(12) United States Patent
Vennemann et al.

(10) Patent No.: US 8,530,493 B2
(45) Date of Patent: Sep. 10, 2013

(54) INDOLOPYRIDINES AS EG5 KINESIN MODULATORS

(75) Inventors: Matthias Vennemann, Constance (DE); Thomas Bär, Reichenau (DE); Jürgen Braunger, Constance (DE); Astrid Zimmermann, Constance (DE); Volker Gekeler, Constance (DE)

(73) Assignee: 4SC AG, Planegg-Martinsried (DE)

( * ) Notice: Subject to any disclaimer, the term of this patent is extended or adjusted under 35 U.S.C. 154(b) by 1129 days.

(21) Appl. No.: 12/280,424

(22) PCT Filed: Feb. 21, 2007

(86) PCT No.: PCT/EP2007/051688
§ 371 (c)(1),
(2), (4) Date: Nov. 18, 2008

(87) PCT Pub. No.: WO2007/096393
PCT Pub. Date: Aug. 30, 2007

(65) Prior Publication Data
US 2009/0233902 A1 Sep. 17, 2009

(30) Foreign Application Priority Data

Feb. 22, 2006 (EP) .................... 06110295
Aug. 16, 2006 (EP) .................... 06119038

(51) Int. Cl.
| A61K 31/435 | (2006.01) |
| A61K 31/44 | (2006.01) |
| A61K 31/41 | (2006.01) |
| A61K 31/40 | (2006.01) |

(52) U.S. Cl.
USPC ........... 514/277; 514/284; 514/359; 514/408; 514/410; 514/422

(58) Field of Classification Search
USPC .................. 514/277, 284, 359, 408, 410, 422
See application file for complete search history.

(56) References Cited

U.S. PATENT DOCUMENTS

| 6,890,933 B1 | 5/2005 | Feng et al. |
| 2003/0113822 A1 | 6/2003 | Westwood et al. |
| 2003/0114432 A1 | 6/2003 | Clare et al. |
| 2004/0242596 A1 | 12/2004 | Kyoung et al. |
| 2005/0004156 A1 | 1/2005 | Feng et al. |
| 2007/0232596 A1 | 10/2007 | Vennemann et al. |

FOREIGN PATENT DOCUMENTS

| EP | 0357122 A2 | 3/1990 |
| WO | 9632003 A2 | 10/1996 |
| WO | 0228865 A2 | 4/2002 |
| WO | 2004004652 A2 | 1/2004 |
| WO | 2004111193 A2 | 12/2004 |
| WO | PCTEP2005054054 R | 11/2005 |
| WO | WO 2006/018435 * | 2/2006 |
| WO | 2006086358 A2 | 8/2006 |
| WO | PCTEP2007051691 R | 5/2007 |
| WO | PCTEP2007055846 R | 6/2007 |
| WO | 2007144384 A1 | 12/2007 |
| WO | 2008006883 A2 | 1/2008 |
| WO | PCTEP2007057195 R | 1/2008 |

OTHER PUBLICATIONS

N. Sunder-Plassmann et al., "Synthesis and Biological Evaluation of New Tetrahydro-β-Carbolines as Inhibitors of the Mitotic Kinesin Eg5", Bioorganic & Medicinal Chemistry, vol. 13 (2005) pp. 6094-6111.

Avakian, et al. "The Synthesis and Microbiological Properties of Beta-(2-Benzothienyl)-theta-aminopropionic Acid." (Journal of American Chemistry Society), 1948, 3075-3076, 70.

Blicke, F. and D. Sheets. "Derivates of Thianaphthene." (Journal of American Chemistry), 1948, 3768-3770, 70.

Hammam, A., et al. "Synthesis of Novel Tricyclic Heterocyclic Compounds as Potential Anticancer Agents Using Chromanone and Thiochromanone as Synthons." (Indian Journal of Chemistry), 2003, 1985-1993, 42B.

Hotha, et al. "HR 22C16: A Potent Small-Molecule Probe for the Dynamics of Cell Division." (Angew Chemistry), 2003, 2481-2484, 115.

Marcus, et al. "Mitotic Kinesin Inhibitors Induce Mitotic Arrest and Cell Death in Taxol-resistant and -sensitive Cancer Cells." (Journal of Biological Chemistry), 2005, 11569-11577, 280:12.

Toth, G., et al. "Fused Heterocycles. Part 3. Synthesis and Stereochemistry of Benzopyrano-and Benzothiapyrano-[4, 3-c] Pyrazoles." (Journal of the Chemical Society), 1989, 319-323, 2.

"GI50 Mean Graph for Compound 652810-NCI Cancer Screen Aug. 2004 Data." (DTP Warehouse), 2004, 1, XP002420061.

\* cited by examiner

*Primary Examiner* — Renee Claytor
(74) *Attorney, Agent, or Firm* — Millen, White, Zelano & Branigan, P.C.

(57) ABSTRACT

Compounds of a certain formula I, in which R1, R2, R3, R4, R5 and R6 have the meanings indicated in the description, are effective compounds with anti-proliferative and/or apoptosis inducing activity.

33 Claims, No Drawings

INDOLOPYRIDINES AS EG5 KINESIN MODULATORS

FIELD OF APPLICATION OF THE INVENTION

The invention relates to indolopyridine derivatives, which can be used in the pharmaceutical industry for the production of pharmaceutical compositions.

KNOWN TECHNICAL BACKGROUND

In the document Hotha et al., Angew. Chem. 2003, 115, 2481-2484 the indolopyridine compound HR22C16 is described as inhibitor of cell division by targeting Eg5.

EP357122 contains, inter alia, indolopyridine, benzofuranopyridine and benzothienopyridine derivatives as cytostatic compounds.

In the International Applications WO9632003 and WO0228865 indolopyridine derivatives are described with PDE inhibitory activity.

In the International Application WO 2004/004652, inter alia, trans-10-(3-hydroxy-phenyl)-2-methyl-3a,4,9,10-tetrahydro-2,9,10a-triaza-cyclopenta[b]fluorene-1,3-dione is described in a crystallized complex with the kinesin spindle protein (KSP).

In the US-application US 2005/0004156 indolopyridine derivatives, specifically monastroline derivatives, are described as Eg5 inhibitors.

In Bioorg. Med. Chem. 13 (2005) 6094-6111 tetrahydro-β-carbolines are described as Eg5 inhibitors.

In J. Org. Chem., vol. 59, no. 6, 1994, p. 1583-1585 and Chem. Pharm. Bull., vol. 42, no. 10, 1994, p. 2108-2112 the reaction of tetrahydro-β-carboline-3-carboxylic acids with isocyanates and isothiocyanates is described.

In J. Med. Chem., vol. 46, no. 21, 2003, p. 4525-4532 indolopyridine derivatives are described with PDE5 inhibitory activity.

The International Application WO 2005/089752 describes tetracyclic carboline derivatives as inhibitors of VEGF production.

DE19744257 describes 2H-pyrrolo[3,4-c]-beta-carbolines as tyrosin kinase inhibitors, which can be used in the treatment of malignant diseases.

DESCRIPTION OF THE INVENTION

It has now been found, that the indolopyridine derivatives, which are described in greater details below, differ from prior art compounds by unanticipated structural features and have surprising and particularly advantageous properties.

Thus, for example, the compounds according to this invention can act as inhibitors of Eg5 kinesin.

In more detail, it has been unexpectedly found that these derivatives are potent and highly efficacious inhibitors of cellular (hyper)proliferation and/or cell-cycle specific inducers of apoptosis in cancer cells. Therefore, these compounds can be particular useful for treating (hyper)proliferative diseases and/or disorders responsive to the induction of apoptosis, notably cancer. By having a cell-cycle specific mode of action, these derivatives should have a higher therapeutic index compared to standard chemotherapeutic drugs targeting basic cellular molecules like DNA.

Thus, for example, the compounds according to this invention are expected to be useful in targeted cancer therapy.

The invention thus relates in a first aspect (aspect A) to compounds of formula I

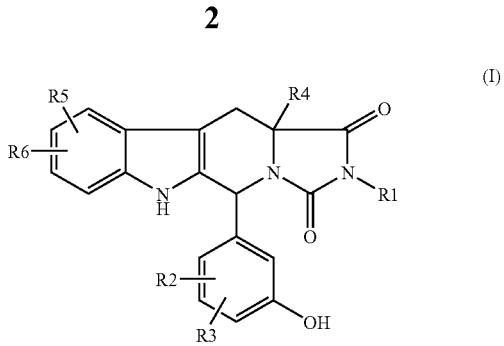

in which
R1 is 1-4C-alkyl, 3-7C-cycloalkyl, 2-4C-alkenyl, 2-4C-alkinyl, 3-7C-cycloalkyl-1-4C-alkyl, or 2-7C-alkyl substituted by R11, in which
R11 is —N(R111)R112, or halogen, in which
R111 is hydrogen, 1-4C-alkyl, 2-4C-alkenyl, 2-4C-alkinyl, 3-7C-cycloalkyl, 3-7C-cycloalkyl-1-4C-alkyl, hydroxy-2-4C-alkyl, 1-4C-alkoxy-2-4C-alkyl, 1N-(1-4C-alkyl)-pyrazolyl, 1N-(H)-pyrazolyl, isoxazolyl, or completely or partially fluorine-substituted 1-4C-alkyl,
R112 is hydrogen, 1-4C-alkyl, 3-7C-cycloalkyl, or 3-7C-cycloalkyl-1-4C-alkyl,
or R111 and R112 together and with inclusion of the nitrogen atom, to which they are bonded, form a ring Het, in which
Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N-(R113)-piperazin-1-yl, 4N-(R113)-homopiperazin-1-yl, 2,5-dihydro-pyrrol-1-yl, 1,2,3,6-tetrahydropyridin-1-yl, pyrrol-1-yl, pyrazol-1-yl, imidazol-1-yl, triazol-1-yl, or tetrazol-1-yl, in which
R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl,
wherein said Het may be optionally substituted by one or two substituents independently selected from fluorine and 1-4C-alkyl,
R2 is hydrogen, 1-4C-alkyl, halogen, trifluoromethyl, 1-4C-alkoxy or hydroxyl,
R3 is hydrogen, 1-4C-alkyl, halogen, trifluoromethyl or 1-4C-alkoxy,
R4 is 1-4C-alkyl, 3-7C-cycloalkyl or 3-7C-cycloalkyl-1-4C-alkyl,
R5 is 1-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy,
R6 is hydrogen, 1-4C-alkyl or halogen,
and the salts, stereoisomers and the salts of the stereoisomers of these compounds.

The invention further relates, in a second aspect (aspect B), which is an embodiment of aspect A, to compounds of formula I,
in which
R1 is 1-4C-alkyl, 3-7C-cycloalkyl, 3-7C-cycloalkyl-1-4C-alkyl, or 2-7C-alkyl substituted by R11, in which
R11 is —N(R111)R112, or halogen, in which
R11 is hydrogen, 1-4C-alkyl, 3-7C-cycloalkyl, 3-7C-cycloalkyl-1-4C-alkyl, hydroxy-2-4C-alkyl, 1-4C-alkoxy-2-4C-alkyl, or completely or partially fluorine-substituted 1-4C-alkyl, R112 is hydrogen, 1-4C-alkyl, 3-7C-cycloalkyl, or 3-7C-cycloalkyl-1-4C-alkyl, or R111 and R112 together and with inclusion of the nitrogen atom, to which they are bonded, form a ring Het, in which Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N-(R113)-piperazin-1-yl, 4N-(R113)-homopiperazin-1-yl, pyrrol-1-yl, pyrazol-1-yl, imidazol-1-yl, triazol-1-yl, or tetrazol-1-yl, in which R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl, wherein said Het may be optionally substituted by one or two substituents independently selected from fluorine and 1-4C-alkyl, R2 is hydrogen, 1-4C-alkyl, halogen, trifluoromethyl, 1-4C-alkoxy or hydroxyl, R3 is hydrogen, 1-4C-alkyl, halogen, trifluoromethyl or 1-4C-alkoxy, R4 is 1-4C-alkyl, 3-7C-cycloalkyl or 3-7C-cycloalkyl-1-4C-alkyl, R5 is 1-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, R6 is hydrogen, 1-4C-alkyl or halogen, and the salts, stereoisomers and the salts of the stereoisomers of these compounds.

The invention further relates, in a third aspect (aspect C), which is also an embodiment of aspect A, to compounds of formula I, in which R1 is 1-4C-alkyl, 3-7C-cycloalkyl, 3-7C-cycloalkyl-1-4C-alkyl, or 2-7C-alkyl substituted by R11, in which R11 is —N(R11)R112, in which R111 is hydrogen, 1-4C-alkyl, 3-7C-cycloalkyl or 3-7C-cycloalkyl-1-4C-alkyl, R112 is hydrogen, 1-4C-alkyl, 3-7C-cycloalkyl or 3-7C-cycloalkyl-1-4C-alkyl, or R111 and R112 together and with inclusion of the nitrogen atom, to which they are bonded, form a ring Het, in which Het is piperidin-1-yl, morpholin-4-yl, thiomorpholin-4-yl, S-oxo-thiomorpholin-4-yl, S,S-dioxothiomorpholin-4-yl, pyrrolidin-1-yl, 4N-(R113)-piperazin-1-yl, pyrrol-1-yl, pyrazol-1-yl, imidazol-1-yl or triazol-1-yl, in which R113 is 1-4C-alkyl, 3-7C-cycloalkyl or 3-7C-cycloalkyl-1-4C-alkyl, R2 is hydrogen, 1-4C-alkyl, halogen, trifluoromethyl, 1-4C-alkoxy or hydroxyl, R3 is hydrogen, 1-4C-alkyl, halogen, trifluoromethyl or 1-4C-alkoxy, R4 is 1-4C-alkyl, 3-7C-cycloalkyl or 3-7C-cycloalkyl-1-4C-alkyl, R5 is 1-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, R6 is hydrogen, 1-4C-alkyl or halogen, and the salts, stereoisomers and the salts of the stereoisomers of these compounds.

As used herein, "alkyl" alone or as part of another group refers to both branched and straight chain saturated aliphatic hydrocarbon groups having the specified numbers of carbon atoms, such as for example:

1-4C-Alkyl is a straight-chain or branched alkyl radical having 1 to 4 carbon atoms. Examples are the butyl, isobutyl, sec-butyl, tert-butyl, propyl, isopropyl, ethyl and methyl radicals, of which propyl, isopropyl, and, particularly, ethyl and methyl are more worthy to be mentioned.

2-7C-Alkyl is a straight-chain or branched alkyl radical having 2 to 7 carbon atoms. Examples are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, isopropyl, and, in particular, the propyl and ethyl radicals.

2-4C-Alkyl is a straight-chain or branched alkyl radical having 2 to 4 carbon atoms. Examples are the butyl, isobutyl, sec-butyl, tert-butyl, isopropyl, and, particularly, the propyl and ethyl radical.

Halogen within the meaning of the present invention is iodine or, in particular, bromine, chlorine or fluorine.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy, ethoxy and methoxy radicals, of which propoxy, isopropoxy, and, particularly, ethoxy and methoxy are more worthy to be mentioned.

The term "cycloalkyl" alone or as part of another group refers to a monocyclic saturated aliphatic hydrocarbon group having the specified numbers of ring carbon atoms, such as for example:

3-7C-Cycloalkyl stands for cyclopropyl, cyclobutyl, cyclopentyl, cyclohexyl and cycloheptyl, of which cyclopropyl, cyclobutyl and cyclopentyl are in particular to be mentioned.

3-7C-Cycloalkyl-1-4C-alkyl stands for one of the abovementioned 1-4C-alkyl radicals, which is substituted by one of the abovementioned 3-7C-cycloalkyl radicals. Examples which may be mentioned are the 3-7C-cycloalkylmethyl radicals, such as e.g. cyclopropylmethyl, cyclobutylmethyl or cyclopentylmethyl, of which cyclopropylmethyl is in particular to be mentioned.

2-4C-Alkenyl is a straight chain or branched alkenyl radical having 2 to 4 carbon atoms. Examples are the 2-butenyl, 3-butenyl (homoallyl), 1-propenyl, 2-propenyl (allyl) and the ethenyl (vinyl) radicals.

2-4C-Alkinyl is a straight chain or branched alkinyl radical having 2 to 4 carbon atoms. Examples are the 2-butinyl, 3-butinyl (homopropargyl), 1-propinyl, 2-propinyl (propargyl), 1-methyl-2-propinyl (1-methyl-propargyl) and the ethinyl radicals.

2-4C-Alkoxy represents radicals which, in addition to the oxygen atom, contain a straight-chain or branched alkyl radical having 2 to 4 carbon atoms. Examples which may be mentioned are the butoxy, isobutoxy, sec-butoxy, tert-butoxy, propoxy, isopropoxy and particularly the ethoxy radicals.

1-4C-Alkoxy-2-4C-alkoxy represents one of the abovementioned 2-4C-alkoxy radicals, which is substituted by one of the abovementioned 1-4C-alkoxy radicals. Examples which may be mentioned are the 2-methoxyethoxy, 2-ethoxyethoxy and the 2-isopropoxyethoxy radicals.

Hydroxy-2-4C-alkoxy represents one of the abovementioned 2-4C-alkoxy radicals, which is substituted by a hydroxyl radical. Examples which may be mentioned are the 2-hydroxyethoxy and the 3-hydroxypropoxy radicals.

3-7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopentyloxy are in particular to be mentioned.

3-7C-Cycloalkyl-1-4C-alkoxy stands for one of the abovementioned 1-4C-alkoxy radicals substituted by one of the abovementioned 3-7C-cycloalkyl radicals. Examples which may be mentioned are the 3-7C-cycloalkylmethoxy radicals, such as e.g. cyclopropylmethoxy, cyclobutylmethoxy or cyclopentylmethoxy, of which cyclopropylmethoxy is in particular to be mentioned.

Completely or predominantly fluorine-substituted 1-4C-alkoxy is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the trifluoromethoxy and the difluoromethoxy radicals are preferred. "Predominantly" in this connection means that more than half of the hydrogen atoms of the 1-4C-alkoxy groups are replaced by fluorine atoms.

Phenyl-1-4C-alkoxy represents one of the abovementioned 1-4C-alkoxy radicals, which is substituted by a phenyl radical. Examples which may be mentioned are the phenethoxy and the benzyloxy radicals.

1-4C-Alkylcarbonyl is a carbonyl group, to which one of the abovementioned 1-4C-alkyl radicals is bonded. An example is the acetyl radical ($CH_3CO$—).

1N-(1-4C-alkyl)-pyrazolyl or 1N-(H)-pyrazolyl, respectively, stands for a pyrazolyl radical which is substituted on the ring nitrogen atom in 1-position with 1-4C-alkyl or hydrogen, respectively; such as especially the 1-methyl-pyrazol-5-yl or 1-methyl-pyrazol-3-yl radical.

As completely or partially fluorine-substituted 1-4C-alkyl, for example, the 2,2,3,3,3-pentafluoropropyl, the perfluoroethyl, the 1,2,2-trifluoroethyl, the 1,1,2,2-tetrafluoroethyl, the 2,2,2-trifluoroethyl, the trifluoromethyl, the difluoromethyl, the monofluoromethyl, the 2-fluoroethyl and the 2,2-difluoroethyl radicals may be mentioned, particularly the 2,2,2-trifluoroethyl, 2,2-difluoroethyl and 2-fluoroethyl radicals.

Het is optionally substituted by one or two substituents independently selected from 1-4C-alkyl and fluorine, and is piperidin-1-yl, morpholin-4-yl, thiomorpholin-4-yl, S-oxothiomorpholin-4-yl, S,S-dioxothiomorpholin-4-yl, pyrrolidin-1-yl, azetidin-1-yl, homopiperidin-1-yl, 4N-(R113)-piperazin-1-yl, 4N-(R113)-homopiperazin-1-yl, 2,5-dihydropyrrol-1-yl, 1,2,3,6-tetrahydropyridin-1-yl, pyrrol-1-yl, pyrazol-1-yl, imidazol-1-yl, triazol-1-yl, or tetrazol-1-yl, in which R21 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl,
in particular
R21 is hydrogen, 1-3C-alkyl, cyclopropyl, cyclopropylmethyl, 1-2C-alkylcarbonyl, or partially fluorine-substituted 1-3C-alkyl (e.g. 2-fluoroethyl, 2,2,2-trifluoroethyl or, particularly, 2,2-difluoroethyl).

In a first embodiment, Het is piperidin-1-yl, morpholin-4-yl, pyrrolidin-1-yl or azetidin-1-yl.

In a second embodiment, Het is 4N-(R113)-piperazin-1-yl, in which
R21 is hydrogen, methyl, ethyl, isopropyl, cyclopropyl, cyclopropylmethyl, 1-2C-alkylcarbonyl, 2-fluoroethyl, 2,2,2-trifluoroethyl or 2,2-difluoroethyl;
such as e.g. 4-methyl-piperazin-1-yl or 4-acetyl-piperazin-1-yl.

In a third embodiment, Het is optionally substituted by one or two substituents independently selected from methyl and fluorine, and is piperidin-1-yl, pyrrolidin-1-yl, azetidin-1-yl or homopiperidin-1-yl; such as e.g. piperidin-1-yl, pyrrolidin-1-yl or azetidin-1-yl, or 4-methyl-piperidin-1-yl, 4-fluoro-piperidin-1-yl, 4,4-difluoro-piperidin-1-yl, (S)-3-fluoro-pyrrolidin-1-yl, (R)-3-fluoro-pyrrolidin-1-yl, 3,3-difluoro-pyrrolidin-1-yl, 3-fluoro-azetidin-1-yl or 3,3-difluoro-azetidin-1-yl.

In a fourth embodiment, Het is pyrazol-1-yl, imidazol-1-yl or triazol-1-yl, especially imidazol-1-yl.

In a fifth embodiment, Het is 2,5-dihydro-pyrrol-1-yl or 1,2,3,6-tetrahydropyridin-1-yl.

Amino-1-4C-alkyl denotes abovementioned 1-4C-alkyl radicals which are substituted by an amino group. Examples which may be mentioned are the aminomethyl, the 2-aminoethyl and the 3-aminopropyl radicals.

Hydroxy-2-4C-alkyl denotes abovementioned 2-4C-alkyl radicals which are substituted by a hydroxyl group. Examples which may be mentioned are the 2-hydroxyethyl and the 3-hydroxypropyl radicals.

1-4C-Alkoxy-2-4C-alkyl denotes abovementioned 2-4C-alkyl radicals which are substituted by one of the abovementioned 1-4C-alkoxy radicals. Examples which may be mentioned are the 2-methoxyethyl and the 3-methoxypropyl radicals.

Mono- or di-1-4C-alkylamino radicals contain, in addition to the nitrogen atom, one or two of the abovementioned 1-4C-alkyl radicals. Examples which may be mentioned are mono-1-4C-alkylamino radicals, like methylamino, ethylamino or isopropylamino, and di-1-4C-alkylamino radicals, like dimethylamino, diethylamino or diisopropylamino.

Mono- or di-1-4C-alkylamino-1-4C-alkyl represents one of the aforementioned 1-4C-alkyl groups, which is substituted by one of the aforementioned mono- or di-1-4C-alkylamino groups. Examples which may be mentioned are the methylamino-methyl, dimethylamino-methyl, 2-methylamino-ethyl, 2-dimethylamino-ethyl, 3-methylamino-propyl or 3-dimethylamino-propyl radicals.

4N-(R113)-piperazin-1-yl or 4N-(R113)-homopiperazin-1-yl stands for a piperazin-1-yl or homopiperazin-1-yl radical, respectively, which is substituted by R113 on the ring nitrogen atom in 4-position. The term 2-(R11)-ethyl stands for ethyl which is substituted in 2-position by R11. The term 3-(R11)-propyl stands for propyl which is substituted in 3-position by R11. The term 4-(R11)-butyl stands for butyl which is substituted in 4-position by R11.

In general and unless otherwise mentioned, the heterocyclic radicals include all the possible isomeric forms thereof, e.g. the positional isomers thereof. Thus, for example, the term triazol-1-yl includes [1,2,3]triazol-1-yl, [1,3,4]triazol-1-yl and [1,2,4]triazol-1-yl, or the term isoxazolyl includes isoxazol-3-yl, isoxazol-4-yl and isoxazol-5-yl.

Constituents which are optionally substituted as stated herein, may be substituted, unless otherwise noted, at any possible position.

Unless otherwise noted, the carbocyclic radicals mentioned herein may be substituted by its substituents or parent molecular groups at any possible position.

The heterocyclic groups mentioned herein may be substituted by their given substituents or parent molecular groups, unless otherwise noted, at any possible position, such as e.g. at any substitutable ring carbon or ring nitrogen atom.

Unless otherwise noted, rings containing quaternizable amino- or imino-type ring nitrogen atoms (—N=) may be preferably not quaternized on these amino- or imino-type ring nitrogen atoms by the mentioned substituents or parent molecular groups.

When any variable occurs more than one time in any constituent, each definition is independent.

Suitable salts for compounds of formula I according to this invention—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid such as (−)-L-malic acid or (+)-D-malic acid, fumaric acid, succinic acid, oxalic acid, tartaric acid such as (+)-L-tartaric acid or (−)-D-tartaric acid or meso-tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

In the context of the foregoing, as further acids, which may be used in the preparation of possible salts of compounds of formula I, can be mentioned, for example, any selected from adipic acid, L-ascorbic acid, L-aspartic acid, benzenesulfonic acid, 4-acetamido-benzoic acid, (+)-camphoric acid, (+)camphor-10-sulfonic acid, caprylic acid (octanoic acid), dodecyl-sulfonic acid, ethane-1,2-disulfonic acid, ethanesulfonic acid, 2-hydroxy-ethanesulfonic acid, formic acid, galactaric acid, gentisic acid, D-glucoheptonic acid, D-glucuronic acid, glutamic acid, 2-oxo-glutaric acid, hippuric acid, lactic acid such as D-lactic acid or L-lactic acid, malonic acid, mandelic acid such as (+)-mandelic acid or (−)-mandelic acid, naphthalene-1,5-disulfonic acid, naphthalene-2-sulfonic acid, nicotinic acid, palmitic acid, pyroglutamic acid such as L-pyroglutamic acid, hydroiodic acid, cyclamic acid, thiocyanic acid, 2,2-dichloroacetic acid, glycerophosphoric acid, 1-hydroxy-2-naphthoic acid, salicyclic acid, 4-aminosalicyclic acid, glycolic acid, oleic acid, glutaric acid, cinnamic acid, capronic acid, isobutyric acid, propionic acid, capric acid, undecylenic acid and orotic acid.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Salts which are unsuitable for pharmaceutical uses but which can be employed, for example, for the isolation or purification of free compounds of formula I or their pharmaceutically acceptable salts, are also included.

Pharmacologically intolerable salts, which can be obtained, for example, as process products during the preparation of the compounds according to this invention on an industrial scale, are converted into pharmacologically tolerable salts by processes known to the person skilled in the art.

According to expert's knowledge the compounds of formula I according to this invention as well as their salts may contain, e.g. when isolated in crystalline form, varying amounts of solvents. Included within the scope of the invention are therefore all solvates and in particular all hydrates of the compounds of formula I according to this invention as well as all solvates and in particular all hydrates of the salts of the compounds of formula I according to this invention.

In one embodiment of this invention, salts of compounds of formula I include a salt of a compound of formula I with hydrochloric acid (a hydrochloride salt).

In another embodiment of this invention, salts of compounds of formula I include hydrochloride, phosphate, citrate, tartrate, mesylate, tosylate and sulphate.

The substituents R2 and R3 of compounds of formula I can be attached in the ortho, meta or para position with respect to the binding position in which the phenyl ring is bonded to the scaffold. In one embodiment R3 is hydrogen. In a particular embodiment R2 and R3 are both hydrogen.

The substituents R5 and R6 may be attached, unless otherwise noted, at any position of the benzene moiety of the scaffold, whereby preference is given to the attachment of none of R5 and R6 to the 8-position of the scaffold. In one embodiment, R5 is attached in the 5-position of the scaffold; in another embodiment, R5 is attached in the 7-position of the scaffold; and in yet another embodiment R5 is attached in the 6-position of the scaffold; wherein, especially, R6 is hydrogen, respectively; or wherein R6 is fluorine, respectively. In a particular embodiment, R5 is attached in the 6-position of the scaffold. In a more particular embodiment, R5 is attached in the 6-position of the scaffold, and R6 is hydrogen. In another embodiment, R5 is attached in the 6-position of the scaffold, and R6 is attached to the 7-position of the scaffold and is fluorine. In yet another embodiment, R5 is attached in the 6-position of the scaffold, and R6 is attached to the 5-position of the scaffold and is fluorine.

Numbering:

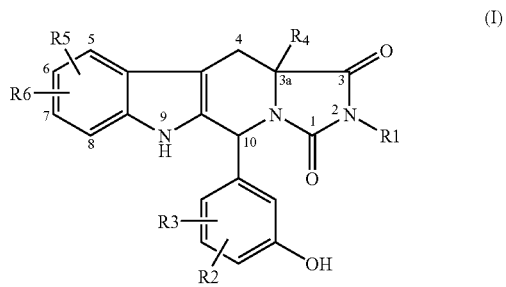

(I)

The compounds of formula I are chiral compounds having chiral centers at least in positions 3a and 10.

The invention includes all conceivable stereoisomers, like e.g. diastereomers and enantiomers, in substantially pure form as well as in any mixing ratio, including the racemates, as well as the salts thereof.

Thus, substantially pure stereoisomers of the compounds according to this invention, particularly substantially pure stereoisomers of the following examples, are all part of the present invention and may be obtained according to procedures customary to the skilled person, e.g. by separation of corresponding mixtures, by using stereochemically pure starting materials and/or by stereoselective synthesis.

Preference is given hereby to those compounds of formula I, which have with respect to the positions 3a and 10 the same configuration as shown in formula I*:

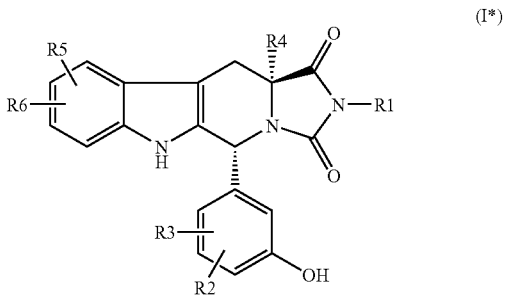

(I*)

If, for example, in compounds of formula I* R4 has the meaning methyl or ethyl, then the configuration according to the rules of Cahn, Ingold and Prelog—is S in the 3a position and R in the 10 position.

If, for example, in compounds of formula I* R4 has the meaning isopropyl or cyclopropyl, then the configuration—according to the rules of Cahn, Ingold and Prelog—is R in the 3a position and R in the 10 position.

Furthermore, compounds of the formula I also worthy to be mentioned are those which have, with respect to the positions 3a and 10, the same configuration as shown in formula I**:

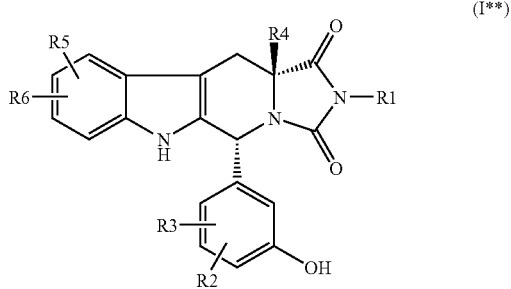

If, for example, in compounds of formula I** R4 has the meaning methyl or ethyl, then the configuration—according to the rules of Cahn, Ingold and Prelog—is R in the 3a position and R in the 10 position.

If, for example, in compounds of formula I** R4 has the meaning isopropyl or cyclopropyl, then the configuration—according to the rules of Cahn, Ingold and Prelog—is S in the 3a position and R in the 10 position.

Further on, compounds of the formula I also to be mentioned are those which have, with respect to the positions 3a and 10, the same configuration as shown in formula I* or I**:

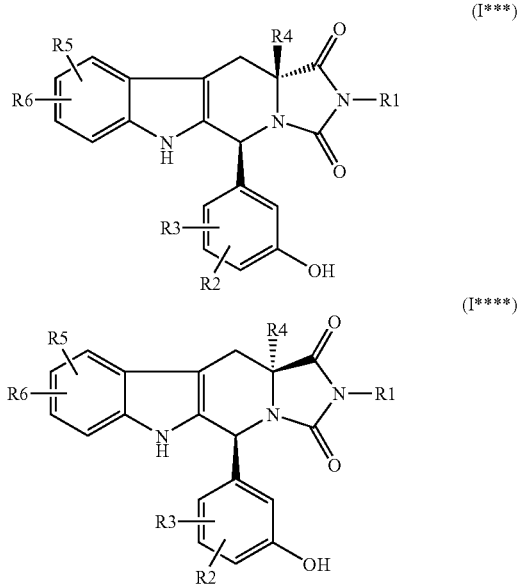

If, for example, in compounds of formula I*** R4 has the meaning methyl or ethyl, then the configuration—according to the rules of Cahn, Ingold and Prelog—is R in the 3a position and S in the 10 position.

If, for example, in compounds of formula I*** R4 has the meaning isopropyl or cyclopropyl, then the configuration—according to the rules of Cahn, Ingold and Prelog—is S in the 3a position and S in the 10 position.

If, for example, in compounds of formula I**** R4 has the meaning methyl or ethyl, then the configuration—according to the rules of Cahn, Ingold and Prelog—is S in the 3a position and S in the 10 position.

If, for example, in compounds of formula I**** R4 has the meaning isopropyl or cyclopropyl, then the configuration—according to the rules of Cahn, Ingold and Prelog—is R in the 3a position and S in the 10 position.

In this connection, in another embodiment, preference is given to those compounds of formula I which have with respect to the positions 3a and 10 the same absolute configuration as the compound (−)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione having the specific optical rotation $[\alpha]^{20}_D = -159°$ (c=0.5400, methanol), as well as the salts thereof.

In general, enantiomerically pure compounds of this invention may be prepared according to art-known processes, such as e.g. via asymmetric syntheses, for example by preparation and separation of appropriate diastereoisomeric compounds/intermediates, which can be separated by known methods (e.g. by chromatographic separation or (fractional) crystallization from a suitable solvent), or by using chiral synthons or chiral reagents; by chromatographic separation of the corresponding racemic compounds on chiral separating columns; by means of diastereomeric salt formation of the racemic compounds with optically active acids (such as e.g. those mentioned later in this application) or bases, subsequent resolution of the salts and release of the desired compound from the salt; by derivatization of the corresponding racemic compounds with chiral auxiliary reagents, subsequent diastereomer separation and removal of the chiral auxiliary group; by kinetic resolution of a racemate (e.g. by enzymatic resolution); by enantioselective (preferential) crystallization (or crystallization by entrainment) from a conglomerate of enantiomorphous crystals under suitable conditions; or by (fractional) crystallization from a suitable solvent in the presence of a chiral auxiliary.

Preferably, enantiomerically pure compounds may be obtained starting from known enantiomerically pure starting compounds via synthesis of diastereomeric intermediates which can be separated by known methods (e.g. by chromatographic separation or crystallization), or by chromatographic resolution of the corresponding racemate on an appropriate chiral separating column.

The enantiomers having the formula I* and the salts thereof are a preferred part of the invention.

In the context of this invention, hyperproliferation and analogous terms are used to describe aberrant/dysregulated cellular growth, a hallmark of diseases like cancer. This hyperproliferation might be caused by single or multiple cellular/molecular alterations in respective cells and can be, in context of a whole organism, of benign or malignant behaviour. Inhibition of cell proliferation and analogous terms is used herein to denote an ability of the compound to retard the growth of and/or kill a cell contacted with that compound as compared to cells not contacted with that compound. Most preferable this inhibition of cell proliferation is 100%, meaning that proliferation of all cells is stopped and/or cells undergo programmed cell death. In some preferred embodiments the contacted cell is a neoplastic cell. A neoplastic cell is defined as a cell with aberrant cell proliferation and/or the potential to metastasize to different tissues or organs. A benign neoplasia is described by hyperproliferation of cells, incapable of forming an aggressive, metastasizing tumor in-vivo. In contrast, a malignant neoplasia is described by cells with different cellular and biochemical abnormalities, e.g. capable of forming tumor metastasis. The acquired functional abnormalities of malignant neoplastic cells (also defined as "hallmarks of cancer") are limitless replicative potential, self-sufficiency in growth signals, insensitivity to anti-growth signals, evasion from apoptosis, sustained angiogenesis and tissue invasion and metastasis.

Inducer of apoptosis and analogous terms are used herein to identify a compound which induces programmed cell death in cells contacted with that compound. Apoptosis is defined by complex biochemical events within the contacted cell, such as the activation of cystein specific proteinases ("caspases") and the fragmentation of chromatin. Induction of apoptosis in cells contacted with the compound might not necessarily be coupled with inhibition of cell proliferation. Preferably, the inhibition of cell proliferation and/or induction of apoptosis is specific to cells with aberrant cell growth (hyperproliferation). Thus, compared to cells with aberrant cell growth, normal proliferating or arrested cells are less sensitive or even insensitive to the proliferation inhibiting or apoptosis inducing activity of the compound. Finally, cytotoxic is used in a more general sense to identify compounds which kill cells by various mechanisms, including the induction of apoptosis/programmed cell death in a cell cycle dependent or cell-cycle independent manner.

Cell cycle specific and analogous terms are used herein to identify a compound as inducing apoptosis/killing only in proliferating cells actively passing a specific phase of the cell cycle, but not in resting, non-dividing cells. Continuously proliferating cells are typical for diseases like cancer and characterized by cells passing all phases of the cell division cycle, namely in the G ("gap") 1, S ("DNA synthesis"), G2 and M ("mitosis") phase.

Compounds according to aspect A of this invention worthy to be mentioned are those compounds of formula I, in which R1 is 1-4C-alkyl, cyclopropyl, cyclopropylmethyl, 2-4C-alkenyl, 2-4C-alkinyl, or 2-4C-alkyl substituted by R11, in which R11 is —N(R111)R112, or halogen, in which R111 is hydrogen, 1-4C-alkyl, 2-4C-alkenyl, 2-4C-alkinyl, cyclopropyl, cyclobutyl, cyclopropylmethyl, hydroxy-2-4C-alkyl, 1-2C-alkoxy-2-4C-alkyl, isoxazolyl, 1N-(1-3C-alkyl)-pyrazolyl, or mono-, di- or tri-fluorine-substituted 1-4C-alkyl, R112 is hydrogen, 1-4C-alkyl, cyclopropyl, or cyclopropylmethyl, or R111 and R112 together and with inclusion of the nitrogen atom, to which they are bonded, form a ring Het, in which Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N-(R113)-piperazin-1-yl, 4N-(R113)-homopiperazin-1-yl, 2,5-dihydro-pyrrol-1-yl, 1,2,3,6-tetrahydropyridin-1-yl, pyrrol-1-yl, pyrazol-1-yl, imidazol-1-yl, triazol-1-yl, or tetrazol-1-yl, in which R113 is hydrogen, 1-3C-alkyl, cyclopropyl, cyclopropylmethyl, 1-3C-alkylcarbonyl, 2-fluoroethyl, 2,2-difluoroethyl, or 2,2,2-trifluoroethyl, wherein said Het may be optionally substituted by one or two substituents independently selected from fluorine and methyl, R2 is hydrogen, R3 is hydrogen, R4 is methyl or ethyl, in particular, R4 is methyl, R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy, in particular, R5 is chlorine, bromine, fluorine, methoxy, ethoxy, difluoromethoxy or trifluoromethoxy, R6 is hydrogen or fluorine, wherein R5 is bonded to the 5-, 7- or, particularly, 6-position of the scaffold, and wherein R6 is bonded to the 5- or 7-position of the scaffold, and the salts, stereoisomers and the salts of the stereoisomers of these compounds.

Compounds according to aspect A of this invention more worthy to be mentioned are those compounds of formula I, in which R1 is methyl, vinyl, 2-(R11)-ethyl, or 3-(R11)-propyl, in which R11 is —N(R111)R112, fluorine, chlorine, or bromine, in which either R111 is hydrogen, and R112 is hydrogen, or R111 is methyl, ethyl, propyl, isopropyl, isobutyl, tertbutyl, vinyl, allyl, propargyl, 1-methyl-propargyl, cyclopropyl, cyclobutyl, cyclopropylmethyl, 2-hydroxyethyl, isoxazolyl, 1N-(methyl)-pyrazolyl, 2-methoxyethyl, 2-fluoroethyl, 2,2-difluoroethyl, or 2,2,2-trifluoroethyl, and R112 is hydrogen, or R111 is methyl, ethyl, propyl, isopropyl, isobutyl, tertbutyl, vinyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and R112 is methyl, or R111 is ethyl, propyl, isopropyl, isobutyl, tertbutyl, vinyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and R112 is ethyl, isopropyl, or cyclopropyl, or R111 and R112 together and with inclusion of the nitrogen atom, to which they are bonded, form a ring Het, in which Het is piperidin-1-yl, morpholin-4-yl, thiomorpholin-4-yl, pyrrolidin-1-yl, azetidin-1-yl, homopiperidin-1-yl, 4N-(R113)-piperazin-1-yl, 4N-(R113)-homopiperazin-1-yl, 2,5-dihydro-pyrrol-1-yl, 1,2,3,6-tetrahydropyridin-1-yl, pyrrol-1-yl, pyrazol-1-yl, imidazol-1-yl, triazol-1-yl, or tetrazol-1-yl, in which R113 is hydrogen, methyl, ethyl, propyl, isopropyl, acetyl, 2-fluoroethyl, 2,2-difluoroethyl, or 2,2,2-trifluoroethyl, wherein said Het may be optionally substituted by one or two substituents independently selected from fluorine and methyl, R2 is hydrogen, R3 is hydrogen, R4 is methyl, R5 is chlorine, bromine, fluorine, ethoxy, methoxy, difluoromethoxy or trifluoromethoxy, in more particular, R5 is chlorine, bromine, ethoxy, methoxy or difluoromethoxy, R6 is hydrogen or fluorine,
wherein R5 is bonded to the 6-position of the scaffold, and
wherein R6 is bonded to the 5- or 7-position of the scaffold,
and the salts, stereoisomers and the salts of the stereoisomers
of these compounds.

Compounds according to aspect A of this invention in particular worthy to be mentioned are those compounds of formula I, in which
R1 is 2-(R11)-ethyl, or 3-(R11)-propyl, in which
R11 is —N(R111)R112, in which
either
R111 is hydrogen, and
R112 is hydrogen,
or
R111 is methyl, ethyl, propyl, isopropyl, isobutyl, tertbutyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is hydrogen,
or
R111 is methyl, ethyl, propyl, isopropyl, isobutyl, tertbutyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is methyl,
or
R111 is ethyl, propyl, isopropyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is ethyl,
or
R111 and R112 together and with inclusion of the nitrogen atom, to which they are bonded, form a ring Het, in which
either
Het is piperidin-1-yl, morpholin-4-yl, pyrrolidin-1-yl, azetidin-1-yl, homopiperidin-1-yl, 4N-(R113)piperazin-1-yl, 4N-(R113)-homopiperazin-1-yl, 2,5-dihydro-pyrrol-1-yl, 1,2,3,6-tetrahydropyridin-1-yl, 4-methyl-piperidin-1-yl, 4-fluoro-piperidin-1-yl, 4,4-difluoropiperidin-1-yl, (S)-3-fluoro-pyrrolidin-1-yl, (R)-3-fluoro-pyrrolidin-1-yl, or 3,3-difluoro-pyrrolidin-1-yl, in which
R113 is methyl or acetyl,
or
Het is pyrazol-1-yl, or imidazol-1-yl,
R2 is hydrogen,
R3 is hydrogen,
R4 is methyl,
R5 is chlorine, bromine, fluorine, ethoxy, methoxy, difluoromethoxy or trifluoromethoxy, in more particular,
R5 is chlorine, bromine, ethoxy, methoxy or difluoromethoxy,
R6 is hydrogen or fluorine,
wherein R5 is bonded to the 6-position of the scaffold, and
wherein R6 is bonded to the 5- or, particularly, 7-position of the scaffold,
and the salts, stereoisomers and the salts of the stereoisomers of these compounds.

Compounds according to aspect A of this invention in more particular worthy to be mentioned are those compounds of formula I, in which
R1 is 2-(R11)-ethyl, or 3-(R11)-propyl, in which
R11 is —N(R111)R112, in which
either
R111 is methyl, ethyl, isopropyl, isobutyl, tertbutyl, allyl, cyclopropyl, cyclobutyl, cyclopropylmethyl, 2-hydroxyethyl, or 2-methoxyethyl, and
R112 is hydrogen,
or
R111 is methyl, ethyl, isopropyl, allyl, cyclopropyl, cyclobutyl, cyclopropylmethyl, 2-hydroxyethyl, or 2-methoxyethyl, and
R112 is methyl,
or
R111 is ethyl, 2-hydroxyethyl, or 2-methoxyethyl, and
R112 is ethyl,
or
R111 and R112 together and with inclusion of the nitrogen atom, to which they are bonded, form a ring Het, in which
Het is piperidin-1-yl, pyrrolidin-1-yl, azetidin-1-yl, 2,5-dihydro-pyrrol-1-yl, or 1,2,3,6-tetrahydropyridin-1-yl,
R2 is hydrogen,
R3 is hydrogen,
R4 is methyl,
R5 is chlorine, bromine, ethoxy, methoxy or difluoromethoxy,
R6 is hydrogen or fluorine,
wherein R5 is bonded to the 6-position of the scaffold, and
wherein R6 is bonded to the 7-position of the scaffold,
and the salts, stereoisomers and the salts of the stereoisomers of these compounds.

Compounds according to aspect A of this invention to be emphasized are those compounds of formula I*, in which
R1 is 2-(R11)-ethyl, or 3-(R11)-propyl, in which
R11 is —N(R111)R112, in which
either
R111 is methyl, ethyl, isopropyl, isobutyl, tertbutyl, allyl, cyclopropyl, cyclobutyl, cyclopropylmethyl, 2-hydroxyethyl, or 2-methoxyethyl, and
R112 is hydrogen,
or
R111 is methyl, ethyl, isopropyl, allyl, cyclopropyl, cyclobutyl, cyclopropylmethyl, 2-hydroxyethyl, or 2-methoxyethyl, and
R112 is methyl,
or
R111 is ethyl, 2-hydroxyethyl, or 2-methoxyethyl, and
R112 is ethyl,
or
R111 and R112 together and with inclusion of the nitrogen atom, to which they are bonded, form a ring Het, in which
Het is piperidin-1-yl, pyrrolidin-1-yl, azetidin-1-yl, 2,5-dihydro-pyrrol-1-yl, or 1,2,3,6-tetrahydropyridin-1-yl,
R2 is hydrogen,
R3 is hydrogen,
R4 is methyl,
R5 is chlorine, bromine, ethoxy, methoxy or difluoromethoxy,
R6 is hydrogen,
wherein R5 is bonded to the 6-position of the scaffold,
and the salts, stereoisomers and the salts of the stereoisomers of these compounds.

Compounds according to aspect B of this invention worthy to be mentioned are those compounds of formula I, in which
R1 is 1-4C-alkyl, cyclopropyl, cyclopropylmethyl, or 2-4C-alkyl substituted by R11, in which
R11 is —N(R111)R112, or halogen, in which
R111 is hydrogen, 1-4C-alkyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, R112 is hydrogen, 1-4C-alkyl, cyclopropyl, or cyclopropylmethyl,
or R111 and R112 together and with inclusion of the nitrogen atom, to which they are bonded, form a ring Het, in which
Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N-(R113)-piperazin-1-yl, 4N-(R113)-homopiperazin-1-yl, pyrrol-1-yl, pyrazol-1-yl, imidazol-1-yl, triazol-1-yl, or tetrazol-1-yl, in which
R113 is hydrogen, 1-3C-alkyl, cyclopropyl, cyclopropylmethyl, 1-3C-alkylcarbonyl, 2-fluoroethyl, 2,2-difluoroethyl, or 2,2,2-trifluoroethyl,
wherein said Het may be optionally substituted by one or two substituents independently selected from fluorine and 1-3C-alkyl,
R2 is hydrogen,
R3 is hydrogen,
R4 is 1-4C-alkyl, cyclopropyl or cyclopropylmethyl,
R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
R6 is hydrogen,
wherein R5 is bonded to the 5-, 7- or, particularly, 6-position of the scaffold,
and the salts, stereoisomers and the salts of the stereoisomers of these compounds.

Compounds according to aspect B of this invention more worthy to be mentioned are those compounds of formula I, in which
R1 is methyl, ethyl, propyl, isopropyl, cyclopropyl, cyclopropylmethyl, ethyl substituted by R11, propyl substituted by R11, or butyl substituted by R11, in which
R11 is —N(R111)R112, fluorine, chlorine, or bromine, in which
either
R111 is hydrogen, and
R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is methyl,
or
R111 is ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is ethyl, isopropyl, or cyclopropyl,
or
R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, azetidin-1-yl, homopiperidin-1-yl, 4N-(R113)-piperazin-1-yl, 4N-(R113)-homopiperazin-1-yl, pyrrol-1-yl, pyrazol-1-yl, imidazol-1-yl, triazol-1-yl, or tetrazol-1-yl, in which
R113 is hydrogen, methyl, ethyl, propyl, isopropyl, acetyl, 2-fluoroethyl, 2,2-difluoroethyl, or 2,2,2-trifluoroethyl,
wherein said Het may be optionally substituted by one or two substituents independently selected from fluorine and methyl,
R2 is hydrogen,
R3 is hydrogen,
R4 is methyl, ethyl, propyl, isopropyl, cyclopropyl or cyclopropylmethyl, in particular,
R4 is methyl, ethyl, isopropyl or cyclopropyl, in more particular,
R4 is methyl or ethyl, in yet more particular,
R4 is methyl,
R5 is chlorine, bromine, fluorine, ethoxy, methoxy, propoxy, isopropoxy, cyclopropylmethoxy, or completely or predominantly fluorine-substituted 1-2C-alkoxy, in particular,
R5 is chlorine, bromine, fluorine, ethoxy, methoxy, difluoromethoxy or trifluoromethoxy, in more particular,
R5 is chlorine, bromine, ethoxy, methoxy or difluoromethoxy,
R6 is hydrogen,
wherein R5 is bonded to the 6-position of the scaffold,
and the salts, stereoisomers and the salts of the stereoisomers of these compounds.

Compounds according to aspect B of this invention in particular worthy to be mentioned are those compounds of formula I*, in which
R1 is methyl, 2-(R11)-ethyl, or 3-(R11)-propyl, in which
R11 is —N(R111)R112, in which
either
R111 is hydrogen, and
R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is methyl,
or
R111 is ethyl, propyl, isopropyl, cyclopropyl, 2-hydroxyethyl, 2-methoxyethyl, 2-fluoroethyl, 2,2-difluoroethyl, or 2,2,2-trifluoroethyl, and
R112 is ethyl,
or
R111 and R112 together and with inclusion of the nitrogen atom, to which they are bonded, form a ring Het, in which
either
Het is piperidin-1-yl, morpholin-4-yl, pyrrolidin-1-yl, azetidin-1-yl, or 4N-(R113)-piperazin-1-yl, in which
R113 is hydrogen, methyl, ethyl, isopropyl, acetyl, 2-fluoroethyl, 2,2-difluoroethyl, or 2,2,2-trifluoroethyl,
wherein said Het may be optionally substituted by one or two substituents independently selected from fluorine and methyl,
or
Het is pyrazol-1-yl, imidazol-1-yl, or triazol-1-yl,
R2 is hydrogen,
R3 is hydrogen,
R4 is methyl, ethyl, isopropyl or cyclopropyl,
in particular,
R4 is methyl or ethyl, in more particular,
R4 is methyl,
R5 is chlorine, bromine, fluorine, ethoxy, methoxy, propoxy, isopropoxy, cyclopropylmethoxy, or completely or predominantly fluorine-substituted 1-2C-alkoxy, in particular,
R5 is chlorine, bromine, fluorine, ethoxy, methoxy, difluoromethoxy or trifluoromethoxy, in more particular,
R5 is chlorine, bromine, ethoxy, methoxy or difluoromethoxy,
R6 is hydrogen,
wherein R5 is bonded to 6-position of the scaffold,
and the salts of these compounds.

Compounds according to aspect B of this invention in more particular worthy to be mentioned are those compounds of formula I*, in which
R1 is 2-(R11)-ethyl, or 3-(R11)-propyl, in which
R11 is —N(R111)R112, in which
either
R111 is hydrogen, and
R112 is hydrogen,
or
R111 is methyl, ethyl, propyl, isopropyl, isobutyl, cyclopropyl, cyclobutyl, or cyclopropylmethyl, and
R112 is hydrogen,
or
R111 is methyl, ethyl, isopropyl, or cyclopropyl, and
R112 is methyl,
or
R111 is ethyl, isopropyl, or cyclopropyl, and
R112 is ethyl,
or
R111 and R112 together and with inclusion of the nitrogen atom, to which they are bonded, form a ring Het, in which
either
Het is piperidin-1-yl, morpholin-4-yl, pyrrolidin-1-yl, azetidin-1-yl, 4N-(R113)-piperazin-1-yl, 4-methylpiperidin-1-yl, 4-fluoro-piperidin-1-yl, 4,4-difluoropiperidin-1-yl, (S)-3-fluoro-pyrrolidin-1-yl, (R)-3-fluoro-pyrrolidin-1-yl, 3,3-difluoro-pyrrolidin-1-yl, 3-fluoro-azetidin-1-yl, or 3,3-difluoro-azetidin-1-yl, in which
R113 is hydrogen, methyl, or acetyl,
or
Het is pyrazol-1-yl, or imidazol-1-yl,
R2 is hydrogen,
R3 is hydrogen,
R4 is methyl, ethyl, isopropyl or cyclopropyl,
in particular,
R4 is methyl or ethyl,
in more particular,
R4 is methyl,
R5 is chlorine, bromine, fluorine, ethoxy, methoxy, or completely or predominantly fluorine-substituted 1-2C-alkoxy, in particular
R5 is chlorine, bromine, fluorine, ethoxy, methoxy, difluoromethoxy or trifluoromethoxy, in more particular,
R5 is chlorine, bromine, ethoxy, methoxy or difluoromethoxy,
in yet more particular,
R5 is chlorine, ethoxy, methoxy or difluoromethoxy,
R6 is hydrogen,
wherein R5 is bonded to the 6-position of the scaffold,
and the salts of these compounds.

In one embodiment of aspect B of this invention (embodiment B1), compounds according to aspect B of this invention to be emphasized are those compounds of formula I, in which
R1 is methyl, ethyl, propyl, isopropyl, isobutyl, cyclopropyl, cyclopropylmethyl, ethyl substituted by R11, propyl substituted by R11, or butyl substituted by R11, in which
R11 is —N(R111)R112, or halogen, in which
either
R111 is hydrogen, and
R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is methyl,
or
R111 is ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is ethyl, isopropyl, or cyclopropyl,
or
R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, azetidin-1-yl, homopiperidin-1-yl, 4N-(R113)-piperazin-1-yl, 4N-(R113)-homopiperazin-1-yl, pyrrol-1-yl, pyrazol-1-yl, imidazol-1-yl, triazol-1-yl, or tetrazol-1-yl, in which
R113 is hydrogen, methyl, ethyl, propyl, isopropyl, cyclopropyl, cyclopropylmethyl, 1-2C-alkylcarbonyl, 2-fluoroethyl, 2,2-difluoroethyl, or 2,2,2-trifluoroethyl,
wherein said Het may be optionally substituted by one or two substituents independently selected from fluorine and methyl,
R2 is hydrogen,
R3 is hydrogen,
R4 is methyl,
R5 is methyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
in particular,
R5 is chlorine, bromine, fluorine, ethoxy, methoxy, propoxy, isopropoxy, cyclopropylmethoxy, difluoromethoxy or trifluoromethoxy, in more particular,
R5 is chlorine, bromine, fluorine, ethoxy, methoxy, difluoromethoxy or trifluoromethoxy, in yet more particular,
R5 is chlorine, bromine, ethoxy, methoxy or difluoromethoxy,
R6 is hydrogen,
wherein R5 is bonded to the 5-, 7- or, particularly, 6-position of the scaffold,
and the salts of these compounds.

Compounds according to embodiment B1 of aspect B of this invention worthy to be mentioned are those compounds of formula I*, in which
R1 is methyl, 2-(R11)-ethyl, or 3-(R11)-propyl, in which
R11 is —N(R111)R112, fluorine, chlorine, or bromine, in which
either
R111 is hydrogen, and R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is methyl,
or
R111 is ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is ethyl,
or
R111 and R112 together and with inclusion of the nitrogen atom, to which they are bonded, form a ring Het, in which either
Het is piperidin-1-yl, morpholin-4-yl, thiomorpholin-4-yl, pyrrolidin-1-yl, azetidin-1-yl, homopiperidin-1-yl, 4N-(R113)-piperazin-1-yl, or 4N-(R113)-homopiperazin-1-yl, in which
R113 is hydrogen, methyl, ethyl, isopropyl, acetyl, 2-fluoroethyl, 2,2-difluoroethyl, or 2,2,2-trifluoroethyl,
wherein said Het may be optionally substituted by one or two substituents independently selected from fluorine and methyl,
or
Het is pyrazol-1-yl, imidazol-1-yl, or triazol-1-yl,
R2 is hydrogen,
R3 is hydrogen,
R4 is methyl,
R5 is chlorine, bromine, fluorine, ethoxy, methoxy, propoxy, isopropoxy, cyclopropylmethoxy, or completely or predominantly fluorine-substituted 1-2C-alkoxy,
in particular,
R5 is chlorine, bromine, fluorine, ethoxy, methoxy, difluoromethoxy or trifluoromethoxy,
in more particular,
R5 is chlorine, bromine, ethoxy, methoxy or difluoromethoxy,
R6 is hydrogen,
wherein R5 is bonded to the 6-position of the scaffold,
and the salts of these compounds.

Compounds according to embodiment B1 of aspect B of this invention more worthy to be mentioned are those compounds of formula I*, in which
R1 is methyl, 2-(R11)-ethyl, or 3-(R11)-propyl, in which
R11 is —N(R111)R112, in which
either
R111 is hydrogen, and
R112 is hydrogen,
or
R111 is methyl, ethyl, propyl, isopropyl, isobutyl, cyclopropyl, cyclobutyl, cyclopropylmethyl, 2-fluoroethyl, 2,2-difluoroethyl, or 2,2,2-trifluoroethyl, and
R112 is hydrogen,
or
R111 is methyl, ethyl, propyl, isopropyl, isobutyl, cyclopropyl, cyclobutyl, cyclopropylmethyl, 2-fluoroethyl, 2,2-difluoroethyl, or 2,2,2-trifluoroethyl, and R112 is methyl,
or
R111 is ethyl, propyl, isopropyl, cyclopropyl, 2-fluoroethyl, 2,2-difluoroethyl, or 2,2,2-trifluoroethyl, and
R112 is ethyl,
or
R111 and R112 together and with inclusion of the nitrogen atom, to which they are bonded, form a ring Het, in which either
Het is piperidin-1-yl, morpholin-4-yl, pyrrolidin-1-yl, azetidin-1-yl, 4N-(R113)-piperazin-1-yl, 4-methylpiperidin-1-yl, 4-fluoro-piperidin-1-yl, 4,4-difluoro-piperidin-1-yl, (S)-3-fluoro-pyrrolidin-1-yl, (R)-3-fluoro-pyrrolidin-1-yl, 3,3-difluoro-pyrrolidin-1-yl, 3-fluoro-azetidin-1-yl, or 3,3-difluoro-azetidin-1-yl, in which
R113 is hydrogen, methyl, ethyl, isopropyl, acetyl, 2-fluoroethyl, 2,2-difluoroethyl, or 2,2,2-trifluoroethyl,
or
Het is pyrazol-1-yl, or imidazol-1-yl,
R2 is hydrogen,
R3 is hydrogen,
R4 is methyl,
R5 is chlorine, bromine, fluorine, ethoxy, methoxy, or completely or predominantly fluorine-substituted 1-2C-alkoxy,
R6 is hydrogen,
wherein R5 is bonded to the 6-position of the scaffold;
in a more particular individual embodiment,
R5 is chlorine,
in another more particular individual embodiment,
R5 is methoxy,
in another more particular individual embodiment,
R5 is ethoxy,
in another more particular individual embodiment,
R5 is difluoromethoxy;
and the salts of these compounds.

Compounds according to embodiment B1 of aspect B of this invention in particular worthy to be mentioned are those compounds of formula I*, in which
R1 is methyl, 2-(R11)-ethyl, or 3-(R11)-propyl, in which
R11 is —N(R111)R112, in which
either
R111 is hydrogen, and
R112 is hydrogen,
or
R111 is methyl, and
R112 is hydrogen,
or
R111 is ethyl, and
R112 is hydrogen,
or
R111 is isopropyl, and
R112 is hydrogen,
or
R111 is isobutyl, and
R112 is hydrogen,
or
R111 is cyclopropyl, and
R112 is hydrogen,
or
R111 is cyclobutyl, and
R112 is hydrogen,
or
R111 is cyclopropylmethyl, and
R112 is hydrogen,
or
R111 is methyl, and
R112 is methyl, or
R111 is ethyl, and
R112 is methyl,
or
R111 is isopropyl, and
R112 is methyl,
or
R111 is ethyl, and
R112 is ethyl,
or
R111 and R112 together and with inclusion of the nitrogen atom, to which they are bonded, form a ring Het, in which
Het is piperidin-1-yl, morpholin-4-yl, pyrrolidin-1-yl, azetidin-1-yl, 4-methyl-piperazin-1-yl, 4-acetylpiperazin-1-yl, 4-methyl-piperidin-1-yl, 4-fluoro-piperidin-1-yl, 4,4-difluoro-piperidin-1-yl, (S)-3-fluoro-pyrrolidin-1-yl, (R)-3-fluoro-pyrrolidin-1-yl, 3,3-difluoro-pyrrolidin-1-yl, 3-fluoro-azetidin-1-yl, 3,3-difluoro-azetidin-1-yl, or imidazol-1-yl,
R2 is hydrogen,
R3 is hydrogen,
R4 is methyl,
R5 is chlorine, bromine, fluorine, ethoxy, methoxy, difluoromethoxy or trifluoromethoxy,
in particular,
R5 is chlorine, bromine, ethoxy, methoxy or difluoromethoxy,
R6 is hydrogen,
wherein R5 is bonded to the 6-position of the scaffold;
in a more particular individual embodiment,
R5 is chlorine,
in another more particular individual embodiment,
R5 is methoxy,
in another more particular individual embodiment,
R5 is ethoxy,
in another more particular individual embodiment,
R5 is difluoromethoxy;
and the salts of these compounds.

Compounds according to embodiment B1 of aspect B of this invention in more particular worthy to be mentioned are those compounds of formula I*, in which
R1 is 2-(R11)-ethyl, in which
R11 is —N(R111)R112, in which
either
R111 is hydrogen, and
R112 is hydrogen,
or
R111 is methyl, and
R112 is hydrogen,
or
R111 is ethyl, and
R112 is hydrogen,
or
R111 is isopropyl, and
R112 is hydrogen,
or
R111 is isobutyl, and
R112 is hydrogen,
or
R111 is cyclopropyl, and
R112 is hydrogen,
or
R111 is cyclobutyl, and
R112 is hydrogen,
or
R111 is cyclopropylmethyl, and
R112 is hydrogen,
or
R111 is methyl, and
R112 is methyl,
or
R111 is ethyl, and
R112 is methyl,
or
R111 is isopropyl, and
R112 is methyl,
or
R2 and R3 together and with inclusion of the nitrogen atom, to which they are bonded, form a ring HetB, in which
HetB is piperidin-1-yl, morpholin-4-yl, pyrrolidin-1-yl, azetidin-1-yl, 4-methyl-piperazin-1-yl, 4-acetylpiperazin-1-yl, or 3,3-difluoro-pyrrolidin-1-yl,
R2 is hydrogen,
R3 is hydrogen,
R4 is methyl,
R5 is chlorine, bromine, fluorine, ethoxy, methoxy, difluoromethoxy or trifluoromethoxy,
in particular,
R5 is chlorine, bromine, ethoxy, methoxy or difluoromethoxy,
R6 is hydrogen,
wherein R5 is bonded to the 6-position of the scaffold;
in a more particular individual embodiment,
R5 is chlorine,
in another more particular individual embodiment,
R5 is methoxy,
in another more particular individual embodiment,
R5 is ethoxy,
in another more particular individual embodiment,
R5 is difluoromethoxy;
and the salts of these compounds.

Compounds according to aspect C of this invention worthy to be mentioned are those compounds of formula I, in which
R1 is 1-4C-alkyl, cyclopropyl, cyclopropylmethyl, or 2-4C-alkyl substituted by R11, in which
R11 is —N(R111)R112, in which
R111 is hydrogen, 1-4C-alkyl, cyclopropyl or cyclopropylmethyl,
R112 is hydrogen, 1-4C-alkyl, cyclopropyl or cyclopropylmethyl,
or R111 and R112 together and with inclusion of the nitrogen atom, to which they are bonded, form a ring Het, in which
Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, 4N-(R113)-piperazin-1-yl, pyrrol-1-yl, pyrazol-1-yl, imidazol-1-yl or triazol-1-yl, in which
R113 is 1-4C-alkyl, cyclopropyl or cyclopropylmethyl,
R2 is hydrogen,
R3 is hydrogen,
R4 is 1-4C-alkyl, cyclopropyl or cyclopropylmethyl,
R5 is 1-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-5C-cycloalkoxy, 3-5C-cycloalkyl-1-4C-alkoxy, or completely or predominantly fluorine-substituted 1-4C-alkoxy,
R6 is hydrogen,
and the salts, stereoisomers and the salts of the stereoisomers of these compounds.

Compounds according to aspect C of this invention more worthy to be mentioned are those compounds of formula I, in which
R1 is methyl, ethyl, propyl, isopropyl, cyclopropyl, cyclopropylmethyl, or 2-4C-alkyl substituted by R11, in which
R11 is —N(R111)R112, in which R111 is hydrogen, methyl, ethyl, propyl, isopropyl, cyclopropyl or cyclopropylmethyl,
R112 is hydrogen, methyl, ethyl, propyl, isopropyl, cyclopropyl or cyclopropylmethyl,
or R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, 4N-(R113)-piperazin-1-yl, pyrrol-1-yl, pyrazol-1-yl, imidazol-1-yl or triazol-1-yl, in which
R113 is methyl, ethyl, propyl, isopropyl, cyclopropyl or cyclopropylmethyl,
R2 is hydrogen,
R3 is hydrogen,
R4 is methyl, ethyl, propyl, isopropyl, cyclopropyl or cyclopropylmethyl,
R5 is 1-4C-alkyl, halogen, 1-4C-alkoxy, trifluoromethyl, phenyl-1-2C-alkoxy, 1-4C-alkoxy-2-3C-alkoxy, 3-5C-cycloalkoxy, 3-5C-cycloalkyl-1-2C-alkoxy, or completely or predominantly fluorine-substituted 1-4C-alkoxy,
R6 is hydrogen,
wherein R5 is bonded to the 5-, 7- or 6-position of the scaffold,
and the salts, stereoisomers and the salts of the stereoisomers of these compounds.

Compounds according to aspect C of this invention in particular worthy to be mentioned are those compounds of formula I*, in which
R1 is methyl, ethyl, propyl, isopropyl, cyclopropyl, cyclopropylmethyl, or 2-4C-alkyl substituted by R11, in which
R11 is —N(R111)R112, in which
R111 is hydrogen, methyl, ethyl, propyl, isopropyl, cyclopropyl or cyclopropylmethyl,
R112 is hydrogen, methyl, ethyl, propyl, isopropyl, cyclopropyl or cyclopropylmethyl,
or R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, 4N-(R113)-piperazin-1-yl, pyrrol-1-yl, pyrazol-1-yl, imidazol-1-yl or triazol-1-yl, in which
R113 is methyl, ethyl, propyl, isopropyl, cyclopropyl or cyclopropylmethyl,
R2 is hydrogen,
R3 is hydrogen,
R4 is methyl, ethyl, propyl, isopropyl, cyclopropyl or cyclopropylmethyl,
R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
R6 is hydrogen,
wherein R5 is bonded to the 5-, 7- or 6-position of the scaffold,
and the salts these compounds.

Compounds according to aspect C of this invention in more particular worthy to be mentioned are those compounds of formula I*, in which
R1 is methyl, ethyl, ethyl substituted by R11, propyl substituted by R11, or butyl substituted by R11, in which
R11 is —N(R111)R112, in which
R111 is hydrogen, methyl or ethyl,
R112 is hydrogen, methyl or ethyl,
or R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, 4N-(R113)-piperazin-1-yl, pyrrol-1-yl, pyrazol-1-yl, imidazol-1-yl or triazol-1-yl, in which
R113 is methyl,
R2 is hydrogen,
R3 is hydrogen,
R4 is methyl, ethyl, propyl, isopropyl, cyclopropyl or cyclopropylmethyl,
R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
R6 is hydrogen,
wherein R5 is bonded to the 5-, 7- or, particularly, 6-position of the scaffold,
and the salts of these compounds.

Compounds according to aspect C of this invention in further more particular worthy to be mentioned are those compounds of formula I*, in which
R1 is methyl, 2-(R11)-ethyl, or 3-(R11)-propyl, in which
R11 is —N(R111)R112, in which
R111 is methyl,
R112 is methyl,
or R111 and R112 together and with inclusion of the nitrogen atom, to which they are bonded, form a ring Het, in which
Het is piperidin-1-yl, morpholin-4-yl, pyrrolidin-1-yl, 4-methyl-piperazin-1-yl, pyrazol-1-yl, imidazol-1-yl or triazol-1-yl, in which
R2 is hydrogen,
R3 is hydrogen,
R4 is methyl, ethyl, isopropyl or cyclopropyl,
R5 is methyl, fluorine, chlorine, bromine, methoxy, ethoxy, propoxy, isopropoxy, trifluoromethyl, 2-methoxy-ethoxy, cyclopropylmethoxy, difluoromethoxy or trifluoromethoxy,
R6 is hydrogen,
wherein R5 is bonded to the 6-position of the scaffold,
and the salts of these compounds.

In one embodiment of aspect C of this invention (embodiment C1), compounds according to aspect C of this invention to be emphasized are those compounds of formula I*, in which
R1 is methyl, ethyl, propyl, isopropyl, cyclopropyl, cyclopropylmethyl, or 2-4C-alkyl substituted by R11, in which
R11 is —N(R111)R112, in which
R111 is hydrogen, methyl, ethyl, propyl, isopropyl, cyclopropyl or cyclopropylmethyl,
R112 is hydrogen, methyl, ethyl, propyl, isopropyl, cyclopropyl or cyclopropylmethyl,
or R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, 4N-(R113)-piperazin-1-yl, pyrrol-1-yl, pyrazol-1-yl, imidazol-1-yl or triazol-1-yl, in which
R113 is methyl,
R2 is hydrogen,
R3 is hydrogen,
R4 is methyl,
R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
R6 is hydrogen,
wherein R5 is bonded to the 5-, 7- or 6-position of the scaffold,
and the salts of these compounds.

Compounds according to embodiment C1 of aspect C of this invention worthy to be mentioned are those compounds of formula I*, in which
R1 is methyl, ethyl, or 2-4C-alkyl substituted by R11, in which
R11 is —N(R111)R112, in which
R111 is hydrogen or methyl,
R112 is hydrogen or methyl,
or R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, 4-methyl-piperazin-1-yl, pyrrol-1-yl, pyrazol-1-yl, imidazol-1-yl or triazol-1-yl, in which
R2 is hydrogen,
R3 is hydrogen,
R4 is methyl,
R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
R6 is hydrogen,
wherein R5 is bonded to the 5-, 7- or, particularly, 6-position of the scaffold,
and the salts of these compounds.

Compounds according to embodiment C1 of aspect C of this invention more worthy to be mentioned are those compounds of formula I*, in which
R1 is methyl, ethyl substituted by R11, propyl substituted by R11, or butyl substituted by R11, in which
R11 is —N(R111)R112, in which
R111 is hydrogen or methyl,
R112 is hydrogen or methyl,
or R111 and R112 together and with inclusion of the nitrogen atom, to which they are bonded, form a ring Het, in which
Het is piperidin-1-yl, morpholin-4-yl, pyrrolidin-1-yl, 4-methyl-piperazin-1-yl, pyrazol-1-yl, imidazol-1-yl or triazol-1-yl, in which
R2 is hydrogen,
R3 is hydrogen,
R4 is methyl,
R5 is methyl, fluorine, chlorine, bromine, methoxy, ethoxy, propoxy, isopropoxy, trifluoromethyl, 2-methoxy-ethoxy, cyclopropylmethoxy, cyclopropyloxy, or completely or predominantly fluorine-substituted 1-2C-alkoxy,
R6 is hydrogen,
wherein R5 is bonded to the 5-, 7- or, particularly, 6-position of the scaffold,
and the salts of these compounds.

Compounds according to embodiment C1 of aspect C of this invention in particular worthy to be mentioned are those compounds of formula I*, in which
R1 is methyl, 2-(R11)-ethyl, or 3-(R11)-propyl, in which
R11 is —N(R111)R112, in which
R111 is methyl,
R112 is methyl,
or R111 and R112 together and with inclusion of the nitrogen atom, to which they are bonded, form a ring Het, in which
Het is piperidin-1-yl, morpholin-4-yl, pyrrolidin-1-yl, 4-methyl-piperazin-1-yl, pyrazol-1-yl, imidazol-1-yl or triazol-1-yl, in which
R2 is hydrogen,
R3 is hydrogen,
R4 is methyl,
R5 is methyl, fluorine, chlorine, bromine, methoxy, ethoxy, propoxy, isopropoxy, trifluoromethyl, 2-methoxy-ethoxy, cyclopropylmethoxy, difluoromethoxy or trifluoromethoxy,
R6 is hydrogen,
wherein R5 is bonded to the 6-position of the scaffold,
and the salts of these compounds.

Compounds according to embodiment C1 of aspect C of this invention in more particular worthy to be mentioned are those compounds of formula I*, in which
R1 is methyl, 2-(R11)-ethyl, or 3-(R11)-propyl, in which
R11 is —N(R111)R112, in which
R111 is methyl,
R112 is methyl,
or R111 and R112 together and with inclusion of the nitrogen atom, to which they are bonded, form a ring Het, in which
Het is morpholin-4-yl, pyrrolidin-1-yl, 4-methyl-piperazin-1-yl or imidazol-1-yl, in which
R2 is hydrogen,
R3 is hydrogen,
R4 is methyl,
R5 is chlorine, bromine, methoxy, ethoxy, or 2-methoxy-ethoxy,
R6 is hydrogen,
wherein R5 is bonded to the 6-position of the scaffold,
and the salts of these compounds.

In another embodiment of aspect C of this invention (embodiment C2), compounds according to aspect B of this invention to be emphasized are those compounds of formula I*, in which
R1 is methyl, ethyl, propyl, isopropyl, cyclopropyl, cyclopropylmethyl, or 2-4C-alkyl substituted by R11, in which
R11 is —N(R111)R112, in which
R111 is hydrogen, methyl, ethyl, propyl, isopropyl, cyclopropyl or cyclopropylmethyl,
R112 is hydrogen, methyl, ethyl, propyl, isopropyl, cyclopropyl or cyclopropylmethyl,
or R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, 4N-(R113)-piperazin-1-yl, pyrrol-1-yl, pyrazol-1-yl, imidazol-1-yl or triazol-1-yl, in which
R113 is methyl,
R2 is hydrogen,
R3 is hydrogen,
R4 is ethyl,
R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
R6 is hydrogen,
wherein R5 is bonded to the 5-, 7- or 6-position of the scaffold,
and the salts of these compounds.

Compounds according to embodiment C2 of aspect C of this invention worthy to be mentioned are those compounds of formula I*, in which
R1 is methyl, ethyl, or 2-4C-alkyl substituted by R11, in which
R11 is —N(R111)R112, in which
R111 is hydrogen or methyl,
R112 is hydrogen or methyl,
or R111 and R112 together and with inclusion of the nitrogen atom, to which they are bonded, form a ring Het, in which Het is piperidin-1-yl, morpholin-4-yl, thiomorpholin-4-yl, pyrrolidin-1-yl, 4-methyl-piperazin-1-yl, pyrrol-1-yl, pyrazol-1-yl, imidazol-1-yl or triazol-1-yl, in which
R2 is hydrogen,
R3 is hydrogen,
R4 is ethyl,
R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
R6 is hydrogen,
wherein R5 is bonded to the 5-, 7- or, particularly, 6-position of the scaffold,
and the salts of these compounds.

Compounds according to embodiment C2 of aspect C of this invention more worthy to be mentioned are those compounds of formula I*, in which
R1 is methyl, ethyl substituted by R11, propyl substituted by R11, or butyl substituted by R11, in which
R11 is —N(R111)R112, in which
R111 is hydrogen or methyl,
R112 is hydrogen or methyl,
or R111 and R112 together and with inclusion of the nitrogen atom, to which they are bonded, form a ring Het, in which
Het is piperidin-1-yl, morpholin-4-yl, pyrrolidin-1-yl, 4-methyl-piperazin-1-yl, pyrazol-1-yl, imidazol-1-yl or triazol-1-yl, in which
R2 is hydrogen,
R3 is hydrogen,
R4 is ethyl,
R5 is methyl, fluorine, chlorine, bromine, methoxy, ethoxy, propoxy, isopropoxy, trifluoromethyl, 2-methoxy-ethoxy, cyclopropylmethoxy, cyclopropyloxy, or completely or predominantly fluorine-substituted 1-2C-alkoxy,
R6 is hydrogen,
wherein R5 is bonded to the 5-, 7- or, particularly, 6-position of the scaffold,
and the salts of these compounds.

Compounds according to embodiment C2 of aspect C of this invention in particular worthy to be mentioned are those compounds of formula I*, in which
R1 is methyl, 2-(R11)-ethyl, or 3-(R11)-propyl, in which
R11 is —N(R111)R112, in which
R111 is methyl,
R112 is methyl,
or R111 and R112 together and with inclusion of the nitrogen atom, to which they are bonded, form a ring Het, in which
Het is piperidin-1-yl, morpholin-4-yl, pyrrolidin-1-yl, 4-methyl-piperazin-1-yl, pyrazol-1-yl, imidazol-1-yl or triazol-1-yl, in which
R2 is hydrogen,
R3 is hydrogen,
R4 is ethyl,
R5 is methyl, fluorine, chlorine, bromine, methoxy, ethoxy, propoxy, isopropoxy, trifluoromethyl, 2-methoxy-ethoxy, cyclopropylmethoxy, difluoromethoxy or trifluoromethoxy,
R6 is hydrogen,
wherein R5 is bonded to the 6-position of the scaffold,
and the salts of these compounds.

Compounds according to embodiment C2 of aspect C of this invention in more particular worthy to be mentioned are those compounds of formula I*, in which
R1 is methyl, 2-(R11)-ethyl, or 3-(R11)-propyl, in which
R11 is —N(R111)R112, in which
R111 is methyl,
R112 is methyl,
or R111 and R112 together and with inclusion of the nitrogen atom, to which they are bonded, form a ring Het, in which
Het is morpholin-4-yl, pyrrolidin-1-yl, 4-methyl-piperazin-1-yl or imidazol-1-yl, in which
R2 is hydrogen,
R3 is hydrogen,
R4 is ethyl,
R5 is chlorine, bromine, methoxy, ethoxy, or 2-methoxy-ethoxy,
R6 is hydrogen,
wherein R5 is bonded to the 6-position of the scaffold,
and the salts of these compounds.

In yet another embodiment of aspect C of this invention (embodiment C3), compounds according to aspect B of this invention to be emphasized are those compounds of formula I*, in which
R1 is methyl, ethyl, propyl, isopropyl, cyclopropyl, cyclopropylmethyl, or 2-4C-alkyl substituted by R11, in which
R11 is —N(R111)R112, in which
R111 is hydrogen, methyl, ethyl, propyl, isopropyl, cyclopropyl or cyclopropylmethyl,
R112 is hydrogen, methyl, ethyl, propyl, isopropyl, cyclopropyl or cyclopropylmethyl,
or R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, 4N-(R113)-piperazin-1-yl, pyrrol-1-yl, pyrazol-1-yl, imidazol-1-yl or triazol-1-yl, in which
R113 is methyl,
R2 is hydrogen,
R3 is hydrogen,
R4 is isopropyl,
R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
R6 is hydrogen,
wherein R5 is bonded to the 5-, 7- or 6-position of the scaffold,
and the salts of these compounds.

Compounds according to embodiment C3 of aspect C of this invention worthy to be mentioned are those compounds of formula I*, in which
R1 is methyl, ethyl, or 2-4C-alkyl substituted by R11, in which
R11 is —N(R111)R112, in which
R111 is hydrogen or methyl,
R112 is hydrogen or methyl,
or R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, 4-methyl-piperazin-1-yl, pyrrol-1-yl, pyrazol-1-yl, imidazol-1-yl or triazol-1-yl, in which
R2 is hydrogen,
R3 is hydrogen,
R4 is isopropyl,
R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
R6 is hydrogen,
wherein R5 is bonded to the 5-, 7- or, particularly, 6-position of the scaffold,
and the salts of these compounds.

Compounds according to embodiment C3 of aspect C of this invention more worthy to be mentioned are those compounds of formula I*, in which R1 is methyl, ethyl substituted by R11, propyl substituted by R11, or butyl substituted by R11, in which
R11 is —N(R111)R112, in which
R111 is hydrogen or methyl,
R112 is hydrogen or methyl,
or R111 and R112 together and with inclusion of the nitrogen atom, to which they are bonded, form a ring Het, in which
Het is piperidin-1-yl, morpholin-4-yl, pyrrolidin-1-yl, 4-methyl-piperazin-1-yl, pyrazol-1-yl, imidazol-1-yl or triazol-1-yl, in which
R2 is hydrogen,
R3 is hydrogen,
R4 is isopropyl,
R5 is methyl, fluorine, chlorine, bromine, methoxy, ethoxy, propoxy, isopropoxy, trifluoromethyl, 2-methoxy-ethoxy, cyclopropylmethoxy, cyclopropyloxy, or completely or predominantly fluorine-substituted 1-2C-alkoxy,
R6 is hydrogen,
wherein R5 is bonded to the 5-, 7- or, particularly, 6-position of the scaffold,
and the salts of these compounds.

Compounds according to embodiment C3 of aspect C of this invention in particular worthy to be mentioned are those compounds of formula I*, in which R1 is methyl, 2-(R11)-ethyl, or 3-(R11)-propyl, in which
R11 is —N(R111)R112, in which
R111 is methyl,
R112 is methyl,
or R111 and R112 together and with inclusion of the nitrogen atom, to which they are bonded, form a ring Het, in which
Het is piperidin-1-yl, morpholin-4-yl, pyrrolidin-1-yl, 4-methyl-piperazin-1-yl, pyrazol-1-yl, imidazol-1-yl or triazol-1-yl, in which
R2 is hydrogen,
R3 is hydrogen,
R4 is isopropyl,
R5 is methyl, fluorine, chlorine, bromine, methoxy, ethoxy, propoxy, isopropoxy, trifluoromethyl, 2-methoxy-ethoxy, cyclopropylmethoxy, difluoromethoxy or trifluoromethoxy,
R6 is hydrogen,
wherein R5 is bonded to the 6-position of the scaffold,
and the salts of these compounds.

Compounds according to embodiment C3 of aspect C of this invention in more particular worthy to be mentioned are those compounds of formula I*, in which R1 is methyl, 2-(R11)-ethyl, or 3-(R11)-propyl, in which
R11 is —N(R111)R112, in which
R111 is methyl,
R112 is methyl,
or R111 and R112 together and with inclusion of the nitrogen atom, to which they are bonded, form a ring Het, in which
Het is morpholin-4-yl, pyrrolidin-1-yl, 4-methyl-piperazin-1-yl or imidazol-1-yl, in which
R2 is hydrogen,
R3 is hydrogen,
R4 is isopropyl,
R5 is chlorine, bromine, methoxy, ethoxy, or 2-methoxy-ethoxy,
R6 is hydrogen,
wherein R5 is bonded to the 6-position of the scaffold,
and the salts of these compounds.

In still yet another embodiment of aspect C of this invention (embodiment C4), compounds according to aspect B of this invention to be emphasized are those compounds of formula I*, in which R1 is methyl, ethyl, propyl, isopropyl, cyclopropyl, cyclopropylmethyl, or 2-4C-alkyl substituted by R11, in which
R11 is —N(R111)R112, in which
R111 is hydrogen, methyl, ethyl, propyl, isopropyl, cyclopropyl or cyclopropylmethyl,
R112 is hydrogen, methyl, ethyl, propyl, isopropyl, cyclopropyl or cyclopropylmethyl,
or R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, 4N-(R113)-piperazin-1-yl, pyrrol-1-yl, pyrazol-1-yl, imidazol-1-yl or triazol-1-yl, in which
R113 is methyl,
R2 is hydrogen,
R3 is hydrogen,
R4 is cyclopropyl,
R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
R6 is hydrogen,
wherein R5 is bonded to the 5-, 7- or 6-position of the scaffold,
and the salts of these compounds.

Compounds according to embodiment C4 of aspect C of this invention worthy to be mentioned are those compounds of formula I*, in which R1 is methyl, ethyl, or 2-4C-alkyl substituted by R11, in which
R11 is —N(R111)R112, in which
R111 is hydrogen or methyl,
R112 is hydrogen or methyl,
or R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, 4-methyl-piperazin-1-yl, pyrrol-1-yl, pyrazol-1-yl, imidazol-1-yl or triazol-1-yl, in which
R2 is hydrogen,
R3 is hydrogen,
R4 is cyclopropyl,
R5 is methyl, ethyl, propyl, isopropyl, fluorine, chlorine, bromine, methoxy, ethoxy, propoxy, isopropoxy, trifluoromethyl, 2-methoxy-ethoxy, cyclopropyloxy, cyclopropylmethoxy, or completely or predominantly fluorine-substituted 1-2C-alkoxy,
R6 is hydrogen,
wherein R5 is bonded to the 5-, 7- or, particularly, 6-position of the scaffold,
and the salts of these compounds.

Compounds according to embodiment C4 of aspect C of this invention more worthy to be mentioned are those compounds of formula I*, in which R1 is methyl, ethyl substituted by R11, propyl substituted by R11, or butyl substituted by R11, in which
R11 is —N(R111)R112, in which
R111 is hydrogen or methyl,
R112 is hydrogen or methyl,
or R111 and R112 together and with inclusion of the nitrogen atom, to which they are bonded, form a ring Het, in which
Het is piperidin-1-yl, morpholin-4-yl, pyrrolidin-1-yl, 4-methyl-piperazin-1-yl, pyrazol-1-yl, imidazol-1-yl or triazol-1-yl, in which R2 is hydrogen,
R3 is hydrogen,
R4 is cyclopropyl,
R5 is methyl, fluorine, chlorine, bromine, methoxy, ethoxy, propoxy, isopropoxy, trifluoromethyl, 2-methoxy-ethoxy, cyclopropylmethoxy, cyclopropyloxy, or completely or predominantly fluorine-substituted 1-2C-alkoxy,
R6 is hydrogen,
wherein R5 is bonded to the 5-, 7- or, particularly, 6-position of the scaffold,
and the salts of these compounds.

Compounds according to embodiment C4 of aspect C of this invention in particular worthy to be mentioned are those compounds of formula I*, in which
R1 is methyl, 2-(R11)-ethyl, or 3-(R11)-propyl, in which
R11 is —N(R111)R112, in which
R111 is methyl,
R112 is methyl,
or R111 and R112 together and with inclusion of the nitrogen atom, to which they are bonded, form a ring Het, in which
Het is piperidin-1-yl, morpholin-4-yl, pyrrolidin-1-yl, 4-methyl-piperazin-1-yl, pyrazol-1-yl, imidazol-1-yl or triazol-1-yl, in which
R2 is hydrogen,
R3 is hydrogen,
R4 is cyclopropyl,
R5 is methyl, fluorine, chlorine, bromine, methoxy, ethoxy, propoxy, isopropoxy, trifluoromethyl, 2-methoxy-ethoxy, cyclopropylmethoxy, difluoromethoxy or trifluoromethoxy,
R6 is hydrogen,
wherein R5 is bonded to the 6-position of the scaffold,
and the salts of these compounds.

Compounds according to embodiment C4 of aspect C of this invention in more particular worthy to be mentioned are those compounds of formula I*, in which
R1 is methyl, 2-(R11)-ethyl, or 3-(R11)-propyl, in which
R11 is —N(R111)R112, in which
R111 is methyl,
R112 is methyl,
or R111 and R112 together and with inclusion of the nitrogen atom, to which they are bonded, form a ring Het, in which
Het is morpholin-4-yl, pyrrolidin-1-yl, 4-methyl-piperazin-1-yl or imidazol-1-yl, in which
R2 is hydrogen,
R3 is hydrogen,
R4 is cyclopropyl,
R5 is chlorine, bromine, methoxy, ethoxy, or 2-methoxy-ethoxy,
R6 is hydrogen,
wherein R5 is bonded to the 6-position of the scaffold,
and the salts of these compounds.

A special interest in the compounds according to this invention refers to those compounds of formula I which are included—within the scope of this invention—by one or, when possible, by a combination of more of the following special embodiments:

A special embodiment (embodiment 1) of the compounds of formula I according to this invention refers to those compounds of formula I, in which
R1 is methyl.
A special embodiment (embodiment 2) of the compounds of formula I according to this invention refers to those compounds of formula I, in which
R1 is ethyl.
A special embodiment (embodiment 3) of the compounds of formula I according to this invention refers to those compounds of formula I, in which
R1 is 2-(R11)-ethyl.
A special embodiment (embodiment 4) of the compounds of formula I according to this invention refers to those compounds of formula I, in which
R1 is 3-(R11)-propyl.
A special embodiment (embodiment 5) of the compounds of formula I according to this invention refers to those compounds of formula I, in which
R1 is 4-(R11)-butyl.
Another special embodiment (embodiment 6) of the compounds of formula I according to this invention refers to those compounds of formula I, in which
R1 is 2-dimethylamino-ethyl.
Another special embodiment (embodiment 7) of the compounds of formula I according to this invention refers to those compounds of formula I, in which
R1 is 2-(N-ethyl-N-methyl-amino)-ethyl.
Another special embodiment (embodiment 8) of the compounds of formula I according to this invention refers to those compounds of formula I, in which
R1 is 2-(N-isopropyl-N-methyl-amino)-ethyl.
Another special embodiment (embodiment 9) of the compounds of formula I according to this invention refers to those compounds of formula I, in which
R1 is 2-[N-(2-hydroxyethyl)-N-methyl-amino]-ethyl.
Another special embodiment (embodiment 10) of the compounds of formula I according to this invention refers to those compounds of formula I, in which
R1 is 2-[N-(2-methoxyethyl)-N-methyl-amino]-ethyl.
Another special embodiment (embodiment 11) of the compounds of formula I according to this invention refers to those compounds of formula I, in which
R1 is 2-(N-allyl-N-methyl-amino)-ethyl.
Another special embodiment (embodiment 12) of the compounds of formula I according to this invention refers to those compounds of formula I, in which
R1 is 2-(N-methyl-N-propargylamino)-ethyl.
Another special embodiment (embodiment 13) of the compounds of formula I according to this invention refers to those compounds of formula I, in which
R1 is 2-[N-ethyl-N-(2-hydroxyethyl)-amino]-ethyl.
Another special embodiment (embodiment 14) of the compounds of formula I according to this invention refers to those compounds of formula I, in which
R1 is 2-[N-ethyl-N-(2-methoxyethyl)-amino]-ethyl.
Another special embodiment (embodiment 15) of the compounds of formula I according to this invention refers to those compounds of formula I, in which
R1 is 2-diethylamino-ethyl.
Another special embodiment (embodiment 16) of the compounds of formula I according to this invention refers to those compounds of formula I, in which
R1 is 2-methylamino-ethyl.
Another special embodiment (embodiment 17) of the compounds of formula I according to this invention refers to those compounds of formula I, in which
R1 is 2-ethylamino-ethyl.
Another special embodiment (embodiment 18) of the compounds of formula I according to this invention refers to those compounds of formula I, in which
R1 is 2-isopropylamino-ethyl.
Another special embodiment (embodiment 19) of the compounds of formula I according to this invention refers to those compounds of formula I, in which R1 is 2-isobutylamino-ethyl.

Another special embodiment (embodiment 20) of the compounds of formula I according to this invention refers to those compounds of formula I, in which
R1 is 2-cyclopropylamino-ethyl.

Another special embodiment (embodiment 21) of the compounds of formula I according to this invention refers to those compounds of formula I, in which
R1 is 2-cyclobutylamino-ethyl.

Another special embodiment (embodiment 22) of the compounds of formula I according to this invention refers to those compounds of formula I, in which
R1 is 2-(cyclopropylmethyl)amino-ethyl.

Another special embodiment (embodiment 23) of the compounds of formula I according to this invention refers to those compounds of formula I, in which
R1 is 2-morpholin-4-yl-ethyl.

Another special embodiment (embodiment 24) of the compounds of formula I according to this invention refers to those compounds of formula I, in which
R1 is 2-pyrrolidin-1-yl-ethyl.

Another special embodiment (embodiment 25) of the compounds of formula I according to this invention refers to those compounds of formula I, in which
R1 is 2-azetidin-1-yl-ethyl.

Another special embodiment (embodiment 26) of the compounds of formula I according to this invention refers to those compounds of formula I, in which
R1 is 2-piperidin-1-yl-ethyl.

Another special embodiment (embodiment 27) of the compounds of formula I according to this invention refers to those compounds of formula I, in which
R1 is 2-(4-methyl-piperidin-1-yl)-ethyl.

Another special embodiment (embodiment 28) of the compounds of formula I according to this invention refers to those compounds of formula I, in which
R1 is 2-homopiperidin-1-yl-ethyl.

Another special embodiment (embodiment 29) of the compounds of formula I according to this invention refers to those compounds of formula I, in which
R1 is 2-(2,5-dihydropyrrol-1-yl)-ethyl.

Another special embodiment (embodiment 30) of the compounds of formula I according to this invention refers to those compounds of formula I, in which
R1 is 2-(1,2,3,6-tetrahydropyridin-1-yl)-ethyl.

Another special embodiment (embodiment 31) of the compounds of formula I according to this invention refers to those compounds of formula I, in which
R1 is 2-imidazol-1-yl-ethyl.

Another special embodiment (embodiment 32) of the compounds of formula I according to this invention refers to those compounds of formula I, in which
R1 is 2-(4-methyl-piperazin-1-yl)-ethyl.

Another special embodiment (embodiment 33) of the compounds of formula I according to this invention refers to those compounds of formula I, in which
R1 is 2-(4-acetyl-piperazin-1-yl)-ethyl.

Another special embodiment (embodiment 34) of the compounds of formula I according to this invention refers to those compounds of formula I, in which
R1 is 2-amino-ethyl.

Another special embodiment (embodiment 35) of the compounds of formula I according to this invention refers to those compounds of formula I, in which
R1 is 2-[(2-hydroxyethyl)-amino]-ethyl.

Another special embodiment (embodiment 36) of the compounds of formula I according to this invention refers to those compounds of formula I, in which
R1 is 2-[(2-methoxyethyl)-amino]-ethyl.

Another special embodiment (embodiment 37) of the compounds of formula I according to this invention refers to those compounds of formula I, in which
R1 is 2-tertbutylamino-ethyl.

Another special embodiment (embodiment 38) of the compounds of formula I according to this invention refers to those compounds of formula I, in which
R1 is 2-allylamino-ethyl.

Another special embodiment (embodiment 39) of the compounds of formula I according to this invention refers to those compounds of formula I, in which
R1 is 2-propargylamino-ethyl.

Another special embodiment (embodiment 40) of the compounds of formula I according to this invention refers to those compounds of formula I, in which
R1 is 2-[(1-methylpropargyl)-amino]-ethyl.

Another special embodiment (embodiment 41) of the compounds of formula I according to this invention refers to those compounds of formula I, in which
R1 is 2-[(2,2-difluoroethyl)-amino]-ethyl.

Another special embodiment (embodiment 42) of the compounds of formula I according to this invention refers to those compounds of formula I, in which
R1 is 3-dimethylamino-propyl.

Another special embodiment (embodiment 43) of the compounds of formula I according to this invention refers to those compounds of formula I, in which
R1 is 3-ethylamino-propyl.

Another special embodiment (embodiment 44) of the compounds of formula I according to this invention refers to those compounds of formula I, in which
R1 is 3-imidazol-1-yl-propyl.

Another special embodiment (embodiment 45) of the compounds of formula I according to this invention refers to those compounds of formula I, in which
R1 is 3-(N-ethyl-N-methyl-amino)-propyl.

Another special embodiment (embodiment 46) of the compounds of formula I according to this invention refers to those compounds of formula I, in which
R1 is 3-(N-isopropyl-N-methyl-amino)-propyl.

Another special embodiment (embodiment 47) of the compounds of formula I according to this invention refers to those compounds of formula I, in which
R1 is 3-[N-(2-hydroxyethyl)-N-methyl-amino]-propyl.

Another special embodiment (embodiment 48) of the compounds of formula I according to this invention refers to those compounds of formula I, in which
R1 is 3-[N-(2-methoxyethyl)-N-methyl-amino]-propyl.

Another special embodiment (embodiment 49) of the compounds of formula I according to this invention refers to those compounds of formula I, in which
R1 is 3-(N-allyl-N-methyl-amino)-propyl.

Another special embodiment (embodiment 50) of the compounds of formula I according to this invention refers to those compounds of formula I, in which
R1 is 3-(N-methyl-N-propargylamino)-propyl.

Another special embodiment (embodiment 51) of the compounds of formula I according to this invention refers to those compounds of formula I, in which
R1 is 3-[N-ethyl-N-(2-hydroxyethyl)-amino]-propyl.

Another special embodiment (embodiment 52) of the compounds of formula I according to this invention refers to those compounds of formula I, in which R1 is 3-[N-ethyl-N-(2-methoxyethyl)-amino]-propyl.

Another special embodiment (embodiment 53) of the compounds of formula I according to this invention refers to those compounds of formula I, in which
R1 is 3-diethylamino-propyl.

Another special embodiment (embodiment 54) of the compounds of formula I according to this invention refers to those compounds of formula I, in which
R1 is 3-methylamino-propyl.

Another special embodiment (embodiment 55) of the compounds of formula I according to this invention refers to those compounds of formula I, in which
R1 is 3-isopropylamino-propyl.

Another special embodiment (embodiment 56) of the compounds of formula I according to this invention refers to those compounds of formula I, in which
R1 is 3-isobutylamino-propyl.

Another special embodiment (embodiment 57) of the compounds of formula I according to this invention refers to those compounds of formula I, in which
R1 is 3-cyclopropylamino-propyl.

Another special embodiment (embodiment 58) of the compounds of formula I according to this invention refers to those compounds of formula I, in which
R1 is 3-cyclobutylamino-propyl.

Another special embodiment (embodiment 59) of the compounds of formula I according to this invention refers to those compounds of formula I, in which
R1 is 3-(cyclopropylmethyl)amino-propyl.

Another special embodiment (embodiment 60) of the compounds of formula I according to this invention refers to those compounds of formula I, in which
R1 is 3-morpholin-4-yl-propyl.

Another special embodiment (embodiment 61) of the compounds of formula I according to this invention refers to those compounds of formula I, in which
R1 is 3-pyrrolidin-1-yl-propyl.

Another special embodiment (embodiment 62) of the compounds of formula I according to this invention refers to those compounds of formula I, in which
R1 is 3-azetidin-1-yl-propyl.

Another special embodiment (embodiment 63) of the compounds of formula I according to this invention refers to those compounds of formula I, in which
R1 is 3-piperidin-1-yl-propyl.

Another special embodiment (embodiment 64) of the compounds of formula I according to this invention refers to those compounds of formula I, in which
R1 is 3-(4-methyl-piperidin-1-yl)-propyl.

Another special embodiment (embodiment 65) of the compounds of formula I according to this invention refers to those compounds of formula I, in which
R1 is 3-homopiperidin-1-yl-propyl.

Another special embodiment (embodiment 66) of the compounds of formula I according to this invention refers to those compounds of formula I, in which
R1 is 3-(2,5-dihydropyrrol-1-yl)-propyl.

Another special embodiment (embodiment 67) of the compounds of formula I according to this invention refers to those compounds of formula I, in which
R1 is 3-(1,2,3,6-tetrahydropyridin-1-yl)-propyl.

Another special embodiment (embodiment 68) of the compounds of formula I according to this invention refers to those compounds of formula I, in which
R1 is 3-(4-methyl-piperazin-1-yl)-propyl.

Another special embodiment (embodiment 69) of the compounds of formula I according to this invention refers to those compounds of formula I, in which
R1 is 3-(4-acetyl-piperazin-1-yl)-propyl.

Another special embodiment (embodiment 70) of the compounds of formula I according to this invention refers to those compounds of formula I, in which
R1 is 3-amino-propyl.

Another special embodiment (embodiment 71) of the compounds of formula I according to this invention refers to those compounds of formula I, in which
R1 is 3-[(2-hydroxyethyl)-amino]-propyl.

Another special embodiment (embodiment 72) of the compounds of formula I according to this invention refers to those compounds of formula I, in which
R1 is 3-[(2-methoxyethyl)-amino]-propyl.

Another special embodiment (embodiment 73) of the compounds of formula I according to this invention refers to those compounds of formula I, in which
R1 is 3-tertbutylamino-propyl.

Another special embodiment (embodiment 74) of the compounds of formula I according to this invention refers to those compounds of formula I, in which
R1 is 3-allylamino-propyl.

Another special embodiment (embodiment 75) of the compounds of formula I according to this invention refers to those compounds of formula I, in which
R1 is 3-propargylamino-propyl.

Another special embodiment (embodiment 76) of the compounds of formula I according to this invention refers to those compounds of formula I, in which
R1 is 3-[(1-methylpropargyl)-amino]-propyl.

Another special embodiment (embodiment 77) of the compounds of formula I according to this invention refers to those compounds of formula I, in which
R1 is 3-[(2,2-difluoroethyl)-amino]-propyl.

Another special embodiment (embodiment 78) of the compounds of formula I according to this invention refers to those compounds of formula I, in which
R1 is 4-dimethylamino-butyl.

Another special embodiment (embodiment 79) of the compounds of formula I according to this invention refers to those compounds of formula I, in which
R2 is hydrogen.

Another special embodiment (embodiment 80) of the compounds of formula I according to this invention refers to those compounds of formula I, in which
R3 is hydrogen.

Another special embodiment (embodiment 81) of the compounds of formula I according to this invention refers to those compounds of formula I, in which
R2 and R3 are both hydrogen.

Another special embodiment (embodiment 82) of the compounds of formula I according to this invention refers to those compounds of formula I, in which
R4 is methyl.

Another special embodiment (embodiment 83) of the compounds of formula I according to this invention refers to those compounds of formula I, in which
R4 is ethyl.

Another special embodiment (embodiment 84) of the compounds of formula I according to this invention refers to those compounds of formula I, in which
R4 is isopropyl.

Another special embodiment (embodiment 85) of the compounds of formula I according to this invention refers to those compounds of formula I, in which R4 is cyclopropyl.

Another special embodiment (embodiment 86) of the compounds of formula I according to this invention refers to those compounds of formula I, in which none of R5 and R6 is bonded to the 8-position of the scaffold.

Another special embodiment (embodiment 87) of the compounds of formula I according to this invention refers to those compounds of formula I, in which
R6 is hydrogen.

Another special embodiment (embodiment 88) of the compounds of formula I according to this invention refers to those compounds of formula I, in which
R5 is bonded to the 5-, 6- or 7-position of the scaffold, and
R6 is hydrogen.

Another special embodiment (embodiment 89) of the compounds of formula I according to this invention refers to those compounds of formula I, in which
R5 is bonded to the 6-position of the scaffold, and
R6 is hydrogen.

Another special embodiment (embodiment 90) of the compounds of formula I according to this invention refers to those compounds of formula I, in which
R6 is fluorine.

Another special embodiment (embodiment 91) of the compounds of formula I according to this invention refers to those compounds of formula I, in which
R5 is bonded to the 6-position of the scaffold, and
R6 is bonded to the 5- or, particularly, 7-position of the scaffold, and is fluorine.

Another special embodiment (embodiment 92) of the compounds of formula I according to this invention refers to those compounds of formula I, in which
R5 is bromine, and
R6 is hydrogen.

Another special embodiment (embodiment 93) of the compounds of formula I according to this invention refers to those compounds of formula I, in which
R5 is fluorine, and
R6 is hydrogen.

Another special embodiment (embodiment 94) of the compounds of formula I according to this invention refers to those compounds of formula I, in which
R5 is methyl, and
R6 is hydrogen.

Another special embodiment (embodiment 95) of the compounds of formula I according to this invention refers to those compounds of formula I, in which
R5 is methoxy, and
R6 is hydrogen.

Another special embodiment (embodiment 96) of the compounds of formula I according to this invention refers to those compounds of formula I, in which
R5 is ethoxy, and
R6 is hydrogen.

Another special embodiment (embodiment 97) of the compounds of formula I according to this invention refers to those compounds of formula I, in which
R5 is chlorine, and
R6 is hydrogen.

Another special embodiment (embodiment 98) of the compounds of formula I according to this invention refers to those compounds of formula I, in which
R5 is cyclopropylmethoxy, and
R6 is hydrogen.

Another special embodiment (embodiment 99) of the compounds of formula I according to this invention refers to those compounds of formula I, in which
R5 is 2-methoxyethoxy, and
R6 is hydrogen.

Another special embodiment (embodiment 100) of the compounds of formula I according to this invention refers to those compounds of formula I, in which
R5 is trifluoromethyl, and
R6 is hydrogen.

Another special embodiment (embodiment 101) of the compounds of formula I according to this invention refers to those compounds of formula I, in which
R5 is trifluoromethoxy, and
R6 is hydrogen.

Another special embodiment (embodiment 102) of the compounds of formula I according to this invention refers to those compounds of formula I, in which
R5 is difluoromethoxy, and
R6 is hydrogen.

Another special embodiment (embodiment 103) of the compounds of formula I according to this invention refers to those compounds of formula I, in which
R5 is cyclopropyloxy, and
R6 is hydrogen.

Another special embodiment (embodiment 104) of the compounds of formula I according to this invention refers to those compounds of formula I, in which
R5 is bonded to the 6-position of the scaffold, and is methyl, trifluoromethyl, fluorine, chlorine, bromine, methoxy, ethoxy, 2-methoxy-ethoxy, cyclopropylmethoxy, trifluoromethoxy or difluoromethoxy, and
R6 is hydrogen.

Another special embodiment (embodiment 105) of the compounds of formula I according to this invention refers to those compounds of formula I, in which
R5 is bonded to the 6-position of the scaffold, and is fluorine, chlorine, bromine, methoxy, ethoxy, difluoromethoxy or trifluoromethoxy, and
R6 is hydrogen.

Another special embodiment (embodiment 106) of the compounds of formula I according to this invention refers to those compounds of formula I, in which
R5 is bonded to the 6-position of the scaffold, and is chlorine, bromine, methoxy or ethoxy, and
R6 is hydrogen.

Another special embodiment (embodiment 107) of the compounds of formula I according to this invention refers to those compounds of formula I, in which
R5 is bonded to the 6-position of the scaffold, and is chlorine, bromine, methoxy, ethoxy or difluoromethoxy, and
R6 is hydrogen.

Another special embodiment (embodiment 108) of the compounds of formula I according to this invention refers to those compounds of formula I, in which
R5 is bonded to the 6-position of the scaffold, and is chlorine, bromine, methoxy, ethoxy or difluoromethoxy, and
R6 is bonded to the 5-position of the scaffold, and is fluorine.

Another special embodiment (embodiment 109) of the compounds of formula I according to this invention refers to those compounds of formula I, in which
R5 is bonded to the 6-position of the scaffold, and is chlorine, bromine, methoxy, ethoxy or difluoromethoxy, and
R6 is bonded to the 7-position of the scaffold, and is fluorine.

Another special embodiment (embodiment 110) of the compounds of formula I according to this invention refers to those compounds of formula I, in which R5 is bonded to the 6-position of the scaffold, and is methoxy, and R6 is bonded to the 5-position of the scaffold, and is fluorine.

Another special embodiment (embodiment 111) of the compounds of formula I according to this invention refers to those compounds of formula I, in which R5 is bonded to the 6-position of the scaffold, and is methoxy, and R6 is bonded to the 7-position of the scaffold, and is fluorine.

Another special embodiment (embodiment 112) of the compounds of formula I according to this invention refers to those compounds of formula I, in which R5 is bonded to the 6-position of the scaffold, and is chlorine, and R6 is bonded to the 7-position of the scaffold, and is fluorine.

Another special embodiment (embodiment 113) of the compounds of formula I according to this invention refers to those compounds which are from formula I* as shown above.

Another special embodiment (embodiment 114) of the compounds of formula I according to this invention refers to those compounds which are from formula Ia* as shown below, in which R2 and R3 are both hydrogen.

Another special embodiment (embodiment 115) of the compounds of formula I according to this invention refers to those compounds which are from formula I* as shown above, in which R2 and R3 are both hydrogen, and R1 and R5 have any of the meanings 1.1 to 1.891 indicated in Table 1 given below.

Another special embodiment (embodiment 116) of the compounds of formula I according to this invention refers to those compounds which are from formula Ia* as shown below, in which R2 and R3 are both hydrogen, and R1 and R5 have any of the meanings 1.1 to 1.891 indicated in Table 1 given below.

Among the special embodiments 3 to 5 mentioned afore, embodiments 3 and 4 are to be emphasized, and embodiment 3 is in particular to be emphasized.

Among the special embodiments 79 to 81 mentioned afore, embodiment 81 is to be emphasized.

Among the special embodiments 82 to 85 mentioned afore, embodiments 82 and 83 are to be emphasized, and embodiment 82 is in particular to be emphasized.

Among the special embodiments 86 to 89 mentioned afore, embodiment 89 is to be emphasized.

Among the special embodiments 90 to 91 mentioned afore, embodiment 91 is to be emphasized.

Among the special embodiments 92 to 103 mentioned afore, embodiments 92, 93, 95, 96, 97, 101 and 102 are to be emphasized, and embodiments 92, 95, 96, 97 and 102 are in particular to be emphasized.

Among the special embodiments 104 to 107 mentioned afore, embodiments 105 to 107 are to be emphasized.

Among the special embodiments 108 to 109 mentioned afore, embodiment 109 is to be emphasized, and among the special embodiments 110 to 112, embodiments 111 and 112 are to be emphasized.

It is to be understood that the present invention includes any or all possible combinations and subsets of the special embodiments defined hereinabove.

As illustrative compounds according to this invention the following compounds of formula Ia*,

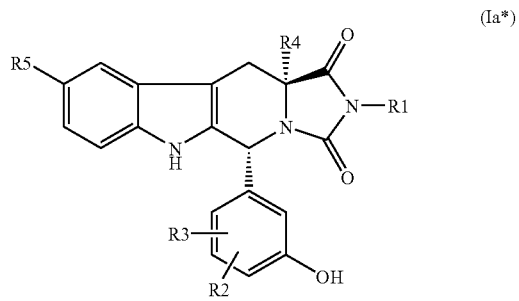

in which
R2 and R3 are both hydrogen, and
R4 is methyl,
and the salts thereof,
may be mentioned by means of the substituent meanings for R1 and R5 in the Table 1 given below.

As further illustrative compounds according to this invention the following compounds of formula Ia*, in which R2 and R3 are both hydrogen, and
R4 is ethyl,
and the salts thereof,
may be mentioned by means of the substituent meanings for R1 and R5 in the Table 1 given below.

As further illustrative compounds according to this invention the following compounds of formula Ia*, in which R2 and R3 are both hydrogen, and
R4 is isopropyl,
and the salts thereof,
may be mentioned by means of the substituent meanings for R1 and R5 in the Table 1 given below.

As further illustrative compounds according to this invention the following compounds of formula Ia*, in which R2 and R3 are both hydrogen, and
R4 is cyclopropyl,
and the salts thereof,
may be mentioned by means of the substituent meanings for R1 and R5 in the Table 1 given below.

As other illustrative compounds according to this invention the following compounds of formula Ib*,

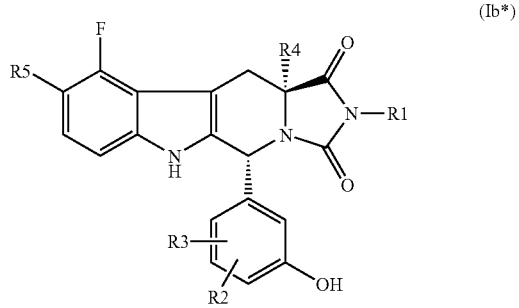

in which
R2 and R3 are both hydrogen, and
R4 is methyl,
and the salts thereof,
may be mentioned by means of the substituent meanings for R1 and R5 in the Table 1 given below.

As other illustrative compounds according to this invention the following compounds of formula Ic*,

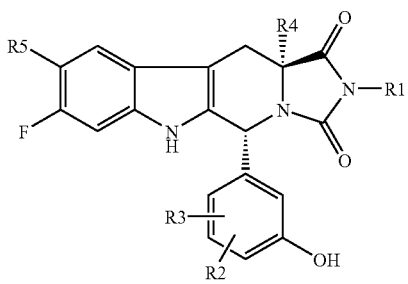

(Ic*)

in which
R2 and R3 are both hydrogen, and
R4 is methyl,
and the salts thereof,
may be mentioned by means of the substituent meanings for R1 and R5 in the Table 1 given below.

Among the foregoing compounds of formulae Ia*, Ib* and Ic* those compounds of formulae Ia*, Ib* and Ic*, in each of which R4 is methyl, are to be emphasized.

Among the foregoing compounds of formulae Ia*, Ib* and Ic* those compounds of formulae Ia* and Ic*, in each of which R4 is methyl, are to be in particular emphasized.

Among the foregoing compounds of formulae Ia*, Ib* and Ic* those compounds of formula Ia*, in which R4 is methyl, are to be in more particular emphasized.

TABLE 1

| No. | R1 | R5 |
|---|---|---|
| 1.1 | methyl | —CH$_3$ |
| 1.2 | methyl | —Br |
| 1.3 | methyl | —F |
| 1.4 | methyl | —OCH$_3$ |
| 1.5 | methyl | —OCH$_2$CH$_3$ |
| 1.6 | methyl | —Cl |
| 1.7 | methyl | —OCH$_2$CH$_2$OCH$_3$ |
| 1.8 | methyl | cyclopropylmethoxy |
| 1.9 | methyl | —CF$_3$ |
| 1.10 | methyl | difluoromethoxy |
| 1.11 | methyl | trifluoromethoxy |
| 1.12 | 2-(dimethylamino)-ethyl | —CH$_3$ |
| 1.13 | 2-(dimethylamino)-ethyl | —Br |
| 1.14 | 2-(dimethylamino)-ethyl | —F |
| 1.15 | 2-(dimethylamino)-ethyl | —OCH$_3$ |
| 1.16 | 2-(dimethylamino)-ethyl | —OCH$_2$CH$_3$ |
| 1.17 | 2-(dimethylamino)-ethyl | —Cl |
| 1.18 | 2-(dimethylamino)-ethyl | —OCH$_2$CH$_2$OCH$_3$ |
| 1.19 | 2-(dimethylamino)-ethyl | cyclopropylmethoxy |
| 1.20 | 2-(dimethylamino)-ethyl | —CF$_3$ |
| 1.21 | 2-(dimethylamino)-ethyl | difluoromethoxy |
| 1.22 | 2-(dimethylamino)-ethyl | trifluoromethoxy |
| 1.23 | 3-(dimethylamino)-propyl | —CH$_3$ |
| 1.24 | 3-(dimethylamino)-propyl | —Br |
| 1.25 | 3-(dimethylamino)-propyl | —F |
| 1.26 | 3-(dimethylamino)-propyl | —OCH$_3$ |
| 1.27 | 3-(dimethylamino)-propyl | —OCH$_2$CH$_3$ |
| 1.28 | 3-(dimethylamino)-propyl | —Cl |
| 1.29 | 3-(dimethylamino)-propyl | —OCH$_2$CH$_2$OCH$_3$ |
| 1.30 | 3-(dimethylamino)-propyl | cyclopropylmethoxy |
| 1.31 | 3-(dimethylamino)-propyl | —CF$_3$ |
| 1.32 | 3-(dimethylamino)-propyl | difluoromethoxy |
| 1.33 | 3-(dimethylamino)-propyl | trifluoromethoxy |
| 1.34 | 2-(morpholin-4-yl)-ethyl | —CH$_3$ |
| 1.35 | 2-(morpholin-4-yl)-ethyl | —Br |
| 1.36 | 2-(morpholin-4-yl)-ethyl | —F |
| 1.37 | 2-(morpholin-4-yl)-ethyl | —OCH$_3$ |
| 1.38 | 2-(morpholin-4-yl)-ethyl | —OCH$_2$CH$_3$ |
| 1.39 | 2-(morpholin-4-yl)-ethyl | —Cl |
| 1.40 | 2-(morpholin-4-yl)-ethyl | —OCH$_2$CH$_2$OCH$_3$ |
| 1.41 | 2-(morpholin-4-yl)-ethyl | cyclopropylmethoxy |

TABLE 1-continued

| No. | R1 | R5 |
|---|---|---|
| 1.42 | 2-(morpholin-4-yl)-ethyl | —CF$_3$ |
| 1.43 | 2-(morpholin-4-yl)-ethyl | difluoromethoxy |
| 1.44 | 2-(morpholin-4-yl)-ethyl | trifluoromethoxy |
| 1.45 | 2-(pyrrolidin-1-yl)-ethyl | —CH$_3$ |
| 1.46 | 2-(pyrrolidin-1-yl)-ethyl | —Br |
| 1.47 | 2-(pyrrolidin-1-yl)-ethyl | —F |
| 1.48 | 2-(pyrrolidin-1-yl)-ethyl | —OCH$_3$ |
| 1.49 | 2-(pyrrolidin-1-yl)-ethyl | —OCH$_2$CH$_3$ |
| 1.50 | 2-(pyrrolidin-1-yl)-ethyl | —Cl |
| 1.51 | 2-(pyrrolidin-1-yl)-ethyl | —OCH$_2$CH$_2$OCH$_3$ |
| 1.52 | 2-(pyrrolidin-1-yl)-ethyl | cyclopropylmethoxy |
| 1.53 | 2-(pyrrolidin-1-yl)-ethyl | —CF$_3$ |
| 1.54 | 2-(pyrrolidin-1-yl)-ethyl | difluoromethoxy |
| 1.55 | 2-(pyrrolidin-1-yl)-ethyl | trifluoromethoxy |
| 1.56 | 2-(imidazol-1-yl)-ethyl | —CH$_3$ |
| 1.57 | 2-(imidazol-1-yl)-ethyl | —Br |
| 1.58 | 2-(imidazol-1-yl)-ethyl | —F |
| 1.59 | 2-(imidazol-1-yl)-ethyl | —OCH$_3$ |
| 1.60 | 2-(imidazol-1-yl)-ethyl | —OCH$_2$CH$_3$ |
| 1.61 | 2-(imidazol-1-yl)-ethyl | —Cl |
| 1.62 | 2-(imidazol-1-yl)-ethyl | —OCH$_2$CH$_2$OCH$_3$ |
| 1.63 | 2-(imidazol-1-yl)-ethyl | cyclopropylmethoxy |
| 1.64 | 2-(imidazol-1-yl)-ethyl | —CF$_3$ |
| 1.65 | 2-(imidazol-1-yl)-ethyl | difluoromethoxy |
| 1.66 | 2-(imidazol-1-yl)-ethyl | trifluoromethoxy |
| 1.67 | 2-(4-methyl-piperazin-1-yl)-ethyl | —CH$_3$ |
| 1.68 | 2-(4-methyl-piperazin-1-yl)-ethyl | —Br |
| 1.69 | 2-(4-methyl-piperazin-1-yl)-ethyl | —F |
| 1.70 | 2-(4-methyl-piperazin-1-yl)-ethyl | —OCH$_3$ |
| 1.71 | 2-(4-methyl-piperazin-1-yl)-ethyl | —OCH$_2$CH$_3$ |
| 1.72 | 2-(4-methyl-piperazin-1-yl)-ethyl | —Cl |
| 1.73 | 2-(4-methyl-piperazin-1-yl)-ethyl | —OCH$_2$CH$_2$OCH$_3$ |
| 1.74 | 2-(4-methyl-piperazin-1-yl)-ethyl | cyclopropylmethoxy |
| 1.75 | 2-(4-methyl-piperazin-1-yl)-ethyl | —CF$_3$ |
| 1.76 | 2-(4-methyl-piperazin-1-yl)-ethyl | difluoromethoxy |
| 1.77 | 2-(4-methyl-piperazin-1-yl)-ethyl | trifluoromethoxy |
| 1.78 | 3-(morpholin-4-yl)-propyl | —CH$_3$ |
| 1.79 | 3-(morpholin-4-yl)-propyl | —Br |
| 1.80 | 3-(morpholin-4-yl)-propyl | —F |
| 1.81 | 3-(morpholin-4-yl)-propyl | —OCH$_3$ |
| 1.82 | 3-(morpholin-4-yl)-propyl | —OCH$_2$CH$_3$ |
| 1.83 | 3-(morpholin-4-yl)-propyl | —Cl |
| 1.84 | 3-(morpholin-4-yl)-propyl | —OCH$_2$CH$_2$OCH$_3$ |
| 1.85 | 3-(morpholin-4-yl)-propyl | cyclopropylmethoxy |
| 1.86 | 3-(morpholin-4-yl)-propyl | —CF$_3$ |
| 1.87 | 3-(morpholin-4-yl)-propyl | difluoromethoxy |
| 1.88 | 3-(morpholin-4-yl)-propyl | trifluoromethoxy |
| 1.89 | 3-(pyrrolidin-1-yl)-propyl | —CH$_3$ |
| 1.90 | 3-(pyrrolidin-1-yl)-propyl | —Br |
| 1.91 | 3-(pyrrolidin-1-yl)-propyl | —F |
| 1.92 | 3-(pyrrolidin-1-yl)-propyl | —OCH$_3$ |
| 1.93 | 3-(pyrrolidin-1-yl)-propyl | —OCH$_2$CH$_3$ |
| 1.94 | 3-(pyrrolidin-1-yl)-propyl | —Cl |
| 1.95 | 3-(pyrrolidin-1-yl)-propyl | —OCH$_2$CH$_2$OCH$_3$ |
| 1.96 | 3-(pyrrolidin-1-yl)-propyl | cyclopropylmethoxy |
| 1.97 | 3-(pyrrolidin-1-yl)-propyl | —CF$_3$ |
| 1.98 | 3-(pyrrolidin-1-yl)-propyl | difluoromethoxy |
| 1.99 | 3-(pyrrolidin-1-yl)-propyl | trifluoromethoxy |
| 1.100 | 3-(imidazol-1-yl)-propyl | —CH$_3$ |
| 1.101 | 3-(imidazol-1-yl)-propyl | —Br |
| 1.102 | 3-(imidazol-1-yl)-propyl | —F |
| 1.103 | 3-(imidazol-1-yl)-propyl | —OCH$_3$ |
| 1.104 | 3-(imidazol-1-yl)-propyl | —OCH$_2$CH$_3$ |
| 1.105 | 3-(imidazol-1-yl)-propyl | —Cl |
| 1.106 | 3-(imidazol-1-yl)-propyl | —OCH$_2$CH$_2$OCH$_3$ |
| 1.107 | 3-(imidazol-1-yl)-propyl | cyclopropylmethoxy |
| 1.108 | 3-(imidazol-1-yl)-propyl | —CF$_3$ |
| 1.109 | 3-(imidazol-1-yl)-propyl | difluoromethoxy |
| 1.110 | 3-(imidazol-1-yl)-propyl | trifluoromethoxy |
| 1.111 | 3-(4-methyl-piperazin-1-yl)-propyl | —CH$_3$ |
| 1.112 | 3-(4-methyl-piperazin-1-yl)-propyl | —Br |
| 1.113 | 3-(4-methyl-piperazin-1-yl)-propyl | —F |
| 1.114 | 3-(4-methyl-piperazin-1-yl)-propyl | —OCH$_3$ |
| 1.115 | 3-(4-methyl-piperazin-1-yl)-propyl | —OCH$_2$CH$_3$ |
| 1.116 | 3-(4-methyl-piperazin-1-yl)-propyl | —Cl |
| 1.117 | 3-(4-methyl-piperazin-1-yl)-propyl | —OCH$_2$CH$_2$OCH$_3$ |
| 1.118 | 3-(4-methyl-piperazin-1-yl)-propyl | cyclopropylmethoxy |
| 1.119 | 3-(4-methyl-piperazin-1-yl)-propyl | —CF$_3$ |

TABLE 1-continued

| No. | R1 | R5 |
|---|---|---|
| 1.120 | 3-(4-methyl-piperazin-1-yl)-propyl | difluoromethoxy |
| 1.121 | 3-(4-methyl-piperazin-1-yl)-propyl | trifluoromethoxy |
| 1.122 | 3-amino-propyl | —CH$_3$ |
| 1.123 | 3-amino-propyl | —Br |
| 1.124 | 3-amino-propyl | —F |
| 1.125 | 3-amino-propyl | —OCH$_3$ |
| 1.126 | 3-amino-propyl | —OCH$_2$CH$_3$ |
| 1.127 | 3-amino-propyl | —Cl |
| 1.128 | 3-amino-propyl | —OCH$_2$CH$_2$OCH$_3$ |
| 1.129 | 3-amino-propyl | cyclopropylmethoxy |
| 1.130 | 3-amino-propyl | trifluoromethyl |
| 1.131 | 3-amino-propyl | difluoromethoxy |
| 1.132 | 3-amino-propyl | trifluoromethoxy |
| 1.133 | 2-amino-ethyl | —CH$_3$ |
| 1.134 | 2-amino-ethyl | —Br |
| 1.135 | 2-amino-ethyl | —F |
| 1.136 | 2-amino-ethyl | —OCH$_3$ |
| 1.137 | 2-amino-ethyl | —OCH$_2$CH$_3$ |
| 1.138 | 2-amino-ethyl | —Cl |
| 1.139 | 2-amino-ethyl | —OCH$_2$CH$_2$OCH$_3$ |
| 1.140 | 2-amino-ethyl | cyclopropylmethoxy |
| 1.141 | 2-amino-ethyl | trifluoromethyl |
| 1.142 | 2-amino-ethyl | difluoromethoxy |
| 1.143 | 2-amino-ethyl | trifluoromethoxy |
| 1.144 | 2-(methylamino)-ethyl | —CH$_3$ |
| 1.145 | 2-(methylamino)-ethyl | —Br |
| 1.146 | 2-(methylamino)-ethyl | —F |
| 1.147 | 2-(methylamino)-ethyl | —OCH$_3$ |
| 1.148 | 2-(methylamino)-ethyl | —OCH$_2$CH$_3$ |
| 1.149 | 2-(methylamino)-ethyl | —Cl |
| 1.150 | 2-(methylamino)-ethyl | —OCH$_2$CH$_2$OCH$_3$ |
| 1.151 | 2-(methylamino)-ethyl | cyclopropylmethoxy |
| 1.152 | 2-(methylamino)-ethyl | trifluoromethyl |
| 1.153 | 2-(methylamino)-ethyl | difluoromethoxy |
| 1.154 | 2-(methylamino)-ethyl | trifluoromethoxy |
| 1.155 | 2-(ethylamino)-ethyl | —CH$_3$ |
| 1.156 | 2-(ethylamino)-ethyl | —Br |
| 1.157 | 2-(ethylamino)-ethyl | —F |
| 1.158 | 2-(ethylamino)-ethyl | —OCH$_3$ |
| 1.159 | 2-(ethylamino)-ethyl | —OCH$_2$CH$_3$ |
| 1.160 | 2-(ethylamino)-ethyl | —Cl |
| 1.161 | 2-(ethylamino)-ethyl | —OCH$_2$CH$_2$OCH$_3$ |
| 1.162 | 2-(ethylamino)-ethyl | cyclopropylmethoxy |
| 1.163 | 2-(ethylamino)-ethyl | trifluoromethyl |
| 1.164 | 2-(ethylamino)-ethyl | difluoromethoxy |
| 1.165 | 2-(ethylamino)-ethyl | trifluoromethoxy |
| 1.166 | 2-(azetidin-1-yl)-ethyl | —CH$_3$ |
| 1.167 | 2-(azetidin-1-yl)-ethyl | —Br |
| 1.168 | 2-(azetidin-1-yl)-ethyl | —F |
| 1.169 | 2-(azetidin-1-yl)-ethyl | —OCH$_3$ |
| 1.170 | 2-(azetidin-1-yl)-ethyl | —OCH$_2$CH$_3$ |
| 1.171 | 2-(azetidin-1-yl)-ethyl | —Cl |
| 1.172 | 2-(azetidin-1-yl)-ethyl | —OCH$_2$CH$_2$OCH$_3$ |
| 1.173 | 2-(azetidin-1-yl)-ethyl | cyclopropylmethoxy |
| 1.174 | 2-(azetidin-1-yl)-ethyl | trifluoromethyl |
| 1.175 | 2-(azetidin-1-yl)-ethyl | difluoromethoxy |
| 1.176 | 2-(azetidin-1-yl)-ethyl | trifluoromethoxy |
| 1.177 | 2-(4-acetyl-piperazin-1-yl)-ethyl | —CH$_3$ |
| 1.178 | 2-(4-acetyl-piperazin-1-yl)-ethyl | —Br |
| 1.179 | 2-(4-acetyl-piperazin-1-yl)-ethyl | —F |
| 1.180 | 2-(4-acetyl-piperazin-1-yl)-ethyl | —OCH$_3$ |
| 1.181 | 2-(4-acetyl-piperazin-1-yl)-ethyl | —OCH$_2$CH$_3$ |
| 1.182 | 2-(4-acetyl-piperazin-1-yl)-ethyl | —Cl |
| 1.183 | 2-(4-acetyl-piperazin-1-yl)-ethyl | —OCH$_2$CH$_2$OCH$_3$ |
| 1.184 | 2-(4-acetyl-piperazin-1-yl)-ethyl | cyclopropylmethoxy |
| 1.185 | 2-(4-acetyl-piperazin-1-yl)-ethyl | trifluoromethyl |
| 1.186 | 2-(4-acetyl-piperazin-1-yl)-ethyl | difluoromethoxy |
| 1.187 | 2-(4-acetyl-piperazin-1-yl)-ethyl | trifluoromethoxy |
| 1.188 | 2-(3,3-difluoropyrrolidin-1-yl)-ethyl | —CH$_3$ |
| 1.189 | 2-(3,3-difluoropyrrolidin-1-yl)-ethyl | —Br |
| 1.190 | 2-(3,3-difluoropyrrolidin-1-yl)-ethyl | —F |
| 1.191 | 2-(3,3-difluoropyrrolidin-1-yl)-ethyl | —OCH$_3$ |
| 1.192 | 2-(3,3-difluoropyrrolidin-1-yl)-ethyl | —OCH$_2$CH$_3$ |
| 1.193 | 2-(3,3-difluoropyrrolidin-1-yl)-ethyl | —Cl |
| 1.194 | 2-(3,3-difluoropyrrolidin-1-yl)-ethyl | —OCH$_2$CH$_2$OCH$_3$ |
| 1.195 | 2-(3,3-difluoropyrrolidin-1-yl)-ethyl | cyclopropylmethoxy |
| 1.196 | 2-(3,3-difluoropyrrolidin-1-yl)-ethyl | trifluoromethyl |
| 1.197 | 2-(3,3-difluoropyrrolidin-1-yl)-ethyl | difluoromethoxy |
| 1.198 | 2-(3,3-difluoropyrrolidin-1-yl)-ethyl | trifluoromethoxy |
| 1.199 | 2-(2-fluoroethylamino)-ethyl | —CH$_3$ |
| 1.200 | 2-(2-fluoroethylamino)-ethyl | —Br |
| 1.201 | 2-(2-fluoroethylamino)-ethyl | —F |
| 1.202 | 2-(2-fluoroethylamino)-ethyl | —OCH$_3$ |
| 1.203 | 2-(2-fluoroethylamino)-ethyl | —OCH$_2$CH$_3$ |
| 1.204 | 2-(2-fluoroethylamino)-ethyl | —Cl |
| 1.205 | 2-(2-fluoroethylamino)-ethyl | —OCH$_2$CH$_2$OCH$_3$ |
| 1.206 | 2-(2-fluoroethylamino)-ethyl | cyclopropylmethoxy |
| 1.207 | 2-(2-fluoroethylamino)-ethyl | trifluoromethyl |
| 1.208 | 2-(2-fluoroethylamino)-ethyl | difluoromethoxy |
| 1.209 | 2-(2-fluoroethylamino)-ethyl | trifluoromethoxy |
| 1.210 | 2-(2,2-difluoroethylamino)-ethyl | —CH$_3$ |
| 1.211 | 2-(2,2-difluoroethylamino)-ethyl | —Br |
| 1.212 | 2-(2,2-difluoroethylamino)-ethyl | —F |
| 1.213 | 2-(2,2-difluoroethylamino)-ethyl | —OCH$_3$ |
| 1.214 | 2-(2,2-difluoroethylamino)-ethyl | —OCH$_2$CH$_3$ |
| 1.215 | 2-(2,2-difluoroethylamino)-ethyl | —Cl |
| 1.216 | 2-(2,2-difluoroethylamino)-ethyl | —OCH$_2$CH$_2$OCH$_3$ |
| 1.217 | 2-(2,2-difluoroethylamino)-ethyl | cyclopropylmethoxy |
| 1.218 | 2-(2,2-difluoroethylamino)-ethyl | trifluoromethyl |
| 1.219 | 2-(2,2-difluoroethylamino)-ethyl | difluoromethoxy |
| 1.220 | 2-(2,2-difluoroethylamino)-ethyl | trifluoromethoxy |
| 1.221 | 2-(2,2,2-trifluoroethylamino)-ethyl | —CH$_3$ |
| 1.222 | 2-(2,2,2-trifluoroethylamino)-ethyl | —Br |
| 1.223 | 2-(2,2,2-trifluoroethylamino)-ethyl | —F |
| 1.224 | 2-(2,2,2-trifluoroethylamino)-ethyl | —OCH$_3$ |
| 1.225 | 2-(2,2,2-trifluoroethylamino)-ethyl | —OCH$_2$CH$_3$ |
| 1.226 | 2-(2,2,2-trifluoroethylamino)-ethyl | —Cl |
| 1.227 | 2-(2,2,2-trifluoroethylamino)-ethyl | —OCH$_2$CH$_2$OCH$_3$ |
| 1.228 | 2-(2,2,2-trifluoroethylamino)-ethyl | cyclopropylmethoxy |
| 1.229 | 2-(2,2,2-trifluoroethylamino)-ethyl | trifluoromethyl |
| 1.230 | 2-(2,2,2-trifluoroethylamino)-ethyl | difluoromethoxy |
| 1.231 | 2-(2,2,2-trifluoroethylamino)-ethyl | trifluoromethoxy |
| 1.232 | 2-(isopropylamino)-ethyl | —CH$_3$ |
| 1.233 | 2-(isopropylamino)-ethyl | —Br |
| 1.234 | 2-(isopropylamino)-ethyl | —F |
| 1.235 | 2-(isopropylamino)-ethyl | —OCH$_3$ |
| 1.236 | 2-(isopropylamino)-ethyl | —OCH$_2$CH$_3$ |
| 1.237 | 2-(isopropylamino)-ethyl | —Cl |
| 1.238 | 2-(isopropylamino)-ethyl | —OCH$_2$CH$_2$OCH$_3$ |
| 1.239 | 2-(isopropylamino)-ethyl | cyclopropylmethoxy |
| 1.240 | 2-(isopropylamino)-ethyl | trifluoromethyl |
| 1.241 | 2-(isopropylamino)-ethyl | difluoromethoxy |
| 1.242 | 2-(isopropylamino)-ethyl | trifluoromethoxy |
| 1.243 | 2-(isobutylamino)-ethyl | —CH$_3$ |
| 1.244 | 2-(isobutylamino)-ethyl | —Br |
| 1.245 | 2-(isobutylamino)-ethyl | —F |
| 1.246 | 2-(isobutylamino)-ethyl | —OCH$_3$ |
| 1.247 | 2-(isobutylamino)-ethyl | —OCH$_2$CH$_3$ |
| 1.248 | 2-(isobutylamino)-ethyl | —Cl |
| 1.249 | 2-(isobutylamino)-ethyl | —OCH$_2$CH$_2$OCH$_3$ |
| 1.250 | 2-(isobutylamino)-ethyl | cyclopropylmethoxy |
| 1.251 | 2-(isobutylamino)-ethyl | trifluoromethyl |
| 1.252 | 2-(isobutylamino)-ethyl | difluoromethoxy |
| 1.253 | 2-(isobutylamino)-ethyl | trifluoromethoxy |
| 1.254 | 2-(N-cyclopropylmethyl-amino)-ethyl | —CH$_3$ |
| 1.255 | 2-(N-cyclopropylmethyl-amino)-ethyl | —Br |
| 1.256 | 2-(N-cyclopropylmethyl-amino)-ethyl | —F |
| 1.257 | 2-(N-cyclopropylmethyl-amino)-ethyl | —OCH$_3$ |
| 1.258 | 2-(N-cyclopropylmethyl-amino)-ethyl | —OCH$_2$CH$_3$ |
| 1.259 | 2-(N-cyclopropylmethyl-amino)-ethyl | —Cl |
| 1.260 | 2-(N-cyclopropylmethyl-amino)-ethyl | —OCH$_2$CH$_2$OCH$_3$ |
| 1.261 | 2-(N-cyclopropylmethyl-amino)-ethyl | cyclopropylmethoxy |
| 1.262 | 2-(N-cyclopropylmethyl-amino)-ethyl | trifluoromethyl |
| 1.263 | 2-(N-cyclopropylmethyl-amino)-ethyl | difluoromethoxy |
| 1.264 | 2-(N-cyclopropylmethyl-amino)-ethyl | trifluoromethoxy |
| 1.265 | 2-(cyclopropylamino)-ethyl | —CH$_3$ |
| 1.266 | 2-(cyclopropylamino)-ethyl | —Br |
| 1.267 | 2-(cyclopropylamino)-ethyl | —F |
| 1.268 | 2-(cyclopropylamino)-ethyl | —OCH$_3$ |
| 1.269 | 2-(cyclopropylamino)-ethyl | —OCH$_2$CH$_3$ |
| 1.270 | 2-(cyclopropylamino)-ethyl | —Cl |
| 1.271 | 2-(cyclopropylamino)-ethyl | —OCH$_2$CH$_2$OCH$_3$ |
| 1.272 | 2-(cyclopropylamino)-ethyl | cyclopropylmethoxy |
| 1.273 | 2-(cyclopropylamino)-ethyl | trifluoromethyl |
| 1.274 | 2-(cyclopropylamino)-ethyl | difluoromethoxy |
| 1.275 | 2-(cyclopropylamino)-ethyl | trifluoromethoxy |

TABLE 1-continued

| No. | R1 | R5 |
|---|---|---|
| 1.276 | 2-(cyclobutylamino)-ethyl | —CH₃ |
| 1.277 | 2-(cyclobutylamino)-ethyl | —Br |
| 1.278 | 2-(cyclobutylamino)-ethyl | —F |
| 1.279 | 2-(cyclobutylamino)-ethyl | —OCH₃ |
| 1.280 | 2-(cyclobutylamino)-ethyl | —OCH₂CH₃ |
| 1.281 | 2-(cyclobutylamino)-ethyl | —Cl |
| 1.282 | 2-(cyclobutylamino)-ethyl | —OCH₂CH₂OCH₃ |
| 1.283 | 2-(cyclobutylamino)-ethyl | cyclopropylmethoxy |
| 1.284 | 2-(cyclobutylamino)-ethyl | trifluoromethyl |
| 1.285 | 2-(cyclobutylamino)-ethyl | difluoromethoxy |
| 1.286 | 2-(cyclobutylamino)-ethyl | trifluoromethoxy |
| 1.287 | 2-(N-ethyl-N-methyl-amino)-ethyl | —CH₃ |
| 1.288 | 2-(N-ethyl-N-methyl-amino)-ethyl | —Br |
| 1.289 | 2-(N-ethyl-N-methyl-amino)-ethyl | —F |
| 1.290 | 2-(N-ethyl-N-methyl-amino)-ethyl | —OCH₃ |
| 1.291 | 2-(N-ethyl-N-methyl-amino)-ethyl | —OCH₂CH₃ |
| 1.292 | 2-(N-ethyl-N-methyl-amino)-ethyl | —Cl |
| 1.293 | 2-(N-ethyl-N-methyl-amino)-ethyl | —OCH₂CH₂OCH₃ |
| 1.294 | 2-(N-ethyl-N-methyl-amino)-ethyl | cyclopropylmethoxy |
| 1.295 | 2-(N-ethyl-N-methyl-amino)-ethyl | trifluoromethyl |
| 1.296 | 2-(N-ethyl-N-methyl-amino)-ethyl | difluoromethoxy |
| 1.297 | 2-(N-ethyl-N-methyl-amino)-ethyl | trifluoromethoxy |
| 1.298 | 2-(diethylamino)-ethyl | —CH₃ |
| 1.299 | 2-(diethylamino)-ethyl | —Br |
| 1.300 | 2-(diethylamino)-ethyl | —F |
| 1.301 | 2-(diethylamino)-ethyl | —OCH₃ |
| 1.302 | 2-(diethylamino)-ethyl | —OCH₂CH₃ |
| 1.303 | 2-(diethylamino)-ethyl | —Cl |
| 1.304 | 2-(diethylamino)-ethyl | —OCH₂CH₂OCH₃ |
| 1.305 | 2-(diethylamino)-ethyl | cyclopropylmethoxy |
| 1.306 | 2-(diethylamino)-ethyl | trifluoromethyl |
| 1.307 | 2-(diethylamino)-ethyl | difluoromethoxy |
| 1.308 | 2-(diethylamino)-ethyl | trifluoromethoxy |
| 1.309 | 2-(N-isopropyl-N-methyl-amino)-ethyl | —CH₃ |
| 1.310 | 2-(N-isopropyl-N-methyl-amino)-ethyl | —Br |
| 1.311 | 2-(N-isopropyl-N-methyl-amino)-ethyl | —F |
| 1.312 | 2-(N-isopropyl-N-methyl-amino)-ethyl | —OCH₃ |
| 1.313 | 2-(N-isopropyl-N-methyl-amino)-ethyl | —OCH₂CH₃ |
| 1.314 | 2-(N-isopropyl-N-methyl-amino)-ethyl | —Cl |
| 1.315 | 2-(N-isopropyl-N-methyl-amino)-ethyl | —OCH₂CH₂OCH₃ |
| 1.316 | 2-(N-isopropyl-N-methyl-amino)-ethyl | cyclopropylmethoxy |
| 1.317 | 2-(N-isopropyl-N-methyl-amino)-ethyl | trifluoromethyl |
| 1.318 | 2-(N-isopropyl-N-methyl-amino)-ethyl | difluoromethoxy |
| 1.319 | 2-(N-isopropyl-N-methyl-amino)-ethyl | trifluoromethoxy |
| 1.320 | 2-((R)-3-fluoro-pyrrolidin-1-yl)-ethyl | —CH₃ |
| 1.321 | 2-((R)-3-fluoro-pyrrolidin-1-yl)-ethyl | —Br |
| 1.322 | 2-((R)-3-fluoro-pyrrolidin-1-yl)-ethyl | —F |
| 1.323 | 2-((R)-3-fluoro-pyrrolidin-1-yl)-ethyl | —OCH₃ |
| 1.324 | 2-((R)-3-fluoro-pyrrolidin-1-yl)-ethyl | —OCH₂CH₃ |
| 1.325 | 2-((R)-3-fluoro-pyrrolidin-1-yl)-ethyl | —Cl |
| 1.326 | 2-((R)-3-fluoro-pyrrolidin-1-yl)-ethyl | —OCH₂CH₂OCH₃ |
| 1.327 | 2-((R)-3-fluoro-pyrrolidin-1-yl)-ethyl | cyclopropylmethoxy |
| 1.328 | 2-((R)-3-fluoro-pyrrolidin-1-yl)-ethyl | trifluoromethyl |
| 1.329 | 2-((R)-3-fluoro-pyrrolidin-1-yl)-ethyl | difluoromethoxy |
| 1.330 | 2-((R)-3-fluoro-pyrrolidin-1-yl)-ethyl | trifluoromethoxy |
| 1.331 | 2-((S)-3-fluoro-pyrrolidin-1-yl)-ethyl | —CH₃ |
| 1.332 | 2-((S)-3-fluoro-pyrrolidin-1-yl)-ethyl | —Br |
| 1.333 | 2-((S)-3-fluoro-pyrrolidin-1-yl)-ethyl | —F |
| 1.334 | 2-((S)-3-fluoro-pyrrolidin-1-yl)-ethyl | —OCH₃ |
| 1.335 | 2-((S)-3-fluoro-pyrrolidin-1-yl)-ethyl | —OCH₂CH₃ |
| 1.336 | 2-((S)-3-fluoro-pyrrolidin-1-yl)-ethyl | —Cl |
| 1.337 | 2-((S)-3-fluoro-pyrrolidin-1-yl)-ethyl | —OCH₂CH₂OCH₃ |
| 1.338 | 2-((S)-3-fluoro-pyrrolidin-1-yl)-ethyl | cyclopropylmethoxy |
| 1.339 | 2-((S)-3-fluoro-pyrrolidin-1-yl)-ethyl | trifluoromethyl |
| 1.340 | 2-((S)-3-fluoro-pyrrolidin-1-yl)-ethyl | difluoromethoxy |
| 1.341 | 2-((S)-3-fluoro-pyrrolidin-1-yl)-ethyl | trifluoromethoxy |
| 1.342 | 2-(4-methyl-piperidin-1-yl)-ethyl | —CH₃ |
| 1.343 | 2-(4-methyl-piperidin-1-yl)-ethyl | —Br |
| 1.344 | 2-(4-methyl-piperidin-1-yl)-ethyl | —F |
| 1.345 | 2-(4-methyl-piperidin-1-yl)-ethyl | —OCH₃ |
| 1.346 | 2-(4-methyl-piperidin-1-yl)-ethyl | —OCH₂CH₃ |
| 1.347 | 2-(4-methyl-piperidin-1-yl)-ethyl | —Cl |
| 1.348 | 2-(4-methyl-piperidin-1-yl)-ethyl | —OCH₂CH₂OCH₃ |
| 1.349 | 2-(4-methyl-piperidin-1-yl)-ethyl | cyclopropylmethoxy |
| 1.350 | 2-(4-methyl-piperidin-1-yl)-ethyl | trifluoromethyl |
| 1.351 | 2-(4-methyl-piperidin-1-yl)-ethyl | difluoromethoxy |
| 1.352 | 2-(4-methyl-piperidin-1-yl)-ethyl | trifluoromethoxy |
| 1.353 | 3-(methylamino)-propyl | —CH₃ |
| 1.354 | 3-(methylamino)-propyl | —Br |
| 1.355 | 3-(methylamino)-propyl | —F |
| 1.356 | 3-(methylamino)-propyl | —OCH₃ |
| 1.357 | 3-(methylamino)-propyl | —OCH₂CH₃ |
| 1.358 | 3-(methylamino)-propyl | —Cl |
| 1.359 | 3-(methylamino)-propyl | —OCH₂CH₂OCH₃ |
| 1.360 | 3-(methylamino)-propyl | cyclopropylmethoxy |
| 1.361 | 3-(methylamino)-propyl | trifluoromethyl |
| 1.362 | 3-(methylamino)-propyl | difluoromethoxy |
| 1.363 | 3-(methylamino)-propyl | trifluoromethoxy |
| 1.364 | 3-(ethylamino)-propyl | —CH₃ |
| 1.365 | 3-(ethylamino)-propyl | —Br |
| 1.366 | 3-(ethylamino)-propyl | —F |
| 1.367 | 3-(ethylamino)-propyl | —OCH₃ |
| 1.368 | 3-(ethylamino)-propyl | —OCH₂CH₃ |
| 1.369 | 3-(ethylamino)-propyl | —Cl |
| 1.370 | 3-(ethylamino)-propyl | —OCH₂CH₂OCH₃ |
| 1.371 | 3-(ethylamino)-propyl | cyclopropylmethoxy |
| 1.372 | 3-(ethylamino)-propyl | trifluoromethyl |
| 1.373 | 3-(ethylamino)-propyl | difluoromethoxy |
| 1.374 | 3-(ethylamino)-propyl | trifluoromethoxy |
| 1.375 | 3-(azetidin-1-yl)-propyl | —CH₃ |
| 1.376 | 3-(azetidin-1-yl)-propyl | —Br |
| 1.377 | 3-(azetidin-1-yl)-propyl | —F |
| 1.378 | 3-(azetidin-1-yl)-propyl | —OCH₃ |
| 1.379 | 3-(azetidin-1-yl)-propyl | —OCH₂CH₃ |
| 1.380 | 3-(azetidin-1-yl)-propyl | —Cl |
| 1.381 | 3-(azetidin-1-yl)-propyl | —OCH₂CH₂OCH₃ |
| 1.382 | 3-(azetidin-1-yl)-propyl | cyclopropylmethoxy |
| 1.383 | 3-(azetidin-1-yl)-propyl | trifluoromethyl |
| 1.384 | 3-(azetidin-1-yl)-propyl | difluoromethoxy |
| 1.385 | 3-(azetidin-1-yl)-propyl | trifluoromethoxy |
| 1.386 | 3-(4-acetyl-piperazin-1-yl)-propyl | —CH₃ |
| 1.387 | 3-(4-acetyl-piperazin-1-yl)-propyl | —Br |
| 1.388 | 3-(4-acetyl-piperazin-1-yl)-propyl | —F |
| 1.389 | 3-(4-acetyl-piperazin-1-yl)-propyl | —OCH₃ |
| 1.390 | 3-(4-acetyl-piperazin-1-yl)-propyl | —OCH₂CH₃ |
| 1.391 | 3-(4-acetyl-piperazin-1-yl)-propyl | —Cl |
| 1.392 | 3-(4-acetyl-piperazin-1-yl)-propyl | —OCH₂CH₂OCH₃ |
| 1.393 | 3-(4-acetyl-piperazin-1-yl)-propyl | cyclopropylmethoxy |
| 1.394 | 3-(4-acetyl-piperazin-1-yl)-propyl | trifluoromethyl |
| 1.395 | 3-(4-acetyl-piperazin-1-yl)-propyl | difluoromethoxy |
| 1.396 | 3-(4-acetyl-piperazin-1-yl)-propyl | trifluoromethoxy |
| 1.397 | 3-(3,3-difluoropyrrolidin-1-yl)-propyl | —CH₃ |
| 1.398 | 3-(3,3-difluoropyrrolidin-1-yl)-propyl | —Br |
| 1.399 | 3-(3,3-difluoropyrrolidin-1-yl)-propyl | —F |
| 1.400 | 3-(3,3-difluoropyrrolidin-1-yl)-propyl | —OCH₃ |
| 1.401 | 3-(3,3-difluoropyrrolidin-1-yl)-propyl | —OCH₂CH₃ |
| 1.402 | 3-(3,3-difluoropyrrolidin-1-yl)-propyl | —Cl |
| 1.403 | 3-(3,3-difluoropyrrolidin-1-yl)-propyl | —OCH₂CH₂OCH₃ |
| 1.404 | 3-(3,3-difluoropyrrolidin-1-yl)-propyl | cyclopropylmethoxy |
| 1.405 | 3-(3,3-difluoropyrrolidin-1-yl)-propyl | trifluoromethyl |
| 1.406 | 3-(3,3-difluoropyrrolidin-1-yl)-propyl | difluoromethoxy |
| 1.407 | 3-(3,3-difluoropyrrolidin-1-yl)-propyl | trifluoromethoxy |
| 1.408 | 3-(2-fluoroethylamino)-propyl | —CH₃ |
| 1.409 | 3-(2-fluoroethylamino)-propyl | —Br |
| 1.410 | 3-(2-fluoroethylamino)-propyl | —F |
| 1.411 | 3-(2-fluoroethylamino)-propyl | —OCH₃ |
| 1.412 | 3-(2-fluoroethylamino)-propyl | —OCH₂CH₃ |
| 1.413 | 3-(2-fluoroethylamino)-propyl | —Cl |
| 1.414 | 3-(2-fluoroethylamino)-propyl | —OCH₂CH₂OCH₃ |
| 1.415 | 3-(2-fluoroethylamino)-propyl | cyclopropylmethoxy |
| 1.416 | 3-(2-fluoroethylamino)-propyl | trifluoromethyl |
| 1.417 | 3-(2-fluoroethylamino)-propyl | difluoromethoxy |
| 1.418 | 3-(2-fluoroethylamino)-propyl | trifluoromethoxy |
| 1.419 | 3-(2,2-difluoroethylamino)-propyl | —CH₃ |
| 1.420 | 3-(2,2-difluoroethylamino)-propyl | —Br |
| 1.421 | 3-(2,2-difluoroethylamino)-propyl | —F |
| 1.422 | 3-(2,2-difluoroethylamino)-propyl | —OCH₃ |
| 1.423 | 3-(2,2-difluoroethylamino)-propyl | —OCH₂CH₃ |
| 1.424 | 3-(2,2-difluoroethylamino)-propyl | —Cl |
| 1.425 | 3-(2,2-difluoroethylamino)-propyl | —OCH₂CH₂OCH₃ |
| 1.426 | 3-(2,2-difluoroethylamino)-propyl | cyclopropylmethoxy |
| 1.427 | 3-(2,2-difluoroethylamino)-propyl | trifluoromethyl |
| 1.428 | 3-(2,2-difluoroethylamino)-propyl | difluoromethoxy |
| 1.429 | 3-(2,2-difluoroethylamino)-propyl | trifluoromethoxy |
| 1.430 | 3-(2,2,2-trifluoroethylamino)-propyl | —CH₃ |
| 1.431 | 3-(2,2,2-trifluoroethylamino)-propyl | —Br |

TABLE 1-continued

| No. | R1 | R5 |
|---|---|---|
| 1.432 | 3-(2,2,2-trifluoroethylamino)-propyl | —F |
| 1.433 | 3-(2,2,2-trifluoroethylamino)-propyl | —OCH$_3$ |
| 1.434 | 3-(2,2,2-trifluoroethylamino)-propyl | —OCH$_2$CH$_3$ |
| 1.435 | 3-(2,2,2-trifluoroethylamino)-propyl | —Cl |
| 1.436 | 3-(2,2,2-trifluoroethylamino)-propyl | —OCH$_2$CH$_2$OCH$_3$ |
| 1.437 | 3-(2,2,2-trifluoroethylamino)-propyl | cyclopropylmethoxy |
| 1.438 | 3-(2,2,2-trifluoroethylamino)-propyl | trifluoromethyl |
| 1.439 | 3-(2,2,2-trifluoroethylamino)-propyl | difluoromethoxy |
| 1.440 | 3-(2,2,2-trifluoroethylamino)-propyl | trifluoromethoxy |
| 1.441 | 3-(isopropylamino)-propyl | —CH$_3$ |
| 1.442 | 3-(isopropylamino)-propyl | —Br |
| 1.443 | 3-(isopropylamino)-propyl | —F |
| 1.444 | 3-(isopropylamino)-propyl | —OCH$_3$ |
| 1.445 | 3-(isopropylamino)-propyl | —OCH$_2$CH$_3$ |
| 1.446 | 3-(isopropylamino)-propyl | —Cl |
| 1.447 | 3-(isopropylamino)-propyl | —OCH$_2$CH$_2$OCH$_3$ |
| 1.448 | 3-(isopropylamino)-propyl | cyclopropylmethoxy |
| 1.449 | 3-(isopropylamino)-propyl | trifluoromethyl |
| 1.450 | 3-(isopropylamino)-propyl | difluoromethoxy |
| 1.451 | 3-(isopropylamino)-propyl | trifluoromethoxy |
| 1.452 | 3-(isobutylamino)-propyl | —CH$_3$ |
| 1.453 | 3-(isobutylamino)-propyl | —Br |
| 1.454 | 3-(isobutylamino)-propyl | —F |
| 1.455 | 3-(isobutylamino)-propyl | —OCH$_3$ |
| 1.456 | 3-(isobutylamino)-propyl | —OCH$_2$CH$_3$ |
| 1.457 | 3-(isobutylamino)-propyl | —Cl |
| 1.458 | 3-(isobutylamino)-propyl | —OCH$_2$CH$_2$OCH$_3$ |
| 1.459 | 3-(isobutylamino)-propyl | cyclopropylmethoxy |
| 1.460 | 3-(isobutylamino)-propyl | trifluoromethyl |
| 1.461 | 3-(isobutylamino)-propyl | difluoromethoxy |
| 1.462 | 3-(isobutylamino)-propyl | trifluoromethoxy |
| 1.463 | 3-(N-cyclopropylmethyl-amino)-propyl | —CH$_3$ |
| 1.464 | 3-(N-cyclopropylmethyl-amino)-propyl | —Br |
| 1.465 | 3-(N-cyclopropylmethyl-amino)-propyl | —F |
| 1.466 | 3-(N-cyclopropylmethyl-amino)-propyl | —OCH$_3$ |
| 1.467 | 3-(N-cyclopropylmethyl-amino)-propyl | —OCH$_2$CH$_3$ |
| 1.468 | 3-(N-cyclopropylmethyl-amino)-propyl | —Cl |
| 1.469 | 3-(N-cyclopropylmethyl-amino)-propyl | —OCH$_2$CH$_2$OCH$_3$ |
| 1.470 | 3-(N-cyclopropylmethyl-amino)-propyl | cyclopropylmethoxy |
| 1.471 | 3-(N-cyclopropylmethyl-amino)-propyl | trifluoromethyl |
| 1.472 | 3-(N-cyclopropylmethyl-amino)-propyl | difluoromethoxy |
| 1.473 | 3-(N-cyclopropylmethyl-amino)-propyl | trifluoromethoxy |
| 1.474 | 3-(cyclopropylamino)-propyl | —CH$_3$ |
| 1.475 | 3-(cyclopropylamino)-propyl | —Br |
| 1.476 | 3-(cyclopropylamino)-propyl | —F |
| 1.477 | 3-(cyclopropylamino)-propyl | —OCH$_3$ |
| 1.478 | 3-(cyclopropylamino)-propyl | —OCH$_2$CH$_3$ |
| 1.479 | 3-(cyclopropylamino)-propyl | —Cl |
| 1.480 | 3-(cyclopropylamino)-propyl | —OCH$_2$CH$_2$OCH$_3$ |
| 1.481 | 3-(cyclopropylamino)-propyl | cyclopropylmethoxy |
| 1.482 | 3-(cyclopropylamino)-propyl | trifluoromethyl |
| 1.483 | 3-(cyclopropylamino)-propyl | difluoromethoxy |
| 1.484 | 3-(cyclopropylamino)-propyl | trifluoromethoxy |
| 1.485 | 3-(cyclobutylamino)-propyl | —CH$_3$ |
| 1.486 | 3-(cyclobutylamino)-propyl | —Br |
| 1.487 | 3-(cyclobutylamino)-propyl | —F |
| 1.488 | 3-(cyclobutylamino)-propyl | —OCH$_3$ |
| 1.489 | 3-(cyclobutylamino)-propyl | —OCH$_2$CH$_3$ |
| 1.490 | 3-(cyclobutylamino)-propyl | —Cl |
| 1.491 | 3-(cyclobutylamino)-propyl | —OCH$_2$CH$_2$OCH$_3$ |
| 1.492 | 3-(cyclobutylamino)-propyl | cyclopropylmethoxy |
| 1.493 | 3-(cyclobutylamino)-propyl | trifluoromethyl |
| 1.494 | 3-(cyclobutylamino)-propyl | difluoromethoxy |
| 1.495 | 3-(cyclobutylamino)-propyl | trifluoromethoxy |
| 1.496 | 3-(N-ethyl-N-methyl-amino)-propyl | —CH$_3$ |
| 1.497 | 3-(N-ethyl-N-methyl-amino)-propyl | —Br |
| 1.498 | 3-(N-ethyl-N-methyl-amino)-propyl | —F |
| 1.499 | 3-(N-ethyl-N-methyl-amino)-propyl | —OCH$_3$ |
| 1.500 | 3-(N-ethyl-N-methyl-amino)-propyl | —OCH$_2$CH$_3$ |
| 1.501 | 3-(N-ethyl-N-methyl-amino)-propyl | —Cl |
| 1.502 | 3-(N-ethyl-N-methyl-amino)-propyl | —OCH$_2$CH$_2$OCH$_3$ |
| 1.503 | 3-(N-ethyl-N-methyl-amino)-propyl | cyclopropylmethoxy |
| 1.504 | 3-(N-ethyl-N-methyl-amino)-propyl | trifluoromethyl |
| 1.505 | 3-(N-ethyl-N-methyl-amino)-propyl | difluoromethoxy |
| 1.506 | 3-(N-ethyl-N-methyl-amino)-propyl | trifluoromethoxy |
| 1.507 | 3-(diethylamino)-propyl | —CH$_3$ |
| 1.508 | 3-(diethylamino)-propyl | —Br |
| 1.509 | 3-(diethylamino)-propyl | —F |
| 1.510 | 3-(diethylamino)-propyl | —OCH$_3$ |
| 1.511 | 3-(diethylamino)-propyl | —OCH$_2$CH$_3$ |
| 1.512 | 3-(diethylamino)-propyl | —Cl |
| 1.513 | 3-(diethylamino)-propyl | —OCH$_2$CH$_2$OCH$_3$ |
| 1.514 | 3-(diethylamino)-propyl | cyclopropylmethoxy |
| 1.515 | 3-(diethylamino)-propyl | trifluoromethyl |
| 1.516 | 3-(diethylamino)-propyl | difluoromethoxy |
| 1.517 | 3-(diethylamino)-propyl | trifluoromethoxy |
| 1.518 | 3-(N-isopropyl-N-methyl-amino)-propyl | —CH$_3$ |
| 1.519 | 3-(N-isopropyl-N-methyl-amino)-propyl | —Br |
| 1.520 | 3-(N-isopropyl-N-methyl-amino)-propyl | —F |
| 1.521 | 3-(N-isopropyl-N-methyl-amino)-propyl | —OCH$_3$ |
| 1.522 | 3-(N-isopropyl-N-methyl-amino)-propyl | —OCH$_2$CH$_3$ |
| 1.523 | 3-(N-isopropyl-N-methyl-amino)-propyl | —Cl |
| 1.524 | 3-(N-isopropyl-N-methyl-amino)-propyl | —OCH$_2$CH$_2$OCH$_3$ |
| 1.525 | 3-(N-isopropyl-N-methyl-amino)-propyl | cyclopropylmethoxy |
| 1.526 | 3-(N-isopropyl-N-methyl-amino)-propyl | trifluoromethyl |
| 1.527 | 3-(N-isopropyl-N-methyl-amino)-propyl | difluoromethoxy |
| 1.528 | 3-(N-isopropyl-N-methyl-amino)-propyl | trifluoromethoxy |
| 1.529 | 3-((R)-3-fluoro-pyrrolidin-1-yl)-propyl | —CH$_3$ |
| 1.530 | 3-((R)-3-fluoro-pyrrolidin-1-yl)-propyl | —Br |
| 1.531 | 3-((R)-3-fluoro-pyrrolidin-1-yl)-propyl | —F |
| 1.532 | 3-((R)-3-fluoro-pyrrolidin-1-yl)-propyl | —OCH$_3$ |
| 1.533 | 3-((R)-3-fluoro-pyrrolidin-1-yl)-propyl | —OCH$_2$CH$_3$ |
| 1.534 | 3-((R)-3-fluoro-pyrrolidin-1-yl)-propyl | —Cl |
| 1.535 | 3-((R)-3-fluoro-pyrrolidin-1-yl)-propyl | —OCH$_2$CH$_2$OCH$_3$ |
| 1.536 | 3-((R)-3-fluoro-pyrrolidin-1-yl)-propyl | cyclopropylmethoxy |
| 1.537 | 3-((R)-3-fluoro-pyrrolidin-1-yl)-propyl | trifluoromethyl |
| 1.538 | 3-((R)-3-fluoro-pyrrolidin-1-yl)-propyl | difluoromethoxy |
| 1.539 | 3-((R)-3-fluoro-pyrrolidin-1-yl)-propyl | trifluoromethoxy |
| 1.540 | 3-((S)-3-fluoro-pyrrolidin-1-yl)-propyl | —CH$_3$ |
| 1.541 | 3-((S)-3-fluoro-pyrrolidin-1-yl)-propyl | —Br |
| 1.542 | 3-((S)-3-fluoro-pyrrolidin-1-yl)-propyl | —F |
| 1.543 | 3-((S)-3-fluoro-pyrrolidin-1-yl)-propyl | —OCH$_3$ |
| 1.544 | 3-((S)-3-fluoro-pyrrolidin-1-yl)-propyl | —OCH$_2$CH$_3$ |
| 1.545 | 3-((S)-3-fluoro-pyrrolidin-1-yl)-propyl | —Cl |
| 1.546 | 3-((S)-3-fluoro-pyrrolidin-1-yl)-propyl | —OCH$_2$CH$_2$OCH$_3$ |
| 1.547 | 3-((S)-3-fluoro-pyrrolidin-1-yl)-propyl | cyclopropylmethoxy |
| 1.548 | 3-((S)-3-fluoro-pyrrolidin-1-yl)-propyl | trifluoromethyl |
| 1.549 | 3-((S)-3-fluoro-pyrrolidin-1-yl)-propyl | difluoromethoxy |
| 1.550 | 3-((S)-3-fluoro-pyrrolidin-1-yl)-propyl | trifluoromethoxy |
| 1.551 | 3-(4-methyl-piperidin-1-yl)-propyl | —CH$_3$ |
| 1.552 | 3-(4-methyl-piperidin-1-yl)-propyl | —Br |
| 1.553 | 3-(4-methyl-piperidin-1-yl)-propyl | —F |
| 1.554 | 3-(4-methyl-piperidin-1-yl)-propyl | —OCH$_3$ |
| 1.555 | 3-(4-methyl-piperidin-1-yl)-propyl | —OCH$_2$CH$_3$ |
| 1.556 | 3-(4-methyl-piperidin-1-yl)-propyl | —Cl |
| 1.557 | 3-(4-methyl-piperidin-1-yl)-propyl | —OCH$_2$CH$_2$OCH$_3$ |
| 1.558 | 3-(4-methyl-piperidin-1-yl)-propyl | cyclopropylmethoxy |
| 1.559 | 3-(4-methyl-piperidin-1-yl)-propyl | trifluoromethyl |
| 1.560 | 3-(4-methyl-piperidin-1-yl)-propyl | difluoromethoxy |
| 1.561 | 3-(4-methyl-piperidin-1-yl)-propyl | trifluoromethoxy |
| 1.562 | 3-[N-(2-hydroxyethyl)-amino]-propyl | —CH$_3$ |
| 1.563 | 3-[N-(2-hydroxyethyl)-amino]-propyl | —Br |
| 1.564 | 3-[N-(2-hydroxyethyl)-amino]-propyl | —F |
| 1.565 | 3-[N-(2-hydroxyethyl)-amino]-propyl | —OCH$_3$ |
| 1.566 | 3-[N-(2-hydroxyethyl)-amino]-propyl | —OCH$_2$CH$_3$ |
| 1.567 | 3-[N-(2-hydroxyethyl)-amino]-propyl | —Cl |
| 1.568 | 3-[N-(2-hydroxyethyl)-amino]-propyl | —OCH$_2$CH$_2$OCH$_3$ |
| 1.569 | 3-[N-(2-hydroxyethyl)-amino]-propyl | cyclopropylmethoxy |
| 1.570 | 3-[N-(2-hydroxyethyl)-amino]-propyl | trifluoromethyl |
| 1.571 | 3-[N-(2-hydroxyethyl)-amino]-propyl | difluoromethoxy |
| 1.572 | 3-[N-(2-hydroxyethyl)-amino]-propyl | trifluoromethoxy |
| 1.573 | 3-[N-(2-methoxyethyl)-amino]-propyl | —CH$_3$ |
| 1.574 | 3-[N-(2-methoxyethyl)-amino]-propyl | —Br |
| 1.575 | 3-[N-(2-methoxyethyl)-amino]-propyl | —F |
| 1.576 | 3-[N-(2-methoxyethyl)-amino]-propyl | —OCH$_3$ |
| 1.577 | 3-[N-(2-methoxyethyl)-amino]-propyl | —OCH$_2$CH$_3$ |
| 1.578 | 3-[N-(2-methoxyethyl)-amino]-propyl | —Cl |
| 1.579 | 3-[N-(2-methoxyethyl)-amino]-propyl | —OCH$_2$CH$_2$OCH$_3$ |
| 1.580 | 3-[N-(2-methoxyethyl)-amino]-propyl | cyclopropylmethoxy |
| 1.581 | 3-[N-(2-methoxyethyl)-amino]-propyl | trifluoromethyl |
| 1.582 | 3-[N-(2-methoxyethyl)-amino]-propyl | difluoromethoxy |
| 1.583 | 3-[N-(2-methoxyethyl)-amino]-propyl | trifluoromethoxy |
| 1.584 | 3-(tertbutylamino)-propyl | —CH$_3$ |
| 1.585 | 3-(tertbutylamino)-propyl | —Br |
| 1.586 | 3-(tertbutylamino)-propyl | —F |
| 1.587 | 3-(tertbutylamino)-propyl | —OCH$_3$ |

TABLE 1-continued

| No. | R1 | R5 |
|---|---|---|
| 1.588 | 3-(tertbutylamino)-propyl | —OCH$_2$CH$_3$ |
| 1.589 | 3-(tertbutylamino)-propyl | —Cl |
| 1.590 | 3-(tertbutylamino)-propyl | —OCH$_2$CH$_2$OCH$_3$ |
| 1.591 | 3-(tertbutylamino)-propyl | cyclopropylmethoxy |
| 1.592 | 3-(tertbutylamino)-propyl | trifluoromethyl |
| 1.593 | 3-(tertbutylamino)-propyl | difluoromethoxy |
| 1.594 | 3-(tertbutylamino)-propyl | trifluoromethoxy |
| 1.595 | 3-(allylamino)-propyl | —CH$_3$ |
| 1.596 | 3-(allylamino)-propyl | —Br |
| 1.597 | 3-(allylamino)-propyl | —F |
| 1.598 | 3-(allylamino)-propyl | —OCH$_3$ |
| 1.599 | 3-(allylamino)-propyl | —OCH$_2$CH$_3$ |
| 1.600 | 3-(allylamino)-propyl | —Cl |
| 1.601 | 3-(allylamino)-propyl | —OCH$_2$CH$_2$OCH$_3$ |
| 1.602 | 3-(allylamino)-propyl | cyclopropylmethoxy |
| 1.603 | 3-(allylamino)-propyl | trifluoromethyl |
| 1.604 | 3-(allylamino)-propyl | difluoromethoxy |
| 1.605 | 3-(allylamino)-propyl | trifluoromethoxy |
| 1.606 | 3-(propargylamino)-propyl | —CH$_3$ |
| 1.607 | 3-(propargylamino)-propyl | —Br |
| 1.608 | 3-(propargylamino)-propyl | —F |
| 1.609 | 3-(propargylamino)-propyl | —OCH$_3$ |
| 1.610 | 3-(propargylamino)-propyl | —OCH$_2$CH$_3$ |
| 1.611 | 3-(propargylamino)-propyl | —Cl |
| 1.612 | 3-(propargylamino)-propyl | —OCH$_2$CH$_2$OCH$_3$ |
| 1.613 | 3-(propargylamino)-propyl | cyclopropylmethoxy |
| 1.614 | 3-(propargylamino)-propyl | trifluoromethyl |
| 1.615 | 3-(propargylamino)-propyl | difluoromethoxy |
| 1.616 | 3-(propargylamino)-propyl | trifluoromethoxy |
| 1.617 | 3-(N-allyl-N-methyl-amino)-propyl | —CH$_3$ |
| 1.618 | 3-(N-allyl-N-methyl-amino)-propyl | —Br |
| 1.619 | 3-(N-allyl-N-methyl-amino)-propyl | —F |
| 1.620 | 3-(N-allyl-N-methyl-amino)-propyl | —OCH$_3$ |
| 1.621 | 3-(N-allyl-N-methyl-amino)-propyl | —OCH$_2$CH$_3$ |
| 1.622 | 3-(N-allyl-N-methyl-amino)-propyl | —Cl |
| 1.623 | 3-(N-allyl-N-methyl-amino)-propyl | —OCH$_2$CH$_2$OCH$_3$ |
| 1.624 | 3-(N-allyl-N-methyl-amino)-propyl | cyclopropylmethoxy |
| 1.625 | 3-(N-allyl-N-methyl-amino)-propyl | trifluoromethyl |
| 1.626 | 3-(N-allyl-N-methyl-amino)-propyl | difluoromethoxy |
| 1.627 | 3-(N-allyl-N-methyl-amino)-propyl | trifluoromethoxy |
| 1.628 | 3-(N-methyl-N-propargyl-amino)-propyl | —CH$_3$ |
| 1.629 | 3-(N-methyl-N-propargyl-amino)-propyl | —Br |
| 1.630 | 3-(N-methyl-N-propargyl-amino)-propyl | —F |
| 1.631 | 3-(N-methyl-N-propargyl-amino)-propyl | —OCH$_3$ |
| 1.632 | 3-(N-methyl-N-propargyl-amino)-propyl | —OCH$_2$CH$_3$ |
| 1.633 | 3-(N-methyl-N-propargyl-amino)-propyl | —Cl |
| 1.634 | 3-(N-methyl-N-propargyl-amino)-propyl | —OCH$_2$CH$_2$OCH$_3$ |
| 1.635 | 3-(N-methyl-N-propargyl-amino)-propyl | cyclopropylmethoxy |
| 1.636 | 3-(N-methyl-N-propargyl-amino)-propyl | trifluoromethyl |
| 1.637 | 3-(N-methyl-N-propargyl-amino)-propyl | difluoromethoxy |
| 1.638 | 3-(N-methyl-N-propargyl-amino)-propyl | trifluoromethoxy |
| 1.639 | 3-[N-(2-hydroxyethyl)-N-methyl-amino]-propyl | —CH$_3$ |
| 1.640 | 3-[N-(2-hydroxyethyl)-N-methyl-amino]-propyl | —Br |
| 1.641 | 3-[N-(2-hydroxyethyl)-N-methyl-amino]-propyl | —F |
| 1.642 | 3-[N-(2-hydroxyethyl)-N-methyl-amino]-propyl | —OCH$_3$ |
| 1.643 | 3-[N-(2-hydroxyethyl)-N-methyl-amino]-propyl | —OCH$_2$CH$_3$ |
| 1.644 | 3-[N-(2-hydroxyethyl)-N-methyl-amino]-propyl | —Cl |
| 1.645 | 3-[N-(2-hydroxyethyl)-N-methyl-amino]-propyl | —OCH$_2$CH$_2$OCH$_3$ |
| 1.646 | 3-[N-(2-hydroxyethyl)-N-methyl-amino]-propyl | cyclopropylmethoxy |
| 1.647 | 3-[N-(2-hydroxyethyl)-N-methyl-amino]-propyl | trifluoromethyl |
| 1.648 | 3-[N-(2-hydroxyethyl)-N-methyl-amino]-propyl | difluoromethoxy |
| 1.649 | 3-[N-(2-hydroxyethyl)-N-methyl-amino]-propyl | trifluoromethoxy |
| 1.650 | 3-[N-(2-methoxyethyl)-N-methyl-amino]-propyl | —CH$_3$ |
| 1.651 | 3-[N-(2-methoxyethyl)-N-methyl-amino]-propyl | —Br |
| 1.652 | 3-[N-(2-methoxyethyl)-N-methyl-amino]-propyl | —F |
| 1.653 | 3-[N-(2-methoxyethyl)-N-methyl-amino]-propyl | —OCH$_3$ |
| 1.654 | 3-[N-(2-methoxyethyl)-N-methyl-amino]-propyl | —OCH$_2$CH$_3$ |
| 1.655 | 3-[N-(2-methoxyethyl)-N-methyl-amino]-propyl | —Cl |
| 1.656 | 3-[N-(2-methoxyethyl)-N-methyl-amino]-propyl | —OCH$_2$CH$_2$OCH$_3$ |
| 1.657 | 3-[N-(2-methoxyethyl)-N-methyl-amino]-propyl | cyclopropylmethoxy |
| 1.658 | 3-[N-(2-methoxyethyl)-N-methyl-amino]-propyl | trifluoromethyl |
| 1.659 | 3-[N-(2-methoxyethyl)-N-methyl-amino]-propyl | difluoromethoxy |
| 1.660 | 3-[N-(2-methoxyethyl)-N-methyl-amino]-propyl | trifluoromethoxy |
| 1.661 | 3-[N-ethyl-N-(2-hydroxyethyl)-amino]-propyl | —CH$_3$ |
| 1.662 | 3-[N-ethyl-N-(2-hydroxyethyl)-amino]-propyl | —Br |
| 1.663 | 3-[N-ethyl-N-(2-hydroxyethyl)-amino]-propyl | —F |
| 1.664 | 3-[N-ethyl-N-(2-hydroxyethyl)-amino]-propyl | —OCH$_3$ |
| 1.665 | 3-[N-ethyl-N-(2-hydroxyethyl)-amino]-propyl | —OCH$_2$CH$_3$ |
| 1.666 | 3-[N-ethyl-N-(2-hydroxyethyl)-amino]-propyl | —Cl |
| 1.667 | 3-[N-ethyl-N-(2-hydroxyethyl)-amino]-propyl | —OCH$_2$CH$_2$OCH$_3$ |
| 1.668 | 3-[N-ethyl-N-(2-hydroxyethyl)-amino]-propyl | cyclopropylmethoxy |
| 1.669 | 3-[N-ethyl-N-(2-hydroxyethyl)-amino]-propyl | trifluoromethyl |
| 1.670 | 3-[N-ethyl-N-(2-hydroxyethyl)-amino]-propyl | difluoromethoxy |
| 1.671 | 3-[N-ethyl-N-(2-hydroxyethyl)-amino]-propyl | trifluoromethoxy |
| 1.672 | 3-[N-ethyl-N-(2-methoxyethyl)-amino]-propyl | —CH$_3$ |
| 1.673 | 3-[N-ethyl-N-(2-methoxyethyl)-amino]-propyl | —Br |
| 1.674 | 3-[N-ethyl-N-(2-methoxyethyl)-amino]-propyl | —F |
| 1.675 | 3-[N-ethyl-N-(2-methoxyethyl)-amino]-propyl | —OCH$_3$ |
| 1.676 | 3-[N-ethyl-N-(2-methoxyethyl)-amino]-propyl | —OCH$_2$CH$_3$ |
| 1.677 | 3-[N-ethyl-N-(2-methoxyethyl)-amino]-propyl | —Cl |
| 1.678 | 3-[N-ethyl-N-(2-methoxyethyl)-amino]-propyl | —OCH$_2$CH$_2$OCH$_3$ |
| 1.679 | 3-[N-ethyl-N-(2-methoxyethyl)-amino]-propyl | cyclopropylmethoxy |
| 1.680 | 3-[N-ethyl-N-(2-methoxyethyl)-amino]-propyl | trifluoromethyl |
| 1.681 | 3-[N-ethyl-N-(2-methoxyethyl)-amino]-propyl | difluoromethoxy |
| 1.682 | 3-[N-ethyl-N-(2-methoxyethyl)-amino]-propyl | trifluoromethoxy |
| 1.683 | 3-(piperidin-1-yl)-propyl | —CH$_3$ |
| 1.684 | 3-(piperidin-1-yl)-propyl | —Br |
| 1.685 | 3-(piperidin-1-yl)-propyl | —F |
| 1.686 | 3-(piperidin-1-yl)-propyl | —OCH$_3$ |
| 1.687 | 3-(piperidin-1-yl)-propyl | —OCH$_2$CH$_3$ |
| 1.688 | 3-(piperidin-1-yl)-propyl | —Cl |
| 1.689 | 3-(piperidin-1-yl)-propyl | —OCH$_2$CH$_2$OCH$_3$ |
| 1.690 | 3-(piperidin-1-yl)-propyl | cyclopropylmethoxy |
| 1.691 | 3-(piperidin-1-yl)-propyl | trifluoromethyl |
| 1.692 | 3-(piperidin-1-yl)-propyl | difluoromethoxy |
| 1.693 | 3-(piperidin-1-yl)-propyl | trifluoromethoxy |
| 1.694 | 3-(homopiperidin-1-yl)-propyl | —CH$_3$ |
| 1.695 | 3-(homopiperidin-1-yl)-propyl | —Br |
| 1.696 | 3-(homopiperidin-1-yl)-propyl | —F |
| 1.697 | 3-(homopiperidin-1-yl)-propyl | —OCH$_3$ |
| 1.698 | 3-(homopiperidin-1-yl)-propyl | —OCH$_2$CH$_3$ |

TABLE 1-continued

| No. | R1 | R5 |
|---|---|---|
| 1.699 | 3-(homopiperidin-1-yl)-propyl | —Cl |
| 1.700 | 3-(homopiperidin-1-yl)-propyl | —OCH$_2$CH$_2$OCH$_3$ |
| 1.701 | 3-(homopiperidin-1-yl)-propyl | cyclopropylmethoxy |
| 1.702 | 3-(homopiperidin-1-yl)-propyl | trifluoromethyl |
| 1.703 | 3-(homopiperidin-1-yl)-propyl | difluoromethoxy |
| 1.704 | 3-(homopiperidin-1-yl)-propyl | trifluoromethoxy |
| 1.705 | 3-(2,5-dihydropyrrol-1-yl)-propyl | —CH$_3$ |
| 1.706 | 3-(2,5-dihydropyrrol-1-yl)-propyl | —Br |
| 1.707 | 3-(2,5-dihydropyrrol-1-yl)-propyl | —F |
| 1.708 | 3-(2,5-dihydropyrrol-1-yl)-propyl | —OCH$_3$ |
| 1.709 | 3-(2,5-dihydropyrrol-1-yl)-propyl | —OCH$_2$CH$_3$ |
| 1.710 | 3-(2,5-dihydropyrrol-1-yl)-propyl | —Cl |
| 1.711 | 3-(2,5-dihydropyrrol-1-yl)-propyl | —OCH$_2$CH$_2$OCH$_3$ |
| 1.712 | 3-(2,5-dihydropyrrol-1-yl)-propyl | cyclopropylmethoxy |
| 1.713 | 3-(2,5-dihydropyrrol-1-yl)-propyl | trifluoromethyl |
| 1.714 | 3-(2,5-dihydropyrrol-1-yl)-propyl | difluoromethoxy |
| 1.715 | 3-(2,5-dihydropyrrol-1-yl)-propyl | trifluoromethoxy |
| 1.716 | 3-(1,2,3,6-tetrahydropyridin-1-yl)-propyl | —CH$_3$ |
| 1.717 | 3-(1,2,3,6-tetrahydropyridin-1-yl)-propyl | —Br |
| 1.718 | 3-(1,2,3,6-tetrahydropyridin-1-yl)-propyl | —F |
| 1.719 | 3-(1,2,3,6-tetrahydropyridin-1-yl)-propyl | —OCH$_3$ |
| 1.720 | 3-(1,2,3,6-tetrahydropyridin-1-yl)-propyl | —OCH$_2$CH$_3$ |
| 1.721 | 3-(1,2,3,6-tetrahydropyridin-1-yl)-propyl | —Cl |
| 1.722 | 3-(1,2,3,6-tetrahydropyridin-1-yl)-propyl | —OCH$_2$CH$_2$OCH$_3$ |
| 1.723 | 3-(1,2,3,6-tetrahydropyridin-1-yl)-propyl | cyclopropylmethoxy |
| 1.724 | 3-(1,2,3,6-tetrahydropyridin-1-yl)-propyl | trifluoromethyl |
| 1.725 | 3-(1,2,3,6-tetrahydropyridin-1-yl)-propyl | difluoromethoxy |
| 1.726 | 3-(1,2,3,6-tetrahydropyridin-1-yl)-propyl | trifluoromethoxy |
| 1.727 | 2-[N-(2-hydroxyethyl)-amino]-ethyl | —CH$_3$ |
| 1.728 | 2-[N-(2-hydroxyethyl)-amino]-ethyl | —Br |
| 1.729 | 2-[N-(2-hydroxyethyl)-amino]-ethyl | —F |
| 1.730 | 2-[N-(2-hydroxyethyl)-amino]-ethyl | —OCH$_3$ |
| 1.731 | 2-[N-(2-hydroxyethyl)-amino]-ethyl | —OCH$_2$CH$_3$ |
| 1.732 | 2-[N-(2-hydroxyethyl)-amino]-ethyl | —Cl |
| 1.733 | 2-[N-(2-hydroxyethyl)-amino]-ethyl | —OCH$_2$CH$_2$OCH$_3$ |
| 1.734 | 2-[N-(2-hydroxyethyl)-amino]-ethyl | cyclopropylmethoxy |
| 1.735 | 2-[N-(2-hydroxyethyl)-amino]-ethyl | trifluoromethyl |
| 1.736 | 2-[N-(2-hydroxyethyl)-amino]-ethyl | difluoromethoxy |
| 1.737 | 2-[N-(2-hydroxyethyl)-amino]-ethyl | trifluoromethoxy |
| 1.738 | 2-[N-(2-methoxyethyl)-amino]-ethyl | —CH$_3$ |
| 1.739 | 2-[N-(2-methoxyethyl)-amino]-ethyl | —Br |
| 1.740 | 2-[N-(2-methoxyethyl)-amino]-ethyl | —F |
| 1.741 | 2-[N-(2-methoxyethyl)-amino]-ethyl | —OCH$_3$ |
| 1.742 | 2-[N-(2-methoxyethyl)-amino]-ethyl | —OCH$_2$CH$_3$ |
| 1.743 | 2-[N-(2-methoxyethyl)-amino]-ethyl | —Cl |
| 1.744 | 2-[N-(2-methoxyethyl)-amino]-ethyl | —OCH$_2$CH$_2$OCH$_3$ |
| 1.745 | 2-[N-(2-methoxyethyl)-amino]-ethyl | cyclopropylmethoxy |
| 1.746 | 2-[N-(2-methoxyethyl)-amino]-ethyl | trifluoromethyl |
| 1.747 | 2-[N-(2-methoxyethyl)-amino]-ethyl | difluoromethoxy |
| 1.748 | 2-[N-(2-methoxyethyl)-amino]-ethyl | trifluoromethoxy |
| 1.749 | 2-(tertbutylamino)-ethyl | —CH$_3$ |
| 1.750 | 2-(tertbutylamino)-ethyl | —Br |
| 1.751 | 2-(tertbutylamino)-ethyl | —F |
| 1.752 | 2-(tertbutylamino)-ethyl | —OCH$_3$ |
| 1.753 | 2-(tertbutylamino)-ethyl | —OCH$_2$CH$_3$ |
| 1.754 | 2-(tertbutylamino)-ethyl | —Cl |
| 1.755 | 2-(tertbutylamino)-ethyl | —OCH$_2$CH$_2$OCH$_3$ |
| 1.756 | 2-(tertbutylamino)-ethyl | cyclopropylmethoxy |
| 1.757 | 2-(tertbutylamino)-ethyl | trifluoromethyl |
| 1.758 | 2-(tertbutylamino)-ethyl | difluoromethoxy |
| 1.759 | 2-(tertbutylamino)-ethyl | trifluoromethoxy |
| 1.760 | 2-(allylamino)-ethyl | —CH$_3$ |
| 1.761 | 2-(allylamino)-ethyl | —Br |
| 1.762 | 2-(allylamino)-ethyl | —F |
| 1.763 | 2-(allylamino)-ethyl | —OCH$_3$ |
| 1.764 | 2-(allylamino)-ethyl | —OCH$_2$CH$_3$ |
| 1.765 | 2-(allylamino)-ethyl | —Cl |
| 1.766 | 2-(allylamino)-ethyl | —OCH$_2$CH$_2$OCH$_3$ |
| 1.767 | 2-(allylamino)-ethyl | cyclopropylmethoxy |
| 1.768 | 2-(allylamino)-ethyl | trifluoromethyl |
| 1.769 | 2-(allylamino)-ethyl | difluoromethoxy |
| 1.770 | 2-(allylamino)-ethyl | trifluoromethoxy |
| 1.771 | 2-(propargylamino)-ethyl | —CH$_3$ |
| 1.772 | 2-(propargylamino)-ethyl | —Br |
| 1.773 | 2-(propargylamino)-ethyl | —F |
| 1.774 | 2-(propargylamino)-ethyl | —OCH$_3$ |
| 1.775 | 2-(propargylamino)-ethyl | —OCH$_2$CH$_3$ |
| 1.776 | 2-(propargylamino)-ethyl | —Cl |
| 1.777 | 2-(propargylamino)-ethyl | —OCH$_2$CH$_2$OCH$_3$ |
| 1.778 | 2-(propargylamino)-ethyl | cyclopropylmethoxy |
| 1.779 | 2-(propargylamino)-ethyl | trifluoromethyl |
| 1.780 | 2-(propargylamino)-ethyl | difluoromethoxy |
| 1.781 | 2-(propargylamino)-ethyl | trifluoromethoxy |
| 1.782 | 2-(N-allyl-N-methyl-amino)-ethyl | —CH$_3$ |
| 1.783 | 2-(N-allyl-N-methyl-amino)-ethyl | —Br |
| 1.784 | 2-(N-allyl-N-methyl-amino)-ethyl | —F |
| 1.785 | 2-(N-allyl-N-methyl-amino)-ethyl | —OCH$_3$ |
| 1.786 | 2-(N-allyl-N-methyl-amino)-ethyl | —OCH$_2$CH$_3$ |
| 1.787 | 2-(N-allyl-N-methyl-amino)-ethyl | —Cl |
| 1.788 | 2-(N-allyl-N-methyl-amino)-ethyl | —OCH$_2$CH$_2$OCH$_3$ |
| 1.789 | 2-(N-allyl-N-methyl-amino)-ethyl | cyclopropylmethoxy |
| 1.790 | 2-(N-allyl-N-methyl-amino)-ethyl | trifluoromethyl |
| 1.791 | 2-(N-allyl-N-methyl-amino)-ethyl | difluoromethoxy |
| 1.792 | 2-(N-allyl-N-methyl-amino)-ethyl | trifluoromethoxy |
| 1.793 | 2-(N-methyl-N-propargyl-amino)-ethyl | —CH$_3$ |
| 1.794 | 2-(N-methyl-N-propargyl-amino)-ethyl | —Br |
| 1.795 | 2-(N-methyl-N-propargyl-amino)-ethyl | —F |
| 1.796 | 2-(N-methyl-N-propargyl-amino)-ethyl | —OCH$_3$ |
| 1.797 | 2-(N-methyl-N-propargyl-amino)-ethyl | —OCH$_2$CH$_3$ |
| 1.798 | 2-(N-methyl-N-propargyl-amino)-ethyl | —Cl |
| 1.799 | 2-(N-methyl-N-propargyl-amino)-ethyl | —OCH$_2$CH$_2$OCH$_3$ |
| 1.800 | 2-(N-methyl-N-propargyl-amino)-ethyl | cyclopropylmethoxy |
| 1.801 | 2-(N-methyl-N-propargyl-amino)-ethyl | trifluoromethyl |
| 1.802 | 2-(N-methyl-N-propargyl-amino)-ethyl | difluoromethoxy |
| 1.803 | 2-(N-methyl-N-propargyl-amino)-ethyl | trifluoromethoxy |
| 1.804 | 2-[N-(2-hydroxyethyl)-N-methyl-amino]-ethyl | —CH$_3$ |
| 1.805 | 2-[N-(2-hydroxyethyl)-N-methyl-amino]-ethyl | —Br |
| 1.806 | 2-[N-(2-hydroxyethyl)-N-methyl-amino]-ethyl | —F |
| 1.807 | 2-[N-(2-hydroxyethyl)-N-methyl-amino]-ethyl | —OCH$_3$ |
| 1.808 | 2-[N-(2-hydroxyethyl)-N-methyl-amino]-ethyl | —OCH$_2$CH$_3$ |
| 1.809 | 2-[N-(2-hydroxyethyl)-N-methyl-amino]-ethyl | —Cl |
| 1.810 | 2-[N-(2-hydroxyethyl)-N-methyl-amino]-ethyl | —OCH$_2$CH$_2$OCH$_3$ |
| 1.811 | 2-[N-(2-hydroxyethyl)-N-methyl-amino]-ethyl | cyclopropylmethoxy |
| 1.812 | 2-[N-(2-hydroxyethyl)-N-methyl-amino]-ethyl | trifluoromethyl |
| 1.813 | 2-[N-(2-hydroxyethyl)-N-methyl-amino]-ethyl | difluoromethoxy |
| 1.814 | 2-[N-(2-hydroxyethyl)-N-methyl-amino]-ethyl | trifluoromethoxy |
| 1.815 | 2-[N-(2-methoxyethyl)-N-methyl-amino]-ethyl | —CH$_3$ |
| 1.816 | 2-[N-(2-methoxyethyl)-N-methyl-amino]-ethyl | —Br |
| 1.817 | 2-[N-(2-methoxyethyl)-N-methyl-amino]-ethyl | —F |
| 1.818 | 2-[N-(2-methoxyethyl)-N-methyl-amino]-ethyl | —OCH$_3$ |
| 1.819 | 2-[N-(2-methoxyethyl)-N-methyl-amino]-ethyl | —OCH$_2$CH$_3$ |
| 1.820 | 2-[N-(2-methoxyethyl)-N-methyl-amino]-ethyl | —Cl |
| 1.821 | 2-[N-(2-methoxyethyl)-N-methyl-amino]-ethyl | —OCH$_2$CH$_2$OCH$_3$ |
| 1.822 | 2-[N-(2-methoxyethyl)-N-methyl-amino]-ethyl | cyclopropylmethoxy |
| 1.823 | 2-[N-(2-methoxyethyl)-N-methyl-amino]-ethyl | trifluoromethyl |
| 1.824 | 2-[N-(2-methoxyethyl)-N-methyl-amino]-ethyl | difluoromethoxy |
| 1.825 | 2-[N-(2-methoxyethyl)-N-methyl-amino]-ethyl | trifluoromethoxy |
| 1.826 | 2-[N-ethyl-N-(2-hydroxyethyl)-amino]-ethyl | —CH$_3$ |
| 1.827 | 2-[N-ethyl-N-(2-hydroxyethyl)-amino]-ethyl | —Br |
| 1.828 | 2-[N-ethyl-N-(2-hydroxyethyl)-amino]-ethyl | —F |

TABLE 1-continued

| No. | R1 | R5 |
|---|---|---|
| 1.829 | 2-[N-ethyl-N-(2-hydroxyethyl)-amino]-ethyl | —OCH₃ |
| 1.830 | 2-[N-ethyl-N-(2-hydroxyethyl)-amino]-ethyl | —OCH₂CH₃ |
| 1.831 | 2-[N-ethyl-N-(2-hydroxyethyl)-amino]-ethyl | —Cl |
| 1.832 | 2-[N-ethyl-N-(2-hydroxyethyl)-amino]-ethyl | —OCH₂CH₂OCH₃ |
| 1.833 | 2-[N-ethyl-N-(2-hydroxyethyl)-amino]-ethyl | cyclopropylmethoxy |
| 1.834 | 2-[N-ethyl-N-(2-hydroxyethyl)-amino]-ethyl | trifluoromethyl |
| 1.835 | 2-[N-ethyl-N-(2-hydroxyethyl)-amino]-ethyl | difluoromethoxy |
| 1.836 | 2-[N-ethyl-N-(2-hydroxyethyl)-amino]-ethyl | trifluoromethoxy |
| 1.837 | 2-[N-ethyl-N-(2-methoxyethyl)-amino]-ethyl | —CH₃ |
| 1.838 | 2-[N-ethyl-N-(2-methoxyethyl)-amino]-ethyl | —Br |
| 1.839 | 2-[N-ethyl-N-(2-methoxyethyl)-amino]-ethyl | —F |
| 1.840 | 2-[N-ethyl-N-(2-methoxyethyl)-amino]-ethyl | —OCH₃ |
| 1.841 | 2-[N-ethyl-N-(2-methoxyethyl)-amino]-ethyl | —OCH₂CH₃ |
| 1.842 | 2-[N-ethyl-N-(2-methoxyethyl)-amino]-ethyl | —Cl |
| 1.843 | 2-[N-ethyl-N-(2-methoxyethyl)-amino]-ethyl | —OCH₂CH₂OCH₃ |
| 1.844 | 2-[N-ethyl-N-(2-methoxyethyl)-amino]-ethyl | cyclopropylmethoxy |
| 1.845 | 2-[N-ethyl-N-(2-methoxyethyl)-amino]-ethyl | trifluoromethyl |
| 1.846 | 2-[N-ethyl-N-(2-methoxyethyl)-amino]-ethyl | difluoromethoxy |
| 1.847 | 2-[N-ethyl-N-(2-methoxyethyl)-amino]-ethyl | trifluoromethoxy |
| 1.848 | 2-(piperidin-1-yl)-ethyl | —CH₃ |
| 1.849 | 2-(piperidin-1-yl)-ethyl | —Br |
| 1.850 | 2-(piperidin-1-yl)-ethyl | —F |
| 1.851 | 2-(piperidin-1-yl)-ethyl | —OCH₃ |
| 1.852 | 2-(piperidin-1-yl)-ethyl | —OCH₂CH₃ |
| 1.853 | 2-(piperidin-1-yl)-ethyl | —Cl |
| 1.854 | 2-(piperidin-1-yl)-ethyl | —OCH₂CH₂OCH₃ |
| 1.855 | 2-(piperidin-1-yl)-ethyl | cyclopropylmethoxy |
| 1.856 | 2-(piperidin-1-yl)-ethyl | trifluoromethyl |
| 1.857 | 2-(piperidin-1-yl)-ethyl | difluoromethoxy |
| 1.858 | 2-(piperidin-1-yl)-ethyl | trifluoromethoxy |
| 1.859 | 2-(homopiperidin-1-yl)-ethyl | —CH₃ |
| 1.860 | 2-(homopiperidin-1-yl)-ethyl | —Br |
| 1.861 | 2-(homopiperidin-1-yl)-ethyl | —F |
| 1.862 | 2-(homopiperidin-1-yl)-ethyl | —OCH₃ |
| 1.863 | 2-(homopiperidin-1-yl)-ethyl | —OCH₂CH₃ |
| 1.864 | 2-(homopiperidin-1-yl)-ethyl | —Cl |
| 1.865 | 2-(homopiperidin-1-yl)-ethyl | —OCH₂CH₂OCH₃ |
| 1.866 | 2-(homopiperidin-1-yl)-ethyl | cyclopropylmethoxy |
| 1.867 | 2-(homopiperidin-1-yl)-ethyl | trifluoromethyl |
| 1.868 | 2-(homopiperidin-1-yl)-ethyl | difluoromethoxy |
| 1.869 | 2-(homopiperidin-1-yl)-ethyl | trifluoromethoxy |
| 1.870 | 2-(2,5-dihydropyrrol-1-yl)-ethyl | —CH₃ |
| 1.871 | 2-(2,5-dihydropyrrol-1-yl)-ethyl | —Br |
| 1.872 | 2-(2,5-dihydropyrrol-1-yl)-ethyl | —F |
| 1.873 | 2-(2,5-dihydropyrrol-1-yl)-ethyl | —OCH₃ |
| 1.874 | 2-(2,5-dihydropyrrol-1-yl)-ethyl | —OCH₂CH₃ |
| 1.875 | 2-(2,5-dihydropyrrol-1-yl)-ethyl | —Cl |
| 1.876 | 2-(2,5-dihydropyrrol-1-yl)-ethyl | —OCH₂CH₂OCH₃ |
| 1.877 | 2-(2,5-dihydropyrrol-1-yl)-ethyl | cyclopropylmethoxy |
| 1.878 | 2-(2,5-dihydropyrrol-1-yl)-ethyl | trifluoromethyl |
| 1.879 | 2-(2,5-dihydropyrrol-1-yl)-ethyl | difluoromethoxy |
| 1.880 | 2-(2,5-dihydropyrrol-1-yl)-ethyl | trifluoromethoxy |
| 1.881 | 2-(1,2,3,6-tetrahydropyridin-1-yl)-ethyl | —CH₃ |
| 1.882 | 2-(1,2,3,6-tetrahydropyridin-1-yl)-ethyl | —Br |
| 1.883 | 2-(1,2,3,6-tetrahydropyridin-1-yl)-ethyl | —F |
| 1.884 | 2-(1,2,3,6-tetrahydropyridin-1-yl)-ethyl | —OCH₃ |
| 1.885 | 2-(1,2,3,6-tetrahydropyridin-1-yl)-ethyl | —OCH₂CH₃ |
| 1.886 | 2-(1,2,3,6-tetrahydropyridin-1-yl)-ethyl | —Cl |
| 1.887 | 2-(1,2,3,6-tetrahydropyridin-1-yl)-ethyl | —OCH₂CH₂OCH₃ |
| 1.888 | 2-(1,2,3,6-tetrahydropyridin-1-yl)-ethyl | cyclopropylmethoxy |
| 1.889 | 2-(1,2,3,6-tetrahydropyridin-1-yl)-ethyl | trifluoromethyl |
| 1.890 | 2-(1,2,3,6-tetrahydropyridin-1-yl)-ethyl | difluoromethoxy |
| 1.891 | 2-(1,2,3,6-tetrahydropyridin-1-yl)-ethyl | trifluoromethoxy |

Exemplary compounds according to the present invention may include, without being restricted thereto, any compound selected from 1. (3aS,10R)-6-Ethoxy-10-(3-hydroxy-phenyl)-2,3a-dimethyl-3a,4,9,10-tetrahydro-2,9,10a-triaza-cyclopenta[b]fluorene-1,3-dione
2. (3aS,10R)-10-(3-Hydroxy-phenyl)-6-(2-methoxy-ethoxy)-2,3a-dimethyl-3a,4,9,10-tetrahydro-2,9,10a-triaza-cyclopenta[b]fluorene-1,3-dione
3. (3aS,10R)-10-(3-Hydroxy-phenyl)-6-methoxy-2,3a-dimethyl-3a,4,9,10-tetrahydro-2,9,10a-triaza-cyclopenta[b]fluorene-1,3-dione
4. (3aS,10R)-6-Bromo-10-(3-hydroxy-phenyl)-2,3a-dimethyl-3a,4,9,10-tetrahydro-2,9,10a-triaza-cyclopenta[b]fluorene-1,3-dione
5. (3aS,10R)-6-Chloro-10-(3-hydroxy-phenyl)-2,3a-dimethyl-3a,4,9,10-tetrahydro-2,9,10a-triaza-cyclopenta[b]fluorene-1,3-dione
6. (3aS,10R)-2-(2-Dimethylamino-ethyl)-10-(3-hydroxyphenyl)-6-(2-methoxy-ethoxy)-3a-methyl-3a,4,9,10-tetrahydro-2,9,10a-triaza-cyclopenta[b]fluorene-1,3-dione
7. (3aS,10R)-2-(2-Dimethylamino-ethyl)-10-(3-hydroxyphenyl)-6-methoxy-3a-methyl-3a,4,9,10-tetrahydro-2,9,10a-triaza-cyclopenta[b]fluorene-1,3-dione
8. (3aS,10R)-6-Bromo-2-(2-dimethylamino-ethyl)-10-(3-hydroxy-phenyl)-3a-methyl-3a,4,9,10-tetrahydro-2,9,10a-triaza-cyclopenta[b]fluorene-1,3-dione
9. (3aS,10R)-6-Chloro-2-(2-dimethylamino-ethyl)-10-(3-hydroxy-phenyl)-3a-methyl-3a,4,9,10-tetrahydro-2,9,10a-triaza-cyclopenta[b]fluorene-1,3-dione
10. (3aS,10R)-10-(3-Hydroxy-phenyl)-6-methoxy-3a-methyl-2-(2-morpholin-4-yl-ethyl)-3a,4,9,10-tetrahydro-2,9,10a-triaza-cyclopenta[b]fluorene-1,3-dione
11. (3aS,10R)-10-(3-Hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione
12. (3aS,10R)-10-(3-Hydroxy-phenyl)-6-methoxy-3a-methyl-2-[2-(4-methyl-piperazin-1-yl)-ethyl]-3a,4,9,10-tetrahydro-2,9,10a-triaza-cyclopenta[b]fluorene-1,3-dione
13. (3aS,10R)-10-(3-Hydroxy-phenyl)-2-(2-imidazol-1-ylethyl)-6-methoxy-3a-methyl-3a,4,9,10-tetrahydro-2,9,10a-triaza-cyclopenta[b]fluorene-1,3-dione
14. (3aS,10R)-2-(4-Dimethylamino-butyl)-10-(3-hydroxyphenyl)-6-methoxy-3a-methyl-3a,4,9,10-tetrahydro-2,9,10a-triaza-cyclopenta[b]fluorene-1,3-dione
15. (3aS,10R)-2-(3-Dimethylamino-propyl)-10-(3-hydroxyphenyl)-6-methoxy-3a-methyl-3a,4,9,10-tetrahydro-2,9,10a-triaza-cyclopenta[b]fluorene-1,3-dione
16. (3aS,10R)-6-Chloro-2-(3-dimethylamino-propyl)-10-(3-hydroxy-phenyl)-3a-methyl-3a,4,9,10-tetrahydro-2,9,10a-triaza-cyclopenta[b]fluorene-1,3-dione
17. (3aS,10R)-6-Chloro-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione
18. (3aS,10R)-2-(2-Dimethylamino-ethyl)-3a-ethyl-10-(3-hydroxy-phenyl)-6-methoxy-3a,4,9,10-tetrahydro-2,9,10a-triaza-cyclopenta[b]fluorene-1,3-dione 19. (3aS,10R)-2-(3-Dimethylamino-propyl)-3a-ethyl-10-(3-hydroxy-phenyl)-6-methoxy-3a,4,9,10-tetrahydro-2,9,10a-triaza-cyclopenta[b]fluorene-1,3-dione
20. (3aS,10R)-10-(3-Hydroxy-phenyl)-2-(3-imidazol-1-yl-propyl)-6-methoxy-3a-methyl-3a,4,9,10-tetrahydro-2,9,10a-triaza-cyclopenta[b]fluorene-1,3-dione
21. (3aS,10R)-6-Cyclopropylmethoxy-10-(3-hydroxy-phenyl)-2,3a-dimethyl-3a,4,9,10-tetrahydro-2,9,10a-triaza-cyclopenta[b]fluorene-1,3-dione
22. (3aS,10R)-2-(2-Bromo-ethyl)-6-ethoxy-10-(3-hydroxy-phenyl)-3a-methyl-3a,4,9,10-tetrahydro-2,9,10a-triaza-cyclopenta[b]fluorene-1,3-dione
23. (3aS,10R)-2-(2-Dimethylamino-ethyl)-6-ethoxy-10-(3-hydroxy-phenyl)-3a-methyl-3a,4,9,10-tetrahydro-2,9,10a-triaza-cyclopenta[b]fluorene-1,3-dione
24. (3aS,10R)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione
25. (3aS,10R)-2-(2-Amino-ethyl)-10-(3-hydroxy-phenyl)-6-methoxy-3a-methyl-3a,4,9,10-tetrahydro-2,9,10a-triaza-cyclopenta[b]fluorene-1,3-dione
26. (3aS,10R)-2-(2-Bromo-ethyl)-6-chloro-10-(3-hydroxy-phenyl)-3a-methyl-3a,4,9,10-tetrahydro-2,9,10a-triaza-cyclopenta[b]fluorene-1,3-dione
27. (3aS,10R)-1'-(3-Hydroxy-phenyl)-6-methoxy-3a-methyl-2-(2-methylamino-ethyl)-3a,4,9,10-tetrahydro-2,9,10a-triaza-cyclopenta[b]fluorene-1,3-dione
28. (3aS,10R)-6-Chloro-10-(3-hydroxy-phenyl)-3a-methyl-2-(2-methylamino-ethyl)-3a,4,9,10-tetrahydro-2,9,10a-triaza-cyclopenta[b]fluorene-1,3-dione
29. (3aS,10R)-2-(2-Azetidin-1-yl-ethyl)-6-chloro-10-(3-hydroxy-phenyl)-3a-methyl-3a,4,9,10-tetrahydro-2,9,10a-triaza-cyclopenta[b]fluorene-1,3-dione
30. (3aS,10R)-2-(2-Amino-ethyl)-6-chloro-10-(3-hydroxy-phenyl)-3a-methyl-3a,4,9,10-tetrahydro-2,9,10a-triaza-cyclopenta[b]fluorene-1,3-dione
31. (3aS,10R)-6-Chloro-10-(3-hydroxy-phenyl)-2-(2-imidazol-1-yl-ethyl)-3a-methyl-3a,4,9,10-tetrahydro-2,9,10a-triaza-cyclopenta[b]fluorene-1,3-dione
32. (3aS,10R)-2-[2-(4-Acetyl-piperazin-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione
33. (3aS,10R)-2-(2-Azetidin-1-yl-ethyl)-10-(3-hydroxy-phenyl)-6-methoxy-3a-methyl-3a,4,9,10-tetrahydro-2,9,10a-triaza-cyclopenta[b]fluorene-1,3-dione
34. (3aS,10R)-2-[2-(3,3-Difluoro-pyrrolidin-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione
35. (3aS,10R)-2-(2-Ethylamino-ethyl)-10-(3-hydroxy-phenyl)-6-methoxy-3a-methyl-3a,4,9,10-tetrahydro-2,9,10a-triaza-cyclopenta[b]fluorene-1,3-dione
36. (3aS,10R)-2-(2-Bromo-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
37. (3aS,10R)-6-Chloro-2-(2-ethylamino-ethyl)-10-(3-hydroxy-phenyl)-3a-methyl-3a,4,9,10-tetrahydro-2,9,10a-triaza-cyclopenta[b]fluorene-1,3-dione
38. (3aS,10R)-6-Chloro-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione
39. (3aS,10R)-6-Chloro-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione
40. (3aS,10R)-6-Chloro-2-[2-(ethyl-methyl-amino)-ethyl]-10-(3-hydroxy-phenyl)-3a-methyl-3a,4,9,10-tetrahydro-2,9,10a-triaza-cyclopenta[b]fluorene-1,3-dione
41. (3aS,10R)-6-Ethoxy-10-(3-hydroxy-phenyl)-3a-methyl-2-(2-methylamino-ethyl)-3a,4,9,10-tetrahydro-2,9,10a-triaza-cyclopenta[b]fluorene-1,3-dione
42. (3aS,10R)-6-(1,1-Difluoro-methoxy)-10-(3-hydroxy-phenyl)-3a-methyl-2-(2-methylamino-ethyl)-3a,4,9,10-tetrahydro-2,9,10a-triaza-cyclopenta[b]fluorene-1,3-dione
43. (3aS,10R)-6-(1,1-Difluoro-methoxy)-2-(2-dimethylamino-ethyl)-10-(3-hydroxy-phenyl)-3a-methyl-3a,4,9,10-tetrahydro-2,9,10a-triaza-cyclopenta[b]fluorene-1,3-dione
44. (3aS,10R)-2-(2-Azetidin-1-yl-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
45. (3aS,10R)-2-(2-Amino-ethyl)-6-ethoxy-10-(3-hydroxy-phenyl)-3a-methyl-3a,4,9,10-tetrahydro-2,9,10a-triaza-cyclopenta[b]fluorene-1,3-dione
46. (3aS,10R)-2-(2-Azetidin-1-yl-ethyl)-6-ethoxy-10-(3-hydroxy-phenyl)-3a-methyl-3a,4,9,10-tetrahydro-2,9,10a-triaza-cyclopenta[b]fluorene-1,3-dione
47. (3aS,10R)-1'-(3-Hydroxy-phenyl)-2-(2-isopropylamino-ethyl)-6-methoxy-3a-methyl-3a,4,9,10-tetrahydro-2,9,10a-triaza-cyclopenta[b]fluorene-1,3-dione
48. (3aS,10R)-2-[2-(Cyclopropylmethyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione
49. (3aS,10R)-10-(3-Hydroxy-phenyl)-2-(2-isobutylamino-ethyl)-6-methoxy-3a-methyl-3a,4,9,10-tetrahydro-2,9,10a-triaza-cyclopenta[b]fluorene-1,3-dione
50. (3aS,10R)-2-(2-Cyclobutylamino-ethyl)-10-(3-hydroxy-phenyl)-6-methoxy-3a-methyl-3a,4,9,10-tetrahydro-2,9,10a-triaza-cyclopenta[b]fluorene-1,3-dione
51. (3aS,10R)-2-(3-Ethylamino-propyl)-10-(3-hydroxy-phenyl)-6-methoxy-3a-methyl-3a,4,9,10-tetrahydro-2,9,10a-triaza-cyclopenta[b]fluorene-1,3-dione
52. (3aS,10R)-2-[2-(Ethyl-methyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione and
53. (3aS,10R)-2-(2-Cyclopropylamino-ethyl)-10-(3-hydroxy-phenyl)-6-methoxy-3a-methyl-3a,4,9,10-tetrahydro-2,9,10a-triaza-cyclopenta[b]fluorene-1,3-dione,
and the salts thereof.

Other exemplary compounds according to the present invention may include, without being restricted thereto, any compound selected from 54. (3aS,10R)-6-Bromo-2-(2-bromo-ethyl)-10-(3-hydroxy-phenyl)-3a-methyl-3a,4,9,10-tetrahydro-2,9,10a-triaza-cyclopenta[b]fluorene-1,3-dione
55. (3aS,10R)-2-(3-Chloro-propyl)-10-(3-hydroxy-phenyl)-6-methoxy-3a-methyl-3a,4,9,10-tetrahydro-2,9,10a-triaza-cyclopenta[b]fluorene-1,3-dione
56. (3aS,10R)-2-(3-Chloro-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
57. (3aS,10R)-6-Chloro-2-(3-chloro-propyl)-10-(3-hydroxy-phenyl)-3a-methyl-3a,4,9,10-tetrahydro-2,9,10a-triaza-cyclopenta[b]fluorene-1,3-dione
58. (3aS,10R)-6-Bromo-2-(3-chloro-propyl)-10-(3-hydroxy-phenyl)-3a-methyl-3a,4,9,10-tetrahydro-2,9,10a-triaza-cyclopenta[b]fluorene-1,3-dione
59. (3aS,10R)-2-(3-Chloro-propyl)-6-ethoxy-10-(3-hydroxy-phenyl)-3a-methyl-3a,4,9,10-tetrahydro-2,9,10a-triaza-cyclopenta[b]fluorene-1,3-dione
60. (3aS,10R)-2-(2-Bromo-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 61. (3aS,10R)-2-(2-Bromo-ethyl)-6-chloro-7-fluoro-10-(3-hydroxy-phenyl)-3a-methyl-3a,4,9,10-tetrahydro-2,9,10a-triaza-cyclopenta[b]fluorene-1,3-dione
62. (3aS,10R)-2-(2-Bromo-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
63. (3aS,10R)-2-(3-Chloro-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
64. (3aS,10R)-6-Chloro-2-(3-chloro-propyl)-7-fluoro-10-(3-hydroxy-phenyl)-3a-methyl-3a,4,9,10-tetrahydro-2,9,10a-triaza-cyclopenta[b]fluorene-1,3-dione
65. (3aS,10R)-2-(3-Chloro-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
66. (3aS,10R)-2-(2-Dimethylamino-ethyl)-6-hydroxy-10-(3-hydroxy-phenyl)-3a-methyl-3a,4,9,10-tetrahydro-2,9,10a-triaza-cyclopenta[b]fluorene-1,3-dione
67. (3aS,10R)-10-(3-Hydroxy-phenyl)-2-(3-isopropylamino-propyl)-6-methoxy-3a-methyl-3a,4,9,10-tetrahydro-2,9,10a-triaza-cyclopenta[b]fluorene-1,3-dione
68. (3aS,10R)-2-[2-(3,6-Dihydro-2H-pyridin-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione
69. (3aS,10R)-2-(2-Diethylamino-ethyl)-10-(3-hydroxy-phenyl)-6-methoxy-3a-methyl-3a,4,9,10-tetrahydro-2,9,10a-triaza-cyclopenta[b]fluorene-1,3-dione
70. (3aS,10R)-10-(3-Hydroxy-phenyl)-2-[2-(isopropyl-methyl-amino)-ethyl]-6-methoxy-3a-methyl-3a,4,9,10-tetrahydro-2,9,10a-triaza-cyclopenta[b]fluorene-1,3-dione
71. (3aS,10R)-10-(3-Hydroxy-phenyl)-6-methoxy-3a-methyl-2-(2-piperidin-1-yl-ethyl)-3a,4,9,10-tetrahydro-2,9,10a-triaza-cyclopenta[b]fluorene-1,3-dione
72. (3aS,10R)-2-(2-tert-Butylamino-ethyl)-10-(3-hydroxy-phenyl)-6-methoxy-3a-methyl-3a,4,9,10-tetrahydro-2,9,10a-triaza-cyclopenta[b]fluorene-1,3-dione
73. (3aS,10R)-2-[2-(2,2-Difluoro-ethylamino)-ethyl]-10-(3-hydroxy-phenyl)-6-methoxy-3a-methyl-3a,4,9,10-tetrahydro-2,9,10a-triaza-cyclopenta[b]fluorene-1,3-dione
74. (3aS,10R)-2-(2-Azepan-1-yl-ethyl)-10-(3-hydroxy-phenyl)-6-methoxy-3a-methyl-3a,4,9,10-tetrahydro-2,9,10a-triaza-cyclopenta[b]fluorene-1,3-dione
75. (3aS,10R)-10-(3-Hydroxy-phenyl)-6-methoxy-3a-methyl-2-[2-(4-methyl-piperidin-1-yl)-ethyl]-3a,4,9,10-tetrahydro-2,9,10a-triaza-cyclopenta[b]fluorene-1,3-dione
76. (3aS,10R)-10-(3-Hydroxy-phenyl)-6-methoxy-3a-methyl-2-(3-methylamino-propyl)-3a,4,9,10-tetrahydro-2,9,10a-triaza-cyclopenta[b]fluorene-1,3-dione
77. (3aS,10R)-2-[3-(Ethyl-methyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione
78. (3aS,10R)-2-{2-[Ethyl-(2-hydroxy-ethyl)-amino]-ethyl}-10-(3-hydroxy-phenyl)-6-methoxy-3a-methyl-3a,4,9,10-tetrahydro-2,9,10a-triaza-cyclopenta[b]fluorene-1,3-dione
79. (3aS,10R)-2-{2-[Ethyl-(2-methoxy-ethyl)-amino]-ethyl}-10-(3-hydroxy-phenyl)-6-methoxy-3a-methyl-3a,4,9,10-tetrahydro-2,9,10a-triaza-cyclopenta[b]fluorene-1,3-dione
80. (3aS,10R)-2-[2-(Allyl-methyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione
81. (3aS,10R)-10-(3-Hydroxy-phenyl)-6-methoxy-3a-methyl-2-[2-(methyl-prop-2-ynyl-amino)-ethyl]-3a,4,9,10-tetrahydro-2,9,10a-triaza-cyclopenta[b]fluorene-1,3-dione
82. (3aS,10R)-2-[2-(2-Hydroxy-ethylamino)-ethyl]-10-(3-hydroxy-phenyl)-6-methoxy-3a-methyl-3a,4,9,10-tetrahydro-2,9,10a-triaza-cyclopenta[b]fluorene-1,3-dione
83. (3aS,10R)-10-(3-Hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione
84. (3aS,10R)-2-(2-Allylamino-ethyl)-10-(3-hydroxy-phenyl)-6-methoxy-3a-methyl-3a,4,9,10-tetrahydro-2,9,10a-triaza-cyclopenta[b]fluorene-1,3-dione
85. (3aS,10R)-10-(3-Hydroxy-phenyl)-6-methoxy-3a-methyl-2-(2-prop-2-ynylamino-ethyl)-3a,4,9,110-tetrahydro-2,9,10a-triaza-cyclopenta[b]fluorene-1,3-dione
86. (3aS,10R)-2-(3-Cyclobutylamino-propyl)-10-(3-hydroxy-phenyl)-6-methoxy-3a-methyl-3a,4,9,10-tetrahydro-2,9,10a-triaza-cyclopenta[b]fluorene-1,3-dione
87. (3aS,10R)-2-(3-Azetidin-1-yl-propyl)-10-(3-hydroxy-phenyl)-6-methoxy-3a-methyl-3a,4,9,10-tetrahydro-2,9,10a-triaza-cyclopenta[b]fluorene-1,3-dione
88. (3aS,10R)-2-[3-(Allyl-methyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione
89. (3aS,10R)-2-{3-[Ethyl-(2-hydroxy-ethyl)-amino]-propyl}-10-(3-hydroxy-phenyl)-6-methoxy-3a-methyl-3a,4,9,10-tetrahydro-2,9,10a-triaza-cyclopenta[b]fluorene-1,3-dione
90. (3aS,10R)-2-{3-[Ethyl-(2-methoxy-ethyl)-amino]-propyl}-10-(3-hydroxy-phenyl)-6-methoxy-3a-methyl-3a,4,9,10-tetrahydro-2,9,10a-triaza-cyclopenta[b]fluorene-1,3-dione
91. (3aS,10R)-10-(3-Hydroxy-phenyl)-6-methoxy-3a-methyl-2-[2-(1-methyl-1H-pyrazol-3-ylamino)ethyl]-3a,4,9,10-tetrahydro-2,9,10a-triaza-cyclopenta[b]fluorene-1,3-dione
92. (3aS,10R)-10-(3-Hydroxy-phenyl)-2-(3-isobutylamino-propyl)-6-methoxy-3a-methyl-3a,4,9,10-tetrahydro-2,9,10a-triaza-cyclopenta[b]fluorene-1,3-dione
93. (3aS,10R)-2-(3-Cyclopropylamino-propyl)-10-(3-hydroxy-phenyl)-6-methoxy-3a-methyl-3a,4,9,10-tetrahydro-2,9,10a-triaza-cyclopenta[b]fluorene-1,3-dione
94. (3aS,10R)-10-(3-Hydroxy-phenyl)-2-[3-(isopropyl-methyl-amino)-propyl]-6-methoxy-3a-methyl-3a,4,9,10-tetrahydro-2,9,10a-triaza-cyclopenta[b]fluorene-1,3-dione
95. (3aS,10R)-2-[3-(Cyclopropylmethyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione
96. (3aS,10R)-10-(3-Hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione
97. (3aS,10R)-2-(2-tert-Butylamino-ethyl)-6-chloro-10-(3-hydroxy-phenyl)-3a-methyl-3a,4,9,10-tetrahydro-2,9,10a-triaza-cyclopenta[b]fluorene-1,3-dione
98. (3aS,10R)-6-Chloro-10-(3-hydroxy-phenyl)-3a-methyl-2-[2-(4-methyl-piperidin-1-yl)-ethyl]-3a,4,9,10-tetrahydro-2,9,10a-triaza-cyclopenta[b]fluorene-1,3-dione
99. (3aS,10R)-6-Chloro-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione
100. (3aS,10R)-6-Chloro-2-[2-(3,6-dihydro-2H-pyridin-1-yl)-ethyl]-10-(3-hydroxy-phenyl)-3a-methyl-3a,4,9,10-tetrahydro-2,9,10a-triaza-cyclopenta[b]fluorene-1,3-dione
101. (3aS,10R)-6-Chloro-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione 102. (3aS,10R)-6-Chloro-2-(2-cyclopropylamino-ethyl)-10-(3-hydroxy-phenyl)-3a-methyl-3a,4,9,10-tetrahydro-2,9,10a-triaza-cyclopenta[b]fluorene-1,3-dione
103. (3aS,10R)-6-Chloro-2-(2-cyclobutylamino-ethyl)-10-(3-hydroxy-phenyl)-3a-methyl-3a,4,9,10-tetrahydro-2,9,10a-triaza-cyclopenta[b]fluorene-1,3-dione
104. (3aS,10R)-2-(2-Azepan-1-yl-ethyl)-6-chloro-10-(3-hydroxy-phenyl)-3a-methyl-3a,4,9,10-tetrahydro-2,9,10a-triaza-cyclopenta[b]fluorene-1,3-dione
105. (3aS,10R)-10-(3-Hydroxy-phenyl)-6-methoxy-3a-methyl-2-(3-piperidin-1-yl-propyl)-3a,4,9,10-tetrahydro-2,9,10a-triaza-cyclopenta[b]fluorene-1,3-dione
106. (3aS,10R)-2-[3-(3,6-Dihydro-2H-pyridin-1-yl)-propyl]-10-(3-hydroxy-phenyl)-6-methoxy-3a-methyl-3a,4,9,10-tetrahydro-2,9,10a-triaza-cyclopenta[b]fluorene-1,3-dione
107. (3aS,10R)-2-(3-Diethylamino-propyl)-10-(3-hydroxy-phenyl)-6-methoxy-3a-methyl-3a,4,9,10-tetrahydro-2,9,10a-triaza-cyclopenta[b]fluorene-1,3-dione
108. (3aS,10R)-6-Chloro-2-[2-(cyclopropylmethyl-amino)-ethyl]-10-(3-hydroxy-phenyl)-3a-methyl-3a,4,9,10-tetrahydro-2,9,10a-triaza-cyclopenta[b]fluorene-1,3-dione
109. (3aS,10R)-6-Chloro-2-[2-(2,5-dihydro-pyrrol-1-yl)-ethyl]-10-(3-hydroxy-phenyl)-3a-methyl-3a,4,9,10-tetrahydro-2,9,10a-triaza-cyclopenta[b]fluorene-1,3-dione
110. (3aS,10R)-6-Chloro-2-(2-diethylamino-ethyl)-10-(3-hydroxy-phenyl)-3a-methyl-3a,4,9,10-tetrahydro-2,9,10a-triaza-cyclopenta[b]fluorene-1,3-dione
111. (3aS,10R)-6-Chloro-10-(3-hydroxy-phenyl)-3a-methyl-2-[2-(4-methyl-piperazin-1-yl)-ethyl]-3a,4,9,10-tetrahydro-2,9,10a-triaza-cyclopenta[b]fluorene-1,3-dione
112. (3aS,10R)-10-(3-Hydroxy-phenyl)-6-methoxy-3a-methyl-2-[3-(4-methyl-piperidin-1-yl)-propyl]-3a,4,9,10-tetrahydro-2,9,10a-triaza-cyclopenta[b]fluorene-1,3-dione
113. (3aS,10R)-2-(3-Azepan-1-yl-propyl)-10-(3-hydroxy-phenyl)-6-methoxy-3a-methyl-3a,4,9,10-tetrahydro-2,9,10a-triaza-cyclopenta[b]fluorene-1,3-dione
114. (3aS,10R)-2-[2-(4-Acetyl-piperazin-1-yl)-ethyl]-6-chloro-10-(3-hydroxy-phenyl)-3a-methyl-3a,4,9,10-tetrahydro-2,9,10a-triaza-cyclopenta[b]fluorene-1,3-dione
115. (3aS,10R)-2-(2-Allylamino-ethyl)-6-chloro-10-(3-hydroxy-phenyl)-3a-methyl-3a,4,9,10-tetrahydro-2,9,10a-triaza-cyclopenta[b]fluorene-1,3-dione
116. (3aS,10R)-6-Chloro-10-(3-hydroxy-phenyl)-3a-methyl-2-[2-(methyl-prop-2-ynyl-amino)-ethyl]-3a,4,9,10-tetrahydro-2,9,10a-triaza-cyclopenta[b]fluorene-1,3-dione
117. (3aS,10R)-2-[2-(Allyl-methyl-amino)-ethyl]-6-chloro-10-(3-hydroxy-phenyl)-3a-methyl-3a,4,9,10-tetrahydro-2,9,10a-triaza-cyclopenta[b]fluorene-1,3-dione
118. (3aS,10R)-2-{2-[(2-Hydroxy-ethyl)-methyl-amino]-ethyl}-10-(3-hydroxy-phenyl)-6-methoxy-3a-methyl-3a,4,9,10-tetrahydro-2,9,10a-triaza-cyclopenta[b]fluorene-1,3-dione
119. (3aS,10R)-2-[2-(2,5-Dihydro-pyrrol-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione
120. (3aS,10R)-6-Chloro-10-(3-hydroxy-phenyl)-3a-methyl-2-(2-morpholin-4-yl-ethyl)-3a,4,9,10-tetrahydro-2,9,10a-triaza-cyclopenta[b]fluorene-1,3-dione
121. (3aS,10R)-6-Chloro-2-{2-[ethyl-(2-methoxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione
122. (3aS,10R)-6-Chloro-2-[2-(2-hydroxy-ethylamino)-ethyl]-10-(3-hydroxy-phenyl)-3a-methyl-3a,4,9,10-tetrahydro-2,9,10a-triaza-cyclopenta[b]fluorene-1,3-dione
123. (3aS,10R)-6-Chloro-2-[2-(2,2-difluoro-ethylamino)-ethyl]-10-(3-hydroxy-phenyl)-3a-methyl-3a,4,9,10-tetrahydro-2,9,10a-triaza-cyclopenta[b]fluorene-1,3-dione
124. (3aS,10R)-6-Chloro-2-{2-[ethyl-(2-hydroxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione
125. (3aS,10R)-6-Chloro-10-(3-hydroxy-phenyl)-3a-methyl-2-[2-(1-methyl-1H-pyrazol-3-ylamino)ethyl]-3a,4,9,10-tetrahydro-2,9,10a-triaza-cyclopenta[b]fluorene-1,3-dione
126. (3aS,10R)-6-Chloro-2-{2-[(2-hydroxy-ethyl)-methyl-amino]-ethyl}-10-(3-hydroxy-phenyl)-3a-methyl-3a,4,9,10-tetrahydro-2,9,10a-triaza-cyclopenta[b]fluorene-1,3-dione
127. (3aS,10R)-6-Chloro-10-(3-hydroxy-phenyl)-3a-methyl-2-(2-prop-2-ynylamino-ethyl)-3a,4,9,10-tetrahydro-2,9,10a-triaza-cyclopenta[b]fluorene-1,3-dione
128. (3aS,10R)-6-Chloro-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione
129. (3aS,10R)-6-Chloro-2-[2-(3,3-difluoro-pyrrolidin-1-yl)-ethyl]-10-(3-hydroxy-phenyl)-3a-methyl-3a,4,9,10-tetrahydro-2,9,10a-triaza-cyclopenta[b]fluorene-1,3-dione
130. (3aS,10R)-6-Chloro-10-(3-hydroxy-phenyl)-3a-methyl-2-(3-methylamino-propyl)-3a,4,9,10-tetrahydro-2,9,10a-triaza-cyclopenta[b]fluorene-1,3-dione
131. (3aS,10R)-6-Chloro-2-(3-ethylamino-propyl)-10-(3-hydroxy-phenyl)-3a-methyl-3a,4,9,10-tetrahydro-2,9,10a-triaza-cyclopenta[b]fluorene-1,3-dione
132. (3aS,10R)-6-Chloro-2-{3-[(2-hydroxy-ethyl)-methyl-amino]-propyl}-10-(3-hydroxy-phenyl)-3a-methyl-3a,4,9,10-tetrahydro-2,9,10a-triaza-cyclopenta[b]fluorene-1,3-dione
133. (3aS,10R)-6-Chloro-10-(3-hydroxy-phenyl)-2-[3-(isopropyl-methyl-amino)-propyl]-3a-methyl-3a,4,9,10-tetrahydro-2,9,10a-triaza-cyclopenta[b]fluorene-1,3-dione
134. (3aS,10R)-10-(3-Hydroxy-phenyl)-6-methoxy-3a-methyl-2-[2-(2-methyl-2H-pyrazol-3-ylamino)ethyl]-3a,4,9,10-tetrahydro-2,9,10a-triaza-cyclopenta[b]fluorene-1,3-dione
135. (3aS,10R)-6-Chloro-10-(3-hydroxy-phenyl)-2-(3-isobutylamino-propyl)-3a-methyl-3a,4,9,10-tetrahydro-2,9,10a-triaza-cyclopenta[b]fluorene-1,3-dione
136. (3aS,10R)-6-Chloro-10-(3-hydroxy-phenyl)-3a-methyl-2-[3-((R and S)1-methyl-prop-2-ynylamino)-propyl]-3a,4,9,10-tetrahydro-2,9,10a-triaza-cyclopenta[b]fluorene-1,3-dione
137. (3aS,10R)-6-Chloro-2-(3-diethylamino-propyl)-10-(3-hydroxy-phenyl)-3a-methyl-3a,4,9,10-tetrahydro-2,9,10a-triaza-cyclopenta[b]fluorene-1,3-dione
138. (3aS,10R)-6-Chloro-2-(3-cyclobutylamino-propyl)-10-(3-hydroxy-phenyl)-3a-methyl-3a,4,9,10-tetrahydro-2,9,10a-triaza-cyclopenta[b]fluorene-1,3-dione
139. (3aS,10R)-2-(3-Allylamino-propyl)-6-chloro-10-(3-hydroxy-phenyl)-3a-methyl-3a,4,9,10-tetrahydro-2,9,10a-triaza-cyclopenta[b]fluorene-1,3-dione
140. (3aS,10R)-6-Chloro-2-[3-(ethyl-methyl-amino)-propyl]-10-(3-hydroxy-phenyl)-3a-methyl-3a,4,9,10-tetrahydro-2,9,10a-triaza-cyclopenta[b]fluorene-1,3-dione
141. (3aS,10R)-2-(3-Azetidin-1-yl-propyl)-6-chloro-10-(3-hydroxy-phenyl)-3a-methyl-3a,4,9,10-tetrahydro-2,9,10a-triaza-cyclopenta[b]fluorene-1,3-dione
142. (3aS,10R)-2-[3-(2,2-Difluoro-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione 143. (3aS,10R)-2-{3-[(2-Hydroxy-ethyl)-methyl-amino]-propyl}-10-(3-hydroxy-phenyl)-6-methoxy-3a-methyl-3a,4,9,10-tetrahydro-2,9,10a-triaza-cyclopenta[b]fluorene-1,3-dione 144. (3aS,10R)-10-(3-Hydroxy-phenyl)-6-methoxy-3a-methyl-2-[3-(methyl-prop-2-ynyl-amino)propyl]-3a,4,9,10-tetrahydro-2,9,10a-triaza-cyclopenta[b]fluorene-1,3-dione 145. (3aS,10R)-2-[3-(2-Hydroxy-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione 146. (3aS,10R)-2-(3-Allylamino-propyl)-10-(3-hydroxy-phenyl)-6-methoxy-3a-methyl-3a,4,9,10-tetrahydro-2,9,10a-triaza-cyclopenta[b]fluorene-1,3-dione 147. (3aS,10R)-10-(3-Hydroxy-phenyl)-6-methoxy-3a-methyl-2-(3-prop-2-ynylamino-propyl)-3a,4,9,10-tetrahydro-2,9,10a-triaza-cyclopenta[b]fluorene-1,3-dione 148. (3aS,10R)-10-(3-Hydroxy-phenyl)-6-methoxy-3a-methyl-2-(3-morpholin-4-yl-propyl)-3a,4,9,10-tetrahydro-2,9,10a-triaza-cyclopenta[b]fluorene-1,3-dione 149. (3aS,10R)-2-[3-(2,5-Dihydro-pyrrol-1-yl)-propyl]-10-(3-hydroxy-phenyl)-6-methoxy-3a-methyl-3a,4,9,10-tetrahydro-2,9,10a-triaza-cyclopenta[b]fluorene-1,3-dione 150. (3aS,10R)-10-(3-Hydroxy-phenyl)-6-methoxy-3a-methyl-2-[3-(4-methyl-piperazin-1-yl)-propyl]-3a,4,9,10-tetrahydro-2,9,10a-triaza-cyclopenta[b]fluorene-1,3-dione 151. (3aS,10R)-2-[3-(4-Acetyl-piperazin-1-yl)-propyl]-10-(3-hydroxy-phenyl)-6-methoxy-3a-methyl-3a,4,9,10-tetrahydro-2,9,10a-triaza-cyclopenta[b]fluorene-1,3-dione 152. (3aS,10R)-6-Ethoxy-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione 153. (3aS,10R)-6-Ethoxy-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione 154. (3aS,10R)-2-[2-(Cyclopropylmethyl-amino)-ethyl]-6-ethoxy-10-(3-hydroxy-phenyl)-3a-methyl-3a,4,9,10-tetrahydro-2,9,10a-triaza-cyclopenta[b]fluorene-1,3-dione 155. (3aS,10R)-2-(2-Cyclobutylamino-ethyl)-6-ethoxy-10-(3-hydroxy-phenyl)-3a-methyl-3a,4,9,10-tetrahydro-2,9,10a-triaza-cyclopenta[b]fluorene-1,3-dione 156. (3aS,10R)-2-(2-tert-Butylamino-ethyl)-6-ethoxy-10-(3-hydroxy-phenyl)-3a-methyl-3a,4,9,10-tetrahydro-2,9,10a-triaza-cyclopenta[b]fluorene-1,3-dione 157. (3aS,10R)-2-(2-Allylamino-ethyl)-6-ethoxy-10-(3-hydroxy-phenyl)-3a-methyl-3a,4,9,10-tetrahydro-2,9,10a-triaza-cyclopenta[b]fluorene-1,3-dione 158. (3aS,10R)-6-Ethoxy-2-[2-(ethyl-methyl-amino)-ethyl]-10-(3-hydroxy-phenyl)-3a-methyl-3a,4,9,10-tetrahydro-2,9,10a-triaza-cyclopenta[b]fluorene-1,3-dione 159. (3aS,10R)-6-Ethoxy-2-[2-(2-hydroxy-ethylamino)-ethyl]-10-(3-hydroxy-phenyl)-3a-methyl-3a,4,9,10-tetrahydro-2,9,10a-triaza-cyclopenta[b]fluorene-1,3-dione 160. (3aS,10R)-6-Ethoxy-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione 161. (3aS,10R)-2-(2-Cyclopropylamino-ethyl)-6-ethoxy-10-(3-hydroxy-phenyl)-3a-methyl-3a,4,9,10-tetrahydro-2,9,10a-triaza-cyclopenta[b]fluorene-1,3-dione 162. (3aS,10R)-2-(2-Diethylamino-ethyl)-6-ethoxy-10-(3-hydroxy-phenyl)-3a-methyl-3a,4,9,10-tetrahydro-2,9,10a-triaza-cyclopenta[b]fluorene-1,3-dione 163. (3aS,10R)-6-Ethoxy-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione 164. (3aS,10R)-6-Ethoxy-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione 165. (3aS,10R)-2-[2-(3,6-Dihydro-2H-pyridin-1-yl)-ethyl]-6-ethoxy-10-(3-hydroxy-phenyl)-3a-methyl-3a,4,9,10-tetrahydro-2,9,10a-triaza-cyclopenta[b]fluorene-1,3-dione 166. (3aS,10R)-2-(2-Azepan-1-yl-ethyl)-6-ethoxy-10-(3-hydroxy-phenyl)-3a-methyl-3a,4,9,10-tetrahydro-2,9,10a-triaza-cyclopenta[b]fluorene-1,3-dione 167. (3aS,10R)-2-(3-tert-Butylamino-propyl)-10-(3-hydroxy-phenyl)-6-methoxy-3a-methyl-3a,4,9,10-tetrahydro-2,9,10a-triaza-cyclopenta[b]fluorene-1,3-dione 168. (3aS,10R)-6-Chloro-2-{3-[ethyl-(2-hydroxy-ethyl)-amino]-propyl}-10-(3-hydroxy-phenyl)-3a-methyl-3a,4,9,10-tetrahydro-2,9,10a-triaza-cyclopenta[b]fluorene-1,3-dione 169. (3aS,10R)-2-[3-(Allyl-methyl-amino)-propyl]-6-chloro-10-(3-hydroxy-phenyl)-3a-methyl-3a,4,9,10-tetrahydro-2,9,10a-triaza-cyclopenta[b]fluorene-1,3-dione 170. (3aS,10R)-6-Chloro-10-(3-hydroxy-phenyl)-3a-methyl-2-[3-(methyl-prop-2-ynyl-amino)-propyl]-3a,4,9,10-tetrahydro-2,9,10a-triaza-cyclopenta[b]fluorene-1,3-dione 171. (3aS,10R)-6-Chloro-10-(3-hydroxy-phenyl)-3a-methyl-2-(3-morpholin-4-yl-propyl)-3a,4,9,10-tetrahydro-2,9,10a-triaza-cyclopenta[b]fluorene-1,3-dione 172. (3aS,10R)-6-Chloro-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione 173. (3aS,10R)-6-Chloro-2-[3-(2,5-dihydro-pyrrol-1-yl)-propyl]-10-(3-hydroxy-phenyl)-3a-methyl-3a,4,9,10-tetrahydro-2,9,10a-triaza-cyclopenta[b]fluorene-1,3-dione 174. (3aS,10R)-6-Chloro-2-[3-(3,6-dihydro-2H-pyridin-1-yl)-propyl]-10-(3-hydroxy-phenyl)-3a-methyl-3a,4,9,10-tetrahydro-2,9,10a-triaza-cyclopenta[b]fluorene-1,3-dione 175. (3aS,10R)-6-Chloro-10-(3-hydroxy-phenyl)-3a-methyl-2-[3-(4-methyl-piperazin-1-yl)-propyl]-3a,4,9,10-tetrahydro-2,9,10a-triaza-cyclopenta[b]fluorene-1,3-dione 176. (3aS,10R)-2-(3-Diethylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione 177. (3aS,10R)-6-(1,1-Difluoro-methoxy)-2-{3-[ethyl-(2-hydroxy-ethyl)-amino]-propyl}-10-(3-hydroxyphenyl)-3a-methyl-3a,4,9,10-tetrahydro-2,9,10a-triaza-cyclopenta[b]fluorene-1,3-dione 178. (3aS,10R)-6-(1,1-Difluoro-methoxy)-2-{3-[ethyl-(2-methoxy-ethyl)-amino]-propyl}-10-(3-hydroxyphenyl)-3a-methyl-3a,4,9,10-tetrahydro-2,9,10a-triaza-cyclopenta[b]fluorene-1,3-dione 179. (3aS,10R)-6-(1,1-Difluoro-methoxy)-10-(3-hydroxy-phenyl)-2-[3-(isopropyl-methyl-amino)propyl]-3a-methyl-3a,4,9,10-tetrahydro-2,9,10a-triaza-cyclopenta[b]fluorene-1,3-dione 180. (3aS,10R)-2-(3-Azepan-1-yl-propyl)-6-chloro-10-(3-hydroxy-phenyl)-3a-methyl-3a,4,9,10-tetrahydro-2,9,10a-triaza-cyclopenta[b]fluorene-1,3-dione 181. (3aS,10R)-6-Chloro-10-(3-hydroxy-phenyl)-3a-methyl-2-(3-piperidin-1-yl-propyl)-3a,4,9,10-tetrahydro-2,9,10a-triaza-cyclopenta[b]fluorene-1,3-dione 182. (3aS,10R)-2-(3-tert-Butylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione 183. (3aS,10R)-6-(1,1-Difluoro-methoxy)-10-(3-hydroxy-phenyl)-3a-methyl-2-[3-(methyl-prop-2-ynylamino)-propyl]-3a,4,9,10-tetrahydro-2,9,10a-triaza-cyclopenta[b]fluorene-1,3-dione
184. (3aS,10R)-2-[3-(Allyl-methyl-amino)-propyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
185. (3aS,10R)-6-Chloro-10-(3-hydroxy-phenyl)-2-[3-(2-methoxy-ethylamino)-propyl]-3a-methyl-3a,4,9,10-tetrahydro-2,9,10a-triaza-cyclopenta[b]fluorene-1,3-dione
186. (3aS,10R)-6-Ethoxy-10-(3-hydroxy-phenyl)-3a-methyl-2-(3-methylamino-propyl)-3a,4,9,10-tetrahydro-2,9,10a-triaza-cyclopenta[b]fluorene-1,3-dione
187. (3aS,10R)-6-Ethoxy-2-(3-ethylamino-propyl)-10-(3-hydroxy-phenyl)-3a-methyl-3a,4,9,10-tetrahydro-2,9,10a-triaza-cyclopenta[b]fluorene-1,3-dione
188. (3aS,10R)-2-[3-(Cyclopropylmethyl-amino)-propyl]-6-ethoxy-10-(3-hydroxy-phenyl)-3a-methyl-3a,4,9,10-tetrahydro-2,9,10a-triaza-cyclopenta[b]fluorene-1,3-dione
189. (3aS,10R)-6-Ethoxy-10-(3-hydroxy-phenyl)-2-[3-(2-methoxy-ethylamino)-propyl]-3a-methyl-3a,4,9,10-tetrahydro-2,9,10a-triaza-cyclopenta[b]fluorene-1,3-dione
190. (3aS,10R)-2-(3-Cyclopropylamino-propyl)-6-ethoxy-10-(3-hydroxy-phenyl)-3a-methyl-3a,4,9,10-tetrahydro-2,9,10a-triaza-cyclopenta[b]fluorene-1,3-dione
191. (3aS,10R)-2-(3-Allylamino-propyl)-6-ethoxy-10-(3-hydroxy-phenyl)-3a-methyl-3a,4,9,10-tetrahydro-2,9,10a-triaza-cyclopenta[b]fluorene-1,3-dione
192. (3aS,10R)-6-Ethoxy-2-[3-(ethyl-methyl-amino)-propyl]-10-(3-hydroxy-phenyl)-3a-methyl-3a,4,9,10-tetrahydro-2,9,10a-triaza-cyclopenta[b]fluorene-1,3-dione
193. (3aS,10R)-6-Ethoxy-2-{3-[(2-hydroxy-ethyl)-methyl-amino]-propyl}-10-(3-hydroxy-phenyl)-3a-methyl-3a,4,9,10-tetrahydro-2,9,10a-triaza-cyclopenta[b]fluorene-1,3-dione
194. (3aS,10R)-6-Ethoxy-2-{3-[ethyl-(2-hydroxy-ethyl)-amino]-propyl}-10-(3-hydroxy-phenyl)-3a-methyl-3a,4,9,10-tetrahydro-2,9,10a-triaza-cyclopenta[b]fluorene-1,3-dione
195. (3aS,10R)-6-Ethoxy-2-{3-[ethyl-(2-methoxy-ethyl)-amino]-propyl}-10-(3-hydroxy-phenyl)-3a-methyl-3a,4,9,10-tetrahydro-2,9,10a-triaza-cyclopenta[b]fluorene-1,3-dione
196. (3aS,10R)-2-[3-(Allyl-methyl-amino)-propyl]-6-ethoxy-10-(3-hydroxy-phenyl)-3a-methyl-3a,4,9,10-tetrahydro-2,9,10a-triaza-cyclopenta[b]fluorene-1,3-dione
197. (3aS,10R)-6-Ethoxy-10-(3-hydroxy-phenyl)-2-[3-(isopropyl-methyl-amino)-propyl]-3a-methyl-3a,4,9,10-tetrahydro-2,9,10a-triaza-cyclopenta[b]fluorene-1,3-dione
198. (3aS,10R)-2-(3-Azetidin-1-yl-propyl)-6-ethoxy-10-(3-hydroxy-phenyl)-3a-methyl-3a,4,9,10-tetrahydro-2,9,10a-triaza-cyclopenta[b]fluorene-1,3-dione
199. (3aS,10R)-6-(1,1-Difluoro-methoxy)-10-(3-hydroxy-phenyl)-2-(3-isobutylamino-propyl)-3a-methyl-3a,4,9,10-tetrahydro-2,9,10a-triaza-cyclopenta[b]fluorene-1,3-dione
200. (3aS,10R)-2-[3-(Cyclopropylmethyl-amino)-propyl]-6-(1,1-difluoro-methoxy)-10-(3-hydroxyphenyl)-3a-methyl-3a,4,9,10-tetrahydro-2,9,10a-triaza-cyclopenta[b]fluorene-1,3-dione
201. (3aS,10R)-6-(1,1-Difluoro-methoxy)-2-[3-(2-hydroxy-ethylamino)-propyl]-10-(3-hydroxy-phenyl)-3a-methyl-3a,4,9,10-tetrahydro-2,9,10a-triaza-cyclopenta[b]fluorene-1,3-dione
202. (3aS,10R)-2-(3-Cyclopropylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
203. (3aS,10R)-6-(1,1-Difluoro-methoxy)-10-(3-hydroxy-phenyl)-3a-methyl-2-(3-methylaminopropyl)-3a,4,9,10-tetrahydro-2,9,10a-triaza-cyclopenta[b]fluorene-1,3-dione
204. (3aS,10R)-6-(1,1-Difluoro-methoxy)-2-(3-ethylamino-propyl)-10-(3-hydroxy-phenyl)-3a-methyl-3a,4,9,10-tetrahydro-2,9,10a-triaza-cyclopenta[b]fluorene-1,3-dione
205. (3aS,10R)-6-(1,1-Difluoro-methoxy)-10-(3-hydroxy-phenyl)-2-[3-(2-methoxy-ethylamino)propyl]-3a-methyl-3a,4,9,10-tetrahydro-2,9,10a-triaza-cyclopenta[b]fluorene-1,3-dione
206. (3aS,10R)-2-(3-Allylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
207. (3aS,10R)-6-Ethoxy-10-(3-hydroxy-phenyl)-3a-methyl-2-(3-morpholin-4-yl-propyl)-3a,4,9,10-tetrahydro-2,9,10a-triaza-cyclopenta[b]fluorene-1,3-dione
208. (3aS,10R)-2-[3-(3,6-Dihydro-2H-pyridin-1-yl)-propyl]-6-ethoxy-10-(3-hydroxy-phenyl)-3a-methyl-3a,4,9,10-tetrahydro-2,9,10a-triaza-cyclopenta[b]fluorene-1,3-dione
209. (3aS,10R)-2-[3-(4-Acetyl-piperazin-1-yl)-propyl]-6-ethoxy-10-(3-hydroxy-phenyl)-3a-methyl-3a,4,9,10-tetrahydro-2,9,10a-triaza-cyclopenta[b]fluorene-1,3-dione
210. (3aS,10R)-2-(3-Azepan-1-yl-propyl)-6-ethoxy-10-(3-hydroxy-phenyl)-3a-methyl-3a,4,9,10-tetrahydro-2,9,10a-triaza-cyclopenta[b]fluorene-1,3-dione
211. (3aS,10R)-6-Bromo-10-(3-hydroxy-phenyl)-3a-methyl-2-(3-methylamino-propyl)-3a,4,9,10-tetrahydro-2,9,10a-triaza-cyclopenta[b]fluorene-1,3-dione
212. (3aS,10R)-6-Bromo-2-(3-ethylamino-propyl)-10-(3-hydroxy-phenyl)-3a-methyl-3a,4,9,10-tetrahydro-2,9,10a-triaza-cyclopenta[b]fluorene-1,3-dione
213. (3aS,10R)-6-Bromo-10-(3-hydroxy-phenyl)-2-(3-isobutylamino-propyl)-3a-methyl-3a,4,9,10-tetrahydro-2,9,10a-triaza-cyclopenta[b]fluorene-1,3-dione
214. (3aS,10R)-6-Bromo-10-(3-hydroxy-phenyl)-2-[3-(2-methoxy-ethylamino)-propyl]-3a-methyl-3a,4,9,10-tetrahydro-2,9,10a-triaza-cyclopenta[b]fluorene-1,3-dione
215. (3aS,10R)-6-Bromo-2-(3-cyclopropylamino-propyl)-10-(3-hydroxy-phenyl)-3a-methyl-3a,4,9,10-tetrahydro-2,9,10a-triaza-cyclopenta[b]fluorene-1,3-dione
216. (3aS,10R)-6-Bromo-2-[3-(ethyl-methyl-amino)-propyl]-10-(3-hydroxy-phenyl)-3a-methyl-3a,4,9,10-tetrahydro-2,9,10a-triaza-cyclopenta[b]fluorene-1,3-dione
217. (3aS,10R)-6-Bromo-2-{3-[ethyl-(2-methoxy-ethyl)-amino]-propyl}-10-(3-hydroxy-phenyl)-3a-methyl-3a,4,9,10-tetrahydro-2,9,10a-triaza-cyclopenta[b]fluorene-1,3-dione
218. (3aS,10R)-6-Bromo-10-(3-hydroxy-phenyl)-2-[3-(isopropyl-methyl-amino)-propyl]-3a-methyl-3a,4,9,10-tetrahydro-2,9,10a-triaza-cyclopenta[b]fluorene-1,3-dione
219. (3aS,10R)-6-Bromo-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione
220. (3aS,10R)-2-[3-(4-Acetyl-piperazin-1-yl)-propyl]-6-bromo-10-(3-hydroxy-phenyl)-3a-methyl-3a,4,9,10-tetrahydro-2,9,10a-triaza-cyclopenta[b]fluorene-1,3-dione
221. (3aS,10R)-6-Ethoxy-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione 222. (3aS,10R)-2-[3-(2,5-Dihydro-pyrrol-1-yl)-propyl]-6-ethoxy-10-(3-hydroxy-phenyl)-3a-methyl-3a,4,9,10-tetrahydro-2,9,10a-triaza-cyclopenta[b]fluorene-1,3-dione
223. (3aS,10R)-6-Ethoxy-10-(3-hydroxy-phenyl)-3a-methyl-2-(3-piperidin-1-yl-propyl)-3a,4,9,10-tetrahydro-2,9,10a-triaza-cyclopenta[b]fluorene-1,3-dione
224. (3aS,10R)-6-Ethoxy-10-(3-hydroxy-phenyl)-3a-methyl-2-[3-(4-methyl-piperidin-1-yl)-propyl]-3a,4,9,10-tetrahydro-2,9,10a-triaza-cyclopenta[b]fluorene-1,3-dione
225. (3aS,10R)-6-Ethoxy-10-(3-hydroxy-phenyl)-3a-methyl-2-(3-prop-2-ynylamino-propyl)-3a,4,9,10-tetrahydro-2,9,10a-triaza-cyclopenta[b]fluorene-1,3-dione
226. (3aS,10R)-2-(3-Dimethylamino-propyl)-6-ethoxy-10-(3-hydroxy-phenyl)-3a-methyl-3a,4,9,10-tetrahydro-2,9,10a-triaza-cyclopenta[b]fluorene-1,3-dione
227. (3aS,10R)-6-Ethoxy-10-(3-hydroxy-phenyl)-3a-methyl-2-[3-(methyl-prop-2-ynyl-amino)-propyl]-3a,4,9,10-tetrahydro-2,9,10a-triaza-cyclopenta[b]fluorene-1,3-dione
228. (3aS,10R)-6-Bromo-2-(3-diethylamino-propyl)-10-(3-hydroxy-phenyl)-3a-methyl-3a,4,9,10-tetrahydro-2,9,10a-triaza-cyclopenta[b]fluorene-1,3-dione
229. (3aS,10R)-6-Ethoxy-10-(3-hydroxy-phenyl)-3a-methyl-2-[3-(4-methyl-piperazin-1-yl)-propyl]-3a,4,9,10-tetrahydro-2,9,10a-triaza-cyclopenta[b]fluorene-1,3-dione
230. (3aS,10R)-6-Bromo-2-(3-dimethylamino-propyl)-10-(3-hydroxy-phenyl)-3a-methyl-3a,4,9,10-tetrahydro-2,9,10a-triaza-cyclopenta[b]fluorene-1,3-dione
231. (3aS,10R)-6-Bromo-2-{3-[ethyl-(2-hydroxy-ethyl)-amino]-propyl}-10-(3-hydroxy-phenyl)-3a-methyl-3a,4,9,10-tetrahydro-2,9,10a-triaza-cyclopenta[b]fluorene-1,3-dione
232. (3aS,10R)-6-Bromo-2-[3-(3,6-dihydro-2H-pyridin-1-yl)-propyl]-10-(3-hydroxy-phenyl)-3a-methyl-3a,4,9,10-tetrahydro-2,9,10a-triaza-cyclopenta[b]fluorene-1,3-dione
233. (3aS,10R)-6-Bromo-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione
234. (3aS,10R)-6-Bromo-2-[3-(cyclopropylmethyl-amino)-propyl]-10-(3-hydroxy-phenyl)-3a-methyl-3a,4,9,10-tetrahydro-2,9,10a-triaza-cyclopenta[b]fluorene-1,3-dione
235. (3aS,10R)-6-Bromo-2-[3-(2-hydroxy-ethylamino)-propyl]-10-(3-hydroxy-phenyl)-3a-methyl-3a,4,9,10-tetrahydro-2,9,10a-triaza-cyclopenta[b]fluorene-1,3-dione
236. (3aS,10R)-6-(1,1-Difluoro-methoxy)-10-(3-hydroxy-phenyl)-3a-methyl-2-(3-morpholin-4-ylpropyl)-3a,4,9,10-tetrahydro-2,9,10a-triaza-cyclopenta[b]fluorene-1,3-dione
237. (3aS,10R)-6-(1,1-Difluoro-methoxy)-10-(3-hydroxy-phenyl)-3a-methyl-2-(3-pyrrolidin-1-ylpropyl)-3a,4,9,10-tetrahydro-2,9,10a-triaza-cyclopenta[b]fluorene-1,3-dione
238. (3aS,10R)-6-(1,1-Difluoro-methoxy)-2-[3-(2,5-dihydro-pyrrol-1-yl)-propyl]-10-(3-hydroxy-phenyl)-3a-methyl-3a,4,9,10-tetrahydro-2,9,10a-triaza-cyclopenta[b]fluorene-1,3-dione
239. (3aS,10R)-6-(1,1-Difluoro-methoxy)-10-(3-hydroxy-phenyl)-3a-methyl-2-(3-piperidin-1-ylpropyl)-3a,4,9,10-tetrahydro-2,9,10a-triaza-cyclopenta[b]fluorene-1,3-dione
240. (3aS,10R)-6-(1,1-Difluoro-methoxy)-10-(3-hydroxy-phenyl)-3a-methyl-2-[3-(4-methyl-piperazin-1-yl)-propyl]-3a,4,9,10-tetrahydro-2,9,10a-triaza-cyclopenta[b]fluorene-1,3-dione
241. (3aS,10R)-2-[3-(4-Acetyl-piperazin-1-yl)-propyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
242. (3aS,10R)-6-(1,1-Difluoro-methoxy)-2-[3-(3,6-dihydro-2H-pyridin-1-yl)-propyl]-10-(3-hydroxyphenyl)-3a-methyl-3a,4,9,10-tetrahydro-2,9,10a-triaza-cyclopenta[b]fluorene-1,3-dione
243. (3aS,10R)-2-(3-Azepan-1-yl-propyl)-6-(1,1-difluoromethoxy)-10-(3-hydroxy-phenyl)-3a-methyl-3a,4,9,10-tetrahydro-2,9,10a-triaza-cyclopenta[b]fluorene-1,3-dione
244. (3aS,10R)-6-(1,1-Difluoro-methoxy)-10-(3-hydroxy-phenyl)-3a-methyl-2-[3-(4-methyl-piperidin-1-yl)-propyl]-3a,4,9,10-tetrahydro-2,9,10a-triaza-cyclopenta[b]fluorene-1,3-dione
245. (3aS,10R)-7-Fluoro-2-[2-(2-hydroxy-ethylamino)-ethyl]-10-(3-hydroxy-phenyl)-6-methoxy-3a-methyl-3a,4,9,10-tetrahydro-2,9,10a-triaza-cyclopenta[b]fluorene-1,3-dione
246. (3aS,10R)-7-Fluoro-2-{2-[(2-hydroxy-ethyl)-methyl-amino]-ethyl}-10-(3-hydroxy-phenyl)-6-methoxy-3a-methyl-3a,4,9,10-tetrahydro-2,9,10a-triaza-cyclopenta[b]fluorene-1,3-dione
247. (3aS,10R)-6-(1,1-Difluoro-methoxy)-2-[3-(ethyl-methyl-amino)-propyl]-10-(3-hydroxy-phenyl)-3a-methyl-3a,4,9,10-tetrahydro-2,9,10a-triaza-cyclopenta[b]fluorene-1,3-dione
248. (3aS,10R)-7-Fluoro-10-(3-hydroxy-phenyl)-6-methoxy-3a-methyl-2-(2-methylamino-ethyl)-3a,4,9,10-tetrahydro-2,9,10a-triaza-cyclopenta[b]fluorene-1,3-dione
249. (3aS,10R)-2-(2-Ethylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
250. (3aS,10R)-7-Fluoro-10-(3-hydroxy-phenyl)-2-(2-isopropylamino-ethyl)-6-methoxy-3a-methyl-3a,4,9,10-tetrahydro-2,9,10a-triaza-cyclopenta[b]fluorene-1,3-dione
251. (3aS,10R)-2-[2-(Cyclopropylmethyl-amino)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
252. (3aS,10R)-7-Fluoro-10-(3-hydroxy-phenyl)-2-(2-isobutylamino-ethyl)-6-methoxy-3a-methyl-3a,4,9,10-tetrahydro-2,9,10a-triaza-cyclopenta[b]fluorene-1,3-dione
253. (3aS,10R)-7-Fluoro-10-(3-hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione
254. (3aS,10R)-2-(2-Allylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
255. (3aS,10R)-2-(2-Dimethylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
256. (3aS,10R)-2-(2-tert-Butylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
257. (3aS,10R)-2-[2-(Ethyl-methyl-amino)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
258. (3aS,10R)-2-(2-Diethylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 259. (3aS,10R)-7-Fluoro-10-(3-hydroxy-phenyl)-2-[2-(isopropyl-methyl-amino)-ethyl]-6-methoxy-3a-methyl-3a,4,9,10-tetrahydro-2,9,10a-triaza-cyclopenta[b]fluorene-1,3-dione
260. (3aS,10R)-7-Fluoro-10-(3-hydroxy-phenyl)-6-methoxy-3a-methyl-2-(2-morpholin-4-yl-ethyl)-3a,4,9,10-tetrahydro-2,9,10a-triaza-cyclopenta[b]fluorene-1,3-dione
261. (3aS,10R)-7-Fluoro-10-(3-hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione
262. (3aS,10R)-2-[2-(2,5-Dihydro-pyrrol-1-yl)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
263. (3aS,10R)-7-Fluoro-10-(3-hydroxy-phenyl)-6-methoxy-3a-methyl-2-(2-piperidin-1-yl-ethyl)-3a,4,9,10-tetrahydro-2,9,10a-triaza-cyclopenta[b]fluorene-1,3-dione
264. (3aS,10R)-7-Fluoro-10-(3-hydroxy-phenyl)-6-methoxy-3a-methyl-2-[2-(4-methyl-piperidin-1-yl)ethyl]-3a,4,9,10-tetrahydro-2,9,10a-triaza-cyclopenta[b]fluorene-1,3-dione
265. (3aS,10R)-2-[2-(3,6-Dihydro-2H-pyridin-1-yl)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
266. (3aS,10R)-7-Fluoro-10-(3-hydroxy-phenyl)-6-methoxy-3a-methyl-2-[2-(4-methyl-piperazin-1-yl)ethyl]-3a,4,9,10-tetrahydro-2,9,10a-triaza-cyclopenta[b]fluorene-1,3-dione
267. (3aS,10R)-2-[2-(4-Acetyl-piperazin-1-yl)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
268. (3aS,10R)-6-(1,1-Difluoro-methoxy)-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione
269. (3aS,10R)-6-(1,1-Difluoro-methoxy)-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione
270. (3aS,10R)-2-[2-(Cyclopropylmethyl-amino)-ethyl]-6-(1,1-difluoro-methoxy)-10-(3-hydroxyphenyl)-3a-methyl-3a,4,9,10-tetrahydro-2,9,10a-triaza-cyclopenta[b]fluorene-1,3-dione
271. (3aS,10R)-6-(1,1-Difluoro-methoxy)-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione
272. (3aS,10R)-2-(2-Cyclobutylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
273. (3aS,10R)-2-(2-tert-Butylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
274. (3aS,10R)-2-(2-Allylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
275. (3aS,10R)-6-(1,1-Difluoro-methoxy)-2-[2-(ethyl-methyl-amino)-ethyl]-10-(3-hydroxy-phenyl)-3a-methyl-3a,4,9,10-tetrahydro-2,9,10a-triaza-cyclopenta[b]fluorene-1,3-dione
276. (3aS,10R)-2-(2-Diethylamino-ethyl)-6-(1,1-difluoromethoxy)-10-(3-hydroxy-phenyl)-3a-methyl-3a,4,9,10-tetrahydro-2,9,10a-triaza-cyclopenta[b]fluorene-1,3-dione
277. (3aS,10R)-6-(1,1-Difluoro-methoxy)-2-{2-[ethyl-(2-hydroxy-ethyl)-amino]-ethyl}-10-(3-hydroxyphenyl)-3a-methyl-3a,4,9,10-tetrahydro-2,9,10a-triaza-cyclopenta[b]fluorene-1,3-dione
278. (3aS,10R)-6-(1,1-Difluoro-methoxy)-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione
279. (3aS,10R)-6-(1,1-Difluoro-methoxy)-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione
280. (3aS,10R)-6-(1,1-Difluoro-methoxy)-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione
281. (3aS,10R)-2-[2-(3,6-dihydro-2H-pyridin-1-yl)-ethyl]-10-(3-hydroxyphenyl)-3a-methyl-3a,4,9,10-tetrahydro-2,9,10a-triaza-cyclopenta[b]fluorene-1,3-dione
282. (3aS,10R)-2-(2-Azepan-1-yl-ethyl)-6-(1,1-difluoromethoxy)-10-(3-hydroxy-phenyl)-3a-methyl-3a,4,9,10-tetrahydro-2,9,10a-triaza-cyclopenta[b]fluorene-1,3-dione
283. (3aS,10R)-2-(2-Amino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
284. (3aS,10R)-6-(1,1-Difluoro-methoxy)-2-(2-ethylamino-ethyl)-10-(3-hydroxy-phenyl)-3a-methyl-3a,4,9,10-tetrahydro-2,9,10a-triaza-cyclopenta[b]fluorene-1,3-dione
285. (3aS,10R)-6-(1,1-Difluoro-methoxy)-2-[2-(2-hydroxy-ethylamino)-ethyl]-10-(3-hydroxy-phenyl)-3a-methyl-3a,4,9,10-tetrahydro-2,9,10a-triaza-cyclopenta[b]fluorene-1,3-dione
286. (3aS,10R)-2-(2-Cyclopropylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
287. (3aS,10R)-6-(1,1-Difluoro-methoxy)-10-(3-hydroxy-phenyl)-3a-methyl-2-(2-prop-2-ynylamino-ethyl)-3a,4,9,10-tetrahydro-2,9,10a-triaza-cyclopenta[b]fluorene-1,3-dione
288. (3aS,10R)-6-(1,1-Difluoro-methoxy)-2-{2-[(2-hydroxy-ethyl)-methyl-amino]-ethyl}-10-(3-hydroxyphenyl)-3a-methyl-3a,4,9,10-tetrahydro-2,9,10a-triaza-cyclopenta[b]fluorene-1,3-dione
289. (3aS,10R)-6-(1,1-Difluoro-methoxy)-2-{2-[ethyl-(2-methoxy-ethyl)-amino]-ethyl}-10-(3-hydroxyphenyl)-3a-methyl-3a,4,9,10-tetrahydro-2,9,10a-triaza-cyclopenta[b]fluorene-1,3-dione
290. (3aS,10R)-2-[2-(Allyl-methyl-amino)-ethyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
291. (3aS,10R)-6-(1,1-Difluoro-methoxy)-10-(3-hydroxy-phenyl)-3a-methyl-2-[2-(methyl-prop-2-ynylamino)-ethyl]-3a,4,9,10-tetrahydro-2,9,10a-triaza-cyclopenta[b]fluorene-1,3-dione
292. (3aS,10R)-6-(1,1-Difluoro-methoxy)-10-(3-hydroxy-phenyl)-3a-methyl-2-(2-morpholin-4-ylethyl)-3a,4,9,10-tetrahydro-2,9,10a-triaza-cyclopenta[b]fluorene-1,3-dione 293. (3aS,10R)-6-(1,1-Difluoro-methoxy)-10-(3-hydroxy-phenyl)-3a-methyl-2-[2-(4-methyl-piperidin-1-yl)-ethyl]-3a,4,9,10-tetrahydro-2,9,10a-triaza-cyclopenta[b]fluorene-1,3-dione
294. (3aS,10R)-6-(1,1-Difluoro-methoxy)-10-(3-hydroxy-phenyl)-3a-methyl-2-[2-(4-methyl-piperazin-1-yl)-ethyl]-3a,4,9,10-tetrahydro-2,9,10a-triaza-cyclopenta[b]fluorene-1,3-dione
295. (3aS,10R)-2-[2-(4-Acetyl-piperazin-1-yl)-ethyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
296. (3aS,10R)-6-Ethoxy-2-(2-ethylamino-ethyl)-10-(3-hydroxy-phenyl)-3a-methyl-3a,4,9,10-tetrahydro-2,9,10a-triaza-cyclopenta[b]fluorene-1,3-dione
297. (3aS,10R)-6-Ethoxy-2-{2-[(2-hydroxy-ethyl)-methyl-amino]-ethyl}-10-(3-hydroxy-phenyl)-3a-methyl-3a,4,9,10-tetrahydro-2,9,10a-triaza-cyclopenta[b]fluorene-1,3-dione
298. (3aS,10R)-6-Ethoxy-2-{2-[ethyl-(2-hydroxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione
299. (3aS,10R)-6-Ethoxy-2-{2-[ethyl-(2-methoxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione
300. (3aS,10R)-2-[2-(Allyl-methyl-amino)-ethyl]-6-ethoxy-10-(3-hydroxy-phenyl)-3a-methyl-3a,4,9,10-tetrahydro-2,9,10a-triaza-cyclopenta[b]fluorene-1,3-dione
301. (3aS,10R)-6-Ethoxy-10-(3-hydroxy-phenyl)-3a-methyl-2-[2-(methyl-prop-2-ynyl-amino)-ethyl]-3a,4,9,10-tetrahydro-2,9,10a-triaza-cyclopenta[b]fluorene-1,3-dione
302. (3aS,10R)-6-Ethoxy-10-(3-hydroxy-phenyl)-3a-methyl-2-[2-(4-methyl-piperidin-1-yl)-ethyl]-3a,4,9,10-tetrahydro-2,9,10a-triaza-cyclopenta[b]fluorene-1,3-dione
303. (3aS,10R)-7-Fluoro-10-(3-hydroxy-phenyl)-6-methoxy-3a-methyl-2-(3-methylamino-propyl)-3a,4,9,10-tetrahydro-2,9,10a-triaza-cyclopenta[b]fluorene-1,3-dione
304. (3aS,10R)-2-[3-(Cyclopropylmethyl-amino)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
305. (3aS,10R)-7-Fluoro-2-[3-(2-hydroxy-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione
306. (3aS,10R)-7-Fluoro-10-(3-hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione
307. (3aS,10R)-2-(3-Cyclopropylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
308. (3aS,10R)-2-(3-tert-Butylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
309. (3aS,10R)-7-Fluoro-10-(3-hydroxy-phenyl)-6-methoxy-3a-methyl-2-(3-prop-2-ynylamino-propyl)-3a,4,9,10-tetrahydro-2,9,10a-triaza-cyclopenta[b]fluorene-1,3-dione
310. (3aS,10R)-2-(3-Dimethylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
311. (3aS,10R)-2-[3-(Ethyl-methyl-amino)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
312. (3aS,10R)-7-Fluoro-2-{3-[(2-hydroxy-ethyl)-methyl-amino]-propyl}-10-(3-hydroxy-phenyl)-6-methoxy-3a-methyl-3a,4,9,10-tetrahydro-2,9,10a-triaza-cyclopenta[b]fluorene-1,3-dione
313. (3aS,10R)-2-(3-Diethylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
314. (3aS,10R)-6-(1,1-Difluoro-methoxy)-2-(3-dimethylamino-propyl)-10-(3-hydroxy-phenyl)-3a-methyl-3a,4,9,10-tetrahydro-2,9,10a-triaza-cyclopenta[b]fluorene-1,3-dione
315. (3aS,10R)-2-{3-[Ethyl-(2-hydroxy-ethyl)-amino]-propyl}-7-fluoro-10-(3-hydroxy-phenyl)-6-methoxy-3a-methyl-3a,4,9,10-tetrahydro-2,9,10a-triaza-cyclopenta[b]fluorene-1,3-dione
316. (3aS,10R)-2-{3-[Ethyl-(2-methoxy-ethyl)-amino]-propyl}-7-fluoro-10-(3-hydroxy-phenyl)-6-methoxy-3a-methyl-3a,4,9,10-tetrahydro-2,9,10a-triaza-cyclopenta[b]fluorene-1,3-dione
317. (3aS,10R)-2-[3-(Allyl-methyl-amino)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
318. (3aS,10R)-7-Fluoro-10-(3-hydroxy-phenyl)-6-methoxy-3a-methyl-2-[3-(methyl-prop-2-ynylamino)-propyl]-3a,4,9,10-tetrahydro-2,9,10a-triaza-cyclopenta[b]fluorene-1,3-dione
319. (3aS,10R)-7-Fluoro-10-(3-hydroxy-phenyl)-2-[3-(isopropyl-methyl-amino)-propyl]-6-methoxy-3a-methyl-3a,4,9,10-tetrahydro-2,9,10a-triaza-cyclopenta[b]fluorene-1,3-dione
320. (3aS,10R)-2-(3-Azetidin-1-yl-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
321. (3aS,10R)-7-Fluoro-10-(3-hydroxy-phenyl)-6-methoxy-3a-methyl-2-(3-morpholin-4-yl-propyl)-3a,4,9,10-tetrahydro-2,9,10a-triaza-cyclopenta[b]fluorene-1,3-dione
322. (3aS,10R)-7-Fluoro-10-(3-hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione
323. (3aS,10R)-2-[3-(2,5-Dihydro-pyrrol-1-yl)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
324. (3aS,10R)-7-Fluoro-10-(3-hydroxy-phenyl)-6-methoxy-3a-methyl-2-(3-piperidin-1-yl-propyl)-3a,4,9,10-tetrahydro-2,9,10a-triaza-cyclopenta[b]fluorene-1,3-dione
325. (3aS,10R)-7-Fluoro-10-(3-hydroxy-phenyl)-6-methoxy-3a-methyl-2-[3-(4-methyl-piperazin-1-yl)propyl]-3a,4,9,10-tetrahydro-2,9,10a-triaza-cyclopenta[b]fluorene-1,3-dione
326. (3aS,10R)-2-[3-(3,6-Dihydro-2H-pyridin-1-yl)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
327. (3aS,10R)-7-Fluoro-10-(3-hydroxy-phenyl)-6-methoxy-3a-methyl-2-[3-(4-methyl-piperidin-1-yl)propyl]-3a,4,9,10-tetrahydro-2,9,10a-triaza-cyclopenta[b]fluorene-1,3-dione 328. (3aS,10R)-2-[3-(4-Acetyl-piperazin-1-yl)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione 329. (3aS,10R)-2-(3-Azepan-1-yl-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 330. (3aS,10R)-2-(3-Ethylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 331. (3aS,10R)-7-Fluoro-10-(3-hydroxy-phenyl)-2-(3-isopropylamino-propyl)-6-methoxy-3a-methyl-3a,4,9,10-tetrahydro-2,9,10a-triaza-cyclopenta[b]fluorene-1,3-dione 332. (3aS,10R)-7-Fluoro-10-(3-hydroxy-phenyl)-2-(3-isobutylamino-propyl)-6-methoxy-3a-methyl-3a,4,9,10-tetrahydro-2,9,10a-triaza-cyclopenta[b]fluorene-1,3-dione 333. (3aS,10R)-2-(3-Cyclobutylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 334. (3aS,10R)-2-(3-Allylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 335. (3aS,10R)-6-Chloro-2-(3-dimethylamino-propyl)-7-fluoro-10-(3-hydroxy-phenyl)-3a-methyl-3a,4,9,10-tetrahydro-2,9,10a-triaza-cyclopenta[b]fluorene-1,3-dione 336. (3aS,10R)-6-Chloro-2-(2-diethylamino-ethyl)-7-fluoro-10-(3-hydroxy-phenyl)-3a-methyl-3a,4,9,10-tetrahydro-2,9,10a-triaza-cyclopenta[b]fluorene-1,3-dione 337. (3aS,10R)-6-Chloro-7-fluoro-10-(3-hydroxy-phenyl)-3a-methyl-2-(2-methylamino-ethyl)-3a,4,9,10-tetrahydro-2,9,10a-triaza-cyclopenta[b]fluorene-1,3-dione 338. (3aS,10R)-6-Chloro-2-(2-ethylamino-ethyl)-7-fluoro-10-(3-hydroxy-phenyl)-3a-methyl-3a,4,9,10-tetrahydro-2,9,10a-triaza-cyclopenta[b]fluorene-1,3-dione 339. (3aS,10R)-6-Chloro-7-fluoro-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione 340. (3aS,10R)-6-Chloro-7-fluoro-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione 341. (3aS,10R)-6-Chloro-2-[2-(cyclopropylmethyl-amino)-ethyl]-7-fluoro-10-(3-hydroxy-phenyl)-3a-methyl-3a,4,9,10-tetrahydro-2,9,10a-triaza-cyclopenta[b]fluorene-1,3-dione 342. (3aS,10R)-6-Chloro-7-fluoro-2-[2-(2-hydroxy-ethylamino)-ethyl]-10-(3-hydroxy-phenyl)-3a-methyl-3a,4,9,10-tetrahydro-2,9,10a-triaza-cyclopenta[b]fluorene-1,3-dione 343. (3aS,10R)-6-Chloro-7-fluoro-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione 344. (3aS,10R)-6-Chloro-2-(2-cyclobutylamino-ethyl)-7-fluoro-10-(3-hydroxy-phenyl)-3a-methyl-3a,4,9,10-tetrahydro-2,9,10a-triaza-cyclopenta[b]fluorene-1,3-dione 345. (3aS,10R)-2-(2-tert-Butylamino-ethyl)-6-chloro-7-fluoro-10-(3-hydroxy-phenyl)-3a-methyl-3a,4,9,10-tetrahydro-2,9,10a-triaza-cyclopenta[b]fluorene-1,3-dione 346. (3aS,10R)-2-(2-Allylamino-ethyl)-6-chloro-7-fluoro-10-(3-hydroxy-phenyl)-3a-methyl-3a,4,9,10-tetrahydro-2,9,10a-triaza-cyclopenta[b]fluorene-1,3-dione 347. (3aS,10R)-6-Chloro-2-[2-(ethyl-methyl-amino)-ethyl]-7-fluoro-10-(3-hydroxy-phenyl)-3a-methyl-3a,4,9,10-tetrahydro-2,9,10a-triaza-cyclopenta[b]fluorene-1,3-dione 348. (3aS,10R)-6-Chloro-7-fluoro-2-{2-[(2-hydroxy-ethyl)-methyl-amino]-ethyl}-10-(3-hydroxyphenyl)-3a-methyl-3a,4,9,10-tetrahydro-2,9,10a-triaza-cyclopenta[b]fluorene-1,3-dione 349. (3aS,10R)-6-Chloro-2-{2-[ethyl-(2-hydroxy-ethyl)-amino]-ethyl}-7-fluoro-10-(3-hydroxy-phenyl)-3a-methyl-3a,4,9,10-tetrahydro-2,9,10a-triaza-cyclopenta[b]fluorene-1,3-dione 350. (3aS,10R)-6-Chloro-2-{2-[ethyl-(2-methoxy-ethyl)-amino]-ethyl}-7-fluoro-10-(3-hydroxy-phenyl)-3a-methyl-3a,4,9,10-tetrahydro-2,9,10a-triaza-cyclopenta[b]fluorene-1,3-dione 351. (3aS,10R)-6-Chloro-7-fluoro-10-(3-hydroxy-phenyl)-3a-methyl-2-[2-(methyl-prop-2-ynyl-amino)ethyl]-3a,4,9,10-tetrahydro-2,9,10a-triaza-cyclopenta[b]fluorene-1,3-dione 352. (3aS,10R)-6-Chloro-7-fluoro-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione 353. (3aS,10R)-6-Chloro-7-fluoro-10-(3-hydroxy-phenyl)-3a-methyl-2-(2-morpholin-4-yl-ethyl)-3a,4,9,10-tetrahydro-2,9,10a-triaza-cyclopenta[b]fluorene-1,3-dione 354. (3aS,10R)-6-Chloro-7-fluoro-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione 355. (3aS,10R)-6-Chloro-2-[2-(2,5-dihydro-pyrrol-1-yl)-ethyl]-7-fluoro-10-(3-hydroxy-phenyl)-3a-methyl-3a,4,9,10-tetrahydro-2,9,10a-triaza-cyclopenta[b]fluorene-1,3-dione 356. (3aS,10R)-6-Chloro-7-fluoro-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione 357. (3aS,10R)-6-Chloro-7-fluoro-10-(3-hydroxy-phenyl)-3a-methyl-2-[2-(4-methyl-piperidin-1-yl)ethyl]-3a,4,9,10-tetrahydro-2,9,10a-triaza-cyclopenta[b]fluorene-1,3-dione 358. (3aS,10R)-6-Chloro-2-[2-(3,6-dihydro-2H-pyridin-1-yl)-ethyl]-7-fluoro-10-(3-hydroxy-phenyl)-3a-methyl-3a,4,9,10-tetrahydro-2,9,10a-triaza-cyclopenta[b]fluorene-1,3-dione 359. (3aS,10R)-6-Chloro-7-fluoro-10-(3-hydroxy-phenyl)-3a-methyl-2-[2-(4-methyl-piperazin-1-yl)ethyl]-3a,4,9,10-tetrahydro-2,9,10a-triaza-cyclopenta[b]fluorene-1,3-dione 360. (3aS,10R)-2-[2-(4-Acetyl-piperazin-1-yl)-ethyl]-6-chloro-7-fluoro-10-(3-hydroxy-phenyl)-3a-methyl-3a,4,9,10-tetrahydro-2,9,10a-triaza-cyclopenta[b]fluorene-1,3-dione 361. (3aS,10R)-2-(2-Azepan-1-yl-ethyl)-6-chloro-7-fluoro-10-(3-hydroxy-phenyl)-3a-methyl-3a,4,9,10-tetrahydro-2,9,10a-triaza-cyclopenta[b]fluorene-1,3-dione 362. (3aS,10R)-2-[2-(Allyl-methyl-amino)-ethyl]-6-chloro-7-fluoro-10-(3-hydroxy-phenyl)-3a-methyl-3a,4,9,10-tetrahydro-2,9,10a-triaza-cyclopenta[b]fluorene-1,3-dione 363. (3aS,10R)-2-(3-Allylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione 364. (3aS,10R)-2-[3-(Ethyl-methyl-amino)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione 365. (3aS,10R)-2-{3-[Ethyl-(2-methoxy-ethyl)-amino]-propyl}-5-fluoro-10-(3-hydroxy-phenyl)-6-methoxy-3a-methyl-3a,4,9,10-tetrahydro-2,9,10a-triaza-cyclopenta[b]fluorene-1,3-dione 366. (3aS,10R)-5-Fluoro-10-(3-hydroxy-phenyl)-6-methoxy-3a-methyl-2-(3-piperidin-1-yl-propyl)-3a,4,9,10-tetrahydro-2,9,10a-triaza-cyclopenta[b]fluorene-1,3-dione
367. (3aS,10R)-5-Fluoro-10-(3-hydroxy-phenyl)-6-methoxy-3a-methyl-2-[3-(4-methyl-piperidin-1-yl)propyl]-3a,4,9,10-tetrahydro-2,9,10a-triaza-cyclopenta[b]fluorene-1,3-dione
368. (3aS,10R)-2-[3-(3,6-Dihydro-2H-pyridin-1-yl)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
369. (3aS,10R)-6-Bromo-2-(3-cyclobutylamino-propyl)-10-(3-hydroxy-phenyl)-3a-methyl-3a,4,9,10-tetrahydro-2,9,10a-triaza-cyclopenta[b]fluorene-1,3-dione
370. (3aS,10R)-6-Bromo-2-{3-[(2-hydroxy-ethyl)-methyl-amino]-propyl}-10-(3-hydroxy-phenyl)-3a-methyl-3a,4,9,10-tetrahydro-2,9,10a-triaza-cyclopenta[b]fluorene-1,3-dione
371. (3aS,10R)-2-[3-(Allyl-methyl-amino)-propyl]-6-bromo-10-(3-hydroxy-phenyl)-3a-methyl-3a,4,9,10-tetrahydro-2,9,10a-triaza-cyclopenta[b]fluorene-1,3-dione
372. (3aS,10R)-6-Bromo-10-(3-hydroxy-phenyl)-3a-methyl-2-[3-(methyl-prop-2-ynyl-amino)-propyl]-3a,4,9,10-tetrahydro-2,9,10a-triaza-cyclopenta[b]fluorene-1,3-dione
373. (3aS,10R)-6-Bromo-10-(3-hydroxy-phenyl)-3a-methyl-2-(3-piperidin-1-yl-propyl)-3a,4,9,10-tetrahydro-2,9,10a-triaza-cyclopenta[b]fluorene-1,3-dione
374. (3aS,10R)-2-(3-Azepan-1-yl-propyl)-6-bromo-10-(3-hydroxy-phenyl)-3a-methyl-3a,4,9,10-tetrahydro-2,9,10a-triaza-cyclopenta[b]fluorene-1,3-dione
375. (3aS,10R)-6-Bromo-10-(3-hydroxy-phenyl)-3a-methyl-2-[3-(4-methyl-piperazin-1-yl)-propyl]-3a,4,9,10-tetrahydro-2,9,10a-triaza-cyclopenta[b]fluorene-1,3-dione
376. (3aS,10R)-6-Bromo-2-[2-(cyclopropylmethyl-amino)-ethyl]-10-(3-hydroxy-phenyl)-3a-methyl-3a,4,9,10-tetrahydro-2,9,10a-triaza-cyclopenta[b]fluorene-1,3-dione
377. (3aS,10R)-6-Bromo-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione
378. (3aS,10R)-6-Bromo-2-(2-tert-butylamino-ethyl)-10-(3-hydroxy-phenyl)-3a-methyl-3a,4,9,10-tetrahydro-2,9,10a-triaza-cyclopenta[b]fluorene-1,3-dione
379. (3aS,10R)-6-Bromo-2-{2-[ethyl-(2-hydroxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione
380. (3aS,10R)-6-Bromo-2-{2-[ethyl-(2-methoxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione
381. (3aS,10R)-2-[2-(Allyl-methyl-amino)-ethyl]-6-bromo-10-(3-hydroxy-phenyl)-3a-methyl-3a,4,9,10-tetrahydro-2,9,10a-triaza-cyclopenta[b]fluorene-1,3-dione
382. (3aS,10R)-6-Bromo-10-(3-hydroxy-phenyl)-3a-methyl-2-[2-(methyl-prop-2-ynyl-amino)-ethyl]-3a,4,9,10-tetrahydro-2,9,10a-triaza-cyclopenta[b]fluorene-1,3-dione
383. (3aS,10R)-2-(2-Allylamino-ethyl)-6-bromo-10-(3-hydroxy-phenyl)-3a-methyl-3a,4,9,10-tetrahydro-2,9,10a-triaza-cyclopenta[b]fluorene-1,3-dione
384. (3aS,10R)-6-Bromo-2-{2-[(2-hydroxy-ethyl)-methyl-amino]-ethyl}-10-(3-hydroxy-phenyl)-3a-methyl-3a,4,9,10-tetrahydro-2,9,10a-triaza-cyclopenta[b]fluorene-1,3-dione
385. (3aS,10R)-6-Bromo-2-(2-diethylamino-ethyl)-10-(3-hydroxy-phenyl)-3a-methyl-3a,4,9,10-tetrahydro-2,9,10a-triaza-cyclopenta[b]fluorene-1,3-dione
386. (3aS,10R)-6-Bromo-10-(3-hydroxy-phenyl)-3a-methyl-2-[2-(4-methyl-piperazin-1-yl)-ethyl]-3a,4,9,10-tetrahydro-2,9,10a-triaza-cyclopenta[b]fluorene-1,3-dione
387. (3aS,10R)-2-[2-(4-Acetyl-piperazin-1-yl)-ethyl]-6-bromo-10-(3-hydroxy-phenyl)-3a-methyl-3a,4,9,10-tetrahydro-2,9,10a-triaza-cyclopenta[b]fluorene-1,3-dione
388. (3aS,10R)-6-Bromo-10-(3-hydroxy-phenyl)-3a-methyl-2-(2-morpholin-4-yl-ethyl)-3a,4,9,10-tetrahydro-2,9,10a-triaza-cyclopenta[b]fluorene-1,3-dione
389. (3aS,10R)-6-Bromo-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione
390. (3aS,10R)-6-Bromo-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione
391. (3aS,10R)-6-Bromo-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione
392. (3aS,10R)-6-Chloro-10-(3-hydroxy-phenyl)-2-(3-isopropylamino-propyl)-3a-methyl-3a,4,9,10-tetrahydro-2,9,10a-triaza-cyclopenta[b]fluorene-1,3-dione
393. (3aS,10R)-6-Bromo-2-(2-ethylamino-ethyl)-10-(3-hydroxy-phenyl)-3a-methyl-3a,4,9,10-tetrahydro-2,9,10a-triaza-cyclopenta[b]fluorene-1,3-dione
394. (3aS,10R)-6-Bromo-10-(3-hydroxy-phenyl)-3a-methyl-2-(2-methylamino-ethyl)-3a,4,9,10-tetrahydro-2,9,10a-triaza-cyclopenta[b]fluorene-1,3-dione
395. (3aS,10R)-6-Bromo-2-[2-(3,6-dihydro-2H-pyridin-1-yl)-ethyl]-10-(3-hydroxy-phenyl)-3a-methyl-3a,4,9,10-tetrahydro-2,9,10a-triaza-cyclopenta[b]fluorene-1,3-dione
396. (3aS,10R)-2-(2-Azepan-1-yl-ethyl)-6-bromo-10-(3-hydroxy-phenyl)-3a-methyl-3a,4,9,10-tetrahydro-2,9,10a-triaza-cyclopenta[b]fluorene-1,3-dione
397. (3aS,10R)-6-Chloro-2-{3-[ethyl-(2-methoxy-ethyl)-amino]-propyl}-10-(3-hydroxy-phenyl)-3a-methyl-3a,4,9,10-tetrahydro-2,9,10a-triaza-cyclopenta[b]fluorene-1,3-dione
398. (3aS,10R)-2-(2-Azepan-1-yl-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
399. (3aS,10R)-2-[2-(4-Acetyl-piperazin-1-yl)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
400. (3aS,10R)-5-Fluoro-10-(3-hydroxy-phenyl)-6-methoxy-3a-methyl-2-[2-(4-methyl-piperazin-1-yl)ethyl]-3a,4,9,10-tetrahydro-2,9,10a-triaza-cyclopenta[b]fluorene-1,3-dione
401. (3aS,10R)-2-[2-(3,6-Dihydro-2H-pyridin-1-yl)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
402. (3aS,10R)-5-Fluoro-10-(3-hydroxy-phenyl)-6-methoxy-3a-methyl-2-[2-(4-methyl-piperidin-1-yl)ethyl]-3a,4,9,10-tetrahydro-2,9,10a-triaza-cyclopenta[b]fluorene-1,3-dione
403. (3aS,10R)-5-Fluoro-10-(3-hydroxy-phenyl)-6-methoxy-3a-methyl-2-(2-piperidin-1-yl-ethyl)-3a,4,9,10-tetrahydro-2,9,10a-triaza-cyclopenta[b]fluorene-1,3-dione
404. (3aS,10R)-2-[2-(2,5-Dihydro-pyrrol-1-yl)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione 405. (3aS,10R)-5-Fluoro-10-(3-hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione
406. (3aS,10R)-5-Fluoro-10-(3-hydroxy-phenyl)-6-methoxy-3a-methyl-2-(2-methylamino-ethyl)-3a,4,9,10-tetrahydro-2,9,10a-triaza-cyclopenta[b]fluorene-1,3-dione
407. (3aS,10R)-2-(2-Ethylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
408. (3aS,10R)-5-Fluoro-10-(3-hydroxy-phenyl)-2-(2-isopropylamino-ethyl)-6-methoxy-3a-methyl-3a,4,9,10-tetrahydro-2,9,10a-triaza-cyclopenta[b]fluorene-1,3-dione
409. (3aS,10R)-5-Fluoro-10-(3-hydroxy-phenyl)-2-(2-isobutylamino-ethyl)-6-methoxy-3a-methyl-3a,4,9,10-tetrahydro-2,9,10a-triaza-cyclopenta[b]fluorene-1,3-dione
410. (3aS,10R)-2-[2-(Cyclopropylmethyl-amino)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
411. (3aS,10R)-2-[2-(2,5-Dihydro-pyrrol-1-yl)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
412. (3aS,10R)-5-Fluoro-10-(3-hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione
413. (3aS,10R)-2-(2-Cyclobutylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
414. (3aS,10R)-2-(2-tert-Butylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
415. (3aS,1R)-2-(2-Allylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
416. (3aS,10R)-5-Fluoro-10-(3-hydroxy-phenyl)-6-methoxy-3a-methyl-2-(2-prop-2-ynylamino-ethyl)-3a,4,9,10-tetrahydro-2,9,10a-triaza-cyclopenta[b]fluorene-1,3-dione
417. (3aS,10R)-2-(2-Dimethylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
418. (3aS,10R)-2-[2-(Ethyl-methyl-amino)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
419. (3aS,10R)-5-Fluoro-2-{2-[(2-hydroxy-ethyl)-methyl-amino]-ethyl}-10-(3-hydroxy-phenyl)-6-methoxy-3a-methyl-3a,4,9,10-tetrahydro-2,9,10a-triaza-cyclopenta[b]fluorene-1,3-dione
420. (3aS,10R)-2-(2-Diethylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
421. (3aS,10R)-2-{2-[Ethyl-(2-hydroxy-ethyl)-amino]-ethyl}-5-fluoro-10-(3-hydroxy-phenyl)-6-methoxy-3a-methyl-3a,4,9,10-tetrahydro-2,9,10a-triaza-cyclopenta[b]fluorene-1,3-dione
422. (3aS,10R)-2-{2-[Ethyl-(2-methoxy-ethyl)-amino]-ethyl}-5-fluoro-10-(3-hydroxy-phenyl)-6-methoxy-3a-methyl-3a,4,9,10-tetrahydro-2,9,10a-triaza-cyclopenta[b]fluorene-1,3-dione
423. (3aS,10R)-2-[2-(Allyl-methyl-amino)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
424. (3aS,10R)-5-Fluoro-10-(3-hydroxy-phenyl)-6-methoxy-3a-methyl-2-[2-(methyl-prop-2-ynylamino)-ethyl]-3a,4,9,10-tetrahydro-2,9,10a-triaza-cyclopenta[b]fluorene-1,3-dione
425. (3aS,10R)-5-Fluoro-10-(3-hydroxy-phenyl)-2-[2-(isopropyl-methyl-amino)-ethyl]-6-methoxy-3a-methyl-3a,4,9,10-tetrahydro-2,9,10a-triaza-cyclopenta[b]fluorene-1,3-dione
426. (3aS,10R)-2-(2-Cyclobutylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
427. (3aS,10R)-5-Fluoro-10-(3-hydroxy-phenyl)-6-methoxy-3a-methyl-2-(3-methylamino-propyl)-3a,4,9,10-tetrahydro-2,9,10a-triaza-cyclopenta[b]fluorene-1,3-dione
428. (3aS,10R)-2-(3-Ethylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
429. (3aS,10R)-5-Fluoro-10-(3-hydroxy-phenyl)-2-(3-isopropylamino-propyl)-6-methoxy-3a-methyl-3a,4,9,10-tetrahydro-2,9,10a-triaza-cyclopenta[b]fluorene-1,3-dione
430. (3aS,10R)-5-Fluoro-10-(3-hydroxy-phenyl)-2-(3-isobutylamino-propyl)-6-methoxy-3a-methyl-3a,4,9,10-tetrahydro-2,9,10a-triaza-cyclopenta[b]fluorene-1,3-dione
431. (3aS,10R)-2-[3-(Cyclopropylmethyl-amino)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
432. (3aS,10R)-5-Fluoro-2-[3-(2-hydroxy-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione
433. (3aS,10R)-5-Fluoro-10-(3-hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione
434. (3aS,10R)-2-(3-Cyclopropylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
435. (3aS,10R)-2-(3-Cyclobutylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
436. (3aS,10R)-2-(3-tert-Butylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
437. (3aS,10R)-5-Fluoro-10-(3-hydroxy-phenyl)-6-methoxy-3a-methyl-2-(3-prop-2-ynylamino-propyl)-3a,4,9,10-tetrahydro-2,9,10a-triaza-cyclopenta[b]fluorene-1,3-dione
438. (3aS,10R)-2-(3-Dimethylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
439. (3aS,10R)-5-Fluoro-2-{3-[(2-hydroxy-ethyl)-methyl-amino]-propyl}-10-(3-hydroxy-phenyl)-6-methoxy-3a-methyl-3a,4,9,10-tetrahydro-2,9,10a-triaza-cyclopenta[b]fluorene-1,3-dione
440. (3aS,10R)-2-(3-Diethylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
441. (3aS,10R)-2-{3-[Ethyl-(2-hydroxy-ethyl)-amino]-propyl}-5-fluoro-10-(3-hydroxy-phenyl)-6-methoxy-3a-methyl-3a,4,9,10-tetrahydro-2,9,10a-triaza-cyclopenta[b]fluorene-1,3-dione 442. (3aS,10R)-2-[3-(Allyl-methyl-amino)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
443. (3aS,10R)-5-Fluoro-10-(3-hydroxy-phenyl)-6-methoxy-3a-methyl-2-[3-(methyl-prop-2-ynylamino)-propyl]-3a,4,9,10-tetrahydro-2,9,10a-triaza-cyclopenta[b]fluorene-1,3-dione
444. (3aS,10R)-5-Fluoro-10-(3-hydroxy-phenyl)-2-[3-(isopropyl-methyl-amino)-propyl]-6-methoxy-3a-methyl-3a,4,9,10-tetrahydro-2,9,10a-triaza-cyclopenta[b]fluorene-1,3-dione
445. (3aS,10R)-5-Fluoro-10-(3-hydroxy-phenyl)-6-methoxy-3a-methyl-2-(3-morpholin-4-yl-propyl)-3a,4,9,10-tetrahydro-2,9,10a-triaza-cyclopenta[b]fluorene-1,3-dione
446. (3aS,10R)-5-Fluoro-10-(3-hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione
447. (3aS,10R)-2-[3-(2,5-Dihydro-pyrrol-1-yl)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
448. (3aS,10R)-5-Fluoro-10-(3-hydroxy-phenyl)-6-methoxy-3a-methyl-2-[3-(4-methyl-piperazin-1-yl)propyl]-3a,4,9,10-tetrahydro-2,9,10a-triaza-cyclopenta[b]fluorene-1,3-dione
449. (3aS,10R)-2-[3-(4-Acetyl-piperazin-1-yl)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
450. (3aS,10R)-2-(3-Azepan-1-yl-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
451. (3aS,10R)-2-{2-[Ethyl-(2-hydroxy-ethyl)-amino]-ethyl}-7-fluoro-10-(3-hydroxy-phenyl)-6-methoxy-3a-methyl-3a,4,9,10-tetrahydro-2,9,10a-triaza-cyclopenta[b]fluorene-1,3-dione
452. (3aS,10R)-2-[2-(Allyl-methyl-amino)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
453. (3aS,10R)-6-(1,1-Difluoro-methoxy)-2-{3-[(2-hydroxy-ethyl)-methyl-amino]-propyl}-10-(3-hydroxy-phenyl)-3a-methyl-3a,4,9,10-tetrahydro-2,9,10a-triaza-cyclopenta[b]fluorene-1,3-dione
454. (3aS,10R)-2-{2-[Ethyl-(2-methoxy-ethyl)-amino]-ethyl}-7-fluoro-10-(3-hydroxy-phenyl)-6-methoxy-3a-methyl-3a,4,9,10-tetrahydro-2,9,10a-triaza-cyclopenta[b]fluorene-1,3-dione
455. (3aS,10R)-7-Fluoro-10-(3-hydroxy-phenyl)-6-methoxy-3a-methyl-2-[2-(methyl-prop-2-ynylamino)-ethyl]-3a,4,9,10-tetrahydro-2,9,10a-triaza-cyclopenta[b]fluorene-1,3-dione
456. (3aS,10R)-6-Chloro-7-fluoro-10-(3-hydroxy-phenyl)-3a-methyl-2-(3-methylamino-propyl)-3a,4,9,10-tetrahydro-2,9,10a-triaza-cyclopenta[b]fluorene-1,3-dione
457. (3aS,10R)-6-Chloro-2-(3-ethylamino-propyl)-7-fluoro-10-(3-hydroxy-phenyl)-3a-methyl-3a,4,9,10-tetrahydro-2,9,10a-triaza-cyclopenta[b]fluorene-1,3-dione
458. (3aS,10R)-6-Chloro-7-fluoro-10-(3-hydroxy-phenyl)-2-(3-isopropylamino-propyl)-3a-methyl-3a,4,9,10-tetrahydro-2,9,10a-triaza-cyclopenta[b]fluorene-1,3-dione
459. (3aS,10R)-6-Chloro-7-fluoro-10-(3-hydroxy-phenyl)-2-(3-isobutylamino-propyl)-3a-methyl-3a,4,9,10-tetrahydro-2,9,10a-triaza-cyclopenta[b]fluorene-1,3-dione
460. (3aS,10R)-6-Chloro-2-[3-(cyclopropylmethyl-amino)-propyl]-7-fluoro-10-(3-hydroxy-phenyl)-3a-methyl-3a,4,9,10-tetrahydro-2,9,10a-triaza-cyclopenta[b]fluorene-1,3-dione
461. (3aS,10R)-6-Chloro-7-fluoro-2-[3-(2-hydroxy-ethylamino)-propyl]-10-(3-hydroxy-phenyl)-3a-methyl-3a,4,9,10-tetrahydro-2,9,10a-triaza-cyclopenta[b]fluorene-1,3-dione
462. (3aS,10R)-6-Chloro-7-fluoro-10-(3-hydroxy-phenyl)-2-[3-(2-methoxy-ethylamino)-propyl]-3a-methyl-3a,4,9,10-tetrahydro-2,9,10a-triaza-cyclopenta[b]fluorene-1,3-dione
463. (3aS,10R)-6-Chloro-2-(3-cyclobutylamino-propyl)-7-fluoro-10-(3-hydroxy-phenyl)-3a-methyl-3a,4,9,10-tetrahydro-2,9,10a-triaza-cyclopenta[b]fluorene-1,3-dione
464. (3aS,10R)-2-(3-tert-Butylamino-propyl)-6-chloro-7-fluoro-10-(3-hydroxy-phenyl)-3a-methyl-3a,4,9,10-tetrahydro-2,9,10a-triaza-cyclopenta[b]fluorene-1,3-dione
465. (3aS,10R)-2-(3-Allylamino-propyl)-6-chloro-7-fluoro-10-(3-hydroxy-phenyl)-3a-methyl-3a,4,9,10-tetrahydro-2,9,10a-triaza-cyclopenta[b]fluorene-1,3-dione
466. (3aS,10R)-6-Chloro-7-fluoro-10-(3-hydroxy-phenyl)-3a-methyl-2-(3-prop-2-ynylamino-propyl)-3a,4,9,10-tetrahydro-2,9,10a-triaza-cyclopenta[b]fluorene-1,3-dione
467. (3aS,10R)-6-Chloro-2-[3-(ethyl-methyl-amino)-propyl]-7-fluoro-10-(3-hydroxy-phenyl)-3a-methyl-3a,4,9,10-tetrahydro-2,9,10a-triaza-cyclopenta[b]fluorene-1,3-dione
468. (3aS,10R)-6-Chloro-7-fluoro-2-{3-[(2-hydroxy-ethyl)-methyl-amino]-propyl}-10-(3-hydroxyphenyl)-3a-methyl-3a,4,9,10-tetrahydro-2,9,10a-triaza-cyclopenta[b]fluorene-1,3-dione
469. (3aS,10R)-6-Chloro-2-(3-diethylamino-propyl)-7-fluoro-10-(3-hydroxy-phenyl)-3a-methyl-3a,4,9,10-tetrahydro-2,9,10a-triaza-cyclopenta[b]fluorene-1,3-dione
470. (3aS,10R)-6-Chloro-2-{3-[ethyl-(2-hydroxy-ethyl)-amino]-propyl}-7-fluoro-10-(3-hydroxy-phenyl)-3a-methyl-3a,4,9,10-tetrahydro-2,9,10a-triaza-cyclopenta[b]fluorene-1,3-dione
471. (3aS,10R)-6-Chloro-2-{3-[ethyl-(2-methoxy-ethyl)-amino]-propyl}-7-fluoro-10-(3-hydroxyphenyl)-3a-methyl-3a,4,9,10-tetrahydro-2,9,10a-triaza-cyclopenta[b]fluorene-1,3-dione
472. (3aS,10R)-2-[3-(Allyl-methyl-amino)-propyl]-6-chloro-7-fluoro-10-(3-hydroxy-phenyl)-3a-methyl-3a,4,9,10-tetrahydro-2,9,10a-triaza-cyclopenta[b]fluorene-1,3-dione
473. (3aS,10R)-6-Chloro-7-fluoro-10-(3-hydroxy-phenyl)-3a-methyl-2-[3-(methyl-prop-2-ynyl-amino)propyl]-3a,4,9,10-tetrahydro-2,9,10a-triaza-cyclopenta[b]fluorene-1,3-dione
474. (3aS,10R)-6-Chloro-7-fluoro-10-(3-hydroxy-phenyl)-2-[3-(isopropyl-methyl-amino)-propyl]-3a-methyl-3a,4,9,10-tetrahydro-2,9,10a-triaza-cyclopenta[b]fluorene-1,3-dione 475. (3aS,10R)-6-Chloro-7-fluoro-10-(3-hydroxy-phenyl)-3a-methyl-2-(3-morpholin-4-yl-propyl)-3a,4,9,10-tetrahydro-2,9,10a-triaza-cyclopenta[b]fluorene-1,3-dione
476. (3aS,10R)-6-Chloro-7-fluoro-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione
477. (3aS,10R)-6-Chloro-2-[3-(2,5-dihydro-pyrrol-1-yl)-propyl]-7-fluoro-10-(3-hydroxy-phenyl)-3a-methyl-3a,4,9,10-tetrahydro-2,9,10a-triaza-cyclopenta[b]fluorene-1,3-dione
478. (3aS,10R)-6-Chloro-7-fluoro-10-(3-hydroxy-phenyl)-3a-methyl-2-(3-piperidin-1-yl-propyl)-3a,4,9,10-tetrahydro-2,9,10a-triaza-cyclopenta[b]fluorene-1,3-dione
479. (3aS,10R)-6-Chloro-7-fluoro-10-(3-hydroxy-phenyl)-3a-methyl-2-[3-(4-methyl-piperidin-1-yl)propyl]-3a,4,9,10-tetrahydro-2,9,10a-triaza-cyclopenta[b]fluorene-1,3-dione
480. (3aS,10R)-6-Chloro-2-[3-(3,6-dihydro-2H-pyridin-1-yl)-propyl]-7-fluoro-10-(3-hydroxy-phenyl)-3a-methyl-3a,4,9,10-tetrahydro-2,9,10a-triaza-cyclopenta[b]fluorene-1,3-dione
481. (3aS,10R)-6-Chloro-7-fluoro-10-(3-hydroxy-phenyl)-3a-methyl-2-[3-(4-methyl-piperazin-1-yl)propyl]-3a,4,9,10-tetrahydro-2,9,10a-triaza-cyclopenta[b]fluorene-1,3-dione
482. (3aS,10R)-2-[3-(4-Acetyl-piperazin-1-yl)-propyl]-6-chloro-7-fluoro-10-(3-hydroxy-phenyl)-3a-methyl-3a,4,9,10-tetrahydro-2,9,10a-triaza-cyclopenta[b]fluorene-1,3-dione
483. (3aS,10R)-2-(3-Azepan-1-yl-propyl)-6-chloro-7-fluoro-10-(3-hydroxy-phenyl)-3a-methyl-3a,4,9,10-tetrahydro-2,9,10a-triaza-cyclopenta[b]fluorene-1,3-dione
484. (3aS,10R)-6-Bromo-10-(3-hydroxy-phenyl)-3a-methyl-2-(3-morpholin-4-yl-propyl)-3a,4,9,10-tetrahydro-2,9,10a-triaza-cyclopenta[b]fluorene-1,3-dione
485. (3aS,10R)-6-Bromo-10-(3-hydroxy-phenyl)-3a-methyl-2-[3-(4-methyl-piperidin-1-yl)-propyl]-3a,4,9,10-tetrahydro-2,9,10a-triaza-cyclopenta[b]fluorene-1,3-dione
486. (3aS,10R)-6-Bromo-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione
487. (3aS,10R)-6-Bromo-10-(3-hydroxy-phenyl)-3a-methyl-2-[2-(4-methyl-piperidin-1-yl)-ethyl]-3a,4,9,10-tetrahydro-2,9,10a-triaza-cyclopenta[b]fluorene-1,3-dione
488. (3aS,10R)-6-Chloro-2-[3-(cyclopropylmethyl-amino)-propyl]-10-(3-hydroxy-phenyl)-3a-methyl-3a,4,9,10-tetrahydro-2,9,10a-triaza-cyclopenta[b]fluorene-1,3-dione
489. (3aS,10R)-2-(3-tert-Butylamino-propyl)-6-chloro-10-(3-hydroxy-phenyl)-3a-methyl-3a,4,9,10-tetrahydro-2,9,10a-triaza-cyclopenta[b]fluorene-1,3-dione and
490. (3aS,10R)-10-(3-Hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione,
and the salts thereof.

The compounds according to the invention can be prepared e.g. as described exemplarily as follows and according to the following specified reaction steps, or, particularly, in a manner as described by way of example in the following examples, or analogously or similarly thereto according to preparation procedures or synthesis strategies known to the person skilled in the art.

As shown in the synthesis route outlined in scheme 1 below, ester compounds of formula IV (particularly, the ethyl esters or, especially, methyl esters of formula IV), in which R4, R5 and R6 have the meanings given above, are condensed and cyclized in a Pictet-Spengler reaction with benzaldehydes of formula III, in which R2 and R3 have the meanings mentioned above, to give the corresponding compounds of formulae IIa and/or IIb mostly as a mixture. Said Pictet-Spengler reaction can be carried out as it is known to the skilled person or as described in the following examples, advantageously in the presence of a suitable acid as a catalyst or promotor (e.g. trifluoroacetic acid) in a suitable solvent, for example toluene or, particularly dichloromethane, at elevated temperature or room temperature.

Compounds of formula IV, in which R is methyl or ethyl, and R4, R5 and R6 have the meanings given above, are known or can be prepared analogously or similarly to known procedures or are accessible as described later.

Compounds of formula III are known or can be obtained in a known manner, for example by formylation of appropriate aromatic compounds, e.g. via hydroxymethylation and subsequent oxidation to the aldehyde, or by reduction of appropriate benzoic acid derivatives to the aldehyde.

Reaction scheme 1:

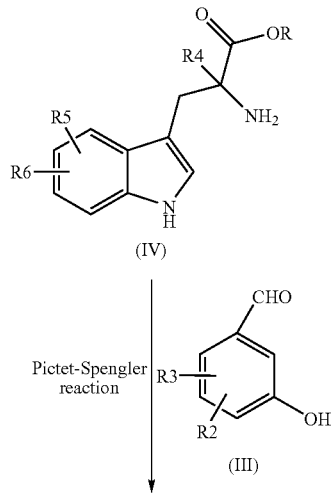

-continued

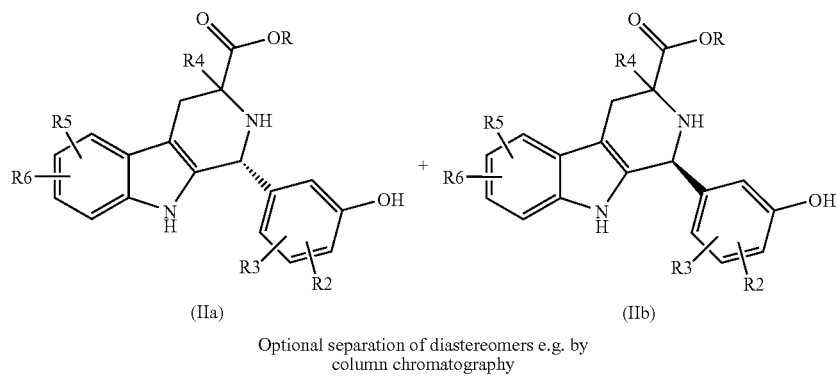

(IIa)          (IIb)

Optional separation of diastereomers e.g. by column chromatography

The compounds of formula IV can be employed in the abovementioned Pictet-Spengler reaction as racemate or enantiomerically pure compounds. Depending thereon, the mixture obtained can contain the compounds of formulae IIa and IIb as diastereomers or as diastereomeric racemates.

Said mixture can be optionally separated in a manner habitual per se to the skilled person, such as, for example, diastereomeric compounds of formulae IIa and IIb can be separated e.g. by column chromatography.

If appropriate, said mixture can be also used in the next step without further separation of the diastereoisomers. Then, separation of diastereomers can be carried out subsequently to one of the following steps.

When the compounds of formula IV are employed as racemic mixture in the abovementioned Pictet-Spengler reaction, the racemate comprising the enantiomeric compounds of formulae IIa' and IIb' can be obtained preferentially or in excess from said reaction.

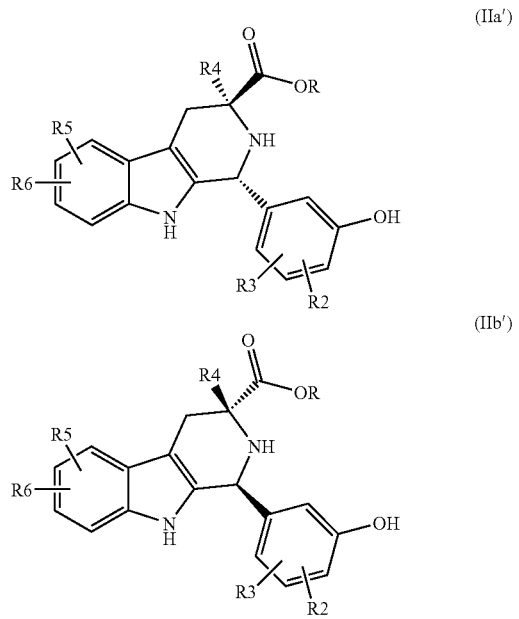

(IIa')

(IIb')

Starting from the appropriate pure enantiomers of the compounds of formula IV, corresponding compounds of either formula IIa' or formula IIb' (depending from the configuration of the starting compound of formula IV) can be obtained preferentially. Thus, e.g. when (S)-α-methyltryptophan methyl ester derivatives [i.e. (S)-2-amino-3-(1H-indol-3-yl)-2-methyl-propionic acid methyl ester derivatives] are employed in the abovementioned Pictet-Spengler reaction, corresponding compounds of formula IIa' are obtained preferentially.

Compounds of formulae IIa' and IIb' can be separated from diastereomeric compounds in a manner habitual per se to the skilled person, such as, for example, by column chromatography. Likewise, compounds of formula IIa' may be separated from enantiomeric compounds of formula IIb' by processes known to the skilled person, such as, for example, by column chromatography on chiral support material (such as described by way of example in the following examples or analogously or similarly thereto), or by means of diastereomeric salt formation of the racemic compounds with optically active acids (such as e.g. those mentioned later in this application).

Compounds of formula IIa' or IIb', e.g. in enantiomerically pure form or as racemic mixture or with corresponding diastereomers co-generated in the Pictet-Spengler reaction above, can be reacted with isocyanates of formula R1-N=C=O or with corresponding activated carbamic acid esters, such as, for example, N-hydroxysuccinimid-activated urethanes, like e.g. $H_3C$—NH—C(O)—OR, in which R is 1N-succinimidyl, in a Hydantoin synthesis as shown in reaction scheme 2 to give the corresponding desired hydantoins of formula I* (from compounds of formula IIa') or I*** (from compounds of formula IIb'). Said Hydantoin synthesis can be performed in an art-known manner or as described in the following examples, e.g. in the presence of microwaves.

Reaction scheme 2:

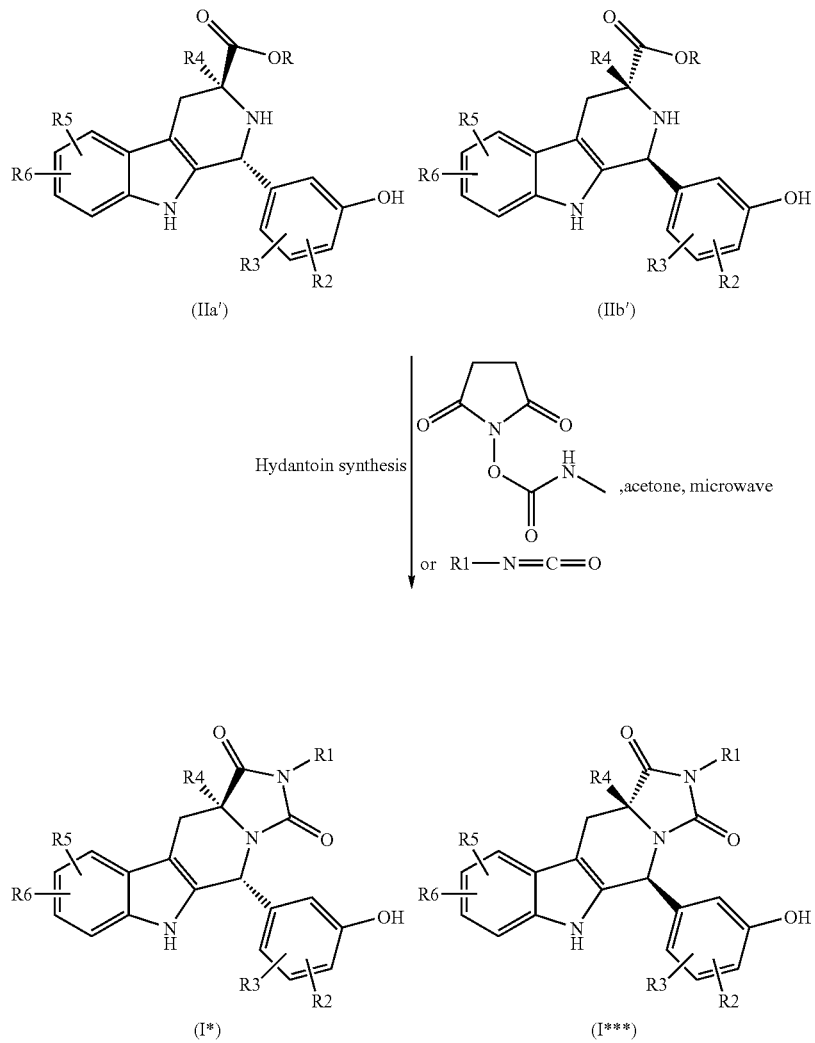

Isocyanates of formula R1-N=C=O, in which R1 has the meanings given above, are known or can be obtained analogously or similarly to known procedures. Thus, e.g. compounds of formula R1-N=C=O, in which R1 is 2-7C-alkyl substituted by —N(R111)R112, can be obtained from compounds of formula R1-N=C=O, in which R1 is 2-7C-alkyl substituted by a suitable leaving group, such as e.g. bromine, by nucleophilic substitution reaction with corresponding amines of formula —H(R111)R112 in a manner habitual per se to the skilled person or similarly as described by way of example in the following example. Yet thus, isocyanates of this invention may be obtained by substitution reaction using isocyanate salts, e.g. according the procedure given in B. Akhlaghinia, Synthesis, 2005, 1955-1958 starting from the corresponding alcohols, thiols or trimethylsilyl ethers by reaction with triphenylphosphine/2,3-dichloro-5,6-dicyanobenzoquinone/Bu$_4$NOCN in acetonitrile. Still yet thus, isocyanates of this invention may be obtained from the corresponding amine compounds by art-known isocyanate synthesis.

Alternatively, particularly when R1 is different from methyl, compounds of formula IIa' or IIb', e.g. in enantiomerically pure form or as racemic mixture or with corresponding diastereomers co-generated in the Pictet-Spengler reaction above, can be converted into the corresponding urea compounds of formula VIa' (from compounds of formula IIa') or VIb' (from compounds of formula IIb') as shown in reaction scheme 3. This urea synthesis can be carried out in a manner as it is known for the skilled person or as described in the following examples, e.g. following the reaction steps outlined in reaction scheme 4. The compounds of formula VI can be then cyclized to give the corresponding desired compounds of formula I* (from compounds of formula IIa') or I*** (from compounds of formula IIb'). This cyclization can be carried out in a manner as it is known for the skilled person or as described in the following examples.

Reaction scheme 3:

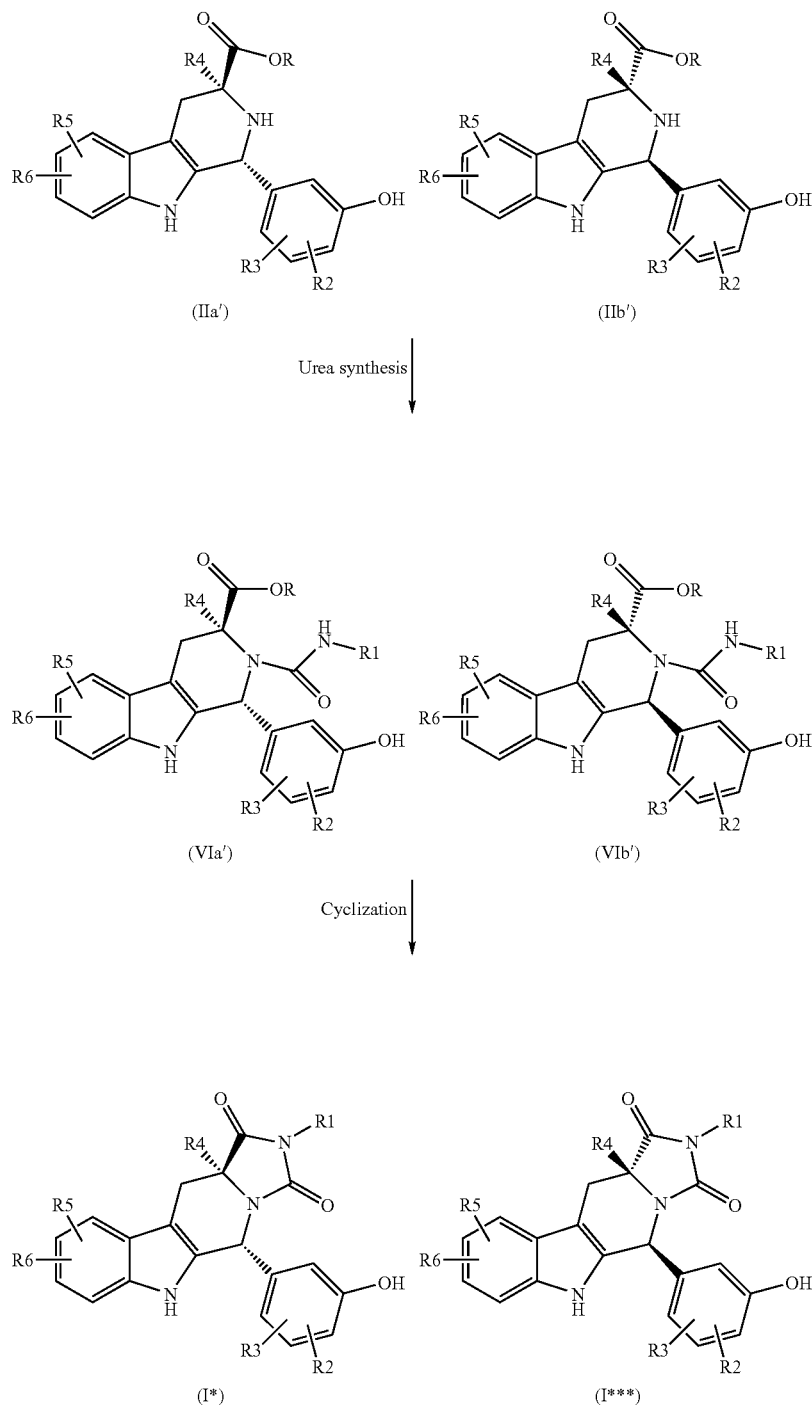

Compounds of formulae I* and I*** can be separated from diastereomeric compounds in a manner habitual per se to the skilled person, such as, for example, by column chromatography. When the compounds of formulae I* and I*** are obtained as racemic mixture, the enantiomerically pure compounds may be accessible by art-known separation techniques, such as e.g. those described above.

Compounds of formula VIa' or VIb' can be obtained from corresponding compounds of formula IIa' or IIb' as shown in reaction scheme 4 firstly by reaction with compounds of formula L-C(O)—X, in which X and L are suitable leaving groups, such as e.g. X is chlorine and L is 4-nitro-phenol, to give corresponding compounds of formula Va' or Vb', which are then reacted with amines of formula R1-NH$_2$, in which R1 has the meanings given above, to give corresponding compounds of formula VIa' or VIb'. These reactions can be carried out in a manner as it is known for the skilled person or as described in the following examples.

Reaction scheme 4:

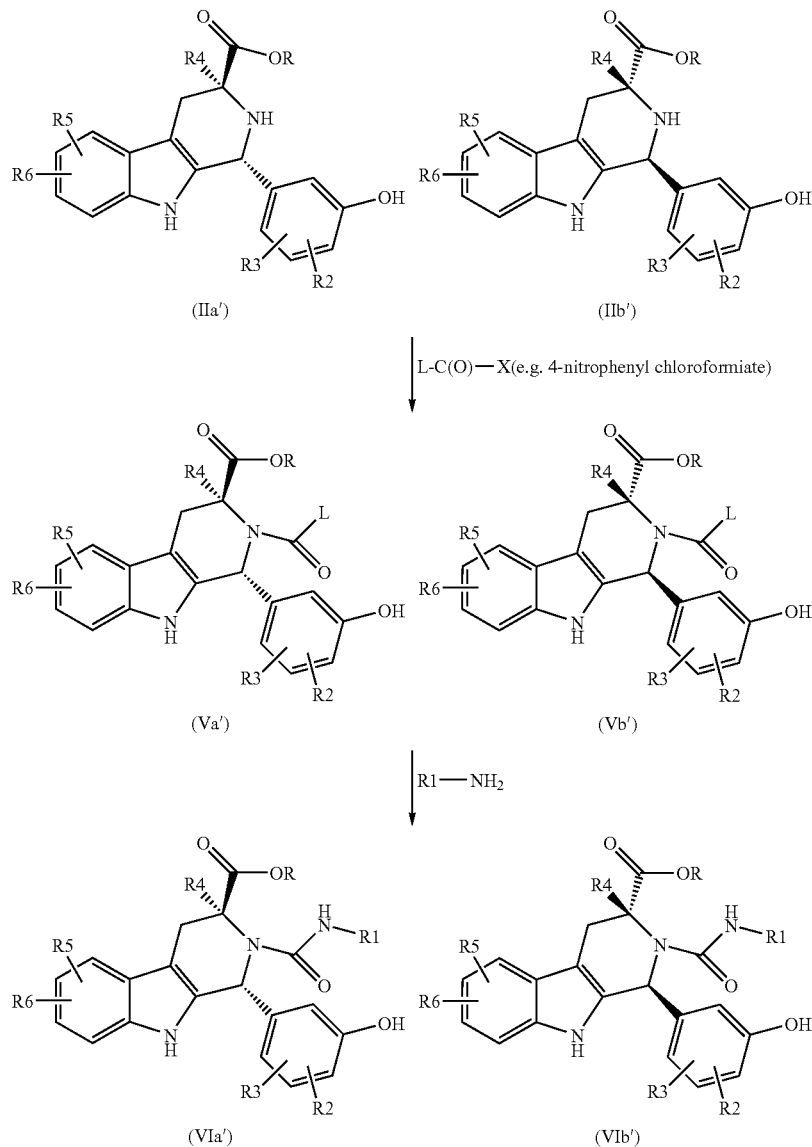

Compounds of formula I, in which R2, R3, R4, R5 and R6 have the meanings given above and R1 is 2-7C-alkyl (advantageously 2-4C-alkyl) substituted by X, in which X is a suitable leaving group, e.g. chlorine or bromine, can be reacted in a nucleophilic substitution reaction with amines of formula HN(R111)R112, in which R11 and R112 stand for the groups given above, which—if necessary—can be temporarily protected by appropriate protecting groups (such as e.g. free amino functions can be temporarily protected by the tert-butyloxycarbonyl (Boc) protecting group), to prepare corresponding compounds of formula I, in which R1 is 2-7C-alkyl substituted by —N(R111)R112. This nucleophilic substitution reaction can be carried out in a manner habitual per se for the skilled person or as described in the following examples or analogously or similarly thereto, e.g. in a suitable solvent (e.g. acetonitrile, methanol or tetrahydrofuran or the like) optionally in the presence of a suitable base or optionally in the presence of microwaves using an excess of the amine of formula HN(R111)R112 at atmospheric or elevated pressure (e.g. in a sealed container) at room temperature, at elevated temperature, at the boiling/reflux temperature or at the microwave super heated boiling temperature of the solvent(s) used.

Compounds of formula I, in which R2, R3, R4, R5 and R6 have the meanings given above and R1 is 2-7C-alkyl (advantageously 2-4C-alkyl) substituted by X, in which X is a suitable leaving group, e.g. chlorine or bromine, can be obtained by Hydantoin synthesis as described herein using the corresponding isocyanate of formula R1-NCO. In more detail, said Hydantoin synthesis is carried out in a suitable solvent (e.g. a ketone such as, when 2-bromo-ethylisocanate is used, e.g. 2-butanon, or the like) preferably at elevated temperature or at boiling/reflux temperature.

Compounds of formula IV, in which R is methyl or ethyl, and R4, R5 and R6 have the meanings given above, are accessible as shown in reaction scheme 5, and as described by way of example in the following examples, or analogously or similarly thereto.

Starting from compounds of formula X, in which R5 and R6 have the meanings mentioned above, the corresponding compounds of formula VIII can be obtained by aminomethylation reaction (Mannich reaction) customary per se to the person skilled in the art.

Compounds of formula VIII are reacted with compounds of formula IX, in which R is methyl or ethyl and R4 has the meanings given above, in a nucleophilic substitution reaction to give corresponding compounds of formula VII. Said substitution reaction can be carried out as it is known for the skilled person or as described in the following examples, or analogously or similarly thereto.

Compounds of formula VII are subjected to a reduction reaction of the nitro group to obtain corresponding amine compounds of formula VI. Said reduction reaction can be carried out as habitual per se to the skilled person, such as, for example, by catalytic hydrogenation, e.g. in the presence of a noble metal catalyst such as palladium on active carbon or, particularly, Raney nickel. Optionally, a catalytic amount of an acid, such as, for example, hydrochloric acid, can be added to the solvent. Alternatively, the reduction may be carried out using a hydrogen-producing mixture, for example, metals such as zinc, zinc-copper couple or iron with organic acids such as acetic acid or mineral acids such as hydrochloric acid.

Reaction scheme 6:

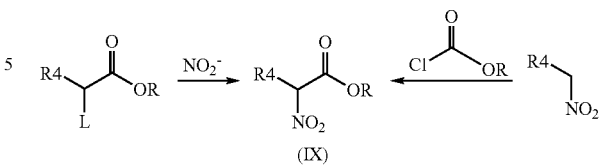

Compounds of formula IX can be prepared by reaction of compounds of formula $R4-CH_2-NO_2$, in which R4 has the meanings given above, e.g. cyclopropyl, with a chloroformic acid ester, such as e.g. described in Ram et al. Synthesis 1986, 133-135, or analogously or similarly thereto.

Alternatively, compounds of formula IX can be prepared by reaction of compounds of formula $R4-C(H)L-CO_2R$, in which L is a suitable leaving group, e.g. iodine, and R4 has the meanings given above, e.g. isopropyl, with a suitable nitrite reagent, e.g. sodium nitrite or silver nitrite, such as e.g. described in J. Am. Chem. Soc. 77, 6654 (1955), or analogously or similarly thereto.

Reaction scheme 5:

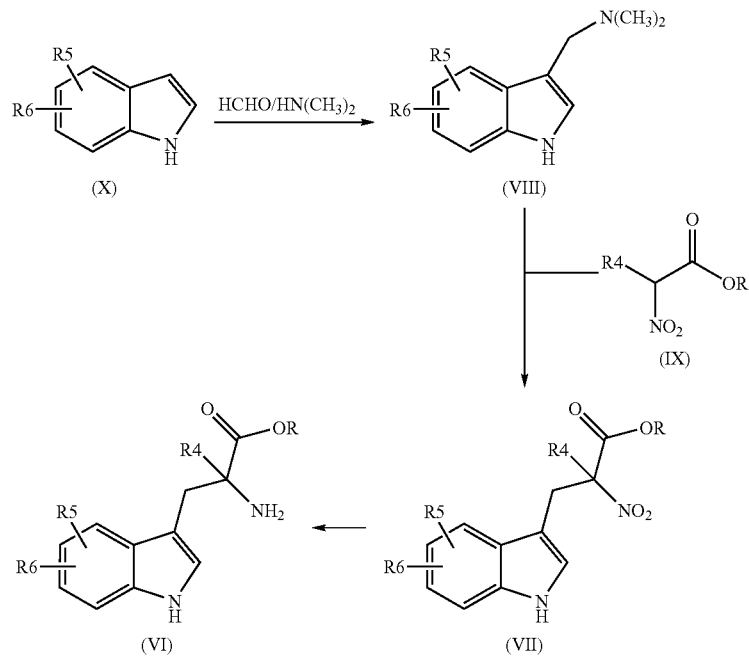

Optionally, ester compounds of formula VI can be converted into the corresponding free acids by art-known saponification reaction. Optionally, the free acids of compounds of formula VI can be also reconverted into the corresponding esters, particularly methyl esters, by art-known esterification reaction, e.g. using thionylchloride/methanol.

Compounds of formula IX are known, commercially available (such as e.g. ethyl 2-nitro-propionate or ethyl 2-nitro-butyrate) or can be obtained according to known procedures.

Methyl 2-nitro-propionate is known e.g. from H. L. Finkbeiner, G. W. Wagner J. Org. Chem. 1963, 28, 215-217).

In more detail, compounds of formula IX, in which R is methyl or ethyl and R4 has the meanings given above, can be obtained as outlined in reaction scheme 6.

Compounds of formula $R4-CH_2-NO_2$ and $R4-C(H)L-CO_2R$ are known or can be obtained analogously or similarly to known procedures (e.g. compounds of formula $R4-C(H)L-CO_2R$ can be obtained via Finkelstein reaction); such as e.g. nitromethyl-cyclopropane can be obtained as described in Helv. Chim. Acta 1982, 65, 137-161 and 2-iodo-3-methyl-butyric acid ethyl ester can be obtained from 2-bromo-3-methyl-butyric acid ethyl ester as described in Org. Lett. 1999, 1, 1419-1422, or analogously or similarly thereto.

Compounds of formula X are known or can be obtained according to known procedures or as described in the following examples or analogously or similarly thereto.

Thus, e.g. 5-methoxy-1H-indole, 5-chloro-1H-indole, 5-bromo-1H-indole, 5-fluoro-1H-indole and 5-trifluoromethyl-1H-indole are commercially available.

Compounds of formula X, which are ether compounds, are obtained from the corresponding alcohol compounds by art-known etherification reaction. Thus, e.g. compounds of formula X, in which R5 is hydroxyl, can be converted into corresponding ether compounds in a manner as described in the following examples, or analogously or similarly thereto.

Thus, e.g. compounds of formula X, in which R5 is hydroxyl, can be converted into the corresponding compounds of formula X, in which R5 is ethoxy, propoxy, isopropoxy, cyclopropylmethoxy, difluoromethoxy or trifluoromethoxy, by alkylating reaction using an appropriate alkylating reagent.

Enantiomerically pure starting compounds according to this invention may be obtained according to art-known processes, such as e.g. from the corresponding racemates according to processes as described above. Therefore enantiomerically pure tryptophans or tryptophan derivatives (e.g. ester derivatives) may be obtained, for example, by means of salt formation of the racemic compounds with optically active acids, preferably carboxylic acids (examples of optically active acids which may be mentioned in this connection, without being restricted thereto, are the enantiomeric forms of mandelic acid, tartaric acid, O,O'-dibenzoyltartaric acid, camphoric acid, quinic acid, glutamic acid, pyroglutamic acid, malic acid, camphorsulfonic acid, 3-bromocamphorsulfonic acid, α-methoxyphenylacetic acid, α-methoxy-α-trifluoromethylphenylacetic acid and 2-phenylpropionic acid), subsequent resolution of the salts [e.g. by (fractional) crystallization from a suitable solvent] and release of the desired compound from the salt; by kinetic resolution of the racemic compounds, such as by enzymatic racemate resolution, e.g. during enzymatic saponification of the corresponding racemic amino acid esters using e.g. a suitable lipase (such as e.g. in analogy to the procedure described by Houng et al. Chirality 1996, 8, 418-422); or by stereoselective amino acid synthesis, e.g. using an appropriate chiral auxiliary; or by chromatographic separation of racemic compounds on chiral separating columns.

Thus, enantiomerically pure tryptophans may be obtained, for example, as described in Tetrahedron Letters 39 (1998), 9589-9592, or analogously or similarly thereto, such as e.g. enantiomerically pure α-methyl-tryptophans, α-ethyl-tryptophans or α-isopropyl-tryptophans may be obtained as described therein starting from N-Boc-(3-bromomethyl)-indole and enantiomerically pure alanine, 2-amino-butyric acid or valine, respectively.

In more detailed example, enantiomerically pure 5-methoxy-α-methyl-tryptophane methyl ester can be obtained by chromatographic separation of the corresponding racemate on chiral separating columns, such as e.g. Daicel CHIRALPAK AD-RH or Daicel CHIRALPAK AD-H; or by means of salt formation of the corresponding racemate with optically active acids, such as e.g. mandelic acid, pyroglutamic acid or, particularly, (S,S)-di-p-anisoyl-tartaric acid, subsequent resolution of the salt [e.g. by (fractional) crystallization from a suitable solvent, such as e.g. ethyl acetate, acetone or, particularly, methanol/water] and release of the desired compound from the salt.

It is to be understood for the skilled worker, that certain compounds according to this invention may be converted into further compounds of this invention by art-known synthesis strategies and reactions habitual per se to a person of ordinary skill in the art.

Therefore, optionally, compounds of formula I can be converted into further compounds of formula I by methods known to one of ordinary skill in the art. More specifically, for example, from compounds of the formula I in which a) R113 is hydrogen, the corresponding N-alkylated compounds may obtained by reductive amination or nucleophilic substitution reaction;
b) R111 and/or R112 are hydrogen, the corresponding N-alkylated compounds may be obtained by reductive amination or nucleophilic substitution reaction.
c) R11 is chlorine or bromine, the corresponding compounds, in which R11 is —N(R111)R112, may be obtained by nucleophilic substitution reaction with amines of formula HN(R111)R112.

The methods mentioned under a) to c) can be expediently carried out analogously to the methods known to the person skilled in the art or as described by way of example in the following examples. Optionally, compounds of the formula I can be converted into their salts, or, optionally, salts of the compounds of the formula I can be converted into the free compounds. Corresponding processes are customary for the skilled person.

When one of the final steps or purification is carried out under the presence of an inorganic or organic acid (e.g. hydrochloric, trifluoroacetic, acetic or formic acid or the like), the compounds of formula I may be obtained—depending on their individual chemical nature and the individual nature of the acid used—as free base or containing said acid in an stoechiometric or non-stoechiometric quantity. The amount of the acid contained can be determined according to art-known procedures, e.g. by titration or NMR.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, $3^{rd}$ Ed.) or in "Protecting Groups (Thieme Foundations Organic Chemistry Series N Group" by P. Kocienski (Thieme Medical Publishers, 2000).

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts can be obtained by dissolving the free compound in a suitable solvent (e.g. a ketone, such as acetone, methyl ethyl ketone or methyl isobutyl ketone, an ether, such as diethyl ether, diisopropyl ether, tetrahydrofuran or dioxane, a chlorinated hydrocarbon, such as methylene chloride or chloroform, a low-molecular-weight aliphatic alcohol, such as methanol, ethanol or isopropanol, or an ester, such as ethyl acetate) which contains the desired acid or base, or to which the desired acid or base is then added. The salts can be obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art may be familiar on the basis of his/her knowledge and on the basis of those synthesis routes, which are shown and described within the description of this invention, to find other possible synthesis routes for compounds according to this invention. All these other possible synthesis routes are also part of this invention.

The present invention also relates to intermediates (including their salts, stereoisomers and salts of these stereoisomers), methods and processes, which are disclosed herein and which are useful in synthesizing compounds according to this invention. Thus, the present invention also relates to processes disclosed herein for preparing compounds according to this invention, which processes comprise one or more steps of converting and/or reacting the mentioned intermediates with the appropriate reaction partners under conditions as disclosed herein.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention as defined by the appended claims.

The following examples serve to illustrate the invention further without restricting it. Likewise, further compounds according to this invention, whose preparation is not explicitly described, can be prepared in an analogous or similar manner or in a manner familiar per se to the person skilled in the art using customary process techniques.

Any or all of the compounds of formula I according to the present invention which are mentioned as final compounds in the following examples, as well as the salts, stereoisomers and salts of the stereoisomers thereof, are a preferred subject of the present invention.

In the examples, m.p. stands for melting point, h for hour(s), min for minutes, conc. for concentrated, calc. for calculated, fnd. for found, EF for elemental formula, MS for mass spectrometry, M for molecular ion in mass spectrometry, and other abbreviations have their meanings customary per se to the skilled person.

Further on, according to common practice in stereochemistry, the symbols RS and SR are used to denote the specific configuration of each of the indicated chiral centers of a racemate. In more detail, for example, the term "(3aSR, 10RS)" stands for a racemate comprising the one enantiomer having the configuration (3aS,10R) and the other enantiomer having the configuration (3aR,10S); yet in more detail, for example, the term "(3aRS,10RS)" stands for a racemate comprising the one enantiomer having the configuration (3aR, 10R) and the other enantiomer having the configuration (3aS, 10S); each of these enantiomers and their salts in pure form as well as their mixtures including the racemic mixtures is part of this invention, whereby with reference to compounds of formula I in which R4 is methyl or ethyl, this enantiomer having the configuration (3aS,10R) is a preferred part of this invention, and whereby with reference to compounds of formula I in which R4 is isopropyl or cyclopropyl, this enantiomer having the configuration (3aR,10R) is a preferred part of this invention.

EXAMPLES

Final Compounds 1. (3aSR,10RS)-6-Ethoxy-10-(3-hydroxy-phenyl)-2, 3a-dimethyl-3a,4,9,10-tetrahydro-2,9,10a-triaza-cyclopenta[b]fluorene-1,3-dione A solution of 125 mg (1RS,3SR)-6-ethoxy-1-(3-hydroxy-phenyl)-3-methyl-2,3,4,9-tetrahydro-1H-betacarboline-3-carboxylic acid methyl ester and 226 mg N-succinimidyl-N-methylcarbamate in a mixture of 5 ml acetonitrile and 1 ml water is heated to 150° C. for 30 min using a microwave reactor. Water and ethylacetate are added to the solution. The aqueous phase is extracted with ethylacetate and the combined organic layers are dried with magnesium sulfate. The solvents are removed under reduced pressure. After purification by column chromatography (toluene/ethylactate 4:1) 15 mg of the title compound are obtained as a colorless foam (MS: m/z (MH$^+$)=406.1).

2. (3aSR,10RS)-10-(3-Hydroxy-phenyl)-6-(2-methoxy-ethoxy)-2,3a-dimethyl-3a,4,9,10-tetrahydro-2,9, 10a-triaza-cyclopenta[b]fluorene-1,3-dione The title compound is prepared similarly as described for example 1 using (1RS,3SR)-1-(3-hydroxyphenyl)-6-(2-methoxy-ethoxy)-3-methyl-2,3,4,9-tetrahydro-1H-beta-carboline-3-carboxylic acid methyl ester as starting material. MS: m/z (MH$^+$)=436.1

3. (3aSR,10RS)-10-(3-Hydroxy-phenyl)-6-methoxy-2,3a-dimethyl-3a,4,9,10-tetrahydro-2,9,10a-triaza-cyclopenta[b]fluorene-1,3-dione The title compound is prepared similarly as described for example 1 using (1RS,3SR)-1-(3-hydroxyphenyl)-6-methoxy-3-methyl-2,3,4,9-tetrahydro-1H-beta-carboline-3-carboxylic acid methyl ester as starting material. MS: m/z (MH$^+$)=392.1

4. (3aSR,10RS)-6-Bromo-10-(3-hydroxy-phenyl)-2, 3a-dimethyl-3a,4,9,10-tetrahydro-2,9,10a-triaza-cyclopenta[b]fluorene-1,3-dione The title compound is prepared similarly as described for example 1 using compound A4 as starting material. MS: m/z (MH$^+$)=440.0/442.0, m.p.: 248-251° C.

5. (3aSR,10RS)-6-Chloro-10-(3-hydroxy-phenyl)-2, 3a-dimethyl-3a,4,9,10-tetrahydro-2,9,10a-triaza-cyclopenta[b]fluorene-1,3-dione The title compound is prepared similarly as described for example 1 using compound A5 as starting material. MS: m/z (MH$^+$)=396.0, m.p.: 248-250° C.

6. (3aSR,10RS)-2-(2-Dimethylamino-ethyl)-10-(3-hydroxy-phenyl)-6-(2-methoxy-ethoxy)-3a-methyl-3a,4,9,10-tetrahydro-2,9,10a-triaza-cyclopenta[b] fluorene-1,3-dione To a suspension of 100 mg (240 µmol) (1RS,3SR)-1-(3-hydroxy-phenyl)-6-(2-methoxy-ethoxy)-3-methyl-2,3,4,9-tetrahydro-1H-β-carboline-3-carboxylic acid methyl ester in 4 ml dichloromethane are added 126 µl (970 µmol, 4.00 eq.) triethylamine. The solution is cooled to 0° C. and a solution of 123 mg (610 µmol, 2.5 eq.) 4-nitrophenyl chloroformiate in 1 ml dichloromethane is added dropwise. The mixture is stirred for 10 min at 0° C. and for additional 30 min at room temperature. The solution is cooled again to 0° C. and 72.0 µl (660 µmol, 2.7 eq) 2-dimethylaminoethyl amine in 1 ml dichloromethane are added slowly. The mixture is allowed to warm up to room temperature over night. Water and a saturated aqueous solution of sodium carbonate are added and the aqueous layer is extracted with dichloromethane. The combined organic layers are dried with magnesium sulphate and the solvent is removed under reduced pressure (210 mg crude intermediate).

The crude intermediate is dissolved in 5 ml acetone and the solution is heated to 150° C. for 60 min using a microwave reactor. The solvent is removed under reduced pressure. After purification by column chromatography 24.5 mg (3aSR,10RS)-2-(2-dimethylamino-ethyl)-10-(3-hydroxy-phenyl)-6-(2-methoxy-ethoxy)-3a-methyl-3a,4,9,10-tetrahydro-2,9,10a-triaza-cyclopenta[b]fluorene-1,3-dione are obtained (m/z (MH$^+$)=493.2).

7. (3aSR,10RS)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 6, using (1RS,3SR)-1-(3-hydroxyphenyl)-6-methoxy-3-methyl-2,3,4,9-tetrahydro-1H-β-carboline-3-carboxylic acid methyl ester instead of (1RS,3SR)-1-(3-hydroxy-phenyl)-6-(2-methoxy-ethoxy)-3-methyl-2,3,4,9-tetrahydro-1H-β-carboline-3-carboxylic acid methyl ester. m/z (MH$^+$)=449.2

Alternatively, the title compound can be obtained from (+/−)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione (example 24) and dimethylamine as starting materials.

7a. (+)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 30 using (+)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione (example 24a) and dimethylamine as starting materials.

The absolute stereochemistry of (+)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione is tentatively assigned to (3aR,10S)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione.

MS: m/z (MH$^+$)=449.2; $[\alpha]^{20}_D$=+157° (c=0.5400, methanol)

7b. (−)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 30 using (−)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione (example 24b) and dimethylamine as starting materials.

The absolute stereochemistry of (−)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione is tentatively assigned to (3aS,10R)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione.

MS: m/z (MH$^+$)=449.3; $[\alpha]^{20}_D$=−159° (c=0.5400, methanol)

8. (3aSR,10RS)-6-Bromo-2-(2-dimethylamino-ethyl)-10-(3-hydroxy-phenyl)-3a-methyl-3a,4,9,10-tetrahydro-2,9,10a-triaza-cyclopenta[b]fluorene-1,3-dione The title compound is prepared similarly as described for example 6, using (1RS,3SR)-6-bromo-1-(3-hydroxy-phenyl)-3-methyl-2,3,4,9-tetrahydro-1H-β-carboline-3-carboxylic acid methyl ester instead of (1RS,3SR)-1-(3-hydroxy-phenyl)-6-(2-methoxy-ethoxy)-3-methyl-2,3,4,9-tetrahydro-1H-β-carboline-3-carboxylic acid methyl ester. m/z (MH$^+$)=497.2/499.1, mp: 286° C.-288° C.

9. (3aSR,10RS)-6-Chloro-2-(2-dimethylamino-ethyl)-10-(3-hydroxy-phenyl)-3a-methyl-3a,4,9,10-tetrahydro-2,9,10a-triaza-cyclopenta[b]fluorene-1,3-dione The title compound is prepared similarly as described for example 6, using (1RS,3SR)-6-chloro-1-(3-hydroxy-phenyl)-3-methyl-2,3,4,9-tetrahydro-1H-β-carboline-3-carboxylic acid methyl ester instead of (1RS,3SR)-1-(3-hydroxy-phenyl)-6-(2-methoxy-ethoxy)-3-methyl-2,3,4,9-tetrahydro-1H-β-carboline-3-carboxylic acid methyl ester. m/z (MH$^+$)=453.2, mp: 283° C.-286° C.

10. (3aSR,10RS)-10-(3-Hydroxy-phenyl)-6-methoxy-3a-methyl-2-(2-morpholin-4-yl-ethyl)-3a,4,9,10-tetrahydro-2,9,10a-triaza-cyclopenta[b]fluorene-1,3-dione The title compound is prepared similarly as described for example 6, using (1RS,3SR)-1-(3-hydroxyphenyl)-6-methoxy-3-methyl-2,3,4,9-tetrahydro-1H-β-carboline-3-carboxylic acid methyl ester instead of (1RS,3SR)-1-(3-hydroxy-phenyl)-6-(2-methoxy-ethoxy)-3-methyl-2,3,4,9-tetrahydro-1H-β-carboline-3-carboxylic acid methyl ester and N-(2-aminoethyl)-morpholine instead of 2-dimethylaminoethyl amine. m/z (MH$^+$)=491.2, mp: 260° C.-263° C.

11. (3aSR,10RS)-10-(3-Hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione The title compound is prepared similarly as described for example 6, using (1RS,3SR)-1-(3-hydroxyphenyl)-6-methoxy-3-methyl-2,3,4,9-tetrahydro-1H-β-carboline-3-carboxylic acid methyl ester instead of (1RS,3SR)-1-(3-hydroxy-phenyl)-6-(2-methoxy-ethoxy)-3-methyl-2,3,4,9-tetrahydro-1H-β-carboline-3-carboxylic acid methyl ester and 1-(2-aminoethyl)-pyrrolidine instead of 2-dimethylaminoethyl amine. m/z (MH$^+$)=475.2, mp: 252° C.-255° C.

12. (3aSR,10RS)-10-(3-Hydroxy-phenyl)-6-methoxy-3a-methyl-2-[2-(4-methyl-piperazin-1-yl)ethyl]-3a,4,9,10-tetrahydro-2,9,10a-triaza-cyclopenta[b]fluorene-1,3-dione The title compound is prepared similarly as described for example 6, using (1RS,3SR)-1-(3-hydroxyphenyl)-6-methoxy-3-methyl-2,3,4,9-tetrahydro-1H-β-carboline-3-carboxylic acid methyl ester instead of (1RS,3SR)-1-(3-hydroxy-phenyl)-6-(2-methoxy-ethoxy)-3-methyl-2,3,4,9- tetrahydro-1H-β-carboline-3-carboxylic acid methyl ester and 1-(2-aminoethyl)-4-methyl piperazine instead of 2-dimethylaminoethyl amine. m/z (MH$^+$)=504.2, mp: 224° C.-227° C.

13. (3aSR,10RS)-10-(3-Hydroxy-phenyl)-2-(2-imidazol-1-yl-ethyl)-6-methoxy-3a-methyl-3a,4,9,10-tetrahydro-2,9,10a-triaza-cyclopenta[b]fluorene-1,3-dione The title compound is prepared similarly as described for example 6, using (1RS,3SR)-1-(3-hydroxyphenyl)-6-methoxy-3-methyl-2,3,4,9-tetrahydro-1H-β-carboline-3-carboxylic acid methyl ester instead of (1RS,3SR)-1-(3-hydroxy-phenyl)-6-(2-methoxy-ethoxy)-3-methyl-2,3,4,9-tetrahydro-1H-β-carboline-3-carboxylic acid methyl ester and 2-(imidazol-1-yl)-ethyl amine instead of 2-dimethylaminoethyl amine. m/z (MH$^+$)=472.2, mp: 321° C.-324° C.

14. (3aSR,10RS)-2-(4-Dimethylamino-butyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 6, using (1RS,3SR)-1-(3-hydroxyphenyl)-6-methoxy-3-methyl-2,3,4,9-tetrahydro-1H-β-carboline-3-carboxylic acid methyl ester instead of (1RS,3SR)-1-(3-hydroxy-phenyl)-6-(2-methoxy-ethoxy)-3-methyl-2,3,4,9-tetrahydro-1H-β-carboline-3-carboxylic acid methyl ester and 4-(dimethylamino)-butyl amine instead of 2-dimethylaminoethyl amine. m/z (MH$^+$)=477.3.

15. (3aSR,10RS)-2-(3-Dimethylamino-propyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 6, using (1RS,3SR)-1-(3-hydroxyphenyl)-6-methoxy-3-methyl-2,3,4,9-tetrahydro-1H-β-carboline-3-carboxylic acid methyl ester instead of (1RS,3SR)-1-(3-hydroxy-phenyl)-6-(2-methoxy-ethoxy)-3-methyl-2,3,4,9-tetrahydro-1H-β-carboline-3-carboxylic acid methyl ester and 3-dimethylaminopropyl amine instead of 2-dimethylaminoethyl amine. m/z (MH$^+$=463.2), mp: 228° C.-231° C.

Starting from (1RS,3SR)-6-ethoxy-1-(3-hydroxy-phenyl)-3-methyl-2,3,4,9-tetrahydro-1H-beta-carboline-3-carboxylic acid methyl ester but with choice of the appropriate amine as reaction partner, the following compounds may be prepared using similar procedures to those to attain to example 6:
(3aSR,10RS)-2-(2-Dimethylamino-ethyl)-6-ethoxy-10-(3-hydroxy-phenyl)-3a-methyl-3a,4,9,10-tetrahydro-2,9,10a-triaza-cyclopenta[b]fluorene-1,3-dione,
(3aSR,10RS)-6-Ethoxy-10-(3-hydroxy-phenyl)-3a-methyl-2-(2-morpholin-4-yl-ethyl)-3a,4,9,10-tetrahydro-2,9,10a-triaza-cyclopenta[b]fluorene-1,3-dione,
(3aSR,10RS)-6-Ethoxy-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione,
(3aSR,10RS)-6-Ethoxy-10-(3-hydroxy-phenyl)-3a-methyl-2-[2-(4-methyl-piperazin-1-yl)-ethyl]-3a,4,9,10-tetrahydro-2,9,10a-triaza-cyclopenta[b]fluorene-1,3-dione,
(3aSR,10RS)-6-Ethoxy-10-(3-hydroxy-phenyl)-2-(2-imidazol-1-yl-ethyl)-3a-methyl-3a,4,9,10-tetrahydro-2,9,10a-triaza-cyclopenta[b]fluorene-1,3-dione,
(3aSR,10RS)-2-(3-Dimethylamino-propyl)-6-ethoxy-10-(3-hydroxy-phenyl)-3a-methyl-3a,4,9,10-tetrahydro-2,9,10a-triaza-cyclopenta[b]fluorene-1,3-dione.

Starting from (1RS,3SR)-1-(3-hydroxy-phenyl)-6-(2-methoxy-ethoxy)-3-methyl-2,3,4,9-tetrahydro-1H-beta-carboline-3-carboxylic acid methyl ester but with choice of the appropriate amine as reaction partner, the following compounds may be prepared using similar procedures to those to attain to example 6:
(3aSR,10RS)-10-(3-Hydroxy-phenyl)-6-(2-methoxy-ethoxy)-2-(2-morpholin-4-yl-ethyl)-3a-methyl-3a,4,9,10-tetrahydro-2,9,10a-triaza-cyclopenta[b]fluorene-1,3-dione,
(3aSR,10RS)-10-(3-Hydroxy-phenyl)-6-(2-methoxy-ethoxy)-3a-methyl-2-(2-pyrrolidin-1-yl-ethyl)-3a,4,9,10-tetrahydro-2,9,10a-triaza-cyclopenta[b]fluorene-1,3-dione,
(3aSR,10RS)-10-(3-Hydroxy-phenyl)-6-(2-methoxy-ethoxy)-2-[2-(4-methyl-piperazin-1-yl)-ethyl]-3a-methyl-3a,4,9,10-tetrahydro-2,9,10a-triaza-cyclopenta[b]fluorene-1,3-dione,
(3aSR,10RS)-10-(3-Hydroxy-phenyl)-2-(2-imidazol-1-yl-ethyl)-6-(2-methoxy-ethoxy)-3a-methyl-3a,4,9,10-tetrahydro-2,9,10a-triaza-cyclopenta[b]fluorene-1,3-dione,
(3aSR,10RS)-2-(3-Dimethylamino-propyl)-10-(3-hydroxy-phenyl)-6-(2-methoxy-ethoxy)-3a-methyl-3a,4,9,10-tetrahydro-2,9,10a-triaza-cyclopenta[b]fluorene-1,3-dione.

Starting from compound A4 mentioned below but with choice of the appropriate amine as reaction partner, the following compounds may be prepared using similar procedures to those to attain to example 6:
(3aSR,10RS)-6-Chloro-10-(3-hydroxy-phenyl)-2-(2-morpholin-4-yl-ethyl)-3a-methyl-3a,4,9,10-tetrahydro-2,9,10a-triaza-cyclopenta[b]fluorene-1,3-dione,
(3aSR,10RS)-6-Chloro-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione,
(3aSR,10RS)-6-Chloro-10-(3-hydroxy-phenyl)-2-[2-(4-methyl-piperazin-1-yl)-ethyl]-3a-methyl-3a,4,9,10-tetrahydro-2,9,10a-triaza-cyclopenta[b]fluorene-1,3-dione,
(3aSR,10RS)-6-Chloro-10-(3-hydroxy-phenyl)-2-(2-imidazol-1-yl-ethyl)-3a-methyl-3a,4,9,10-tetrahydro-2,9,10a-triaza-cyclopenta[b]fluorene-1,3-dione,
(3aSR,10RS)-6-Chloro-2-(3-dimethylamino-propyl)-10-(3-hydroxy-phenyl)-3a-methyl-3a,4,9,10-tetrahydro-2,9,10a-triaza-cyclopenta[b]fluorene-1,3-dione.

Starting from compound A5 mentioned below but with choice of the appropriate amine as reaction partner, the following compounds may be prepared using similar procedures to those to attain to example 6:
(3aSR,10RS)-6-Bromo-10-(3-hydroxy-phenyl)-2-(2-morpholin-4-yl-ethyl)-3a-methyl-3a,4,9,10-tetrahydro-2,9,10a-triaza-cyclopenta[b]fluorene-1,3-dione,
(3aSR,10RS)-6-Bromo-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione,
(3aSR,10RS)-6-Bromo-10-(3-hydroxy-phenyl)-2-[2-(4-methyl-piperazin-1-yl)-ethyl]-3a-methyl-3a,4,9,10-tetrahydro-2,9,10a-triaza-cyclopenta[b]fluorene-1,3-dione,
(3aSR,10RS)-6-Bromo-10-(3-hydroxy-phenyl)-2-(2-imidazol-1-yl-ethyl)-3a-methyl-3a,4,9,10-tetrahydro-2,9,10a-triaza-cyclopenta[b]fluorene-1,3-dione,
(3aSR,10RS)-6-Bromo-2-(3-dimethylamino-propyl)-10-(3-hydroxy-phenyl)-3a-methyl-3a,4,9,10-tetrahydro-2,9,10a-triaza-cyclopenta[b]fluorene-1,3-dione.

Starting from the appropriate compound A6 to A10 mentioned below, the following compounds may be prepared using similar procedures to those to attain to example 1:
- (3aSR,10RS)-6-Ethoxy-3a-ethyl-10-(3-hydroxy-phenyl)-2-methyl-3a,4,9,10-tetrahydro-2,9,10a-triaza-cyclopenta[b]fluorene-1,3-dione,
- (3aSR,10RS)-3a-Ethyl-10-(3-hydroxy-phenyl)-6-(2-methoxy-ethoxy)-2-methyl-3a,4,9,10-tetrahydro-2,9,10a-triaza-cyclopenta[b]fluorene-1,3-dione,
- (3aSR,10RS)-3a-Ethyl-10-(3-hydroxy-phenyl)-6-methoxy-2-methyl-3a,4,9,10-tetrahydro-2,9,10a-triaza-cyclopenta[b]fluorene-1,3-dione,
- (3aSR,10RS)-6-Bromo-3a-ethyl-10-(3-hydroxy-phenyl)-2-methyl-3a,4,9,10-tetrahydro-2,9,10a-triaza-cyclopenta[b]fluorene-1,3-dione,
- (3aSR,10RS)-6-Chloro-3a-ethyl-10-(3-hydroxy-phenyl)-2-methyl-3a,4,9,10-tetrahydro-2,9,10a-triaza-cyclopenta[b]fluorene-1,3-dione.

Starting from the appropriate compound A6 to A10 mentioned below and with choice of the appropriate amine as reaction partner, the following compounds may be prepared using similar procedures to those to attain to example 6:
- (3aSR,10RS)-2-(2-Dimethylamino-ethyl)-3a-ethyl-10-(3-hydroxy-phenyl)-6-(2-methoxy-ethoxy)-3a,4,9,10-tetrahydro-2,9,10a-triaza-cyclopenta[b]fluorene-1,3-dione,
- (3aSR,10RS)-2-(2-Dimethylamino-ethyl)-3a-ethyl-10-(3-hydroxy-phenyl)-6-methoxy-3a,4,9,10-tetrahydro-2,9,10a-triaza-cyclopenta[b]fluorene-1,3-dione,
- (3aSR,10RS)-6-Bromo-2-(2-dimethylamino-ethyl)-3a-ethyl-10-(3-hydroxy-phenyl)-3a,4,9,10-tetrahydro-2,9,10a-triaza-cyclopenta[b]fluorene-1,3-dione,
- (3aSR,10RS)-6-Chloro-2-(2-dimethylamino-ethyl)-3a-ethyl-10-(3-hydroxy-phenyl)-3a,4,9,10-tetrahydro-2,9,10a-triaza-cyclopenta[b]fluorene-1,3-dione,
- (3aSR,10RS)-3a-Ethyl-10-(3-hydroxy-phenyl)-6-methoxy-2-(2-morpholin-4-yl-ethyl)-3a,4,9,10-tetrahydro-2,9,10a-triaza-cyclopenta[b]fluorene-1,3-dione,
- (3aSR,10RS)-3a-Ethyl-10-(3-hydroxy-phenyl)-6-methoxy-2-(2-pyrrolidin-1-yl-ethyl)-3a,4,9,10-tetrahydro-2,9,10a-triaza-cyclopenta[b]fluorene-1,3-dione,
- (3aSR,10RS)-3a-Ethyl-10-(3-hydroxy-phenyl)-6-methoxy-2-[2-(4-methyl-piperazin-1-yl)-ethyl]-3a,4,9,10-tetrahydro-2,9,10a-triaza-cyclopenta[b]fluorene-1,3-dione,
- (3aSR,10RS)-3a-Ethyl-10-(3-hydroxy-phenyl)-2-(2-imidazol-1-yl-ethyl)-6-methoxy-3a,4,9,10-tetrahydro-2,9,10a-triaza-cyclopenta[b]fluorene-1,3-dione,
- (3aSR,10RS)-2-(4-Dimethylamino-butyl)-3a-ethyl-10-(3-hydroxy-phenyl)-6-methoxy-3a,4,9,10-tetrahydro-2,9,10a-triaza-cyclopenta[b]fluorene-1,3-dione,
- (3aSR,10RS)-2-(3-Dimethylamino-propyl)-3a-ethyl-10-(3-hydroxy-phenyl)-6-methoxy-3a,4,9,10-tetrahydro-2,9,10a-triaza-cyclopenta[b]fluorene-1,3-dione,
- (3aSR,10RS)-2-(2-Dimethylamino-ethyl)-3a-ethyl-6-ethoxy-10-(3-hydroxy-phenyl)-3a,4,9,10-tetrahydro-2,9,10a-triaza-cyclopenta[b]fluorene-1,3-dione,
- (3aSR,10RS)-6-Ethoxy-3a-ethyl-10-(3-hydroxy-phenyl)-2-(2-morpholin-4-yl-ethyl)-3a,4,9,10-tetrahydro-2,9,10a-triaza-cyclopenta[b]fluorene-1,3-dione,
- (3aSR,10RS)-6-Ethoxy-3a-ethyl-10-(3-hydroxy-phenyl)-2-(2-pyrrolidin-1-yl-ethyl)-3a,4,9,10-tetrahydro-2,9,10a-triaza-cyclopenta[b]fluorene-1,3-dione,
- (3aSR,10RS)-6-Ethoxy-3a-ethyl-10-(3-hydroxy-phenyl)-2-[2-(4-methyl-piperazin-1-yl)-ethyl]-3a,4,9,10-tetrahydro-2,9,10a-triaza-cyclopenta[b]fluorene-1,3-dione,
- (3aSR,10RS)-6-Ethoxy-3a-ethyl-10-(3-hydroxy-phenyl)-2-(2-imidazol-1-yl-ethyl)-3a,4,9,10-tetrahydro-2,9,10a-triaza-cyclopenta[b]fluorene-1,3-dione,
- (3aSR,10RS)-2-(3-Dimethylamino-propyl)-6-ethoxy-3a-ethyl-10-(3-hydroxy-phenyl)-3a,4,9,10-tetrahydro-2,9,10a-triaza-cyclopenta[b]fluorene-1,3-dione,
- (3aSR,10RS)-3a-Ethyl-10-(3-hydroxy-phenyl)-6-(2-methoxy-ethoxy)-2-(2-morpholin-4-yl-ethyl)-3a,4,9,10-tetrahydro-2,9,10a-triaza-cyclopenta[b]fluorene-1,3-dione,
- (3aSR,10RS)-3a-Ethyl-10-(3-hydroxy-phenyl)-6-(2-methoxy-ethoxy)-2-(2-pyrrolidin-1-yl-ethyl)-3a,4,9,10-tetrahydro-2,9,10a-triaza-cyclopenta[b]fluorene-1,3-dione,
- (3aSR,10RS)-3a-Ethyl-10-(3-hydroxy-phenyl)-6-(2-methoxy-ethoxy)-2-[2-(4-methyl-piperazin-1-yl)ethyl]-3a,4,9,10-tetrahydro-2,9,10a-triaza-cyclopenta[b]fluorene-1,3-dione,
- (3aSR,10RS)-3a-Ethyl-10-(3-hydroxy-phenyl)-2-(2-imidazol-1-yl-ethyl)-6-(2-methoxy-ethoxy)-3a,4,9,10-tetrahydro-2,9,10a-triaza-cyclopenta[b]fluorene-1,3-dione,
- (3aSR,10RS)-2-(3-Dimethylamino-propyl)-3a-ethyl-10-(3-hydroxy-phenyl)-6-(2-methoxy-ethoxy)-3a,4,9,10-tetrahydro-2,9,10a-triaza-cyclopenta[b]fluorene-1,3-dione,
- (3aSR,10RS)-6-Chloro-3a-ethyl-10-(3-hydroxy-phenyl)-2-(2-morpholin-4-yl-ethyl)-3a,4,9,10-tetrahydro-2,9,10a-triaza-cyclopenta[b]fluorene-1,3-dione,
- (3aSR,10RS)-6-Chloro-3a-ethyl-10-(3-hydroxy-phenyl)-2-(2-pyrrolidin-1-yl-ethyl)-3a,4,9,10-tetrahydro-2,9,10a-triaza-cyclopenta[b]fluorene-1,3-dione,
- (3aSR,10RS)-6-Chloro-3a-ethyl-10-(3-hydroxy-phenyl)-2-[2-(4-methyl-piperazin-1-yl)-ethyl]-3a,4,9,10-tetrahydro-2,9,10a-triaza-cyclopenta[b]fluorene-1,3-dione,
- (3aSR,10RS)-6-Chloro-3a-ethyl-10-(3-hydroxy-phenyl)-2-(2-imidazol-1-yl-ethyl)-3a,4,9,10-tetrahydro-2,9,10a-triaza-cyclopenta[b]fluorene-1,3-dione,
- (3aSR,10RS)-6-Chloro-2-(3-dimethylamino-propyl)-3a-ethyl-10-(3-hydroxy-phenyl)-3a,4,9,10-tetrahydro-2,9,10a-triaza-cyclopenta[b]fluorene-1,3-dione,
- (3aSR,10RS)-6-Bromo-3a-ethyl-10-(3-hydroxy-phenyl)-2-(2-morpholin-4-yl-ethyl)-3a,4,9,10-tetrahydro-2,9,10a-triaza-cyclopenta[b]fluorene-1,3-dione,
- (3aSR,10RS)-6-Bromo-3a-ethyl-10-(3-hydroxy-phenyl)-2-(2-pyrrolidin-1-yl-ethyl)-3a,4,9,10-tetrahydro-2,9,10a-triaza-cyclopenta[b]fluorene-1,3-dione,
- (3aSR,10RS)-6-Bromo-3a-ethyl-10-(3-hydroxy-phenyl)-2-[2-(4-methyl-piperazin-1-yl)-ethyl]-3a,4,9,10-tetrahydro-2,9,10a-triaza-cyclopenta[b]fluorene-1,3-dione,
- (3aSR,10RS)-6-Bromo-3a-ethyl-10-(3-hydroxy-phenyl)-2-(2-imidazol-1-yl-ethyl)-3a,4,9,10-tetrahydro-2,9,10a-triaza-cyclopenta[b]fluorene-1,3-dione,
- (3aSR,10RS)-6-Bromo-2-(3-dimethylamino-propyl)-3a-ethyl-10-(3-hydroxy-phenyl)-3a,4,9,10-tetrahydro-2,9,10a-triaza-cyclopenta[b]fluorene-1,3-dione.

16. (3aSR,10RS)-6-Chloro-2-(3-dimethylamino-propyl)-10-(3-hydroxy-phenyl)-3a-methyl-3a,4,9,10-tetrahydro-2,9,10a-triaza-cyclopenta[b]fluorene-1,3-dione The title compound is prepared similarly as described for example 6 using (1RS,3SR)-6-Chloro-1-(3-hydroxy-phenyl)-3-methyl-2,3,4,9-tetrahydro-1H-beta-carboline-3-carboxylic acid methyl ester and 3-dimethylaminopropyl amine as starting materials. MS: m/z (MH$^+$)=467.2

17. (3aSR,10RS)-6-Chloro-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione The title compound is prepared similarly as described for example 6 using (1RS,3SR)-6-Chloro-1-(3-hydroxy-phenyl)-3-methyl-2,3,4,9-tetrahydro-1H-beta-carboline-3-carboxylic acid methyl ester and 1-(2-aminoethyl)-pyrrolidine as starting materials. MS: m/z (MH$^+$)=479.2

18. (3aSR,10RS)-2-(2-Dimethylamino-ethyl)-3a-ethyl-10-(3-hydroxy-phenyl)-6-methoxy-3a,4,9,10-tetrahydro-2,9,10a-triaza-cyclopenta[b]fluorene-1,3-dione The title compound is prepared similarly as described for example 6 using (1RS,3SR)-3-ethyl-1-(3-hydroxy-phenyl)-6-methoxy-2,3,4,9-tetrahydro-1H-beta-carboline-3-carboxylic acid ethyl ester as starting material. MS: m/z (MH$^+$)=463.2

19. (3aSR,10RS)-2-(3-Dimethylamino-propyl)-3a-ethyl-10-(3-hydroxy-phenyl)-6-methoxy-3a,4,9,10-tetrahydro-2,9,10a-triaza-cyclopenta[b]fluorene-1,3-dione The title compound is prepared similarly as described for example 6 using (1RS,3SR)-3-ethyl-1-(3-hydroxy-phenyl)-6-methoxy-2,3,4,9-tetrahydro-1H-beta-carboline-3-carboxylic acid ethyl ester and 3-dimethylaminopropyl amine as starting materials. MS: m/z (MH$^+$)=477.2

20. (3aSR,10RS)-10-(3-Hydroxy-phenyl)-2-(3-imidazol-1-yl-propyl)-6-methoxy-3a-methyl-3a,4,9,10-tetrahydro-2,9,10a-triaza-cyclopenta[b]fluorene-1,3-dione The title compound is prepared similarly as described for example 6 using N-(3-aminopropyl)-imidazole as starting material. MS: m/z (MH$^+$)=486.2

21. (3aSR,10RS)-6-Cyclopropylmethoxy-10-(3-hydroxy-phenyl)-2,3a-dimethyl-3a,4,9,10-tetrahydro-2,9,10a-triaza-cyclopenta[b]fluorene-1,3-dione The title compound is prepared similarly as described for example 1 using (1RS,3SR)-6-Cyclopropylmethoxy-1-(3-hydroxy-phenyl)-3-methyl-2,3,4,9-tetrahydro-1H-β-carboline-3-carboxylic acid methyl ester as starting material. MS: m/z (MH$^+$)=432.0

22. (3aSR,10RS)-2-(2-Bromo-ethyl)-6-ethoxy-10-(3-hydroxy-phenyl)-3a-methyl-3a,4,9,10-tetrahydro-2,9,10a-triaza-cyclopenta[b]fluorene-1,3-dione To a solution of 500 mg (1.31 mmol) (1RS,3SR)-6-Ethoxy-1-(3-hydroxy-phenyl)-3-methyl-2,3,4,9-tetrahydro-1H-beta-carboline-3-carboxylic acid methyl ester in 25 ml 2-butanon are added 120 μl (1.31 mmol) bromoethyl isocyanate. The mixture is heated to reflux for 24 h. The solvent is removed under reduced pressure. The crude product is purified by column chromatography (silica gel; toluene, ethyl acetate 6:1). 260 mg (40%) of the title compound are obtained as a colorless solid. m.p.: 250-252° C., MS: m/z (MH$^+$)=498.1/500.0

23. (3aSR,10RS)-2-(2-Dimethylamino-ethyl)-6-ethoxy-10-(3-hydroxy-phenyl)-3a-methyl-3a,4,9,10-tetrahydro-2,9,10a-triaza-cyclopenta[b]fluorene-1,3-dione To a suspension of 200 mg (3aSR,10RS)-2-(2-Bromo-ethyl)-6-ethoxy-10-(3-hydroxy-phenyl)-3a-methyl-3a,4,9,10-tetrahydro-2,9,10a-triaza-cyclopenta[b]fluorene-1,3-dione (example 22) in 10 ml acetonitrile are added 200 μl of a 2 M solution of dimethyl amine in tetrahydrofurane and 85 mg sodium carbonate. The mixture is heated to reflux and additional 1 ml of the 2 m solution of dimethyl amine in THF are added. After additional 2 h heating to reflux, another 600 μl of the solution of dimethyl amine in THF are added. The mixture is heated to reflux for 15 h. Water is added and the mixture is extracted with ethyl acetate. The combined organic layers are washed with brine and dried with magnesium sulfate. After removal of the solvent under reduced pressure, the residue is triturated with diisopropyl ether. 82 mg (44%) of title compound are obtained as a colorless solid. MS: m/z (MH$^+$)=463.2

24. (3aSR,10RS)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione To a solution of 3.17 g (1RS,3SR)-1-(3-Hydroxy-phenyl)-6-methoxy-3-methyl-2,3,4,9-tetrahydro-1H-beta-carboline-3-carboxylic acid methyl ester in 35 ml 2-butanon are added 860 μl bromoethyl isocyanate. The mixture is heated to reflux for 7 h and is stirred at room temperature over night. The precipitated compound is filtered and washed with 2-butanon. 3.09 g (74%) of the title compound are obtained. m.p.: 299-302° C., MS: m/z (MH$^+$)=484.0/486.0

24a. (+)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 24 using (−)-1-(3-Hydroxy-phenyl)-6-methoxy-3-methyl-2,3,4,9-tetrahydro-1H-β-carboline-3-carboxylic acid methyl ester as starting material. The absolute stereochemistry of (+)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione is tentatively assigned to (3aR,10S)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione.

MS: m/z (M−H$^+$)=482.1/484.1; $[\alpha]^{20}_D$=+115° (c=0.8550, methanol)

24b. (−)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 24 using (+)-1-(3-Hydroxy-phenyl)-6-methoxy-3-methyl-2,3,4,9-tetrahydro-1H-β-carboline-3-carboxylic acid methyl ester as starting material. The absolute stereochemistry of (−)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione is tentatively assigned to (3aS,10R)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione.

MS: m/z (M−H$^+$)=482.3/484.3; $[\alpha]^{20}_D$=−108° (c=0.5450, methanol)

25. (3aSR,10RS)-2-(2-Amino-ethyl)-10-(3-hydroxy-phenyl)-6-methoxy-3a-methyl-3a,4,9,10-tetrahydro-2,9,10a-triaza-cyclopenta[b]fluorene-1,3-dione To a solution of 150 mg (3aSR,10RS)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione (example 24) in 2 ml methanol are added 1 ml of a 7 M solution of ammonia in methanol. The mixture is heated in a sealed tube to 130° C. for 20 min and to 140° C. for additional 60 min using a microwave reactor. Water is added and the mixture is extracted with ethyl acetate. The combined organic layers are washed with brine and dried with magnesium sulfate. After evaporation of the solvent under reduced pressure, the crude product is purified by column chromatography (silica gel; ethyl acetate, methanol, ammonia 10:0.3:0.2). 90 mg of an oil are obtained which cystallize after trituration with diisopropyl ether. 62 mg (48%) of the title compound are obtained as a colorless solid. MS: m/z (MH$^+$)=421.1

26. (3aSR,10RS)-2-(2-Bromo-ethyl)-6-chloro-10-(3-hydroxy-phenyl)-3a-methyl-3a,4,9,10-tetrahydro-2,9,10a-triaza-cyclopenta[b]fluorene-1,3-dione To a suspension of 1.66 g (5.39 mmol) (1RS,3SR)-6-Chloro-1-(3-hydroxy-phenyl)-3-methyl-2,3,4,9-tetrahydro-1H-beta-carboline-3-carboxylic acid methyl ester in 20 ml 2-butanon are added 490 μl 2-bromoethyl isocyanate. After heating the mixture to reflux for 4 h, additional 490 μl 2-bromoethyl isocyanate are added and the mixture is heated to reflux over night. The solvent is removed at reduced pressure and the residue is dissolved in 20 ml dimethyl formamide. The mixture is stirred at 80° C. for 15 h. The solvent is removed at reduced pressure and the residue is dissolved in ethyl acetate. Water is added and the organic layer is dried with magnesium sulfate. The solvent is removed at reduced pressure and the residue is suspended in a mixture of toluene and ethyl acetate (4:1). The suspension is filtered. 1.35 g (62%) of the title compound are obtained as the precipitate. m.p.: 262-264° C., MS: m/z (MH$^+$)=488.0/490.0

27. (3aSR,10RS)-10-(3-Hydroxy-phenyl)-6-methoxy-3a-methyl-2-(2-methylamino-ethyl)-3a,4,9,10-tetrahydro-2,9,10a-triaza-cyclopenta[b]fluorene-1,3-dione To a solution of 150 mg (3aSR,10RS)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione (example 24) in 5 ml acetonitrile are added 66 mg sodium carbonate and 920 μl of a 2 M solution of methyl amine in tetrahydrofurane. The mixture is heated in a sealed tube to 140° C. for 3 h using a microwave reactor. Water is added and the mixture is extracted with ethyl acetate. The organic layer is dried with magnesium sulfate. The solvent is removed under reduced pressure. After column chromatography (silica gel; ethyl acetate, methanol, ammonia 10:1:0.5) and trituration with diisopropylether, 60 mg of the title compound are obtained as a colorless solid. MS: m/z (MH$^+$)=435.1

28. (3aSR,10RS)-6-Chloro-10-(3-hydroxy-phenyl)-3a-methyl-2-(2-methylamino-ethyl)-3a,4,9,10-tetrahydro-2,9,10a-triaza-cyclopenta[b]fluorene-1,3-dione The title compound is prepared similarly as described for example 27 (426160) using (3aSR,10RS)-2-(2-Bromo-ethyl)-6-chloro-10-(3-hydroxy-phenyl)-3a-methyl-3a,4,9,10-tetrahydro-2,9,10a-triaza-cyclopenta[b]fluorene-1,3-dione (example 26) as starting material. MS: m/z (MH$^+$)=439.1

29. (3aSR,10RS)-2-(2-Azetidin-1-yl-ethyl)-6-chloro-10-(3-hydroxy-phenyl)-3a-methyl-3a,4,9,10-tetrahydro-2,9,10a-triaza-cyclopenta[b]fluorene-1,3-dione To a solution of 200 mg (3aSR,10RS)-2-(2-Bromo-ethyl)-6-chloro-10-(3-hydroxy-phenyl)-3a-methyl-3a,4,9,10-tetrahydro-2,9,10a-triaza-cyclopenta[b]fluorene-1,3-dione (example 26) in 5 ml acetonitrile are added 87 mg sodium carbonate and 83 μl azetidine. The mixture is heated to reflux for 4 h. Water is added and the mixture is extracted with ethyl acetate. The organic layer is dried with magnesium sulfate. The solvent is removed under reduced pressure. After column chromatography (silica gel; ethyl acetate, methanol, ammonia 10:0.2:0.1) and trituration with diisopropylether, 61 mg of the title compound are obtained as a colorless solid. MS: m/z (MH$^+$)=465.1

30. (3aSR,10RS)-2-(2-Amino-ethyl)-6-chloro-10-(3-hydroxy-phenyl)-3a-methyl-3a,4,9,10-tetrahydro-2,9,10a-triaza-cyclopenta[b]fluorene-1,3-dione To a solution of 200 mg (3aSR,10RS)-2-(2-Bromo-ethyl)-6-chloro-10-(3-hydroxy-phenyl)-3a-methyl-3a,4,9,10-tetrahydro-2,9,10a-triaza-cyclopenta[b]fluorene-1,3-dione (example 26) in 3 ml methanol are added 1.2 ml of a 7 M solution of ammonia in methanol. The mixture is heated in a sealed tube to 140° C. for 1 h using a microwave reactor. The solvent is removed under reduced pressure. Water is added and the mixture is extracted with ethyl acetate. The organic layer is dried with magnesium sulfate. The solvent is removed under reduced pressure. The crude product is purified by preparative HPLC. 24 mg of the title compound are obtained. MS: m/z (MH$^+$)=425.1

31. (3aSR,10RS)-6-Chloro-10-(3-hydroxy-phenyl)-2-(2-imidazol-1-yl-ethyl)-3a-methyl-3a,4,9,10-tetrahydro-2,9,10a-triaza-cyclopenta[b]fluorene-1,3-dione The title compound is prepared similarly as described for example 29 using imidazole instead of azetidine as starting material. MS: m/z (MH$^+$)=476.2

32. (3aSR,10RS)-2-[2-(4-Acetyl-piperazin-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 29 using (3aSR,10RS)-2-(2-Bromoethyl)-10-(3-hydroxy-phenyl)-6-methoxy-3a-methyl-3a,4,9,10-tetrahydro-2,9,10a-triaza-cyclopenta[b]-fluorene-1,3-dione (example 24) and N-acetyl piperazine as starting materials. MS: m/z (MH$^+$)=532.1

33. (3aSR,10RS)-2-(2-Azetidin-1-yl-ethyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 29 using (3aSR,10RS)-2-(2-Bromoethyl)-10-(3-hydroxy-phenyl)-6-methoxy-3a-methyl-3a,4,9,10-tetrahydro- 2,9,10a-triaza-cyclopenta[b]-fluorene-1,3-dione (example 24) as starting material. MS: m/z (MH$^+$)=461.1

34. (3aSR,10RS)-2-[2-(3,3-Difluoro-pyrrolidin-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 27 using 3,3-difluoropyrrolidine hydrochloride as starting material. MS: m/z (MH$^+$)=511.1

35. (3aSR,10RS)-2-(2-Ethylamino-ethyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 30 using (3aSR,10RS)-2-(2-Bromoethyl)-10-(3-hydroxy-phenyl)-6-methoxy-3a-methyl-3a,4,9,10-tetrahydro-2,9,10a-triaza-cyclopenta[b]-fluorene-1,3-dione (example 24) and a 2 M solution of ethyl amine in methanol as starting materials.
MS: m/z (MH$^+$)=449.1

36. (3aSR,10RS)-2-(2-Bromo-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione To a solution of 5.5 mg (1RS,3SR)-6-(1,1-difluoro-methoxy)-1-(3-hydroxy-phenyl)-3-methyl-2,3,4,9-tetrahydro-1H-beta-carboline-3-carboxylic acid methyl ester in 10 ml 2-butanon are added 132 µl bromoethyl isocyanate. The mixture is heated to reflux for 30 h. An aqueous solution of sodium bicarbonate is added and the mixture is extracted with ethyl acetate. The organic layer is washed with brine and dried with magnesium sulfate. The solvent is removed at reduced pressure. After column chromatography (silica gel; toluene, ethyl acetate 4:1) and trituration with diisopropylether, 550 mg (61%) of the title compound are obtained as a colorless solid. MS: m/z (MH$^+$)=519.9/522.0

37. (3aSR,10RS)-6-Chloro-2-(2-ethylamino-ethyl)-10-(3-hydroxy-phenyl)-3a-methyl-3a,4,9,10-tetrahydro-2,9,10a-triaza-cyclopenta[b]fluorene-1,3-dione The title compound is prepared similarly as described for example 30 using a 2 M solution of ethyl amine in methanol as starting material. MS: m/z (MH$^+$)=453.2

38. (3aSR,10RS)-6-Chloro-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione The title compound is prepared similarly as described for example 30 using isopropyl amine as starting material. MS: m/z (MH$^+$)=467.2

39. (3aSR,10RS)-6-Chloro-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione The title compound is prepared similarly as described for example 29 using N-isopropyl methyl amine instead of azetidine as starting material. MS: m/z (MH$^+$)=481.2

40. (3aSR,10RS)-6-Chloro-2-[2-(ethyl-methyl-amino)-ethyl]-10-(3-hydroxy-phenyl)-3a-methyl-3a,4,9,10-tetrahydro-2,9,10a-triaza-cyclopenta[b]fluorene-1,3-dione The title compound is prepared similarly as described for example 29 using N-ethyl methyl amine instead of azetidine as starting material. MS: m/z (MH$^+$)=467.1

41. (3aSR,10RS)-6-Ethoxy-10-(3-hydroxy-phenyl)-3a-methyl-2-(2-methylamino-ethyl)-3a,4,9,10-tetrahydro-2,9,10a-triaza-cyclopenta[b]fluorene-1,3-dione The title compound is prepared similarly as described for example 29 using (3aSR,10RS)-2-(2-Bromoethyl)-6-ethoxy-10-(3-hydroxy-phenyl)-3a-methyl-3a,4,9,10-tetrahydro-2,9,10a-triaza-cyclopenta[b]-fluorene-1,3-dione (example 22) and a 2 M solution of methyl amine in tetrahydrofurane instead of azetidine as starting materials. MS: m/z (MH$^+$)=449.1

42. (3aSR,10RS)-6-(1,1-Difluoro-methoxy)-10-(3-hydroxy-phenyl)-3a-methyl-2-(2-methylaminoethyl)-3a,4,9,10-tetrahydro-2,9,10a-triaza-cyclopenta[b]fluorene-1,3-dione The title compound is prepared similarly as described for example 30 using (3aSR,10RS)-2-(2-Bromoethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione (example 36) and a 2 M solution of methyl amine in tetrahydrofurane as starting materials. MS: m/z (MH$^+$)=471.2

43. (3aSR,10RS)-6-(1,1-Difluoro-methoxy)-2-(2-dimethylamino-ethyl)-10-(3-hydroxy-phenyl)-3a-methyl-3a,4,9,10-tetrahydro-2,9,10a-triaza-cyclopenta[b]fluorene-1,3-dione The title compound is prepared similarly as described for example 29 using (3aSR,10RS)-2-(2-Bromoethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione (example 36) and dimethyl amine instead of azetidine as starting materials. MS: m/z (MH$^+$)=485.2

44. (3aSR,10RS)-2-(2-Azetidin-1-yl-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione The title compound is prepared similarly as described for example 29 using (3aSR,10RS)-2-(2-Bromoethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione (example 36) as starting material. MS: m/z (MH$^+$)=497.2

45. (3aSR,10RS)-2-(2-Amino-ethyl)-6-ethoxy-10-(3-hydroxy-phenyl)-3a-methyl-3a,4,9,10-tetrahydro-2,9,10a-triaza-cyclopenta[b]fluorene-1,3-dione The title compound is prepared similarly as described for example 30 using (3aSR,10RS)-2-(2-Bromoethyl)-6-ethoxy-10-(3-hydroxy-phenyl)-3a-methyl-3a,4,9,10-tetrahydro-2,9, 10a-triaza-cyclopenta[b]fluorene-1,3-dione (example 22) as starting material. MS: m/z (MH$^+$)=435.1

46. (3aSR,10RS)-2-(2-Azetidin-1-yl-ethyl)-6-ethoxy-10-(3-hydroxy-phenyl)-3a-methyl-3a,4,9,10-tetrahydro-2,9,10a-triaza-cyclopenta[b]fluorene-1,3-dione The title compound is prepared similarly as described for example 29 using (3aSR,10RS)-2-(2-Bromoethyl)-6-ethoxy-10-(3-hydroxy-phenyl)-3a-methyl-3a,4,9,10-tetrahydro-2,9,10a-triaza-cyclopenta[b]fluorene-1,3-dione as starting material. MS: m/z (MH$^+$)=475.2

47. (3aSR,10RS)-10-(3-Hydroxy-phenyl)-2-(2-isopropylamino-ethyl)-6-methoxy-3a-methyl-3a,4,9,10-tetrahydro-2,9,10a-triaza-cyclopenta[b]fluorene-1,3-dione The title compound is prepared similarly as described for example 30 using (3aSR,10RS)-2-(2-Bromoethyl)-10-(3-hydroxy-phenyl)-6-methoxy-3a-methyl-3a,4,9,10-tetrahydro-2,9,10a-triaza-cyclopenta[b]-fluorene-1,3-dione (example 24) and isopropyl amine as starting materials. MS: m/z (MH$^+$)=463.2

48. (3aSR,10RS)-2-[2-(Cyclopropylmethyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 30 using (3aSR,10RS)-2-(2-Bromoethyl)-10-(3-hydroxy-phenyl)-6-methoxy-3a-methyl-3a,4,9,10-tetrahydro-2,9,10a-triaza-cyclopenta[b]-fluorene-1,3-dione (example 24) and C-cyclopropyl methyl amine as starting materials. MS: m/z (MH$^+$)=475.2

49. (3aSR,10RS)-10-(3-Hydroxy-phenyl)-2-(2-isobutylamino-ethyl)-6-methoxy-3a-methyl-3a,4,9,10-tetrahydro-2,9,10a-triaza-cyclopenta[b]fluorene-1,3-dione The title compound is prepared similarly as described for example 30 using (3aSR,10RS)-2-(2-Bromoethyl)-10-(3-hydroxy-phenyl)-6-methoxy-3a-methyl-3a,4,9,10-tetrahydro-2,9,10a-triaza-cyclopenta[b]-fluorene-1,3-dione (example 24) and isobutyl amine as starting materials. MS: m/z (MH$^+$)=477.2

50. (3aSR,10RS)-2-(2-Cyclobutylamino-ethyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 30 using (3aSR,10RS)-2-(2-Bromoethyl)-10-(3-hydroxy-phenyl)-6-methoxy-3a-methyl-3a,4,9,10-tetrahydro-2,9,10a-triaza-cyclopenta[b]-fluorene-1,3-dione (example 24) and cyclobutyl amine as starting materials. MS: m/z (MH$^+$)=475.2

51. (3aSR,10RS)-2-(3-Ethylamino-propyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 30 using (3aSR,10RS)-2-(2-Bromoethyl)-10-(3-hydroxy-phenyl)-6-methoxy-3a-methyl-3a,4,9,10-tetrahydro-2,9,10a-triaza-cyclopenta[b]-fluorene-1,3-dione (example 24) and ethyl amine as starting materials. MS: m/z (MH$^+$)=463.2

52. (3aSR,10RS)-2-[2-(Ethyl-methyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 30 using (3aSR,10RS)-2-(2-Bromoethyl)-10-(3-hydroxy-phenyl)-6-methoxy-3a-methyl-3a,4,9,10-tetrahydro-2,9,10a-triaza-cyclopenta[b]-fluorene-1,3-dione (example 24) and N-ethyl methyl amine as starting materials. MS: m/z (MH$^+$)=463.2

53. (3aSR,10RS)-2-(2-Cyclopropylamino-ethyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared similarly as described for example 30 using (3aSR,10RS)-2-(2-Bromoethyl)-10-(3-hydroxy-phenyl)-6-methoxy-3a-methyl-3a,4,9,10-tetrahydro-2,9,10a-triaza-cyclopenta[b]-fluorene-1,3-dione (example 24) and cyclopropyl amine as starting materials. MS: m/z (MH$^+$)=461.2

Starting from the appropriate starting compounds mentioned below and with choice of bromoethyl isocyanate as reaction partner, the following compounds may be prepared using similar procedures as described for example 22, 24, 26 or 36:

(3aSR,10RS)-6-Bromo-2-(2-Bromo-ethyl)-10-(3-hydroxy-phenyl)-3a-methyl-3a,4,9,10-tetrahydro-2,9,10a-triaza-cyclopenta[b]fluorene-1,3-dione (3aSR,10RS)-2-(2-Bromo-ethyl)-6-cyclopropylmethoxy-10-(3-hydroxy-phenyl)-3a-methyl-3a,4,9,10-tetrahydro-2,9,10a-triaza-cyclopenta[b]fluorene-1,3-dione (3aSR,10RS)-2-(2-Bromo-ethyl)-10-(3-hydroxy-phenyl)-3a-methyl-6-trifluoromethoxy-3a,4,9,10-tetrahydro-2,9,10a-triaza-cyclopenta[b]fluorene-1,3-dione

54. (3aSR,10RS)-6-Bromo-2-(2-bromo-ethyl)-10-(3-hydroxy-phenyl)-3a-methyl-3a,4,9,10-tetrahydro-2,9,10a-triaza-cyclopenta[b]fluorene-1,3-dione Starting from (1RS,3SR)-6-bromo-1-(3-hydroxy-phenyl)-3-methyl-2,3,4,9-tetrahydro-1H-beta-carboline-3-carboxylic acid methyl ester, the title compound is prepared analogously to the procedure described for example 22. MS: m/z (M−H$^+$)$^-$=531.9/533.8

55. (3aSR,10RS)-2-(3-Chloro-propyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared analogously to the procedure described for example 22, using chloro propyl isocyanate and (1RS,3SR)-1-(3-hydroxy-phenyl)-6-methoxy-3-methyl-2,3,4,9-tetrahydro-1H-betacarboline-3-carboxylic acid methyl ester. MS: m/z (MH$^+$)=454.0

55a. (3aS,10R)-2-(3-Chloro-propyl)-10-(3-hydroxy-phenyl)-6-methoxy-3a-methyl-3a,4,9,10-tetrahydro-2,9,10a-triaza-cyclopenta[b]fluorene-1,3-dione The title compound is prepared analogously to the procedure described for example 22, using chloro propyl isocyanate and (1R,3S)-1-(3-hydroxy-phenyl)-6-methoxy-3-methyl-2,3,4,9-tetrahydro-1H-β-carboline-3-carboxylic acid methyl ester. MS: m/z (MH⁺)=454.0

56. (3aSR,10RS)-2-(3-Chloro-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione The title compound is prepared analogously to the procedure described for example 22, using chloro propyl isocyanate and (1RS,3SR)-6-(1,1-difluoro-methoxy)-1-(3-hydroxy-phenyl)-3-methyl-2,3,4,9-tetrahydro-1H-beta-carboline-3-carboxylic acid methyl ester. MS: m/z (MH⁺)=490.0

57. (3aSR,10RS)-6-Chloro-2-(3-chloro-propyl)-10-(3-hydroxy-phenyl)-3a-methyl-3a,4,9,10-tetrahydro-2,9,10a-triaza-cyclopenta[b]fluorene-1,3-dione The title compound is prepared analogously to the procedure described for example 22, using chloro propyl isocyanate and (1RS,3SR)-6-chloro-1-(3-hydroxy-phenyl)-3-methyl-2,3,4,9-tetrahydro-1H-betacarboline-3-carboxylic acid methyl ester. MS: m/z (MH⁺)=457.9

58. (3aSR,10RS)-6-Bromo-2-(3-chloro-propyl)-10-(3-hydroxy-phenyl)-3a-methyl-3a,4,9,10-tetrahydro-2,9,10a-triaza-cyclopenta[b]fluorene-1,3-dione The title compound is prepared analogously to the procedure described for example 22, using chloro propyl isocyanate and (1RS,3SR)-6-bromo-1-(3-hydroxy-phenyl)-3-methyl-2,3,4,9-tetrahydro-1H-betacarboline-3-carboxylic acid methyl ester. MS: m/z (MH⁺)=501.9/503.9

59. (3aSR,10RS)-2-(3-Chloro-propyl)-6-ethoxy-10-(3-hydroxy-phenyl)-3a-methyl-3a,4,9,10-tetrahydro-2,9,10a-triaza-cyclopenta[b]fluorene-1,3-dione The title compound is prepared analogously to the procedure described for example 22, using chloro propyl isocyanate and (1RS,3SR)-6-ethoxy-1-(3-hydroxy-phenyl)-3-methyl-2,3,4,9-tetrahydro-1H-betacarboline-3-carboxylic acid methyl ester. MS: m/z (MH⁺)=468.1

60. (3aSR,10RS)-2-(2-Bromo-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione Starting from (1RS,3SR)-7-fluoro-1-(3-hydroxy-phenyl)-6-methoxy-2,3,4,9-tetrahydro-1H-betacarboline-3-carboxylic acid methyl ester, the title compound is prepared analogously to the procedure described for example 22. MS: m/z (MH⁺)=502.0

61. (3aSR,10RS)-2-(2-Bromo-ethyl)-6-chloro-7-fluoro-10-(3-hydroxy-phenyl)-3a-methyl-3a,4,9,10-tetrahydro-2,9,10a-triaza-cyclopenta[b]fluorene-1,3-dione Starting from (1RS,3SR)-6-chloro-7-fluoro-1-(3-hydroxy-phenyl)-2,3,4,9-tetrahydro-1H-beta-carboline-3-carboxylic acid methyl ester, the title compound is prepared analogously to the procedure described for example 22. MS: m/z (M−H⁺)⁻=505.9

62. (3aSR,10RS)-2-(2-Bromo-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione Starting from (1RS,3SR)-5-fluoro-1-(3-hydroxy-phenyl)-6-methoxy-2,3,4,9-tetrahydro-1H-betacarboline-3-carboxylic acid methyl ester, the title compound is prepared analogously to the procedure described for example 22. MS: m/z (MH⁺)=501.9/503.8

63. (3aSR,10RS)-2-(3-Chloro-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione The title compound is prepared analogously to the procedure described for example 22, using chloro propyl isocyanate and (1RS,3SR)-7-fluoro-1-(3-hydroxy-phenyl)-6-methoxy-2,3,4,9-tetrahydro-1H-betacarboline-3-carboxylic acid methyl ester. MS: m/z (MH⁺)=472.0

64. (3aSR,10RS)-6-Chloro-2-(3-chloro-propyl)-7-fluoro-10-(3-hydroxy-phenyl)-3a-methyl-3a,4,9,10-tetrahydro-2,9,10a-triaza-cyclopenta[b]fluorene-1,3-dione The title compound is prepared analogously to the procedure described for example 22, using chloro propyl isocyanate and (1RS,3SR)-6-chloro-7-fluoro-1-(3-hydroxy-phenyl)-2,3,4,9-tetrahydro-1H-betacarboline-3-carboxylic acid methyl ester. MS: m/z (M−H⁺)⁻=474.0

65. (3aSR,10RS)-2-(3-Chloro-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione The title compound is prepared analogously to the procedure described for example 22, using chloro propyl isocyanate and (1RS,3SR)-5-fluoro-1-(3-hydroxy-phenyl)-6-methoxy-2,3,4,9-tetrahydro-1H-betacarboline-3-carboxylic acid methyl ester. MS: m/z (MH⁺)=472.0

66. (3aSR,10RS)-2-(2-Dimethylamino-ethyl)-6-hydroxy-10-(3-hydroxy-phenyl)-3a-methyl-3a,4,9,10-tetrahydro-2,9,10a-triaza-cyclopenta[b]fluorene-1,3-dione A solution of 150 mg (3aSR,10RS)-2-(2-dimethylaminoethyl)-10-(3-hydroxy-phenyl)-6-methoxy-3a-methyl-3a,4,9,10-tetrahydro-2,9,10a-triaza-cyclopenta[b]fluorene-1,3-dione (example 7) in 5 ml dichloromethane is cooled to −78° C. 20 ml bor tribromide are added drop wise. The suspension is stirred for 30 min at −78° C. and allowed to warm up to room temperature. After stirring for 1 h at room temperature, the mixture is cooled to 0° C. and an aqueous solution of sodium bicarbonate is added. The organic layer is separated and dried with magnesium sulfate. The solvent is removed at reduced pressure. After column chromatography (silica gel, ethyl acetate, methanol, ammonia 10:0.3:0.2), 49 mg of the title compound are obtained as a colourless foam. MS: m/z (MH⁺)=435.2

General Procedure for the Preparation of the Following Examples 67 to 544

A solution of the designated starting material (1. eq) and the designated amine (20 eq.) in THF is heated to 150° C.

using a sealed tube. In some cases a catalytic amount of sodium iodide is added to accelerate the reaction. The reaction is monitored by LC-MS. After full conversion (24-48 h), the solvent is removed under reduced pressure. The residue is dissolved in dichloromethane and extracted with an aqueous solution of sodium bicarbonate. The organic layer is separated and the solvent is removed. The finial compound is purified by preparative HPLC followed by lyophilization.

| example | chemical name | starting material | amine |
|---|---|---|---|
| 67. | (3aSR,10RS)-10-(3-Hydroxy-phenyl)-2-(3-isopropylamino-propyl)-6-methoxy-3a-methyl-3a,4,9,10-tetrahydro-2,9,10a-triaza-cyclopenta[b]fluorene-1,3-dione | Ex. 55 | 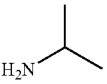 |
| 68. | (3aSR,10RS)-2-[2-(3,6-Dihydro-2H-pyridin-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione | Ex. 24 |  |
| 69. | (3aSR,10RS)-2-(2-Diethylamino-ethyl)-10-(3-hydroxy-phenyl)-6-methoxy-3a-methyl-3a,4,9,10-tetrahydro-2,9,10a-triaza-cyclopenta[b]fluorene-1,3-dione | Ex. 24 | 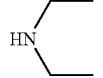 |
| 70. | (3aSR,10RS)-10-(3-Hydroxy-phenyl)-2-[2-(isopropyl-methyl-amino)-ethyl]-6-methoxy-3a-methyl-3a,4,9,10-tetrahydro-2,9,10a-triaza-cyclopenta[b]fluorene-1,3-dione | Ex. 24 | 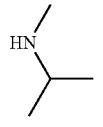 |
| 71. | (3aSR,10RS)-10-(3-Hydroxy-phenyl)-6-methoxy-3a-methyl-2-(2-piperidin-1-yl-ethyl)-3a,4,9,10-tetrahydro-2,9,10a-triaza-cyclopenta[b]fluorene-1,3-dione | Ex. 24 | 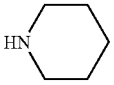 |
| 72. | (3aSR,10RS)-2-(2-tert-Butylamino-ethyl)-10-(3-hydroxy-phenyl)-6-methoxy-3a-methyl-3a,4,9,10-tetrahydro-2,9,10a-triaza-cyclopenta[b]fluorene-1,3-dione | Ex. 24 | 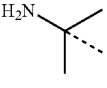 |
| 73. | (3aSR,10RS)-2-[2-(2,2-Difluoro-ethylamino)-ethyl]-10-(3-hydroxy-phenyl)-6-methoxy-3a-methyl-3a,4,9,10-tetrahydro-2,9,10a-triaza-cyclopenta[b]fluorene-1,3-dione | Ex. 24 | 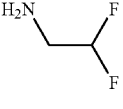 |
| 74. | (3aSR,10RS)-2-(2-Azepan-1-yl-ethyl)-10-(3-hydroxy-phenyl)-6-methoxy-3a-methyl-3a,4,9,10-tetrahydro-2,9,10a-triaza-cyclopenta[b]fluorene-1,3-dione | Ex. 24 | 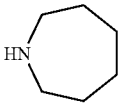 |
| 75. | (3aSR,10RS)-10-(3-Hydroxy-phenyl)-6-methoxy-3a-methyl-2-[2-(4-methyl-piperidin-1-yl)-ethyl]-3a,4,9,10-tetrahydro-2,9,10a-triaza-cyclopenta[b]fluorene-1,3-dione | Ex. 24 | 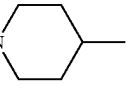 |
| 76. | (3aSR,10RS)-10-(3-Hydroxy-phenyl)-6-methoxy-3a-methyl-2-(3-methylamino-propyl)-3a,4,9,10-tetrahydro-2,9,10a-triaza-cyclopenta[b]fluorene-1,3-dione | Ex. 55 | 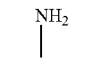 |
| 77. | (3aSR,10RS)-2-[3-(Ethyl-methyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55 | 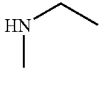 |

| | | | |
|---|---|---|---|
| 78. | (3aSR,10RS)-2-[2-[Ethyl-(2-hydroxy-ethyl)-amino]-ethyl}-10-(3-hydroxy-phenyl)-6-methoxy-3a-methyl-3a,4,9,10-tetrahydro-2,9,10a-triaza-cyclopenta[b]fluorene-1,3-dione | Ex. 24 | |
| 79. | (3aSR,10RS)-2-[2-[Ethyl-(2-methoxy-ethyl)-amino]-ethyl}-10-(3-hydroxy-phenyl)-6-methoxy-3a-methyl-3a,4,9,10-tetrahydro-2,9,10a-triaza-cyclopenta[b]fluorene-1,3-dione | Ex. 24 | 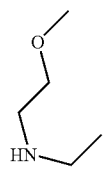 |
| 80. | (3aSR,10RS)-2-[2-(Allyl-methyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione | Ex. 24 |  |
| 81. | (3aSR,10RS)-10-(3-Hydroxy-phenyl)-6-methoxy-3a-methyl-2-[2-(methyl-prop-2-ynyl-amino)-ethyl]-3a,4,9,10-tetrahydro-2,9,10a-triaza-cyclopenta[b]fluorene-1,3-dione | Ex. 24 |  |
| 82. | (3aSR,10RS)-2-[2-(2-Hydroxy-ethylamino)-ethyl]-10-(3-hydroxy-phenyl)-6-methoxy-3a-methyl-3a,4,9,10-tetrahydro-2,9,10a-triaza-cyclopenta[b]fluorene-1,3-dione | Ex. 24 | 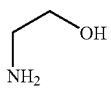 |
| 83. | (3aSR,10RS)-10-(3-Hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione | Ex. 24 | 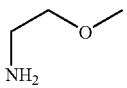 |
| 84. | (3aSR,10RS)-2-(2-Allylamino-ethyl)-10-(3-hydroxy-phenyl)-6-methoxy-3a-methyl-3a,4,9,10-tetrahydro-2,9,10a-triaza-cyclopenta[b]fluorene-1,3-dione | Ex. 24 |  |
| 85. | (3aSR,10RS)-10-(3-Hydroxy-phenyl)-6-methoxy-3a-methyl-2-(2-prop-2-ynylamino-ethyl)-3a,4,9,10-tetrahydro-2,9,10a-triaza-cyclopenta[b]fluorene-1,3-dione | Ex. 24 | 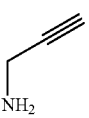 |
| 86. | (3aSR,10RS)-2-(3-Cyclobutylamino-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55 | 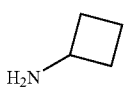 |
| 87. | (3aSR,10RS)-2-(3-Azetidin-1-yl-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55 |  |
| 88. | (3aSR,10RS)-2-[3-(Allyl-methyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55 | 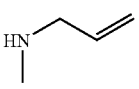 |

| | | | |
|---|---|---|---|
| 89. | (3aSR,10RS)-2-{3-[Ethyl-(2-hydroxy-ethyl)-amino]-propyl}-10-(3-hydroxy-phenyl)-6-methoxy-3a-methyl-3a,4,9,10-tetrahydro-2,9,10a-triaza-cyclopenta[b]fluorene-1,3-dione | Ex. 55 | 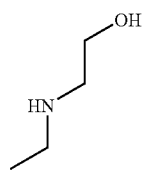 |
| 90. | (3aSR,10RS)-2-{3-[Ethyl-(2-methoxy-ethyl)-amino]-propyl}-10-(3-hydroxy-phenyl)-6-methoxy-3a-methyl-3a,4,9,10-tetrahydro-2,9,10a-triaza-cyclopenta[b]fluorene-1,3-dione | Ex. 55 | 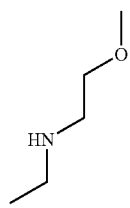 |
| 91. | (3aSR,10RS)-10-(3-Hydroxy-phenyl)-6-methoxy-3a-methyl-2-[2-(1-methyl-1H-pyrazol-3-ylamino)-ethyl]-3a,4,9,10-tetrahydro-2,9,10a-triaza-cyclopenta[b]fluorene-1,3-dione | Ex. 24 | 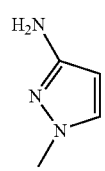 |
| 92. | (3aSR,10RS)-10-(3-Hydroxy-phenyl)-2-(3-isobutylamino-propyl)-6-methoxy-3a-methyl-3a,4,9,10-tetrahydro-2,9,10a-triaza-cyclopenta[b]fluorene-1,3-dione | Ex. 55 | 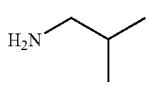 |
| 93. | (3aSR,10RS)-2-(3-Cyclopropylamino-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55 | 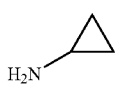 |
| 94. | (3aSR,10RS)-10-(3-Hydroxy-phenyl)-2-[3-(isopropyl-methyl-amino)-propyl]-6-methoxy-3a-methyl-3a,4,9,10-tetrahydro-2,9,10a-triaza-cyclopenta[b]fluorene-1,3-dione | Ex. 55 | 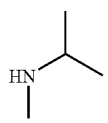 |
| 95. | (3aSR,10RS)-2-[3-(Cyclopropylmethyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55 | 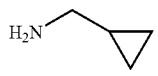 |
| 96. | (3aSR,10RS)-10-(3-Hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione | Ex. 55 |  |
| 97. | (3aSR,10RS)-2-(2-tert-Butylamino-ethyl)-6-chloro-10-(3-hydroxy-phenyl)-3a-methyl-3a,4,9,10-tetrahydro-2,9,10a-triaza-cyclopenta[b]fluorene-1,3-dione | Ex. 26 | 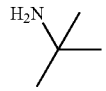 |
| 98. | (3aSR,10RS)-6-Chloro-10-(3-hydroxy-phenyl)-3a-methyl-2-[2-(4-methyl-piperidin-1-yl)-ethyl]-3a,4,9,10-tetrahydro-2,9,10a-triaza-cyclopenta[b]fluorene-1,3-dione | Ex. 26 |  |

| | | | |
|---|---|---|---|
| 99. | (3aSR,10RS)-6-Chloro-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione | Ex. 26 | H₂N-CH₂-CH(CH₃)₂ |
| 100. | (3aSR,10RS)-6-Chloro-2-[2-(3,6-dihydro-2H-pyridin-1-yl)-ethyl]-10-(3-hydroxy-phenyl)-3a-methyl-3a,4,9,10-tetrahydro-2,9,10a-triaza-cyclopenta[b]fluorene-1,3-dione | Ex. 26 | 3,6-dihydro-2H-pyridine (HN ring with double bond) |
| 101. | (3aSR,10RS)-6-Chloro-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione | Ex. 26 | piperidine (HN ring) |
| 102. | (3aSR,10RS)-6-Chloro-2-(2-cyclopropylamino-ethyl)-10-(3-hydroxy-phenyl)-3a-methyl-3a,4,9,10-tetrahydro-2,9,10a-triaza-cyclopenta[b]fluorene-1,3-dione | Ex. 26 | H₂N-cyclopropyl |
| 103. | (3aSR,10RS)-6-Chloro-2-(2-cyclobutylamino-ethyl)-10-(3-hydroxy-phenyl)-3a-methyl-3a,4,9,10-tetrahydro-2,9,10a-triaza-cyclopenta[b]fluorene-1,3-dione | Ex. 26 | H₂N-cyclobutyl |
| 104. | (3aSR,10RS)-2-(2-Azepan-1-yl-ethyl)-6-chloro-10-(3-hydroxy-phenyl)-3a-methyl-3a,4,9,10-tetrahydro-2,9,10a-triaza-cyclopenta[b]fluorene-1,3-dione | Ex. 26 | azepane (HN 7-ring) |
| 105. | (3aSR,10RS)-10-(3-Hydroxy-phenyl)-6-methoxy-3a-methyl-2-(3-piperidin-1-yl-propyl)-3a,4,9,10-tetrahydro-2,9,10a-triaza-cyclopenta[b]fluorene-1,3-dione | Ex. 55 | piperidine (HN ring) |
| 106. | (3aSR,10RS)-2-[3-(3,6-Dihydro-2H-pyridin-1-yl)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55 | 3,6-dihydro-2H-pyridine (HN ring with double bond) |
| 107. | (3aSR,10RS)-2-(3-Diethylamino-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55 | HN(CH₂CH₃)₂ |
| 108. | (3aSR,10RS)-6-Chloro-2-[2-(cyclopropylmethyl-amino)-ethyl]-10-(3-hydroxy-phenyl)-3a-methyl-3a,4,9,10-tetrahydro-2,9,10a-triaza-cyclopenta[b]fluorene-1,3-dione | Ex. 26 | H₂N-CH₂-cyclopropyl |
| 109. | (3aSR,10RS)-6-Chloro-2-[2-(2,5-dihydro-pyrrol-1-yl)-ethyl]-10-(3-hydroxy-phenyl)-3a-methyl-3a,4,9,10-tetrahydro-2,9,10a-triaza-cyclopenta[b]fluorene-1,3-dione | Ex. 26 | 2,5-dihydropyrrole (HN ring with double bond) |
| 110. | (3aSR,10RS)-6-Chloro-2-(2-diethylamino-ethyl)-10-(3-hydroxy-phenyl)-3a-methyl-3a,4,9,10-tetrahydro-2,9,10a-triaza-cyclopenta[b]fluorene-1,3-dione | Ex. 26 | HN(CH₂CH₃)₂ |

-continued

| | | | |
|---|---|---|---|
| 111. | (3aSR,10RS)-6-Chloro-10-(3-hydroxy-phenyl)-3a-methyl-2-[2-(4-methyl-piperazin-1-yl)-ethyl]-3a,4,9,10-tetrahydro-2,9,10a-triaza-cyclopenta[b]fluorene-1,3-dione | Ex. 26 | |
| 112. | (3aSR,10RS)-10-(3-Hydroxy-phenyl)-6-methoxy-3a-methyl-2-[3-(4-methyl-piperidin-1-yl)-propyl]-3a,4,9,10-tetrahydro-2,9,10a-triaza-cyclopenta[b]fluorene-1,3-dione | Ex. 55 | |
| 113. | (3aSR,10RS)-2-(3-Azepan-1-yl)-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55 | |
| 114. | (3aSR,10RS)-2-[2-(4-Acetyl-piperazin-1-yl)-ethyl]-6-chloro-10-(3-hydroxy-phenyl)-3a-methyl-3a,4,9,10-tetrahydro-2,9,10a-triaza-cyclopenta[b]fluorene-1,3-dione | Ex. 26 | |
| 115. | (3aSR,10RS)-2-(2-Allylamino-ethyl)-6-chloro-10-(3-hydroxy-phenyl)-3a-methyl-3a,4,9,10-tetrahydro-2,9,10a-triaza-cyclopenta[b]fluorene-1,3-dione | Ex. 26 | |
| 116. | (3aSR,10RS)-6-Chloro-10-(3-hydroxy-phenyl)-3a-methyl-2-[2-(methyl-prop-2-ynyl-amino)-ethyl]-3a,4,9,10-tetrahydro-2,9,10a-triaza-cyclopenta[b]fluorene-1,3-dione | Ex. 26 | |
| 117. | (3aSR,10RS)-2-[2-(Allyl-methyl-amino)-ethyl]-6-chloro-10-(3-hydroxy-phenyl)-3a-methyl-3a,4,9,10-tetrahydro-2,9,10a-triaza-cyclopenta[b]fluorene-1,3-dione | Ex. 26 | |
| 118. | (3aSR,10RS)-2-{2-[(2-Hydroxy-ethyl)-methyl-amino]-ethyl}-10-(3-hydroxy-phenyl)-6-methoxy-3a-methyl-3a,4,9,10-tetrahydro-2,9,10a-triaza-cyclopenta[b]fluorene-1,3-dione | Ex. 24 | |
| 119. | (3aSR,10RS)-2-[2-(2,5-Dihydro-pyrrol-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione | Ex. 24 | |
| 120. | (3aSR,10RS)-6-Chloro-10-(3-hydroxy-phenyl)-3a-methyl-2-(2-morpholin-4-ylethyl)-3a,4,9,10-tetrahydro-2,9,10a-triaza-cyclopenta[b]fluorene-1,3-dione | Ex. 26 | |
| 121. | (3aSR,10RS)-6-Chloro-2-{2-[ethyl-(2-methoxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione | Ex. 26 | |
| 122. | (3aSR,10RS)-6-Chloro-2-[2-(2-hydroxy-ethylamino)-ethyl]-10-(3-hydroxy-phenyl)-3a-methyl-3a,4,9,10-tetrahydro-2,9,10a-triaza-cyclopenta[b]fluorene-1,3-dione | Ex. 26 | |

| | | | |
|---|---|---|---|
| 123. | (3aSR,10RS)-6-Chloro-2-[2-(2,2-difluoro-ethylamino)-ethyl]-10-(3-hydroxy-phenyl)-3a-methyl-3a,4,9,10-tetrahydro-2,9,10a-triaza-cyclopenta[b]fluorene-1,3-dione | Ex. 26 | H₂N⁓⁓CHF₂ |
| 124. | (3aSR,10RS)-6-Chloro-2-{2-[ethyl-(2-hydroxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione | Ex. 26 | HN(Et)CH₂CH₂OH |
| 125. | (3aSR,10RS)-6-Chloro-10-(3-hydroxy-phenyl)-3a-methyl-2-[2-(1-methyl-1H-pyrazol-3-ylamino)-ethyl]-3a,4,9,10-tetrahydro-2,9,10a-triaza-cyclopenta[b]fluorene-1,3-dione | Ex. 26 | 3-amino-1-methylpyrazole |
| 126. | (3aSR,10RS)-6-Chloro-2-{2-[(2-hydroxy-ethyl)-methyl-amino]-ethyl}-10-(3-hydroxy-phenyl)-3a-methyl-3a,4,9,10-tetrahydro-2,9,10a-triaza-cyclopenta[b]fluorene-1,3-dione | Ex. 26 | HN(Me)CH₂CH₂OH |
| 127. | (3aSR,10RS)-6-Chloro-10-(3-hydroxy-phenyl)-3a-methyl-2-(2-prop-2-ynylamino-ethyl)-3a,4,9,10-tetrahydro-2,9,10a-triaza-cyclopenta[b]fluorene-1,3-dione | Ex. 26 | H₂N-CH₂-C≡CH |
| 128. | (3aSR,10RS)-6-Chloro-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione | Ex. 26 | H₂N-CH₂CH₂-O-CH₃ |
| 129. | (3aSR,10RS)-6-Chloro-2-[2-(3,3-difluoro-pyrrolidin-1-yl)-ethyl]-10-(3-hydroxy-phenyl)-3a-methyl-3a,4,9,10-tetrahydro-2,9,10a-triaza-cyclopenta[b]fluorene-1,3-dione | Ex. 26 | 3,3-difluoropyrrolidine |
| 130. | (3aSR,10RS)-6-Chloro-10-(3-hydroxy-phenyl)-3a-methyl-2-(3-methylamino-propyl)-3a,4,9,10-tetrahydro-2,9,10a-triaza-cyclopenta[b]fluorene-1,3-dione | Ex. 57 | H₂N—CH₃ |
| 131. | (3aSR,10RS)-6-Chloro-2-(3-ethylamino-propyl)-10-(3-hydroxy-phenyl)-3a-methyl-3a,4,9,10-tetrahydro-2,9,10a-triaza-cyclopenta[b]fluorene-1,3-dione | Ex. 57 | H₂N—CH₂CH₃ |
| 132. | (3aSR,10RS)-6-Chloro-2-{3-[(2-hydroxy-ethyl)-methyl-amino]-propyl}-10-(3-hydroxy-phenyl)-3a-methyl-3a,4,9,10-tetrahydro-2,9,10a-triaza-cyclopenta[b]fluorene-1,3-dione | Ex. 57 | CH₃-NH-CH₂CH₂-OH |
| 133. | (3aSR,10RS)-6-Chloro-10-(3-hydroxy-phenyl)-2-[3-(isopropyl-methyl-amino)-propyl]-3a-methyl-3a,4,9,10-tetrahydro-2,9,10a-triaza-cyclopenta[b]fluorene-1,3-dione | Ex. 57 | CH₃-NH-CH(CH₃)₂ |

| | | | |
|---|---|---|---|
| 134. | (3aSR,10RS)-10-(3-Hydroxy-phenyl)-6-methoxy-3a-methyl-2-[2-(2-methyl-2H-pyrazol-3-ylamino)-ethyl]-3a,4,9,10-tetrahydro-2,9,10a-triaza-cyclopenta[b]fluorene-1,3-dione | Ex. 24 | |
| 135. | (3aSR,10RS)-6-Chloro-10-(3-hydroxy-phenyl)-2-(3-isobutylamino-propyl)-3a-methyl-3a,4,9,10-tetrahydro-2,9,10a-triaza-cyclopenta[b]fluorene-1,3-dione | Ex. 57 | |
| 136. | (3aSR,10RS)-6-Chloro-10-(3-hydroxy-phenyl)-3a-methyl-2-[3-((R and S)1-methyl-prop-2-ynylamino)-propyl]-3a,4,9,10-tetrahydro-2,9,10a-triaza-cyclopenta[b]fluorene-1,3-dione | Ex. 57 | |
| 137. | (3aSR,10RS)-6-Chloro-2-(3-diethylamino-propyl)-10-(3-hydroxy-phenyl)-3a-methyl-3a,4,9,10-tetrahydro-2,9,10a-triaza-cyclopenta[b]fluorene-1,3-dione | Ex. 57 | |
| 138. | (3aSR,10RS)-6-Chloro-2-(3-cyclobutylamino-propyl)-10-(3-hydroxy-phenyl)-3a-methyl-3a,4,9,10-tetrahydro-2,9,10a-triaza-cyclopenta[b]fluorene-1,3-dione | Ex. 57 | |
| 139. | (3aSR,10RS)-2-(3-Allylamino-propyl)-6-chloro-10-(3-hydroxy-phenyl)-3a-methyl-3a,4,9,10-tetrahydro-2,9,10a-triaza-cyclopenta[b]fluorene-1,3-dione | Ex. 57 | |
| 140. | (3aSR,10RS)-6-Chloro-2-[3-(ethyl-methyl-amino)-propyl]-10-(3-hydroxy-phenyl)-3a-methyl-3a,4,9,10-tetrahydro-2,9,10a-triaza-cyclopenta[b]fluorene-1,3-dione | Ex. 57 | |
| 141. | (3aSR,10RS)-2-(3-Azetidin-1-yl-propyl)-6-chloro-10-(3-hydroxy-phenyl)-3a-methyl-3a,4,9,10-tetrahydro-2,9,10a-triaza-cyclopenta[b]fluorene-1,3-dione | Ex. 57 | |
| 142. | (3aSR,10RS)-2-[3-(2,2-Difluoro-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55 | |
| 143. | (3aSR,10RS)-2-{3[(2-Hydroxy-ethyl)-methyl-amino]-propyl}-10-(3-hydroxy-phenyl)-6-methoxy-3a-methyl-3a,4,9,10-tetrahydro-2,9,10a-triaza-cyclopenta[b]fluorene-1,3-dione | Ex. 55 | |
| 144. | (3aSR,10RS)-10-(3-Hydroxy-phenyl)-6-methyl-3a-methyl-2-[3-(methyl-prop-2-ynyl-amino)-propyl]-3a,4,9,10-tetrahydro-2,9,10a-triaza-cyclopenta[b]fluorene-1,3-dione | Ex. 55 | |
| 145. | (3aSR,10RS)-2-[3-(2-Hydroxy-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55 | |

-continued

| | | | |
|---|---|---|---|
| 146. | (3aSR,10RS)-2-(3-Allylamino-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55 | H₂N–CH₂–CH=CH₂ |
| 147. | (3aSR,10RS)-10-(3-Hydroxy-phenyl)-6-methoxy-3a-methyl-2-(3-prop-2-ynylamino-propyl)-3a,4,9,10-tetrahydro-2,9,10a-triaza-cyclopenta[b]fluorene-1,3-dione | Ex. 55 | H₂N–CH₂–C≡CH |
| 148. | (3aSR,10RS)-10-(3-Hydroxy-phenyl)-6-methoxy-3a-methyl-2-(3-morpholin-4-yl-propyl)-3a,4,9,10-tetrahydro-2,9,10a-triaza-cyclopenta[b]fluorene-1,3-dione | Ex. 55 | morpholine (HN–CH₂CH₂–O–CH₂CH₂) |
| 149. | (3aSR,10RS)-2-[3-(2,5-Dihydro-pyrrol-1-yl)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55 | 2,5-dihydropyrrole (HN) |
| 150. | (3aSR,10RS)-10-(3-Hydroxy-phenyl)-6-methoxy-3a-methyl-2-[3-(4-methyl-piperazin-1-yl)-propyl]-3a,4,9,10-tetrahydro-2,9,10a-triaza-cyclopenta[b]fluorene-1,3-dione | Ex. 55 | 4-methylpiperazine (HN...N–CH₃) |
| 151. | (3aSR,10RS)-2-[3-(4-Acetyl-piperazin-1-yl)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55 | 4-acetylpiperazine (HN...N–C(=O)CH₃) |
| 152. | (3aSR,10RS)-6-Ethoxy-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione | Ex. 22 | H₂N–CH(CH₃)₂ |
| 153. | (3aSR,10RS)-6-Ethoxy-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione | Ex. 22 | H₂N–CH₂–CH(CH₃)₂ |
| 154. | (3aSR,10RS)-2-[2-(Cyclopropylmethyl-amino)-ethyl]-6-methoxy-10-(3-hydroxy-phenyl)-3a-methyl-3a,4,9,10-tetrahydro-2,9,10a-triaza-cyclopenta[b]fluorene-1,3-dione | Ex. 22 | H₂N–CH₂–cyclopropyl |
| 155. | (3aSR,10RS)-2-(2-Cyclobutylamino-ethyl)-6-ethoxy-10-(3-hydroxy-phenyl)-3a-methyl-3a,4,9,10-tetrahydro-2,9,10a-triaza-cyclopenta[b]fluorene-1,3-dione | Ex. 22 | H₂N–cyclobutyl |
| 156. | (3aSR,10RS)-2-(2-tert-Butylamino-ethyl)-6-ethoxy-10-(3-hydroxy-phenyl)-3a-methyl-3a,4,9,10-tetrahydro-2,9,10a-triaza-cyclopenta[b]fluorene-1,3-dione | Ex. 22 | H₂N–C(CH₃)₃ |
| 157. | (3aSR,10RS)-2-(2-Allylamino-ethyl)-6-ethoxy-10-(3-hydroxy-phenyl)-3a-methyl-3a,4,9,10-tetrahydro-2,9,10a-triaza-cyclopenta[b]fluorene-1,3-dione | Ex. 22 | H₂N–CH₂–CH=CH₂ |

-continued

| | | | |
|---|---|---|---|
| 158. | (3aSR,10RS)-6-Ethoxy-2-[2-(ethyl-methyl-amino)-ethyl]-10-(3-hydroxy-phenyl)-3a-methyl-3a,4,9,10-tetrahydro-2,9,10a-triaza-cyclopenta[b]fluorene-1,3-dione | Ex. 22 |  |
| 159. | (3aSR,10RS)-6-Ethoxy-2-[2-(2-hydroxy-ethylamino)-ethyl]-10-(3-hydroxy-phenyl)-3a-methyl-3a,4,9,10-tetrahydro-2,9,10a-triaza-cyclopenta[b]fluorene-1,3-dione | Ex. 22 | 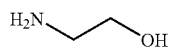 |
| 160. | (3aSR,10RS)-6-Ethoxy-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione | Ex. 22 |  |
| 161. | (3aSR,10RS)-2-(2-Cyclopropylamino-ethyl)-6-ethoxy-10-(3-hydroxy-phenyl)-3a-methyl-3a,4,9,10-tetrahydro-2,9,10a-triaza-cyclopenta[b]fluorene-1,3-dione | Ex. 22 | 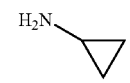 |
| 162. | (3aSR,10RS)-2-(2-Diethylamino-ethyl)-6-ethoxy-10-(3-hydroxy-phenyl)-3a-methyl-3a,4,9,10-tetrahydro-2,9,10a-triaza-cyclopenta[b]fluorene-1,3-dione | Ex. 22 |  |
| 163. | (3aSR,10RS)-6-Ethoxy-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione | Ex. 22 | 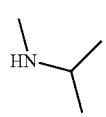 |
| 164. | (3aSR,10RS)-6-Ethoxy-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione | Ex. 22 |  |
| 165. | (3aSR,10RS)-2-[2-(3,6-Dihydro-2H-pyridin-1-yl)-ethyl]-6-ethoxy-10-(3-hydroxy-phenyl)-3a-methyl-3a,4,9,10-tetrahydro-2,9,10a-triaza-cyclopenta[b]fluorene-1,3-dione | Ex. 22 |  |
| 166. | (3aSR,10RS)-2-(2-Azepan-1-yl-ethyl)-6-ethoxy-10-(3-hydroxy-phenyl)-3a-methyl-3a,4,9,10-tetrahydro-2,9,10a-triaza-cyclopenta[b]fluorene-1,3-dione | Ex. 22 |  |
| 167. | (3aSR,10RS)-2-(3-tert-Butylamino-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55 |  |
| 168. | (3aSR,10RS)-6-Chloro-2-{3-[ethyl-(2-hydroxy-ethyl)-amino]-propyl}-10-(3-hydroxy-phenyl)-3a-methyl-3a,4,9,10-tetrahydro-2,9,10a-triaza-cyclopenta[b]fluorene-1,3-dione | Ex. 57 | 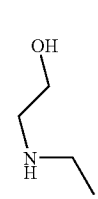 |

-continued

| | | | |
|---|---|---|---|
| 169. | (3aSR,10RS)-2-[3-(Allyl-methyl-amino)-propyl]-6-chloro-10-(3-hydroxy-phenyl)-3a-methyl-3a,4,9,10-tetrahydro-2,9,10a-triaza-cyclopenta[b]fluorene-1,3-dione | Ex. 57 | |
| 170. | (3aSR,10RS)-6-Chloro-10-(3-hydroxy-phenyl)-3a-methyl-2-[3-(methyl-prop-2-ynyl-amino)-propyl]-3a,4,9,10-tetrahydro-2,9,10a-triaza-cyclopenta[b]fluorene-1,3-dione | Ex. 57 | |
| 171. | (3aSR,10RS)-6-Chloro-10-(3-hydroxy-phenyl)-3a-methyl-2-(3-morpholin-4-yl-propyl)-3a,4,9,10-tetrahydro-2,9,10a-triaza-cyclopenta[b]fluorene-1,3-dione | Ex. 57 | |
| 172. | (3aSR,10RS)-6-Chloro-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione | Ex. 57 | |
| 173. | (3aSR,10RS)-6-Chloro-2-[3-(2,5-dihydro-pyrrol-1-yl)-propyl]-10-(3-hydroxy-phenyl)-3a-methyl-3a,4,9,10-tetrahydro-2,9,10a-triaza-cyclopenta[b]fluorene-1,3-dione | Ex. 57 | |
| 174. | (3aSR,10RS)-6-Chloro-2-[3-(3,6-dihydro-2H-pyridin-1-yl)-propyl]-10-(3-hydroxy-phenyl)-3a-methyl-3a,4,9,10-tetrahydro-2,9,10a-triaza-cyclopenta[b]fluorene-1,3-dione | Ex. 57 | |
| 175. | (3aSR,10RS)-6-Chloro-10-(3-hydroxy-phenyl)-3a-methyl-2-[3-(4-methyl-piperazin-1-yl)-propyl]-3a,4,9,10-tetrahydro-2,9,10a-triaza-cyclopenta[b]fluorene-1,3-dione | Ex. 57 | |
| 176. | (3aSR,10RS)-2-(3-Diethylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 56 | |
| 177. | (3aSR,10RS)-6-(1,1-Difluoro-methoxy)-2-{3-[ethyl-(2-hydroxy-ethyl)-amino]-propyl}-10-(3-hydroxy-phenyl)-3a-methyl-3a,4,9,10-tetrahydro-2,9,10a-triaza-cyclopenta[b]fluorene-1,3-dione | Ex. 56 | |
| 178. | (3aSR,10RS)-6-(1,1-Difluoro-methoxy)-2-{3-[ethyl-(2-methoxy-ethyl)-amino]-propyl}-10-(3-hydroxy-phenyl)-3a-methyl-3a,4,9,10-tetrahydro-2,9,10a-triaza-cyclopenta[b]fluorene-1,3-dione | Ex. 56 | |
| 179. | (3aSR,10RS)-6-(1,1-Difluoro-methoxy)-10-(3-hydroxy-phenyl)-2-[3-(isopropyl-methyl-amino)-propyl]-3a-methyl-3a,4,9,10-tetarhydro-2,9,10a-triaza-cyclopenta[b]fluorene-1,3-dione | Ex. 56 | |

| | | | |
|---|---|---|---|
| 180. | (3aSR,10RS)-2-(3-Azepan-1-yl-propyl)-6-chloro-10-(3-hydroxy-phenyl)-3a-methyl-3a,4,9,10-tetrahydro-2,9,10a-triaza-cyclopenta[b]fluorene-1,3-dione | Ex. 57 | 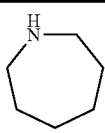 |
| 181. | (3aSR,10RS)-6-Chloro-10-(3-hydroxy-phenyl)-3a-methyl-2-(3-piperidin-1-yl-propyl)-3a,4,9,10-tetrahydro-2,9,10a-triaza-cyclopenta[b]fluorene-1,3-dione | Ex. 57 | 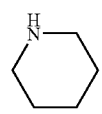 |
| 182. | (3aSR,10RS)-2-(3-tert-Butylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 56 | 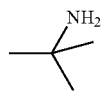 |
| 183. | (3aSR,10RS)-6-(1,1-Difluoro-methoxy)-10-(3-hydroyx-phenyl)-3a-methyl-2-[3-(methyl-prop-2-ynyl-amino)-propyl]-3a,4,9,10-tetrahydro-2,9,10a-triaza-cyclopenta[b]fluorene-1,3-dione | Ex. 56 | 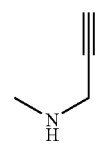 |
| 184. | (3aSR,10RS)-2-[3-(Allyl-methyl-amino)-propyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 56 | 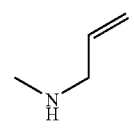 |
| 185. | (3aSR,10RS)-6-Chloro-10-(3-hydroxy-phenyl)-2-[3-(2-methoxy-ethylamino)-propyl]-3a-methyl-3a,4,9,10-tetrahydro-2,9,10a-triaza-cyclopenta[b]fluorene-1,3-dione | Ex. 57 | 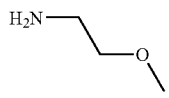 |
| 186. | (3aSR,10RS)-6-Ethoxy-10-(3-hydroxy-phenyl)-3a-methyl-2-(3-methylamino-propyl)-3a,4,9,10-tetrahydro-2,9,10a-triaza-cyclopenta[b]fluorene-1,3-dione | Ex. 59 |  |
| 187. | (3aSR,10RS)-6-Ethoxy-2-(3-ethylamino-propyl)-10-(3-hydroxy-phenyl)-3a-methyl-3a,4,9,10-tetrahydro-2,9,10a-triaza-cyclopenta[b]fluorene-1,3-dione | Ex. 59 | 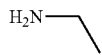 |
| 188. | (3aSR,10RS)-2-[3-(Cyclopropylmethyl-amino)-propyl]-6-ethoxy-10-(3-hydroxy-phenyl)-3a-methyl-3a,4,9,10-tetrahydro-2,9,10a-triaza-cyclopenta[b]fluorene-1,3-dione | Ex. 59 | 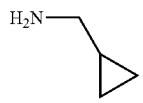 |
| 189. | (3aSR,10RS)-6-Ethoxy-10-(3-hydroyx-phenyl)-2-[3-(2-methoxy-ethylamino)-propyl]-3a-methyl-3a,4,9,10-tetrahydro-2,9,10a-triaza-cyclopenta[b]fluorene-1,3-dione | Ex. 59 | 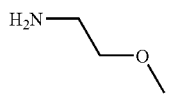 |
| 190. | (3aSR,10RS)-2-(3-Cyclopropylamino-propyl)-6-ethoxy-10-(3-hydroxy-phenyl)-3a-methyl-3a,4,9,10-tetrahydro-2,9,10a-triaza-cyclopenta[b]fluorene-1,3-dione | Ex. 59 | 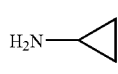 |
| 191. | (3aSR,10RS)-2-(3-Allylamino-propyl)-6-ethoxy-10-(3-hydroxy-phenyl)-3a-methyl-3a,4,9,10-tetrahydro-2,9,10a-triaza-cyclopenta[b]bluorene-1,3-dione | Ex. 59 | 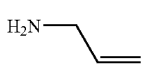 |

| | | | |
|---|---|---|---|
| 192. | (3aSR,10RS)-6-Ethoxy-2-[3-(ethyl-methyl-amino)-propyl]-10-(3-hydroxy-phenyl)-3a-methyl-3a,4,9,10-tetrahydro-2,9,10a-triaza-cyclopenta[b]fluorene-1,3-dione | Ex. 59 | |
| 193. | (3aSR,10RS)-6-Ethoxy-2-{3-[(2-hydrox-ethyl)-methyl-amino]-propyl}-10-(3-hydroxy-phenyl)-3a-methyl-3a,4,9,10-tetrahydro-2,9,10a-triaza-cyclopenta[b]fluorene-1,3-dione | Ex. 59 | |
| 194. | (3aSR,10RS)-6-Ethoxy-2-{3-[ethyl-(2-hydroxy-ethyl)-amino]-propyl}-10-(3-hydroxy-phenyl)-3a-methyl-3a,4,9,10-tetrahydro-2,9,10a-triaza-cyclopenta[b]fluorene-1,3-dione | Ex. 59 | |
| 195. | (3aSR,10RS)-6-Ethoxy-2-{3-[ethyl-(2-methoxy-ethyl)-amino]-propyl}-10-(3-hydroxy-phenyl)-3a-methyl-3a,4,9,10-tetrahydro-2,9,10a-triaza-cyclopenta[b]fluorene-1,3-dione | Ex. 59 | |
| 196. | (3aSR,10RS)-2-[3-(Allyl-methyl-amino)-propyl]-6-ethoxy-10-(3-hydroyx-phenyl)-3a-methyl-3a,4,9,10-tetrahydro-2,9,10a-triaza-cyclopenta[b]fluorene-1,3-dione | Ex. 59 | |
| 197. | (3aSR,10RS)-6-Ethoxy-10-(3-hydroxy-phenyl)-2-[3-(isopropyl-methyl-amino)-propyl]-3a-methyl-3a,4,9,10-tetrahydro-2,9,10a-triaza-cyclpenta[b]fluorene-1,3-dione | Ex. 59 | |
| 198. | (3aSR,10RS)-2-(3-Azetidin-1-yl-propyl)-6-ethoxy-10-(3-hydroxy-phenyl)-3a-methyl-3a,4,9,10-tetrahydro-2,9,10a-triaza-cyclopenta[b]fluorene-1,3-dione | Ex. 59 | |
| 199. | (3aSR,10RS)-6-(1,1-Difluoro-methoxy)-10-(3-hydroxy-phenyl)-2-(3-isobutylamino-propyl)-3a-methyl-3a,4,9,10-tetrahydro-2,9,10a-triaza-cyclopenta[b]fluorene-1,3-dione | Ex. 56 | |
| 200. | (3aSR,10RS)-2-[3-(Cyclopropylmethyl-amino)-propyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 56 | |
| 201. | (3aSR,10RS)-6-(1,1-Difluoro-methoxy)-2-[3-(2-hydroxy-ethylamino)-propyl]-10-(3-hydroxy-phenyl)-3a-methyl-3a,4,9,10-tetrahydro-2,2,10a-triaza-cyclopenta[b]fluorene-1,3-dione | Ex. 56 | |
| 202. | (3aSR,10RS)-2-(3-Cyclopropylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 56 | |

-continued

| | | | |
|---|---|---|---|
| 203. | (3aSR,10RS)-6-(1,1-Difluoro-methoxy)-10-(3-hydroxy-phenyl)-3a-methyl-2-(3-methylamino-propyl)-3a,4,9,10-tetrahydro-2,9,10a-triaza-cyclopenta[b]fluorene-1,3-dione | Ex. 56 | H$_2$N— |
| 204. | (3aSR,10RS)-6-(1,1-Difluoro-methoxy)-2-(3-ethylamino-propyl)-10-(3-hydroxy-phenyl)-3a-methyl-3a,4,9,10-tetrahydro-2,9,10a-triaza-cyclopenta[b]fluorene-1,3-dione | Ex. 56 |  |
| 205. | (3aSR,10RS)-6-(1,1-Difluoro-methoxy)-10-(3-hydroxy-phenyl)-2-[3-(2-methoxy-ethylamino)-propyl]-3a-methyl-3a,4,9,10-tetrahydro-2,9,10a-triaza-cyclopenta[b]fluorene-1,3-dione | Ex. 56 | 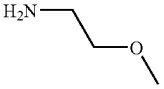 |
| 206. | (3aSR,10RS)-2-(3-Allylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 56 |  |
| 207. | (3aSR,10RS)-6-Ethoxy-10-(3-hydroxy-phenyl)-3a-methyl-2-(3-morpholin-4-yl-propyl)-3a,4,9,10-tetrahydro-2,9,10a-triaza-cyclopenta[b]fluorene-1,3-dione | Ex. 59 | 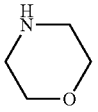 |
| 208. | (3aSR,10RS)-2-[3-(3,6-Dihydro-2H-pyridin-1-yl)-propyl]-6-ethoxy-10-(3-hydroyx-phenyl)-3a-methyl-3a,4,9,10-tetrahydro-2,9,10a-triaza-cyclopenta[b]fluorene-1,3-dione | Ex. 59 | 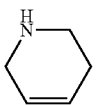 |
| 209. | (3aSR,10RS)-2-[3-(4-Acetyl-piperazin-1-yl)-propyl]-6-ethoxy-10-(3-hydroxy-phenyl)-3a-methyl-3a,4,9,10-tetrahydro-2,9,10a-triaza-cyclopenta[b]fluorene-1,3-dione | Ex. 59 | 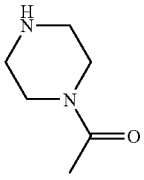 |
| 210. | (3aSR,10RS)-2-(3-Azepan-1-yl-propyl)-6-ethoxy-10-(3-hydroxy-phenyl)-3a-methyl-3a,4,9,10-tetrahydro-2,9,10a-triaza-cyclopenta[b]fluorene-1,3-dione | Ex. 59 | 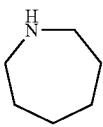 |
| 211. | (3aSR,10RS)-6-Bromo-10-(3-hydroyx-phenyl)-3a-methyl-2-(3-methylamino-propyl)-3a,4,9,10-tetrahydro-2,9,10a-triaza-cyclopenta[b]fluorene-1,3-dione | Ex. 58 | H$_2$N— |
| 212. | (3aSR,10RS)-6-Bromo-2-(3-ethylamino-propyl)-10-(3-hydroxy-phenyl)-3a-methyl-3a,4,9,10-tetrahydro-2,9,10a-triaza-cyclopenta[b]fluorene-1,3-dione | Ex. 58 |  |
| 213. | (3aSR,10RS)-6-Bromo-10-(3-hydroxy-phenyl)-2-(3-isobutylamino-propyl)-3a-methyl-3a,4,9,10-tetrahydro-2,9,10a-triaza-cyclopenta[b]fluorene-1,3-dione | Ex. 58 | 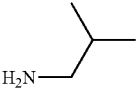 |

| | | | |
|---|---|---|---|
| 214. | (3aSR,10RS)-6-Bromo-10-(3-hydroxy-phenyl)-2-[3-(2-methoxy-ethylamino)-propyl]-3a-methyl-3a,4,9,10-tetrahydro-2,9,10a-triaza-cyclopenta[b]fluorene-1,3-dione | Ex. 58 | H₂N–\–O–\ |
| 215. | (3aSR,10RS)-6-Bromo-2-(3-cyclopropylamino-propyl)-10-(3-hydroxy-phenyl)-3a-methyl-3a,4,9,10-tetrahydro-2,9,10a-triaza-cyclopenta[b]fluorene-1,3-dione | Ex. 58 | H₂N-cyclopropyl |
| 216. | (3aSR,10RS)-6-Bromo-2-[3-(ethyl-methyl-amino)-propyl]-10-(3-hydroxy-phenyl)-3a-methyl-3a,4,9,10-tetrahydro-2,9,10a-triaza-cyclopenta[b]fluorene-1,3-dione | Ex. 58 | CH₃NH-C₂H₅ |
| 217. | (3aSR,10RS)-6-Bromo-2-{3-[ethyl-(2-methoxy-ethyl)-amino]-propyl}-10-(3-hydroxy-phenyl)-3a-methyl-3a,4,9,10-tetrahydro-2,9,10a-triaza-cyclopenta[b]fluorene-1,3-dione | Ex. 58 | CH₃O-CH₂CH₂-NH-C₂H₅ |
| 218. | (3aSR,10RS)-6-Bromo-10-(3-hydroxy-phenyl)-2-[3-(isopropyl-methyl-amino)-propyl]-3a-methyl-3a,4,9,10-tetrahydro-2,9,10a-triaza-cyclopenta[b]fluorene-1,3-dione | Ex. 58 | CH₃NH-iPr |
| 219. | (3aSR,10RS)-6-Bromo-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione | Ex. 58 | pyrrolidine |
| 220. | (3aSR,10RS)-2-[3-(4-Acetyl-piperazin-1-yl)-propyl]-6-bromo-10-(3-hydroxy-phenyl)-3a-methyl-3a,4,9,10-tetrahydro-2,9,10a-triaza-cyclopenta[b]fluorene-1,3-dione | Ex. 58 | 4-acetyl-piperazine |
| 221. | (3aSR,10RS)-6-Ethoxy-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione | Ex. 59 | pyrrolidine |
| 222. | (3aSR,10RS)-2-[3-(2,5-Dihydro-pyrrol-1-yl)-propyl]-6-ethoxy-10-(3-hydroxy-phenyl)-3a-methyl-3a,4,9,10-tetrahydro-2,9,10a-triaza-cyclopenta[b]fluorene-1,3-dione | Ex. 59 | 2,5-dihydropyrrole |
| 223. | (3aSR,10RS)-6-Ethoxy-10-(3-hydroxy-phenyl)-3a-methyl-2-(3-piperidin-1-yl-propyl)-3a,4,9,10-tetrahydro-2,9,10a-triaza-cyclopenta[b]fluorene-1,3-dione | Ex. 59 | piperidine |
| 224. | (3aSR,10RS)-6-Ethoxy-10-(3-hydroxy-phenyl)-3a-methyl-2-[3-(4-methyl-piperidin-1-yl)-propyl]-3a,4,9,10-tetrahydro-2,9,10a-triaza-cyclopenta[b]fluorene-1,3-dione | Ex. 59 | 4-methylpiperidine |

| | | | |
|---|---|---|---|
| 225. | (3aSR,10RS)-6-Ethoxy-10-(3-hydroxy-phenyl)-3a-methyl-2-(3-prop-2-ynylamino-propyl)-3a,4,9,10-tetrahydro-2,9,10a-triaza-cyclopenta[b]fluorene-1,3-dione | Ex. 59 | propargylamine (NH₂–CH₂–C≡CH) |
| 226. | (3aSR,10RS)-2-(3-Dimethylamino-propyl)-6-ethoxy-10-(3-hydroxy-phenyl)-3a-methyl-3a,4,9,10-tetrahydro-2,9,10a-triaza-cyclopenta[b]fluorene-1,3-dione | Ex. 59 | N,N-dimethylamine fragment |
| 227. | (3aSR,10RS)-6-Ethoxy-10-(3-hydroxy-phenyl)-3a-methyl-2-[3-(methyl-prop-2-ynyl-amino)-propyl]-3a,4,9,10-tetrahydro-2,9,10a-triaza-cyclopenta[b]fluorene-1,3-dione | Ex. 59 | N-methyl-propargylamine |
| 228. | (3aSR,10RS)-6-Bromo-2-(3-diethylamino-propyl)-10-(3-hydroxy-phenyl)-3a-methyl-3a,4,9,10-tetrahydro-2,9,10a-triaza-cyclopenta[b]fluorene-1,3-dione | Ex. 58 | diethylamine |
| 229. | (3aSR,10RS)-6-Ethoxy-10-(3-hydroxy-phenyl)-3a-methyl-2-[3-(4-methyl-piperazin-1-yl)-propyl]-3a,4,9,10-tetrahydro-2,9,10a-triaza-cyclopenta[b]fluorene-1,3-dione | Ex. 59 | 4-methylpiperazine |
| 230. | (3aSR,10RS)-6-Bromo-2-(3-dimethylamino-propyl)-10-(3-hydroyx-phenyl)-3a-methyl-3a,4,9,10-tetrahydro-2,9,10a-triaza-cyclopenta[b]fluorene-1,3-dione | Ex. 58 | N,N-dimethylamine fragment |
| 231. | (3aSR,10RS)-6-Bromo-2-{3-[ethyl-(2-hydroxy-ethyl)-amino]-propyl}-10-(3-hydroyx-phenyl)-3a-methyl-3a,4,9,10-tetrahydro-2,9,10a-triaza-cyclopenta[b]fluorene-1,3-dione | Ex. 58 | N-ethyl-2-hydroxyethylamine |
| 232. | (3aSR,10RS)-6-Bromo-2-[3-(3,6-dihydro-2H-pyridin-1-yl)-propyl]-10-(3-hydroxy-phenyl)-3a-methyl-3a,4,9,10-tetrahydro-2,9,10a-triaza-cyclopenta[b]fluorene-1,3-dione | Ex. 58 | 1,2,3,6-tetrahydropyridine |
| 233. | (3aSR,10RS)-6-Bromo-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione | Ex. 54 | isopropylamine |
| 234. | (3aSR,10RS)-6-Bromo-2-[3-(cyclopropylmethyl-amino)-propyl]-10-(3-hydroxy-phenyl)-3a-methyl-3a,4,9,10-tetrahydro-2,9,10a-triaza-cyclopenta[b]fluorene-1,3-dione | Ex. 58 | cyclopropylmethylamine |
| 235. | (3aSR,10RS)-6-Bromo-2-[3-(2-hydroxy-ethylamino)-propyl]-10-(3-hydroxy-phenyl)-3a-methyl-3a,4,9,10-tetrahydro-2,9,10a-triaza-cyclopenta[b]fluorene-1,3-dione | Ex. 58 | 2-aminoethanol |

| | | -continued | |
|---|---|---|---|
| 236. | (3aSR,10RS)-6-(1,1-Difluoro-methoxy)-10-(3-hydroxy-phenyl)-3a-methyl-2-(3-morpholin-4-yl-propyl)-3a,4,9,10-tetrahydro-2,9,10a-triaza-cyclopenta[b]fluorene-1,3-dione | Ex. 56 | 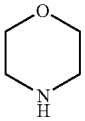 |
| 237. | (3aSR,10RS)-6-(1,1-Difluoro-methoxy)-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione | Ex. 56 | 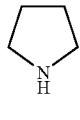 |
| 238. | (3aSR,10RS)-6-(1,1-Difluoro-methoxy)-2-[3-(2,5-dihydro-pyrrol-1-yl)-propyl]-10-(3-hydroxy-phenyl)-3a-methyl-3a,4,9,10-tetrahydro-2,9,10a-triaza-cyclopenta[b]fluorene-1,3-dione | Ex. 56 | 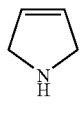 |
| 239. | (3aSR,10RS)-6-(1,1-Difluoro-methoxy)-10-(3-hydroxy-phenyl)-3a-methyl-2-(3-piperidin-1-yl-propyl)-3a,4,9,10-tetrahydro-2,9,10a-triaza-cyclopenta[b]fluorene-1,3-dione | Ex. 56 | 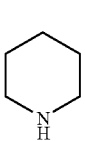 |
| 240. | (3aSR,10RS)-6-(1,1-Difluoro-methoxy)-10-(3-hydroyx-phenyl)-3a-methyl-2-[3-(4-methyl-piperazin-1-yl)-propyl]-3a,4,9,10-tetrahydro-2,9,10a-triaza-cyclopenta[b]fluorene-1,3-dione | Ex. 56 | 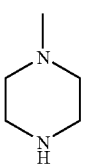 |
| 241. | (3aSR,10RS)-2-[3-(4-Acetyl-piperazin-1-yl)-propyl]-6-(1,1-difluoro-methoxy)-10-(3-hydroxy-phenyl)-3a-methyl-3a,4,9,10-tetrahydro-2,9,10a-triaza-cyclopenta[b]fluoroene-1,3-dione | Ex. 56 | 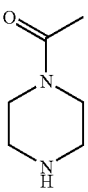 |
| 242. | (3aSR,10RS)-6-(1,1-Difluoro-methoxy)-2-[3-(3,6-dihydro-2H-pyridin-1-yl)-propyl]-10-(3-hydroxy-phenyl)-3a-methyl-3a,4,9,10-tetrahydro-2,9,10a-triaza-cyclopenta[b]fluorene-1,3-dione | Ex. 56 | 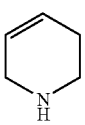 |
| 243. | (3aSR,10RS)-2-(3-Azepan-1-yl-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 56 |  |
| 244. | (3aSR,10RS)-6-(1,1-Difluoro-methoxy)-10-(3-hydroxy-phenyl)-3a-methyl-2-[3-(4-methyl-piperidin-1-yl)-propyl]-3a,4,9,10-tetrahydro-2,9,10a-triaza-cyclopenta[b]fluorene-1,3-dione | Ex. 56 | 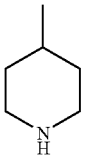 |
| 245. | (3aS,10R)-7-Fluoro-2-[2-(2-hydroxy-ethylamino)-ethyl]-10-(3-hydroxy-phenyl)-6-methoxy-3a-methyl-3a,4,9,10-tetrahydro-2,9,10a-triaza-cyclopenta[b]fluorene-1,3-dione | Ex. 60 | 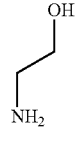 |

-continued

| | | | |
|---|---|---|---|
| 246. | (3aS,10R)-7-Fluoro-2-{2-[(2-hydroxy-ethyl)-methyl-amino]-ethyl}-10-(3-hydroxy-phenyl)-6-methoxy-3a-methyl-3a,4,9,10-tetrahydro-2,9,10a-triaza-cyclopenta[b]fluorene-1,3-dione | Ex. 60 | HN—CH₂CH₂—OH (N-methyl, N-(2-hydroxyethyl)) |
| 247. | (3aSR,10RS)-6-(1,1-Difluoro-methoxy)-2-[3-(ethyl-methyl-amino)-propyl]-10-(3-hydroxy-phenyl)-3a-methyl-3a,4,9,10-tetrahydro-2,9,10a-triaza-cyclopenta[b]fluorene-,3-dione | Ex. 56 | ethyl-methyl-amine |
| 248. | (3aSR,10RS)-7-Fluoro-10-(3-hydroxy-phenyl)-6-methoxy-3a-methyl-2-(2-methylamino-ethyl)-3a,4,9,10-tetrahydro-2,9,10a-triaza-cyclopenta[b]fluorene-1,3-dione | Ex. 60 | CH₃—NH₂ (methylamine) |
| 249. | (3aSR,10RS)-2-(2-Ethylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 | ethylamine |
| 250. | (3aSR,10RS)-7-Fluoro-10-(3-hydroxy-phenyl)-2-(2-isopropylamino-ethyl)-6-methoxy-3a-methyl-3a,4,9,10-tetrahydro-2,9,10a-triaza-cyclopenta[b]fluorene-1,3-dione | Ex. 60 | isopropylamine |
| 251. | (3aSR,10RS)-2-[2-(Cyclopropylmethyl-amino)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 | cyclopropylmethylamine |
| 252. | (3aSR,10RS)-7-Fluoro-10-(3-hydroxy-phenyl)-2-(2-isobutylamino-ethyl)-6-methoxy-3a-methyl-3a,4,9,10-tetrahydro-2,9,10-triaza-cyclopenta[b]fluorene-1,3-dione | Ex. 60 | isobutylamine |
| 253. | (3aSR,10RS)-7-Fluoro-10-(3-hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione | Ex. 60 | 2-methoxyethylamine |
| 254. | (3aSR,10RS)-2-(2-Allylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 | allylamine |
| 255. | (3aSR,10RS)-2-(2-Dimethylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 | dimethylamine |
| 256. | (3aSR,10RS)-2-(2-tert-Butylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 | tert-butylamine |

| | | | |
|---|---|---|---|
| 257. | (3aSR,10RS)-2-[2-(Ethyl-methyl-amino)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 |  |
| 258. | (3aSR,10RS)-2-(2-Diethylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 |  |
| 259. | (3aSR,10RS)-7-Fluoro-10-(3-hydroyx-phenyl)-2-[2-(isopropyl-methyl-amino)-ethyl]-6-methoxy-3a-methyl-3a,4,9,10-tetrahydro-2,9,10a-triaza-cyclopenta[b]fluorene-1,3-dione | Ex. 60 |  |
| 260. | (3aSR,10RS)-7-Fluoro-10-(3-hydroxy-phenyl)-6-methoxy-3a-methyl-2-(2-morpholin-4-yl-ethyl)-3a,4,9,10-tetrahydro-2,9,10a-triaza-cyclopenta[b]fluorene-1,3-dione | Ex. 60 |  |
| 261. | (3aSR,10RS)-7-Fluoro-10-(3-hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione | Ex. 60 |  |
| 262. | (3aSR,10RS)-2-[2-(2,5-Dihydro-pyrrol-1-yl)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 |  |
| 263. | (3aSR,10RS)-7-Fluoro-10-(3-hydroxy-phenyl)-6-methoxy-3a-methyl-2-(2-piperidin-1-yl-ethyl)-3a,4,9,10-tetrahydro-2,9,10a-triaza-cyclopenta[b]fluorene-1,3-dione | Ex. 60 |  |
| 264. | (3aSR,10RS)-7-Fluoro-10-(3-hydroxy-phenyl)-6-methoxy-3a-methyl-2-[2-(4-methyl-piperidin-1-yl)-ethyl]-3a,4,9,10-tetrahydro-2,9,10a-triaza-cyclopenta[b]fluorene-1,3-dione | Ex. 60 | 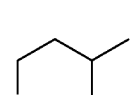 |
| 265. | (3aSR,10RS)-2-[2-(3,6-Dihydro-2H-pyridin-1-yl)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 |  |
| 266. | (3aSR,10RS)-7-Fluoro-10-(3-hydroxy-phenyl)-6-methoxy-3a-methyl-2-[2-(4-methyl-piperazin-1-yl)-ethyl]-3a,4,9,10-tetrahydro-2,9,10a-triaza-cyclopenta[b]fluorene-1,3-dione | Ex. 60 | 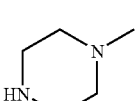 |
| 267. | (3aSR,10RS)-2-[2-(4-Acetyl-piperazin-1-yl)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 | 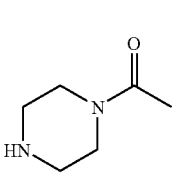 |

-continued

| | | | |
|---|---|---|---|
| 268. | (3aSR,10RS)-6-(1,1-Difluoro-methoxy)-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione | Ex. 36 | H₂N–CH(CH₃)₂ |
| 269. | (3aSR,10RS)-6-(1,1-Difluoro-methoxy)-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione | Ex. 36 | H₂N–CH₂CH(CH₃)₂ |
| 270. | (3aSR,10RS)-2-[2-(Cyclopropylmethyl-amino)-ethyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 36 | H₂N–CH₂–cyclopropyl |
| 271. | (3aSR,10RS)-6-(1,1-Difluoro-methoxy)-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione | Ex. 36 | H₂N–CH₂CH₂–O–CH₃ |
| 272. | (3aSR,10RS)-2-(2-Cyclobutylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 36 | H₂N–cyclobutyl |
| 273. | (3aSR,10RS)-2-(2-tert-Butylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 36 | H₂N–C(CH₃)₃ |
| 274. | (3aSR,10RS)-2-(2-Allylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 36 | H₂N–CH₂–CH=CH₂ |
| 275. | (3aSR,10RS)-6-(1,1-Difluoro-methoxy)-2-[2-(ethyl-methyl-amino)-ethyl]-10-(3-hydroxy-phenyl)-3a-methyl-3a,4,9,10-tetrahydro-2,9,10a-triaza-cyclopenta[b]fluorene-1,3-dione | Ex. 36 | CH₃–NH–CH₂CH₃ |
| 276. | (3aSR,10RS)-2-(2-Diethylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 36 | (CH₃CH₂)₂NH |
| 277. | (3aSR,10RS)-6-(1,1-Difluoro-methoxy)-2-{2-[ethyl-(2-hydroxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione | Ex. 36 | CH₃CH₂–NH–CH₂CH₂–OH |
| 278. | (3aSR,10RS)-6-(1,1-Difluoro-methoxy)-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione | Ex. 36 | CH₃–NH–CH(CH₃)₂ |

| | | | |
|---|---|---|---|
| 279. | (3aSR,10RS)-6-(1,1-Difluoro-methoxy)-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione | Ex. 36 | pyrrolidine (HN-cyclopentane) |
| 280. | (3aSR,10RS)-6-(1,1-Difluoro-methoxy)-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione | Ex. 36 | piperidine (HN-cyclohexane) |
| 281. | (3aSR,10RS)-6-(1,1-Difluoro-methoxy)-2-[2-(3,6-dihydro-2H-pyridin-1-yl)-ethyl]-10-(3-hydroxy-phenyl)-3a-methyl-3a,4,9,10-tetrahydro-2,9,10a-triaza-cyclopenta[b]fluorene-1,3-dione | Ex. 36 | 1,2,3,6-tetrahydropyridine |
| 282. | (3aSR,10RS)-2-(2-Azepan-1-yl-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 36 | azepane |
| 283. | (3aSR,10RS)-2-(2-Amino-ethyl)-6-(1,1-difluoro-methoxy)-10-(3-hydroxy-phenyl)-3a-methyl-3a4,9,10-tetrahydro-2,9,10a-triaza-cyclopenta[b]fluorene-1,3-dione | Ex. 36 | NH$_2$ |
| 284. | (3aSR,10RS)-6-(1,1-Difluoro-methoxy)-2-(2-ethylamino-ethyl)-10-(3-hydroxy-phenyl)-3a-methyl-3a,4,9,10-tetrahydro-2,9,10a-triaza-cyclopenta[b]fluorene-1,3-dione | Ex. 36 | H$_2$N-CH$_2$CH$_3$ |
| 285. | (3aSR,10RS)-6-(1,1-Difluoro-methoxy)-2-[2-(2-hydroxy-ethylamino)-ethyl]-10-(3-hydroxy-phenyl)-3a-methyl-3a,4,9,10-tetrahydro-2,9,10a-triaza-cyclopenta[b]fluorene-1,3-dione | Ex. 36 | H$_2$N-CH$_2$CH$_2$-OH |
| 286. | (3aSR,10RS)-2-(2-Cyclopropylamino-ethyl)-6-(1,1-difluoro-methoxy)-10-(3-hydroxy-phenyl)-3a-methyl-3a,4,9,10-tetrahydro-2,9,10a-triaza-cyclpenta[b]fluorene-1,3-dione | Ex. 36 | H$_2$N-cyclopropyl |
| 287. | (3aSR,10RS)-6-(1,1-Difluoro-methoxy)-10-(3-hydroxy-phenyl)-3a-methyl-2-(2-prop-2-ynylamino-ethyl)-3a,4,9,10-tetrahydro-2,9,10a-triaza-cyclopenta[b]fluorene-1,3-dione | Ex. 36 | H$_2$N-CH$_2$-C≡CH |
| 288. | (3aSR,10RS)-6-(1,1-Difluoro-methoxy)-2-{2-[(2-hydroxy-ethyl)-methyl-amino]-ethyl}-10-(3-hydroxy-phenyl)-3a-methyl-3a,4,9,10-tetrahydro-2,9,10a-triaza-cyclopenta[b]fluorene-1,3-dione | Ex. 36 | CH$_3$-HN-CH$_2$CH$_2$-OH |
| 289. | (3aSR,10RS)-6-(1,1-Difluoro-methoxy)-2-{2-[ethyl-(2-methoxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione | Ex. 36 | CH$_3$CH$_2$-N(H)-CH$_2$CH$_2$-OCH$_3$ |

| | | | |
|---|---|---|---|
| 290. | (3aSR,10RS)-2-[2-(Allyl-methyl-amino)-ethyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 36 | ![structure] HN with N-methyl and allyl |
| 291. | (3aSR,10RS)-6-(1,1-Difluoro-methoxy)-10-(3-hydroxy-phenyl)-3a-methyl-2-[2-(methyl-prop-2-ynyl-amino)-ethyl]-3a,4,9,10-tetrahydro-2,9,10a-triaza-cyclopenta[b]fluorene-1,3-dione | Ex. 36 | ![structure] HN-CH2-C≡CH with methyl |
| 292. | (3aSR,10RS)-6-(1,1-Difluoro-methoxy)-10-(3-hydroxy-phenyl)-3a-methyl-2-(2-morpholin-4-yl-ethyl)-3a,4,9,10-tetrahydro-2,9,10a-triaza-cyclopenta[b]fluorene-1,3-dione | Ex. 36 | ![morpholine] |
| 293. | (3aSR,10RS)-6-(1,1-Difluoro-methoxy)-10-(3-hydroxy-phenyl)-3a-methyl-2-[2-(4-methyl-piperidin-1-yl)-ethyl]-3a,4,9,10-tetrahydro-2,9,10a-triaza-cyclopenta[b]fluorene-1,3-dione | Ex. 36 | ![4-methylpiperidine] |
| 294. | (3aSR,10RS)-6-(1,1-Difluoro-methoxy)-10-(3-hydroxy-phenyl)-3a-methyl-2-[2-(4-methyl-piperazin-1-yl)-ethyl}-3a,4,9,10-tetrahydro-2,9,10a-triaza-cyclopenta[b]fluorene-1,3-dione | Ex. 36 | ![4-methylpiperazine] |
| 295. | (3aSR,10RS)-2-[2-(4-Acetyl-piperazin-1-yl)-ethyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione | Ex. 36 | ![4-acetylpiperazine] |
| 296. | (3aSR,10RS)-6-Ethoxy-2-(2-ethylamino-ethyl)-10-(3-hydroxy-phenyl)-3a-methyl-3a,4,9,10-tetrahydro-2,9,10a-triaza-cyclopenta[b]fluorene-1,3-dione | Ex. 22 | H2N-ethyl |
| 297. | (3aSR,10RS)-6-Ethoxy-2-{2-[(2-hydroxy-ethyl)-methyl-amino]-ethyl}-10-(3-hydroxy-phenyl)-3a-methyl-3a,4,9,10-tetrahydro-2,9,10a-triaza-cyclopenta[b]fluorene-1,3-dione | Ex. 22 | HN(Me)-CH2CH2-OH |
| 298. | (3aSR,10RS)-6-Ethoxy-2-{2-[ethyl-(2-hydroxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione | Ex. 22 | HN(Et)-CH2CH2-OH |
| 299. | (3aSR,10RS)-6-Ethoxy-2-{2-[ethyl-(2-methoxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione | Ex. 22 | HN(Et)-CH2CH2-OMe |
| 300. | (3aSR,10RS)-2-[2-(Allyl-methyl-amino)-ethyl]-6-ethoxy-10-(3-hydroxy-phenyl)-3a-methyl-3a,4,9,10-tetrahydro-2,9,10a-triaza-cyclopenta[b]fluorene-1,3-dione | Ex. 22 | HN(Me)-allyl |

-continued

| | | | |
|---|---|---|---|
| 301. | (3aSR,10RS)-6-Ethoxy-10-(3-hydroxy-phenyl)-3a-methyl-2-[2-(methyl-prop-2-ynyl-amino)-ethyl]-3a,4,9,10-tetrahydro-2,9,10a-triaza-cyclopenta[b]fluorene-1,3-dione | Ex. 22 | HN–CH₂–C≡CH (N-methyl propargylamine) |
| 302. | (3aSR,10RS)-6-Ethoxy-10-(3-hydroxy-phenyl)-3a-methyl-2-[2-(4-methyl-piperidin-1-yl)-ethyl]-3a,4,9,10-tetrahydro-2,9,10a-triaza-cyclopenta[b]fluorene-1,3-dione | Ex. 22 | 4-methylpiperidine (HN-piperidine-4-methyl) |
| 303. | (3aSR,10RS)-7-Fluoro-10-(3-hydroxy-phenyl)-6-methoxy-3a-methyl-2-(3-methylamino-propyl)-3a,4,9,10-tetrahydro-2,9,10a-triaza-cyclopenta[b]fluorene-1,3-dione | Ex. 63 | H₂N–CH₃ (methylamine) |
| 304. | (3aSR,10RS)-2-[3-(Cyclopropylmethyl-amino)-propyl]-7-fluoro-10-(3-hydroyx-phenyl)-6-methoxy-3a-methyl-3a,4,9,10-tetrahydro-2,9,10a-triaza-cyclopenta[b]fluorene-1,3-dione | Ex. 63 | H₂N–CH₂–cyclopropyl |
| 305. | (3aSR,10RS)-7-Fluoro-2-[3-(2-hydroxy-ethylamino)-propyl]-10-(3-hydroyx-phenyl)-6-methoxy-3a-methyl-3a,4,9,10-tetrahydro-2,9,10a-triaza-cyclopenta[b]fluorene-1,3-dione | Ex. 63 | H₂N–CH₂CH₂–OH |
| 306. | (3aSR,10RS)-7-Fluoro-10-(3-hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione | Ex. 63 | H₂N–CH₂CH₂–O–CH₃ |
| 307. | (3aSR,10RS)-2-(3-Cyclopropylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | H₂N–cyclopropyl |
| 308. | (3aSR,10RS)-2-(3-tert-Butylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | H₂N–C(CH₃)₃ (tert-butylamine) |
| 309. | (3aSR,10RS)-7-Fluoro-10-(3-hydroxy-phenyl)-6-methoxy-3a-methyl-2-(3-prop-2-ynylamino-propyl)-3a,4,9,10-tetrahydro-2,9,10a-triaza-cyclopenta[b]fluorene-1,3-dione | Ex. 63 | H₂N–CH₂–C≡CH (propargylamine) |
| 310. | (3aSR,10RS)-2-(3-Dimethylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | HN(CH₃)₂ (dimethylamine) |
| 311. | (3aSR,10RS)-2-[3-(Ethyl-methyl-amino)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | HN(CH₃)(C₂H₅) (N-ethyl-N-methylamine) |

| | | | |
|---|---|---|---|
| 312. | (3aSR,10RS)-7-Fluoro-2-{3-[(2-hydroxy-ethyl)-methyl-amino]-propyl}-10-(3-hydroyx-phenyl)-6-methoxy-3a-methyl-3a,4,9,10-tetrahydro-2,9,10a-triaza-cyclopenta[b]fluorene-1,3-dione | Ex. 63 | HN\\/\\OH (N-methyl, N-(2-hydroxyethyl)) |
| 313. | (3aSR,10RS)-2-(3-Diethylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | HN(Et)(Et) |
| 314. | (3aSR,10RS)-6-(1,1-Difluoro-methoxy)-2-(3-dimethylamino-propyl)-10-(3-hydroxy-phenyl)-3a-methyl-3a,4,9,10-tetrahydro-2,9,10a-triaza-cyclopenta[b]fluorene-1,3-dione | Ex. 56 | HN(Me)(Me) |
| 315. | (3aSR,10RS)-2-{3-[Ethyl-(2-hydroxy-ethyl)-amino]-propyl}-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | HN(Et)(CH2CH2OH) |
| 316. | (3aSR,10RS)-2-{3-[Ethyl-(2-methoxy-ethyl)-amino]-propyl}-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | HN(Et)(CH2CH2OMe) |
| 317. | (3aSR,10RS)-2-[3-(Allyl-methyl-amino)-propyl]-7-fluoro-10-(3-hydroyx-phenyl)-6-methoxy-3a-methyl-3a,4,9,10-tetrahydro-2,9,10a-triaza-cyclopenta[b]fluorene-1,3-dione | Ex. 63 | HN(Me)(allyl) |
| 318. | (3aSR,10RS)-7-Fluoro-10-(3-hydroxy-phenyl)-6-methoxy-3a-methyl-2-[3-(methyl-prop-2-ynyl-amino)-propyl]-3a,4,9,10-tetrahydro-2,9,10a-triaza-cyclopenta[b]fluorene-1,3-dione | Ex. 63 | HN(Me)(CH2C≡CH) |
| 319. | (3aSR,10RS)-7-Fluoro-10-(3-hydroxy-phenyl)-2-[3-(isopropyl-methyl-amino)-propyl]-6-methoxy-3a-methyl-3a,4,9,10-tetrahydro-2,9,10a-triaza-cyclopenta[b]fluorene-1,3-dione | Ex. 63 | HN(Me)(iPr) |
| 320. | (3aSR,10RS)-2-(3-Azetidin-1-yl-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | azetidine (HN in 4-membered ring) |
| 321. | (3aSR,10RS)-7-Fluoro-10-(3-hydroxy-phenyl)-6-methoxy-3a-methyl-2-(3-morpholin-4-yl-propyl)-3a,4,9,10-tetrahydro-2,9,10a-triaza-cyclopenta[b]fluorene-1,3-dione | Ex. 63 | morpholine |
| 322. | (3aSR,10RS)-7-Fluoro-10-(3-hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione | Ex. 63 | pyrrolidine |

| # | Name | Ex. | Structure |
|---|---|---|---|
| 323. | (3aSR,10RS)-2-[3-(2,5-Dihydro-pyrrol-1-yl)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | 2,5-dihydropyrrole |
| 324. | (3aSR,10RS)-7-Fluoro-10-(3-hydroxy-phenyl)-6-methoxy-3a-methyl-2-(3-piperidin-1-yl-propyl)-3a,4,9,10-tetrahydro-2,9,10a-triaza-cyclopenta[b]fluorene-1,3-dione | Ex. 63 | piperidine |
| 325. | (3aSR,10RS)-7-Fluoro-10-(3-hydroxy-phenyl)-6-methoxy-3a-methyl-2-[3-(4-methyl-piperazin-1-yl)-propyl]-3a,4,9,10-tetrahydro-2,9,10a-triaza-cyclopenta[b]fluorene-1,3-dione | Ex. 63 | 4-methylpiperazine |
| 326. | (3aSR,10RS)-2-[3-(3,6-Dihydro-2H-pyridin-1-yl)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | 1,2,3,6-tetrahydropyridine |
| 327. | (3aSR,10RS)-7-Fluoro-10-(3-hydroxy-phenyl)-6-methoxy-3a-methyl-2-[3-(4-methyl-piperidin-1-yl)-propyl]-3a,4,9,10-tetrahydro-2,9,10a-triaza-cyclopenta[b]fluorene-1,3-dione | Ex. 63 | 4-methylpiperidine |
| 328. | (3aSR,10RS)-2-[3-(4-Acetyl-piperazin-1-yl)-propyl]-7-fluoro-10-(3-hydroyx-phenyl)-6-methoxy-3a-methyl-3a,4,9,10-tetrahydro-2,9,10a-triaza-cyclopenta[b]fluorene-1,3-dione | Ex. 63 | 1-acetylpiperazine |
| 329. | (3aSR,10RS)-2-(3-Azepan-1-yl-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | azepane |
| 330. | (3aSR,10RS)-2-(3-Ethylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | ethylamine |
| 331. | (3aSR,10RS)-7-Fluoro-10-(3-hydroxy-phenyl)-2-{3-isopropylamino-propyl)-6-methoxy-3a-methyl-3a,4,9,10-tetrahydro-2,9,10a-triaza-cyclopenta[b]fluorene-1,3-dione | Ex. 63 | isopropylamine |
| 332. | (3aSR,10RS)-7-Fluoro-10-(3-hydroxy-phenyl)-2-(3-isobutylamino-propyl)-6-methoxy-3a-methyl-3a,4,9,10-tetrahydro-2,9,10a-triaza-cyclopenta[b]fluorene-1,3-dione | Ex. 63 | isobutylamine |
| 333. | (3aSR,10RS)-2-(3-Cyclobutylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | cyclobutylamine |

| | | | |
|---|---|---|---|
| 334. | (3aSR,10RS)-2-(3-Allylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 63 | H₂N⁀⁀⁼ |
| 335. | (3aSR,10RS)-6-Chloro-2-(3-dimethylamino-propyl)-7-fluoro-10-(3-hydroxy-phenyl)-3a-methyl-3a,4,9,10-tetrahydro-2,9,10a-triaza-cyclopenta[b]fluorene-1,3-dione | Ex. 64 | HN(CH₃)₂ |
| 336. | (3aSR,10RS)-6-Chloro-2-(2-diethylamino-ethyl)-7-fluoro-10-(3-hydroxy-phenyl)-3a-methyl-3a,4,9,10-tetrahydro-2,9,10a-triaza-cyclopenta[b]fluorene-1,3-dione | Ex. 61 | HN(Et)₂ |
| 337. | (3aSR,10RS)-6-Chloro-7-fluoro-10-(3-hydroxy-phenyl)-3a-methyl-2-(2-methylamino-ethyl)-3a,4,9,10-tetrahydro-2,9,10a-triaza-cyclopenta[b]fluorene-1,3-dione | Ex. 61 | H₂N−CH₃ |
| 338. | (3aSR,10RS)-6-Chloro-2-(2-ethylamino-ethyl)-7-fluoro-10-(3-hydroxy-phenyl)-3a-methyl-3a,4,9,10-tetrahydro-2,9,10a-triaza-cyclopenta[b]fluorene-1,3-dione | Ex. 61 | H₂N−Et |
| 339. | (3aSR,10RS)-6-Chloro-7-fluoro-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione | Ex. 61 | H₂N−iPr |
| 340. | (3aSR,10RS)-6-Chloro-7-fluoro-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione | Ex. 61 | H₂N−iBu |
| 341. | (3aSR,10RS)-6-Chloro-2-[2-(cyclopropylmethyl-amino)-ethyl]-7-fluoro-10-(3-hydroxy-phenyl)-3a-methyl-3a,4,9,10-tetrahydro-2,9,10a-triaza-cyclopenta[b]fluorene-1,3-dione | Ex. 61 | H₂N−CH₂−cPr |
| 342. | (3aSR,10RS)-6-Chloro-7-fluoro-2-[2-(2-hydroxy-ethylamino)-ethyl]-10-(3-hydroxy-phenyl)-3a-methyl-3a,4,9,10-tetrahydro-2,9,10a-triaza-cyclopenta[b]fluorene-1,3-dione | Ex. 61 | H₂N⌒OH |
| 343. | (3aSR,10RS)-6-Chloro-7-fluoro-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione | Ex. 61 | H₂N⌒O−CH₃ |
| 344. | (3aSR,10RS)-6-Chloro-2-(2-cyclobutylamino-ethyl)-7-fluoro-10-(3-hydroxy-phenyl)-3a-methyl-3a,4,9,10-tetrahydro-2,9,10a-triaza-cyclopenta[b]fluorene-1,3-dione | Ex. 61 | H₂N−cyclobutyl |

| | -continued | | |
|---|---|---|---|
| 345. | (3aSR,10RS)-2-(2-tert-Butylamino-ethyl)-6-chloro-7-fluoro-10-(3-hydroxy-phenyl)-3a-methyl-3a,4,9,10-tetrahydro-2,9,10a-triaza-cyclopenta[b]fluorene-1,3-dione | Ex. 61 | $H_2N$—C(CH$_3$)$_3$ |
| 346. | (3aSR,10RS)-2-(2-Allylamino-ethyl)-6-chloro-7-fluoro-10-(3-hydroxy-phenyl)-3a-methyl-3a,4,9,10-tetrahydro-2,9,10a-triaza-cyclopenta[b]fluorene-1,3-dione | Ex. 61 | $H_2N$—CH$_2$—CH=CH$_2$ |
| 347. | (3aSR,10RS)-6-Chloro-2-[2-(ethyl-methyl-amino)-ethyl]-7-fluoro-10-(3-hydroxy-phenyl)-3a-methyl-3a,4,9,10-tetrahydro-2,9,10a-triaza-cyclopenta[b]fluorene-1,3-dione | Ex. 61 | CH$_3$-HN-CH$_2$CH$_3$ |
| 348. | (3aSR,10RS)-6-Chloro-7-fluoro-2-{2-[(2-hydroxy-ethyl)-methyl-amino]-ethyl}-10-(3-hydroxy-phenyl)-3a-methyl-3a,4,9,10-tetrahydro-2,9,10a-triaza-cyclopenta[b]fluorene-1,3-dione | Ex. 61 | CH$_3$-HN-CH$_2$CH$_2$OH |
| 349. | (3aSR,10RS)-6-Chloro-2-{2-[ethyl-(2-hydroxy-ethyl)-amino]-ethyl}-7-fluoro-10-(3-hydroxy-phenyl)-3a-methyl-3a,4,9,10-tetrahydro-2,9,10a-triaza-cyclopenta[b]fluorene-1,3-dione | Ex. 61 | Et-HN-CH$_2$CH$_2$OH |
| 350. | (3aSR,10RS)-6-Chloro-2-{2-[ethyl-(2-methoxy-ethyl)-amino]-ethyl}-7-fluoro-10-(3-hydroxy-phenyl)-3a-methyl-3a,4,9,10-tetrahydro-2,9,10a-triaza-cyclopenta[b]fluorene-1,3-dione | Ex. 61 | Et-HN-CH$_2$CH$_2$OCH$_3$ |
| 351. | (3aSR,10RS)-6-Chloro-7-fluoro-10-(3-hydroxy-phenyl)-3a-methyl-2-[2-(methyl-prop-2-ynyl-amino)-ethyl]-3a,4,9,10-tetrahydro-2,9,10a-triaza-cyclopenta[b]fluorene-1,3-dione | Ex. 61 | CH$_3$-HN-CH$_2$-C≡CH |
| 352. | (3aSR,10RS)-6-Chloro-7-fluoro-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione | Ex. 61 | CH$_3$-HN-CH(CH$_3$)$_2$ |
| 353. | (3aSR,10RS)-6-Chloro-7-fluoro-10-(3-hydroxy-phenyl)-3a-methyl-2-(2-morpholin-4-yl-ethyl)-3a,4,9,10-tetrahydro-2,9,10a-triaza-cyclopenta[b]fluorene-1,3-dione | Ex. 61 | morpholine |
| 354. | (3aSR,10RS)-6-Chloro-7-fluoro-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione | Ex. 61 | pyrrolidine |
| 355. | (3aSR,10RS)-6-Chloro-2-[2-(2,5-dihydro-pyrrol-1-yl)-ethyl]-7-fluoro-10-(3-hydroxy-phenyl)-3a-methyl-3a,4,9,10-tetrahydro-2,9,10a-triaza-cyclopenta[b]fluorene-1,3-dione | Ex. 61 | 3-pyrroline |

| | | | |
|---|---|---|---|
| 356. | (3aSR,10RS)-6-Chloro-7-fluoro-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione | Ex. 61 | |
| 357. | (3aSR,10RS)-6-Chloro-7-fluoro-10-(3-hydroxy-phenyl)-3a-methyl-2-[2-(4-methyl-piperidin-1-yl)-ethyl]-3a,4,9,10-tetrahydro-2,9,10a-triaza-cyclopenta[b]fluorene-1,3-dione | Ex. 61 | |
| 358. | (3aSR,10RS)-6-Chloro-2-[2-(3,6-dihydro-2H-pyridin-1-yl)-ethyl]-7-fluoro-10-(3-hydroxy-phenyl)-3a-methyl-3a,4,9,10-tetrahydro-2,9,10a-triaza-cyclopenta[b]fluorene-1,3-dione | Ex. 61 | |
| 359. | (3aSR,10RS)-6-Chloro-7-fluoro-10-(3-hydroxy-phenyl)-3a-methyl-2-[2-(4-methyl-piperazin-1-yl)-ethyl]-3a,4,9,10-tetrahydro-2,9,10a--triaza-cyclopenta[b]fluorene-1,3-dione | Ex. 61 | |
| 360. | (3aSR,10RS)-2-[2-(4-Acetyl-piperazin-1-yl)-ethyl]-6-chloro-7-fluoro-10-(3-hydroxy-phenyl)-3a-methyl-3a,4,9,10-tetrahydro-2,9,10a-triaza-cyclopenta[b]fluorene-1,3-dione | Ex. 61 | |
| 361. | (3aSR,10RS)-2-(2-Azepan-1-yl-ethyl)-6-chloro-7-fluoro-10-(3-hydroxy-phenyl)-3a-methyl-3a,4,9,10-tetrahydro-2,9,10a-triaza-cyclopenta[b]fluorene-1,3-dione | Ex. 61 | |
| 362. | (3aSR,10RS)-2-[2-(Allyl-methyl-amino)-ethyl]-6-chloro-7-fluoro-10-(3-hydroxy-phenyl)-3a-methyl-3a,4,9,10-tetrahydro-2,9,10a-triaza-cyclopenta[b]fluorene-1,3-dione | Ex. 61 | |
| 363. | (3aSR,10RS)-2-(3-Allylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | |
| 364. | (3aSR,10RS)-2-[3-(Ethyl-methyl-amino)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | |
| 365. | (3aSR,10RS)-2-{3-[Ethyl-(2-methoxy-ethyl)-amino]-propyl}-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | |
| 366. | (3aSR,10RS)-5-Fluoro-10-(3-hydroxy-phenyl)-6-methoxy-3a-methyl-2-(3-piperidin-1-yl-propyl)-3a,4,9,10-tetrahydro-2,9,10a-triaza-cyclopenta[b]fluorene-1,3-dione | Ex. 65 | |

-continued

| | | | |
|---|---|---|---|
| 367. | (3aSR,10RS)-5-Fluoro-10-(3-hydroxy-phenyl)-6-methoxy-3a-methyl-2-[3-(4-methyl-piperidin-1-yl)-propyl]-3a,4,9,10-tetrahydro-2,9,10a-triaza-cyclopenta[b]fluorene-1,3-dione | Ex. 65 | 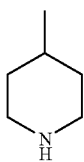 |
| 368. | (3aSR,10RS)-2-[3-(3,6-Dihydro-2H-pyridin-1-yl)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | 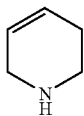 |
| 369. | (3aSR,10RS)-6-Bromo-2-(3-cyclobutylamino-propyl)-10-(3-hydroxy-phenyl)-3a-methyl-3a,4,9,10-tetrahydro-2,9,10a-triaza-cyclopenta[b]fluorene-1,3-dione | Ex. 58 | 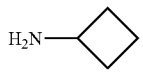 |
| 370. | (3aSR,10RS)-6-Bromo-2-{3-[(2-hydroxy-ethyl)-methyl-amino]-propyl}-10-(3-hydroxy-phenyl)-3a-methyl-3a,4,9,10-tetrahydro-2,9,10a-triaza-cyclopenta[b]fluorene-1,3-dione | Ex. 58 | 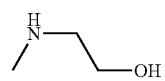 |
| 371. | (3aSR,10RS)-2-[3-(Allyl-methyl-amino)-propyl]-6-bromo-10-(3-hydroxy-phenyl)-3a-methyl-3a,4,9,10-tetrahydro-2,9,10a-triaza-cyclopenta[b]fluorene-1,3-dione | Ex. 58 | 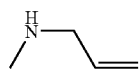 |
| 372. | (3aSR,10RS)-6-Bromo-10-(3-hydroxy-phenyl)-3a-methyl-2-[3-(methyl-prop-2-ynyl-amino)-propyl]-3a,4,9,10-tetrahydro-2,9,10a-triaza-cyclopenta[b]fluorene-1,3-dione | Ex. 58 | 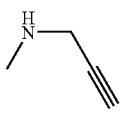 |
| 373. | (3aSR,10RS)-6-Bromo-10-(3-hydroxy-phenyl)-3a-methyl-2-(3-piperidin-1-yl-propyl)-3a,4,9,10-tetrahydro-2,9,10a-triaza-cyclopenta[b]fluorene-1,3-dione | Ex. 58 | 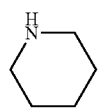 |
| 374. | (3aSR,10RS)-2-(3-Azepan-1-yl-propyl)-6-bromo-10-(3-hydroxy-phenyl)-3a-methyl-3a,4,9,10-tetrahydro-2,9,10a-triaza-cyclopenta[b]fluorene-1,3-dione | Ex. 58 | 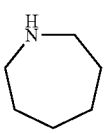 |
| 375. | (3aSR,10RS)-6-Bromo-10-(3-hydroxy-phenyl)-3a-methyl-2-[3-(4-methyl-piperazin-1-yl)-propyl]-3a,4,9,10-tetrahydro-2,9,10a-triaza-cyclopenta[b]fluorene-1,3-dione | Ex. 58 | 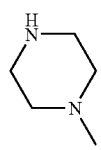 |
| 376. | (3aSR,10RS)-6-Bromo-2-[2-(cyclopropylmethyl-amino)-ethyl]-10-(3-hydroxy-phenyl)-3a-methyl-3a,4,9,10-tetrahydro-2,9,10a-triaza-cyclopenta[b]fluorene-1,3-dione | Ex. 54 | 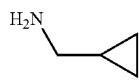 |
| 377. | (3aSR,10RS)-6-Bromo-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione | Ex. 54 | 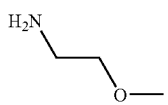 |

-continued

| | | | |
|---|---|---|---|
| 378. | (3aSR,10RS)-6-Bromo-2-(2-tert-butylamino-ethyl)-10-(3-hydroxy-phenyl)-3a-methyl-3a,4,9,10-tetrahydro-2,9,10a-triaza-cyclopenta[b]fluorene-1,3-dione | Ex. 54 | |
| 379. | (3aSR,10RS)-6-Bromo-2-{2-[ethyl-(2-hydroxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione | Ex. 54 | |
| 380. | (3aSR,10RS)-6-Bromo-2-{2-[ethyl-(2-methoxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione | Ex. 54 | |
| 381. | (3aSR,10RS)-2-[2-(Allyl-methyl-amino)-ethyl]-6-bromo-10-(3-hydroxy-phenyl)-3a-methyl-3a,4,9,10-tetrahydro-2,9,10a-triaza-cyclopenta[b]fluorene-1,3-dione | Ex. 54 | |
| 382. | (3aSR,10RS)-6-Bromo-10-(3-hydroxy-phenyl)-3a-methyl-2-[2-(methyl-prop-2-ynyl-amino)-ethyl]-3a,4,9,10-tetrahydro-2,9,10a-triaza-cyclopenta[b]fluorene-1,3-dione | Ex. 54 | |
| 383. | (3aSR,10RS)-2-(2-Allylamino-ethyl)-6-bromo-10-(3-hydroxy-phenyl)-3a-methyl-3a,4,9,10-tetrahydro-2,9,10a-triaza-cyclopenta[b]fluorene-1,3-dione | Ex. 54 | |
| 384. | (3aSR,10RS)-6-Bromo-2-{2-[(2-hydroxy-ethyl)-methyl-amino]-ethyl}-10-(3-hydroxy-phenyl)-3a-methyl-3a,4,9,10-tetrahydro-2,9,10a-triaza-cyclopenta[b]fluorene-1,3-dione | Ex. 54 | |
| 385. | (3aSR,10RS)-6-Bromo-2-(2-diethylamino-ethyl)-10-(3-hydroxy-phenyl)-3a-methyl-3a,4,9,10-tetrahydro-2,9,10a-triaza-cyclopenta[b]fluorene-1,3-dione | Ex. 54 | |
| 386. | (3aSR,10RS)-6-Bromo-10-(3-hydroxy-phenyl)-3a-methyl-2-[2-(4-methyl-piperazin-1-yl)-ethyl]-3a,4,9,10-tetrahydro-2,9,10a-triaza-cyclopenta[b]fluorene-1,3-dione | Ex. 54 | |
| 387. | (3aSR,10RS)-2-[2-(4-Acetyl-piperazin-1-yl)-ethyl]-6-bromo-10-(3-hydroxy-phenyl)-3a-methyl-3a,4,9,10-tetrahydro-2,9,10a-triaza-cyclopenta[b]fluorene-1,3-dione | Ex. 54 | |
| 388. | (3aSR,10RS)-6-Bromo-10-(3-hydroxy-phenyl)-3a-methyl-2-(2-morpholin-4-yl-ethyl)-3a,4,9,10-tetrahydro-2,9,10a-triaza-cyclopenta[b]fluorene-1,3-dione | Ex. 54 | |
| 389. | (3aSR,10RS)-6-Bromo-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione | Ex. 54 | |

| | | | |
|---|---|---|---|
| 390. | (3aSR,10RS)-6-Bromo-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione | Ex. 54 | piperidine |
| 391. | (3aSR,10RS)-6-Bromo-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione | Ex. 54 | isobutylamine |
| 392. | (3aSR,10RS)-6-Chloro-10-(3-hydroxy-phenyl)-2-(3-isopropylamino-propyl)-3a-methyl-3a,4,9,10-tetrahydro-2,9,10a-triaza-cyclopenta[b]fluorene-1,3-dione | Ex. 57 | isopropylamine |
| 393. | (3aSR,10RS)-6-Bromo-2-(2-ethylamino-ethyl)-10-(3-hydroxy-phenyl)-3a-methyl-3a,4,9,10-tetrahydro-2,9,10a-triaza-cyclopenta[b]fluorene-1,3-dione | Ex. 54 | ethylamine |
| 394. | (3aSR,10RS)-6-Bromo-10-(3-hydroxy-phenyl)-3a-methyl-2-(2-methylamino-ethyl)-3a,4,9,10-tetrahydro-2,9,10a-triaza-cyclopenta[b]fluorene-1,3-dione | Ex. 54 | methylamine |
| 395. | (3aSR,10RS)-6-Bromo-2-[2-(3,6-dihydro-2H-pyridin-1-yl)-ethyl]-10-(3-hydroxy-phenyl)-3a-methyl-3a,4,9,10-tetrahydro-2,9,10a-triaza-cyclopenta[b]fluorene-1,3-dione | Ex. 54 | 1,2,3,6-tetrahydropyridine |
| 396. | (3aSR,10RS)-2-(2-Azepan-1-yl-ethyl)-6-bromo-10-(3-hydroxy-phenyl)-3a-methyl-3a,4,9,10-tetrahydro-2,9,10a-triaza-cyclopenta[b]fluorene-1,3-dione | Ex. 54 | azepane |
| 397. | (3aSR,10RS)-6-Chloro-2-{3-[ethyl-(2-methoxy-ethyl)-amino]-propyl}-10-(3-hydroxy-phenyl)-3a-methyl-3a,4,9,10-tetrahydro-2,9,10a-triaza-cyclopenta[b]fluorene-1,3-dione | Ex. 57 | N-ethyl-2-methoxyethylamine |
| 398. | (3aSR,10RS)-2-(2-Azepan-1-yl-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | azepane |
| 399. | (3aSR,10RS)-2-[2-(4-Acetyl-piperazin-1-yl)-ethyl]-5-fluoro-10-(3-hydroxy-phenyl)-6-methoxy-3a-methyl-3a,4,9,10-tetrahydro-2,9,10a-triaza-cyclopenta[b]florene-1,3-dione | Ex. 62 | 1-acetylpiperazine |
| 400. | (3aSR,10RS)-5-Fluoro-10-(3-hydroxy-phenyl)-6-methoxy-3a-methyl-2-[2-(4-methyl-piperazin-1-yl)-ethyl]-3a,4,9,10-tetrahydro-2,9,10a-triaza-cyclopenta[b]fluorene-1,3-dione | Ex. 62 | 1-methylpiperazine |
| 401. | (3aSR,10RS)-2-[2-(3,6-Dihydro-2H-pyridin-1-yl)-ethyl]-5-fluoro-10-(3-hydroyx-phenyl)-6-methoxy-3a-methyl-3a,4,9,10-tetrahydro-2,9,10a-triaza-cyclopenta[b]fluorene-1,3-dione | Ex. 62 | 1,2,3,6-tetrahydropyridine |

-continued

| | | | |
|---|---|---|---|
| 402. | (3aSR,10RS)-5-Fluoro-10-(3-hydroxy-phenyl)-6-methoxy-3a-methyl-2-[2-(4-methyl-piperidin-1-yl)-ethyl]-3a,4,9,10-tetrahydro-2,9,10a-triaza-cyclopenta[b]fluorene-1,3-dione | Ex. 62 | |
| 403. | (3aSR,10RS)-5-Fluoro-10-(3-hydroxy-phenyl)-6-methoxy-3a-methyl-2-(2-piperidin-1-yl-ethyl)-3a,4,9,10-tetrahydro-2,9,10a-triaza-cyclopenta[b]fluorene-1,3-dione | Ex. 62 | |
| 404. | (3aSR,10RS)-2-[2-(2,5-Dihydro-pyrrol-1-yl)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 405. | (3aSR,10RS)-5-Fluoro-10-(3-hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione | Ex. 62 | |
| 406. | (3aSR,10RS)-5-Fluoro-10-(3-hydroxy-phenyl)-6-methoxy-3a-methyl-2-(2-methylamino-ethyl)-3a,4,9,10-tetrahydro-2,9,10a-triaza-cyclopenta[b]fluorene-1,3-dione | Ex. 62 | |
| 407. | (3aSR,10RS)-2-(2-Ethylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 408. | (3aSR,10RS)-5-Fluoro-10-(3-hydroxy-phenyl)-2-{2-isopropylamino-ethyl)-6-methoxy-3a-methyl-3a,4,9,10-tetrahydro-2,9,10a-triaza-cyclopenta[b]fluorene-1,3-dione | Ex. 62 | |
| 409. | (3aSR,10RS)-5-Fluoro-10-(3-hydroxy-phenyl)-2-(2-isobutylamino-ethyl)-6-methoxy-3a-methyl-3a,4,9,10-tetrahydro-2,9,10a-triaza-cyclopenta[b]fluorene-1,3-dione | Ex. 62 | |
| 410. | (3aSR,10RS)-2-[2-(Cyclopropylmethyl-amino)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 411. | (3aSR,10RS)-2-[2-(2,5-Dihydro-pyrrol-1-yl)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 412. | (3aSR,10RS)-5-Fluoro-10-(3-hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione | Ex. 62 | |

-continued

| | | | |
|---|---|---|---|
| 413. | (3aSR,10RS)-2-(2-Cyclobutylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 414. | (3aSR,10RS)-2-(2-tert-Butylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dinone | Ex. 62 | |
| 415. | (3aSR,10RS)-2-(2-Allylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 416. | (3aSR,10RS)-5-Fluoro-10-(3-hydroxy-phenyl)-6-methoxy-3a-methyl-2-(2-prop-2-ynylamino-ethyl)-3a,4,9,10-tetrahydro-2,9,10a-triaza-cyclopenta[b]fluorene-1,3-dione | Ex. 62 | |
| 417. | (3aSR,10RS)-2-(2-Dimethylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 418. | (3aSR,10RS)-2-[2-(Ethyl-methyl-amino)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 419. | (3aSR,10RS)-5-Fluoro-2-{2-[(2-hydroxy-ethyl)-methyl-amino]-ethyl}-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 420. | (3aSR,10RS)-2-(2-Diethylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 421. | (3aSR,10RS)-2-{2-[Ethyl-(2-hydroxy-ethyl)-amino]-ethyl}-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 422. | (3aSR,10RS)-2-{2-[Ethyl-(2-methoxy-ethyl)-amino]-ethyl}-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 423. | (3aSR,10RS)-2-[2-(Allyl-methyl-amino)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |

-continued

| | | | |
|---|---|---|---|
| 424. | (3aSR,10RS)-5-Fluoro-10-(3-hydroxy-phenyl)-6-methoxy-3a-methyl-2-[2-(methyl-prop-2-ynyl-amino)-ethyl]-3a,4,9,10-tetrahydro-2,9,10a-triaza-cyclopenta[b]fluorene-1,3-dione | Ex. 62 | |
| 425. | (3aSR,10RS)-5-Fluoro-10-(3-hydroxy-phenyl)-2-[2-(isopropyl-methyl-amino)-ethyl]-6-methoxy-3a-methyl-3a,4,9,10-tetrahydro-2,9,10a-triaza-cyclopenta[b]fluorene-1,3-dione | Ex. 62 | |
| 426. | (3aSR,10RS)-2-(2-Cyclobutylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 62 | |
| 427. | (3aSR,10RS)-5-Fluoro-10-(3-hydroxy-phenyl)-6-methoxy-3a-methyl-2-(3-methylamino-propyl)-3a,4,9,10-tetrahydro-2,9,10a-triaza-cyclopenta[b]fluorene-1,3-dione | Ex. 65 | |
| 428. | (3aSR,10RS)-2-(3-Ethylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | |
| 429. | (3aSR,10RS)-5-Fluoro-10-(3-hydroxy-phenyl)-2-(3-isopropylamino-propyl)-6-methoxy-3a-methyl-3a,4,9,10-tetrahydro-2,9,10a-triaza-cyclopenta[b]fluorene-1,3-dione | Ex. 65 | |
| 430. | (3aSR,10RS)-5-Fluoro-10-(3-hydroxy-phenyl)-2-(3-isobutylamino-propyl)-6-methoxy-3a-methyl-3a,4,9,10-tetrahydro-2,9,10a-triaza-cyclopenta[b]fluorene-1,3-dione | Ex. 65 | |
| 431. | (3aSR,10RS)-2-[3-(Cyclopropylmethyl-amino)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | |
| 432. | (3aSR,10RS)-5-Fluoro-2-[3-(2-hydroxy-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 65 | |
| 433. | (3aSR,10RS)-5-Fluoro-10-(3-hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione | Ex. 65 | |
| 434. | (3aSR,10RS)-2-(3-Cyclopropylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | |

| | | | |
|---|---|---|---|
| 435. | (3aSR,10RS)-2-(3-Cyclobutylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | 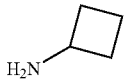 |
| 436. | (3aSR,10RS)-2-(3-tert-Butylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 |  |
| 437. | (3aSR,10RS)-5-Fluoro-10-(3-hydroxy-phenyl)-6-methoxy-3a-methyl-2-(3-prop-2-ynylamino-propyl)-3a,4,9,10-tetrahydro-2,9,10a-triaza-cyclopenta[b]fluorene-1,3-dione | Ex. 65 | 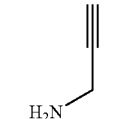 |
| 438. | (3aSR,10RS)-2-(3-Dimethylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | 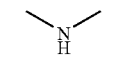 |
| 439. | (3aSR,10RS)-5-Fluoro-2-{3-[(2-hydroxy-ethyl)-methyl-amino]-propyl}-10-(3-hydroxy-phenyl)-6-methoxy-3a-methyl-3a,4,9,10-tetrahydro-2,9,10a-triaza-cyclopenta[b]fluorene-1,3-dione | Ex. 65 | 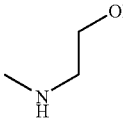 |
| 440. | (3aSR,10RS)-2-(3-Diethylamino-propyl)-5-fluoro-10-(3-hydrox-phenyl)-6-methoxy-3a-methyl-3a,4,9,10-tetrahydro-2,9,10a-triaza-cyclopenta[b]fluorene-1,3-dione | Ex. 65 | 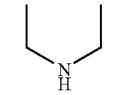 |
| 441. | (3aSR,10RS)-2-{3-[Ethyl-(2-hydroxy-ethyl)-amino]-propyl}-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | 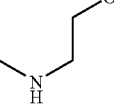 |
| 442. | (3aSR,10RS)-2-[3-(Allyl-methyl-amino)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | 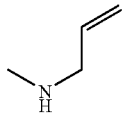 |
| 443. | (3aSR,10RS)-5-Fluoro-10-(3-hydroxy-phenyl)-6-methoxy-3a-methyl-2-[3-(methyl-prop-2-ynyl-amino)-propyl]-3a,4,9,10-tetrahydro-2,9,10a-triaza-cyclopenta[b]fluorene-1,3-dione | Ex. 65 | 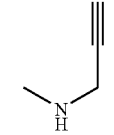 |
| 444. | (3aSR,10RS)-5-Fluoro-10-(3-hydroxy-phenyl)-2-[3-(isopropyl-methyl-amino)-propyl]-6-methoxy-3a-methyl-3a,4,9,10-tetrahydro-2,9,10a-triaza-cyclopenta[b]fluorene-1,3-dione | Ex. 65 | 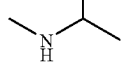 |
| 445. | (3aSR,10RS)-5-Fluoro-10-(3-hydroxy-phenyl)-6-methoxy-3a-methyl-2-(3-morpholin-4-yl-propyl)-3a,4,9,10-tetrahydro-2,9,10a-triaza-cyclopenta[b]fluorene-1,3-dione | Ex. 65 | 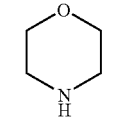 |

| | | | |
|---|---|---|---|
| 446. | (3aSR,10RS)-5-Fluoro-10-(3-hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione | Ex. 65 | 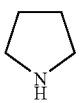 |
| 447. | (3aSR,10RS)-2-[3-(2,5-Dihydro-pyrrol-1-yl)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 | 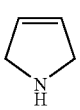 |
| 448. | (3aSR,10RS)-5-Fluoro-10-(3-hydroxy-phenyl)-6-methoxy-3a-methyl-2-[3-(4-methyl-piperazin-1-yl)-propyl]-3a,4,9,10-tetrahydro-2,9,10a-triaza-cyclopenta[b]fluorene-1,3-dione | Ex. 65 | 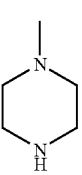 |
| 449. | (3aSR,10RS)-2-[3-(4-Acetyl-piperazin-1-yl)-propyl]-5-fluoro-10-(3-hydroyx-phenyl)-6-methoxy-3a-methyl-3a,4,9,10-tetrahydro-2,9,10a-triaza-cyclopenta[b]fluorene-1,3-dione | Ex. 65 | 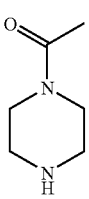 |
| 450. | (3aSR,10RS)-2-(3-Azepan-1-yl-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 65 |  |
| 451. | (3aSR,10RS)-2-{2-[Ethyl-(2-hydroxy-ethyl)-amino]-ethyl}-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 | 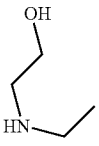 |
| 452. | (3aSR,10RS)-2-[2-(Allyl-methyl-amino)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 | 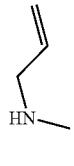 |
| 453. | (3aSR,10RS)-6-(1,1-Difluoro-methoxy)-2-{3-[(2-hydroxy-ethyl)-methyl-amino]-propyl}-10-(3-hydroxy-phenyl)-3a-methyl-3a,4,9,10-tetrahydro-2,9,10a-triaza-cyclopenta[b]fluorene-1,3-dione | Ex. 56 | 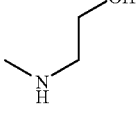 |
| 454. | (3aSR,10RS)-2-{2-[Ethyl-(2-methoxy-ethyl)-amino]-ethyl}-7-fluoro-10-(3-hydroxy-phenyl)-6-methoxy-3a-methyl-3a,4,9,10-tetrahydro-2,9,10a-triaza-cyclopenta[b]fluorene-1,3-dione | Ex. 60 | 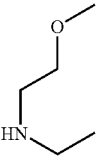 |
| 455. | (3aSR,10RS)-7-Fluoro-10-(3-hydroxy-phenyl)-6-methoxy-3a-methyl-2-[2-(methyl-prop-2-ynyl-amino)-ethyl]-3a,4,9,10-tetrahydro-2,9,10a-triaza-cyclopenta[b]fluorene-1,3-dione | Ex. 60 | 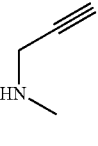 |

| | | | |
|---|---|---|---|
| 456. | (3aSR,10RS)-6-Chloro-7-fluoro-10-(3-hydroxy-phenyl)-3a-methyl-2-(3-methylamino-propyl)-3a,4,9,10-tetrahydro-2,9,10a-triaza-cyclopenta[b]fluorene-1,3-dione | Ex. 64 |  |
| 457. | (3aSR,10RS)-6-Chloro-2-(3-ethylamino-propyl)-7-fluoro-10-(3-hydroxy-phenyl)-3a-methyl-3a,4,9,10-tetrahydro-2,9,10a-triaza-cyclopenta[b]fluorene-1,3-dione | Ex. 64 |  |
| 458. | (3aSR,10RS)-6-Chloro-7-fluoro-10-(3-hydroxy-phenyl)-2-(3-isopropylamino-propyl)-3a-methyl-3a,4,9,10-tetrahydro-2,9,10a-triaza-cyclopenta[b]fluorene-1,3-dione | Ex. 64 |  |
| 459. | (3aSR,10RS)-6-Chloro-7-fluoro-10-(3-hydroxy-phenyl)-2-(3-isobutylamino-propyl)-3a-methyl-3a,4,9,10-tetrahydro-2,9,10a-triaza-cyclopenta[b]fluorene-1,3-dione | Ex. 64 | 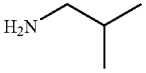 |
| 460. | (3aSR,10RS)-6-Chloro-2-[3-(cyclopropylmethyl-amino)-propyl]-7-fluoro-10-(3-hydroxy-phenyl)-3a-methyl-3a,4,9,10-tetrahydro-2,9,10a-triaza-cyclopenta[b]fluorene-1,3-dione | Ex. 64 | 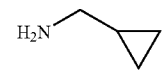 |
| 461. | (3aSR,10RS)-6-Chloro-7-fluoro-2-[3-(2-hydroxy-ethylamino)-propyl]-10-(3-hydroxy-phenyl)-3a-methyl-3a,4,9,10-tetrahydro-2,9,10a-triaza-cyclopenta[b]fluorene-1,3-dione | Ex. 64 | 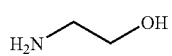 |
| 462. | (3aSR,10RS)-6-Chloro-7-fluoro-10-(3-hydroxy-phenyl)-2-[3-(2-methoxy-ethylamino)-propyl]-3a-methyl-3a,4,9,10-tetrahydro-2,9,10a-triaza-cyclopenta[b]fluorene-1,3-dione | Ex. 64 | 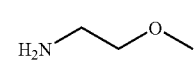 |
| 463. | (3aSR,10RS)-6-Chloro-2-(3-cyclobutylamino-propyl)-7-fluoro-10-(3-hydroxy-phenyl)-3a-methyl-3a,4,9,10-tetrahydro-2,9,10a-triaza-cyclopenta[b]fluorene-1,3-dione | Ex. 64 |  |
| 464. | (3aSR,10RS)-2-(3-tert-Butylamino-propyl)-6-chloro-7-fluoro-10-(3-hydroxy-phenyl)-3a-methyl-3a,4,9,10-tetrahydro-2,9,10a-triaza-cyclopenta[b]fluorene-1,3-dione | Ex. 64 |  |
| 465. | (3aSR,10RS)-2-(3-Allylamino-propyl)-6-chloro-7-fluoro-10-(3-hydroxy-phenyl)-3a-methyl-3a,4,9,10-tetrahydro-2,9,10a-triaza-cyclopenta[b]fluorene-1,3-dione | Ex. 64 | 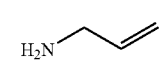 |
| 466. | (3aSR,10RS)-6-Chloro-7-fluoro-10-(3-hydroxy-phenyl)-3a-methyl-2-(3-prop-2-ynylamino-propyl)-3a,4,9,10-tetrahydro-2,9,10a-triaza-cyclopenta[b]fluorene-1,3-dione | Ex. 64 | 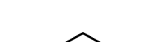 |

| | | | |
|---|---|---|---|
| 467. | (3aSR,10RS)-6-Chloro-2-[3-(ethyl-methyl-amino)-propyl]-7-fluoro-10-(3-hydroxy-phenyl)-3a-methyl-3a,4,9,10-tetrahydro-2,9,10a-triaza-cyclopenta[b]fluorene-1,3-dione | Ex. 64 | |
| 468. | (3aSR,10RS)-6-Chloro-7-fluoro-2-{3-[(2-hydroxy-ethyl)-methyl-amino]-propyl}-10-(3-hydroxy-phenyl)-3a-methyl-3a,4,9,10-tetrahydro-2,9,10a-triaza-cyclopenta[b]fluorene-1,3-dione | Ex. 64 | |
| 469. | (3aSR,10RS)-6-Chloro-2-(3-diethylamino-propyl)-7-fluoro-10-(3-hydroxy-phenyl)-3a-methyl-3a,4,9,10-tetrahydro-2,9,10a-triaza-cyclopenta[b]fluorene-1,3-dione | Ex. 64 | |
| 470. | (3aSR,10RS)-6-Chloro-2-{3-[ethyl-(2-hydroxy-ethyl)-amino]-propyl}-7-fluoro-10-(3-hydroxy-phenyl)-3a-methyl-3a,4,9,10-tetrahydro-2,9,10a-triaza-cyclopenta[b]fluorene-1,3-dione | Ex. 64 | |
| 471. | (3aSR,10RS)-6-Chloro-2-{3-[ethyl-(2-methoxy-ethyl)-amino]-propyl}-7-fluoro-10-(3-hydroxy-phenyl)-3a-methyl-3a,4,9,10-tetrahydro-2,9,10a-triaza-cyclopenta[b]fluorene-1,3-dione | Ex. 64 | |
| 472. | (3aSR,10RS)-2-[3-(Allyl-methyl-amino)-propyl]-6-chloro-7-fluoro-10-(3-hydroyx-phenyl)-3a-methyl-3a,4,9,10-tetrahydro-2,9,10a-triaza-cyclopenta[b]fluorene-1,3-dione | Ex. 64 | |
| 473. | (3aSR,10RS)-6-Chloro-7-fluoro-10-(3-hydroxy-phenyl)-3a-methyl-2-[3-(methyl-prop-2-ynyl-amino)-propyl]-3a,4,9,10-tetrahydro-2,9,10a-triaza-cyclopenta[b]fluorene-1,3-dione | Ex. 64 | |
| 474. | (3aSR,10RS)-6-Chloro-7-fluoro-10-(3-hydroxy-phenyl)-2-[3-(isopropyl-methyl-amino)-propyl]-3a-methyl-3a,4,9,10-tetrahydro-2,9,10a-triaza-cyclopenta[b]fluorene-1,3-dione | Ex. 64 | |
| 475. | (3aSR,10RS)-6-Chloro-7-fluoro-10-(3-hydroxy-phenyl)-3a-methyl-2-(3-morpholin-4-yl-propyl)-3a,4,9,10-tetrahydro-2,9,10a-triaza-cyclopenta[b]fluorene-1,3-dione | Ex. 64 | |
| 476. | (3aSR,10RS)-6-Chloro-7-fluoro-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione | Ex. 64 | |
| 477. | (3aSR,10RS)-6-Chloro-2-[3-(2,5-dihydro-pyrrol-1-yl)-propyl]-7-fluoro-10-(3-hydroxy-phenyl)-3a-methyl-3a,4,9,10-tetrahydro-2,9,10a-triaza-cyclopenta[b]fluorene-1,3-dione | Ex. 64 | |

-continued

| | | | |
|---|---|---|---|
| 478. | (3aSR,10RS)-6-Chloro-7-fluoro-10-(3-hydroxy-phenyl)-3a-methyl-2-(3-piperidin-1-yl-propyl)-3a,4,9,10-tetrahydro-2,9,10a-triaza-cyclopenta[b]fluorene-1,3-dione | Ex. 64 | piperidine |
| 479. | (3aSR,10RS)-6-Chloro-7-fluoro-10-(3-hydroxy-phenyl)-3a-methyl-2-[3-(4-methyl-piperidin-1-yl)-propyl]-3a,4,9,10-tetrahydro-2,9,10a-triaza-cyclopenta[b]fluorene-1,3-dione | Ex. 64 | 4-methylpiperidine |
| 480. | (3aSR,10RS)-6-Chloro-2-[3-(3,6-dihydro-2H-pyridin-1-yl)-propyl]-7-fluoro-10-(3-hydroxy-phenyl)-3a-methyl-3a,4,9,10-tetrahydro-2,9,10a-triaza-cyclopenta[b]fluorene-1,3-dione | Ex. 64 | 1,2,3,6-tetrahydropyridine |
| 481. | (3aSR,10RS)-6-Chloro-7-fluoro-10-(3-hydroxy-phenyl)-3a-methyl-2-[3-(4-methyl-piperazin-1-yl)-propyl]-3a,4,9,10-tetrahydro-2,9,10a-triaza-cyclopenta[b]fluorene-1,3-dione | Ex. 64 | 1-methylpiperazine |
| 482. | (3aSR,10RS)-2-[3-(4-Acetyl-piperazin-1-yl)-propyl]-6-chloro-7-fluoro-10-(3-hydroxy-phenyl)-3a-methyl-3a,4,9,10-tetrahydro-2,9,10a-triaza-cyclopenta[b]fluorene-1,3-dione | Ex. 64 | 1-acetylpiperazine |
| 483. | (3aSR,10RS)-2-(3-Azepan-1-yl-propyl)-6-chloro-7-fluoro-10-(3-hydroyx-phenyl)-3a-methyl-3a,4,9,10-tetrahydro-2,9,10a-triaza-cyclopenta[b]fluorene-1,3-dione | Ex. 64 | azepane |
| 484. | (3aSR,10RS)-6-Bromo-10-(3-hydroxy-phenyl)-3a-methyl-2-(3-morpholin-4-yl-propyl)-3a,4,9,10-tetrahydro-2,9,10a-triaza-cyclopenta[b]fluorene-1,3-dione | Ex. 58 | morpholine |
| 485. | (3aSR,10RS)-6-Bromo-10-(3-hydroxy-phenyl)-3a-methyl-2-[3-(4-methyl-piperidin-1-yl)-propyl]-3a,4,9,10-tetrahydro-2,9,10a-triaza-cyclopenta[b]fluorene-1,3-dione | Ex. 58 | 4-methylpiperidine |
| 486. | (3aSR,10RS)-6-Bromo-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione | Ex. 54 | N-methylisopropylamine |
| 487. | (3aSR,10RS)-6-Bromo-10-(3-hydroxy-phenyl)-3a-methyl-2-[2-(4-methyl-piperidin-1-yl)-ethyl]-3a,4,9,10-tetrahydro-2,9,10a-triaza-cyclopenta[b]fluorene-1,3-dione | Ex. 54 | 4-methylpiperidine |
| 488. | (3aSR,10RS)-6-Chloro-2-[3-(cyclopropylmethyl-amino)-propyl]-10-(3-hydroxy-phenyl)-3a-methyl-3a,4,9,10-tetrahydro-2,9,10a-triaza-cyclopenta[b]fluorene-1,3-dione | Ex. 57 | cyclopropylmethylamine |

| | | | |
|---|---|---|---|
| 489. | (3aSR,10RS)-2-(3-tert-Butylamino-propyl)-6-chloro-10-(3-hydroxy-phenyl)-3a-methyl-3a,4,9,10-tetrahydro-2,9,10a-triaza-cyclopenta[b]fluorene-1,3-dione | Ex. 57 | |
| 490. | (3aS,10R)-10-(3-Hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione | Ex. 55a | |
| 491. | (3aS,10R)-2-(3-Ethylamino-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55a | |
| 492. | (3aS,10R)-10-(3-Hydroxy-phenyl)-2-(3-isopropylamino-propyl)-6-methoxy-3a-methyl-3a,4,9,10-tetrahydro-2,9,10a-triaza-cyclopenta[b]fluorene-1,3-dione | Ex. 55a | |
| 493. | (3aS,10R)-2-(3-Cyclobutylamino-propyl)-10-(3-hydroxy-phenyl)-6-methoxy-3a-methyl-3a,4,9,10-tetrahydro-2,9,10a-triaza-cyclopenta[b]fluorene-,3-dione | Ex. 55a | |
| 494. | (3aS,10R)-2-(3-Diethylamino-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55a | |
| 495. | (3aS,10R)-2-[3-(2,5-Dihydro-pyrrol-1-yl)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55a | |
| 496. | (3aS,10R)-2-[3-(Allyl-methyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55a | |
| 497. | (3aS,10R)-10-(3-Hydroxy-phenyl)-6-methoxy-3a-methyl-2-[3-(methyl-prop-2-ynyl-amino)-propyl]-3a,4,9,10-tetrahydro-2,9,10a-triaza-cyclopenta[b]fluorene-1,3-dione | Ex. 55a | |
| 498. | (3aS,10R)-10-(3-Hydroxy-phenyl)-2-[3-(isopropyl-methyl-amino)-propyl]-6-methoxy-3a-methyl-3a,4,9,10-tetrahydro-2,9,10a-triaza-cyclopenta[b]fluorene-1,3-dione | Ex. 55a | |
| 499. | (3aS,10R)-10-(3-Hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione | Ex. 55a | |
| 500. | (3aS,10R)-10-(3-Hydroxy-phenyl)-6-methoxy-3a-methyl-2-(3-piperidin-1-yl-propyl)-3a,4,9,10-tetrahydro-2,9,10a-triaza-cyclopenta[b]fluorene-1,3-dione | Ex. 55a | |

| | | | |
|---|---|---|---|
| 501. | (3aS,10R)-2-[3-(3,6-Dihydro-2H-pyridin-1-yl)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55a |  |
| 502. | (3aS,10R)-10-(3-Hydroxy-phenyl)-6-methoxy-3a-methyl-2-[3-(4-methyl-piperazin-1-yl)-propyl]-3a,4,9,10-tetrahydro-2,9,10a-triaza-cyclopenta[b]fluorene-1,3-dione | Ex. 55a | 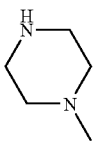 |
| 503. | (3aS,10R)-2-(3-Azepan-1-yl-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55a | 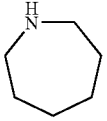 |
| 504. | (3aS,10R)-10-(3-Hydroxy-phenyl)-6-methoxy-3a-methyl-2-(2-methylamino-ethyl)-3a,4,9,10-tetrahydro-2,9,10-a-triaza-cyclopenta[b]fluorene-1,3-dione | Ex. 24b |  |
| 505. | (3aS,10R)-2-(2-Ethylamino-ethyl)-10-(3-hydroxy-phenyl)-6-methoxy-3a-methyl-3a,4,9,10-tetrahydro-2,9,10a-triaza-cyclopenta[b]fluorene-1,3-dione | Ex. 24b |  |
| 506. | (3aS,10R)-10-(3-Hydroxy-phenyl)-2-(2-isobutylamino-etyl)-6-methoxy-3a-methyl-3a,4,9,10-tetrahydro-2,9,10a-triaza-cyclopenta[b]fluorene-1,3-dione | Ex. 24b | 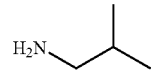 |
| 507. | (3aS,10R)-2-[2-(Cyclopropylmethyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione | Ex. 24b | 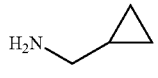 |
| 508. | (3aS,10R)-2-[2-(2-Hydroxy-ethylamino)-ethyl]-10-(3-hydroxy-phenyl)-6-methoxy-3a-methyl-3a,4,9,10-tetrahydro-2,9,10a-triaza-cyclopenta[b]fluorene-1,3-dione | Ex. 24b | 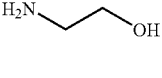 |
| 509. | (3aS,10R)-10-(3-Hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione | Ex. 24b | 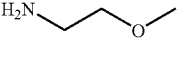 |
| 510. | (3aS,10R)-2-(2-Cyclopropylamino-ethyl)-10-(3-hydroxy-phenyl)-6-methoxy-3a-methyl-3a,4,9,10-tetrahydro-2,9,10a-triaza-cyclopenta[b]fluorene-1,3-dione | Ex. 24b |  |
| 511. | (3aS,10R)-2-(2-Cyclobutylamino-ethyl)-10-(3-hydroxy-phenyl)-6-methoxy-3a-methyl-3a,4,9,10-tetrahydro-2,9,10a-triaza-cyclopenta[b]fluorene-1,3-dione | Ex. 24b |  |
| 512. | (3aS,10R)-2-(2-tert-Butylamino-ethyl)-10-(3-hydroxy-phenyl)-6-methoxy-3a-methyl-3a,4,9,10-tetrahydro-2,9,10a-triaza-cyclopenta[b]fluorene-1,3-dione | Ex. 24b |  |

| | | | |
|---|---|---|---|
| 513. | (3aS,10R)-2-(2-Allylamino-ethyl)-10-(3-hydroxy-phenyl)-6-methoxy-3a-methyl-3a,4,9,10-tetrahydro-2,9,10a-triaza-cyclopenta[b]fluorene-1,3-dione | Ex. 24b | 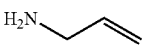 |
| 514. | (3aS,10R)-10-(3-Hydroxy-phenyl)-6-methoxy-3a-methyl-2-(2-prop-2-ynylamino-ethyl)-3a,4,9,10-tetrahydro-2,9,10a-triaza-cyclopenta[b]fluorene-1,3-dione | Ex. 24b | 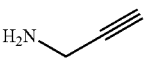 |
| 515. | (3aS,10R)-2-[2-(Ethyl-methyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione | Ex. 24b |  |
| 516. | (3aS,10R)-2-{2-[(2-Hydroxy-ethyl)-methyl-amino]-ethyl}-10-(3-hydroxy-phenyl)-6-methoxy-3a-methyl-3a,4,9,10-tetrahydro-2,9,10a-triaza-cyclopenta[b]fluorene-1,3-dione | Ex. 24b | 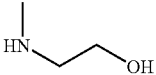 |
| 517. | (3aS,10R)-2-(2-Diethylamino-ethyl)-10-(3-hydroxy-phenyl)-6-methoxy-3a-methyl-3a,4,9,10-tetrahydro-2,9,10a-triaza-cyclopenta[b]fluorene-1,3-dione | Ex. 24b | 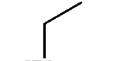 |
| 518. | (3aS,10R)-2-{2-[Ethyl-(2-hydroxy-ethyl)-amino]-ethyl}-10-(3-hydroxy-phenyl)-6-methoxy-3a-methyl-3a,4,9,10-tetrahydro-2,9,10a-triaza-cyclopenta[b]fluorene-1,3-dione | Ex. 24b | 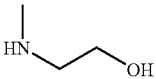 |
| 519. | (3aS,10R)-2-{2-[Ethyl-(2-methoxy-ethyl)-amino]-ethyl}-10-(3-hydroxy-phenyl)-6-methoxy-3a-methyl-3a,4,9,10-tetrahydro-2,9,10a-triaza-cyclopenta[b]fluorene-1,3-dione | Ex. 24b | 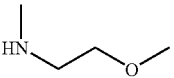 |
| 520. | (3aS,10R)-2-[2-(Allyl-methyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione | Ex. 24b | 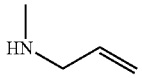 |
| 521. | (3aS,10R)-10-(3-Hydroxy-phenyl)-6-methoxy-3a-methyl-2-[2-(methyl-prop-2-ynyl-amino)-ethyl]-3a,4,9,10-tetrahydro-2,9,10a-triaza-cyclopenta[b]fluorene-1,3-dione | Ex. 24b | 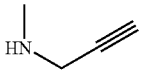 |
| 522. | (3aS,10R)-10-(3-Hydroxy-phenyl)-2-[2-(isopropyl-methyl-amino)-ethyl]-6-methoxy-3a-methyl-3a,4,9,10-tetrahydro-2,9,10a-triaza-cyclopenta[b]fluorene-1,3-dione | Ex. 24b | 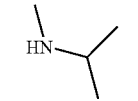 |
| 523. | (3aS,10R)-2-(2-Azetidin-1-yl-ethyl)-10-(3-hydroxy-phenyl)-6-methoxy-3a-methyl-3a,4,9,10-tetrahydro-2,9,10-a-triaza-cyclopenta[b]fluorene-1,3-dione | Ex. 24b |  |
| 524. | (3aS,10R)-10-(3-Hydroxy-phenyl)-6-methoxy-3a-methyl-2-(2-morpholin-4-yl-ethyl)-3a,4,9,10-tetrahydro-2,9,10a-triaza-cyclopenta[b]fluorene-1,3-dione | Ex. 24b | 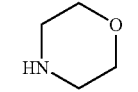 |

-continued

| | | | |
|---|---|---|---|
| 525. | (3aS,10R)-10-(3-Hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione | Ex. 24b | pyrrolidine (HN in 5-membered ring) |
| 526. | (3aS,10R)-10-(3-Hydroxy-phenyl)-6-methoxy-3a-methyl-2-(2-piperidin-1-yl-ethyl)-3a,4,9,10-tetrahydro-2,9,10a-triaza-cyclopenta[b]fluorene-1,3-dione | Ex. 24b | piperidine (HN in 6-membered ring) |
| 527. | (3aS,10R)-10-(3-Hydroxy-phenyl)-6-methoxy-3a-methyl-2-[2-(4-methyl-piperidin-1-yl)-ethyl]-3a,4,9,10-tetrahydro-2,9,10a-triaza-cyclopenta[b]fluorene-1,3-dione | Ex. 24b | 4-methylpiperidine |
| 528. | (3aS,10R)-2-[2-(3,6-Dihydro-2H-pyridin-1-yl)-ethyl]-10-(3-hydroyx-phenyl)-6-methoxy-3a-methyl-3a,4,9,10-tetrahydro-2,9,10a-triaza-cyclopenta[b]fluorene-1,3-dione | Ex. 24b | 1,2,3,6-tetrahydropyridine |
| 529. | (3aS,10R)-10-(3-Hydroxy-phenyl)-6-methoxy-3a-methyl-2-[2-(4-methyl-piperazin-1-yl)-ethyl]-3a,4,9,10-tetrahydro-2,9,10a-triaza-cyclopenta[b]fluorene-1,3-dione | Ex. 24b | 1-methylpiperazine |
| 530. | (3aS,10R)-2-[2-(4-Acetyl-piperazin-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione | Ex. 24b | 1-acetylpiperazine |
| 531. | (3aS,10R)-2-(2-Azepan-1-yl-ethyl)-10-(3-hydroxy-phenyl)-6-methoxy-3a-methyl-3a,4,9,10-tetrahydro-2,9,10a-triaza-cyclopenta[b]fluorene-1,3-dione | Ex. 24b | azepane |
| 532. | (3aS,10R)-10-(3-Hydroxy-phenyl)-2-(2-isopropylamino-ethyl)-6-methoxy-3a-methyl-3a,4,9,10-tetrahydro-2,9,10a-triaza-cyclopenta[b]fluorene-1,3-dione | Ex. 24b | H$_2$N–CH(CH$_3$)$_2$ (isopropylamine) |
| 533. | (3aS,10R)-2-(3-Allylamino-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55a | allylamine (CH$_2$=CH–CH$_2$–NH$_2$) |
| 534. | (3aS,10R)-10-(3-Hydroxy-phenyl)-2-(3-isobutylamino-propyl)-6-methoxy-3a-methyl-3a,4,9,10-tetrahydro-2,9,10a-triaza-cyclopenta[b]fluorene-1,3-dione | Ex. 55a | isobutylamine (H$_2$N–CH$_2$–CH(CH$_3$)$_2$) |
| 535. | (3aS,10R)-2-[3-(Cyclopropylmethyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55a | cyclopropylmethylamine |
| 536. | (3aS,10R)-2-[3-(2-Hydroxy-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55a | ethanolamine (H$_2$N–CH$_2$–CH$_2$–OH) |

| | | | |
|---|---|---|---|
| 537. | (3aS,10R)-2-(3-Cyclopropylamino-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55a | 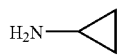 |
| 538. | (3aS,10R)-2-(3-tert-Butylamino-propyl)-10-(3-hydroxy-phenyl)-6-methoxy-3a-methyl-3a,4,9,10-tetrahydro-2,9,10a-triaza-cyclopenta[b]fluorene-1,3-dione | ex. 55a | 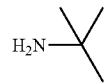 |
| 539. | (3aS,10R)-10-(3-Hydroxy-phenyl)-6-methoxy-3a-methyl-2-(3-prop-2-ynylamino-propyl)-3a,4,9,10-tetrahydro-2,9,10a-triaza-cyclopenta[b]fluorene-1,3-dione | Ex. 55a | 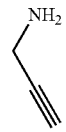 |
| 540. | (3aS,10R)-2-(3-Dimethylamino-propyl)-10-(3-hydroxy-phenyl)-6-methoxy-3a-methyl-3a,4,9,10-tetrahydro-2,9,10a-triaza-cyclopenta[b]fluorene-1,3-dione | Ex. 55a | 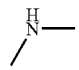 |
| 541. | (3aS,10R)-2-[3-(Ethyl-methyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione | Ex. 55a | 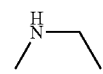 |
| 542. | (3aS,10R)-2-{3-[(2-Hydroxy-ethyl)-methyl-amino]-propyl}-10-(3-hydroxy-phenyl)-6-methoxy-3a-methyl-3a,4,9,10-tetrahydro-2,9,10a-triaza-cyclopenta[b]fluorene-1,3-dione | Ex. 55a | 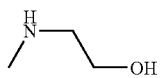 |
| 543. | (3aS,10R)-2-{3-[Ethyl-(2-hydroxy-ethyl)-amino]-propyl}-10-(3-hydroxy-phenyl)-6-methoxy-3a-methyl-3a,4,9,10-tetrahydro-2,9,10a-triaza-cyclopenta[b]fluorene-1,3-dione | Ex. 55a | 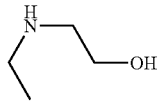 |
| 544. | (3aS,10R)-2-{3-[Ethyl-(2-methoxy-ethyl)-amino]-propyl}-10-(3-hydroxy-phenyl)-6-methoxy-3a-methyl-3a,4,9,10-tetrahydro-2,9,10a-triaza-cyclopenta[b]fluorene-1,3-dione | Ex. 55a | 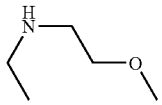 |

| example | structure | MS: m/z (MH$^+$) |
|---|---|---|
| 67. | 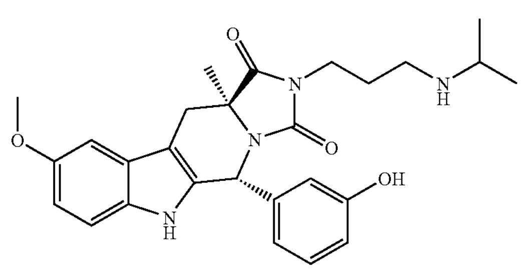 [SMILES: COc1ccc2[nH]c3c(c2c1)C[C@@]1(C)C(=O)N(CCCNC(C)C)C(=O)N1[C@@H]3c1cccc(O)c1] | 477.2 |

-continued
| 68. | 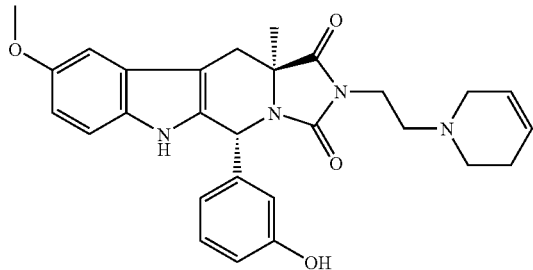 [SMILES: COc1ccc2[nH]c3c(c2c1)C[C@@]1(C)C(=O)N(CCN2CC=CCC2)C(=O)N1[C@@H]3c1cccc(O)c1] | 487.2 |
| 69. | 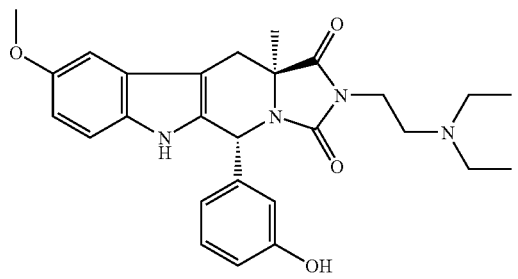 [SMILES: CCN(CC)CCN1C(=O)N2[C@H](c3cccc(O)c3)c3[nH]c4ccc(OC)cc4c3C[C@@]2(C)C1=O] | 477.2 |
| 70. | 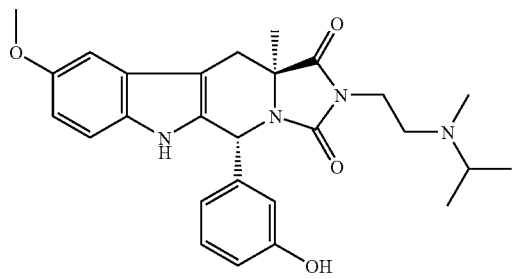 [SMILES: COc1ccc2[nH]c3c(c2c1)C[C@@]1(C)C(=O)N(CCN(C)C(C)C)C(=O)N1[C@@H]3c1cccc(O)c1] | 477.2 |
| 71. | 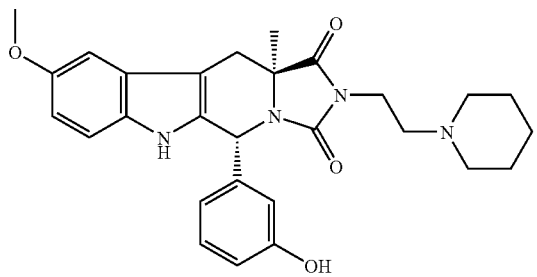 [SMILES: COc1ccc2[nH]c3c(c2c1)C[C@@]1(C)C(=O)N(CCN2CCCCC2)C(=O)N1[C@@H]3c1cccc(O)c1] | 489.2 |
| 72. | 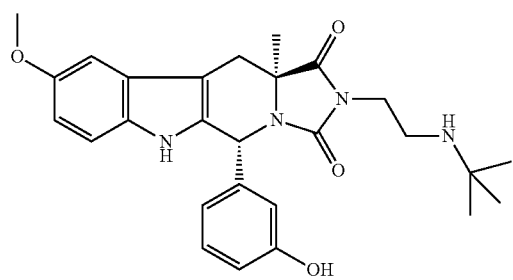 [SMILES: COc1ccc2[nH]c3c(c2c1)C[C@@]1(C)C(=O)N(CCNC(C)(C)C)C(=O)N1[C@@H]3c1cccc(O)c1] | 477.1 |

| | | |
|---|---|---|
| 73. | 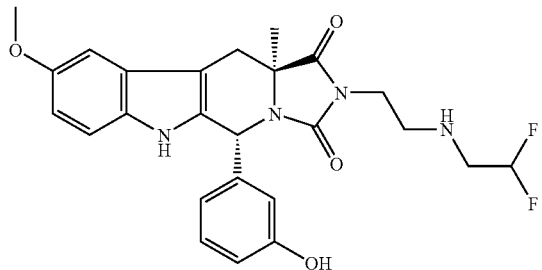 [SMILES: COc1ccc2[nH]c3c(c2c1)C[C@@]1(C)C(=O)N(CCNCC(F)F)C(=O)N1[C@@H]3c1cccc(O)c1] | 485.1 |
| 74. | 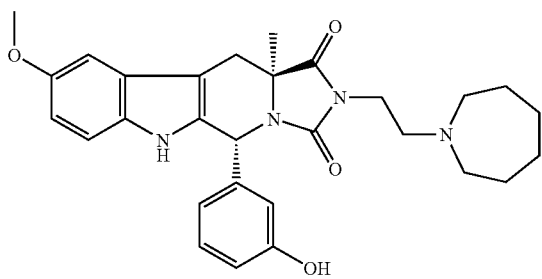 [SMILES: COc1ccc2[nH]c3c(c2c1)C[C@@]1(C)C(=O)N(CCN2CCCCCC2)C(=O)N1[C@@H]3c1cccc(O)c1] | 503.3 |
| 75. | 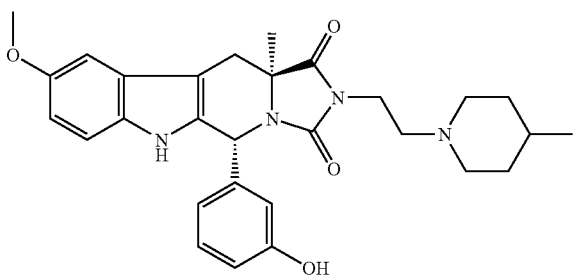 [SMILES: COc1ccc2[nH]c3c(c2c1)C[C@@]1(C)C(=O)N(CCN2CCC(C)CC2)C(=O)N1[C@@H]3c1cccc(O)c1] | 503.3 |
| 76. | 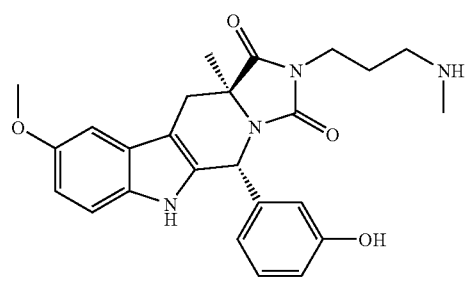 [SMILES: CNCCCN1C(=O)N2[C@H](c3cccc(O)c3)c3[nH]c4ccc(OC)cc4c3C[C@@]2(C)C1=O] | 449.1 |
| 77. | 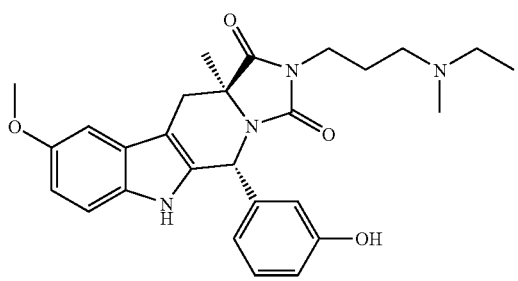 [SMILES: CCN(C)CCCN1C(=O)N2[C@H](c3cccc(O)c3)c3[nH]c4ccc(OC)cc4c3C[C@@]2(C)C1=O] | 477.2 |

| | | |
|---|---|---|
| 78. | 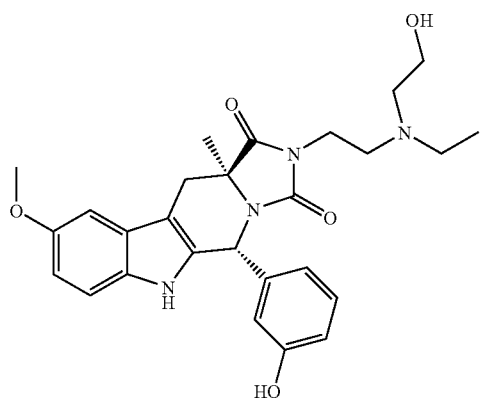 [SMILES: CCN(CCO)CCN1C(=O)N2[C@H](c3cccc(O)c3)c3[nH]c4ccc(OC)cc4c3C[C@@]2(C)C1=O] | 493.2 |
| 79. | 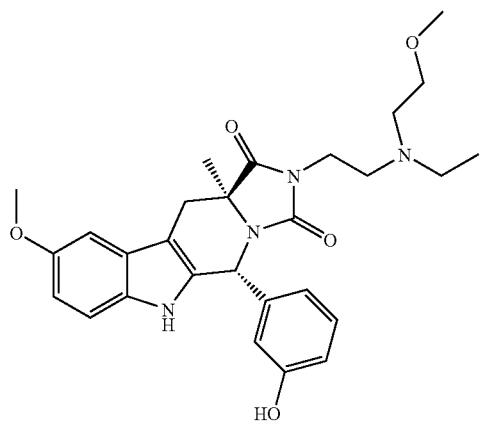 [SMILES: CCN(CCOC)CCN1C(=O)N2[C@H](c3cccc(O)c3)c3[nH]c4ccc(OC)cc4c3C[C@@]2(C)C1=O] | 507.2 |
| 80. | 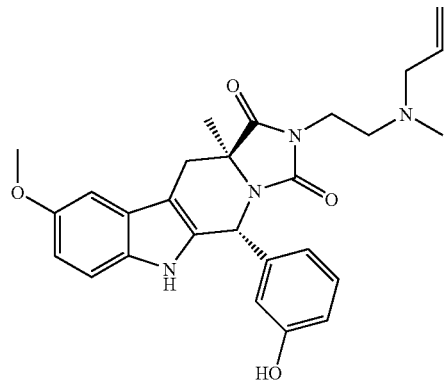 [SMILES: C=CCN(C)CCN1C(=O)N2[C@H](c3cccc(O)c3)c3[nH]c4ccc(OC)cc4c3C[C@@]2(C)C1=O] | 475.2 |
| 81. | 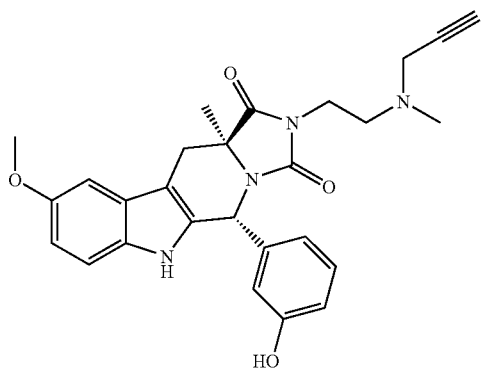 [SMILES: C#CCN(C)CCN1C(=O)N2[C@H](c3cccc(O)c3)c3[nH]c4ccc(OC)cc4c3C[C@@]2(C)C1=O] | 473.2 |

| | | |
|---|---|---|
| 82. | 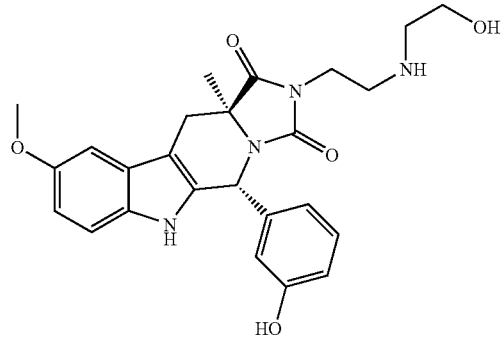 [SMILES: COc1ccc2[nH]c3c(c2c1)C[C@@]1(C)C(=O)N(CCNCCO)C(=O)N1[C@@H]3c1cccc(O)c1] | 465.1 |
| 83. | 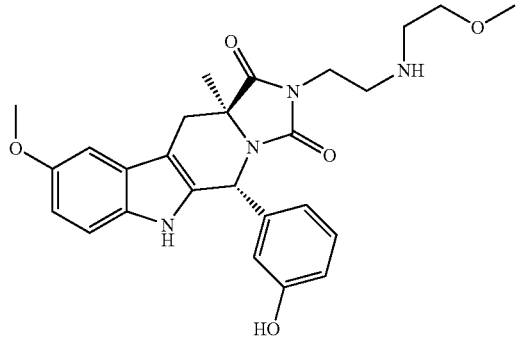 [SMILES: COCCNCCN1C(=O)N2[C@H](c3cccc(O)c3)c3[nH]c4ccc(OC)cc4c3C[C@@]2(C)C1=O] | 479.1 |
| 84. | 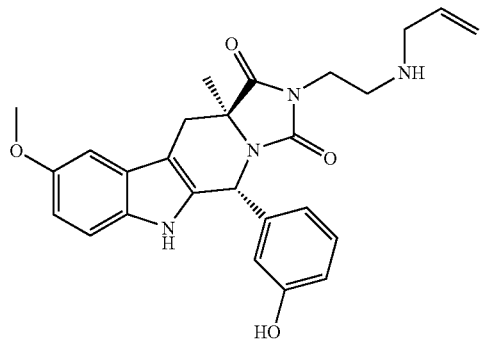 [SMILES: C=CCNCCN1C(=O)N2[C@H](c3cccc(O)c3)c3[nH]c4ccc(OC)cc4c3C[C@@]2(C)C1=O] | 461.1 |
| 85. | 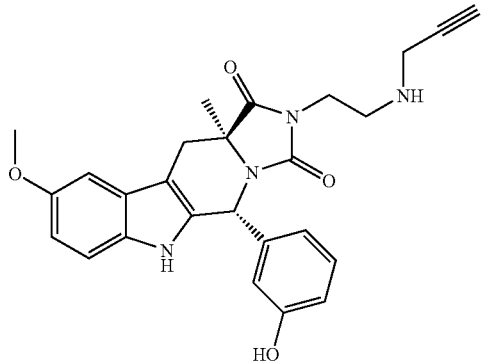 | 459.1 |

| | | |
|---|---|---|
| 86. | 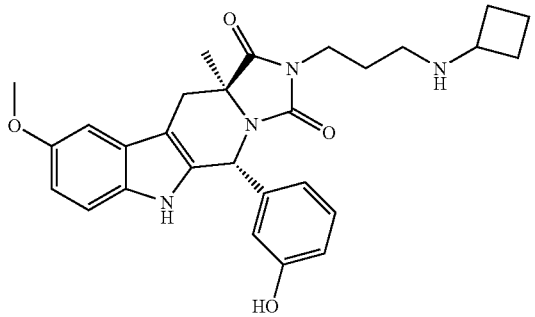 [SMILES: COc1ccc2[nH]c3c(c2c1)C[C@@]1(C)C(=O)N(CCCNC2CCC2)C(=O)N1[C@@H]3c1cccc(O)c1] | 489.2 |
| 87. | 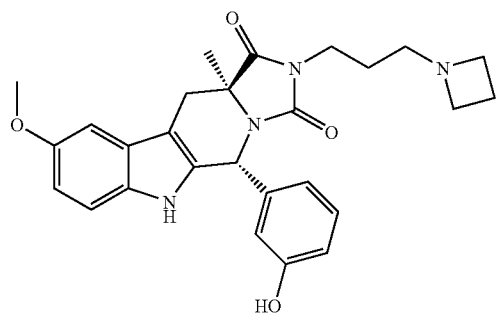 [SMILES: COc1ccc2[nH]c3c(c2c1)C[C@@]1(C)C(=O)N(CCCN2CCC2)C(=O)N1[C@@H]3c1cccc(O)c1] | 475.2 |
| 88. | 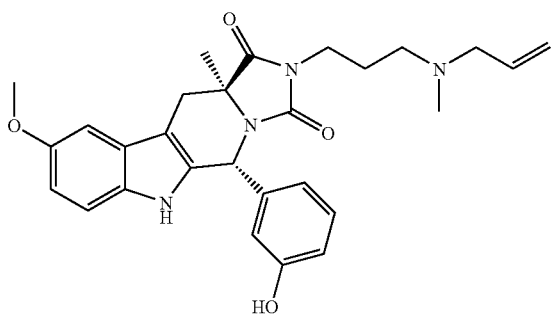 [SMILES: C=CCN(C)CCCN1C(=O)N2[C@H](c3cccc(O)c3)c3[nH]c4ccc(OC)cc4c3C[C@@]2(C)C1=O] | 489.2 |
| 89. | 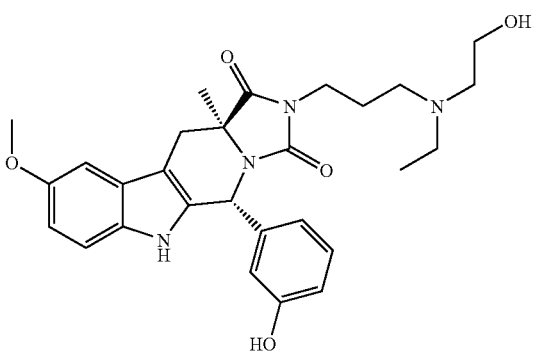 [SMILES: CCN(CCO)CCCN1C(=O)N2[C@H](c3cccc(O)c3)c3[nH]c4ccc(OC)cc4c3C[C@@]2(C)C1=O] | 507.2 |

-continued
| | | |
|---|---|---|
| 90. | 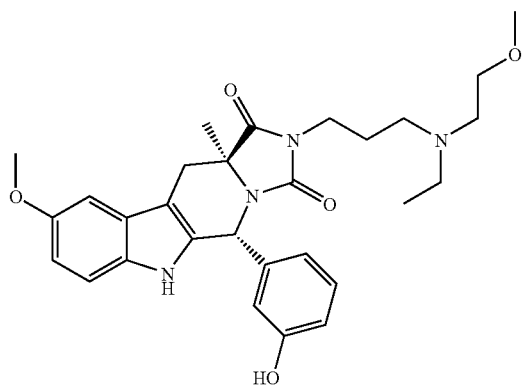 [SMILES: CCN(CCCN1C(=O)N2[C@H](c3cccc(O)c3)c3[nH]c4ccc(OC)cc4c3C[C@@]2(C)C1=O)CCOC] | 521.2 |
| 91. | 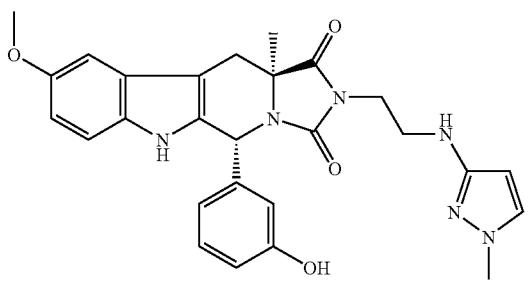 [SMILES: COc1ccc2[nH]c3c(c2c1)C[C@@]1(C)C(=O)N(CCNc2ccn(C)n2)C(=O)N1[C@@H]3c1cccc(O)c1] | 501.2 |
| 92. | 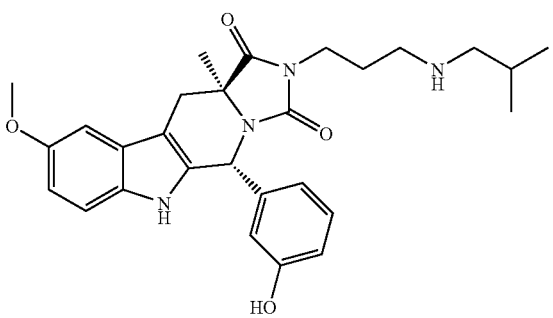 [SMILES: COc1ccc2[nH]c3c(c2c1)C[C@@]1(C)C(=O)N(CCCNCC(C)C)C(=O)N1[C@@H]3c1cccc(O)c1] | 491.1 |
| 93. | 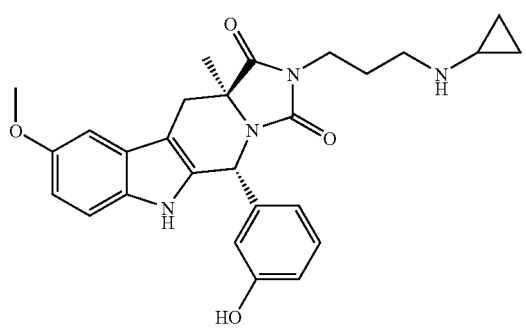 [SMILES: COc1ccc2[nH]c3c(c2c1)C[C@@]1(C)C(=O)N(CCCNC2CC2)C(=O)N1[C@@H]3c1cccc(O)c1] | 475.1 |
| 94. | 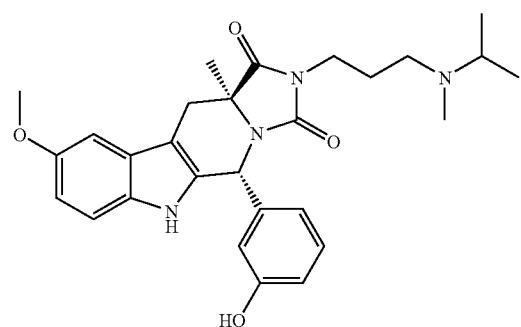 [SMILES: COc1ccc2[nH]c3c(c2c1)C[C@@]1(C)C(=O)N(CCCN(C)C(C)C)C(=O)N1[C@@H]3c1cccc(O)c1] | 491.2 |

| 95. | 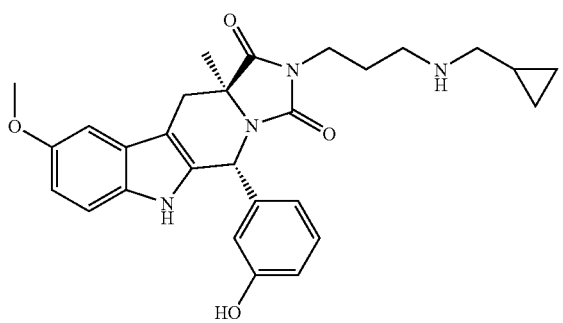 [SMILES: COc1ccc2[nH]c3c(c2c1)C[C@@]1(C)C(=O)N(CCCNCC2CC2)C(=O)N1[C@@H]3c1cccc(O)c1] | 489.2 |
| 96. | 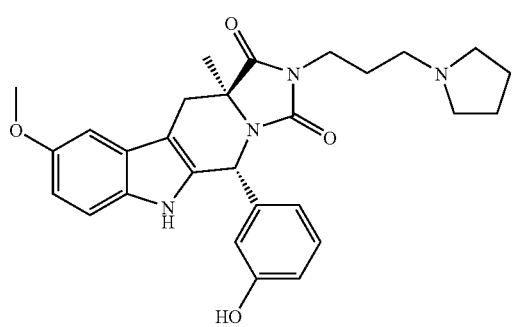 | 489.2 |
| 97. | 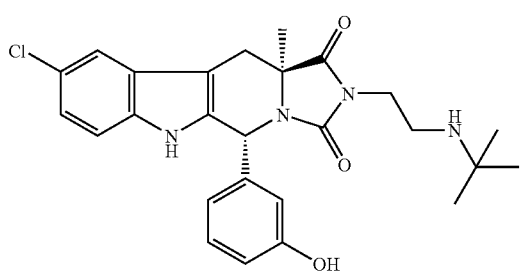 [SMILES: CC(C)(C)NCCN1C(=O)N2[C@H](c3cccc(O)c3)c3[nH]c4ccc(Cl)cc4c3C[C@@]2(C)C1=O] | 481.0 |
| 98. | 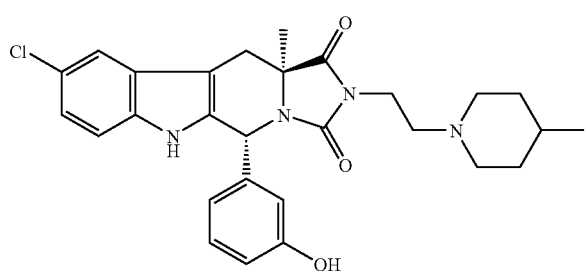 [SMILES: CC1CCN(CCN2C(=O)N3[C@H](c4cccc(O)c4)c4[nH]c5ccc(Cl)cc5c4C[C@@]3(C)C2=O)CC1] | 507.2 |
| 99. | 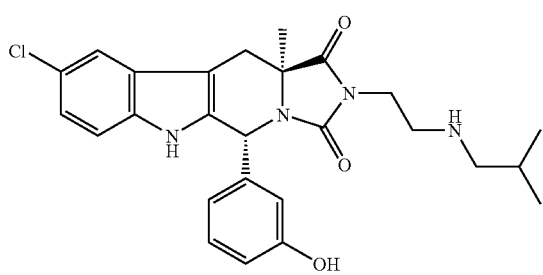 [SMILES: CC(C)CNCCN1C(=O)N2[C@H](c3cccc(O)c3)c3[nH]c4ccc(Cl)cc4c3C[C@@]2(C)C1=O] | 481.1 |

| | | |
|---|---|---|
| 100. | 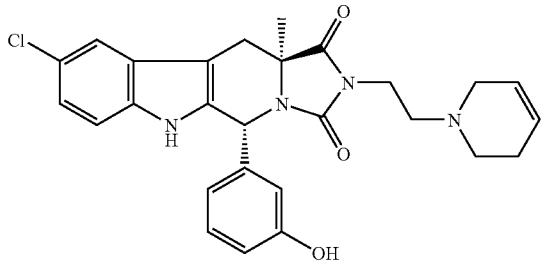 [SMILES: C[C@@]12Cc3c([nH]c4ccc(Cl)cc34)[C@@H](c3cccc(O)c3)N1C(=O)N(CCN1CC=CCC1)C2=O] | 491.1 |
| 101. | 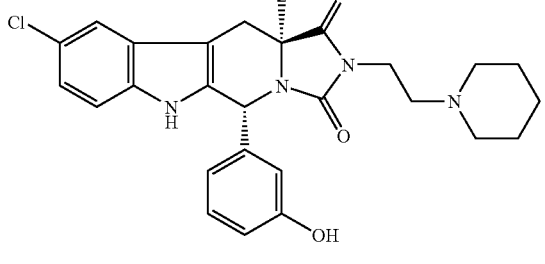 | 493.2 |
| 102. | 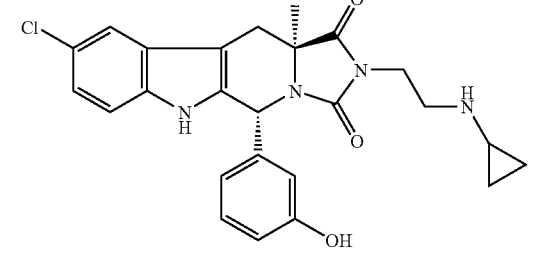 | 465.0 |
| 103. | 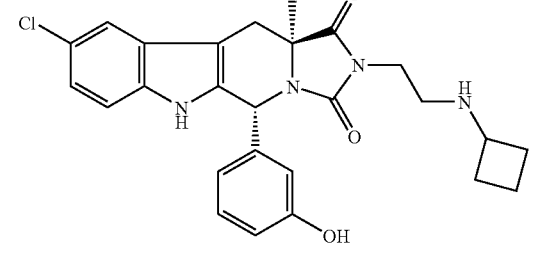 | 479.2 |
| 104. | 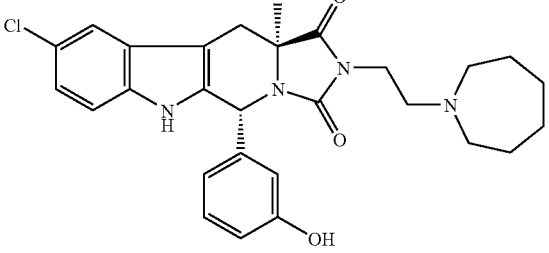 | 507.2 |

| | | |
|---|---|---|
| 105. | 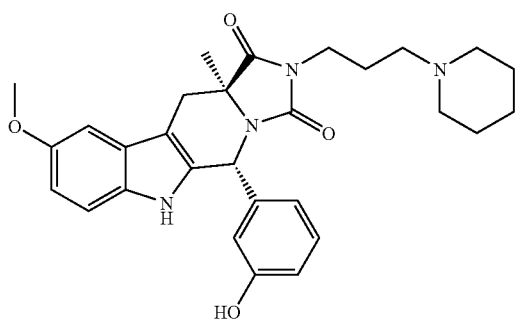 [SMILES: COc1ccc2[nH]c3c(c2c1)C[C@@]1(C)C(=O)N(CCCN2CCCCC2)C(=O)N1[C@@H]3c1cccc(O)c1] | 503.2 |
| 106. | 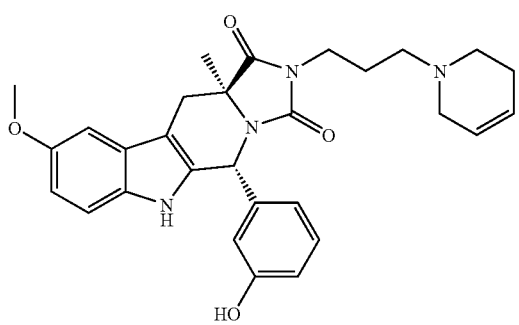 [SMILES: COc1ccc2[nH]c3c(c2c1)C[C@@]1(C)C(=O)N(CCCN2CC=CCC2)C(=O)N1[C@@H]3c1cccc(O)c1] | 501.2 |
| 107. | 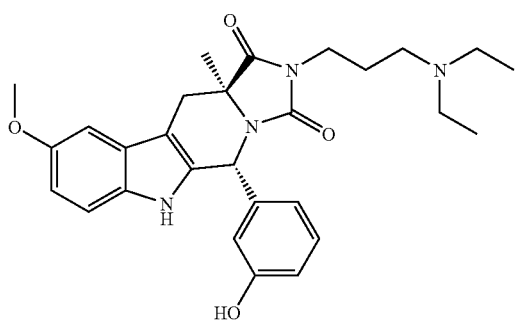 [SMILES: CCN(CC)CCCN1C(=O)N2[C@H](c3cccc(O)c3)c3[nH]c4ccc(OC)cc4c3C[C@@]2(C)C1=O] | 491.3 |
| 108. | 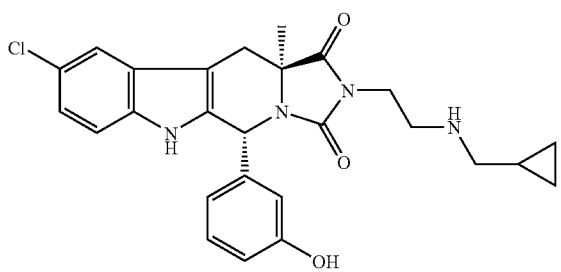 [SMILES: C[C@@]12Cc3c([nH]c4ccc(Cl)cc34)[C@@H](c3cccc(O)c3)N1C(=O)N(CCNCC1CC1)C2=O] | 479.1 |
| 109. | 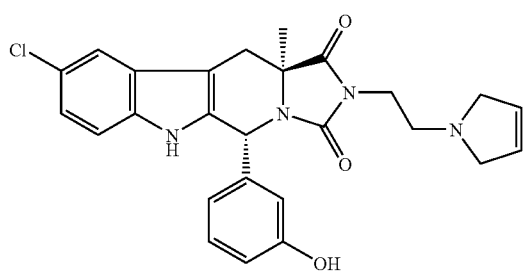 [SMILES: C[C@@]12Cc3c([nH]c4ccc(Cl)cc34)[C@@H](c3cccc(O)c3)N1C(=O)N(CCN1CC=CC1)C2=O] | 477.1 |

-continued
| 110. | 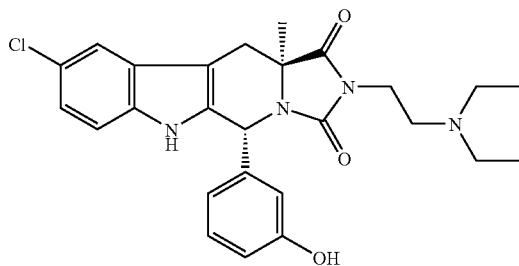 [SMILES: CCN(CC)CCN1C(=O)N2[C@H](c3cccc(O)c3)c3[nH]c4ccc(Cl)cc4c3C[C@@]2(C)C1=O] | 481.1 |
| 111. | 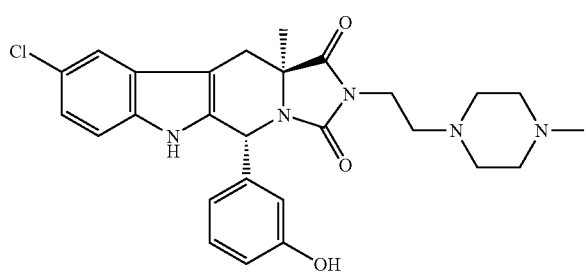 | 508.2 |
| 112. | 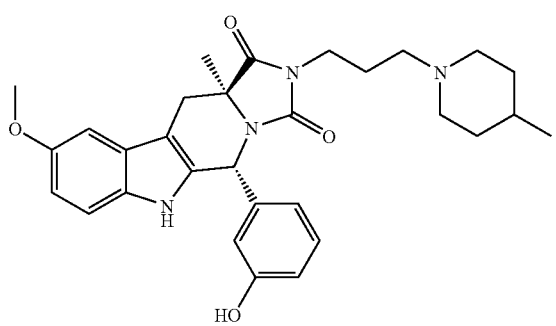 | 517.3 |
| 113. | 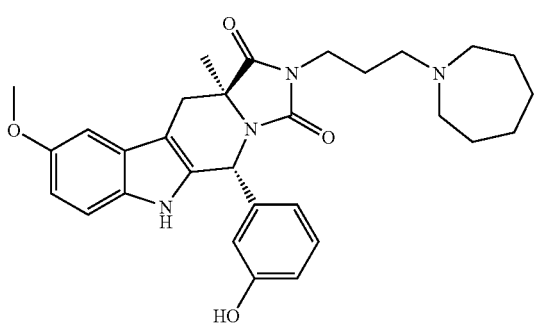 [SMILES: COc1ccc2[nH]c3c(c2c1)C[C@@]1(C)C(=O)N(CCCN2CCCCCC2)C(=O)N1[C@@H]3c1cccc(O)c1] | 517.3 |
| 114. | 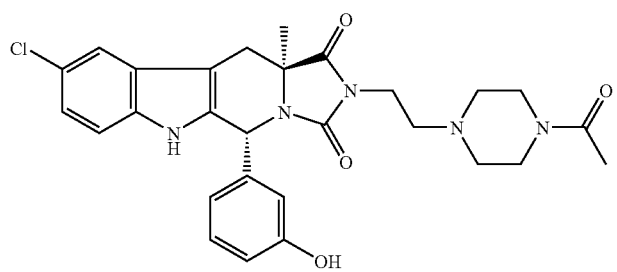 [SMILES: CC(=O)N1CCN(CCN2C(=O)N3[C@H](c4cccc(O)c4)c4[nH]c5ccc(Cl)cc5c4C[C@@]3(C)C2=O)CC1] | 536.2 |

| | | |
|---|---|---|
| 115. | 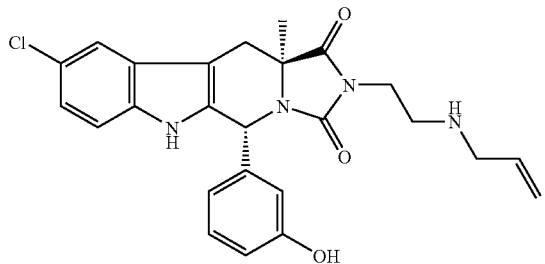 | 465.2 |
| 116. | 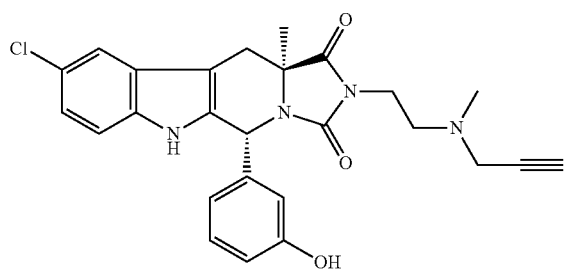 [SMILES: C#CCN(C)CCN1C(=O)N2[C@H](c3cccc(O)c3)c3[nH]c4ccc(Cl)cc4c3C[C@@]2(C)C1=O] | 477.2 |
| 117. | 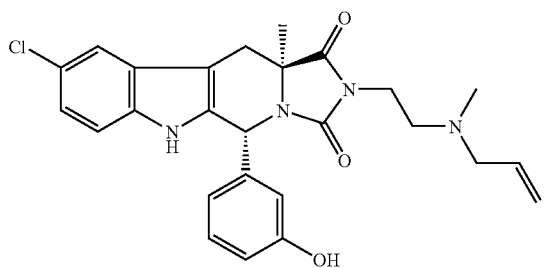 [SMILES: C=CCN(C)CCN1C(=O)N2[C@H](c3cccc(O)c3)c3[nH]c4ccc(Cl)cc4c3C[C@@]2(C)C1=O] | 479.1 |
| 118. | 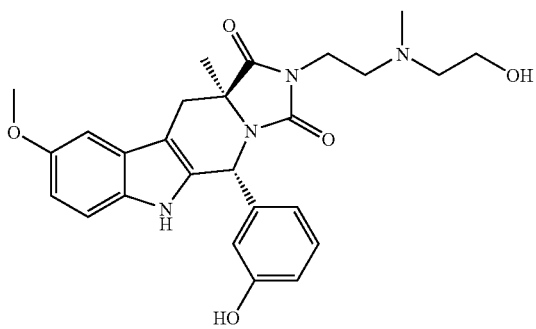 [SMILES: COc1ccc2[nH]c3c(c2c1)C[C@@]1(C)C(=O)N(CCN(C)CCO)C(=O)N1[C@@H]3c1cccc(O)c1] | 479.2 |
| 119. | 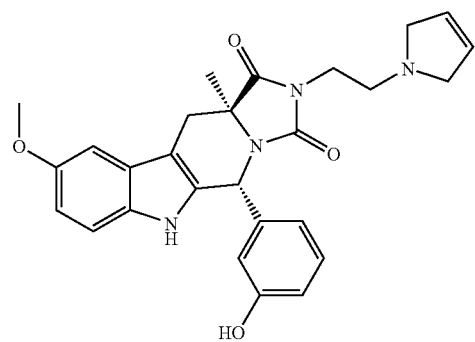 [SMILES: COc1ccc2[nH]c3c(c2c1)C[C@@]1(C)C(=O)N(CCN2CC=CC2)C(=O)N1[C@@H]3c1cccc(O)c1] | 473.1 |

| | | |
|---|---|---|
| 120. | 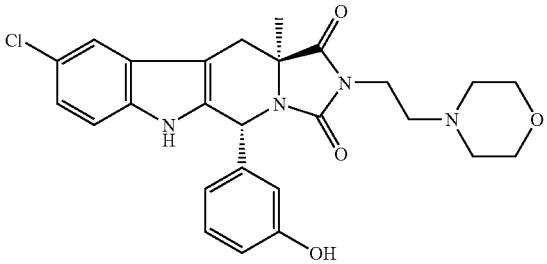 [SMILES: C[C@@]12Cc3c([nH]c4ccc(Cl)cc34)[C@@H](c3cccc(O)c3)N1C(=O)N(CCN1CCOCC1)C2=O] | 495.2 |
| 121. | 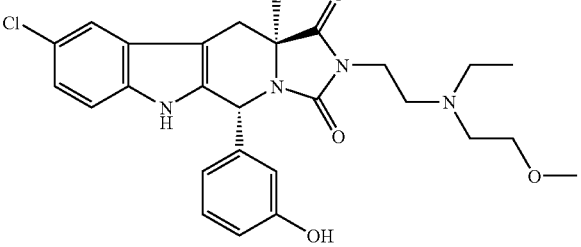 | 511.2 |
| 122. | 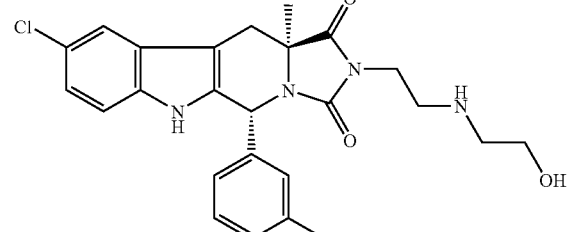 | 469.1 |
| 123. | 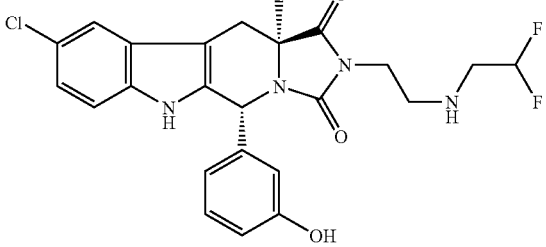 | 489.3 |
| 124. | 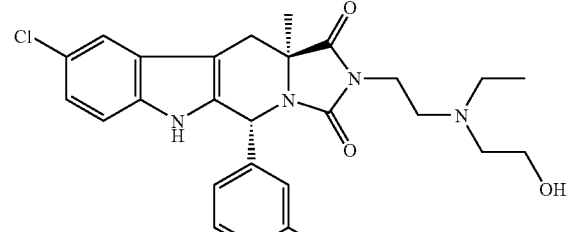 | 497.3 |

| | | |
|---|---|---|
| 125. | 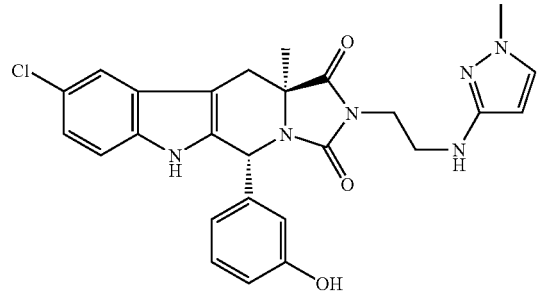 [SMILES: Cn1ccc(NCCN2C(=O)N3[C@H](c4cccc(O)c4)c4[nH]c5ccc(Cl)cc5c4C[C@@]3(C)C2=O)n1] | 505.2 |
| 126. | 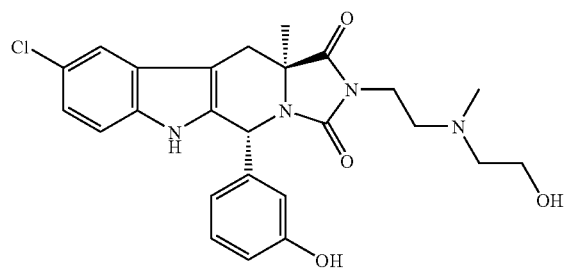 [SMILES: CN(CCO)CCN1C(=O)N2[C@H](c3cccc(O)c3)c3[nH]c4ccc(Cl)cc4c3C[C@@]2(C)C1=O] | 483.1 |
| 127. | 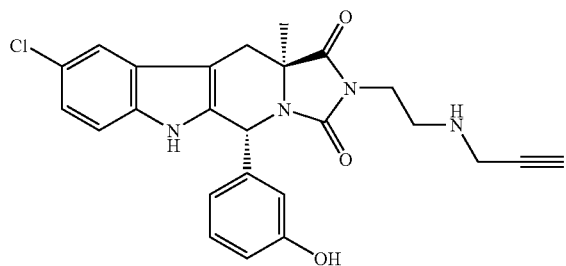 | 463.1 |
| 128. | 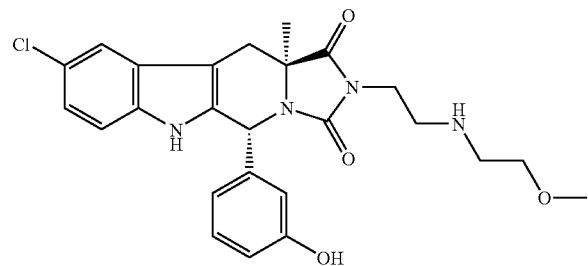 [SMILES: COCCNCCN1C(=O)N2[C@H](c3cccc(O)c3)c3[nH]c4ccc(Cl)cc4c3C[C@@]2(C)C1=O] | 483.2 |
| 129. | 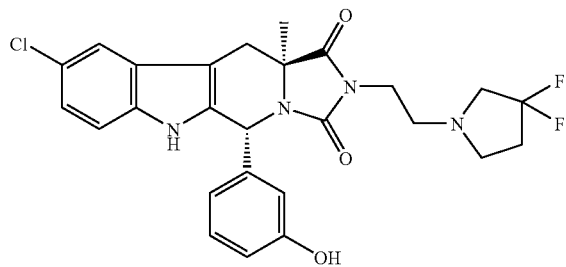 [SMILES: C[C@@]12Cc3c([nH]c4ccc(Cl)cc34)[C@@H](c3cccc(O)c3)N1C(=O)N(CCN1CCC(F)(F)C1)C2=O] | 515.1 |

| | | |
|---|---|---|
| 130. | 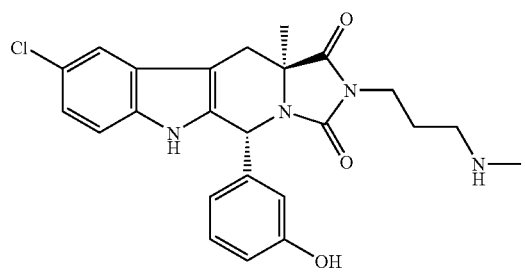 [SMILES: CNCCCN1C(=O)N2[C@H](c3cccc(O)c3)c3[nH]c4ccc(Cl)cc4c3C[C@@]2(C)C1=O] | 453.1 |
| 131. | 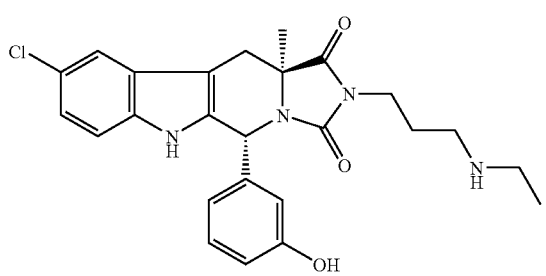 [SMILES: CCNCCCN1C(=O)N2[C@H](c3cccc(O)c3)c3[nH]c4ccc(Cl)cc4c3C[C@@]2(C)C1=O] | 467.1 |
| 132. | 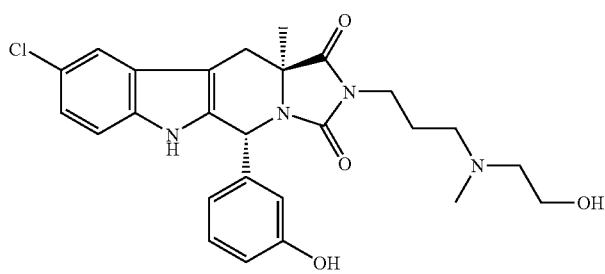 [SMILES: CN(CCO)CCCN1C(=O)N2[C@H](c3cccc(O)c3)c3[nH]c4ccc(Cl)cc4c3C[C@@]2(C)C1=O] | 497.1 |
| 133. | 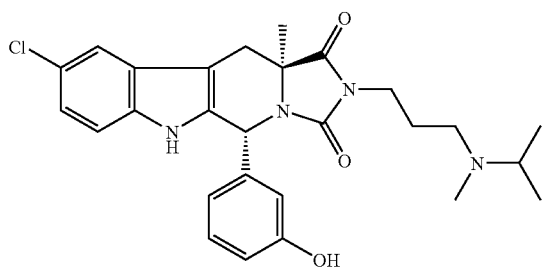 [SMILES: CC(C)N(C)CCCN1C(=O)N2[C@H](c3cccc(O)c3)c3[nH]c4ccc(Cl)cc4c3C[C@@]2(C)C1=O] | 495.2 |
| 134. | 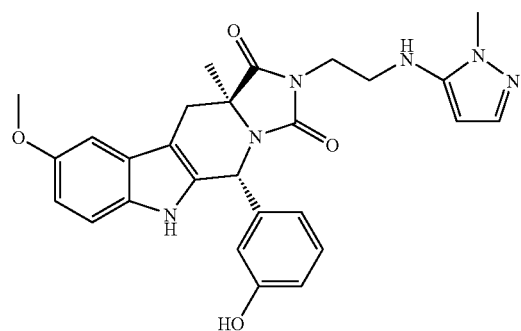 [SMILES: COc1ccc2[nH]c3c(c2c1)C[C@@]1(C)C(=O)N(CCNc2ccnn2C)C(=O)N1[C@@H]3c1cccc(O)c1] | 501.2 |

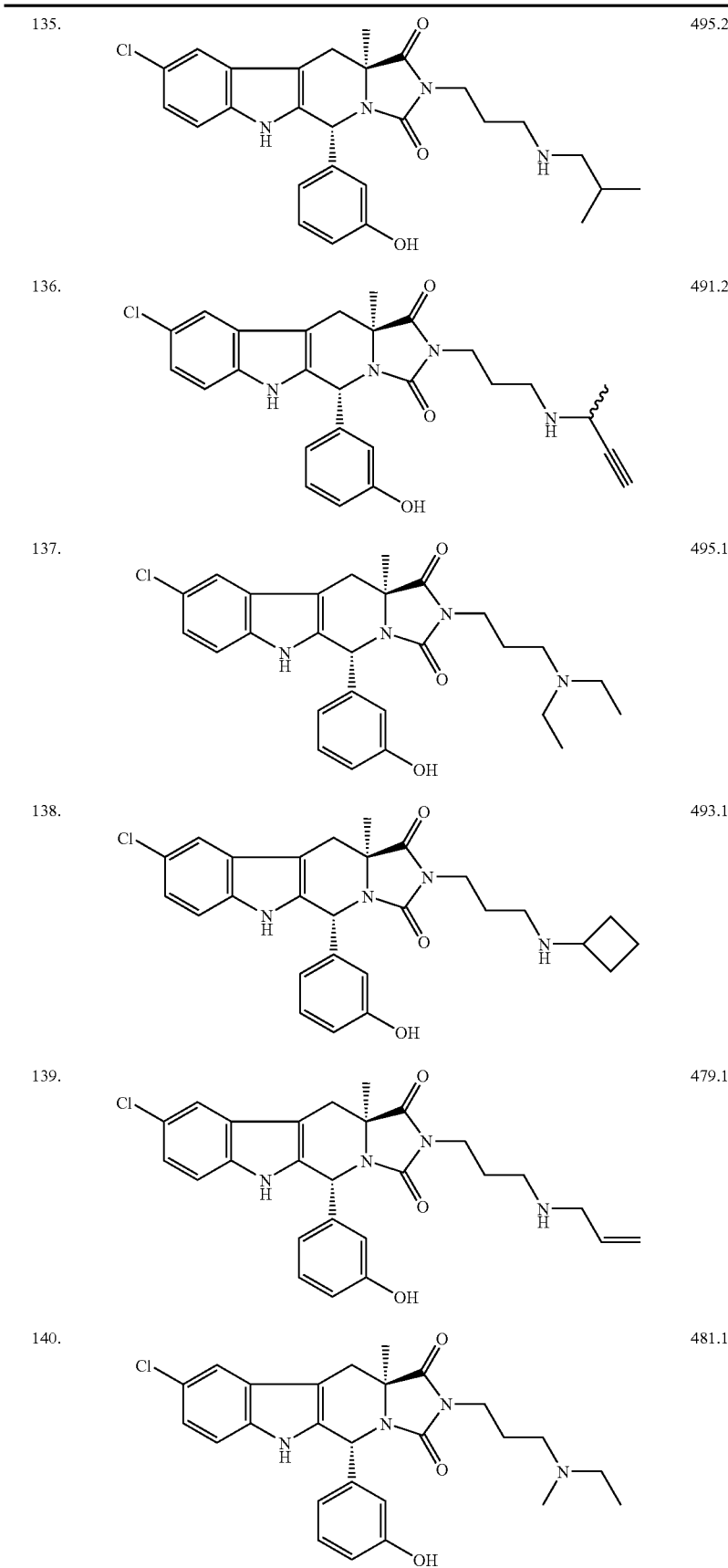

| | | |
|---|---|---|
| 141. | 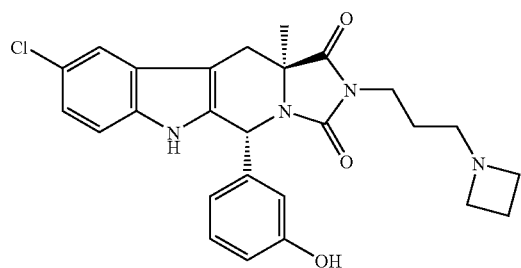 [SMILES: C[C@@]12Cc3c([nH]c4ccc(Cl)cc34)[C@@H](c3cccc(O)c3)N1C(=O)N(CCCN1CCC1)C2=O] | 479.1 |
| 142. | 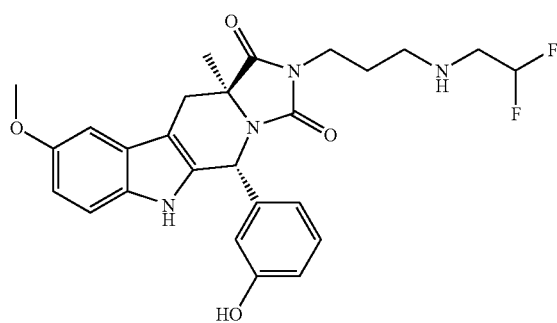 [SMILES: COc1ccc2[nH]c3c(c2c1)C[C@@]1(C)C(=O)N(CCCNCC(F)F)C(=O)N1[C@@H]3c1cccc(O)c1] | 499.1 |
| 143. | 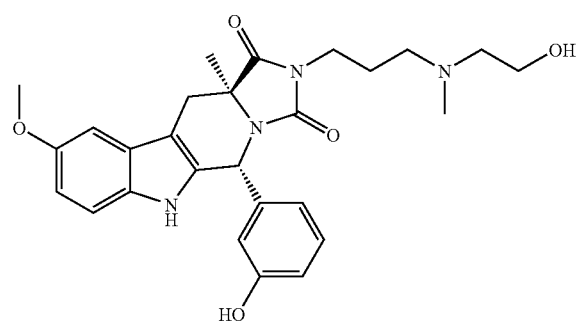 [SMILES: COc1ccc2[nH]c3c(c2c1)C[C@@]1(C)C(=O)N(CCCN(C)CCO)C(=O)N1[C@@H]3c1cccc(O)c1] | 493.2 |
| 144. | 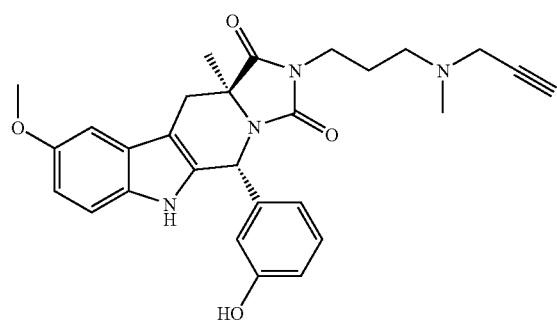 [SMILES: C#CCN(C)CCCN1C(=O)N2[C@H](c3cccc(O)c3)c3[nH]c4ccc(OC)cc4c3C[C@@]2(C)C1=O] | 487.2 |
| 145. | 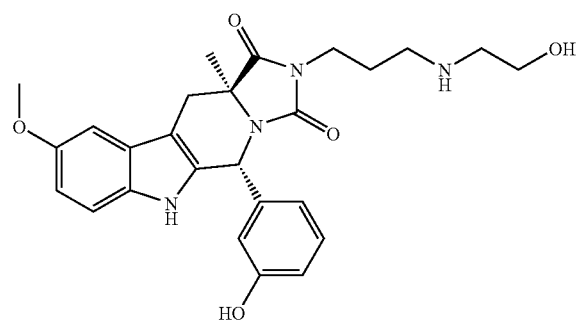 [SMILES: COc1ccc2[nH]c3c(c2c1)C[C@@]1(C)C(=O)N(CCCNCCO)C(=O)N1[C@@H]3c1cccc(O)c1] | 479.1 |

| | | |
|---|---|---|
| 146. | 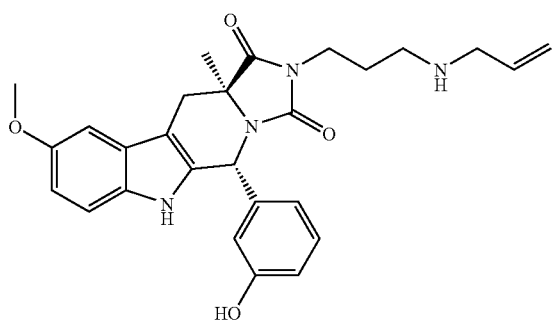 [SMILES: C=CCNCCCN1C(=O)N2[C@H](c3cccc(O)c3)c3[nH]c4ccc(OC)cc4c3C[C@@]2(C)C1=O] | 475.1 |
| 147. | 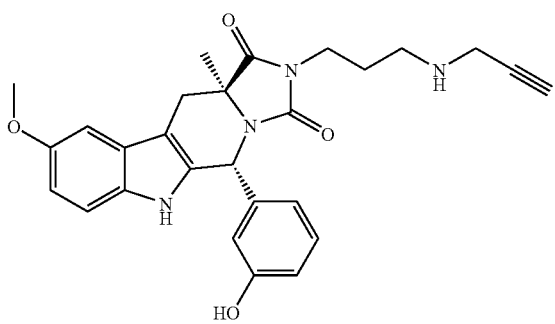 [SMILES: C#CCNCCCN1C(=O)N2[C@H](c3cccc(O)c3)c3[nH]c4ccc(OC)cc4c3C[C@@]2(C)C1=O] | 473.0 |
| 148. | 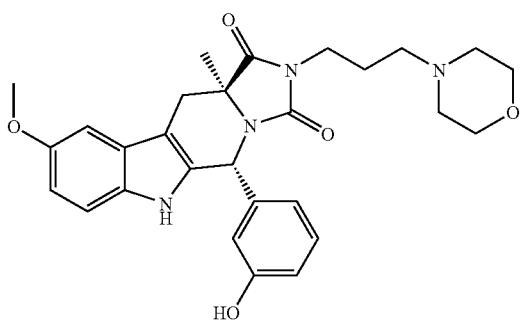 [SMILES: COc1ccc2[nH]c3c(c2c1)C[C@@]1(C)C(=O)N(CCCN2CCOCC2)C(=O)N1[C@@H]3c1cccc(O)c1] | 505.2 |
| 149. | 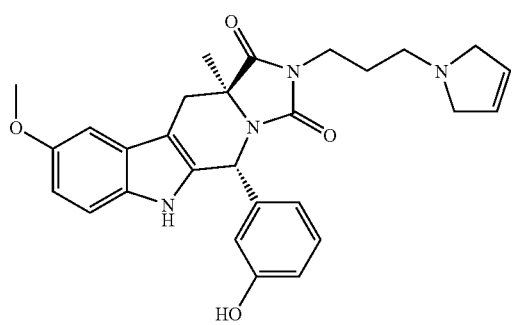 [SMILES: COc1ccc2[nH]c3c(c2c1)C[C@@]1(C)C(=O)N(CCCN2CC=CC2)C(=O)N1[C@@H]3c1cccc(O)c1] | 487.1 |
| 150. | 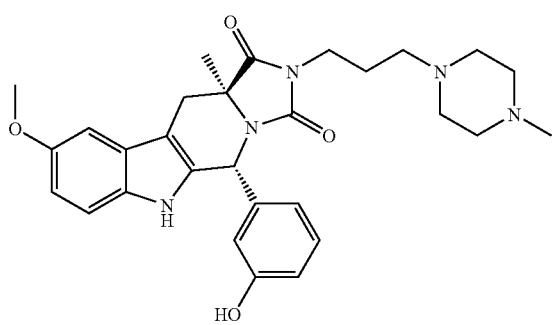 [SMILES: COc1ccc2[nH]c3c(c2c1)C[C@@]1(C)C(=O)N(CCCN2CCN(C)CC2)C(=O)N1[C@@H]3c1cccc(O)c1] | 518.3 |

-continued
| 151. | 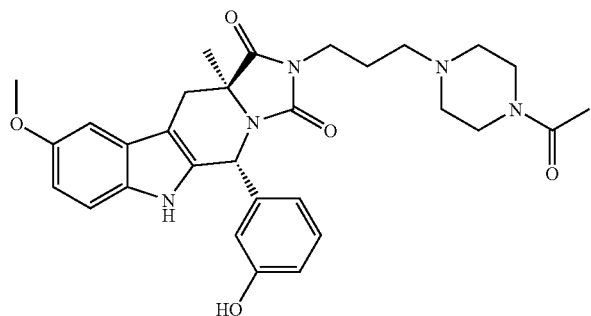 [SMILES: COc1ccc2[nH]c3c(c2c1)C[C@@]1(C)C(=O)N(CCCN2CCN(C(C)=O)CC2)C(=O)N1[C@@H]3c1cccc(O)c1] | 546.2 |
| 152. | 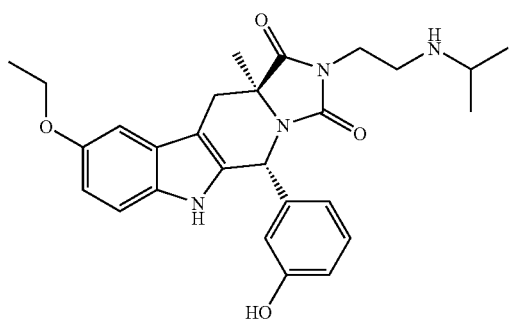 | 477.2 |
| 153. | 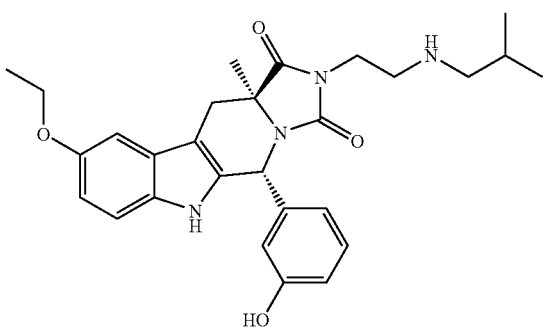 [SMILES: CCOc1ccc2[nH]c3c(c2c1)C[C@@]1(C)C(=O)N(CCNCC(C)C)C(=O)N1[C@@H]3c1cccc(O)c1] | 491.3 |
| 154. | 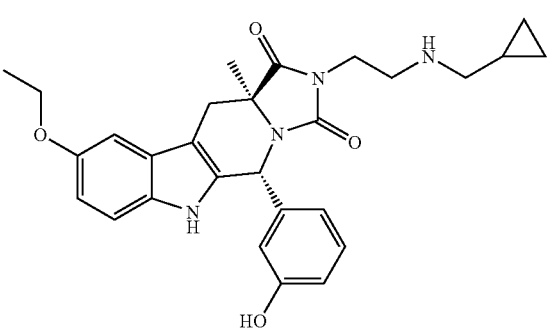 [SMILES: CCOc1ccc2[nH]c3c(c2c1)C[C@@]1(C)C(=O)N(CCNCC2CC2)C(=O)N1[C@@H]3c1cccc(O)c1] | 489.2 |
| 155. | 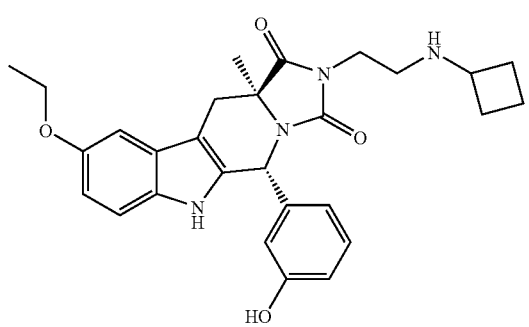 [SMILES: CCOc1ccc2[nH]c3c(c2c1)C[C@@]1(C)C(=O)N(CCNC2CCC2)C(=O)N1[C@@H]3c1cccc(O)c1] | 489.1 |

-continued
| 156. | 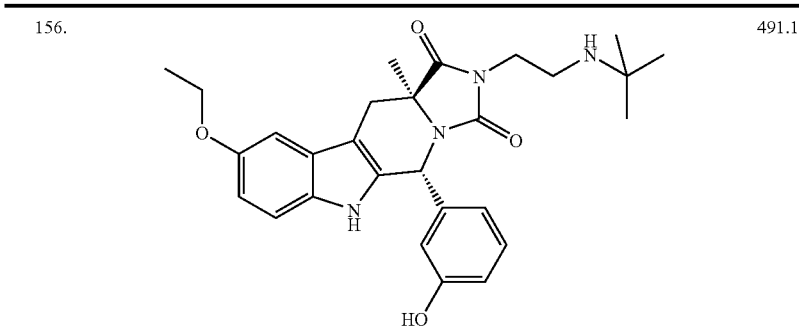 | 491.1 |
| 157. | 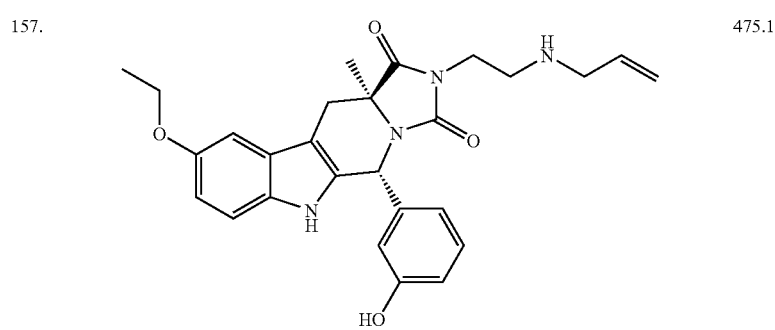 | 475.1 |
| 158. | 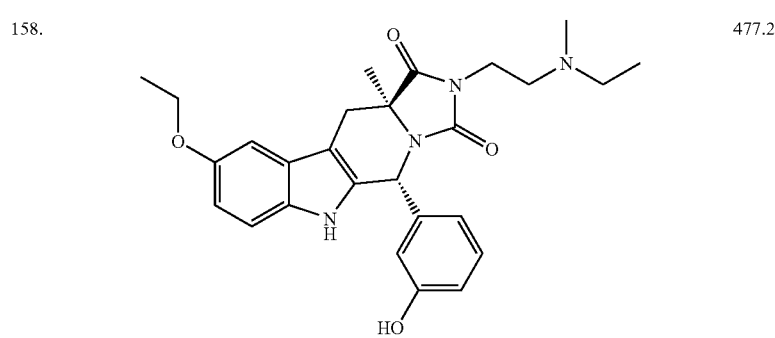 | 477.2 |
| 159. | 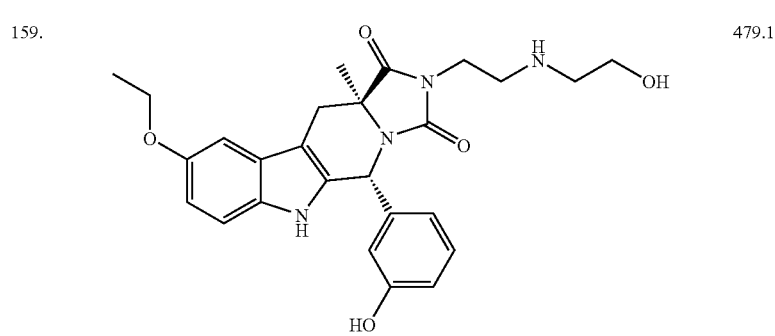 | 479.1 |
| 160. | 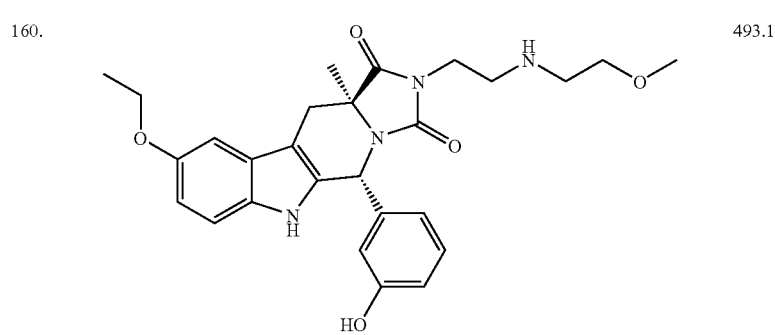 | 493.1 |

161. 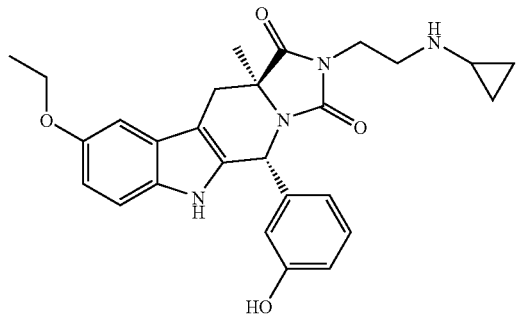 [SMILES: CCOc1ccc2[nH]c3c(c2c1)C[C@@]1(C)C(=O)N(CCNC2CC2)C(=O)N1[C@@H]3c1cccc(O)c1] 475.1
162. 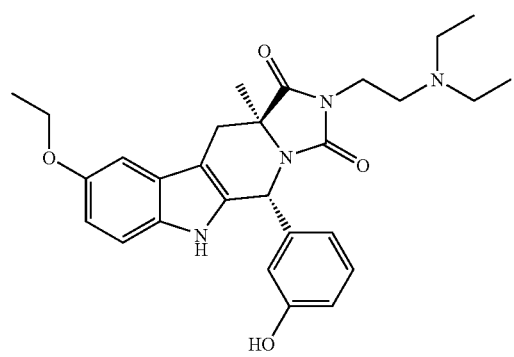 [SMILES: CCOc1ccc2[nH]c3c(c2c1)C[C@@]1(C)C(=O)N(CCN(CC)CC)C(=O)N1[C@@H]3c1cccc(O)c1] 491.2
163. 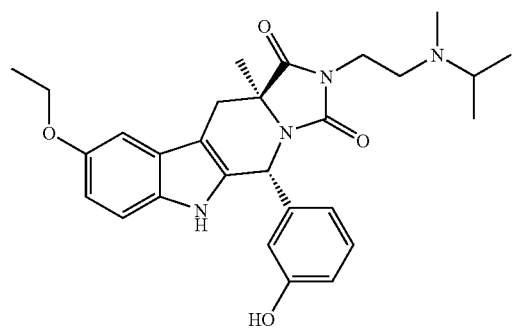 491.2
164. 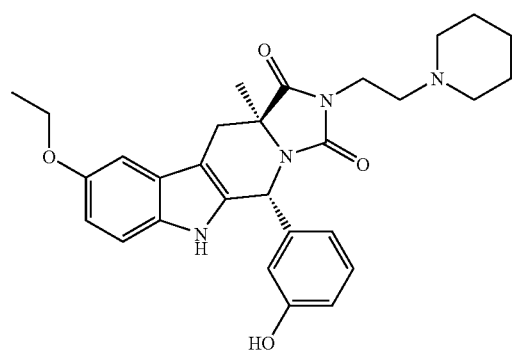 [SMILES: CCOc1ccc2[nH]c3c(c2c1)C[C@@]1(C)C(=O)N(CCN2CCCCC2)C(=O)N1[C@@H]3c1cccc(O)c1] 503.3

| | | |
|---|---|---|
| 165. | 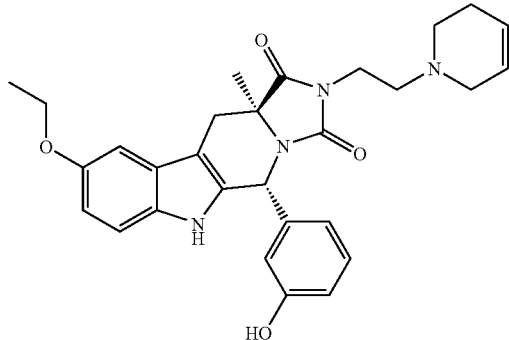 | 501.2 |
| 166. | 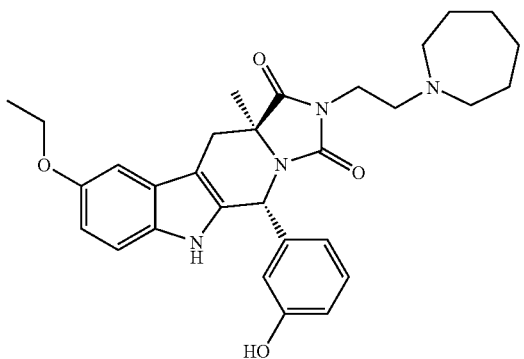 [SMILES: CCOc1ccc2[nH]c3c(c2c1)C[C@@]1(C)C(=O)N(CCN2CCCCCC2)C(=O)N1[C@@H]3c1cccc(O)c1] | 517.2 |
| 167. | 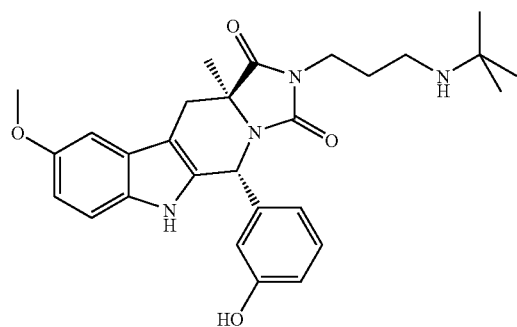 [SMILES: COc1ccc2[nH]c3c(c2c1)C[C@@]1(C)C(=O)N(CCCNC(C)(C)C)C(=O)N1[C@@H]3c1cccc(O)c1] | 491.1 |
| 168. | 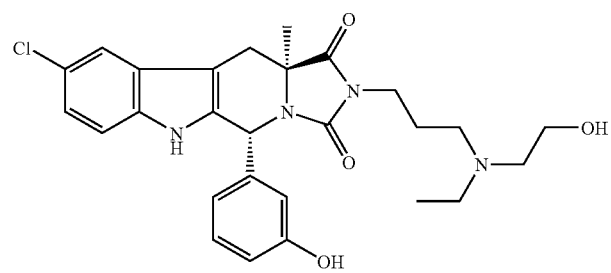 [SMILES: CCN(CCO)CCCN1C(=O)N2[C@H](c3cccc(O)c3)c3[nH]c4ccc(Cl)cc4c3C[C@@]2(C)C1=O] | 511.2 |
| 169. | 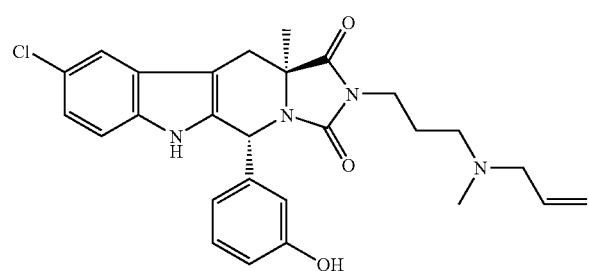 | 493.2 |

-continued
| 170. | 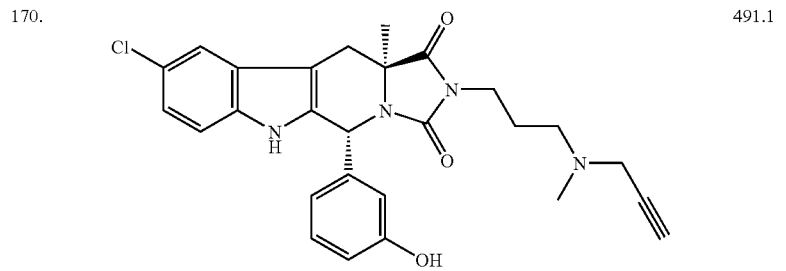 | 491.1 |
| 171. | 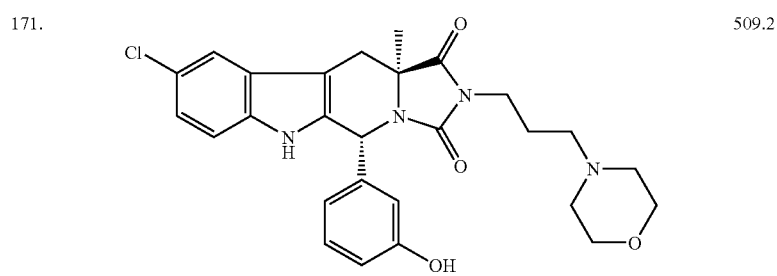 | 509.2 |
| 172. | 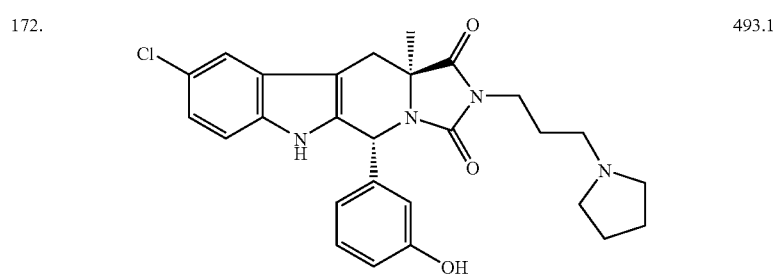 | 493.1 |
| 173. | 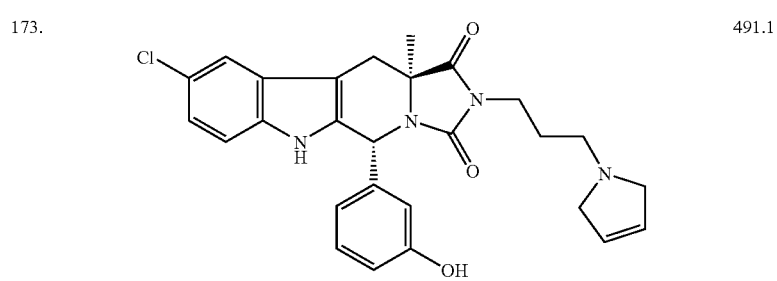 | 491.1 |
| 174. | 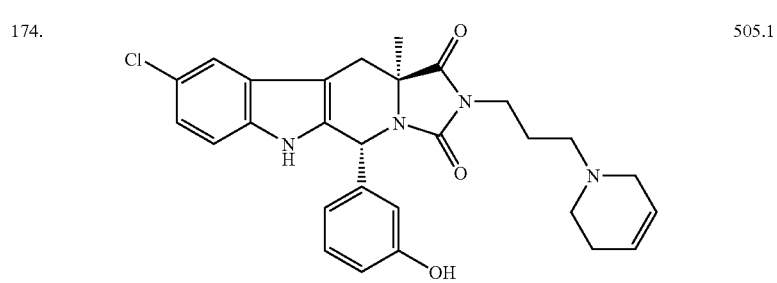 | 505.1 |
| 175. | 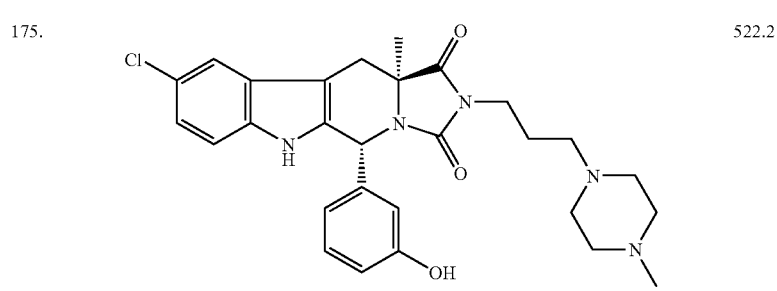 | 522.2 |

-continued
176. 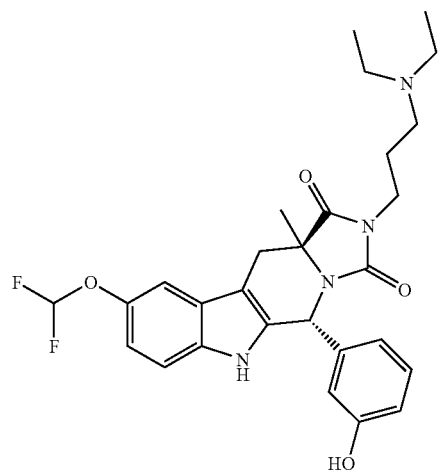 [SMILES: CCN(CC)CCCN1C(=O)N2[C@H](c3cccc(O)c3)c3[nH]c4ccc(OC(F)F)cc4c3C[C@@]2(C)C1=O] 527.2
177. 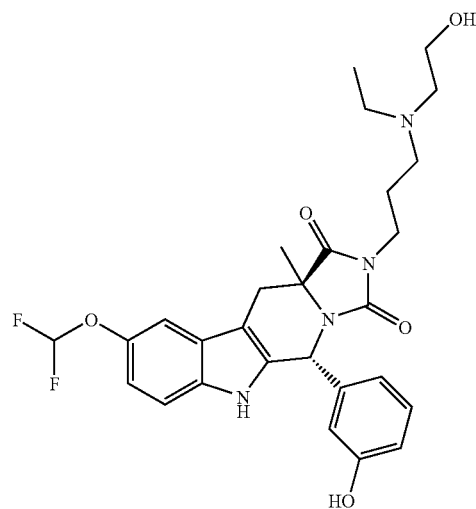 [SMILES: CCN(CCO)CCCN1C(=O)N2[C@H](c3cccc(O)c3)c3[nH]c4ccc(OC(F)F)cc4c3C[C@@]2(C)C1=O] 543.2
178. 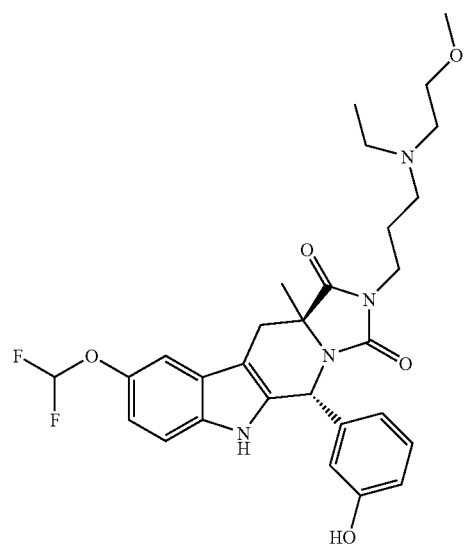 [SMILES: CCN(CCCN1C(=O)N2[C@H](c3cccc(O)c3)c3[nH]c4ccc(OC(F)F)cc4c3C[C@@]2(C)C1=O)CCOC] 557.1

-continued
| 179. | 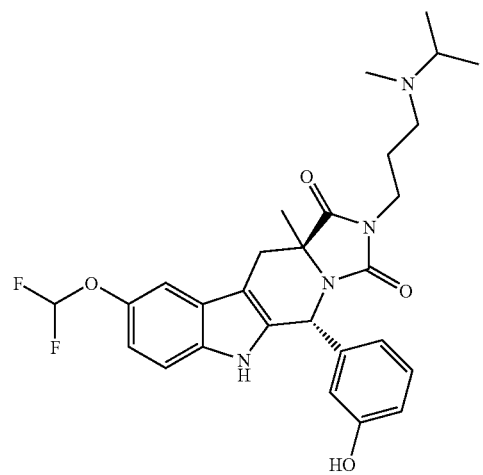 [SMILES: CC(C)N(C)CCCN1C(=O)N2[C@H](c3cccc(O)c3)c3[nH]c4ccc(OC(F)F)cc4c3C[C@@]2(C)C1=O] | 527.2 |
| 180. | 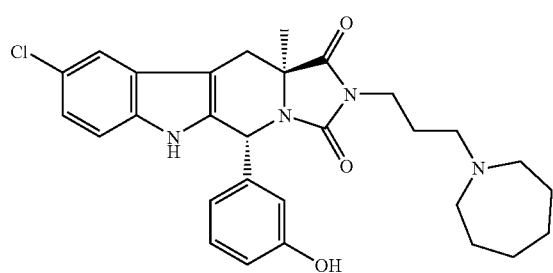 [SMILES: C[C@@]12Cc3c([nH]c4ccc(Cl)cc34)[C@@H](c3cccc(O)c3)N1C(=O)N(CCCN1CCCCCC1)C2=O] | 521.2 |
| 181. | 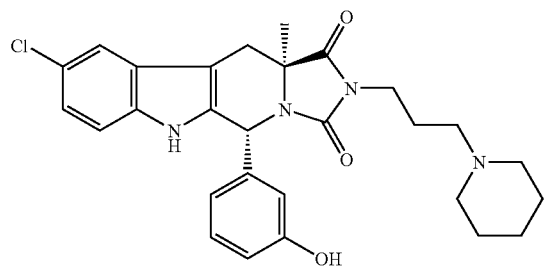 [SMILES: C[C@@]12Cc3c([nH]c4ccc(Cl)cc34)[C@@H](c3cccc(O)c3)N1C(=O)N(CCCN1CCCCC1)C2=O] | 507.2 |
| 182. | 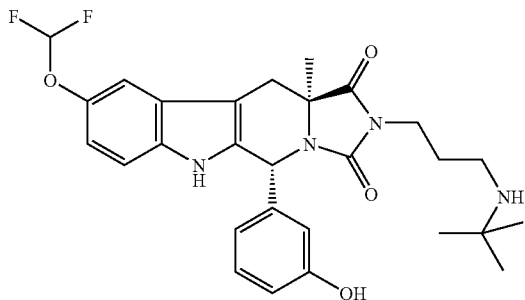 [SMILES: CC(C)(C)NCCCN1C(=O)N2[C@H](c3cccc(O)c3)c3[nH]c4ccc(OC(F)F)cc4c3C[C@@]2(C)C1=O] | 527.1 |

| | | |
|---|---|---|
| 183. | 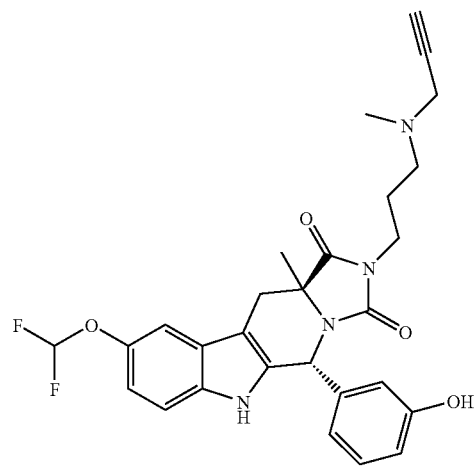 [SMILES: C#CCN(C)CCCN1C(=O)N2[C@H](c3cccc(O)c3)c3[nH]c4ccc(OC(F)F)cc4c3C[C@@]2(C)C1=O] | 523.1 |
| 184. | 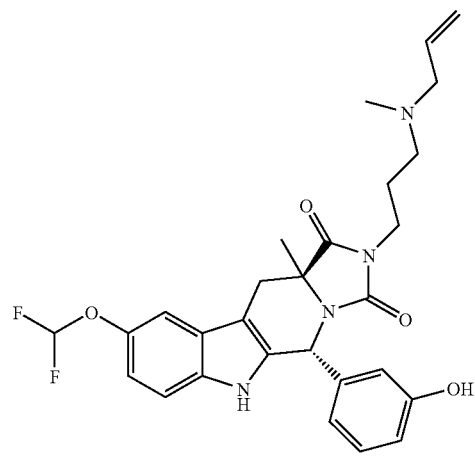 [SMILES: C=CCN(C)CCCN1C(=O)N2[C@H](c3cccc(O)c3)c3[nH]c4ccc(OC(F)F)cc4c3C[C@@]2(C)C1=O] | 525.2 |
| 185. | 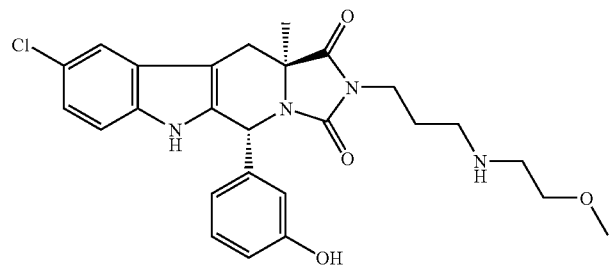 [SMILES: COCCNCCCN1C(=O)N2[C@H](c3cccc(O)c3)c3[nH]c4ccc(Cl)cc4c3C[C@@]2(C)C1=O] | 497.1 |
| 186. | 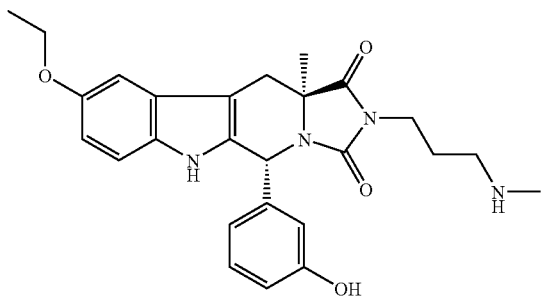 [SMILES: CCOc1ccc2[nH]c3c(c2c1)C[C@@]1(C)C(=O)N(CCCNC)C(=O)N1[C@@H]3c1cccc(O)c1] | 463.2 |

| | | |
|---|---|---|
| 187. | 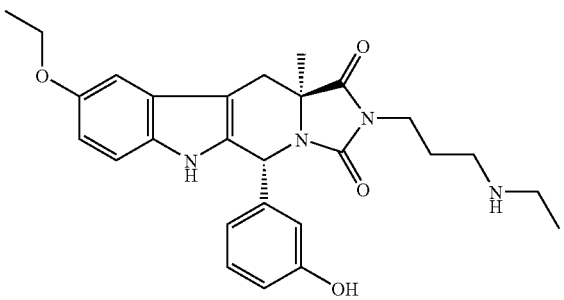 [SMILES: CCNCCCN1C(=O)N2[C@H](c3cccc(O)c3)c3[nH]c4ccc(OCC)cc4c3C[C@@]2(C)C1=O] | 477.2 |
| 188. | 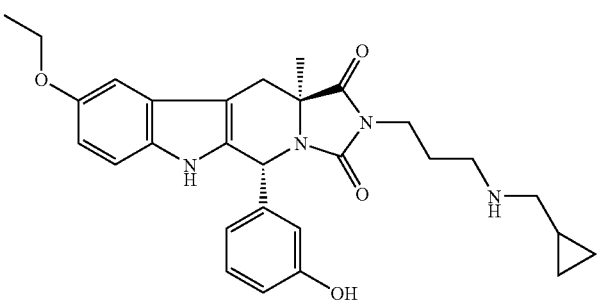 [SMILES: CCOc1ccc2[nH]c3c(c2c1)C[C@@]1(C)C(=O)N(CCCNCC2CC2)C(=O)N1[C@@H]3c1cccc(O)c1] | 503.2 |
| 189. | 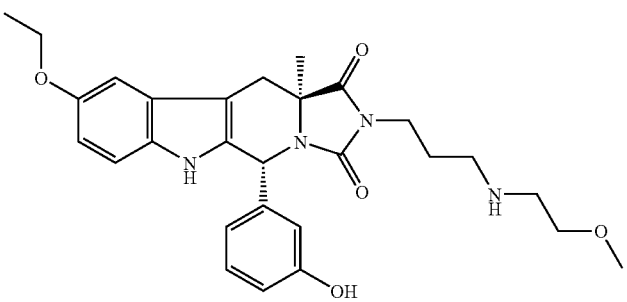 [SMILES: CCOc1ccc2[nH]c3c(c2c1)C[C@@]1(C)C(=O)N(CCCNCCOC)C(=O)N1[C@@H]3c1cccc(O)c1] | 507.2 |
| 190. | 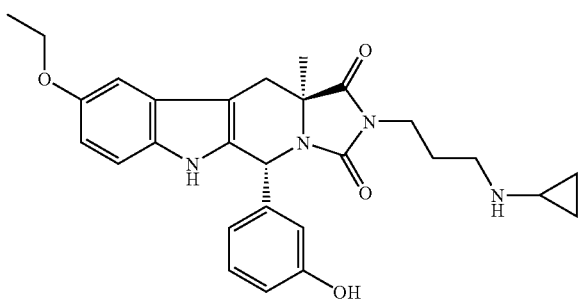 [SMILES: CCOc1ccc2[nH]c3c(c2c1)C[C@@]1(C)C(=O)N(CCCNC2CC2)C(=O)N1[C@@H]3c1cccc(O)c1] | 489.2 |
| 191. | 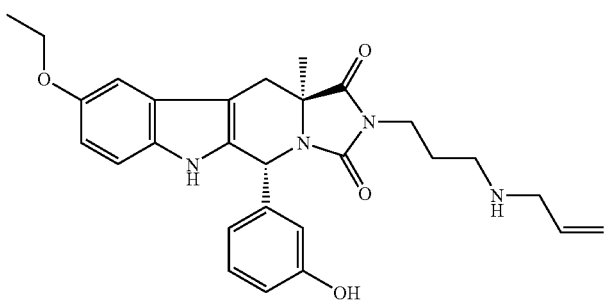 | 489.2 |

| | | |
|---|---|---|
| 192. | 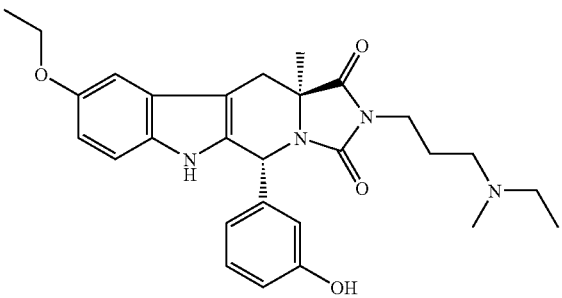 [SMILES: CCOc1ccc2[nH]c3c(c2c1)C[C@@]1(C)C(=O)N(CCCN(C)CC)C(=O)N1[C@@H]3c1cccc(O)c1] | 491.2 |
| 193. | 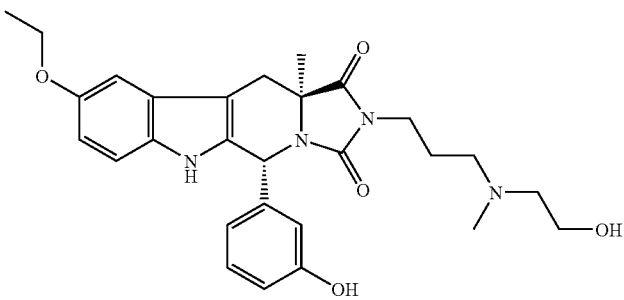 [SMILES: CCOc1ccc2[nH]c3c(c2c1)C[C@@]1(C)C(=O)N(CCCN(C)CCO)C(=O)N1[C@@H]3c1cccc(O)c1] | 507.2 |
| 194. | 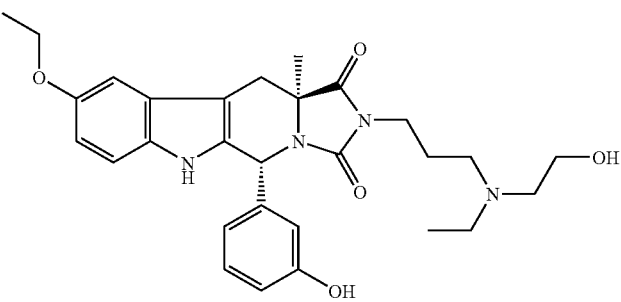 [SMILES: CCOc1ccc2[nH]c3c(c2c1)C[C@@]1(C)C(=O)N(CCCN(CC)CCO)C(=O)N1[C@@H]3c1cccc(O)c1] | 521.3 |
| 195. | 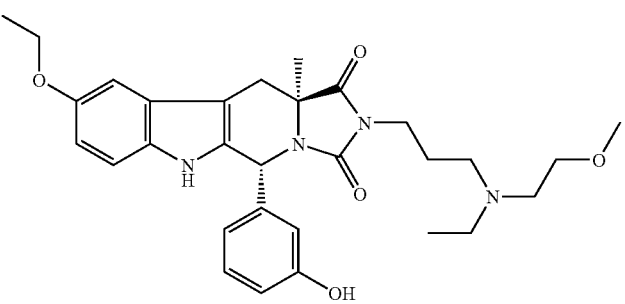 [SMILES: CCOc1ccc2[nH]c3c(c2c1)C[C@@]1(C)C(=O)N(CCCN(CC)CCOC)C(=O)N1[C@@H]3c1cccc(O)c1] | 535.3 |
| 196. | 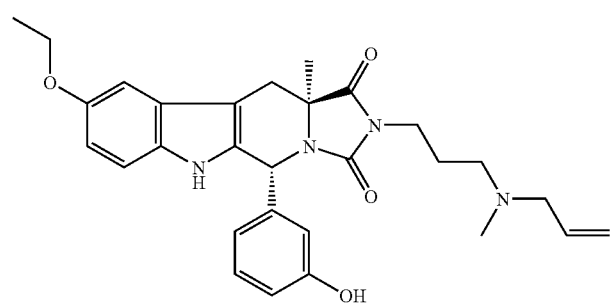 [SMILES: C=CCN(C)CCCN1C(=O)N2[C@H](c3cccc(O)c3)c3[nH]c4ccc(OCC)cc4c3C[C@@]2(C)C1=O] | 503.1 |

| | | |
|---|---|---|
| 197. | 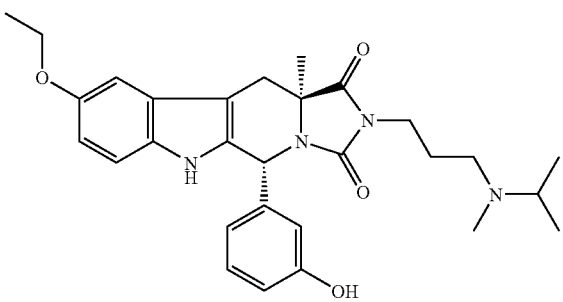 [SMILES: CCOc1ccc2[nH]c3c(c2c1)C[C@@]1(C)C(=O)N(CCCN(C)C(C)C)C(=O)N1[C@@H]3c1cccc(O)c1] | 505.2 |
| 198. | 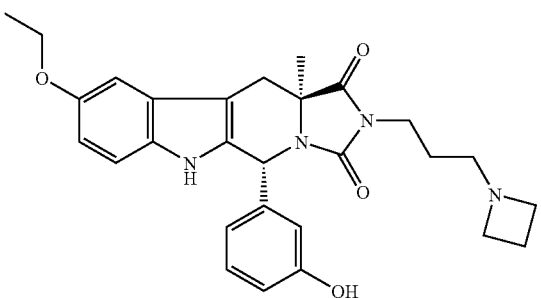 [SMILES: CCOc1ccc2[nH]c3c(c2c1)C[C@@]1(C)C(=O)N(CCCN2CCC2)C(=O)N1[C@@H]3c1cccc(O)c1] | 489.3 |
| 199. | 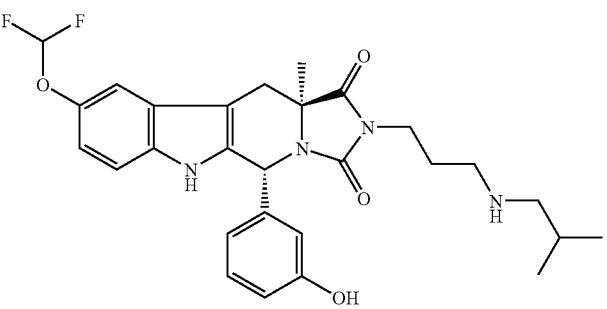 [SMILES: CC(C)CNCCCN1C(=O)N2[C@H](c3cccc(O)c3)c3[nH]c4ccc(OC(F)F)cc4c3C[C@@]2(C)C1=O] | 527.2 |
| 200. | 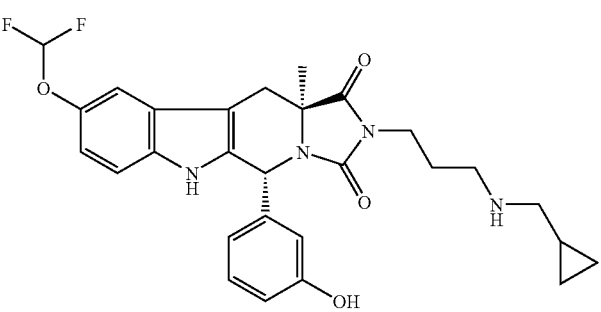 [SMILES: C[C@@]12Cc3c([nH]c4ccc(OC(F)F)cc34)[C@@H](c3cccc(O)c3)N1C(=O)N(CCCNCC1CC1)C2=O] | 525.1 |
| 201. | 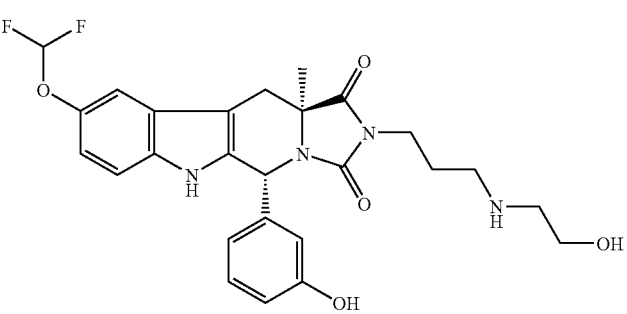 [SMILES: C[C@@]12Cc3c([nH]c4ccc(OC(F)F)cc34)[C@@H](c3cccc(O)c3)N1C(=O)N(CCCNCCO)C2=O] | 515.2 |

| | | |
|---|---|---|
| 202. | 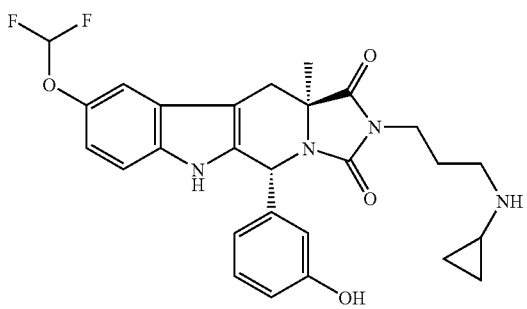 [SMILES: C[C@@]12Cc3c([nH]c4ccc(OC(F)F)cc34)[C@@H](c3cccc(O)c3)N1C(=O)N(CCCNC1CC1)C2=O] | 511.2 |
| 203. | 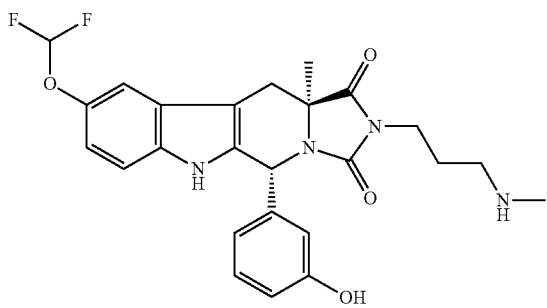 [SMILES: CNCCCN1C(=O)N2[C@H](c3cccc(O)c3)c3[nH]c4ccc(OC(F)F)cc4c3C[C@@]2(C)C1=O] | 485.2 |
| 204. | 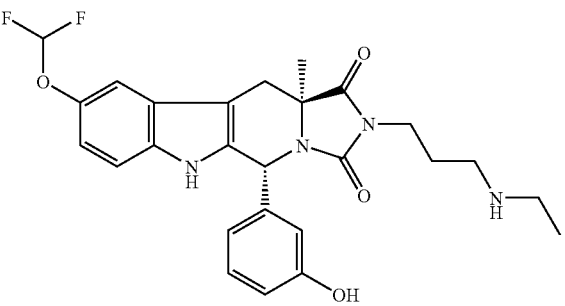 [SMILES: CCNCCCN1C(=O)N2[C@H](c3cccc(O)c3)c3[nH]c4ccc(OC(F)F)cc4c3C[C@@]2(C)C1=O] | 499.1 |
| 205. | 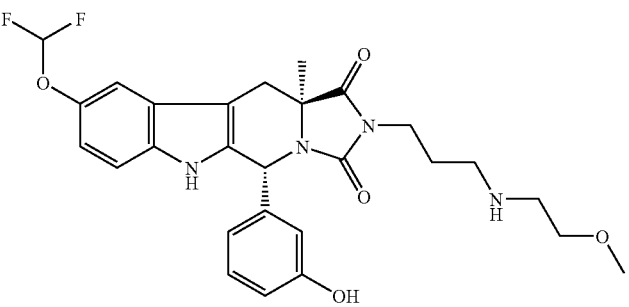 [SMILES: COCCNCCCN1C(=O)N2[C@H](c3cccc(O)c3)c3[nH]c4ccc(OC(F)F)cc4c3C[C@@]2(C)C1=O] | 529.3 |
| 206. | 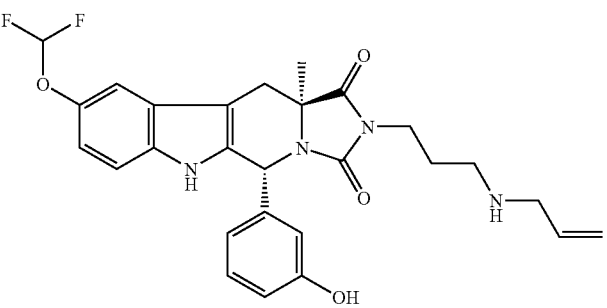 [SMILES: C=CCNCCCN1C(=O)N2[C@H](c3cccc(O)c3)c3[nH]c4ccc(OC(F)F)cc4c3C[C@@]2(C)C1=O] | 511.0 |

-continued
| | | |
|---|---|---|
| 207. | 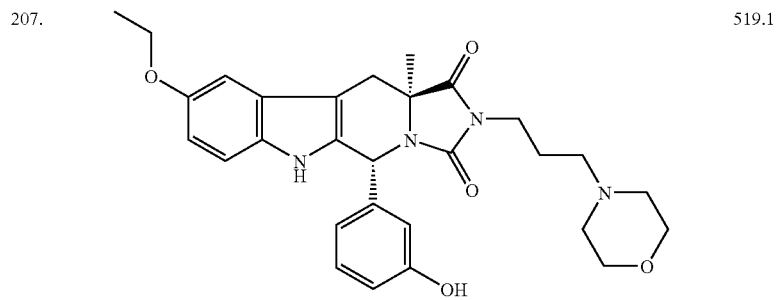 | 519.1 |
| 208. | 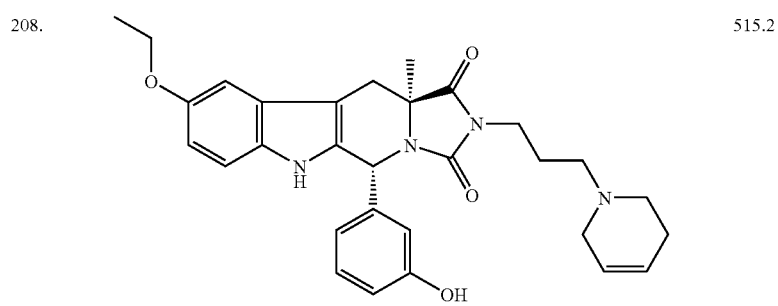 | 515.2 |
| 209. | 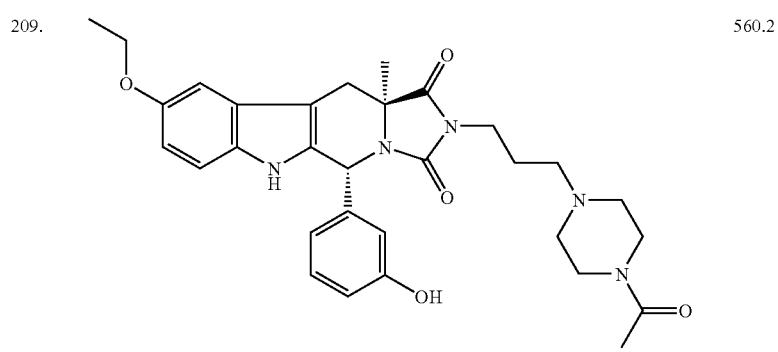 | 560.2 |
| 210. | 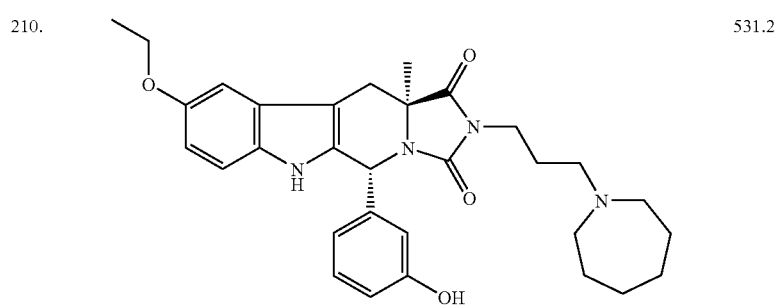 | 531.2 |
| 211. | 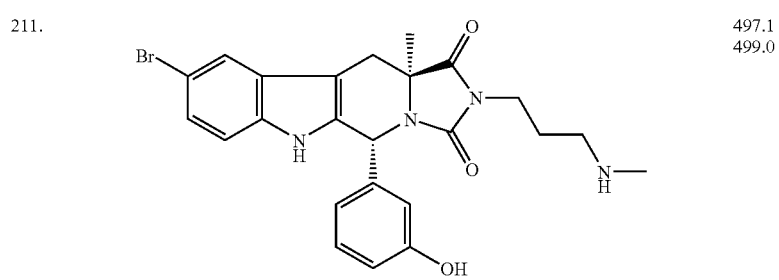 | 497.1<br>499.0 |

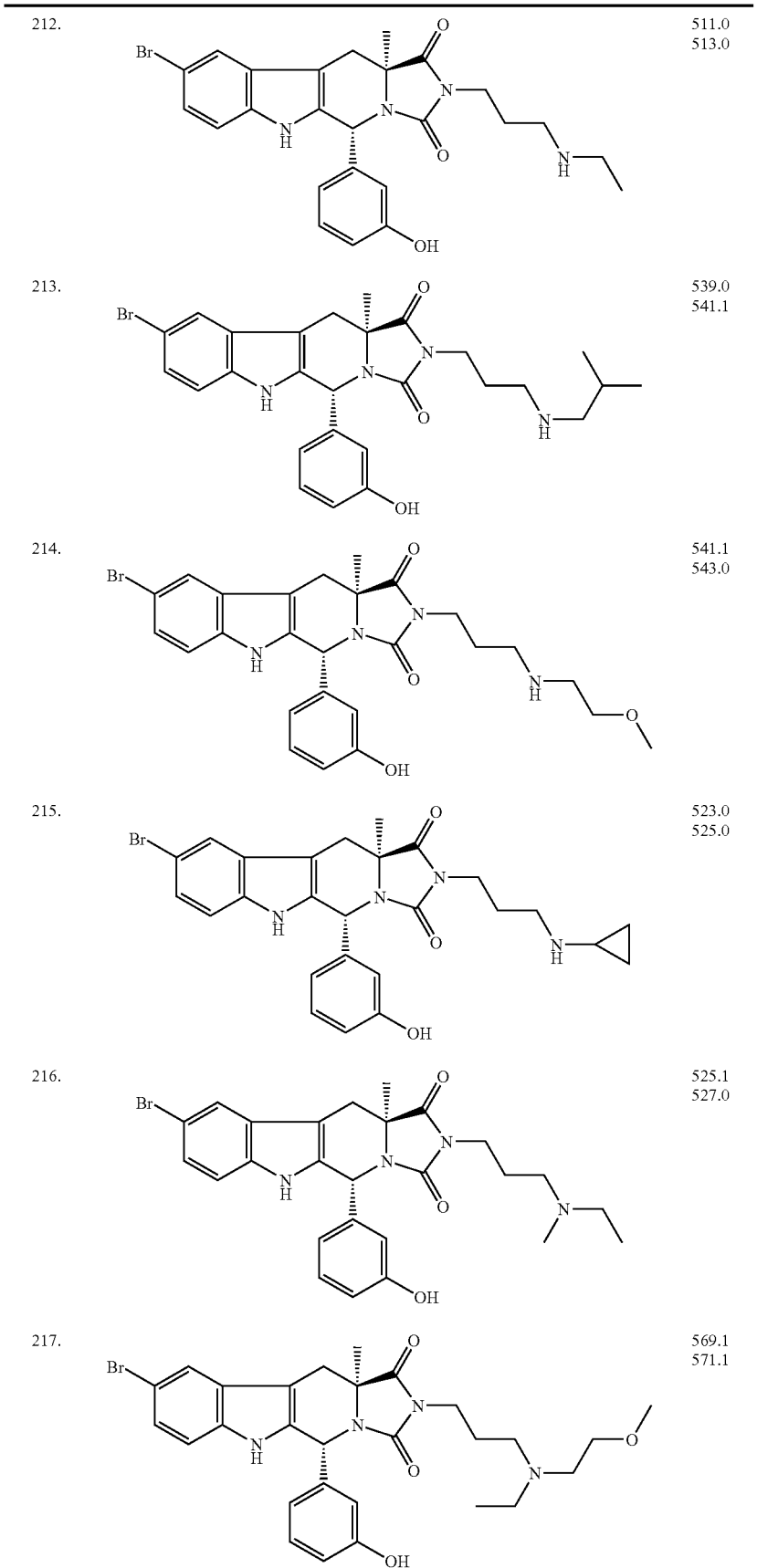

| | | |
|---|---|---|
| 218. | 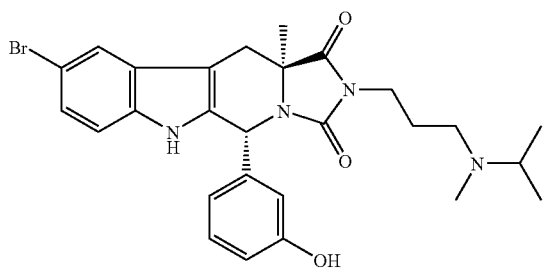 | 539.2<br>541.1 |
| 219. | 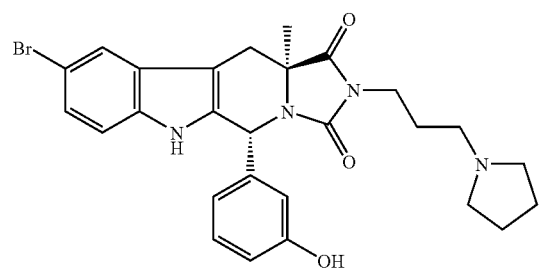 [SMILES: C[C@@]12Cc3c([nH]c4ccc(Br)cc34)[C@@H](c3cccc(O)c3)N1C(=O)N(CCCN1CCCC1)C2=O] | 537.2<br>539.1 |
| 220. | 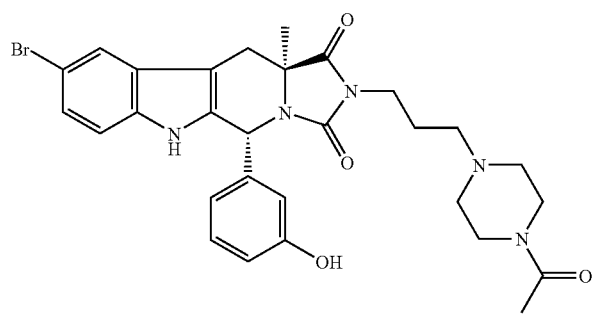 [SMILES: CC(=O)N1CCN(CCCN2C(=O)N3[C@H](c4cccc(O)c4)c4[nH]c5ccc(Br)cc5c4C[C@@]3(C)C2=O)CC1] | 594.1<br>596.1 |
| 221. | 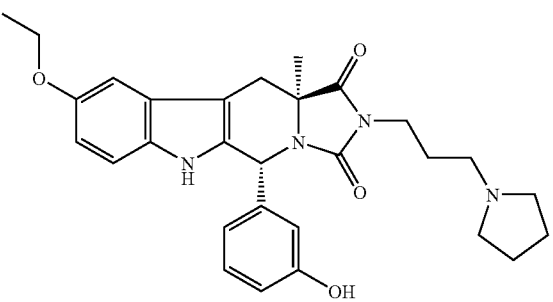 | 503.2 |
| 222. | 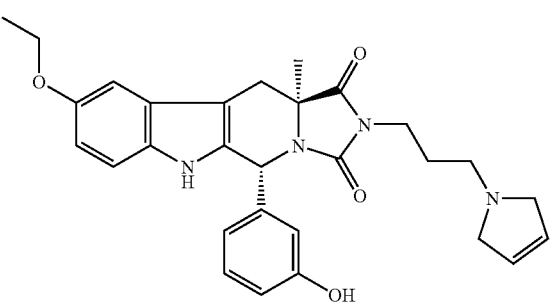 [SMILES: CCOc1ccc2[nH]c3c(c2c1)C[C@@]1(C)C(=O)N(CCCN2CC=CC2)C(=O)N1[C@@H]3c1cccc(O)c1] | 501.2 |

| # | | MW |
|---|---|---|
| 223. | 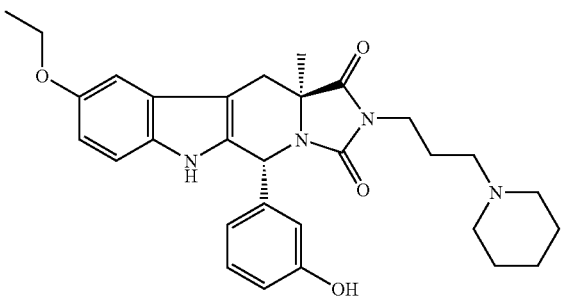 [SMILES: CCOc1ccc2[nH]c3c(c2c1)C[C@@]1(C)C(=O)N(CCCN2CCCCC2)C(=O)N1[C@@H]3c1cccc(O)c1] | 517.2 |
| 224. | 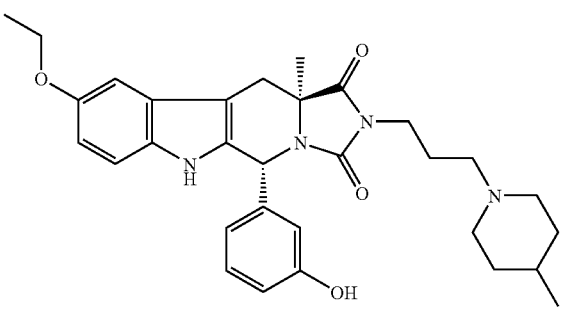 [SMILES: CCOc1ccc2[nH]c3c(c2c1)C[C@@]1(C)C(=O)N(CCCN2CCC(C)CC2)C(=O)N1[C@@H]3c1cccc(O)c1] | 531.2 |
| 225. | 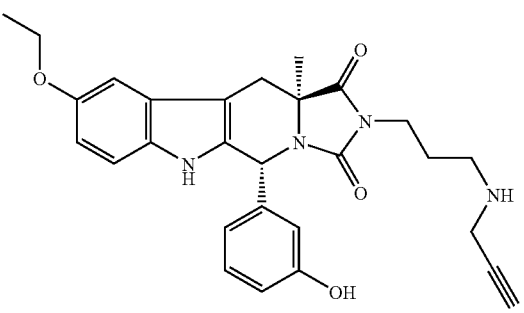 [SMILES: C#CCNCCCN1C(=O)N2[C@H](c3cccc(O)c3)c3[nH]c4ccc(OCC)cc4c3C[C@@]2(C)C1=O] | 487.2 |
| 226. | 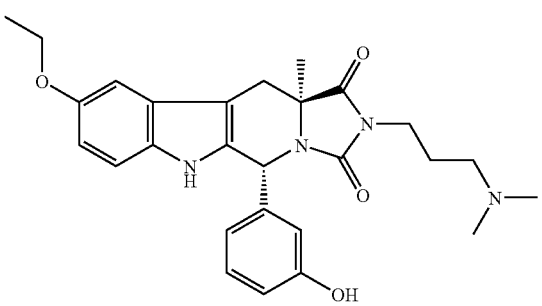 | 477.2 |
| 227. | 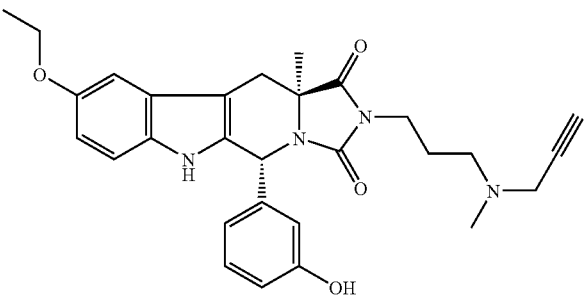 [SMILES: C#CCN(C)CCCN1C(=O)N2[C@H](c3cccc(O)c3)c3[nH]c4ccc(OCC)cc4c3C[C@@]2(C)C1=O] | 501.2 |

-continued
| | | |
|---|---|---|
| 228. | 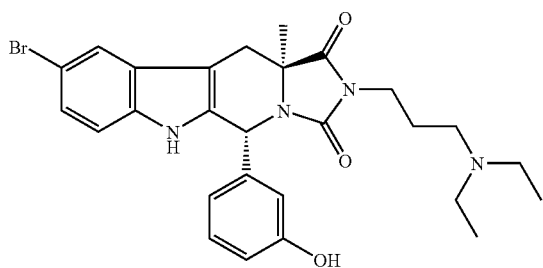 [SMILES: CCN(CC)CCCN1C(=O)N2[C@H](c3cccc(O)c3)c3[nH]c4ccc(Br)cc4c3C[C@@]2(C)C1=O] | 539.1<br>541.1 |
| 229. | 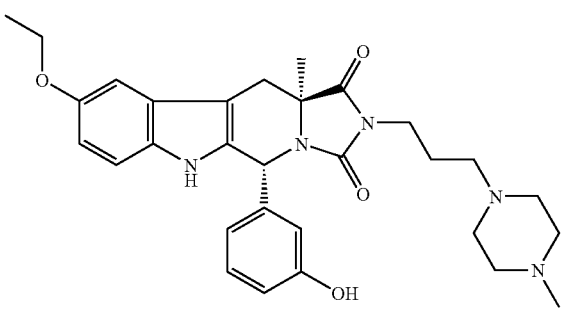 | 532.2 |
| 230. | 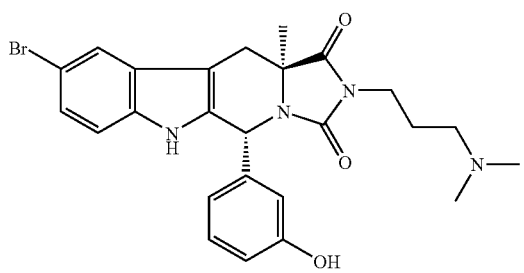 | 511.1<br>513.0 |
| 231. | 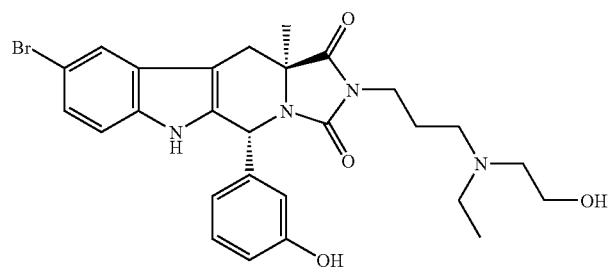 [SMILES: CCN(CCO)CCCN1C(=O)N2[C@H](c3cccc(O)c3)c3[nH]c4ccc(Br)cc4c3C[C@@]2(C)C1=O] | 555.1<br>557.1 |
| 232. | 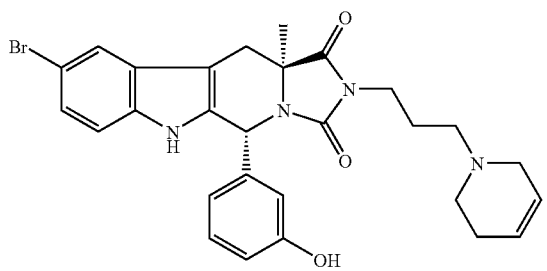 | 549.1<br>551.1 |

| | | |
|---|---|---|
| 233. | 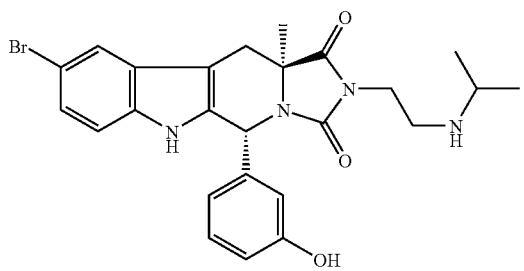 [SMILES: CC(C)NCCN1C(=O)N2[C@H](c3cccc(O)c3)c3[nH]c4ccc(Br)cc4c3C[C@@]2(C)C1=O] | 511.2<br>513.2 |
| 234. | 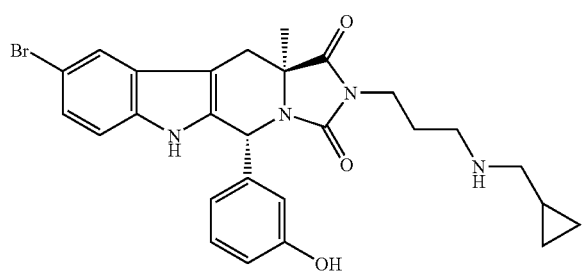 [SMILES: C[C@@]12Cc3c([nH]c4ccc(Br)cc34)[C@@H](c3cccc(O)c3)N1C(=O)N(CCCNCC1CC1)C2=O] | 537.1<br>539.1 |
| 235. | 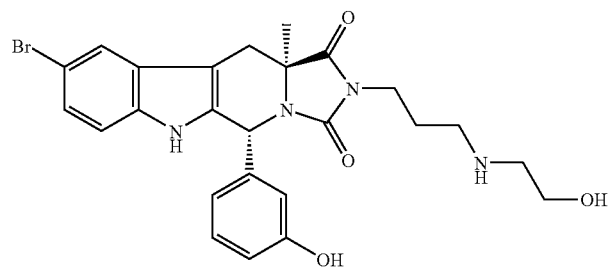 [SMILES: C[C@@]12Cc3c([nH]c4ccc(Br)cc34)[C@@H](c3cccc(O)c3)N1C(=O)N(CCCNCCO)C2=O] | 527.0<br>529.0 |
| 236. | 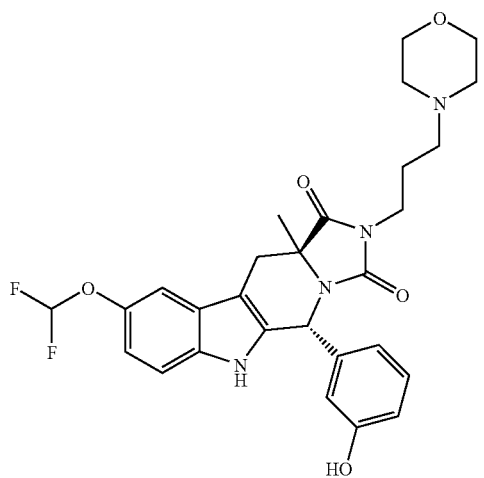 [SMILES: C[C@@]12Cc3c([nH]c4ccc(OC(F)F)cc34)[C@@H](c3cccc(O)c3)N1C(=O)N(CCCN1CCOCC1)C2=O] | 541.1 |

| # | | MS |
|---|---|---|
| 237. | 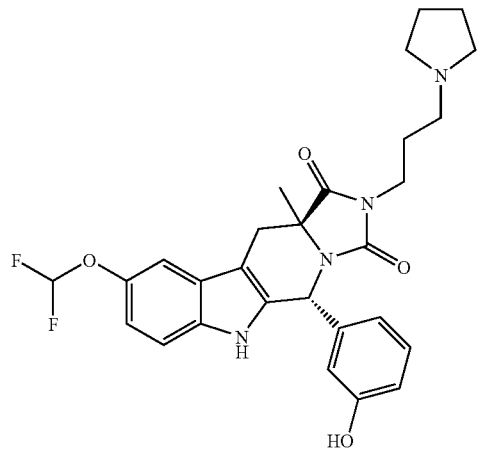 [SMILES: C[C@@]12Cc3c([nH]c4ccc(OC(F)F)cc34)[C@@H](c3cccc(O)c3)N1C(=O)N(CCCN1CCCC1)C2=O] | 525.2 |
| 238. | 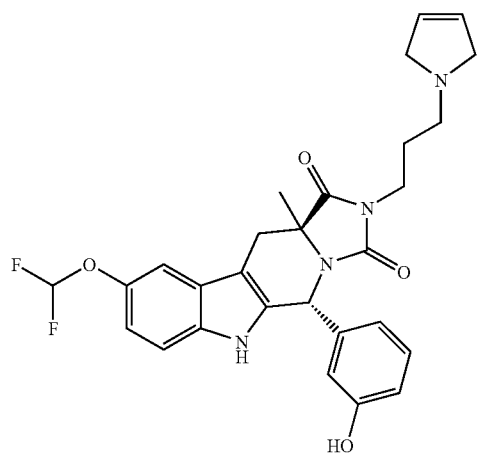 [SMILES: C[C@@]12Cc3c([nH]c4ccc(OC(F)F)cc34)[C@@H](c3cccc(O)c3)N1C(=O)N(CCCN1CC=CC1)C2=O] | 523.2 |
| 239. | 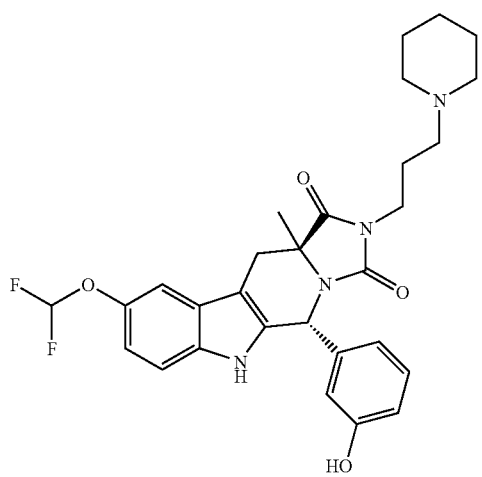 [SMILES: C[C@@]12Cc3c([nH]c4ccc(OC(F)F)cc34)[C@@H](c3cccc(O)c3)N1C(=O)N(CCCN1CCCCC1)C2=O] | 539.2 |

-continued
240.
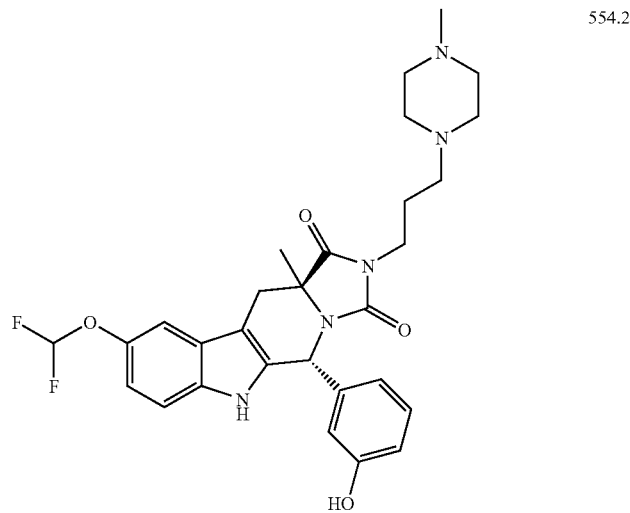
554.2
241.
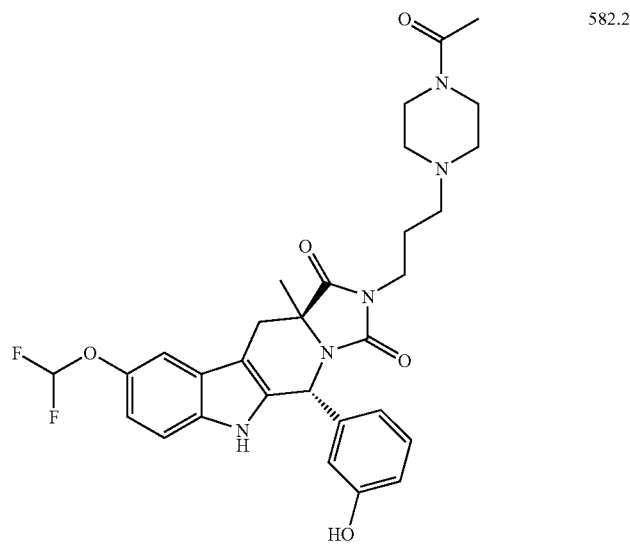
582.2
242.
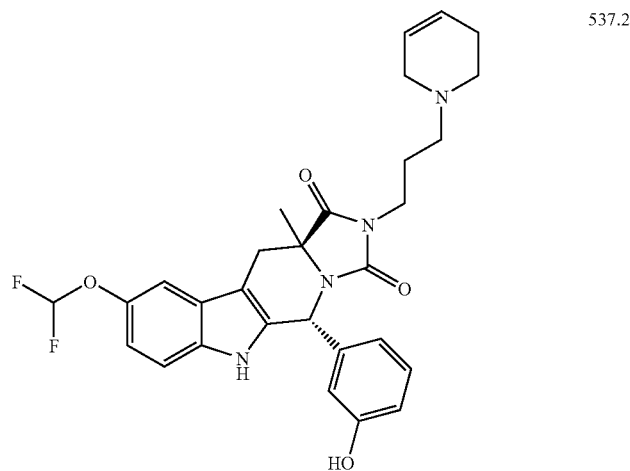
537.2

-continued
243. 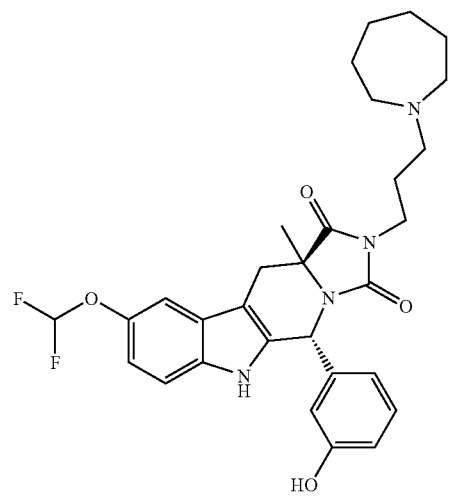 [SMILES: C[C@@]12Cc3c([nH]c4ccc(OC(F)F)cc34)[C@@H](c3cccc(O)c3)N1C(=O)N(CCCN1CCCCCC1)C2=O] 553.2
244. 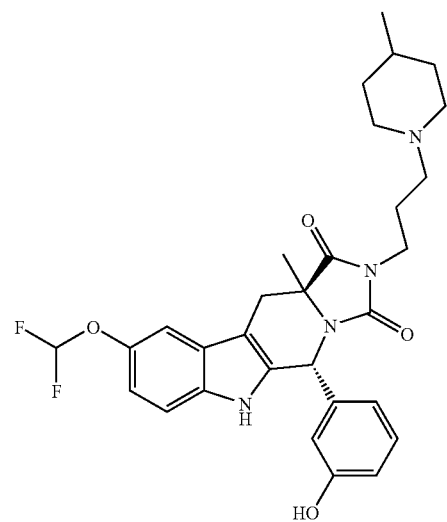 [SMILES: CC1CCN(CCCN2C(=O)N3[C@H](c4cccc(O)c4)c4[nH]c5ccc(OC(F)F)cc5c4C[C@@]3(C)C2=O)CC1] 553.2
245. 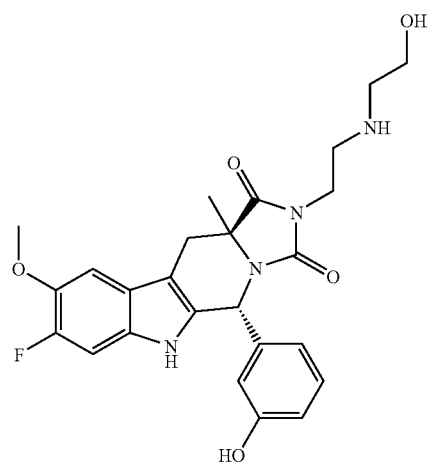 [SMILES: COc1cc2c3c([nH]c2cc1F)[C@@H](c1cccc(O)c1)N1C(=O)N(CCNCCO)C(=O)[C@]1(C)C3] 483.1

| | | |
|---|---|---|
| 246. | 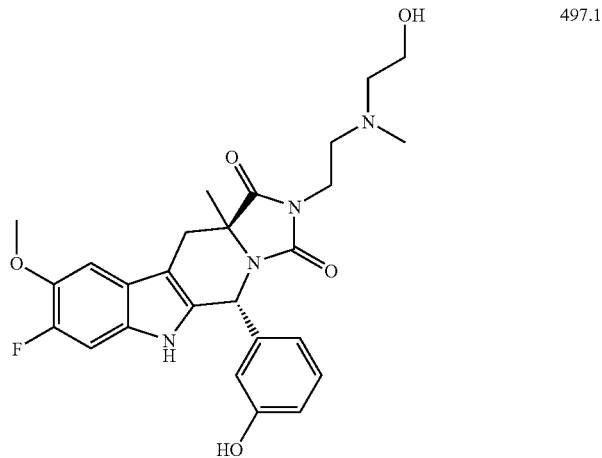 | 497.1 |
| 247. | 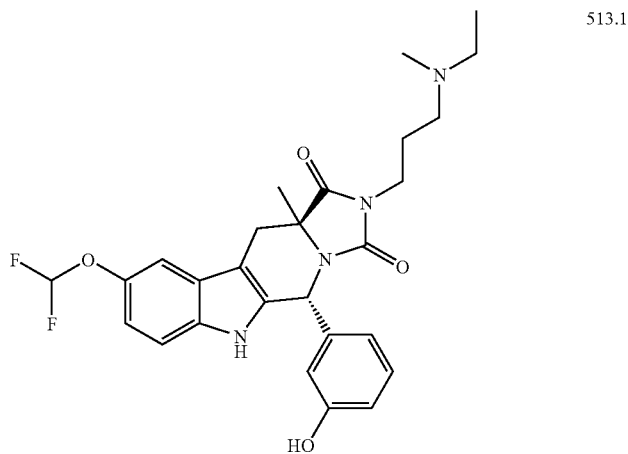 | 513.1 |
| 248. | 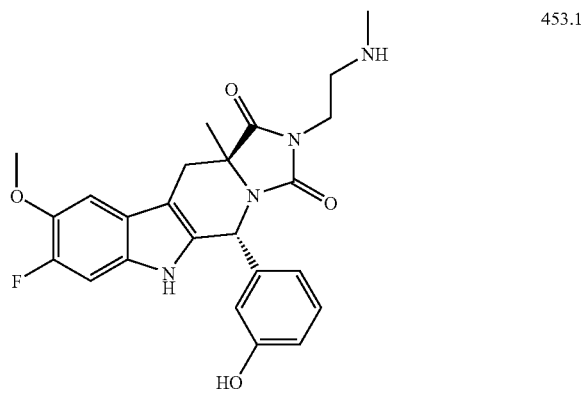 | 453.1 |

| 249. | 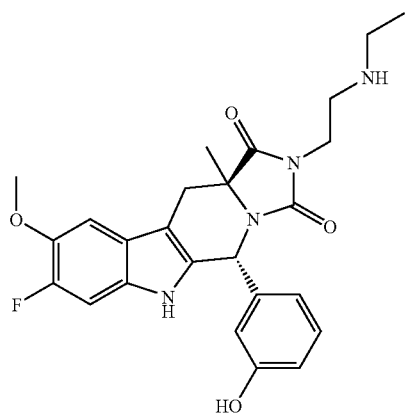 [SMILES: CCNCCN1C(=O)N2[C@H](c3cccc(O)c3)c3[nH]c4cc(F)c(OC)cc4c3C[C@@]2(C)C1=O] | 467.2 |
| 250. | 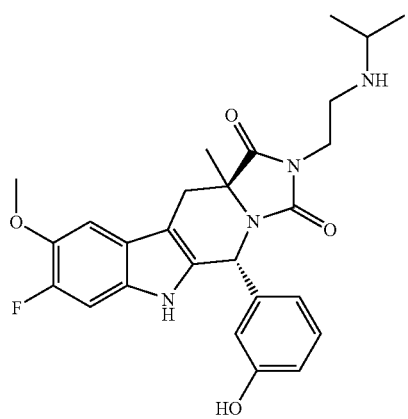 [SMILES: COc1cc2c3c([nH]c2cc1F)[C@@H](c1cccc(O)c1)N1C(=O)N(CCNC(C)C)C(=O)[C@]1(C)C3] | 481.2 |
| 251. | 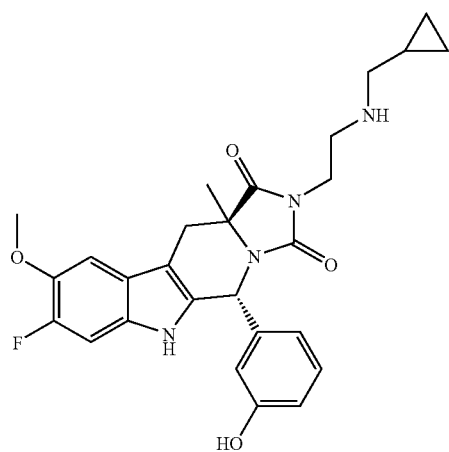 [SMILES: COc1cc2c3c([nH]c2cc1F)[C@@H](c1cccc(O)c1)N1C(=O)N(CCNCC2CC2)C(=O)[C@]1(C)C3] | 493.2 |

-continued
252. 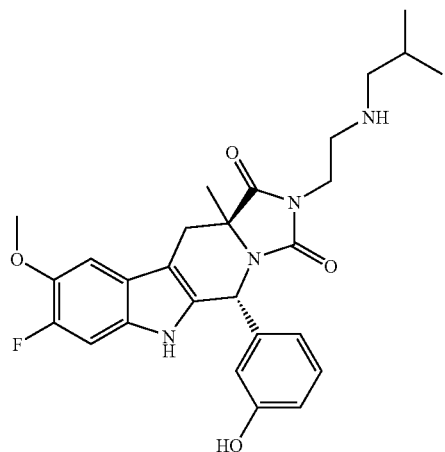 [SMILES: COc1cc2c3c([nH]c2cc1F)[C@@H](c1cccc(O)c1)N1C(=O)N(CCNCC(C)C)C(=O)[C@]1(C)C3] 495.2
253. 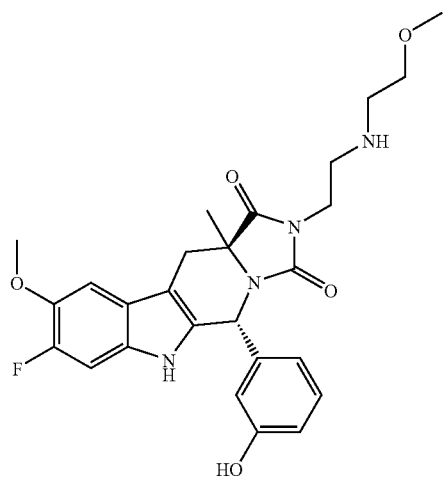 [SMILES: COCCNCCN1C(=O)N2[C@H](c3cccc(O)c3)c3[nH]c4cc(F)c(OC)cc4c3C[C@@]2(C)C1=O] 497.2
254. 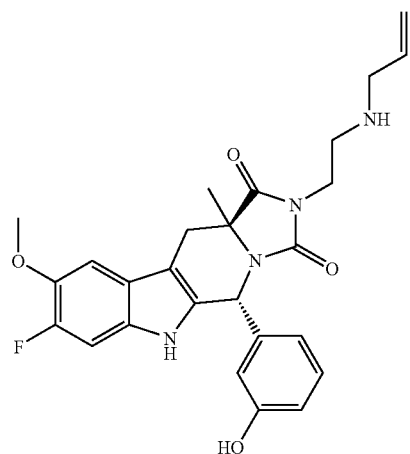 [SMILES: C=CCNCCN1C(=O)N2[C@H](c3cccc(O)c3)c3[nH]c4cc(F)c(OC)cc4c3C[C@@]2(C)C1=O] 479.1

-continued
| 255. | 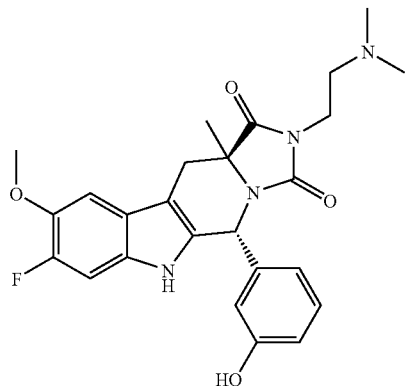 [SMILES: COc1cc2c3c([nH]c2cc1F)[C@@H](c1cccc(O)c1)N1C(=O)N(CCN(C)C)C(=O)[C@]1(C)C3] | 467.2 |
| 256. | 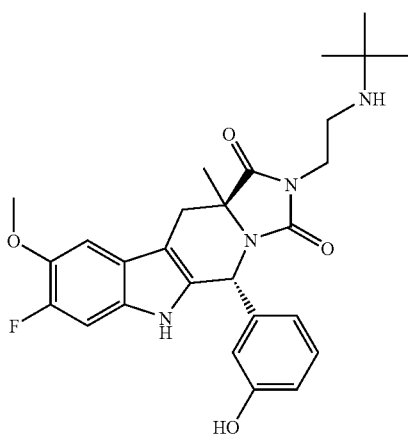 [SMILES: COc1cc2c3c([nH]c2cc1F)[C@@H](c1cccc(O)c1)N1C(=O)N(CCNC(C)(C)C)C(=O)[C@]1(C)C3] | 495.1 |
| 257. | 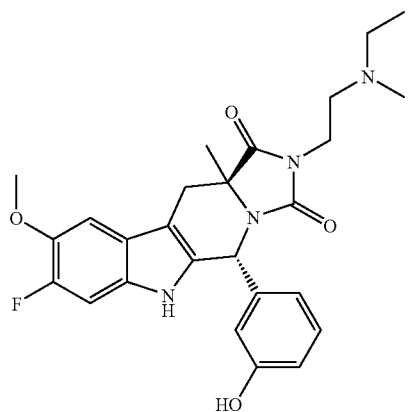 [SMILES: CCN(C)CCN1C(=O)N2[C@H](c3cccc(O)c3)c3[nH]c4cc(F)c(OC)cc4c3C[C@@]2(C)C1=O] | 481.2 |
| 258. | 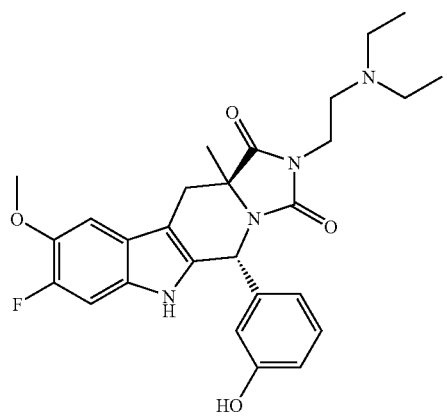 [SMILES: CCN(CC)CCN1C(=O)N2[C@H](c3cccc(O)c3)c3[nH]c4cc(F)c(OC)cc4c3C[C@@]2(C)C1=O] | 495.2 |

| | | |
|---|---|---|
| 259. | 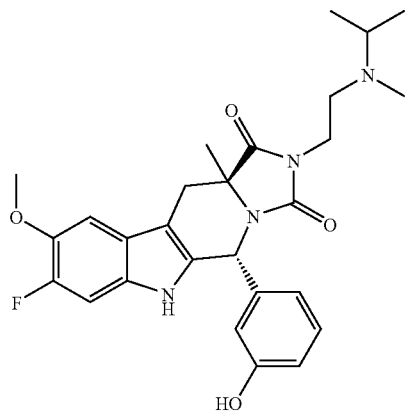 [SMILES: COc1cc2c3c([nH]c2cc1F)[C@@H](c1cccc(O)c1)N1C(=O)N(CCN(C)C(C)C)C(=O)[C@]1(C)C3] | 495.1 |
| 260. | 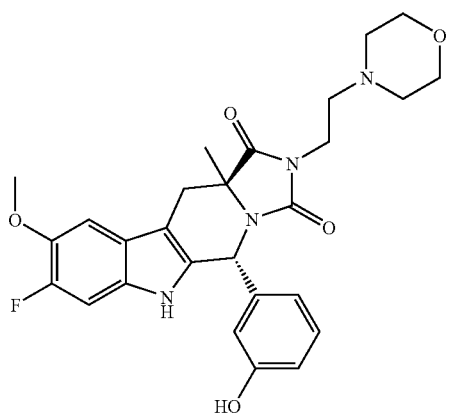 [SMILES: COc1cc2c3c([nH]c2cc1F)[C@@H](c1cccc(O)c1)N1C(=O)N(CCN2CCOCC2)C(=O)[C@]1(C)C3] | 509.2 |
| 261. | 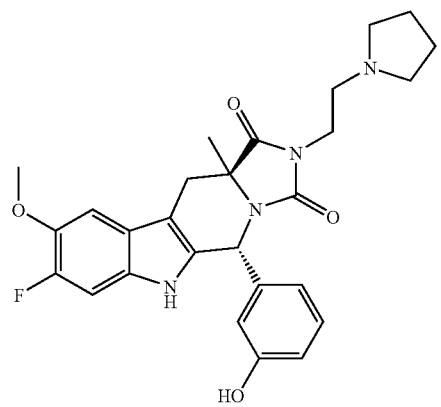 [SMILES: COc1cc2c3c([nH]c2cc1F)[C@@H](c1cccc(O)c1)N1C(=O)N(CCN2CCCC2)C(=O)[C@]1(C)C3] | 493.2 |
| 262. | 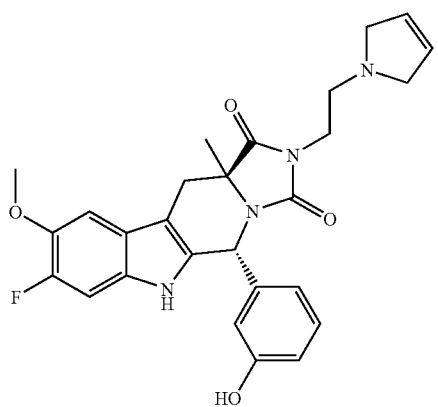 [SMILES: COc1cc2c3c([nH]c2cc1F)[C@@H](c1cccc(O)c1)N1C(=O)N(CCN2CC=CC2)C(=O)[C@]1(C)C3] | 491.1 |

263. 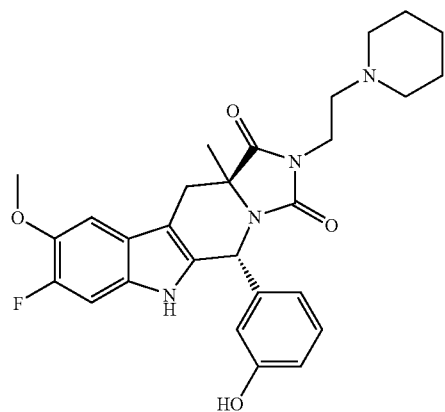 [SMILES: COc1cc2c3c([nH]c2cc1F)[C@@H](c1cccc(O)c1)N1C(=O)N(CCN2CCCCC2)C(=O)[C@]1(C)C3] 507.2
264. 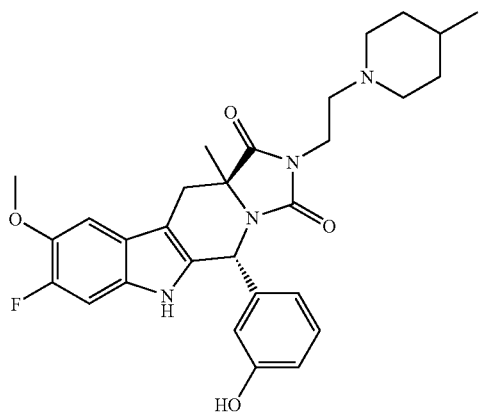 [SMILES: COc1cc2c3c([nH]c2cc1F)[C@@H](c1cccc(O)c1)N1C(=O)N(CCN2CCC(C)CC2)C(=O)[C@]1(C)C3] 521.2
265. 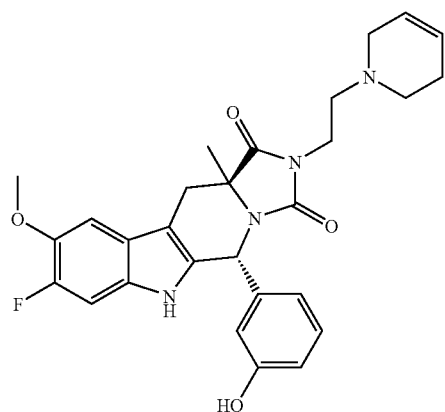 [SMILES: COc1cc2c3c([nH]c2cc1F)[C@@H](c1cccc(O)c1)N1C(=O)N(CCN2CC=CCC2)C(=O)[C@]1(C)C3] 505.2

266. 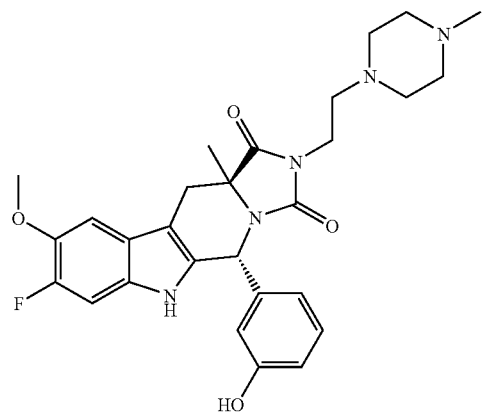 [SMILES: COc1cc2c3c([nH]c2cc1F)[C@@H](c1cccc(O)c1)N1C(=O)N(CCN2CCN(C)CC2)C(=O)[C@]1(C)C3] 522.2
267. 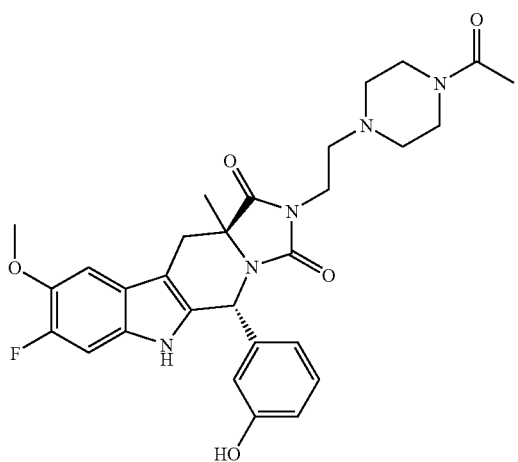 [SMILES: COc1cc2c3c([nH]c2cc1F)[C@@H](c1cccc(O)c1)N1C(=O)N(CCN2CCN(C(C)=O)CC2)C(=O)[C@]1(C)C3] 550.2
268. 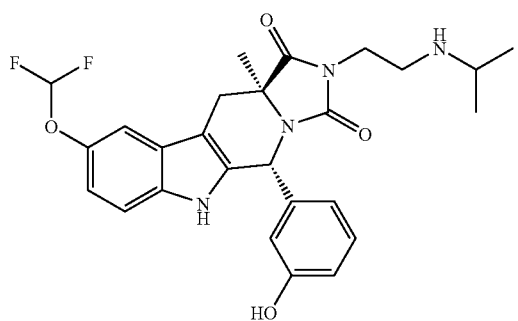 499.2
269. 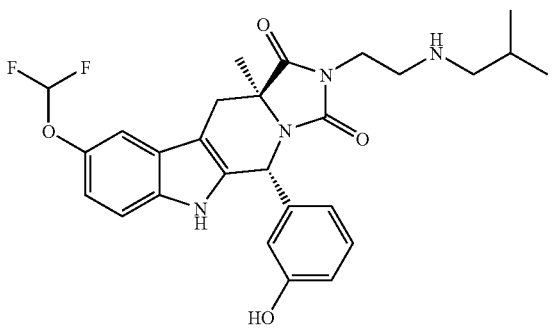 [SMILES: CC(C)CNCCN1C(=O)N2[C@H](c3cccc(O)c3)c3[nH]c4ccc(OC(F)F)cc4c3C[C@@]2(C)C1=O] 513.1

| | | |
|---|---|---|
| 270. | 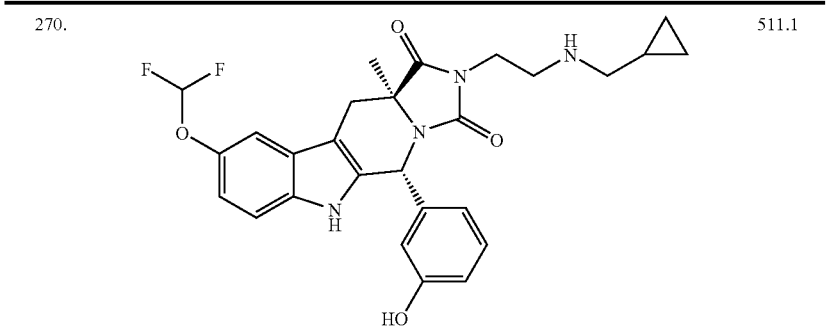 | 511.1 |
| 271. | 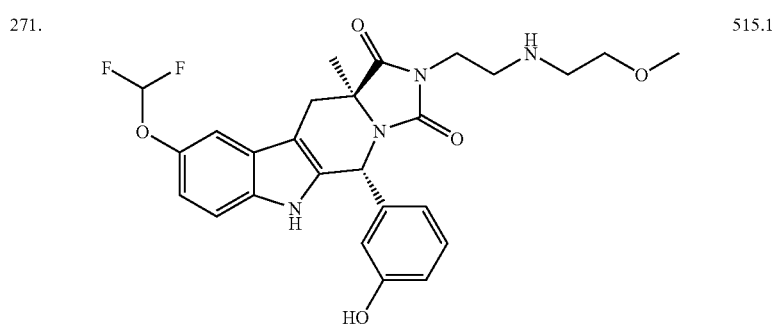 | 515.1 |
| 272. | 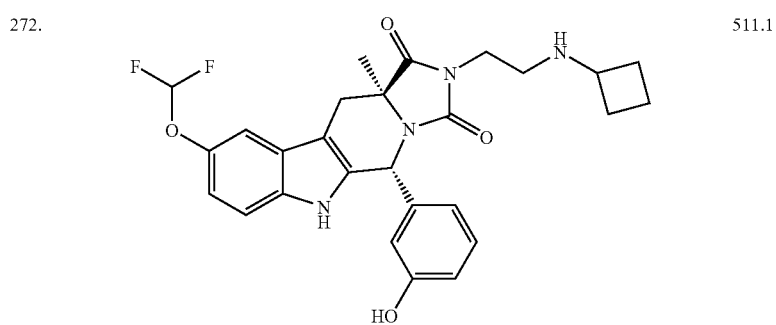 | 511.1 |
| 273. | 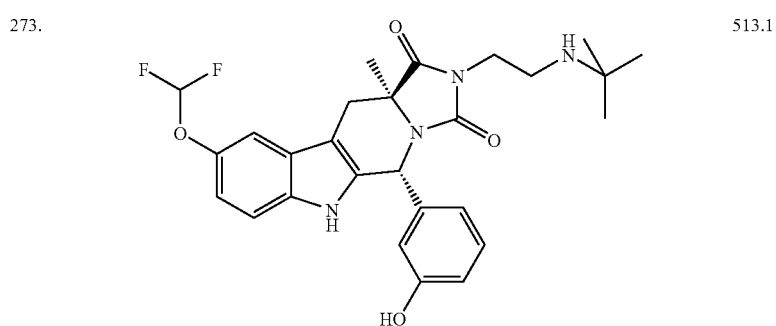 | 513.1 |
| 274. | 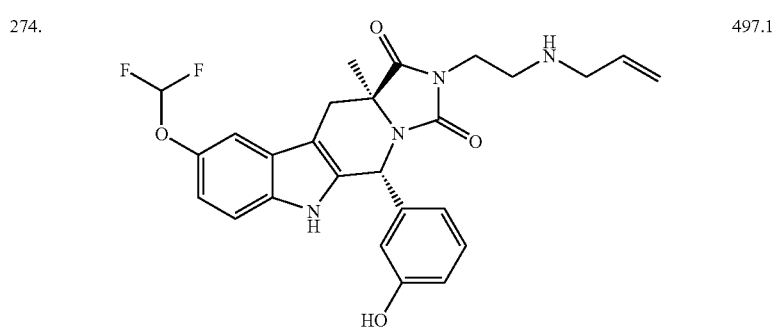 | 497.1 |

275. 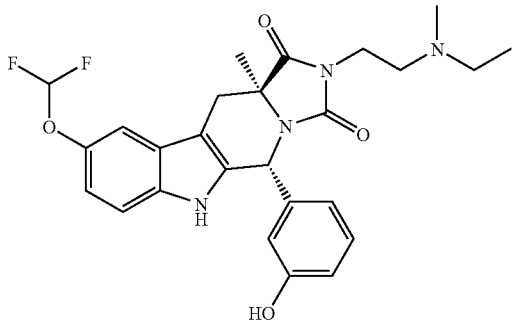 [SMILES: CCN(C)CCN1C(=O)N2[C@H](c3cccc(O)c3)c3[nH]c4ccc(OC(F)F)cc4c3C[C@@]2(C)C1=O] 499.2
276. 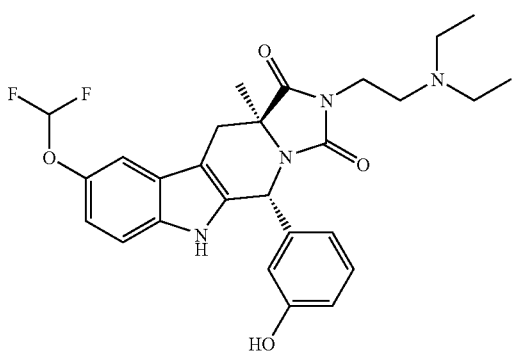 [SMILES: CCN(CC)CCN1C(=O)N2[C@H](c3cccc(O)c3)c3[nH]c4ccc(OC(F)F)cc4c3C[C@@]2(C)C1=O] 513.1
277. 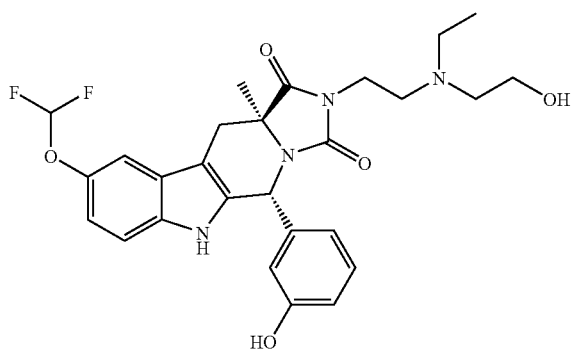 [SMILES: CCN(CCO)CCN1C(=O)N2[C@H](c3cccc(O)c3)c3[nH]c4ccc(OC(F)F)cc4c3C[C@@]2(C)C1=O] 529.2
278. 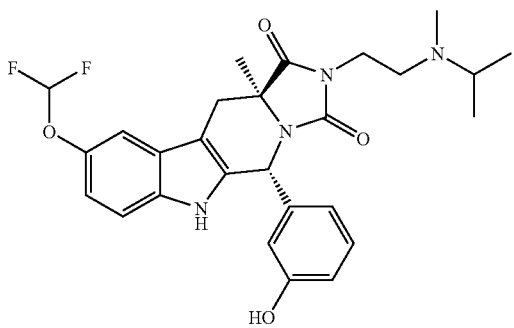 [SMILES: CC(C)N(C)CCN1C(=O)N2[C@H](c3cccc(O)c3)c3[nH]c4ccc(OC(F)F)cc4c3C[C@@]2(C)C1=O] 513.2

| | | |
|---|---|---|
| 279. | 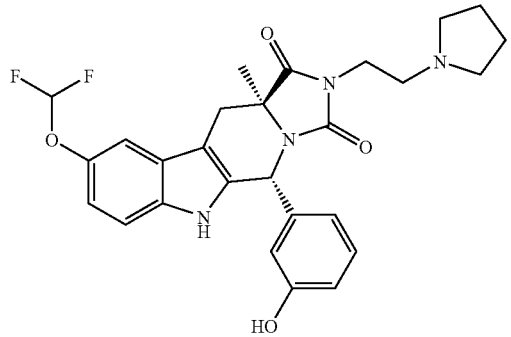 [SMILES: C[C@@]12Cc3c([nH]c4ccc(OC(F)F)cc34)[C@@H](c3cccc(O)c3)N1C(=O)N(CCN1CCCC1)C2=O] | 511.2 |
| 280. | 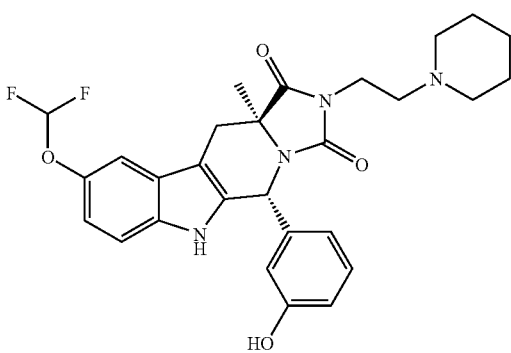 | 525.1 |
| 281. | 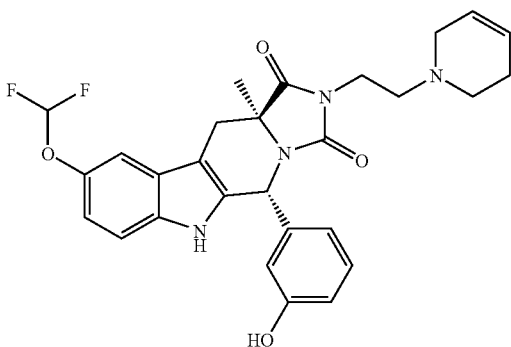 [SMILES: C[C@@]12Cc3c([nH]c4ccc(OC(F)F)cc34)[C@@H](c3cccc(O)c3)N1C(=O)N(CCN1CC=CCC1)C2=O] | 523.1 |
| 282. | 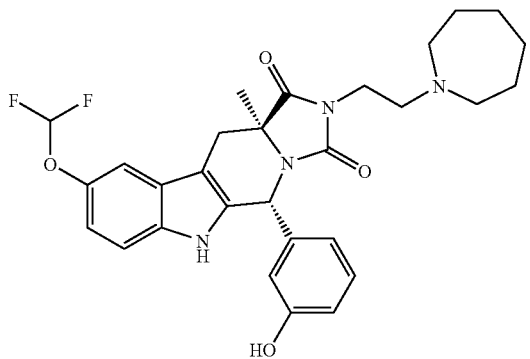 [SMILES: C[C@@]12Cc3c([nH]c4ccc(OC(F)F)cc34)[C@@H](c3cccc(O)c3)N1C(=O)N(CCN1CCCCCC1)C2=O] | 539.2 |

| | | |
|---|---|---|
| 283. | 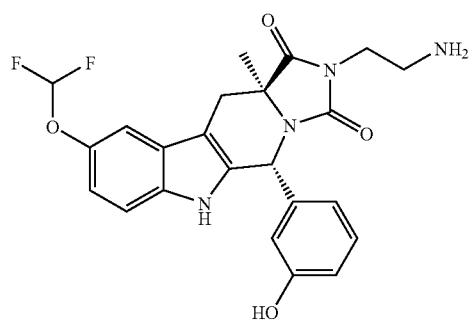 [SMILES: C[C@@]12Cc3c([nH]c4ccc(OC(F)F)cc34)[C@@H](c3cccc(O)c3)N1C(=O)N(CCN)C2=O] | 457.1 |
| 284. | 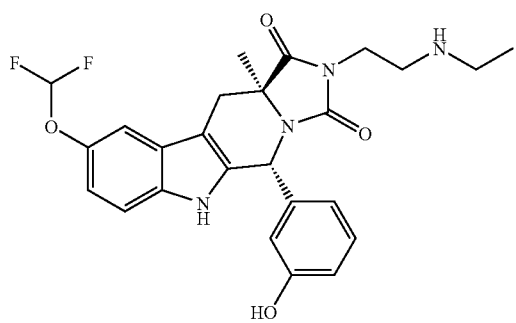 [SMILES: CCNCCN1C(=O)N2[C@H](c3cccc(O)c3)c3[nH]c4ccc(OC(F)F)cc4c3C[C@@]2(C)C1=O] | 485.1 |
| 285. | 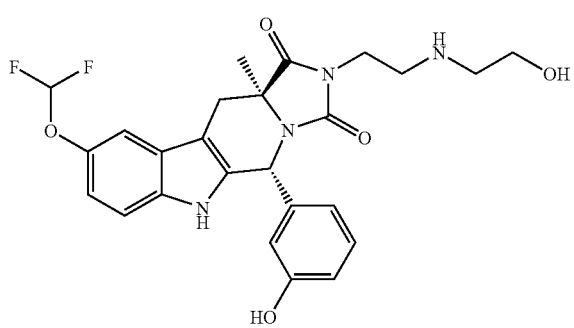 | 501.1 |
| 286. | 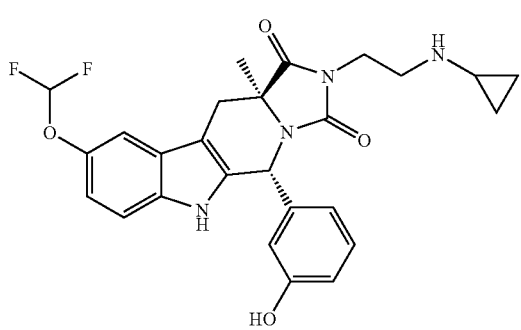 [SMILES: C[C@@]12Cc3c([nH]c4ccc(OC(F)F)cc34)[C@@H](c3cccc(O)c3)N1C(=O)N(CCNC1CC1)C2=O] | 497.2 |
| 287. | 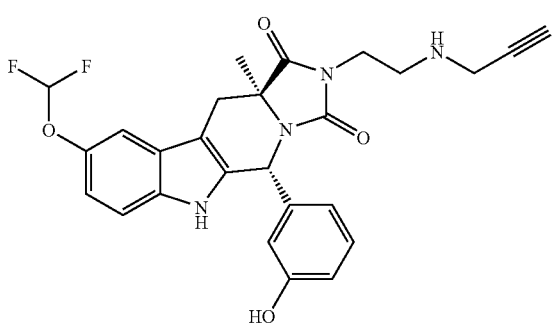 [SMILES: C#CCNCCN1C(=O)N2[C@H](c3cccc(O)c3)c3[nH]c4ccc(OC(F)F)cc4c3C[C@@]2(C)C1=O] | 495.1 |

| | | |
|---|---|---|
| 288. | 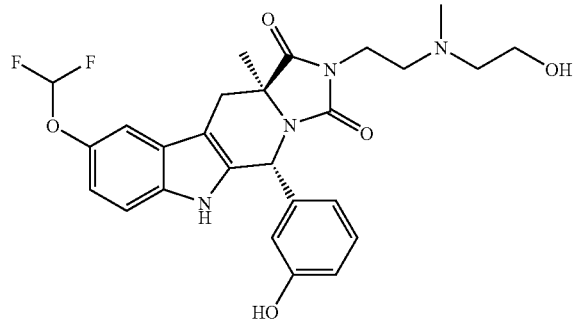 | 515.2 |
| 289. | 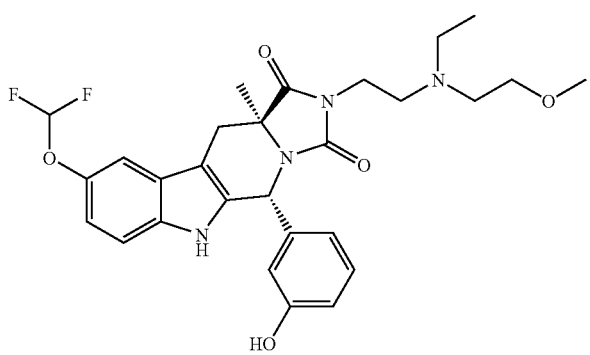 [SMILES: CCN(CCOC)CCN1C(=O)N2[C@H](c3cccc(O)c3)c3[nH]c4ccc(OC(F)F)cc4c3C[C@@]2(C)C1=O] | 543.2 |
| 290. | 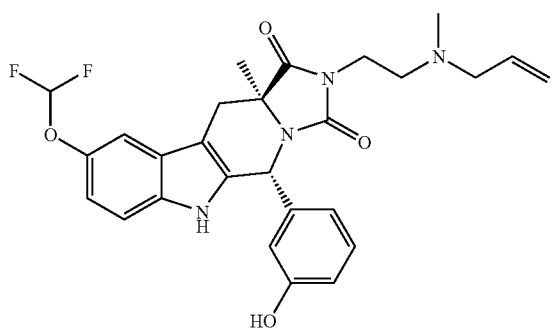 [SMILES: C=CCN(C)CCN1C(=O)N2[C@H](c3cccc(O)c3)c3[nH]c4ccc(OC(F)F)cc4c3C[C@@]2(C)C1=O] | 511.1 |
| 291. | 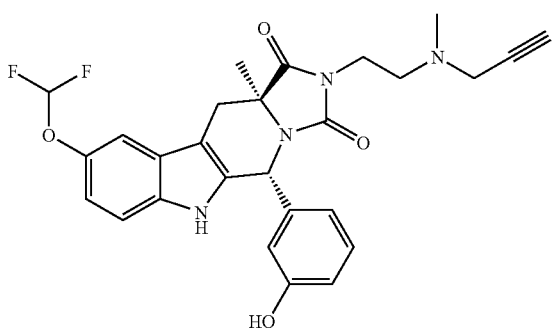 [SMILES: C#CCN(C)CCN1C(=O)N2[C@H](c3cccc(O)c3)c3[nH]c4ccc(OC(F)F)cc4c3C[C@@]2(C)C1=O] | 509.1 |

| | | |
|---|---|---|
| 292. | 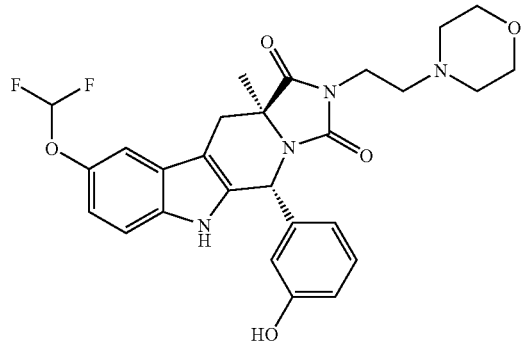 [SMILES: C[C@@]12Cc3c([nH]c4ccc(OC(F)F)cc34)[C@@H](c3cccc(O)c3)N1C(=O)N(CCN1CCOCC1)C2=O] | 527.1 |
| 293. | 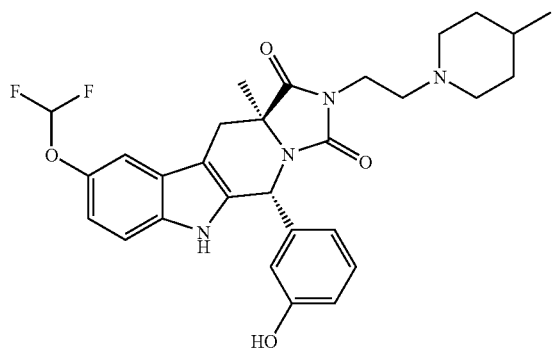 | 539.2 |
| 294. | 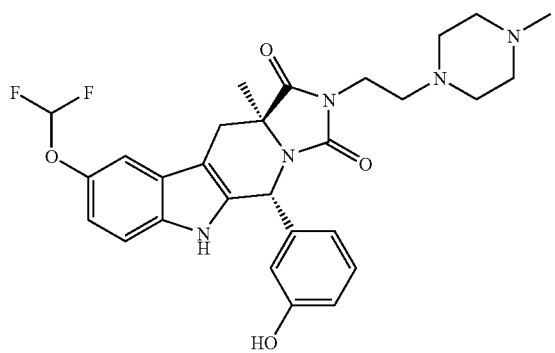 [SMILES: CN1CCN(CCN2C(=O)N3[C@H](c4cccc(O)c4)c4[nH]c5ccc(OC(F)F)cc5c4C[C@@]3(C)C2=O)CC1] | 540.2 |
| 295. | 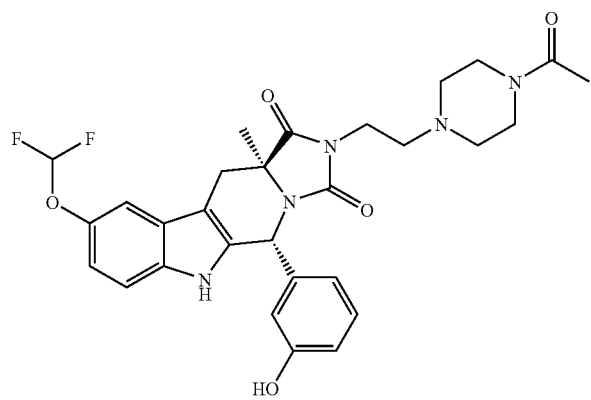 [SMILES: CC(=O)N1CCN(CCN2C(=O)N3[C@H](c4cccc(O)c4)c4[nH]c5ccc(OC(F)F)cc5c4C[C@@]3(C)C2=O)CC1] | 568.2 |

296. 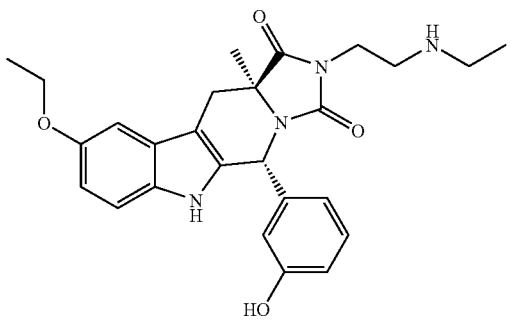 [SMILES: CCNCCN1C(=O)N2[C@H](c3cccc(O)c3)c3[nH]c4ccc(OCC)cc4c3C[C@@]2(C)C1=O] 463.1
297. 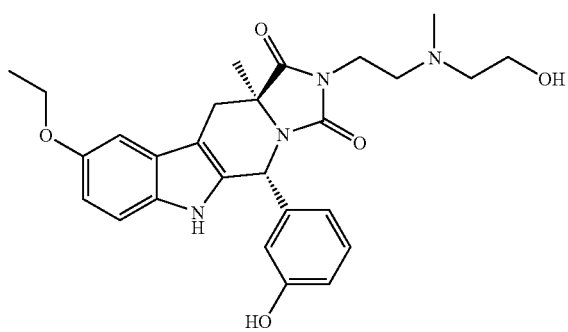 [SMILES: CCOc1ccc2[nH]c3c(c2c1)C[C@@]1(C)C(=O)N(CCN(C)CCO)C(=O)N1[C@@H]3c1cccc(O)c1] 493.2
298. 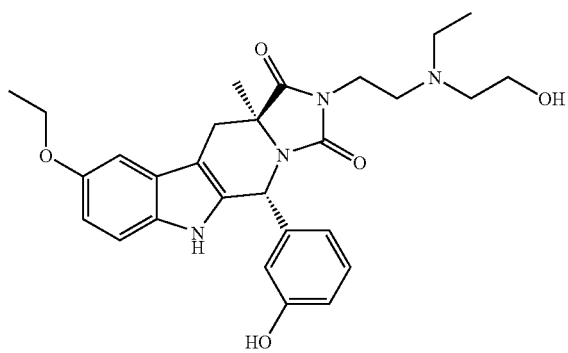 [SMILES: CCOc1ccc2[nH]c3c(c2c1)C[C@@]1(C)C(=O)N(CCN(CC)CCO)C(=O)N1[C@@H]3c1cccc(O)c1] 507.1
299. 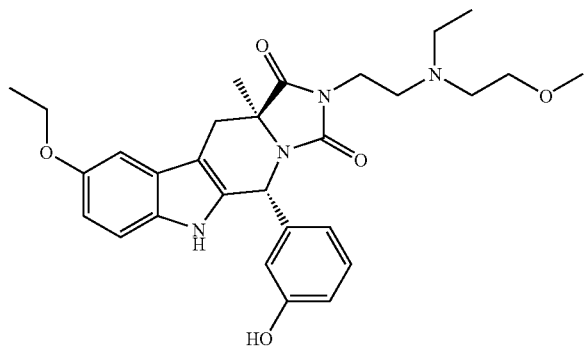 [SMILES: CCOc1ccc2[nH]c3c(c2c1)C[C@@]1(C)C(=O)N(CCN(CC)CCOC)C(=O)N1[C@@H]3c1cccc(O)c1] 521.1

-continued
| 300. | 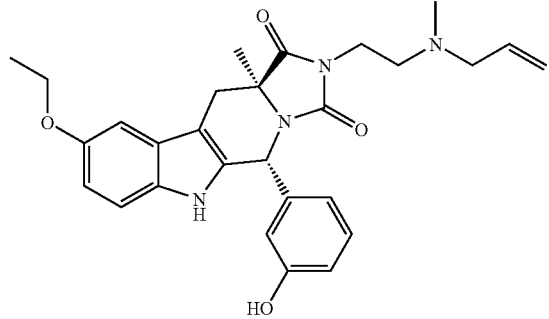 [SMILES: C=CCN(C)CCN1C(=O)N2[C@H](c3cccc(O)c3)c3[nH]c4ccc(OCC)cc4c3C[C@@]2(C)C1=O] | 489.2 |
| 301. | 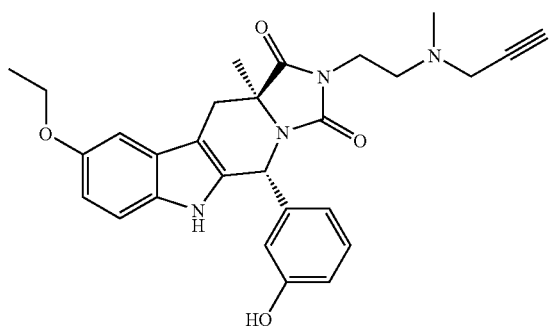 [SMILES: C#CCN(C)CCN1C(=O)N2[C@H](c3cccc(O)c3)c3[nH]c4ccc(OCC)cc4c3C[C@@]2(C)C1=O] | 487.2 |
| 302. | 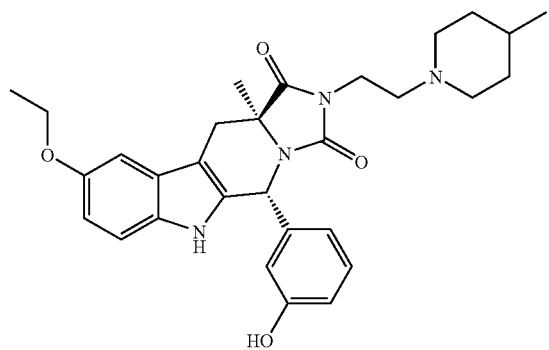 [SMILES: CCOc1ccc2[nH]c3c(c2c1)C[C@@]1(C)C(=O)N(CCN2CCC(C)CC2)C(=O)N1[C@@H]3c1cccc(O)c1] | 517.2 |
| 303. | 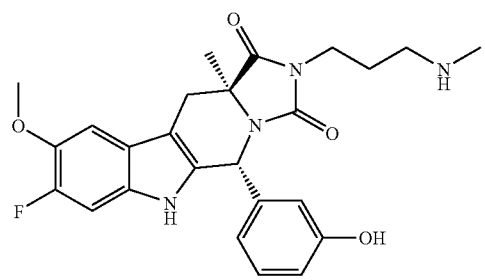 [SMILES: CNCCCN1C(=O)N2[C@H](c3cccc(O)c3)c3[nH]c4cc(F)c(OC)cc4c3C[C@@]2(C)C1=O] | 467.1 |
| 304. | 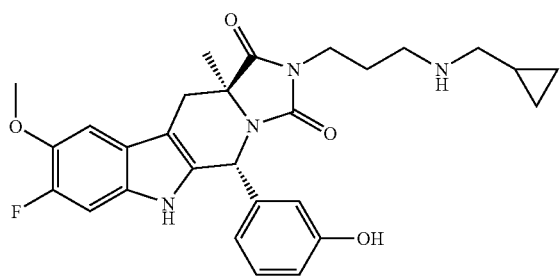 [SMILES: COc1cc2c3c([nH]c2cc1F)[C@@H](c1cccc(O)c1)N1C(=O)N(CCCNCC2CC2)C(=O)[C@]1(C)C3] | 507.1 |

| | | |
|---|---|---|
| 305. | 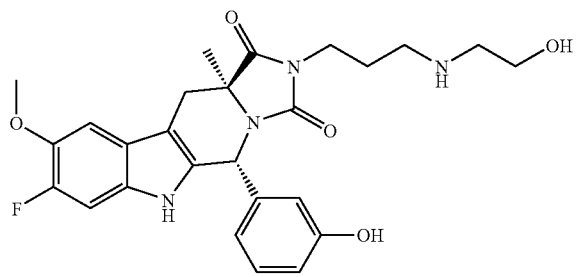 [SMILES: COc1cc2c3c([nH]c2cc1F)[C@@H](c1cccc(O)c1)N1C(=O)N(CCCNCCO)C(=O)[C@]1(C)C3] | 497.0 |
| 306. | 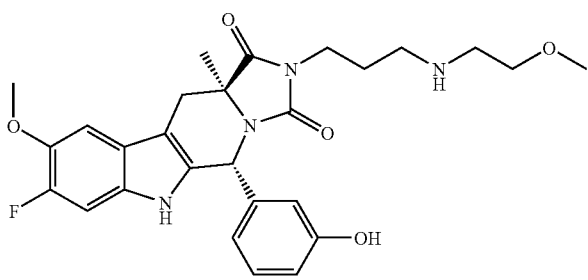 [SMILES: COCCNCCCN1C(=O)N2[C@H](c3cccc(O)c3)c3[nH]c4cc(F)c(OC)cc4c3C[C@@]2(C)C1=O] | 511.1 |
| 307. | 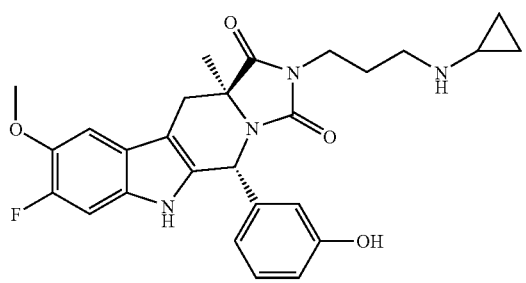 [SMILES: COc1cc2c3c([nH]c2cc1F)[C@@H](c1cccc(O)c1)N1C(=O)N(CCCNC2CC2)C(=O)[C@]1(C)C3] | 493.1 |
| 308. | 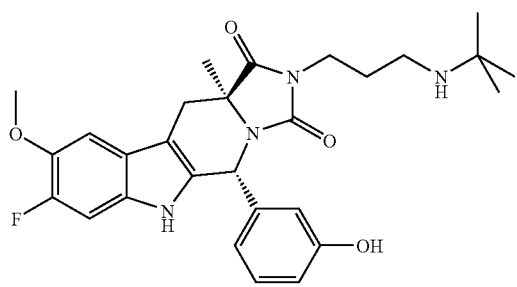 [SMILES: COc1cc2c3c([nH]c2cc1F)[C@@H](c1cccc(O)c1)N1C(=O)N(CCCNC(C)(C)C)C(=O)[C@]1(C)C3] | 509.1 |
| 309. | 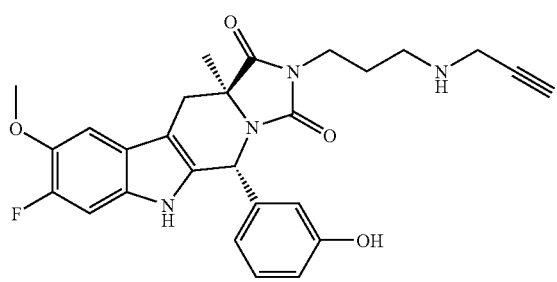 [SMILES: C#CCNCCCN1C(=O)N2[C@H](c3cccc(O)c3)c3[nH]c4cc(F)c(OC)cc4c3C[C@@]2(C)C1=O] | 491.1 |

| | | |
|---|---|---|
| 310. | 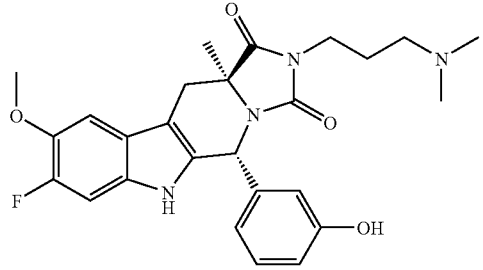 [SMILES: COc1cc2c3c([nH]c2cc1F)[C@@H](c1cccc(O)c1)N1C(=O)N(CCCN(C)C)C(=O)[C@]1(C)C3] | 481.1 |
| 311. | 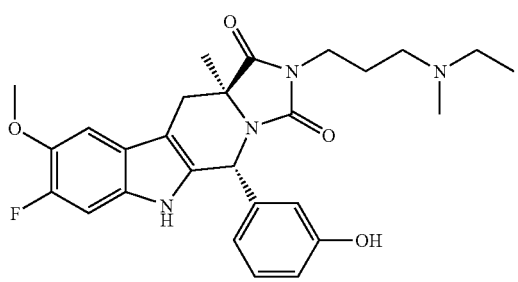 [SMILES: CCN(C)CCCN1C(=O)N2[C@H](c3cccc(O)c3)c3[nH]c4cc(F)c(OC)cc4c3C[C@@]2(C)C1=O] | 495.2 |
| 312. | 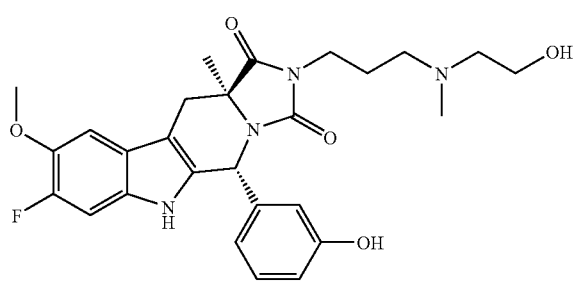 [SMILES: COc1cc2c3c([nH]c2cc1F)[C@@H](c1cccc(O)c1)N1C(=O)N(CCCN(C)CCO)C(=O)[C@]1(C)C3] | 511.1 |
| 313. | 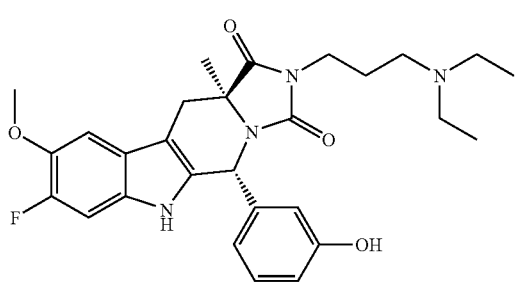 [SMILES: CCN(CC)CCCN1C(=O)N2[C@H](c3cccc(O)c3)c3[nH]c4cc(F)c(OC)cc4c3C[C@@]2(C)C1=O] | 509.1 |
| 314. | 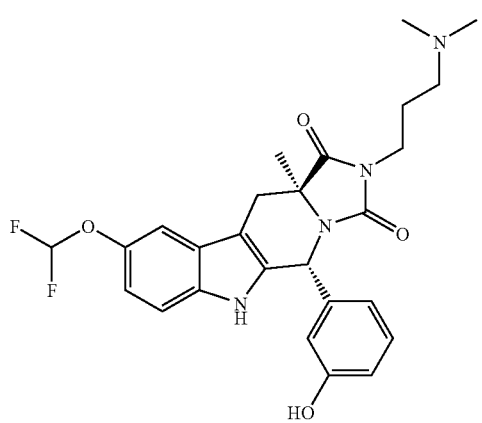 [SMILES: CN(C)CCCN1C(=O)N2[C@H](c3cccc(O)c3)c3[nH]c4ccc(OC(F)F)cc4c3C[C@@]2(C)C1=O] | 499.2 |

| 315. | 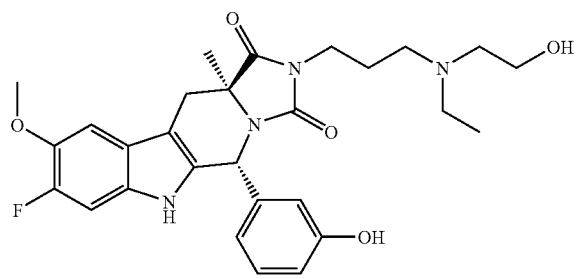 [SMILES: CCN(CCO)CCCN1C(=O)N2[C@H](c3cccc(O)c3)c3[nH]c4cc(F)c(OC)cc4c3C[C@@]2(C)C1=O] | 525.2 |
| 316. | 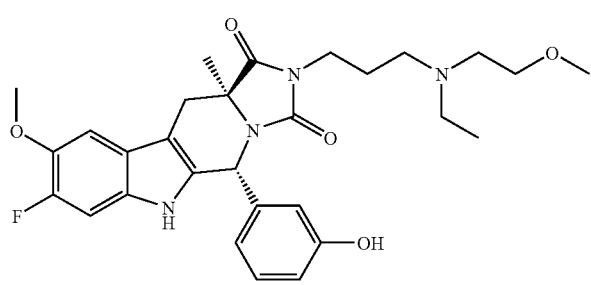 [SMILES: CCN(CCCN1C(=O)N2[C@H](c3cccc(O)c3)c3[nH]c4cc(F)c(OC)cc4c3C[C@@]2(C)C1=O)CCOC] | 539.1 |
| 317. | 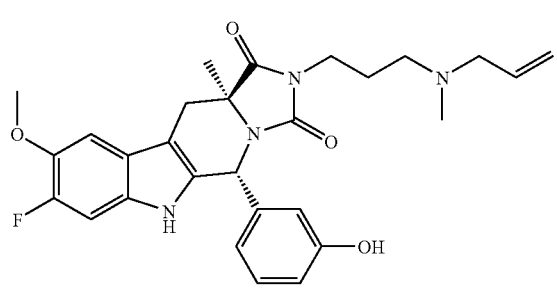 | 507.2 |
| 318. | 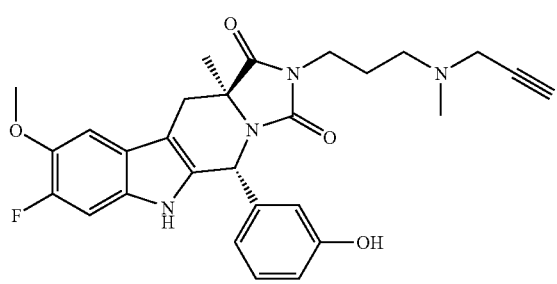 [SMILES: C#CCN(C)CCCN1C(=O)N2[C@H](c3cccc(O)c3)c3[nH]c4cc(F)c(OC)cc4c3C[C@@]2(C)C1=O] | 505.1 |
| 319. | 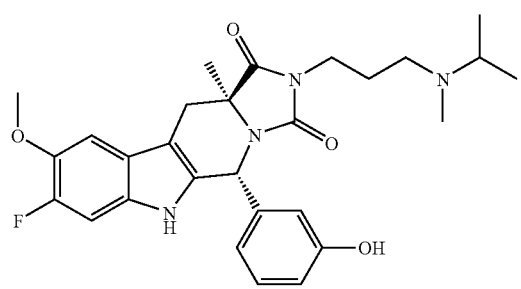 [SMILES: COc1cc2c3c([nH]c2cc1F)[C@@H](c1cccc(O)c1)N1C(=O)N(CCCN(C)C(C)C)C(=O)[C@]1(C)C3] | 509.2 |

| | | |
|---|---|---|
| 320. | 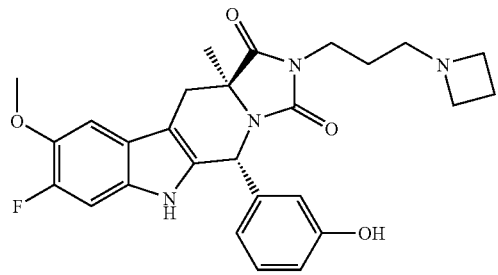 [SMILES: COc1cc2c3c([nH]c2cc1F)[C@@H](c1cccc(O)c1)N1C(=O)N(CCCN2CCC2)C(=O)[C@]1(C)C3] | 493.2 |
| 321. | 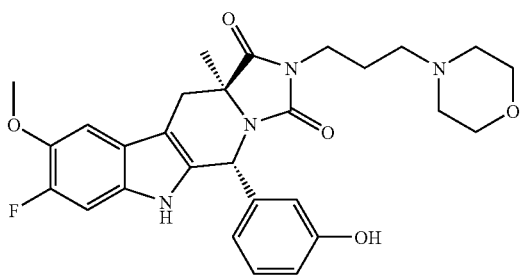 [SMILES: COc1cc2c3c([nH]c2cc1F)[C@@H](c1cccc(O)c1)N1C(=O)N(CCCN2CCOCC2)C(=O)[C@]1(C)C3] | 523.1 |
| 322. | 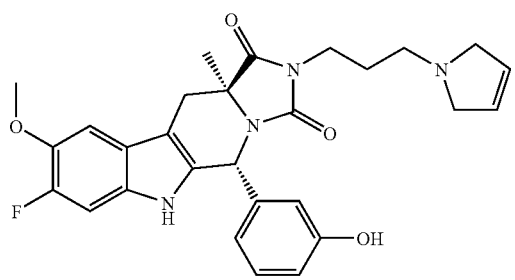 [SMILES: COc1cc2c3c([nH]c2cc1F)[C@@H](c1cccc(O)c1)N1C(=O)N(CCCN2CC=CC2)C(=O)[C@]1(C)C3] | 507.2 |
| 323. | 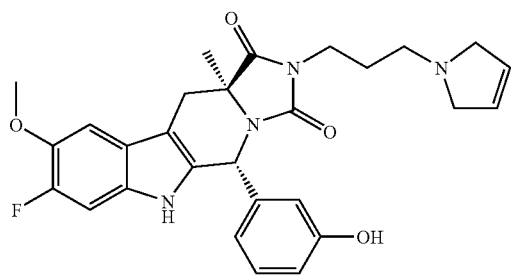 [SMILES: COc1cc2c3c([nH]c2cc1F)[C@@H](c1cccc(O)c1)N1C(=O)N(CCCN2CC=CC2)C(=O)[C@]1(C)C3] | 505.2 |
| 324. | 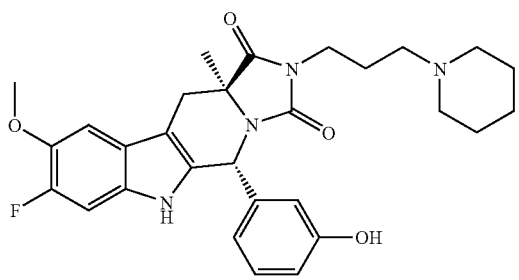 [SMILES: COc1cc2c3c([nH]c2cc1F)[C@@H](c1cccc(O)c1)N1C(=O)N(CCCN2CCCCC2)C(=O)[C@]1(C)C3] | 521.2 |

-continued
| | | |
|---|---|---|
| 325. | 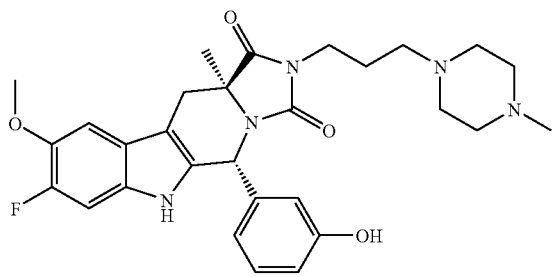 [SMILES: COc1cc2c3c([nH]c2cc1F)[C@@H](c1cccc(O)c1)N1C(=O)N(CCCN2CCN(C)CC2)C(=O)[C@]1(C)C3] | 536.2 |
| 326. | 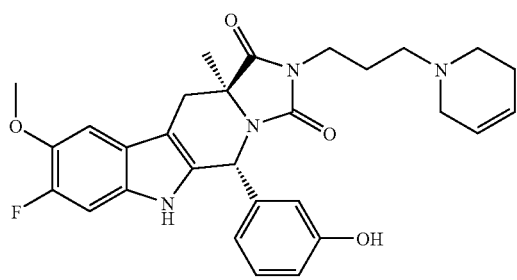 [SMILES: COc1cc2c3c([nH]c2cc1F)[C@@H](c1cccc(O)c1)N1C(=O)N(CCCN2CC=CCC2)C(=O)[C@]1(C)C3] | 519.1 |
| 327. | 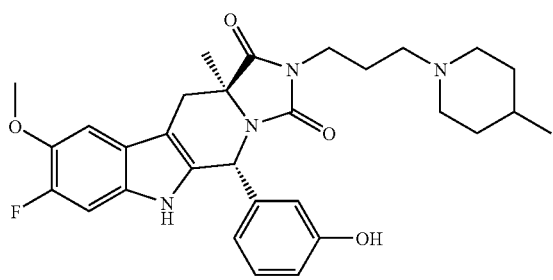 [SMILES: COc1cc2c3c([nH]c2cc1F)[C@@H](c1cccc(O)c1)N1C(=O)N(CCCN2CCC(C)CC2)C(=O)[C@]1(C)C3] | 535.2 |
| 328. | 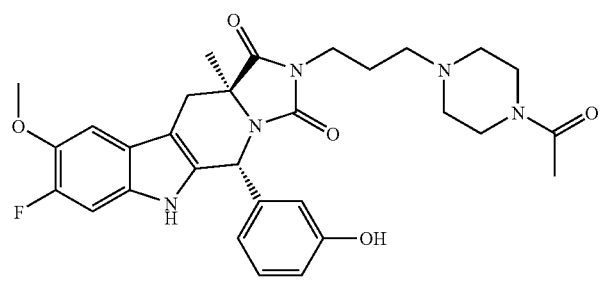 [SMILES: COc1cc2c3c([nH]c2cc1F)[C@@H](c1cccc(O)c1)N1C(=O)N(CCCN2CCN(C(C)=O)CC2)C(=O)[C@]1(C)C3] | 564.2 |
| 329. | 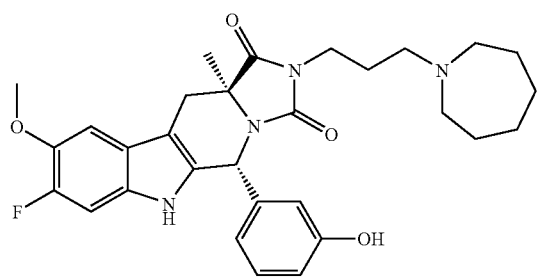 [SMILES: COc1cc2c3c([nH]c2cc1F)[C@@H](c1cccc(O)c1)N1C(=O)N(CCCN2CCCCCC2)C(=O)[C@]1(C)C3] | 535.2 |

| | | |
|---|---|---|
| 330. | 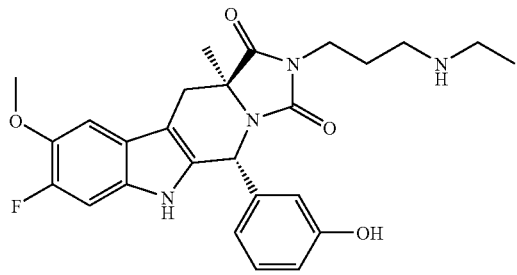 [SMILES: CCNCCCN1C(=O)N2[C@H](c3cccc(O)c3)c3[nH]c4cc(F)c(OC)cc4c3C[C@@]2(C)C1=O] | 481.1 |
| 331. | 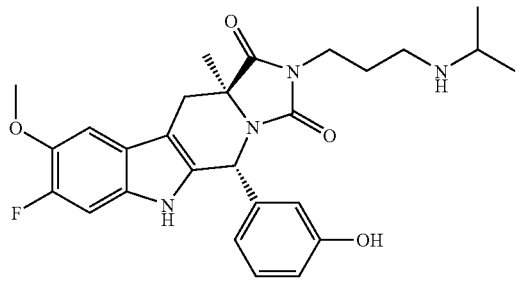 | 495.2 |
| 332. | 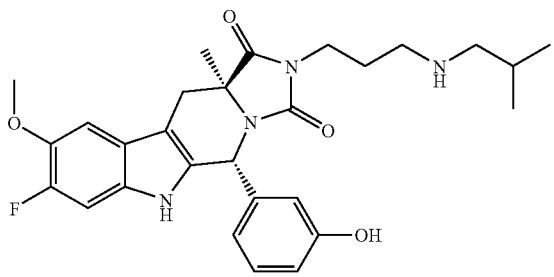 [SMILES: COc1cc2c3c([nH]c2cc1F)[C@@H](c1cccc(O)c1)N1C(=O)N(CCCNCC(C)C)C(=O)[C@]1(C)C3] | 509.1 |
| 333. | 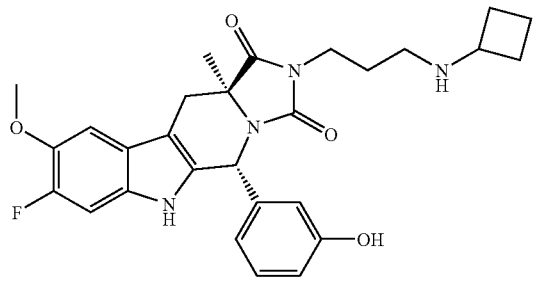 [SMILES: COc1cc2c3c([nH]c2cc1F)[C@@H](c1cccc(O)c1)N1C(=O)N(CCCNC2CCC2)C(=O)[C@]1(C)C3] | 507.1 |
| 334. | 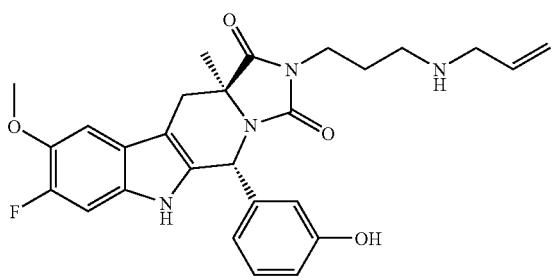 [SMILES: C=CCNCCCN1C(=O)N2[C@H](c3cccc(O)c3)c3[nH]c4cc(F)c(OC)cc4c3C[C@@]2(C)C1=O] | 493.1 |

| | | |
|---|---|---|
| 335. | 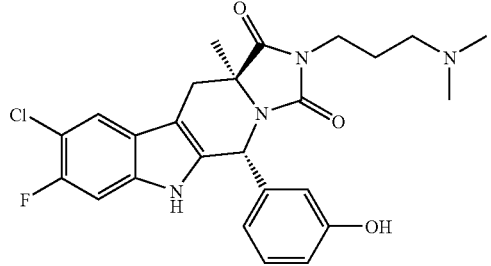 [SMILES: CN(C)CCCN1C(=O)N2[C@H](c3cccc(O)c3)c3[nH]c4cc(F)c(Cl)cc4c3C[C@@]2(C)C1=O] | 485.1 |
| 336. | 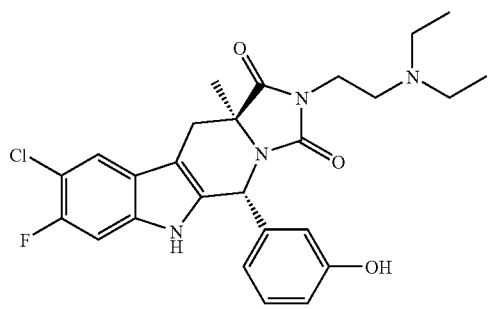 [SMILES: CCN(CC)CCN1C(=O)N2[C@H](c3cccc(O)c3)c3[nH]c4cc(F)c(Cl)cc4c3C[C@@]2(C)C1=O] | 499.1 |
| 337. | 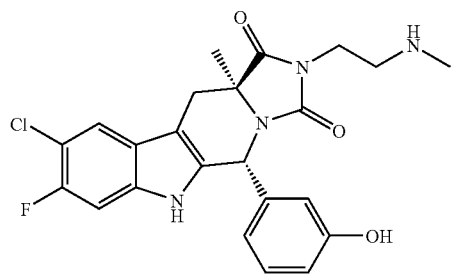 [SMILES: CNCCN1C(=O)N2[C@H](c3cccc(O)c3)c3[nH]c4cc(F)c(Cl)cc4c3C[C@@]2(C)C1=O] | 457.1 |
| 338. | 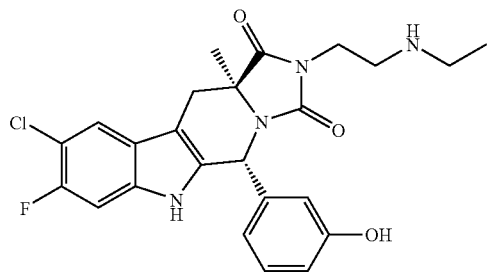 [SMILES: CCNCCN1C(=O)N2[C@H](c3cccc(O)c3)c3[nH]c4cc(F)c(Cl)cc4c3C[C@@]2(C)C1=O] | 471.2 |
| 339. | 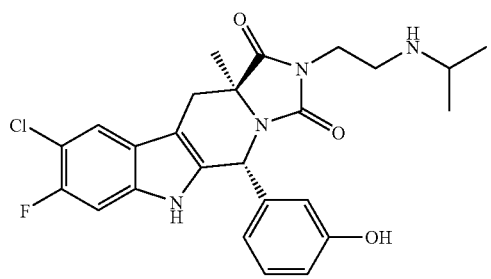 [SMILES: CC(C)NCCN1C(=O)N2[C@H](c3cccc(O)c3)c3[nH]c4cc(F)c(Cl)cc4c3C[C@@]2(C)C1=O] | 485.2 |

-continued
| 340. | 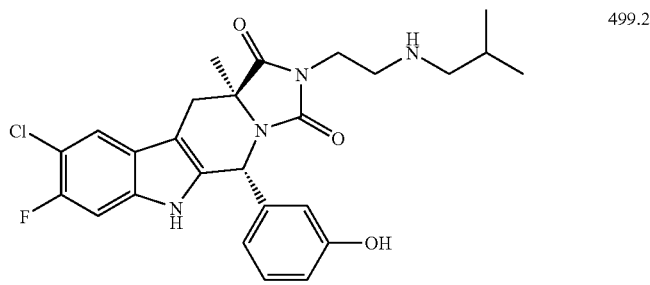 | 499.2 |
| 341. | 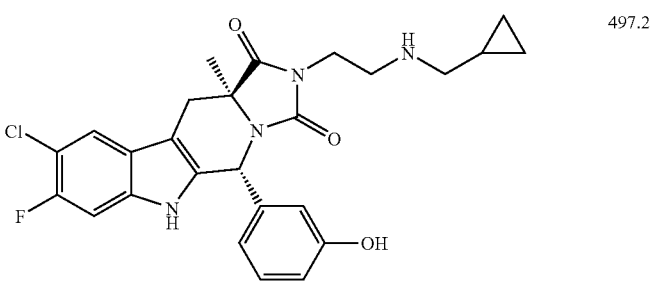 | 497.2 |
| 342. | 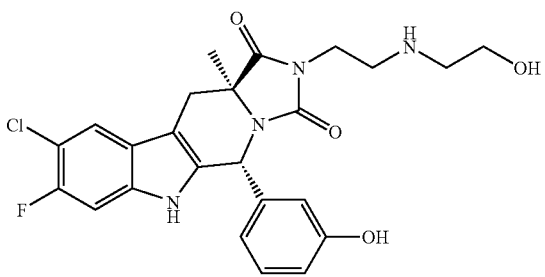 [SMILES: C[C@@]12Cc3c([nH]c4cc(F)c(Cl)cc34)[C@@H](c3cccc(O)c3)N1C(=O)N(CCNCCO)C2=O] | 487.2 |
| 343. | 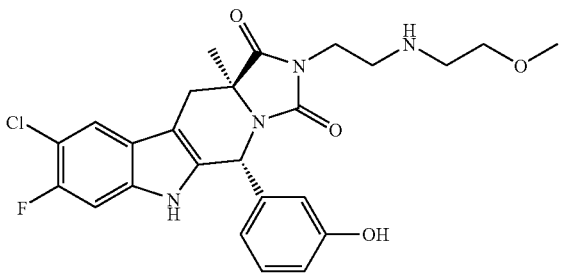 [SMILES: COCCNCCN1C(=O)N2[C@H](c3cccc(O)c3)c3[nH]c4cc(F)c(Cl)cc4c3C[C@@]2(C)C1=O] | 501.2 |
| 344. | 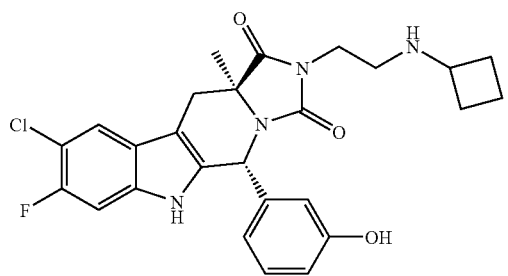 [SMILES: C[C@@]12Cc3c([nH]c4cc(F)c(Cl)cc34)[C@@H](c3cccc(O)c3)N1C(=O)N(CCNC1CCC1)C2=O] | 497.2 |

-continued
| | | |
|---|---|---|
| 345. | 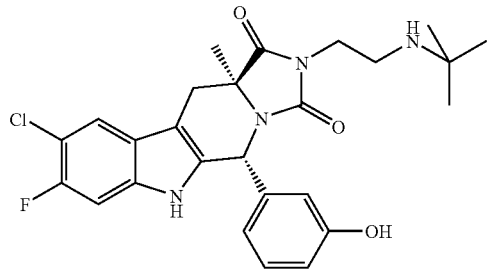 [SMILES: CC(C)(C)NCCN1C(=O)N2[C@H](c3cccc(O)c3)c3[nH]c4cc(F)c(Cl)cc4c3C[C@@]2(C)C1=O] | 499.1 |
| 346. | 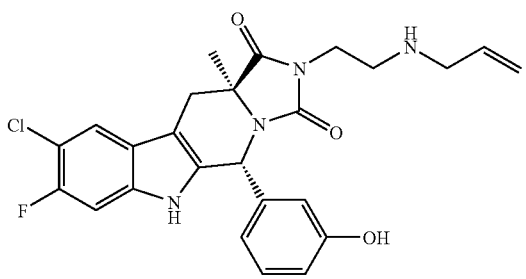 [SMILES: C=CCNCCN1C(=O)N2[C@H](c3cccc(O)c3)c3[nH]c4cc(F)c(Cl)cc4c3C[C@@]2(C)C1=O] | 483.2 |
| 347. | 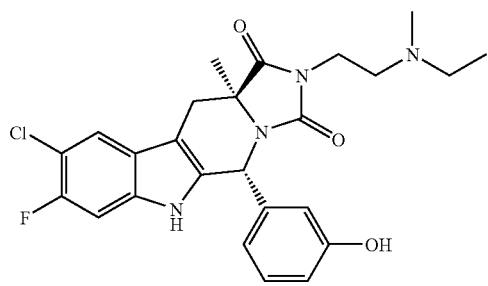 [SMILES: CCN(C)CCN1C(=O)N2[C@H](c3cccc(O)c3)c3[nH]c4cc(F)c(Cl)cc4c3C[C@@]2(C)C1=O] | 485.2 |
| 348. | 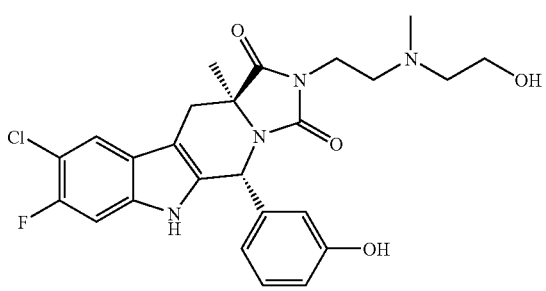 [SMILES: CN(CCO)CCN1C(=O)N2[C@H](c3cccc(O)c3)c3[nH]c4cc(F)c(Cl)cc4c3C[C@@]2(C)C1=O] | 501.2 |
| 349. | 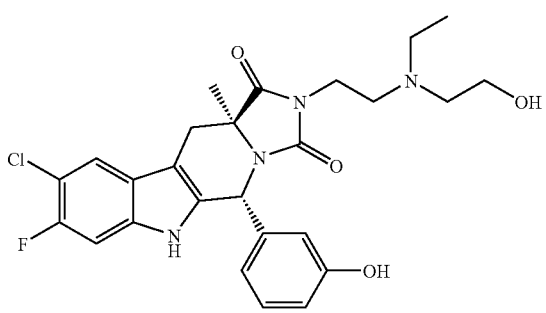 [SMILES: CCN(CCO)CCN1C(=O)N2[C@H](c3cccc(O)c3)c3[nH]c4cc(F)c(Cl)cc4c3C[C@@]2(C)C1=O] | 515.2 |

| | | |
|---|---|---|
| 350. | 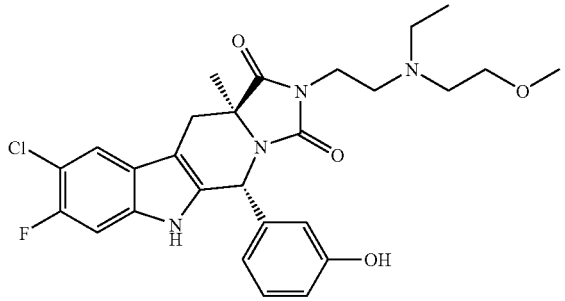 [SMILES: CCN(CCOC)CCN1C(=O)N2[C@H](c3cccc(O)c3)c3[nH]c4cc(F)c(Cl)cc4c3C[C@@]2(C)C1=O] | 529.2 |
| 351. | 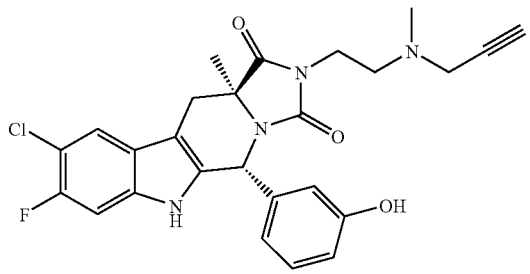 [SMILES: C#CCN(C)CCN1C(=O)N2[C@H](c3cccc(O)c3)c3[nH]c4cc(F)c(Cl)cc4c3C[C@@]2(C)C1=O] | 495.2 |
| 352. | 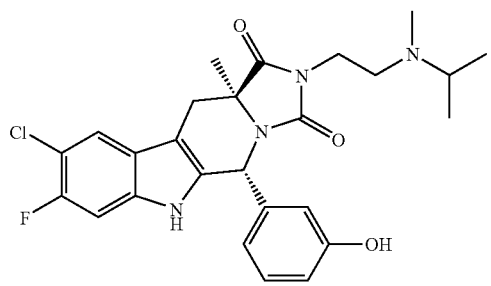 [SMILES: CC(C)N(C)CCN1C(=O)N2[C@H](c3cccc(O)c3)c3[nH]c4cc(F)c(Cl)cc4c3C[C@@]2(C)C1=O] | 499.2 |
| 353. | 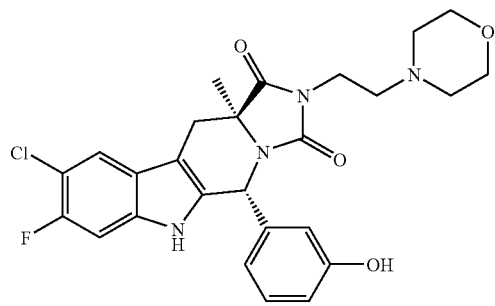 [SMILES: C[C@@]12Cc3c([nH]c4cc(F)c(Cl)cc34)[C@@H](c3cccc(O)c3)N1C(=O)N(CCN1CCOCC1)C2=O] | 513.2 |
| 354. | 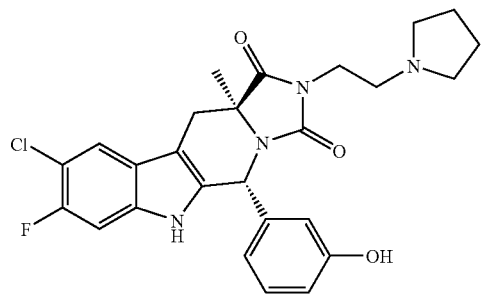 [SMILES: C[C@@]12Cc3c([nH]c4cc(F)c(Cl)cc34)[C@@H](c3cccc(O)c3)N1C(=O)N(CCN1CCCC1)C2=O] | 497.2 |

| | | |
|---|---|---|
| 355. | 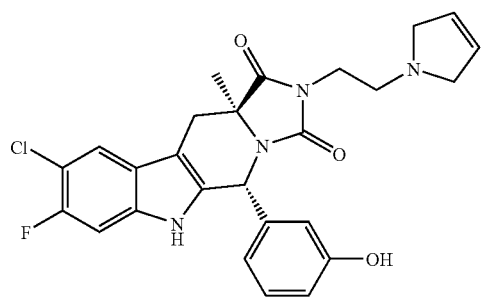 [SMILES: C[C@@]12Cc3c([nH]c4cc(F)c(Cl)cc34)[C@@H](c3cccc(O)c3)N1C(=O)N(CCN1CC=CC1)C2=O] | 495.2 |
| 356. | 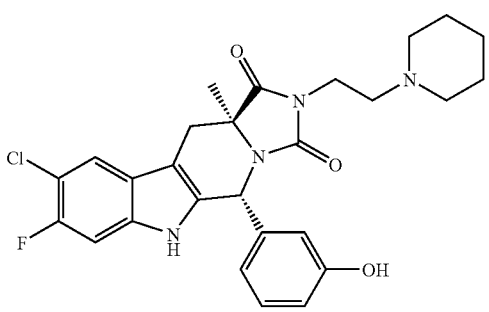 [SMILES: C[C@@]12Cc3c([nH]c4cc(F)c(Cl)cc34)[C@@H](c3cccc(O)c3)N1C(=O)N(CCN1CCCCC1)C2=O] | 511.2 |
| 357. | 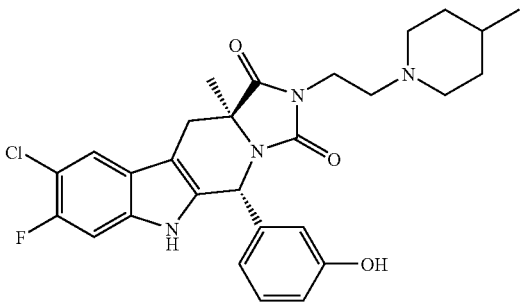 [SMILES: CC1CCN(CCN2C(=O)N3[C@H](c4cccc(O)c4)c4[nH]c5cc(F)c(Cl)cc5c4C[C@@]3(C)C2=O)CC1] | 525.2 |
| 358. | 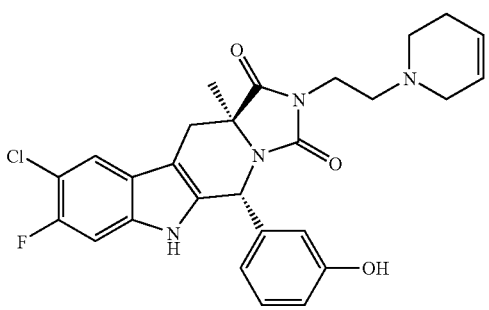 [SMILES: C[C@@]12Cc3c([nH]c4cc(F)c(Cl)cc34)[C@@H](c3cccc(O)c3)N1C(=O)N(CCN1CC=CCC1)C2=O] | 509.2 |
| 359. | 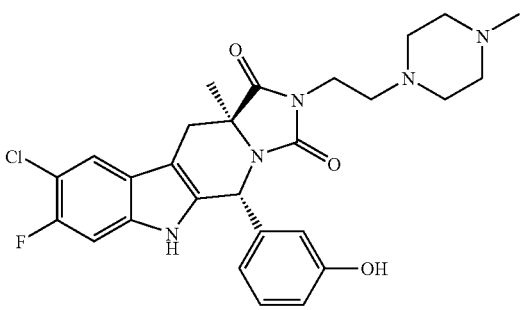 | 526.2 |

360. 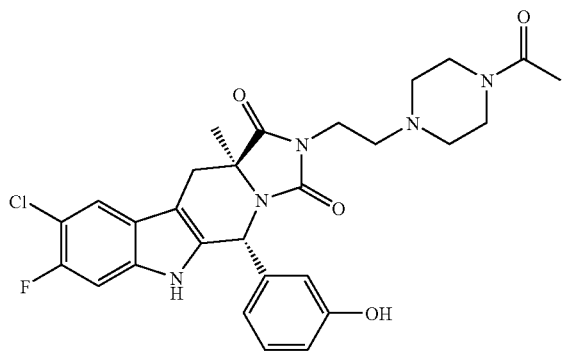 [SMILES: CC(=O)N1CCN(CCN2C(=O)N3[C@H](c4cccc(O)c4)c4[nH]c5cc(F)c(Cl)cc5c4C[C@@]3(C)C2=O)CC1] 554.2
361. 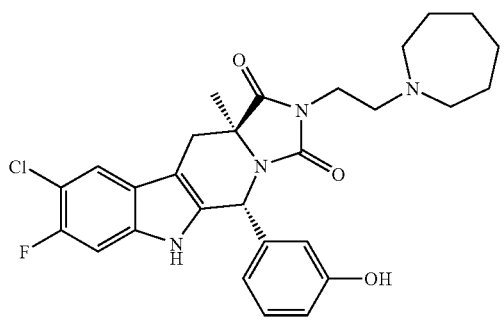 [SMILES: C[C@@]12Cc3c([nH]c4cc(F)c(Cl)cc34)[C@@H](c3cccc(O)c3)N1C(=O)N(CCN1CCCCCC1)C2=O] 525.2
362. 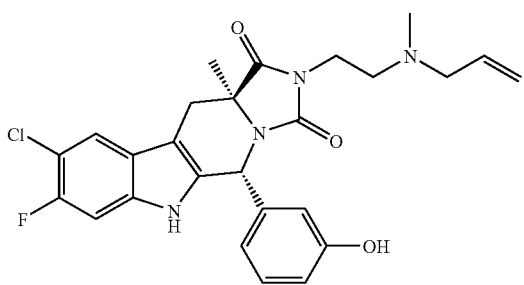 [SMILES: C=CCN(C)CCN1C(=O)N2[C@H](c3cccc(O)c3)c3[nH]c4cc(F)c(Cl)cc4c3C[C@@]2(C)C1=O] 497.2
363. 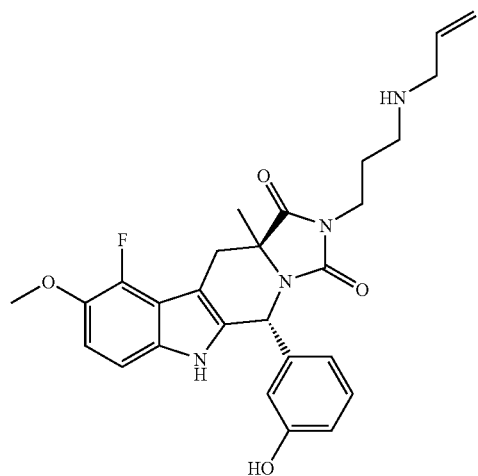 [SMILES: C=CCNCCCN1C(=O)N2[C@H](c3cccc(O)c3)c3[nH]c4ccc(OC)c(F)c4c3C[C@@]2(C)C1=O] 493.2

| | |
|---|---|
| 364. | 495.2 |
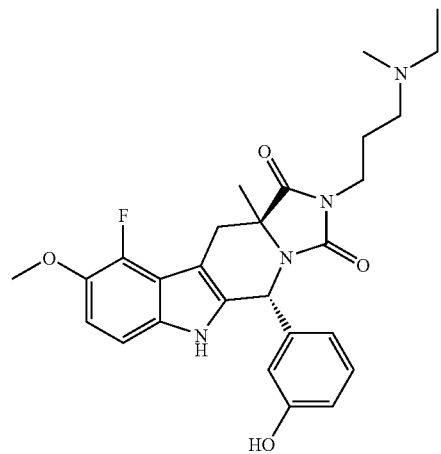 [SMILES: CCN(C)CCCN1C(=O)N2[C@H](c3cccc(O)c3)c3[nH]c4ccc(OC)c(F)c4c3C[C@@]2(C)C1=O]
| | |
|---|---|
| 365. | 539.3 |
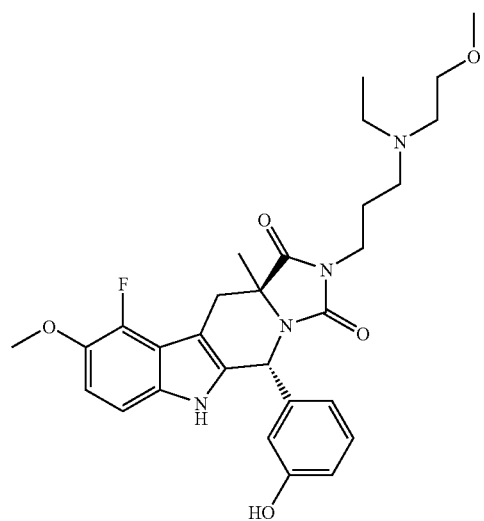
| | |
|---|---|
| 366. | 521.3 |
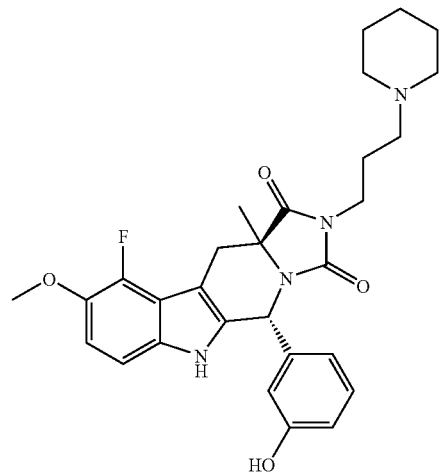 [SMILES: COc1ccc2[nH]c3c(c2c1F)C[C@@]1(C)C(=O)N(CCCN2CCCCC2)C(=O)N1[C@@H]3c1cccc(O)c1]

| 367. | 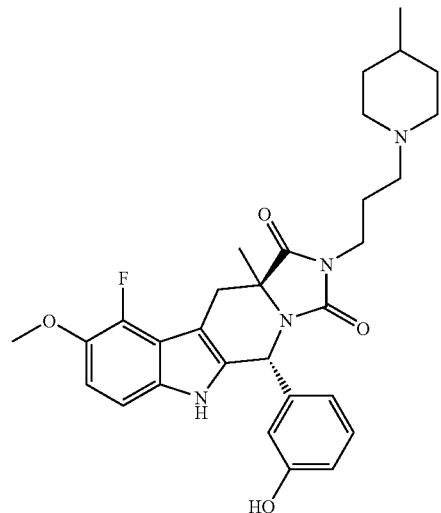 [SMILES: COc1ccc2[nH]c3c(c2c1F)C[C@@]1(C)C(=O)N(CCCN2CCC(C)CC2)C(=O)N1[C@@H]3c1cccc(O)c1] | 535.3 |
| 368. | 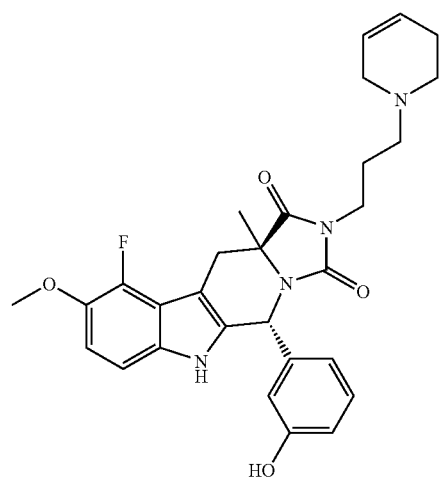 [SMILES: COc1ccc2[nH]c3c(c2c1F)C[C@@]1(C)C(=O)N(CCCN2CC=CCC2)C(=O)N1[C@@H]3c1cccc(O)c1] | 519.2 |
| 369. | 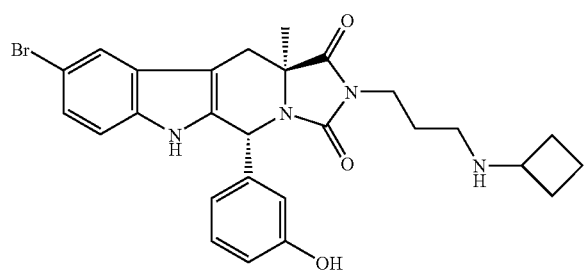 | 537.1<br>539.1 |
| 370. | 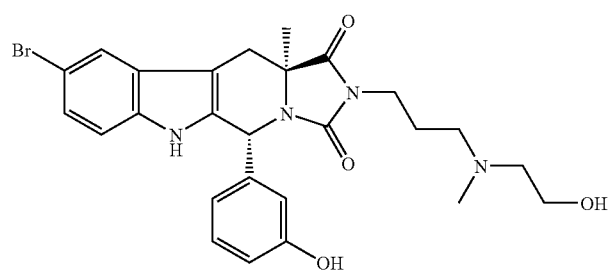 | 541.1<br>543.1 |

-continued
| 371. | 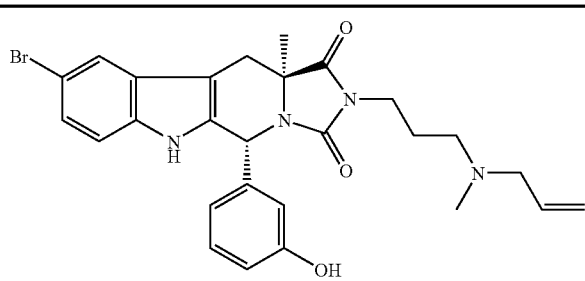 | 537.0 539.1 |
| --- | --- | --- |
| 372. | 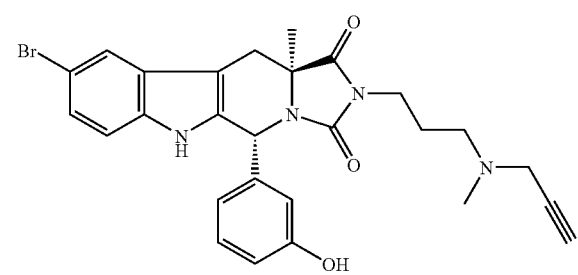 [SMILES: C#CCN(C)CCCN1C(=O)N2[C@H](c3cccc(O)c3)c3[nH]c4ccc(Br)cc4c3C[C@@]2(C)C1=O] | 535.1 537.0 |
| 373. | 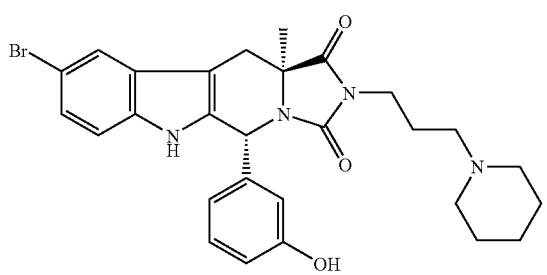 [SMILES: C[C@@]12Cc3c([nH]c4ccc(Br)cc34)[C@@H](c3cccc(O)c3)N1C(=O)N(CCCN1CCCCC1)C2=O] | 551.1 553.2 |
| 374. | 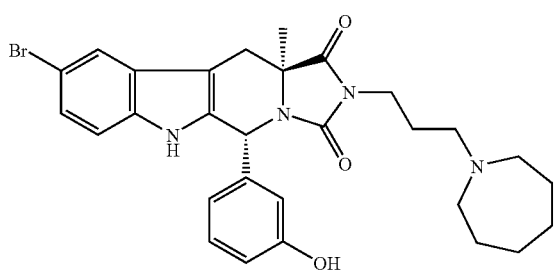 [SMILES: C[C@@]12Cc3c([nH]c4ccc(Br)cc34)[C@@H](c3cccc(O)c3)N1C(=O)N(CCCN1CCCCCC1)C2=O] | 565.2 567.1 |
| 375. | 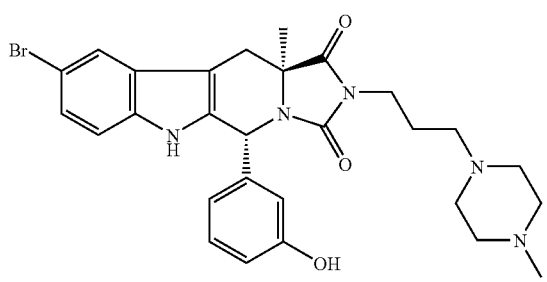 | 566.2 568.1 |
| 376. | 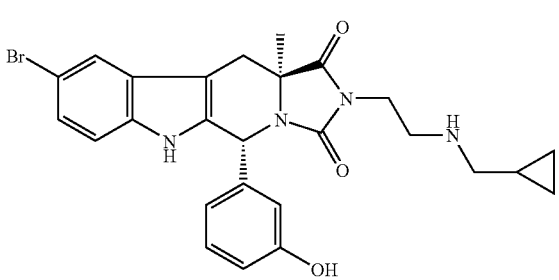 | 523.1 525.1 |

| | | |
|---|---|---|
| 377. | 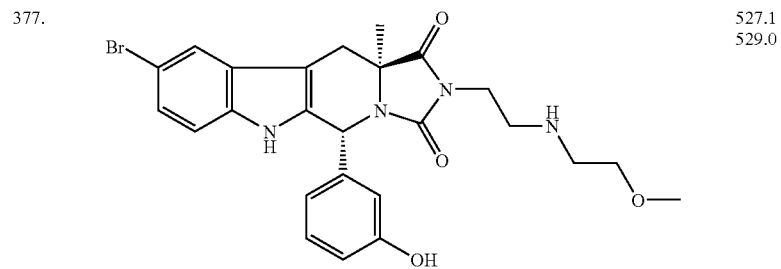 | 527.1<br>529.0 |
| 378. | 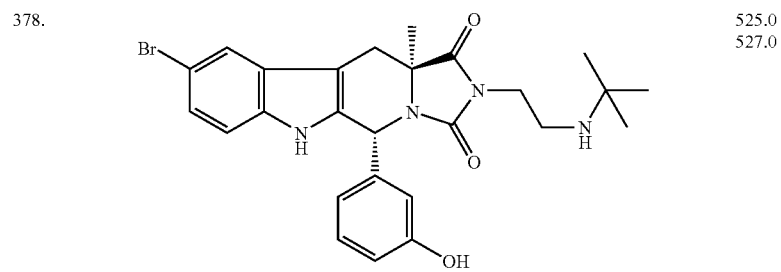 | 525.0<br>527.0 |
| 379. | 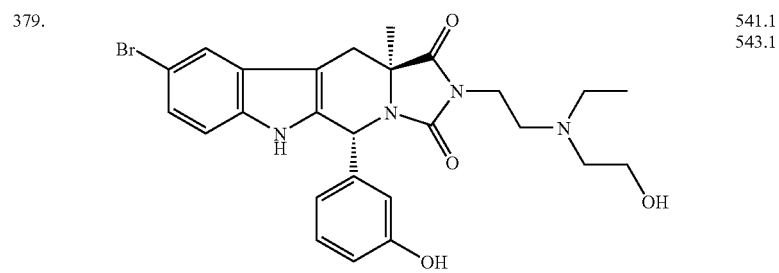 | 541.1<br>543.1 |
| 380. | 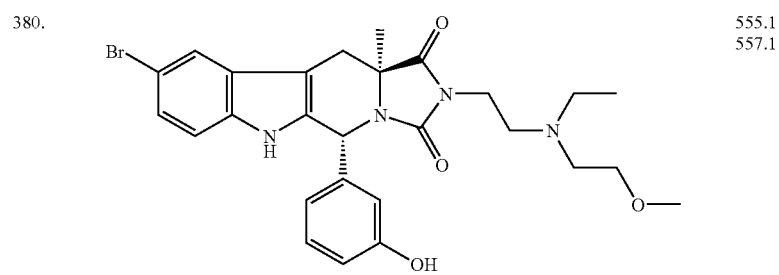 | 555.1<br>557.1 |
| 381. | 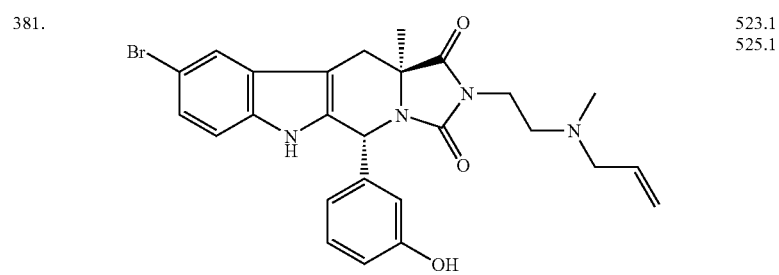 | 523.1<br>525.1 |

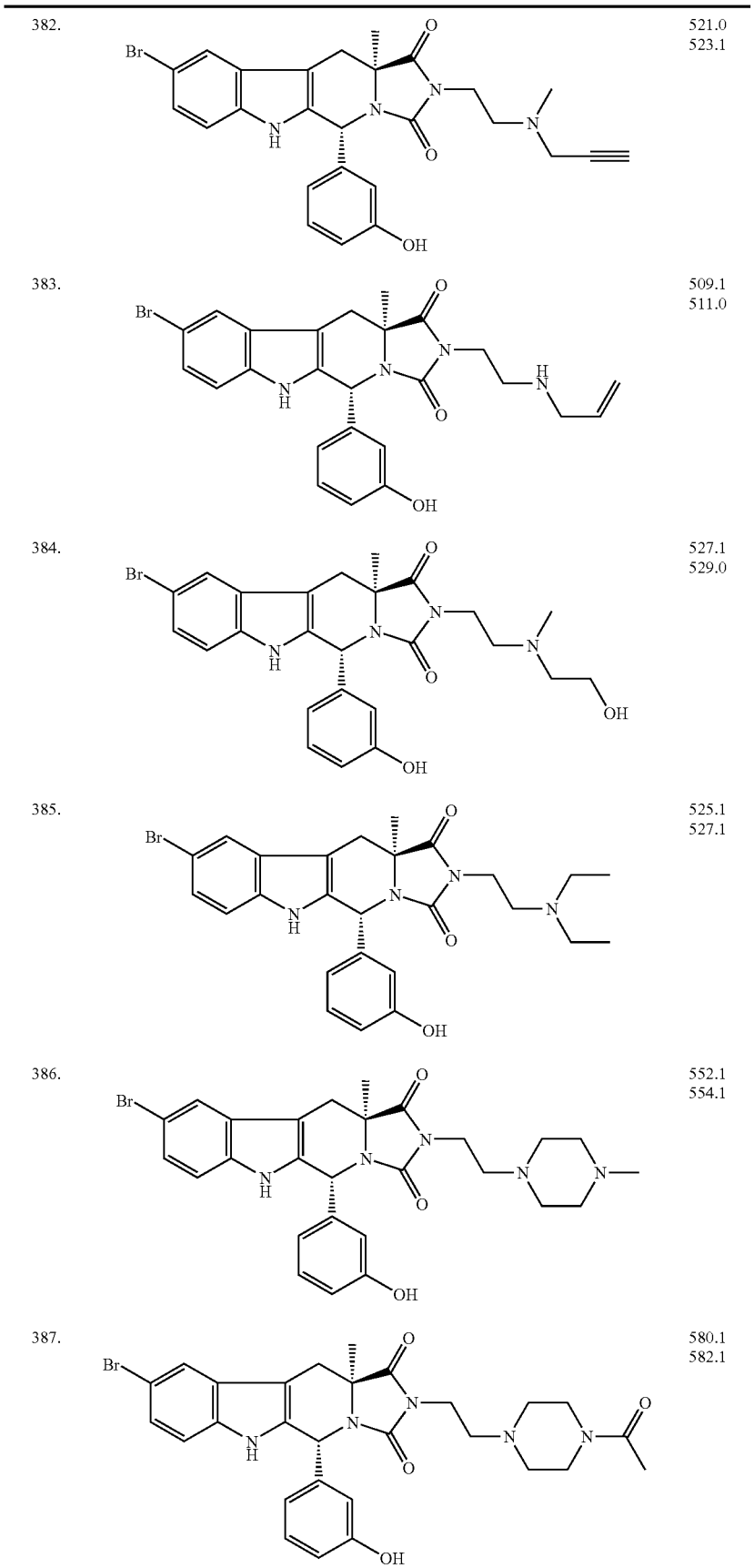

| | | |
|---|---|---|
| 388. | 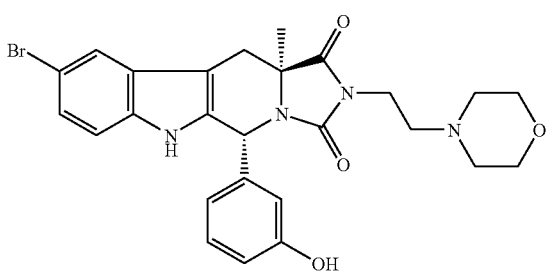 | 529.1<br>541.1 |
| 389. | 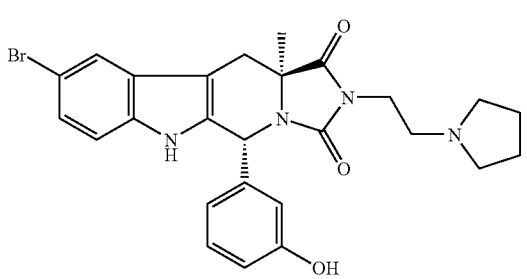 | 523.1<br>525.1 |
| 390. | 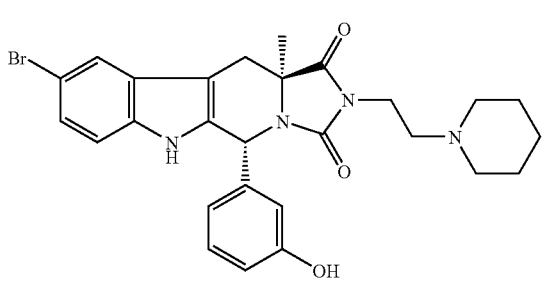 [SMILES: C[C@@]12Cc3c([nH]c4ccc(Br)cc34)[C@@H](c3cccc(O)c3)N1C(=O)N(CCN1CCCCC1)C2=O] | 537.1<br>539.1 |
| 391. | 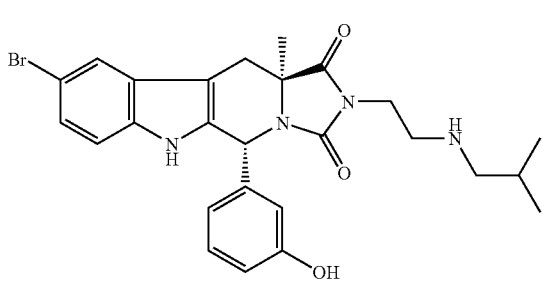 [SMILES: CC(C)CNCCN1C(=O)N2[C@H](c3cccc(O)c3)c3[nH]c4ccc(Br)cc4c3C[C@@]2(C)C1=O] | 525.1<br>527.0 |
| 392. | 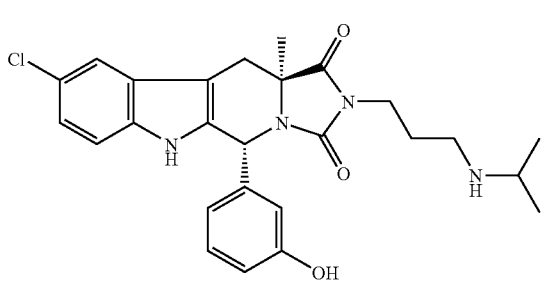 [SMILES: CC(C)NCCCN1C(=O)N2[C@H](c3cccc(O)c3)c3[nH]c4ccc(Cl)cc4c3C[C@@]2(C)C1=O] | 481.1 |

-continued
| 393. | 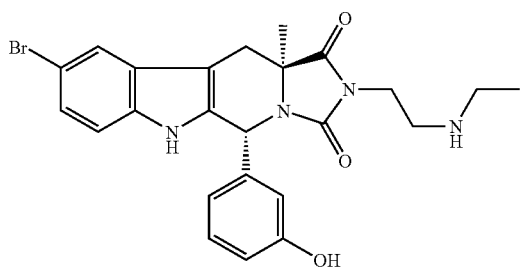 | 497.0 499.0 |
| --- | --- | --- |
| 394. | 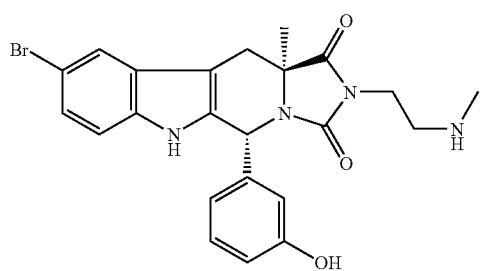 [SMILES: CNCCN1C(=O)N2[C@H](c3cccc(O)c3)c3[nH]c4ccc(Br)cc4c3C[C@@]2(C)C1=O] | 483.0 484.9 |
| 395. | 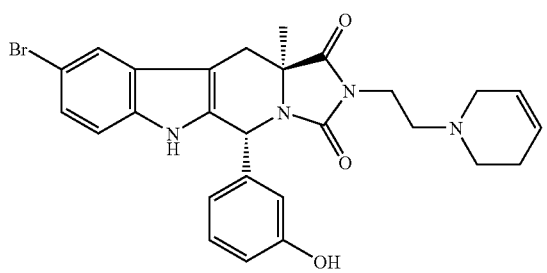 | 535.2 537.1 |
| 396. | 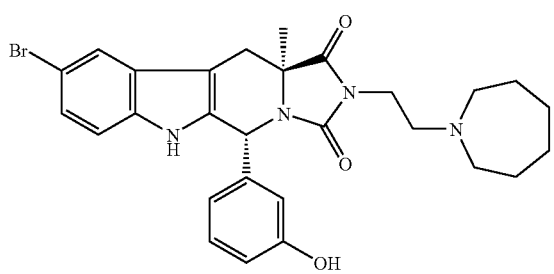 | 551.2 553.2 |
| 397. | 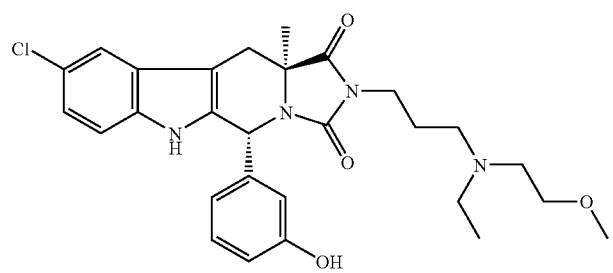 [SMILES: CCN(CCCN1C(=O)N2[C@H](c3cccc(O)c3)c3[nH]c4ccc(Cl)cc4c3C[C@@]2(C)C1=O)CCOC] | 525.2 |

-continued
| | | |
|---|---|---|
| 398. | 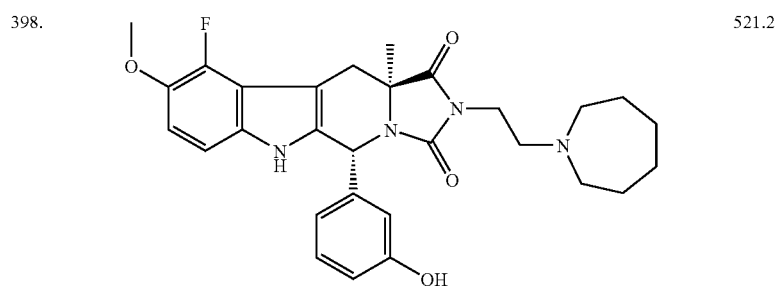 | 521.2 |
| 399. | 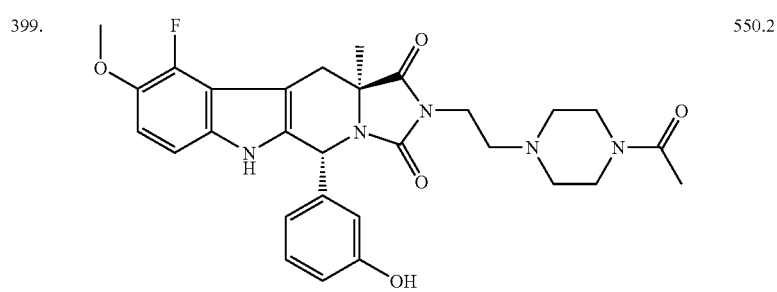 | 550.2 |
| 400. | 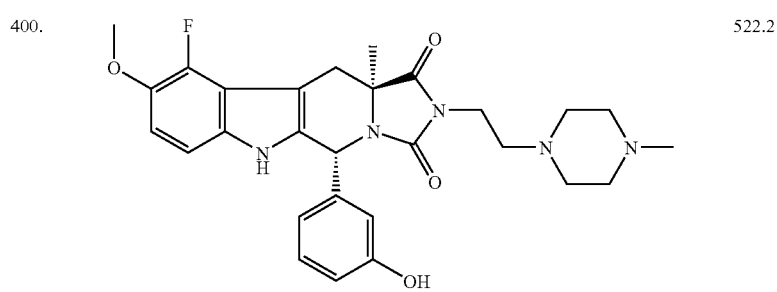 | 522.2 |
| 401. | 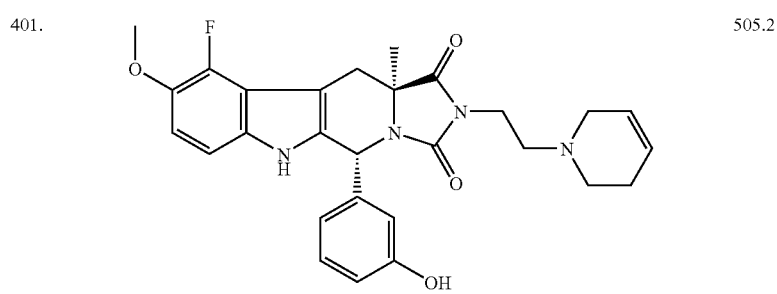 | 505.2 |
| 402. | 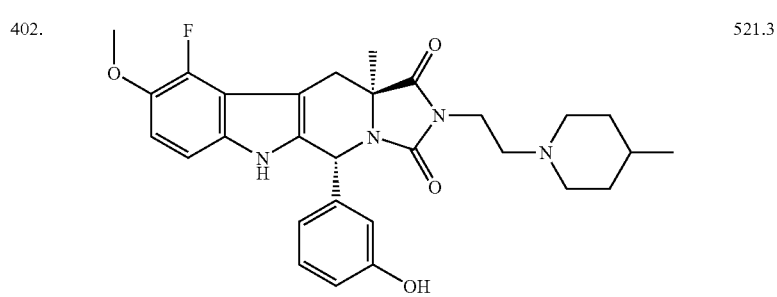 | 521.3 |

403. 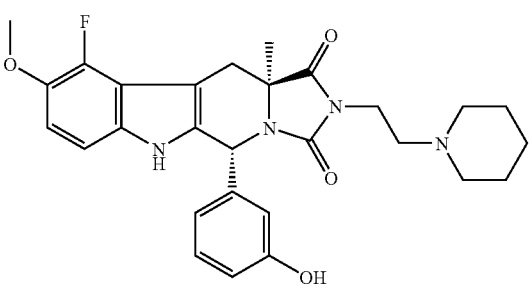 [SMILES: COc1ccc2[nH]c3c(c2c1F)C[C@@]1(C)C(=O)N(CCN2CCCCC2)C(=O)N1[C@@H]3c1cccc(O)c1] 507.2
404. 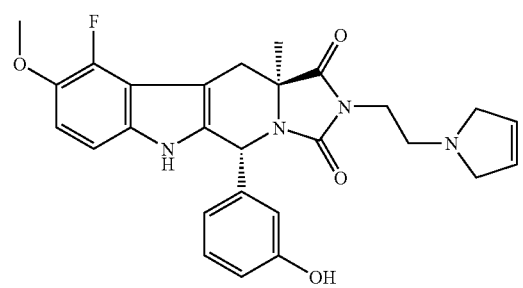 491.2
405. 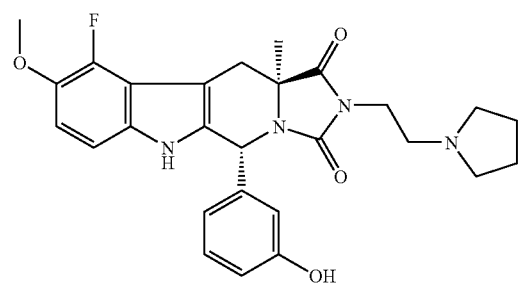 [SMILES: COc1ccc2[nH]c3c(c2c1F)C[C@@]1(C)C(=O)N(CCN2CCCC2)C(=O)N1[C@@H]3c1cccc(O)c1] 493.2
406. 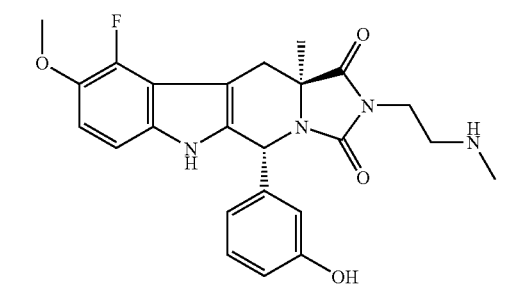 [SMILES: CNCCN1C(=O)N2[C@H](c3cccc(O)c3)c3[nH]c4ccc(OC)c(F)c4c3C[C@@]2(C)C1=O] 453.2
407. 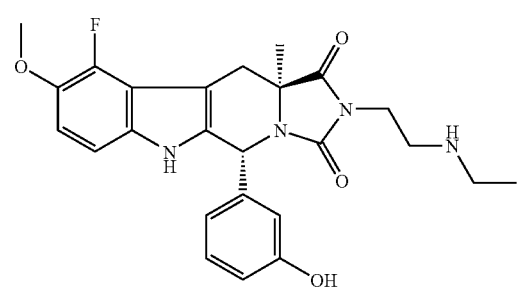 [SMILES: CCNCCN1C(=O)N2[C@H](c3cccc(O)c3)c3[nH]c4ccc(OC)c(F)c4c3C[C@@]2(C)C1=O] 467.2

-continued
| 408. | 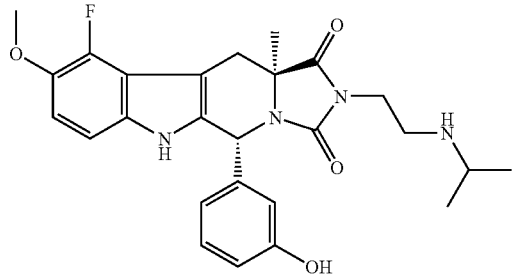 | 481.2 |
| 409. | 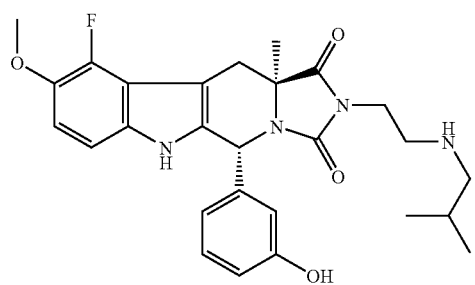 [SMILES: COc1ccc2[nH]c3c(c2c1F)C[C@@]1(C)C(=O)N(CCNCC(C)C)C(=O)N1[C@@H]3c1cccc(O)c1] | 495.2 |
| 410. | 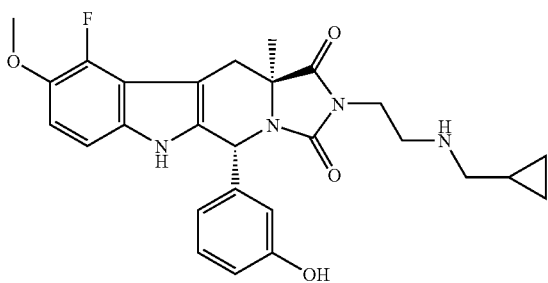 [SMILES: COc1ccc2[nH]c3c(c2c1F)C[C@@]1(C)C(=O)N(CCNCC2CC2)C(=O)N1[C@@H]3c1cccc(O)c1] | 493.2 |
| 411. | 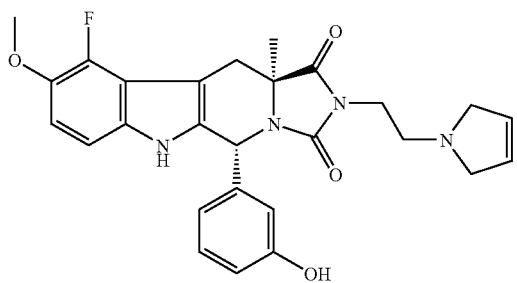 | 483.2 |
| 412. | 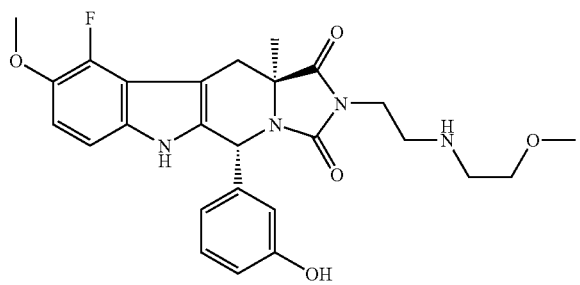 [SMILES: COCCNCCN1C(=O)N2[C@H](c3cccc(O)c3)c3[nH]c4ccc(OC)c(F)c4c3C[C@@]2(C)C1=O] | 497.2 |

| | | |
|---|---|---|
| 413. | 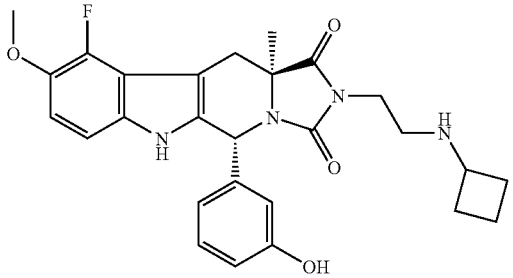 [SMILES: COc1ccc2[nH]c3c(c2c1F)C[C@@]1(C)C(=O)N(CCNC2CCC2)C(=O)N1[C@@H]3c1cccc(O)c1] | 493.2 |
| 414. | 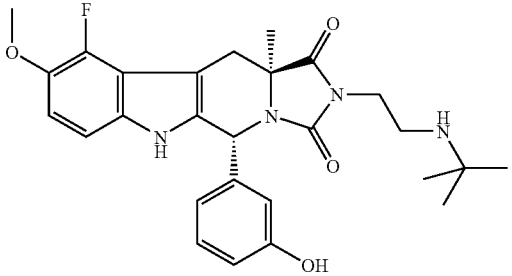 | 495.1 |
| 415. | 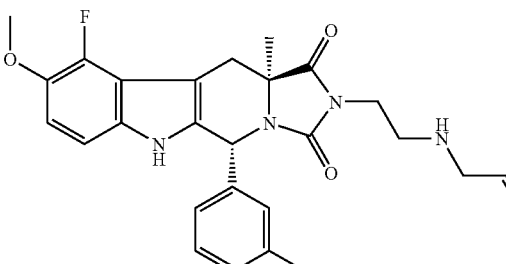 | 479.2 |
| 416. | 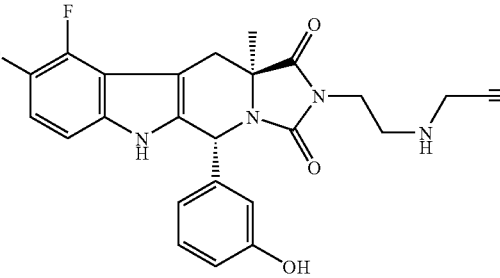 | 477.2 |
| 417. | 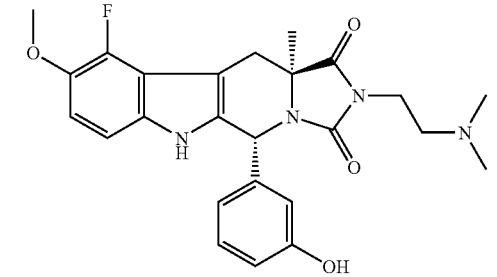 [SMILES: COc1ccc2[nH]c3c(c2c1F)C[C@@]1(C)C(=O)N(CCN(C)C)C(=O)N1[C@@H]3c1cccc(O)c1] | 467.2 |

| | |
|---|---|
| 418. 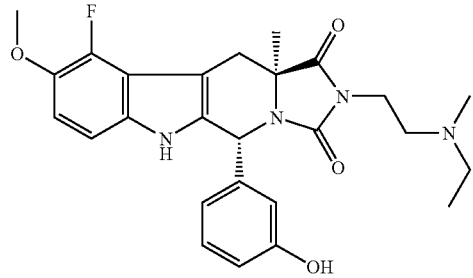 | 481.2 |
| 419. 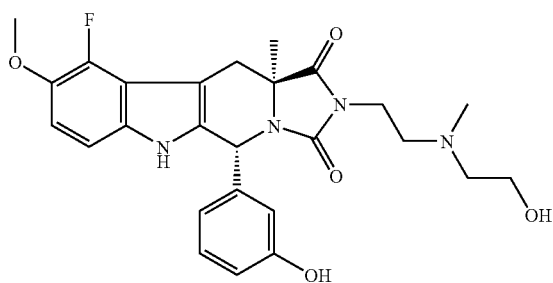 [SMILES: CCN(CCO)CCN1C(=O)N2[C@H](c3cccc(O)c3)c3[nH]c4ccc(OC)c(F)c4c3C[C@@]2(C)C1=O] | 497.2 |
| 420. 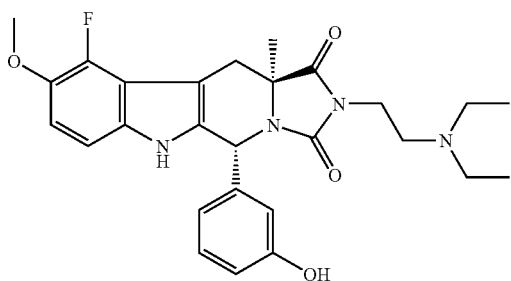 | 495.2 |
| 421. 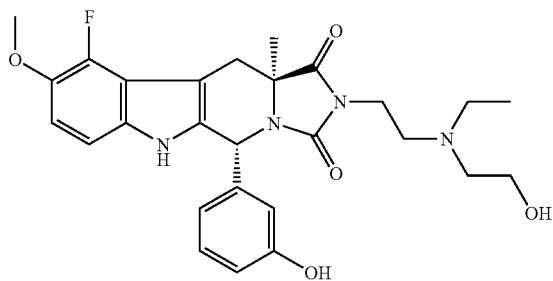 | 511.2 |
| 422. 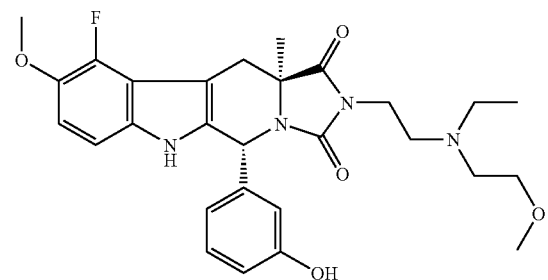 [SMILES: CCN(CCOC)CCN1C(=O)N2[C@H](c3cccc(O)c3)c3[nH]c4ccc(OC)c(F)c4c3C[C@@]2(C)C1=O] | 525.2 |

| 423. | 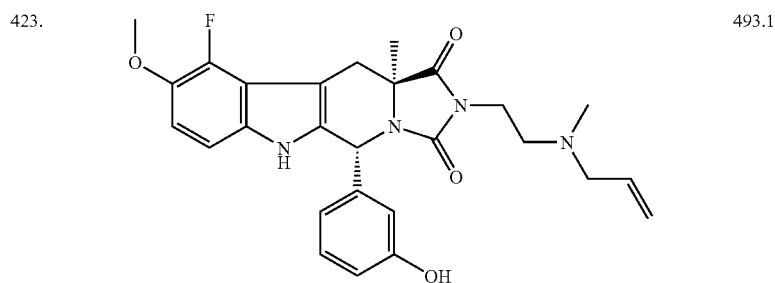 | 493.1 |
| 424. | 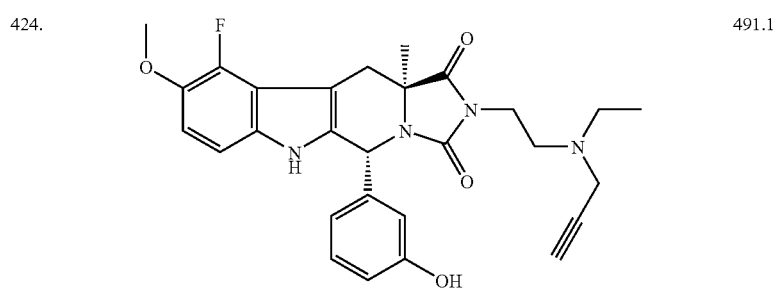 | 491.1 |
| 425. | 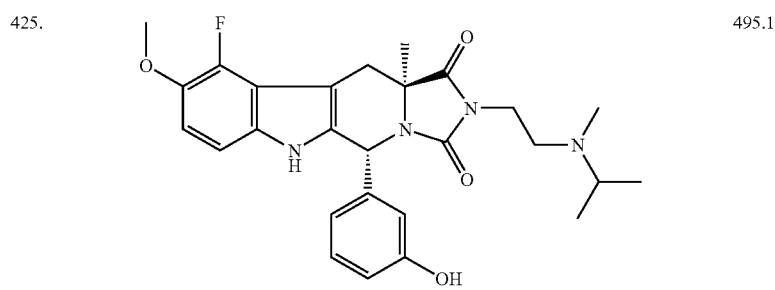 | 495.1 |
| 426. | 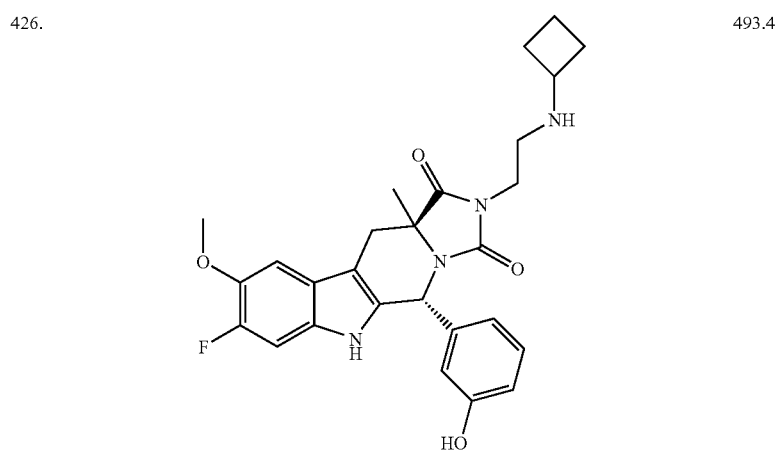 | 493.4 |

-continued
427. 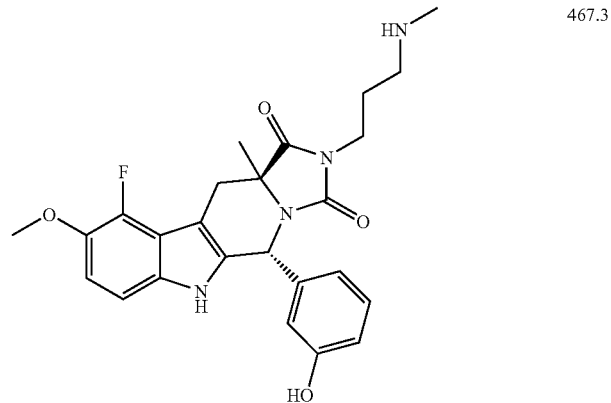 467.3
428. 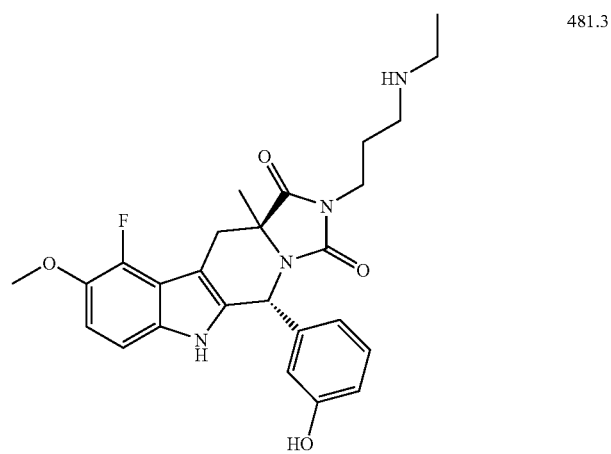 481.3
429. 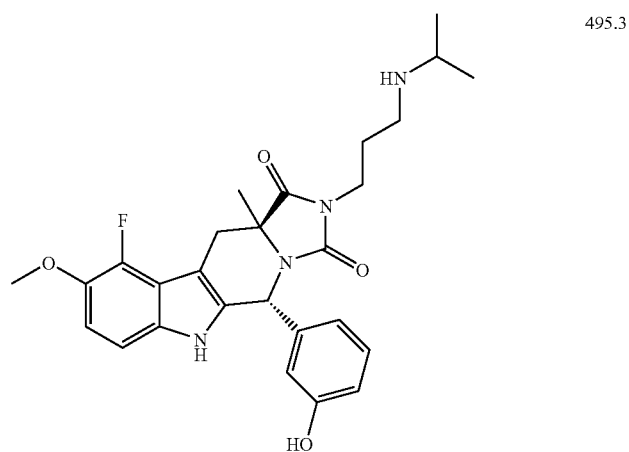 495.3

-continued
| | | |
|---|---|---|
| 430. | 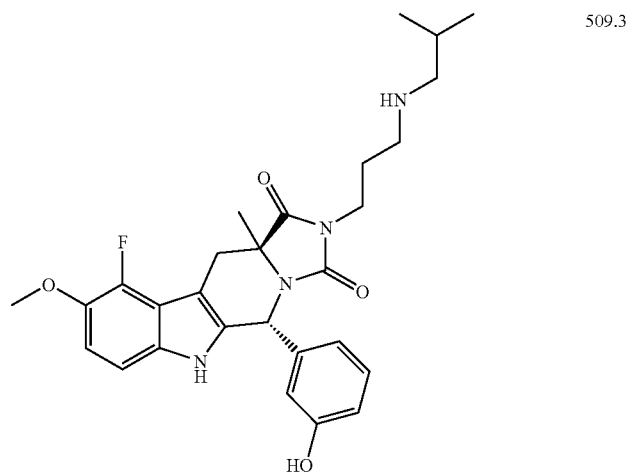 | 509.3 |
| 431. | 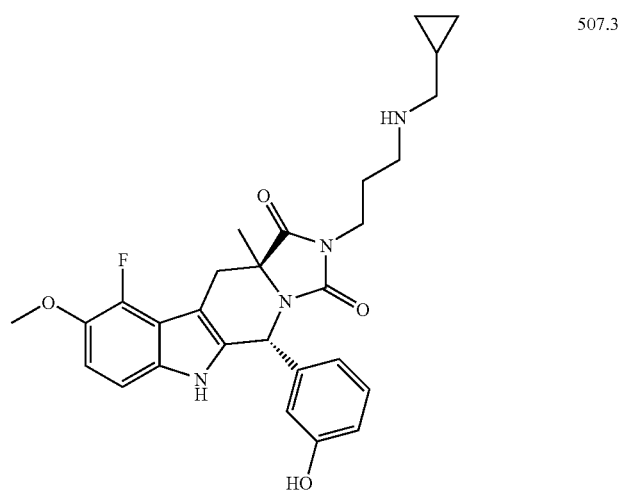 | 507.3 |
| 432. | 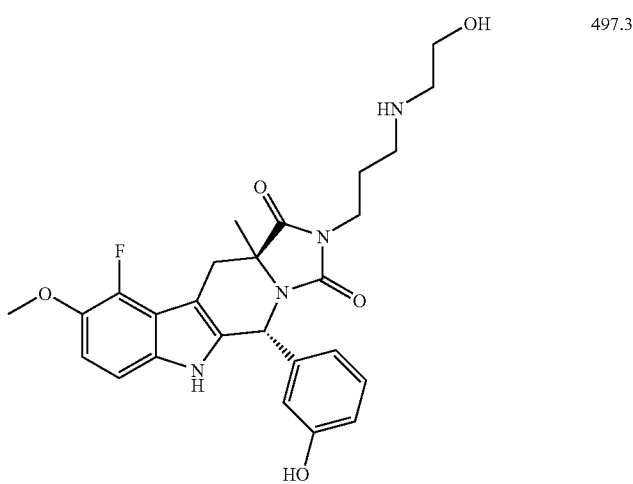 | 497.3 |

| | | |
|---|---|---|
| 433. | 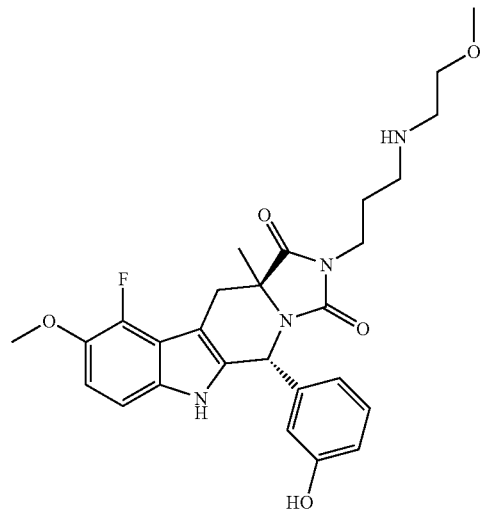 | 511.3 |
| 434. | 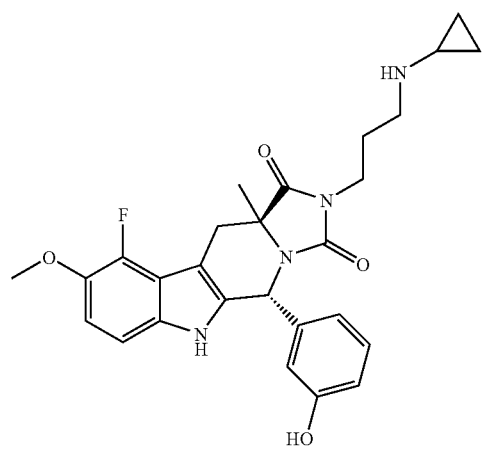 [SMILES: COc1ccc2[nH]c3c(c2c1F)C[C@@]1(C)C(=O)N(CCCNC2CC2)C(=O)N1[C@@H]3c1cccc(O)c1] | 493.3 |
| 435. | 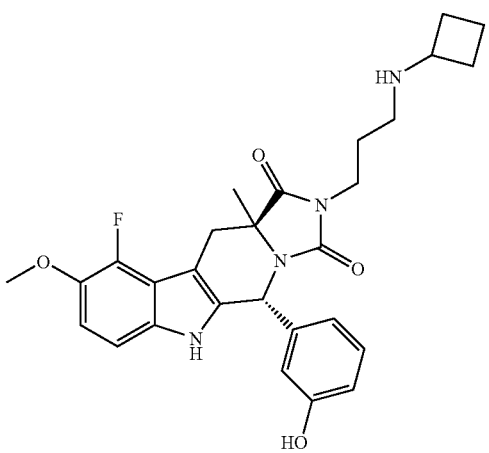 [SMILES: COc1ccc2[nH]c3c(c2c1F)C[C@@]1(C)C(=O)N(CCCNC2CCC2)C(=O)N1[C@@H]3c1cccc(O)c1] | 507.3 |

-continued
| 436. | 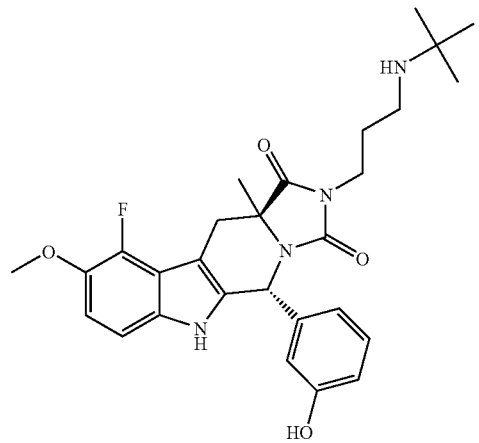 [SMILES: COc1ccc2[nH]c3c(c2c1F)C[C@@]1(C)C(=O)N(CCCNC(C)(C)C)C(=O)N1[C@@H]3c1cccc(O)c1] | 509.3 |
| 437. | 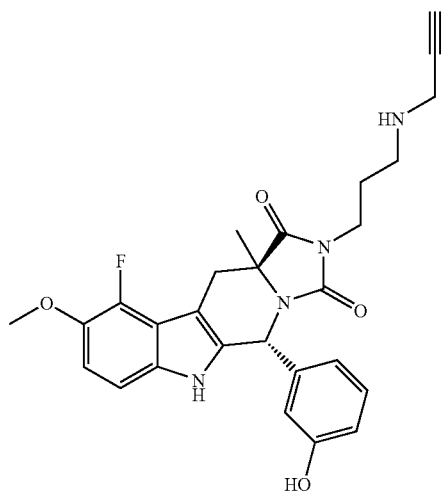 [SMILES: C#CCNCCCN1C(=O)N2[C@H](c3cccc(O)c3)c3[nH]c4ccc(OC)c(F)c4c3C[C@@]2(C)C1=O] | 491.3 |
| 438. | 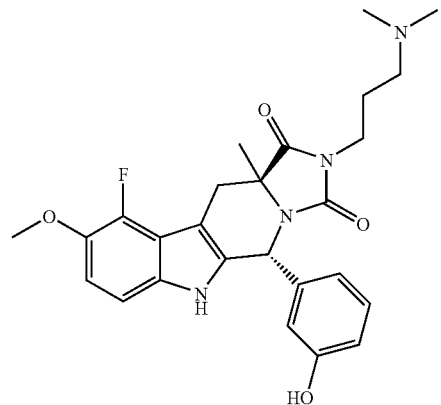 | 481.3 |

| | | |
|---|---|---|
| 439. | 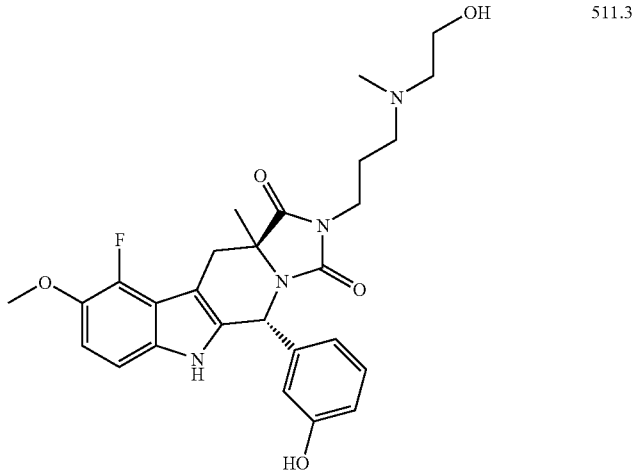 | 511.3 |
| 440. | 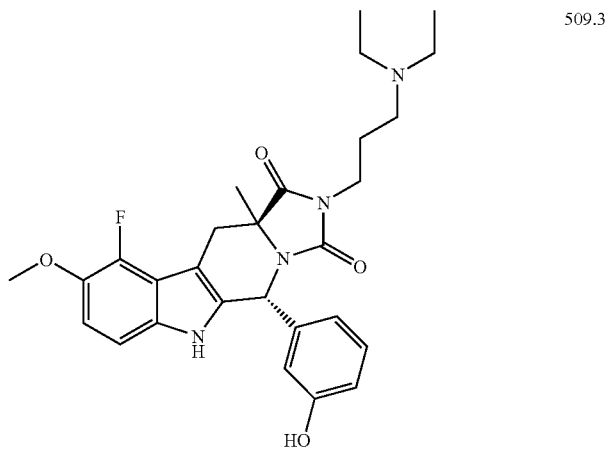 | 509.3 |
| 441. | 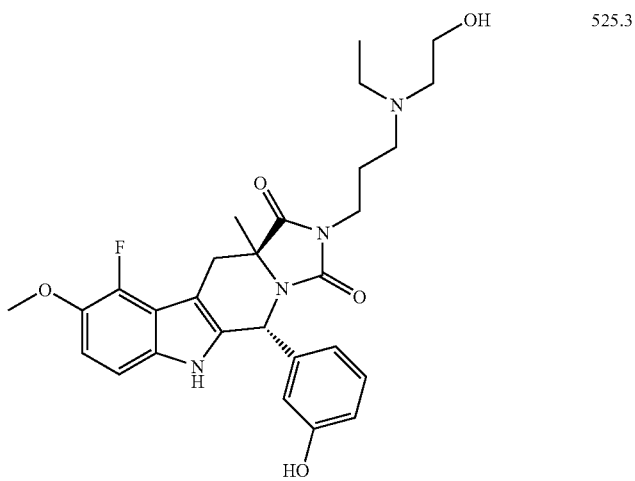 | 525.3 |

| | | |
|---|---|---|
| 442. | 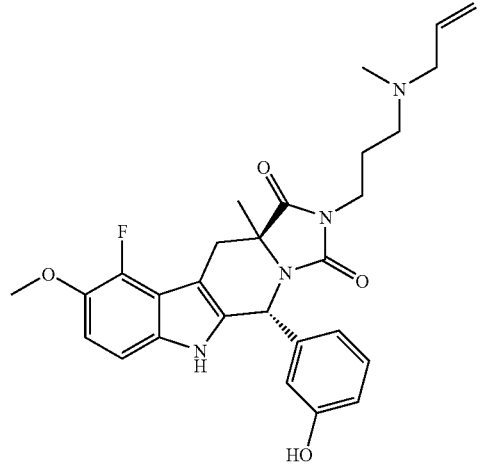 [SMILES: C=CCN(C)CCCN1C(=O)N2[C@H](c3cccc(O)c3)c3[nH]c4ccc(OC)c(F)c4c3C[C@@]2(C)C1=O] | 507.3 |
| 443. | 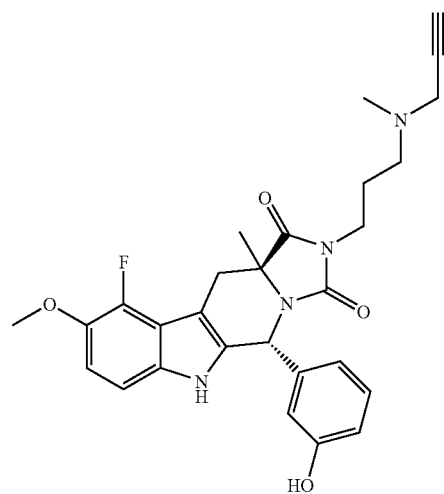 [SMILES: C#CCN(C)CCCN1C(=O)N2[C@H](c3cccc(O)c3)c3[nH]c4ccc(OC)c(F)c4c3C[C@@]2(C)C1=O] | 505.3 |
| 444. | 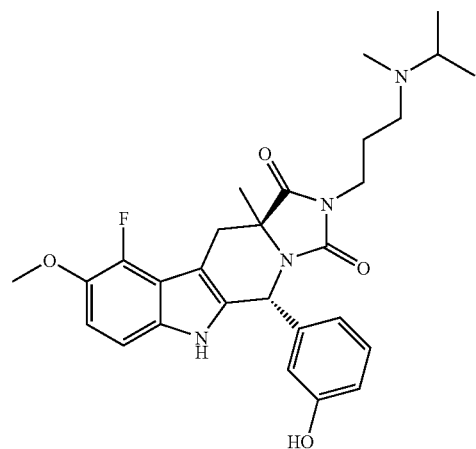 [SMILES: COc1ccc2[nH]c3c(c2c1F)C[C@@]1(C)C(=O)N(CCCN(C)C(C)C)C(=O)N1[C@@H]3c1cccc(O)c1] | 509.3 |

445. 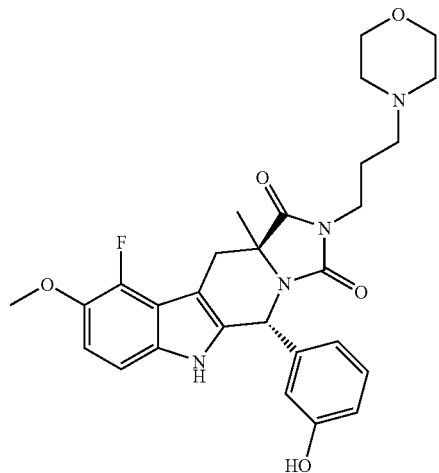 [SMILES: COc1ccc2[nH]c3c(c2c1F)C[C@@]1(C)C(=O)N(CCCN2CCOCC2)C(=O)N1[C@@H]3c1cccc(O)c1] 523.3
446. 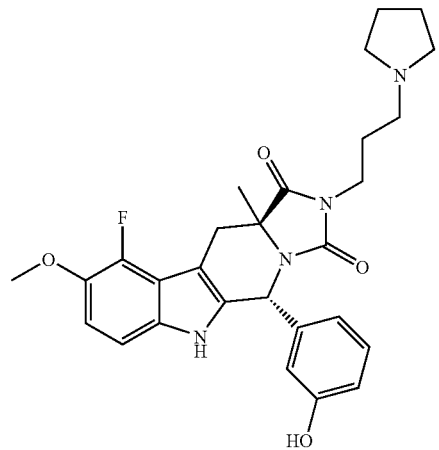 [SMILES: COc1ccc2[nH]c3c(c2c1F)C[C@@]1(C)C(=O)N(CCCN2CCCC2)C(=O)N1[C@@H]3c1cccc(O)c1] 507.3
447. 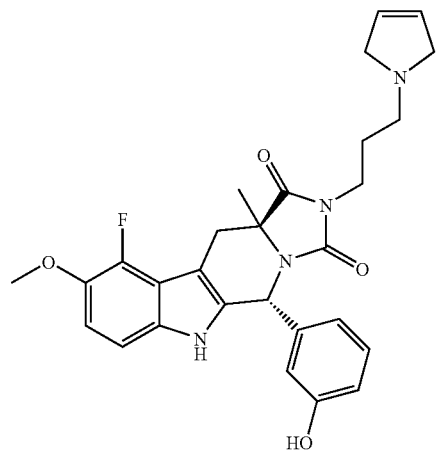 [SMILES: COc1ccc2[nH]c3c(c2c1F)C[C@@]1(C)C(=O)N(CCCN2CC=CC2)C(=O)N1[C@@H]3c1cccc(O)c1] 505.3

| | | |
|---|---|---|
| 448. | 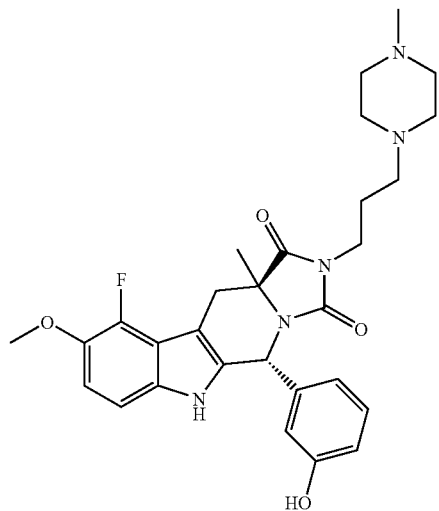 [SMILES: COc1ccc2[nH]c3c(c2c1F)C[C@@]1(C)C(=O)N(CCCN2CCN(C)CC2)C(=O)N1[C@@H]3c1cccc(O)c1] | 536.4 |
| 449. | 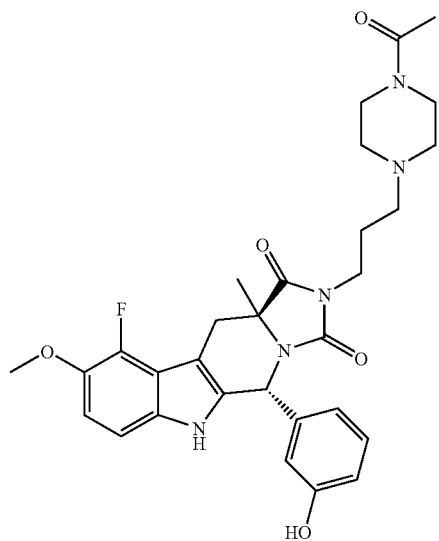 [SMILES: COc1ccc2[nH]c3c(c2c1F)C[C@@]1(C)C(=O)N(CCCN2CCN(C(C)=O)CC2)C(=O)N1[C@@H]3c1cccc(O)c1] | 564.4 |
| 450. | 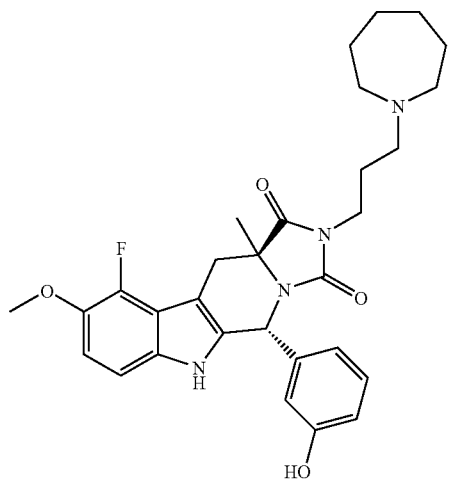 [SMILES: COc1ccc2[nH]c3c(c2c1F)C[C@@]1(C)C(=O)N(CCCN2CCCCCC2)C(=O)N1[C@@H]3c1cccc(O)c1] | 535.3 |

| | | |
|---|---|---|
| 451. | 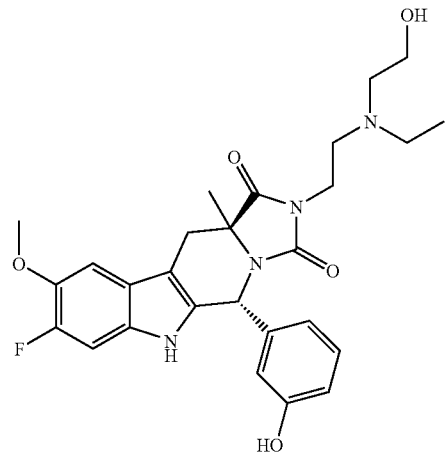 [SMILES: CCN(CCO)CCN1C(=O)N2[C@H](c3cccc(O)c3)c3[nH]c4cc(F)c(OC)cc4c3C[C@@]2(C)C1=O] | 511.3 |
| 452. | 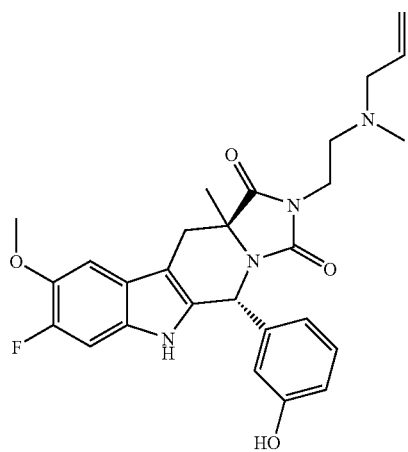 [SMILES: C=CCN(C)CCN1C(=O)N2[C@H](c3cccc(O)c3)c3[nH]c4cc(F)c(OC)cc4c3C[C@@]2(C)C1=O] | 493.3 |
| 453. | 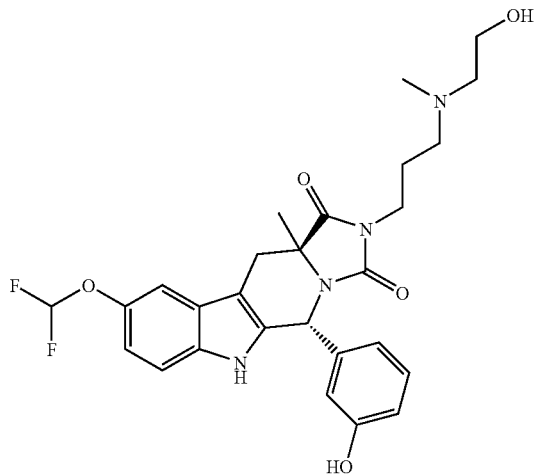 [SMILES: CN(CCO)CCCN1C(=O)N2[C@H](c3cccc(O)c3)c3[nH]c4ccc(OC(F)F)cc4c3C[C@@]2(C)C1=O] | 529.1 |

454. 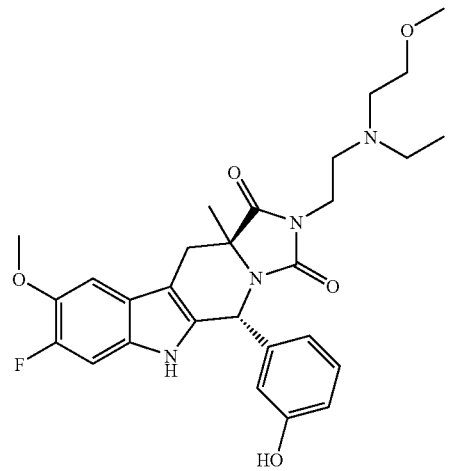 [SMILES: CCN(CCOC)CCN1C(=O)N2[C@H](c3cccc(O)c3)c3[nH]c4cc(F)c(OC)cc4c3C[C@@]2(C)C1=O] 525.1
455. 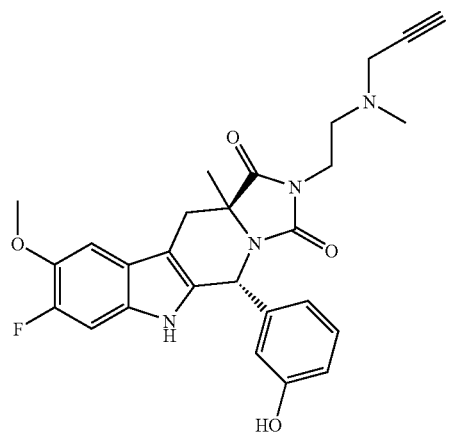 [SMILES: C#CCN(C)CCN1C(=O)N2[C@H](c3cccc(O)c3)c3[nH]c4cc(F)c(OC)cc4c3C[C@@]2(C)C1=O] 491.1
456. 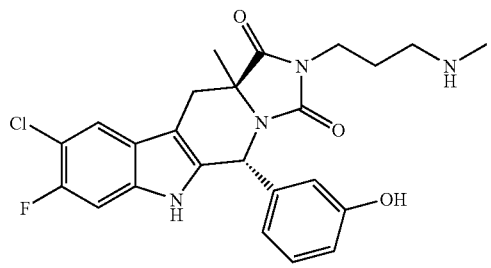 [SMILES: CNCCCN1C(=O)N2[C@H](c3cccc(O)c3)c3[nH]c4cc(F)c(Cl)cc4c3C[C@@]2(C)C1=O] 471.4
457. 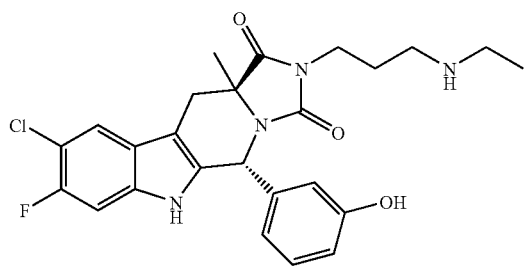 [SMILES: CCNCCCN1C(=O)N2[C@H](c3cccc(O)c3)c3[nH]c4cc(F)c(Cl)cc4c3C[C@@]2(C)C1=O] 485.4

-continued
| | | |
|---|---|---|
| 458. | 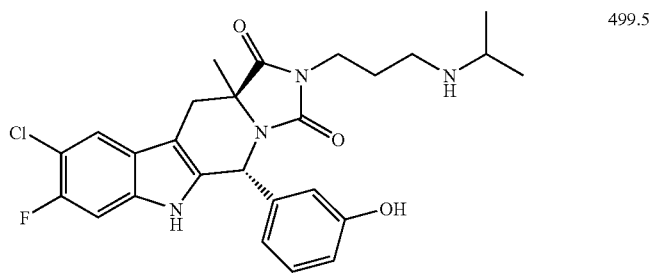 | 499.5 |
| 459. | 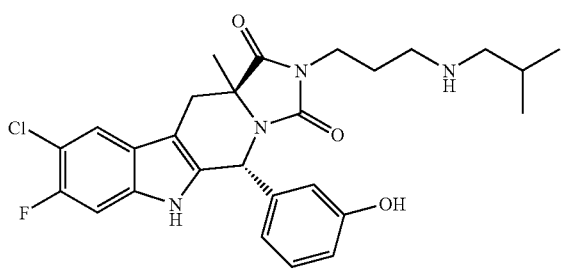 [SMILES: CC(C)CNCCCN1C(=O)N2[C@H](c3cccc(O)c3)c3[nH]c4cc(F)c(Cl)cc4c3C[C@@]2(C)C1=O] | 513.5 |
| 460. | 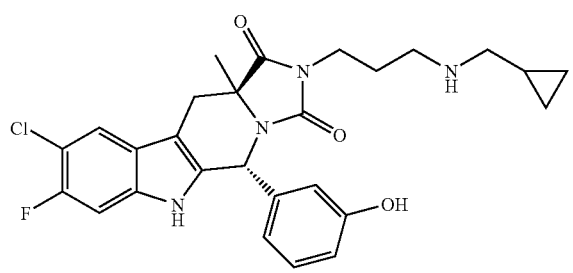 [SMILES: C[C@@]12Cc3c([nH]c4cc(F)c(Cl)cc34)[C@@H](c3cccc(O)c3)N1C(=O)N(CCCNCC1CC1)C2=O] | 511.5 |
| 461. | 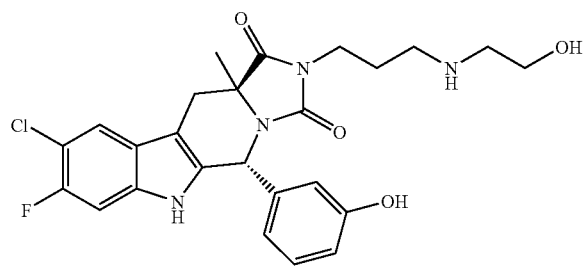 [SMILES: C[C@@]12Cc3c([nH]c4cc(F)c(Cl)cc34)[C@@H](c3cccc(O)c3)N1C(=O)N(CCCNCCO)C2=O] | 501.4 |
| 462. | 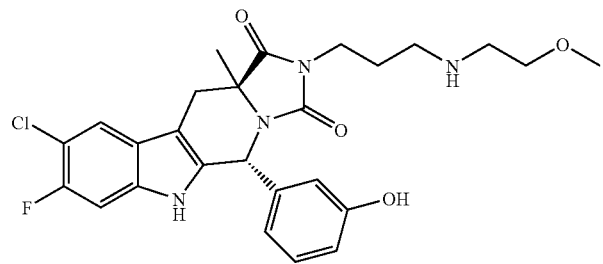 [SMILES: COCCNCCCN1C(=O)N2[C@H](c3cccc(O)c3)c3[nH]c4cc(F)c(Cl)cc4c3C[C@@]2(C)C1=O] | 515.5 |
| 463. | 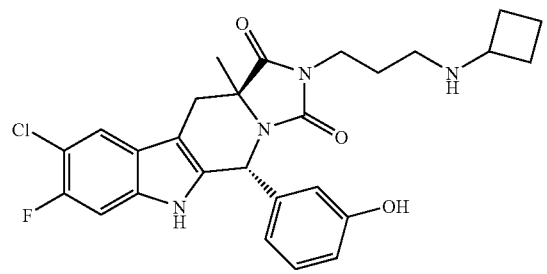 [SMILES: C[C@@]12Cc3c([nH]c4cc(F)c(Cl)cc34)[C@@H](c3cccc(O)c3)N1C(=O)N(CCCNC1CCC1)C2=O] | 511.5 |

464. 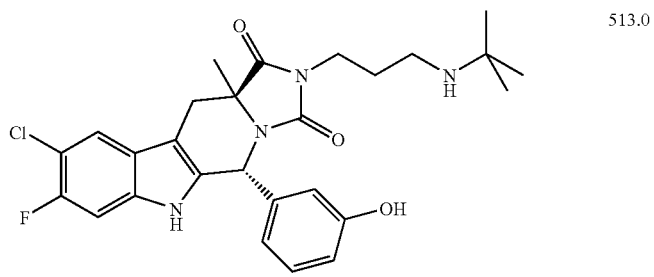 513.0
465. 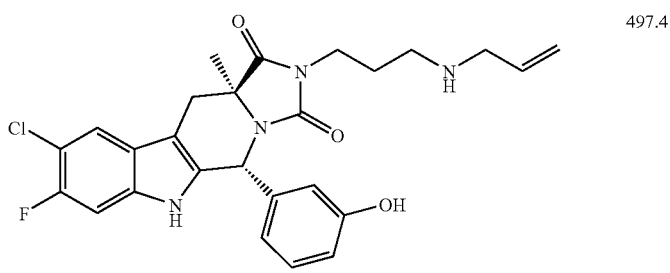 497.4
466. 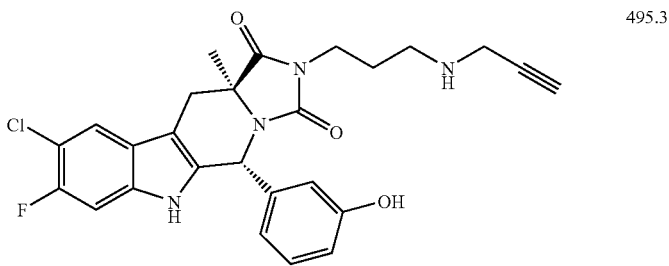 495.3
467. 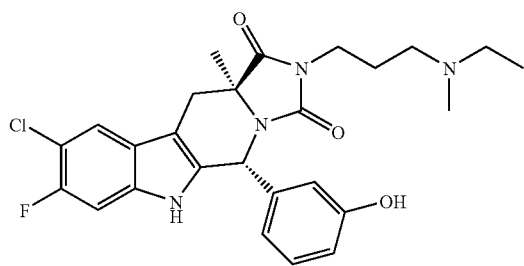 [SMILES: CCN(C)CCCN1C(=O)N2[C@H](c3cccc(O)c3)c3[nH]c4cc(F)c(Cl)cc4c3C[C@@]2(C)C1=O] 499.5
468. 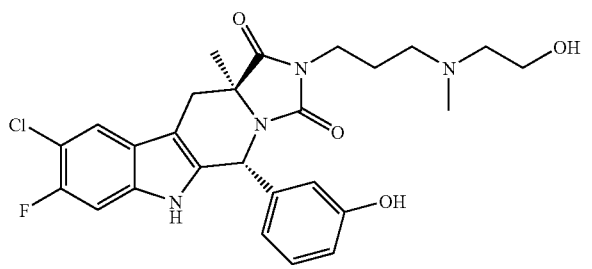 [SMILES: CN(CCO)CCCN1C(=O)N2[C@H](c3cccc(O)c3)c3[nH]c4cc(F)c(Cl)cc4c3C[C@@]2(C)C1=O] 515.4

| | | |
|---|---|---|
| 469. | 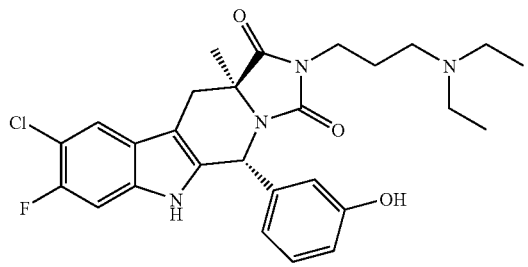 [SMILES: CCN(CC)CCCN1C(=O)N2[C@H](c3cccc(O)c3)c3[nH]c4cc(F)c(Cl)cc4c3C[C@@]2(C)C1=O] | 513.5 |
| 470. | 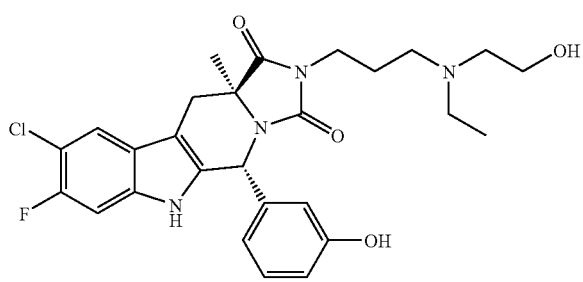 [SMILES: CCN(CCO)CCCN1C(=O)N2[C@H](c3cccc(O)c3)c3[nH]c4cc(F)c(Cl)cc4c3C[C@@]2(C)C1=O] | 529.5 |
| 471. | 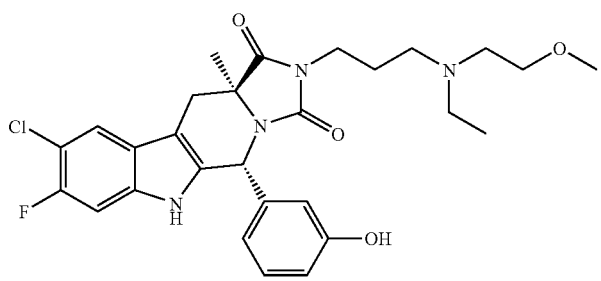 [SMILES: CCN(CCCN1C(=O)N2[C@H](c3cccc(O)c3)c3[nH]c4cc(F)c(Cl)cc4c3C[C@@]2(C)C1=O)CCOC] | 543.5 |
| 472. | 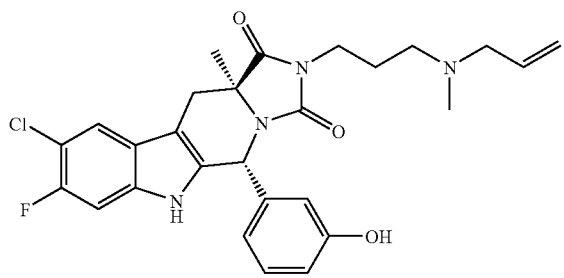 [SMILES: C=CCN(C)CCCN1C(=O)N2[C@H](c3cccc(O)c3)c3[nH]c4cc(F)c(Cl)cc4c3C[C@@]2(C)C1=O] | 511.5 |
| 473. | 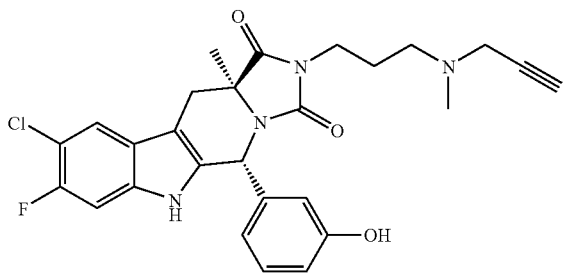 [SMILES: C#CCN(C)CCCN1C(=O)N2[C@H](c3cccc(O)c3)c3[nH]c4cc(F)c(Cl)cc4c3C[C@@]2(C)C1=O] | 509.4 |

| | | |
|---|---|---|
| 474. | 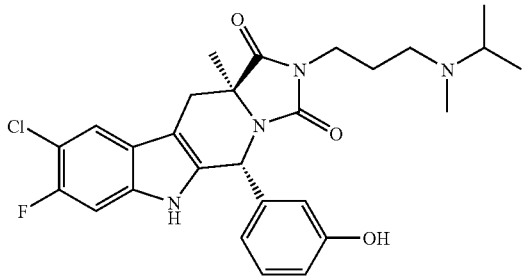 [SMILES: CC(C)N(C)CCCN1C(=O)N2[C@H](c3cccc(O)c3)c3[nH]c4cc(F)c(Cl)cc4c3C[C@@]2(C)C1=O] | 513.1 |
| 475. | 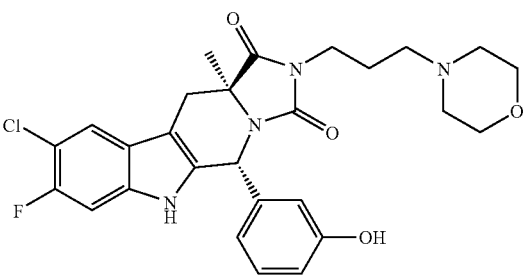 [SMILES: C[C@@]12Cc3c([nH]c4cc(F)c(Cl)cc34)[C@@H](c3cccc(O)c3)N1C(=O)N(CCCN1CCOCC1)C2=O] | 527.5 |
| 476. | 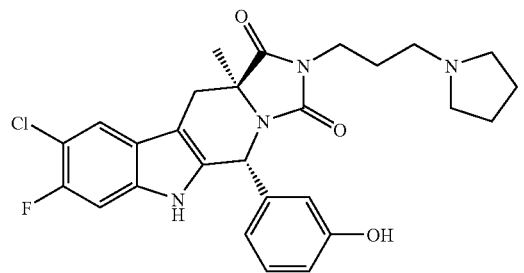 [SMILES: C[C@@]12Cc3c([nH]c4cc(F)c(Cl)cc34)[C@@H](c3cccc(O)c3)N1C(=O)N(CCCN1CCCC1)C2=O] | 511.1 |
| 477. | 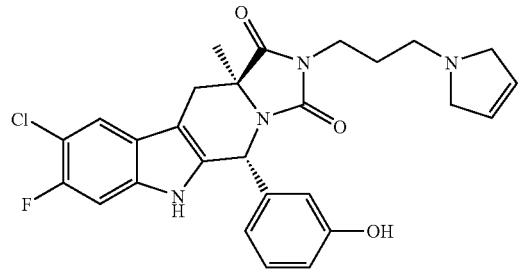 [SMILES: C[C@@]12Cc3c([nH]c4cc(F)c(Cl)cc34)[C@@H](c3cccc(O)c3)N1C(=O)N(CCCN1CC=CC1)C2=O] | 509.4 |
| 478. | 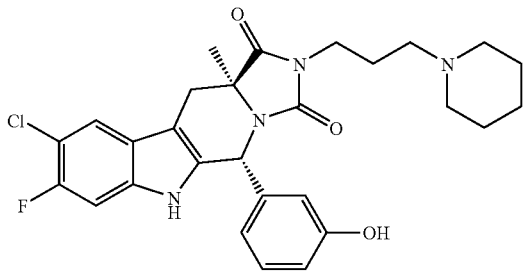 [SMILES: C[C@@]12Cc3c([nH]c4cc(F)c(Cl)cc34)[C@@H](c3cccc(O)c3)N1C(=O)N(CCCN1CCCCC1)C2=O] | 525.5 |

| | | |
|---|---|---|
| 479. | 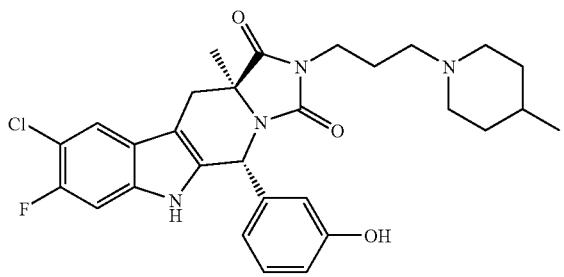 | 539.6 |
| 480. | 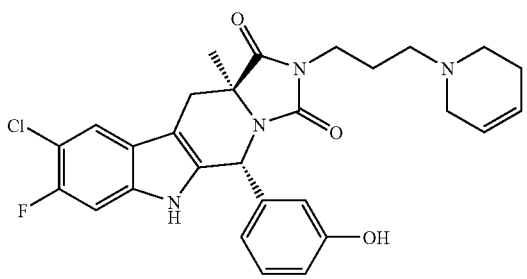 | 523.5 |
| 481. | 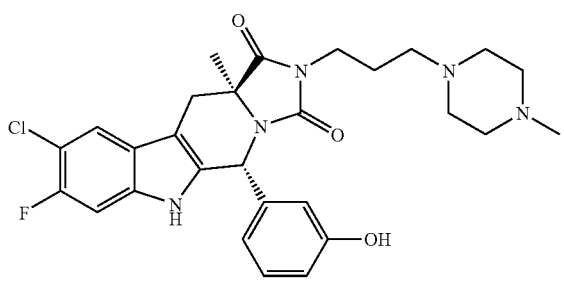 [SMILES: CC1CCN(CCCN2C(=O)N3[C@H](c4cccc(O)c4)c4[nH]c5cc(F)c(Cl)cc5c4C[C@@]3(C)C2=O)CC1] | 540.5 |
| 482. | 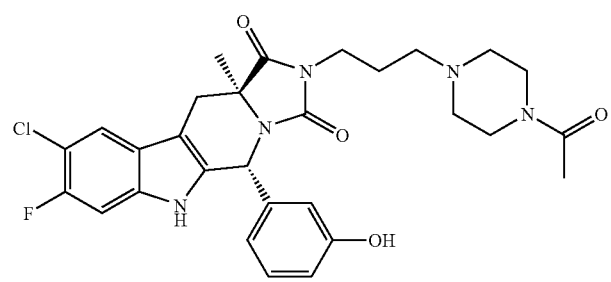 [SMILES: CC(=O)N1CCN(CCCN2C(=O)N3[C@H](c4cccc(O)c4)c4[nH]c5cc(F)c(Cl)cc5c4C[C@@]3(C)C2=O)CC1] | 568.5 |
| 483. | 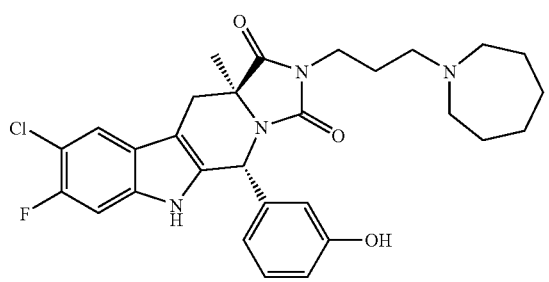 [SMILES: C[C@@]12Cc3c([nH]c4cc(F)c(Cl)cc34)[C@@H](c3cccc(O)c3)N1C(=O)N(CCCN1CCCCCC1)C2=O] | 539.5 |

-continued
| 484. | 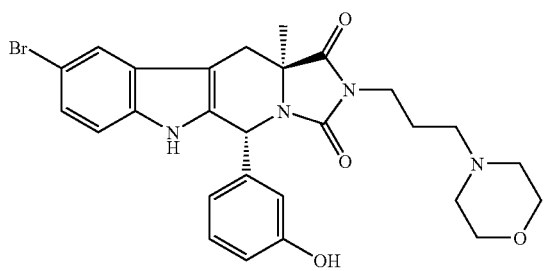 [SMILES: C[C@@]12Cc3c([nH]c4ccc(Br)cc34)[C@@H](c3cccc(O)c3)N1C(=O)N(CCCN1CCOCC1)C2=O] | 553.1 555.0 |
|---|---|---|
| 485. | 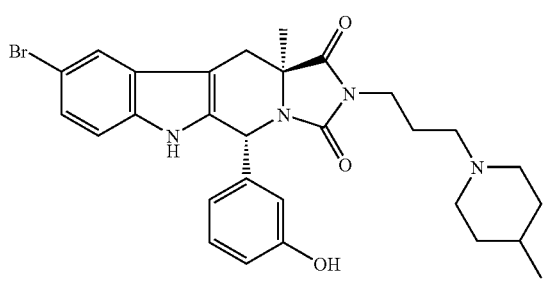 | 565.2 567.1 |
| 486. | 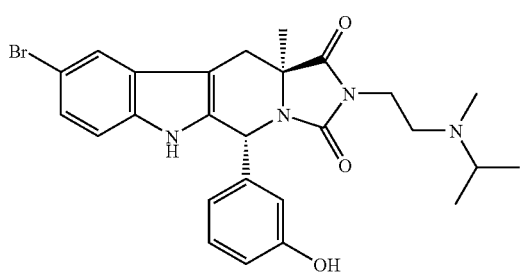 [SMILES: CC(C)N(C)CCN1C(=O)N2[C@H](c3cccc(O)c3)c3[nH]c4ccc(Br)cc4c3C[C@@]2(C)C1=O] | 525.1 527.1 |
| 487. | 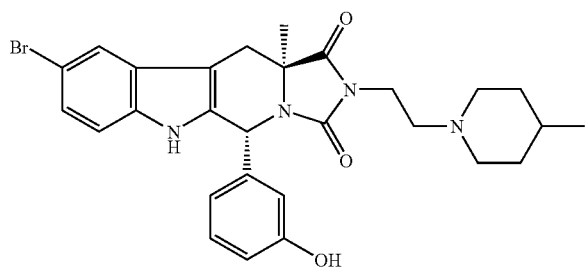 | 551.1 553.1 |
| 488. | 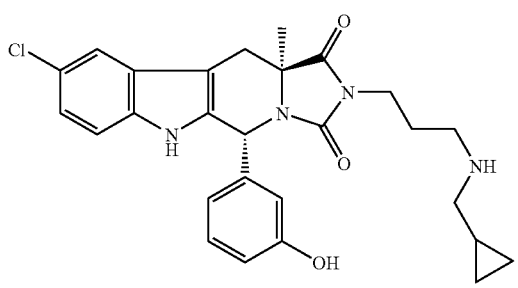 [SMILES: C[C@@]12Cc3c([nH]c4ccc(Cl)cc34)[C@@H](c3cccc(O)c3)N1C(=O)N(CCCNCC1CC1)C2=O] | 493.1 |

| | | |
|---|---|---|
| 489. | 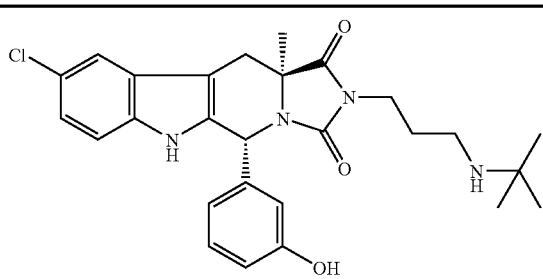 | 495.1 |
| 490. | 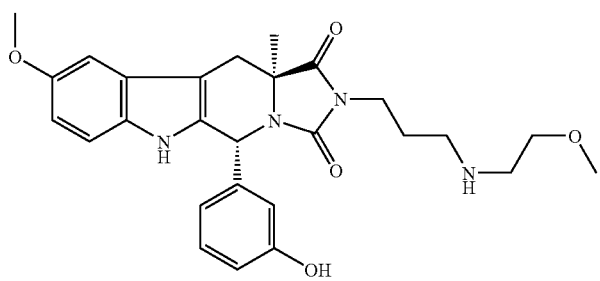 [SMILES: COCCNCCCN1C(=O)N2[C@H](c3cccc(O)c3)c3[nH]c4ccc(OC)cc4c3C[C@@]2(C)C1=O] | 493.1 |
| 491. | 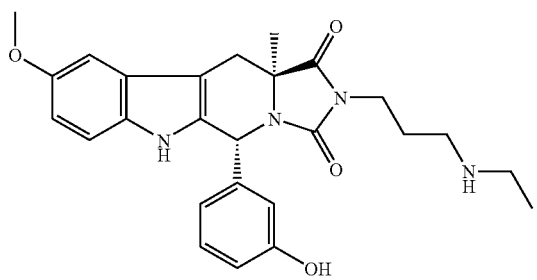 [SMILES: CCNCCCN1C(=O)N2[C@H](c3cccc(O)c3)c3[nH]c4ccc(OC)cc4c3C[C@@]2(C)C1=O] | 463.1 |
| 492. | 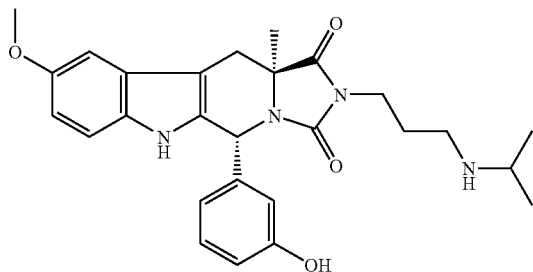 | 477.1 |
| 493. | 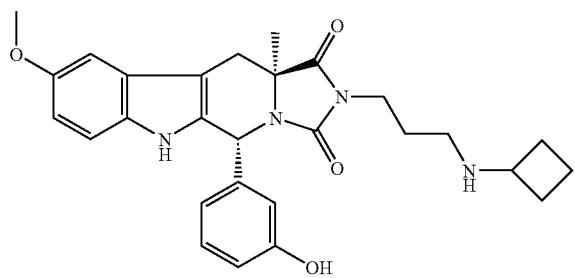 [SMILES: COc1ccc2[nH]c3c(c2c1)C[C@@]1(C)C(=O)N(CCCNC2CCC2)C(=O)N1[C@@H]3c1cccc(O)c1] | 489.1 |

-continued
| | | |
|---|---|---|
| 494. | 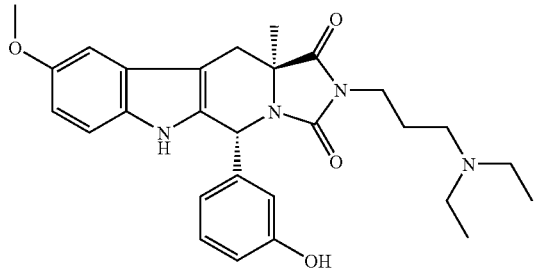 [SMILES: CCN(CC)CCCN1C(=O)N2[C@H](c3cccc(O)c3)c3[nH]c4ccc(OC)cc4c3C[C@@]2(C)C1=O] | 491.1 |
| 495. | 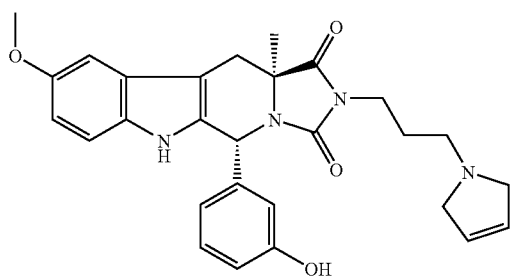 [SMILES: COc1ccc2[nH]c3c(c2c1)C[C@@]1(C)C(=O)N(CCCN2CC=CC2)C(=O)N1[C@@H]3c1cccc(O)c1] | 487.1 |
| 496. | 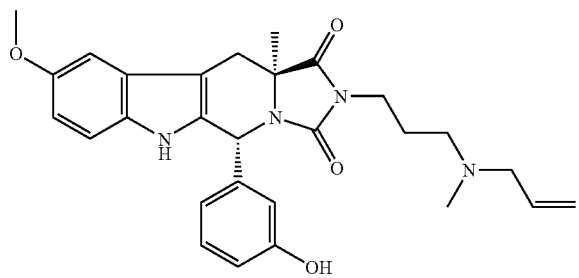 [SMILES: C=CCN(C)CCCN1C(=O)N2[C@H](c3cccc(O)c3)c3[nH]c4ccc(OC)cc4c3C[C@@]2(C)C1=O] | 489.1 |
| 497. | 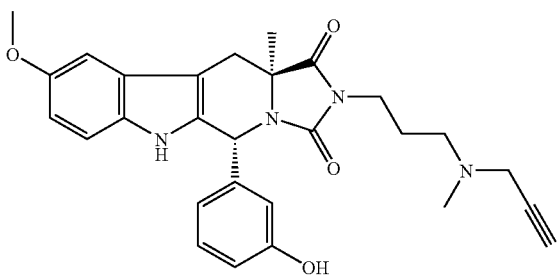 [SMILES: C#CCN(C)CCCN1C(=O)N2[C@H](c3cccc(O)c3)c3[nH]c4ccc(OC)cc4c3C[C@@]2(C)C1=O] | 487.0 |
| 498. | 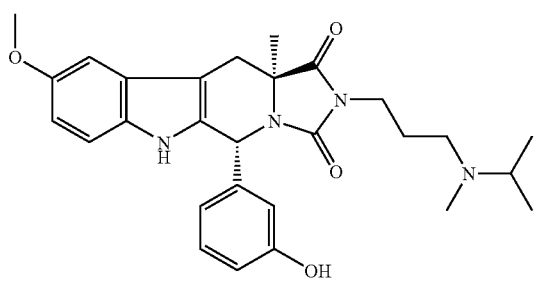 [SMILES: COc1ccc2[nH]c3c(c2c1)C[C@@]1(C)C(=O)N(CCCN(C)C(C)C)C(=O)N1[C@@H]3c1cccc(O)c1] | 491.2 |

-continued
| | | |
|---|---|---|
| 499. | 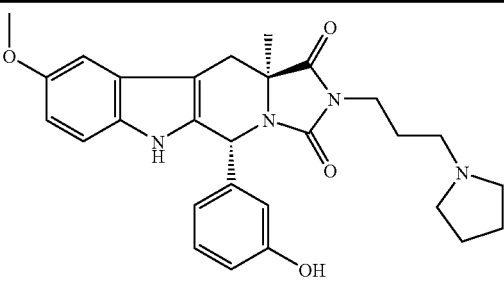 | 489.1 |
| 500. | 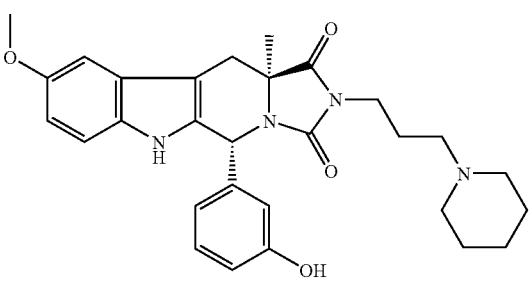 [SMILES: COc1ccc2[nH]c3c(c2c1)C[C@@]1(C)C(=O)N(CCCN2CCCCC2)C(=O)N1[C@@H]3c1cccc(O)c1] | 503.1 |
| 501. | 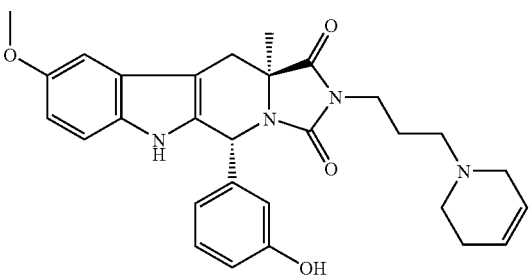 [SMILES: COc1ccc2[nH]c3c(c2c1)C[C@@]1(C)C(=O)N(CCCN2CC=CCC2)C(=O)N1[C@@H]3c1cccc(O)c1] | 501.1 |
| 502. | 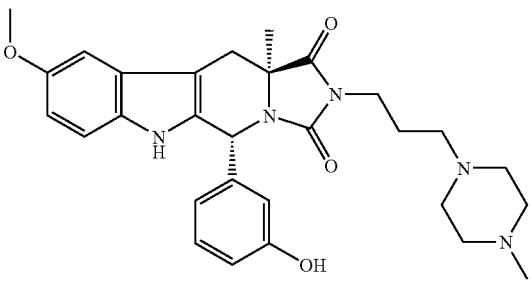 [SMILES: COc1ccc2[nH]c3c(c2c1)C[C@@]1(C)C(=O)N(CCCN2CCN(C)CC2)C(=O)N1[C@@H]3c1cccc(O)c1] | 518.1 |
| 503. | 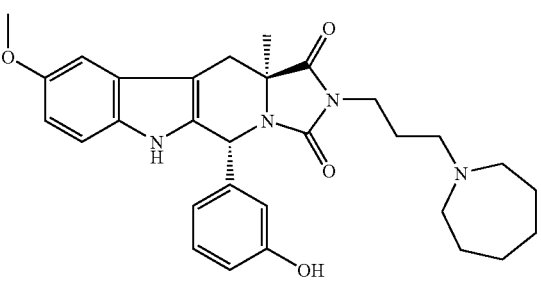 [SMILES: COc1ccc2[nH]c3c(c2c1)C[C@@]1(C)C(=O)N(CCCN2CCCCCC2)C(=O)N1[C@@H]3c1cccc(O)c1] | 517.2 |

-continued
| | | |
|---|---|---|
| 504. | 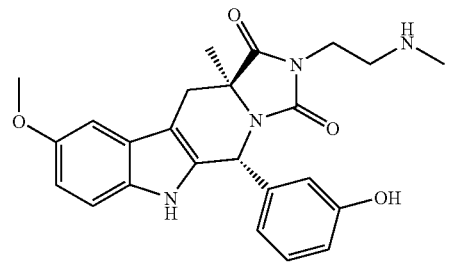 [SMILES: CNCCN1C(=O)N2[C@H](c3cccc(O)c3)c3[nH]c4ccc(OC)cc4c3C[C@@]2(C)C1=O] | 435.0 |
| 505. | 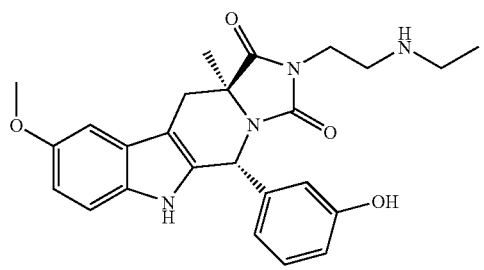 [SMILES: CCNCCN1C(=O)N2[C@H](c3cccc(O)c3)c3[nH]c4ccc(OC)cc4c3C[C@@]2(C)C1=O] | 449.1 |
| 506. | 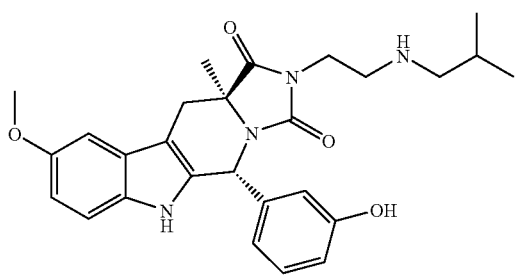 [SMILES: COc1ccc2[nH]c3c(c2c1)C[C@@]1(C)C(=O)N(CCNCC(C)C)C(=O)N1[C@@H]3c1cccc(O)c1] | 477.1 |
| 507. | 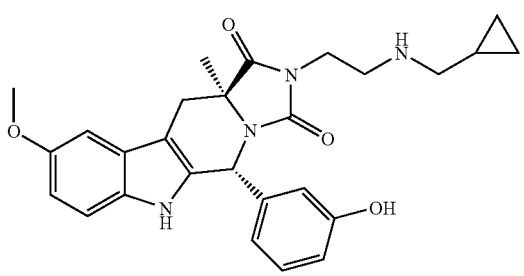 [SMILES: COc1ccc2[nH]c3c(c2c1)C[C@@]1(C)C(=O)N(CCNCC2CC2)C(=O)N1[C@@H]3c1cccc(O)c1] | 475.1 |
| 508. | 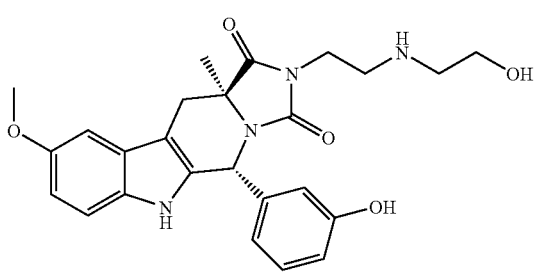 [SMILES: COc1ccc2[nH]c3c(c2c1)C[C@@]1(C)C(=O)N(CCNCCO)C(=O)N1[C@@H]3c1cccc(O)c1] | 465.1 |
| 509. | 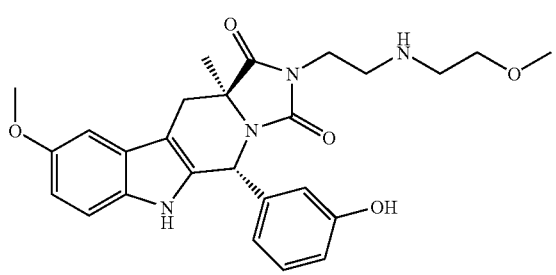 [SMILES: COCCNCCN1C(=O)N2[C@H](c3cccc(O)c3)c3[nH]c4ccc(OC)cc4c3C[C@@]2(C)C1=O] | 479.1 |

-continued
| | | |
|---|---|---|
| 510. | 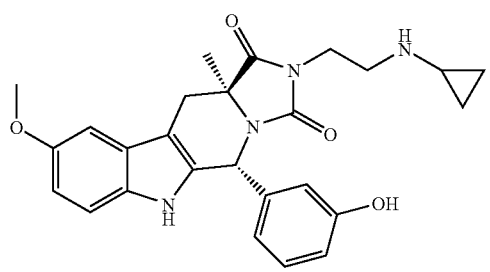 [SMILES: COc1ccc2[nH]c3c(c2c1)C[C@@]1(C)C(=O)N(CCNC2CC2)C(=O)N1[C@@H]3c1cccc(O)c1] | 461.0 |
| 511. | 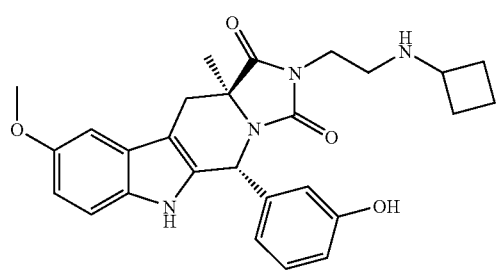 [SMILES: COc1ccc2[nH]c3c(c2c1)C[C@@]1(C)C(=O)N(CCNC2CCC2)C(=O)N1[C@@H]3c1cccc(O)c1] | 475.1 |
| 512. | 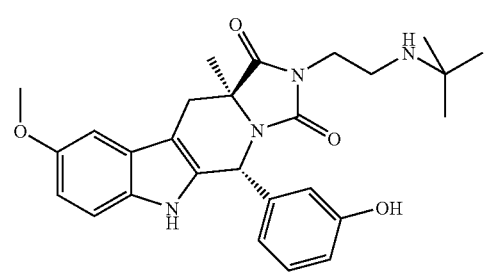 [SMILES: COc1ccc2[nH]c3c(c2c1)C[C@@]1(C)C(=O)N(CCNC(C)(C)C)C(=O)N1[C@@H]3c1cccc(O)c1] | 477.1 |
| 513. | 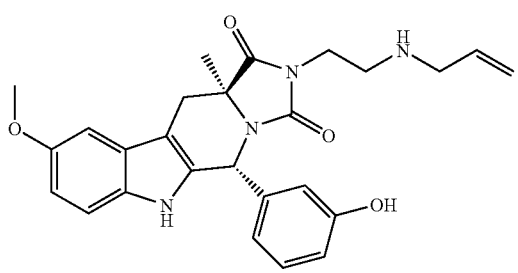 [SMILES: C=CCNCCN1C(=O)N2[C@H](c3cccc(O)c3)c3[nH]c4ccc(OC)cc4c3C[C@@]2(C)C1=O] | 461.1 |
| 514. | 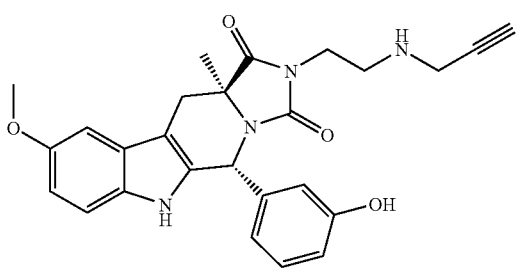 [SMILES: C#CCNCCN1C(=O)N2[C@H](c3cccc(O)c3)c3[nH]c4ccc(OC)cc4c3C[C@@]2(C)C1=O] | 459.0 |

| | | |
|---|---|---|
| 515. | 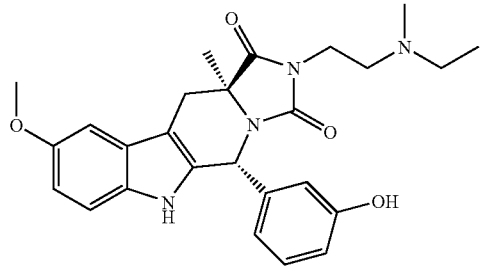 | 463.1 |
| 516. | 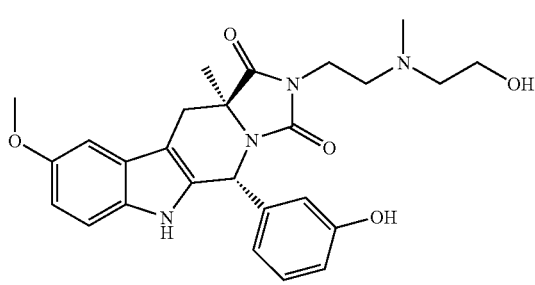 [SMILES: COc1ccc2[nH]c3c(c2c1)C[C@@]1(C)C(=O)N(CCN(C)CCO)C(=O)N1[C@@H]3c1cccc(O)c1] | 479.1 |
| 517. | 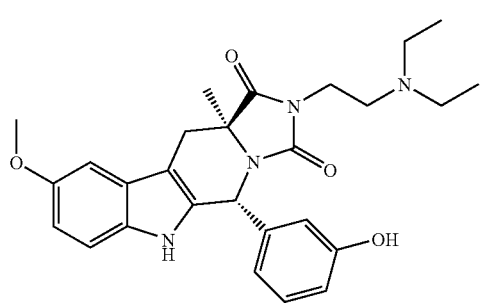 [SMILES: CCN(CC)CCN1C(=O)N2[C@H](c3cccc(O)c3)c3[nH]c4ccc(OC)cc4c3C[C@@]2(C)C1=O] | 477.2 |
| 518. | 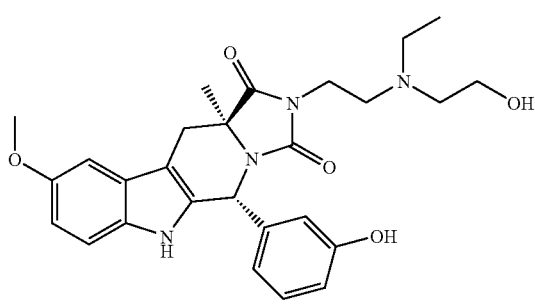 [SMILES: CCN(CCO)CCN1C(=O)N2[C@H](c3cccc(O)c3)c3[nH]c4ccc(OC)cc4c3C[C@@]2(C)C1=O] | 493.1 |
| 519. | 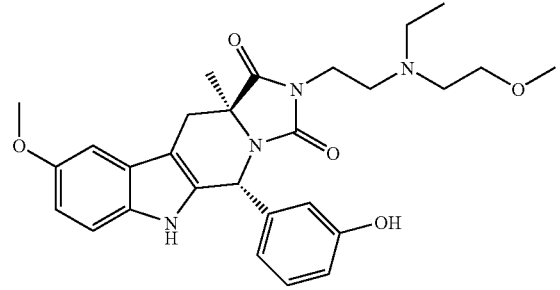 [SMILES: CCN(CCOC)CCN1C(=O)N2[C@H](c3cccc(O)c3)c3[nH]c4ccc(OC)cc4c3C[C@@]2(C)C1=O] | 507.1 |

| | | |
|---|---|---|
| 520. | 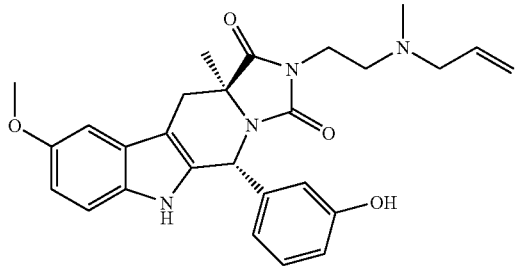 [SMILES: C=CCN(C)CCN1C(=O)N2[C@H](c3cccc(O)c3)c3[nH]c4ccc(OC)cc4c3C[C@@]2(C)C1=O] | 475.1 |
| 521. | 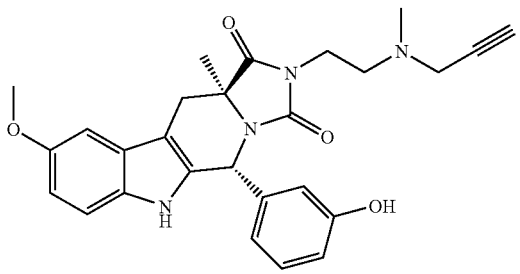 [SMILES: C#CCN(C)CCN1C(=O)N2[C@H](c3cccc(O)c3)c3[nH]c4ccc(OC)cc4c3C[C@@]2(C)C1=O] | 473.1 |
| 522. | 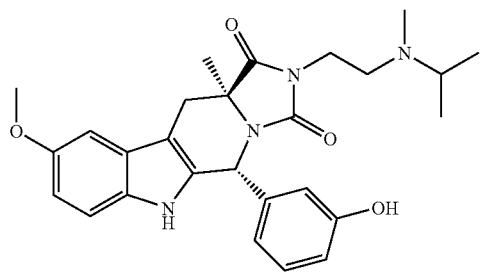 [SMILES: COc1ccc2[nH]c3c(c2c1)C[C@@]1(C)C(=O)N(CCN(C)C(C)C)C(=O)N1[C@@H]3c1cccc(O)c1] | 477.1 |
| 523. | 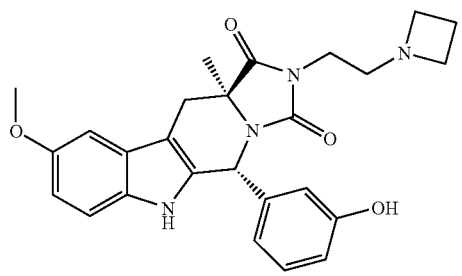 [SMILES: COc1ccc2[nH]c3c(c2c1)C[C@@]1(C)C(=O)N(CCN2CCC2)C(=O)N1[C@@H]3c1cccc(O)c1] | 461.1 |
| 524. | 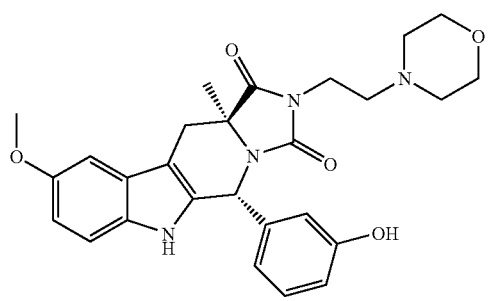 [SMILES: COc1ccc2[nH]c3c(c2c1)C[C@@]1(C)C(=O)N(CCN2CCOCC2)C(=O)N1[C@@H]3c1cccc(O)c1] | 491.1 |

| | | |
|---|---|---|
| 525. | 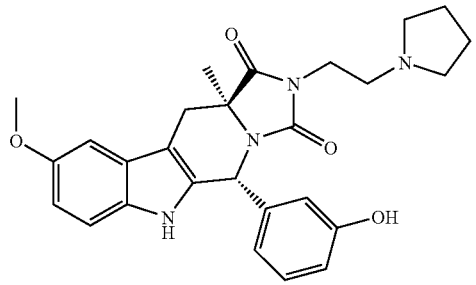 [SMILES: COc1ccc2[nH]c3c(c2c1)C[C@@]1(C)C(=O)N(CCN2CCCC2)C(=O)N1[C@@H]3c1cccc(O)c1] | 475.1 |
| 526. | 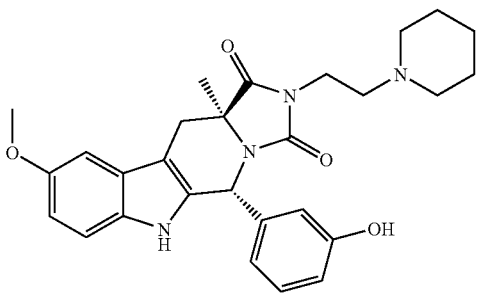 [SMILES: COc1ccc2[nH]c3c(c2c1)C[C@@]1(C)C(=O)N(CCN2CCCCC2)C(=O)N1[C@@H]3c1cccc(O)c1] | 489.1 |
| 527. | 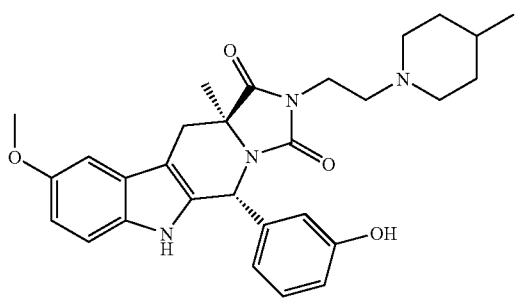 [SMILES: COc1ccc2[nH]c3c(c2c1)C[C@@]1(C)C(=O)N(CCN2CCC(C)CC2)C(=O)N1[C@@H]3c1cccc(O)c1] | 503.1 |
| 528. | 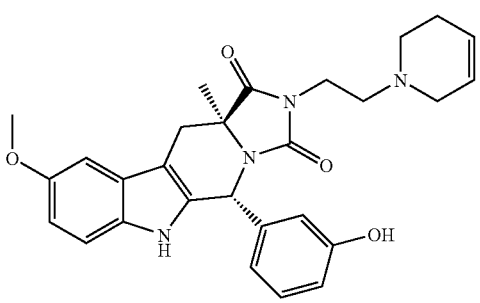 [SMILES: COc1ccc2[nH]c3c(c2c1)C[C@@]1(C)C(=O)N(CCN2CC=CCC2)C(=O)N1[C@@H]3c1cccc(O)c1] | 487.1 |
| 529. | 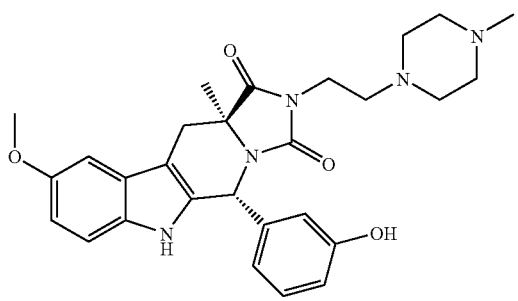 [SMILES: COc1ccc2[nH]c3c(c2c1)C[C@@]1(C)C(=O)N(CCN2CCN(C)CC2)C(=O)N1[C@@H]3c1cccc(O)c1] | 504.1 |

| | | |
|---|---|---|
| 530. | 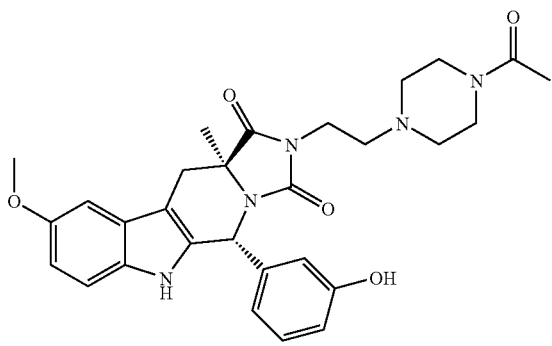 [SMILES: COc1ccc2[nH]c3c(c2c1)C[C@@]1(C)C(=O)N(CCN2CCN(C(C)=O)CC2)C(=O)N1[C@@H]3c1cccc(O)c1] | 532.1 |
| 531. | 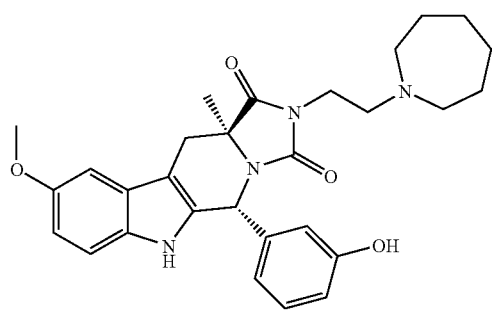 [SMILES: COc1ccc2[nH]c3c(c2c1)C[C@@]1(C)C(=O)N(CCN2CCCCCC2)C(=O)N1[C@@H]3c1cccc(O)c1] | 503.2 |
| 532. | 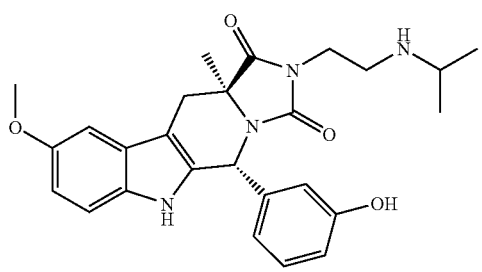 [SMILES: COc1ccc2[nH]c3c(c2c1)C[C@@]1(C)C(=O)N(CCNC(C)C)C(=O)N1[C@@H]3c1cccc(O)c1] | 463.1 |
| 533. | 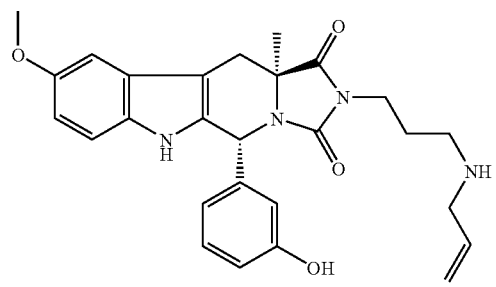 [SMILES: C=CCNCCCN1C(=O)N2[C@H](c3cccc(O)c3)c3[nH]c4ccc(OC)cc4c3C[C@@]2(C)C1=O] | 475.1 |
| 534. | 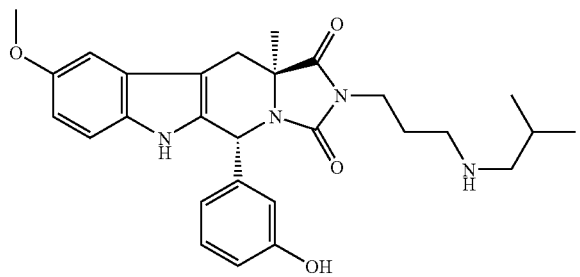 [SMILES: COc1ccc2[nH]c3c(c2c1)C[C@@]1(C)C(=O)N(CCCNCC(C)C)C(=O)N1[C@@H]3c1cccc(O)c1] | 491.2 |

| | | |
|---|---|---|
| 535. | 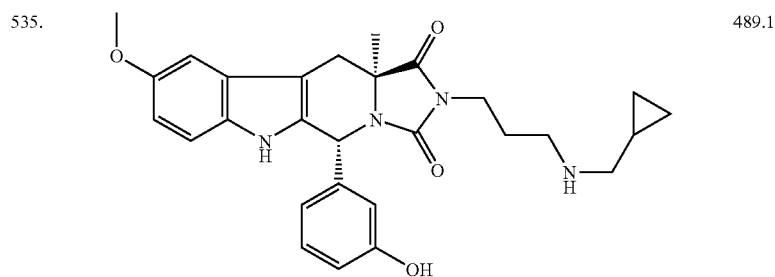 | 489.1 |
| 536. | 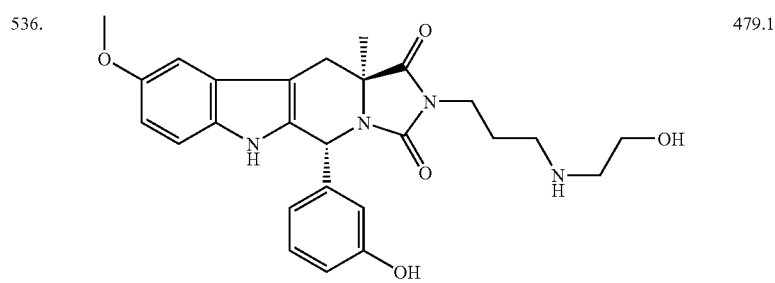 | 479.1 |
| 537. | 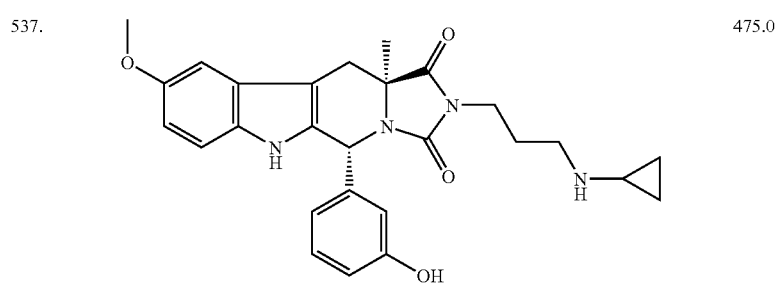 | 475.0 |
| 538. | 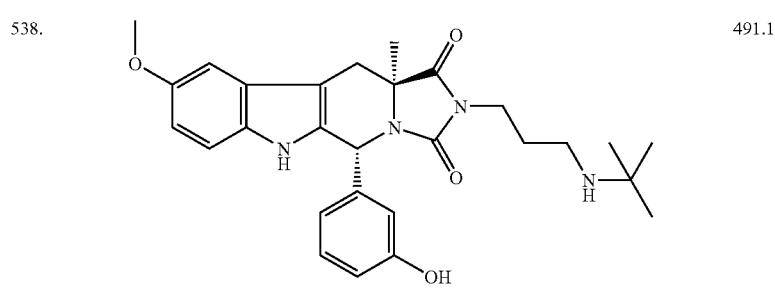 | 491.1 |
| 539. | 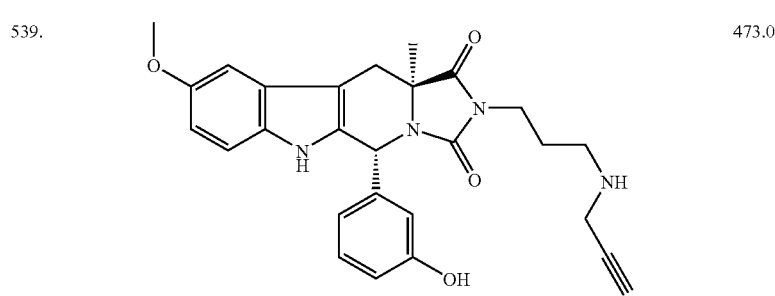 | 473.0 |

-continued

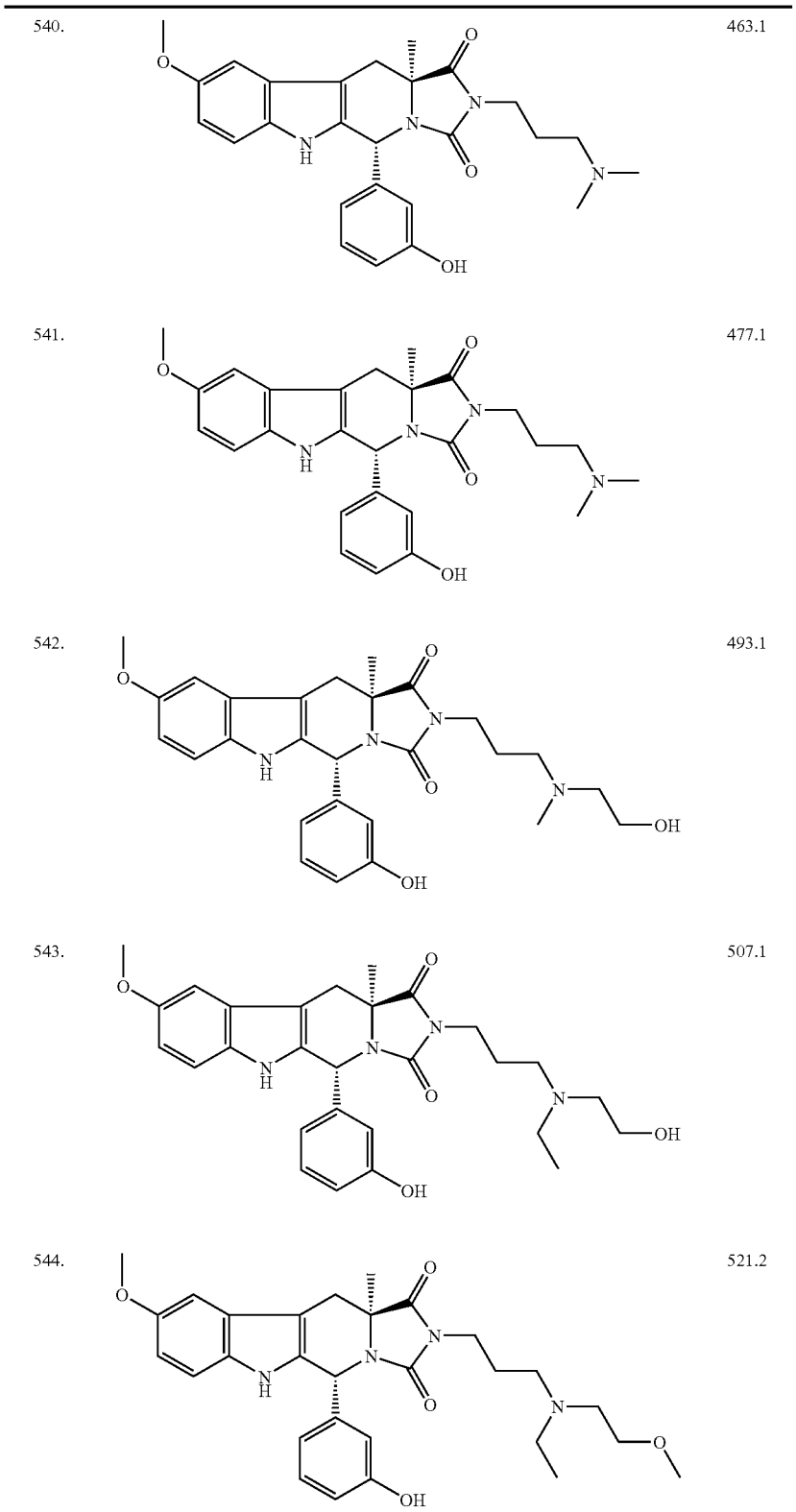

| 540. | 463.1 |
| 541. | 477.1 |
| 542. | 493.1 |
| 543. | 507.1 |
| 544. | 521.2 |

General procedure for the preparation of the salts given in the following table:

A mixture of 100 mg of the appropriate free base, 1.00 equivalents of the corresponding acid and 1 ml of the indicated solvent is heated to reflux. The solution is allowed to cool down to room temperature. The precipitated salt is filtered, washed with solvent and dried at 40° C. under reduced pressure. Some examples contain traces of the solvent.

| name | solvent | m.p. [° C.] |
|---|---|---|
| (3aS,10R)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione, salt with hydrochloric acid | methanol | 259-260 |
| (3aS,10R)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione, salt with methanesulfonic acid | methanol | 174-175 |
| (3aS,10R)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione, salt with p-toluenesulfonic acid | methanol | 274-275 |
| (3aS,10R)-10-(3-Hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione, salt with hydrochloric acid | diisopropyl ether | 156-162 |
| (3aS,10R)-10-(3-Hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione, salt with phosphoric acid | ethanol | 186-191 |
| (3aS,10R)-10-(3-Hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione, salt with sulphuric acid | diisopropyl ether | 105-109 |
| (3aS,10R)-10-(3-Hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione, salt with tartaric acid | ethanol | 196-198 |
| (3aS,10R)-10-(3-Hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione, salt with citric acid | ethanol | 181-184 |
| (3aS,10R)-10-(3-Hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione, salt with hydrochloric acid | ethanol | 291-295 |
| (3aS,10R)-10-(3-Hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione, salt with phosphoric acid | ethanol | 172-176 |
| (3aS,10R)-10-(3-Hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione, salt with sulphuric acid | acetone | >150 decomposition |
| (3aS,10R)-10-(3-Hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione, salt with tartaric acid | ethyl acetate | >120 decomposition |
| (3aS,10R)-10-(3-Hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione, salt with citric acid | ethanol | 170-174 |
| (3aSR,10RS)-6-Ethoxy-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione, salt with hydrochloric acid | ethanol | 291-294 |
| (3aSR,10RS)-6-Ethoxy-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione, salt with citric acid | ethanol | 176-180 |
| (3aSR,10RS)-6-(1,1-Difluoro-methoxy)-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione, salt with hydrochloric acid | ethanol | 240-244 |
| (3aSR,10RS)-6-(1,1-Difluoro-methoxy)-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione, salt with citric acid | ethanol | 133-137 |
| (3aSR,10RS)-6-Bromo-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione, salt with hydrochloric acid | ethanol | 232-236 |
| (3aSR,10RS)-6-Bromo-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione, salt with citric acid | 2-propanol | >119 decomposition |
| (3aS,10R)-10-(3-Hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione, salt with hydrochloric acid | ethanol | 208-212 |
| (3aS,10R)-10-(3-Hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione, salt with phosphoric acid | ethanol | >110 decomposition |
| (3aS,10R)-10-(3-Hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione, salt with tartaric acid | ethanol | 220-222 |
| (3aS,10R)-10-(3-Hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione, salt with citric acid | 2-propanol | >105 decomposition |
| (3aS,10R)-10-(3-Hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione, salt with hydrochloric acid | 2-propanol | 188-192 |
| (3aS,10R)-10-(3-Hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione, salt with phosphoric acid | ethanol | 179-181 |
| (3aS,10R)-10-(3-Hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione, salt with sulphuric acid | ethyl acetate | 205-207 |

| name | solvent | m.p. [° C.] |
|---|---|---|
| (3aS,10R)-10-(3-Hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione, salt with tartaric acid | ethanol | 219-220 |
| (3aS,10R)-10-(3-Hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione, salt with citric acid | ethanol | 174-177 |
| (3aS,10R)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione, salt with phosphoric acid | ethanol | >101 decomposition |
| (3aS,10R)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione, salt with sulphuric acid | acetone | 90-95 |
| (3aS,10R)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione, salt with tartaric acid | ethanol | 197-199 |
| (3aS,10R)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione, salt with citric acid | 2-propanol | >102 decomposition |

Starting Compounds

A1. (1RS,3SR)-1-(3-Hydroxy-phenyl)-6-methoxy-3-methyl-2,3,4,9-tetrahydro-1H-beta-carboline-3-carboxylic acid methyl ester and (1RS,3RS)-1-(3-hydroxy-phenyl)-6-methoxy-3-methyl-2,3,4,9-tetrahydro-1H-beta-carboline-3-carboxylic acid methyl ester To a solution of (+/−)-2-amino-3-(5-methoxy-1H-indol-3-yl)-2-methyl-propionic acid methyl ester (5.178 g, 19.5 mmol) and 3-hydroxybenzaldehyde (2.85 g, 23.4 mmol, 1.2 equiv.) in dry dichloromethane (80 ml) trifluoroacetic acid (1.5 ml, 19.5 mol, 1 equiv.) is added and the mixture is stirred under argon at room temperature. When TLC indicates the disappearance of (+/−)-2-amino-3-(5-methoxy-1H-indol-3-yl)-2-methyl-propionic acid methyl ester (1 day), a little methanol is added to dissolve the product precipitated during the reaction. The mixture is then diluted with dichloromethane (750 ml) and is washed with 2 M aqueous HCl, aqueous NaHCO$_3$ and water, is dried and concentrated. Column chromatography (dichloromethane-ethyl acetate 9:17:1) of the residue gives 5.22 g (73%) of (1RS,3SR)-1-(3-hydroxy-phenyl)-6-methoxy-3-methyl-2,3,4,9-tetrahydro-1H-beta-carboline-3-carboxylic acid methyl ester (m.p. 183-184° C. from ethyl acetate-light petroleum) and 1.07 g (15%) of (1RS,3RS)-1-(3-hydroxy-phenyl)-6-methoxy-3-methyl-2,3,4,9-tetrahydro-1H-beta-carboline-3-carboxylic acid methyl ester (m.p. 175-177° C. from ethyl acetate-light petroleum).

According to NMR experiments (such as the nuclear Overhauser effect), the main product of the Pictet-Spengler reaction is the diasteromer with the configuration (1RS,3SR). This diastereomer has a higher retention factor (silica gel, ethyl acetate-light petroleum ether) than the minor product having the configuration (1RS,3RS).

Enantiomer separation of (1RS,3SR)-1-(3-Hydroxy-phenyl)-6-methoxy-3-methyl-2,3,4,9-tetrahydro-1H-beta-carboline-3-carboxylic acid methyl ester:

58.4 g of racemic (1RS,3SR)-1-(3-Hydroxy-phenyl)-6-methoxy-3-methyl-2,3,4,9-tetrahydro-1H-betacarboline-3-carboxylic acid methyl ester are separated into its enantiomers by preparative HPLC using the following conditions:
column: CHIRALPAK AD 20 µm, 250×50 mm
mobile phase: n-heptane/ethanol/diethylamine 60/40/0.1 (v/v/v)
flow rate: 120 ml/min
detection: UV 315 nm
temperature: 25° C.

29.1 g (−)-1-(3-Hydroxy-phenyl)-6-methoxy-3-methyl-2,3,4,9-tetrahydro-1H-β-carboline-3-carboxylic acid methyl ester {τ=6.5 min, >99.5% ee, $[\alpha]^{20}_D$=−53° (c=0.5200, methanol)} and 27.6 g (+)-1-(3-Hydroxy-phenyl)-6-methoxy-3-methyl-2,3,4,9-tetrahydro-1H-β-carboline-3-carboxylic acid methyl ester {τ=12.7 min, >99.0% ee, $[\alpha]^{20}_D$=+54° (c=0.5150, methanol)} are obtained.

The absolute stereochemistry of (+)-1-(3-Hydroxy-phenyl)-6-methoxy-3-methyl-2,3,4,9-tetrahydro-1H-β-carboline-3-carboxylic acid methyl ester is tentatively assigned to (1R,3S)-1-(3-Hydroxy-phenyl)-6-methoxy-3-methyl-2,3,4,9-tetrahydro-1H-β-carboline-3-carboxylic acid methyl ester.

A2. (1RS,3SR)-6-Ethoxy-1-(3-hydroxy-phenyl)-3-methyl-2,3,4,9-tetrahydro-1H-beta-carboline-3-carboxylic acid methyl ester A mixture of (+/−)-2-amino-3-(5-ethoxy-1H-indol-3-yl)-2-methyl-propionic acid methyl ester (829 mg, 3 mmol), 3-hydroxybenzaldehyde (439 mg, 3.6 mmol) and trifluoroacetic acid (223 µl, 3 mmol) in dry dichloromethane (40 ml) is stirred for 6 h under argon. Methanol (2 ml) is added to dissolve the precipitated product and the mixture is diluted with dichloromethane (150 ml). It is washed with saturated aqueous NaHCO$_3$ (2×50 ml) and water (2×50 ml), is dried, and the solvent is removed under reduced pressure. The residue is purified by column chromatography (dichloromethane-ethyl acetate, 7:1→4:1) to provide (1RS,3SR)-1-(3-hydroxy-phenyl)-6-ethoxy-3-methyl-2,3,4,9-tetrahydro-1H-beta-carboline-3-carboxylic acid methyl ester (1.05 g, 93%). M.p. 173-175° C. (from ethyl acetate-hexane).

A3. (1RS,3SR)-1-(3-Hydroxy-phenyl)-6-(2-methoxy-ethoxy)-3-methyl-2,3,4,9-tetrahydro-1H-beta-carboline-3-carboxylic acid methyl ester and (1RS,3RS)-1-(3-hydroxy-phenyl)-6-(2-methoxy-ethoxy)-3-methyl-2,3,4,9-tetrahydro-1H-beta-carboline-3-carboxylic acid methyl ester To a solution of (+/−)-2-amino-3-[5-(2-methoxy-ethoxy)-1H-indol-3-yl]-2-methyl-propionic acid methyl ester (800 mg, 2.60 mmol) and 3-hydroxybenzaldehyde (383 mg, 3.14 mmol, 1.2 equiv) in dry dichloromethane (20 ml) trifluoroacetic acid (200 µl, 2.6 mmol, 1 equiv) is added and the mixture is stirred under argon at room temperature. When TLC indicated the disappearance of the starting material (1 day), a little methanol is added to dissolve the precipitated product. Then it is diluted with $CH_2Cl_2$ (250 ml) and washed with 2 M aqueous HCl, aqueous $NaHCO_3$ and water, dried, and concentrated. Column chromatography (dichloromethane-ethyl acetate, 7:1→5:1) of the residue gives (1RS,3SR)-1-(3-hydroxy-phenyl)-6-(2-methoxy-ethoxy)-3-methyl-2,3,4,9-tetrahydro-1H-beta-carboline-3-carboxylic acid methyl ester (839 mg, 78%) and (1RS,3RS)-1-(3-hydroxy-phenyl)-6-(2-methoxyethoxy)-3-methyl-2,3,4,9-tetrahydro-1H-beta-carboline-3-carboxylic acid methyl ester (152 mg, 14%).

A4. (1RS,3SR)-6-Chloro-1-(3-hydroxy-phenyl)-3-methyl-2,3,4,9-tetrahydro-1H-beta-carboline-3-carboxylic acid methyl ester Starting from the appropriate starting compounds, the title compound is prepared analogously to the procedure described for compound A1. M.p.: 240-241° C.

A5. (1RS,3SR)-6-Bromo-1-(3-hydroxy-phenyl)-3-methyl-2,3,4,9-tetrahydro-1H-beta-carboline-3-carboxylic acid methyl ester Starting from the appropriate starting compounds, the title compound is prepared analogously to the procedure described for compound A1. m/z ($MH^+$)=415.0/417.1, m.p.: 240-241° C.

Starting from the appropriate compounds B6 to B10, the following compounds A6 to A10 may be prepared using similar procedures to those to attain to compound A1.

A6. (1RS,3SR)-3-Ethyl-1-(3-hydroxy-phenyl)-6-methoxy-2,3,4,9-tetrahydro-1H-beta-carboline-3-carboxylic acid ethyl ester; MS: m/z ($MH^+$)=394.9

A7. (1RS,3SR)-6-Ethoxy-3-ethyl-1-(3-hydroxy-phenyl)-2,3,4,9-tetrahydro-1H-beta-carboline-3-carboxylic acid ethyl ester A8. (1RS,3SR)-3-Ethyl-1-(3-hydroxy-phenyl)-6-(2-methoxy-ethoxy)-2,3,4,9-tetrahydro-1H-betacarboline-3-carboxylic acid ethyl ester A9. (1RS,3SR)-6-Chloro-3-ethyl-1-(3-hydroxy-phenyl)-2,3,4,9-tetrahydro-1H-beta-carboline-3-carboxylic acid ethyl ester A10. (1RS,3SR)-6-Bromo-3-ethyl-1-(3-hydroxy-phenyl)-2,3,4,9-tetrahydro-1H-beta-carboline-3-carboxylic acid ethyl ester A11. (1RS,3SR)-6-Cyclopropylmethoxy-1-(3-hydroxy-phenyl)-3-methyl-2,3,4,9-tetrahydro-1H-β-carboline-3-carboxylic acid methyl ester Starting from the appropriate starting compounds, the title compound is prepared analogously to the procedure described for compound A1. MS: m/z ($MH^+$)=406.9

A12. (1RS,3SR)-6-(1,1-Difluoro-methoxy)-1-(3-hydroxy-phenyl)-3-methyl-2,3,4,9-tetrahydro-1H-β-carboline-3-carboxylic acid methyl ester Starting from the appropriate starting compounds, the title compound is prepared analogously to the procedure described for compound A1. MS: m/z ($MH^+$)=402.9

A13. (1RS,3SR)-6-Trifluoromethoxy-1-(3-hydroxy-phenyl)-3-methyl-2,3,4,9-tetrahydro-1H-β-carboline-3-carboxylic acid methyl ester Starting from the appropriate starting compounds, the title compound may be prepared analogously to the procedure described for compound A1.

Starting from the appropriate compounds B14 to B16, the following compounds A14 to A16 may be prepared using similar procedures to those to attain to compound A1.

A14. (1RS,3SR)-6-Cyclopropylmethoxy-3-ethyl-1-(3-hydroxy-phenyl)-2,3,4,9-tetrahydro-1H-β-carboline-3-carboxylic acid ethyl ester A15. (1RS,3SR)-6-(1,1-Difluoro-methoxy)-3-ethyl-1-(3-hydroxy-phenyl)-2,3,4,9-tetrahydro-1H-β-carboline-3-carboxylic acid ethyl ester A16. (1RS,3SR)-3-Ethyl-1-(3-hydroxy-phenyl)-6-trifluoromethoxy-2,3,4,9-tetrahydro-1H-β-carboline-3-carboxylic acid ethyl ester A17. (1RS,3SR)-5-Fluoro-1-(3-hydroxy-phenyl)-6-methoxy-2,3,4,9-tetrahydro-1H-betacarboline-3-carboxylic acid methyl ester Starting from the appropriate starting compounds, the title compound is prepared analogously to the procedure described for compound A1. m/z ($MH^+$)=385

A18. (1RS,3SR)-7-Fluoro-1-(3-hydroxy-phenyl)-6-methoxy-2,3,4,9-tetrahydro-1H-betacarboline-3-carboxylic acid methyl ester Starting from the appropriate starting compounds, the title compound is prepared analogously to the procedure described for compound A1. m/z ($MH^+$)=385.0

A19. (1RS,3SR)-6-Chloro-7-fluoro-1-(3-hydroxy-phenyl)-2,3,4,9-tetrahydro-1H-beta-carboline-3-carboxylic acid methyl ester Starting from the appropriate starting compounds, the title compound is prepared analogously to the procedure described for compound A1. m/z ($MH^+$)=389

B1. (+/−)-2-Amino-3-(5-methoxy-1H-indol-3-yl)-2-methyl-propionic acid methyl ester To a solution of (+/−)-3-(5-methoxy-1H-indol-3-yl)-2-methyl-2-nitro-propionic acid methyl ester (4.26 g) in methanol (80 mL) wet Raney nickel (ca 12 g) is added, and the mixture is stirred under hydrogen at atmospheric pressure at room temperature overnight. The solid is filtered through Celite, is washed with methanol, and the filtrate is concentrated. Column chromatography of the residue (dichloromethane-methanol, 98:2→95:5) gives the title compound (3.45 g, 90%). M.p. 131-132° C. (from ethyl acetate-light petroleum).

B2. (+/−)-2-Amino-3-(5-ethoxy-1H-indol-3-yl)-2-methyl-propionic acid methyl ester To a stirred solution of (+/−)-3-(5-ethoxy-1H-indol-3-yl)-2-methyl-2-nitro-propionic acid methyl ester (5.3 g, 17.3 mmol) in dry methanol (50 ml) Raney nickel is added and the mixture is stirred at room temperature under $H_2$ at atmospheric pressure overnight. The reaction mixture is filtered through a pad of Celite and the solid is washed with methanol. The filtrate is concentrated and the residue is purified by column chromatography (dichloromethane-methanol, 95:5) to give (+/−)-2-amino-3-(5-ethoxy-1H-indol-3-yl)-2-methyl-propionic acid methyl ester (4.2 g, 90%) as a white crystals. M.p. 165-166° C. (from ethyl acetate-hexane).

B3. (+/−)-2-amino-3-[5-(2-methoxy-ethoxy)-1H-indol-3-yl]-2-methyl-propionic acid methyl ester To a stirred solution of (+/−)-3-[5-(2-methoxy-ethoxy)-1H-indol-3-yl]-2-methyl-2-nitro-propionic acid methyl ester (12.7 g, 37.8 mmol) in dry methanol (200 ml) Raney nickel (ca 20 g) is added and the mixture is stirred at room temperature under H$_2$ at atmospheric pressure overnight. The reaction mixture is filtered through a pad of Celite and the solid is washed with methanol. The filtrate is concentrated and the residue is purified by column chromatography (dichloromethane-methanol, 9:1) to give (+/−)-2-amino-3-[5-(2-methoxy-ethoxy)-1H-indol-3-yl]-2-methyl-propionic acid methyl ester (5.98 g, 52%). M.p. 117-118 (from ethyl acetate-light petroleum).

B4. (+/−)-2-Amino-3-(5-chloro-1H-indol-3-yl)-2-methyl-propionic acid methyl ester Starting from the appropriate starting compounds, the title compound is prepared analogously to the procedure described for compound B1. M.p.: 170° C.

B5. (+/−)-2-Amino-3-(5-bromo-1H-indol-3-yl)-2-methyl-propionic acid methyl ester Starting from the appropriate starting compounds, the title compound is prepared analogously to the procedure described for compound B1. m/z (MH$^+$)=311.0/313.0, m.p.: 181° C.

Starting from the appropriate compounds C6 to C10, the following compounds B6 to B10 may be prepared using similar procedures to those to attain to compound B1.

B6. (+/−)-2-Amino-2-ethyl-3-(5-methoxy-1H-indol-3-yl)-propionic acid ethyl ester; MS: m/z (MH$^+$)=291.0

B7. (+/−)-2-Amino-3-(5-ethoxy-1H-indol-3-yl)-2-ethyl-propionic acid ethyl ester

B8. (+/−)-2-Amino-2-ethyl-3-[5-(2-methoxy-ethoxy)-1H-indol-3-yl]-propionic acid ethyl ester B9. (+/−)-2-Amino-3-(5-chloro-1H-indol-3-yl)-2-ethyl-propionic acid ethyl ester B10. (+/−)-2-Amino-3-(5-bromo-1H-indol-3-yl)-2-ethyl-propionic acid ethyl ester B11. (RS)-2-Amino-3-(5-cyclopropylmethoxy-1H-indol-3-yl)-2-methyl-propionic acid methyl ester Starting from the appropriate starting compounds, the title compound is prepared analogously to the procedure described for compound B1. M.p. 172° C. (from dichloromethane-light petroleum). $^1$H-NMR (CDCl$_3$): 0.36 (m, 2H, cyclopropyl CH$_2$), 0.64 (m, 2H, cyclopropyl CH$_2$), 1.26 (m, 1H, cyclopropyl CH), 1.44 (s, 3H, CMe), 2.95 and 3.23 (2d, 2H, CCH$_2$), 3.61 (s, 3H, OMe), 3.84 (d, 2H, CH$_2$O), 6.85-7.3 (m, 4H, aromatic), 7.95 (bs, 1H, NH).

B12. (RS)-2-Amino-3-[5-(1,1-difluoro-methoxy)-1H-indol-3-yl]-2-methyl-propionic acid methyl ester Starting from the appropriate starting compounds, the title compound is prepared analogously to the procedure described for compound B1. M.p. 140-142° C. (from ethyl acetate-light petroleum). $^1$H-NMR (CDCl$_3$): 1.46 (s, 3H, CMe), 2.93 and 3.30 (2d, 2H, J=14.3 Hz, CH$_2$), 3.60 (bs, 2H, NH$_2$), 3.66 (s, 3H, OMe), 6.53 (t, 1H, J$_{H,F}$=75 Hz, CHF$_2$), 6.95 (dd, 1H, aromatic), 7.08 (bs, 1H, NH), 7.30 (m, 3H, aromatic). $^{13}$C-NMR (CDCl$_3$): 26.2 (CCH$_3$), 36.1 (CH$_2$), 52.2 (OMe), 58.6 (CNH$_2$), 109.6, 112.1, 115.0, 125.5 (aromatic CHs), 109.9, 128.2, 133.9, 144.9 (quaternary aromatic carbons), 168.1 (COOMe).

B13. (RS)-2-Amino-3-(5-trifluoromethoxy-1H-indol-3-yl)-2-methyl-propionic acid methyl ester Starting from the appropriate starting compounds, the title compound may be prepared analogously to the procedure described for compound B1.

Starting from the appropriate compounds C14 to C16, the following compounds B14 to B16 may be prepared using similar procedures to those to attain to compound B1.

B14. (+/−)-2-Amino-3-(5-cyclopropylmethoxy-1H-indol-3-yl)-2-ethyl-propionic acid ethyl ester B15. (+/−)-2-Amino-3-[5-(1,1-difluoro-methoxy)-1H-indol-3-yl]-2-ethyl-propionic acid ethyl ester B16. (+/−)-2-Amino-2-ethyl-3-(5-trifluoromethoxy-1H-indol-3-yl)-propionic acid ethyl ester B17. (RS)-2-Amino-2-(5-methoxy-1H-indol-3-ylmethyl)-3-methyl-butyric acid ethyl ester Starting from the appropriate starting compounds, the title compound is prepared analogously to the procedure described for compound B1. MS: m/z (MH$^+$)=305.0

B18. (RS)-2-Amino-3-(4-fluoro-5-methoxy-1H-indol-3-yl)-2-methyl-propionic acid methyl ester Starting from the appropriate starting compounds, the title compound is prepared analogously to the procedure described for compound B1. m/z (MH$^+$)=264

B19. (RS)-2-Amino-3-(6-fluoro-5-methoxy-1H-indol-3-yl)-2-methyl-propionic acid methyl ester Starting from the appropriate starting compounds, the title compound is prepared analogously to the procedure described for compound B1. m/z (MH$^+$)=264

B20. (RS)-2-Amino-3-(5-chloro-6-fluoro-1H-indol-3-yl)-2-methyl-propionic acid methyl ester Starting from the appropriate starting compounds, the title compound is prepared analogously to the procedure described for compound B1. m/z (MH$^+$)=284.8

C1. (+/−)-3-(5-Methoxy-1H-indol-3-yl)-2-methyl-2-nitro-propionic acid methyl ester A solution of commercially available 5-methoxy gramine (6.24 g) and commercially available methyl 2-nitro-propionate (4.07 g) in a mixture of toluene (50 ml) and N,N-dimethylformamide (2 ml) is refluxed for one day while bubbling argon through the reaction mixture. The solvent is evaporated, the residue is taken up in dichloromethane (300 ml), is washed subsequently with 2 M aqueous HCl, 2 M aqueous NaOH, and water, is dried and concentrated. Column chromatography of the residue (toluene-acetone, 98:2→95:5) gives the title compound (3.42 g, 38%). M.p. 109-110° C. (from ethyl acetate-light petroleum).

C2. (+/−)-3-(5-Ethoxy-1H-indol-3-yl)-2-methyl-2-nitro-propionic acid methyl ester A mixture of (5-ethoxy-1H-indol-ylmethyl)-dimethyl-amine (2.18 g, 10 mmol) and commercially available methyl 2-nitro-propionate (1.60 g, 12 mmol, 1.2 equiv) in dry toluene (17 ml) is refluxed. When TLC (toluene-acetone, 9:1) indicates the absence of starting material the mixture is cooled and is diluted with chloroform (35 ml). It is subsequently washed with 10% aqueous HCl (2×10 ml), water (10 ml), 5% aqueous NaOH (2×10 ml), water (10 ml), and 20% aqueous $Na_2SO_4$ (10 ml), is dried, and the solvents are removed under reduced pressure. The residue is purified by column chromatography (light petroleum-ethyl acetate, 4:1→7:3) to give (+/−)-3-(5-ethoxy-1H-indol-3-yl)-2-methyl-2-nitro-propionic acid methyl ester (2.07 g, 68%) as a white solid. M.p. 80-82° C. (from ethyl acetate-hexane).

C3. (+/−)-3-[5-(2-Methoxy-ethoxy)-1H-indol-3-yl]-2-methyl-2-nitro-propionic acid methyl ester To a solution of (5-(2-methoxy-ethoxy)-1H-indol-ylmethyl)-dimethyl-amine (15.2 g, 61.4 mmol) in a mixture of toluene (100 ml) and N,N-dimethylformamide (50 ml) methyl 2-nitropropionate (8.5 g, 63.9 mmol) is added. The mixture is refluxed for 2 days with stirring while a rapid stream of argon is passed through the solution. The solvent is evaporated, the residue is taken up in dichloromethane (600 ml), is washed subsequently with 2 M hydrochloric acid, 2 M aqueous NaOH, and water, is dried and evaporated. Column chromatography of the residue (toluene-acetone, 9:1) provides (+/−)-3-[5-(2-methoxy-ethoxy)-1H-indol-3-yl]-2-methyl-2-nitro-propionic acid methyl ester (9.34 g, 45%).

C4. (+/−)-3-(5-Chloro-1H-indol-3-yl)-2-methyl-2-nitro-propionic acid methyl ester Starting from the appropriate starting compounds, the title compound is prepared analogously to the procedure described for compound C1.

C5. (+/−)-3-(5-Bromo-1H-indol-3-yl)-2-methyl-2-nitro-propionic acid methyl ester Starting from the appropriate starting compounds, the title compound is prepared analogously to the procedure described for compound C1.

Starting from ethyl 2-nitrobutyrate and with choice of the appropriate amine compound D1 to D5 as reaction partner, the following compounds C6 to C10 may be prepared using similar procedures to those to attain to compound C1.

C6. (+/−)-2-Ethyl-3-(5-methoxy-1H-indol-3-yl)-2-nitro-propionic acid ethyl ester; MS: m/z (MH$^+$)=320.2

C7. (+/−)-3-(5-Ethoxy-1H-indol-3-yl)-2-ethyl-2-nitro-propionic acid ethyl ester

C8. (+/−)-2-Ethyl-3-[5-(2-methoxy-ethoxy)-1H-indol-3-yl]-2-nitro-propionic acid ethyl ester

C9. (+/−)-3-(5-Chloro-1H-indol-3-yl)-2-ethyl-2-nitro-propionic acid ethyl ester

C10. (+/−)-3-(5-Bromo-1H-indol-3-yl)-2-ethyl-2-nitro-propionic acid ethyl ester

C11. (RS)-3-(5-Cyclopropylmethoxy-1H-indol-3-yl)-2-methyl-2-nitro-propionic acid methyl ester Starting from compound D6, the title compound is prepared analogously to the procedure described for compound C1. $^1$H-NMR (CDCl$_3$): 0.39 (m, 2H, cyclopropyl CH$_2$), 0.68 (m, 2H, cyclopropyl CH$_2$), 1.32 (m, 1H, cyclopropyl CH), 1.74 (s, 3H, CMe), 3.59 and 3.81 (2d, 2H, CCH$_2$), 3.82 (s, 3H, OMe), 3.82-3.87 (m, 2H, CH$_2$O), 6.86-7.3 (m, 4H, aromatic), 8.06 (bs, 1H, NH)

C12. (RS)-3-[5-(1,1-Difluoro-methoxy)-1H-indol-3-yl]-2-methyl-2-nitro-propionic acid methyl ester Starting from compound D7, the title compound is prepared analogously to the procedure described for compound C1. $^1$H-NMR (CDCl$_3$): 1.73 (s, 3H, CMe), 3.57 and 3.75 (2d, 2H, J=15 Hz, CH$_2$), 3.76 (s, 3H, OMe), 6.49 (t, 1H, $J_{H,F}$=75 Hz, CHF$_2$), 6.92-7.36 (m, 3H, aromatic), 8.42 (bs, 1H, NH). $^{13}$C-NMR (CDCl$_3$): 21.3 (CCH$_3$), 32.2 (CH$_2$), 53.5 (OMe), 93.6 (CNO$_2$), 109.4, 112.3, 115.6, 126.2 (aromatic CHs), 107.4, 128.3, 133.6, 145.2 (quaternary aromatic carbons), 168.1 (COOMe)

C13. (RS)-3-(5-Trifluoromethoxy-1H-indol-3-yl)-2-methyl-2-nitro-propionic acid methyl ester Starting from compound D8, the title compound may be prepared analogously to the procedure described for compound C1.

Starting from ethyl 2-nitrobutyrate and with choice of the appropriate amine compound D6 to D8 as reaction partner, the following compounds C14 to C16 may be prepared using similar procedures to those to attain to compound C1.

C14. (+/−)-3-(5-Cyclopropylmethoxy-1H-indol-3-yl)-2-ethyl-2-nitro-propionic acid ethyl ester

C15. (+/−)-3-[5-(1,1-Difluoro-methoxy)-1H-indol-3-yl]-2-ethyl-2-nitro-propionic acid ethyl ester

C16. (+/−)-2-Ethyl-2-nitro-3-(5-trifluoromethoxy-1H-indol-3-yl)-propionic acid ethyl ester

C17. (RS)-2-(5-Methoxy-1H-indol-3-ylmethyl)-3-methyl-2-nitro-butyric acid ethyl ester Starting from 3-methyl-2-nitro-butyric acid ethyl ester and compound D1, the title compound is prepared analogously to the procedure described for compound C1. In this case 1 equivalent potassium hydrogen carbonate is added to the reaction mixture. MS: m/z (MH$^+$)=334.9

C18. (RS)-3-(4-Fluoro-5-methoxy-1H-indol-3-yl)-2-methyl-2-nitro-propionic acid methyl ester Starting from the appropriate starting compounds, the title compound is prepared analogously to the procedure described for compound C1. m/z (MH$^+$)=310.7

C19. (RS)-3-(6-Fluoro-5-methoxy-1H-indol-3-yl)-2-methyl-2-nitro-propionic acid methyl ester Starting from the appropriate starting compounds, the title compound is prepared analogously to the procedure described for compound C1. m/z (MH$^+$)=310.6

C20. (RS)-3-(6-Chloro-5-methoxy-1H-indol-3-yl)-2-methyl-2-nitro-propionic acid methyl ester Starting from the appropriate starting compounds, the title compound is prepared analogously to the procedure described for compound C1. m/z (M–H$^+$)$^-$=313.2

D1. (5-Methoxy-1H-indol-3-ylmethyl)-dimethyl-amine

The title compound (5-methoxy-gramine) is commercially available.

D2. (5-Ethoxy-1H-indol-3-ylmethyl)-dimethyl-amine

A mixture of 5-ethoxy-indole (7.84 g, 48.7 mmol), 40% aqueous dimethylamine (9.25 ml, 73 mmol, 1.5 equiv), and 96% acetic acid (30 ml) is stirred at 0° C., then 36% aqueous formaldehyde solution (6.33 ml, 82.7 mmol, 1.7 equiv) is added drop wise. The mixture is allowed to come to room temperature, and after stirring overnight TLC (dichloromethane-methanol, 4:1) indicates the absence of starting material. 10% Aqueous NaOH (150 ml) is added and the mixture is stirred at room temperature for 2 h. It is then extracted with dichloromethane (4×200 ml), the organic layer is dried and concentrated. The residue is purified by column chromatography (dichloromethane-methanol, 4:1→methanol-aqueous ammonia 50:1) to give crude product (10.18 g, 96%), which is crystallized from acetone to provide pure (5-ethoxy-1H-indol-ylmethyl)-dimethyl-amine (10.2 g, 96%) as white crystals. M.p. 95-97° C.

D3. [5-(2-Methoxy-ethoxy)-1H-indol-3-ylmethyl]-dimethyl-amine

A solution of 5-(2-methoxy-ethoxy)-indole (2.06 g, 11.0 mmol) in acetic acid (7 ml) and 40% aqueous dimethylamine (2.1 ml) is cooled to 0° C., and 36% aqueous formaldehyde (1.38 ml) (pre-cooled to 0° C.) is added drop wise. The mixture is stirred at room temperature overnight, 2 M hydrochloric acid is added, and the mixture is washed with dichloromethane. The aqueous layer is made alkaline with 10% NaOH, and is extracted with dichloromethane. The combined organic layer is washed with water, is dried and concentrated. The residue is purified by column chromatography (dichloromethane-methanol, 4:1→dichloromethane-methanol-water-aqueous ammonia, 10:20:1:1) to afford [5-(2-methoxy-ethoxy)-1H-indol-ylmethyl]-dimethyl-amine (2.42 g, 90%). M.p. 163-164° C. (from toluene-N,N-dimethylformamide).

D4. (5-Chloro-1H-indol-3-ylmethyl)-dimethyl-amine

Starting from the appropriate starting compounds, the title compound is prepared analogously to the procedure described for compound D2 or D3. M.p.: 127-130° C.

D5. (5-Bromo-1H-indol-3-ylmethyl)-dimethyl-amine

Starting from the appropriate starting compounds, the title compound is prepared analogously to the procedure described for compound D2 or D3. M.p.: 139° C.

D6. (5-Cyclopropylmethoxy-1H-indol-3-ylmethyl)-dimethyl amine

Starting from the appropriate starting compounds, the title compound is prepared analogously to the procedure described for compound D2 or D3. $^1$H-NMR (CDCl$_3$): 0.36 (m, 2H, cyclopropyl CH$_2$), 0.64 (m, 2H, cyclopropyl CH$_2$), 1.26 (m, 1H, cyclopropyl CH), 2.34 (s, 6H, 2 NMe$_2$), 3.8 (m, 2H, CH$_2$O), 6.8-7.4 (m, 4H, aromatic), 8.84 (bs, 1H, NH)

D7. [5-(1,1-Difluoro-methoxy)-1H-indol-3-ylmethyl]-dimethyl amine

Starting from the appropriate starting compounds, the title compound is prepared analogously to the procedure described for compound D2 or D3. $^1$H-NMR (CDCl$_3$+CD$_3$OD): 2.30 (s, 6H, NMe$_2$), 3.66 (s, 2H, CH$_2$), 6.53 (t, 1H, J$_{H,F}$=75 Hz, CHF$_2$), 6.95 (dd, 1H, aromatic), 7.2-7.4 (m, 3H, aromatic). $^{13}$C-NMR (CDCl$_3$): 44.4 (NMe$_2$), 53.6 (CH$_2$), 109.2, 109.7, 112.1, 114.8, 126.6, 128.1, 133.9, 145.0 (aromatic)

D8. [5-Trifluoromethoxy-1H-indol-3-ylmethyl]-dimethyl amine

Starting from the appropriate starting compounds, the title compound may be prepared analogously to the procedure described for compound D2 or D3.

D9. (4-Fluoro-5-methoxy-1H-indol-3-ylmethyl)-dimethyl amine

Starting from the appropriate starting compounds, the title compound is prepared analogously to the procedure described for compound D2 or D3. m/z (MH$^+$)=222.8

D10. (6-Fluoro-5-methoxy-1H-indol-3-ylmethyl)-dimethyl amine

Starting from the appropriate starting compounds, the title compound is prepared analogously to the procedure described for compound D2 or D3. m/z (MH$^+$)=222.6

D11. (5-Chloro-5-fluoro-1H-indol-3-ylmethyl)-dimethyl amine

Starting from the appropriate starting compounds, the title compound is prepared analogously to the procedure described for compound D2 or D3. m/z (MH$^+$)=226.8

E1. 5-Ethoxy-indole

A mixture of commercially available 5-hydroxy-indole (18 g, 13.5 mmol), anhydrous $K_2CO_3$ (93.5 g, 5 equiv) and iodo-ethane (40.5 ml, 3.75 equiv) in acetone (180 mL) is stirred at 50° C. under argon. When TLC (dichloromethane-methanol, 95:5) indicates the disappearance of 5-hydroxy-indole (4 days), the mixture is filtered, the solid is washed with acetone, then the filtrate is concentrated to give 17.67 g (90%) of the title compound, which is sufficiently pure to be used in the next step. M.p. 144-146° C. (from ethanol).

E2. 5-(2-Methoxy-ethoxy)-1H-indole

To a solution of 5-hydroxy-indole (15.2 g, 114 mmol) in 250 ml of dry acetone 2-methoxyethyl iodide (15 ml, 141 mmol, 1.25 equiv) and anhydrous $K_2CO_3$ (46.7 g, 338 mmol, 3 equiv) are added and the mixture is refluxed. Additional amounts of 0.5 equiv of 2-methoxyethyl iodide and $K_2CO_3$ are added each day. After 6 days TLC (toluene-acetone, 9:1) indicates the absence of starting material. The solid is removed by filtration, and the solvent is evaporated. The residue is taken up in dichloromethane (800 ml) and the solution is washed with 2 M aqueous HCl, 10% aqueous $NaHCO_3$, and water. The organic layer is dried and concentrated. Column chromatography (toluene-acetone, 9:1) provides 5-(2-methoxyethoxy)-1H-indole (18.8 g, 86%). M.p. 58-60° C. (from ethyl acetate-light petroleum).

E3. 5-Chloro-1H-indole

The title compound is commercially available.

E4. 5-Bromo-1H-indole

The title compound is commercially available.

E5. 5-Cyclopropylmethoxy-1H-indol

To a solution of 7.3 g 5-hydroxy-indole in 130 ml of dry acetone are added 10.5 ml bromomethyl cyclopropane and 22.7 g anhydrous potassium carbonate. The mixture is heated to reflux for 24 h and an additional amount of 5 ml bromomethyl cyclopropane are added. The mixture is heated to reflux for additional 4 days. The mixture is filtered and the solvent is removed under reduced pressure. The residue is dissolved in dichloro methane and washed with an aqueous solution of hydrochloric acid (2 M), 10% aq. $NaHCO_3$ and water. The organic layer is dried and the solvent is removed under reduced pressure. After purification by column chromatography (silica gel; toluene, acetone 95:5), 9.62 g, 94%) of the title compound are obtained as an oil. $^1$H-NMR ($CDCl_3$): 0.36 (m, 2H, cyclopropyl $CH_2$), 0.64 (m, 2H, cyclopropyl $CH_2$), 1.30 (m, 1H, cyclopropyl CH), 3.83 (d, 2H, J=7.0 Hz, $CH_2O$), 6.45 (s, 1H, aromatic), 6.90 (dd, 1H, aromatic), 7.09-7.27 (m, 3H, aromatic), 8.05 (bs, 1H, NH). $^{13}$C-NMR ($CDCl_3$): 3.1 (2 cyclopropyl $CH_2$), 10.4 (cyclopropyl CH), 74.2 ($CH_2O$), 101.2, 101.6, 104.0, 104.6, 149.8 (aromatic)

E6. 5-(1,1-Difluoro-methoxy)-1H-indol

Chlorodifluoromethane is bubbled trough an ice-cooled solution of 6.65 g 5-hydroxy-indole and 3.69 g tetrabutylammonium iodide in a mixture of 70 ml dioxane and 20 ml of an aqueous solution of sodium hydroxide (50%). After TLC indicating the absence of starting material, 500 ml dichloromethane are added. The mixture is washed with water. The organic layer is dried and the solvent is removed under reduced pressure. After column chromatography (silica gel; toluene, acetone 99:1), 2.19 g (24%) of the title compound are obtained as a colorless liquid. MS: [M+H]: 184.1, [M−H]: 182.0. $^1$H-NMR ($CDCl_3$): 6.48 (t, 1H, $J_{H,F}$=75 Hz, $CHF_2$), 6.52 (m, 1H, aromatic), 6.98 (dd, 1H, aromatic), 7.2-7.4 (m, 3H, aromatic). $^{13}$C-NMR ($CDCl_3$): 103.0, 111.5, 111.9, 115.4, 117.1, 122.2, 126.0, 128.4, 133.6 (aromatic carbons)

E7. 5-Trifluoromethoxy-1H-indol

The title compound may be obtained from 5-hydroxy-1H-indol by trifluoromethylation reaction.

E8. 6-Fluoro-5-methoxy-1H-indole and

E9. 4-Fluoro-5-methoxy-1H-indole

Both title compounds are prepared analogously to a procedure described in WO2003/064413 (p. 91f) for the preparation of 4-fluoro-5-methoxyindole and 6-fluoro-5-methoxyindole as a mixture. In this case, the regioisomeric intermediates (4-fluoro-5-methoxy-2-nitro-phenyl)-acetonitrile and (2-fluoro-3-methoxy-6-nitro-phenyl)-acetonitrile are separated by a sequence of crystallization of (4-fluoro-5-methoxy-2-nitro-phenyl)-acetonitrile (m/z ($MH^+$)=166.1) from 2-propanol followed by crystallization of (2-fluoro-3-methoxy-6-nitro-phenyl)-acetonitrile (m/z ($MH^+$)=166.1) from toluene using the mother liquid of the previous crystallization.

E10. 5-Chloro-6-fluoro-1H-indole

To a suspension of 12.4 g sodium 1-acetyl-6-fluoro-1H-indole-2-sulfonate in 30 ml acetonitrile are added 7.1 g N-chlorsuccinimid. The mixture is stirred at room temperature for 2 hours and heated to 110° C. 450 ml of an aqueous solution of sodium hydroxide (1 M) are added. The solution is stirred at 110° C. for 1 hour and cooled to 0° C. The organic layer is separated and the solvent is removed. After purification of the residue by column chromatography (heptane/methyl tert.-butyl ether), 7.82 g (39%) of the title compound are obtained. m/z $(M-H^+)^-$=168.0

F1. 2-Methoxyethyl iodide

The crude 2-methoxyethyl tosylate is dissolved in 1600 ml of acetone and NaI (300 g, 2 mol, 2 equiv) is added. The mixture is heated to reflux and the progress of the reaction is monitored by TLC (toluene-acetone, 9:1). After 3 h the mixture is cooled to room temperature and the solid is removed by filtration. The solvent is evaporated, the residue is taken up in dichloromethane (700 ml) and is washed with 10% aqueous $Na_2S_2O_3$ and water. The organic layer is dried and the solvent evaporated. The residue is distilled at reduced pressure to yield 108 g (58%) of 2-methoxyethyl iodide. B.p. 34-36° C. at 30 mbar.

G1. Toluene-4-sulfonic acid 2-methoxy-ethyl ester

A slurry of p-toluenesulfonyl chloride (205 g, 1.08 mol) and pyridine (150 mL) is stirred under an argon atmosphere. The temperature is maintained below 5° C. (ice-water bath), while ethylene glycol monomethyl ether (80 ml, 1 mol) is added slowly from a dropping funnel. After the addition is complete, the mixture is stirred for 1 h below 5° C. The mixture is poured into ice-water (1 L) and is extracted with

H1. 3-Methyl-2-nitro-butyric acid ethyl ester

To an ice cooled solution of 5.31 g sodium nitrite and 8 g dried phloroglucinol in 70 ml dimethyl formamide is added a solution of 11.3 g 2-iodo-3-methyl-butyric acid ethyl ester in 30 ml dimethyl formamide. The solution is allowed to warm up to room temperature and is stirred over night. The solvent is removed at reduced pressure. The residue is dissolved in ethyl acetate and washed with water. The organic layer is dried and the solvent is removed. The title compound is obtained as an oil. MS: m/z $(M^+)$=176.1

I1. 2-Iodo-3-methyl-butyric acid ethyl ester

A mixture of 10 g commercially available ethyl-2-bromo isovalerate and 17.8 g sodium iodide in 150 ml acetone are heated to reflux over night. The solvent is removed under reduced pressure. Dichloromethane is added to the residue and the solution is washed with an aqueous solution (10%) of sodium thiosulfate and brine. The organic layer is dried and the solvent is removed under reduced pressure. 11.34 g (93%) of the title compound are obtained as a yellowish oil. MS: m/z $(M^+)$=255.9

J1. Sodium 1-acetyl-6-fluoro-1H-indole-2-sulfonate

A mixture of 14.0 g 6-fluoro-1H-indole-2-sulfonate and 87 ml acetic anhydride are stirred for 20 min at 70° C. 35 ml additional acetic anhydride are added and the temperature is kept at 70° C. for 15 min. Additional 46 ml acetic anhydride are added and the temperature is increased to 110° C. After 1 hour, the temperature is reduced to 90° C. for additional 90 min. After cooling to room temperature, 180 ml diethyl ether are added. The precipitate is filtered and dried under reduced pressure. 12.5 g (76%) of the title compound are obtained as a colourless solid. m/z $(M-H^+)^-$=258

K1. Sodium 6-Fluoro-1H-indole-2-sulfonate

To a solution of 23.4 g sodium bisulfite in 80 ml water a solution of 13.5 g 6-fluoro indole in ethanol is added drop wise. The obtained suspension is stirred at room temperature over night. The precipitate is filtered and washed with cold water, cold methanol and diethyl ether. 7.0 g (29%) of the title compound are obtained as a colourless solid.

Commercial Utility

The compounds according to the present invention have valuable pharmacological properties which can make them commercially applicable. Thus, for example, the compounds according to this invention can act as inhibitors of the mitotic kinesin Eg5 and these compounds are expected to be commercially applicable in the therapy of diseases responsive to the inhibition of this kinesin, such as e.g. those diseases mentioned below. Also, for example, the compounds according to this invention can display cell-cycle dependent, antiproliferative and/or apoptosis inducing activity.

The mitotic kinesin Eg5 is an enzyme essential for the assembly and function of the bipolar mitotic spindle. Eg5 plays essential roles during various phases of mitosis. Drugs that perturb mitosis have proven clinically effective in the treatment of many cancers. Despite the diverse array of essential spindle proteins that could be exploited as targets for the discovery of novel cancer therapies, all spindle-targeted therapeutics in clinical use today act on only one protein, tubulin. Surprisingly, kinesin Eg5 expression is most abundant in proliferating human tissues, whereas it is absent from most postmitotic cells, such as e.g. human central nervous system neurons, consistent with an exclusive or almost confined role for Eg5 in cell proliferation. In contrary to drugs that directly interfere with microtubule dynamic instability, Eg5 kinesin inhibitors are expected not to disrupt microtubule-based cellular processes, e.g. neuronal transport, that are unrelated to proliferation. During mitosis, Eg5 is essentially involved in organizing microtubules into a bipolar structure that forms the mitotic spindle. Experimental perturbation of Eg5 function causes a characteristic malformation or dysfunction of the mitotic spindle, frequently resulting in cell cycle arrest and cell death.

The compounds according to this invention can be used to modulate mitotic spindle formation, thus causing prolonged cell cycle arrest in mitosis, which is frequently followed by apoptosis. By "modulate" herein is meant altering mitotic spindle formation, including increasing and decreasing spindle formation. By "mitotic spindle formation" herein is meant organization of microtubules into bipolar structures by mitotic kinesins. By "dysfunction of the mitotic spindle" herein is meant mitotic arrest and monopolar spindle formation. "Malformation of the mitotic spindle" encompasses the splaying of mitotic spindle poles, or otherwise causing morphological perturbation of the mitotic spindle.

Further on, these compounds can be useful in the treatment of benign or malignant neoplasia. A "neoplasia" is defined by cells displaying aberrant cell proliferation and/or survival and/or a block in differentiation. A "benign neoplasia" is described by hyperproliferation of cells, incapable of forming an aggressive, metastasizing tumor in-vivo. In contrast, a "malignant neoplasia" is described by cells with multiple cellular and biochemical abnormalities, capable of forming a systemic disease, for example forming tumor metastasis in distant organs.

Various diseases are caused by aberrant cell proliferation ("hyperproliferation") as well as evasion from apoptosis. These diseases include e.g. benign hyperplasia like that of the prostate ("BPH") or colon epithelium, psoriasis, glomerulonephritis or osteoarthritis. Most importantly these diseases include malignant neoplasia commonly described as cancer and characterized by tumor cells finally metastasizing into distinct organs or tissues. Malignant neoplasia include solid and hematological tumors. Solid tumors are exemplified by tumors of the breast, bladder, bone, brain, central and peripheral nervous system, colon, endocrine glands (eg thyroid and adrenal cortex), esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva. Malignant neoplasia include inherited cancers exemplified by retinoblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

It is to be noted that a cancer disease as well as a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Neoplastic cell proliferation might affect normal cell behaviour and organ function. For example the formation of new blood vessels, a process described as neovascularization, is induced by tumors or tumor metastases. Compounds according to this invention can be commercially applicable for the treatment of pathophysiological relevant processes caused by benign or neoplastic cell proliferation, such as but not limited to neovascularization by unphysiological proliferation of vascular endothelial cells.

Drug resistance is of particular importance for the frequent failure of standard cancer therapeutics. This drug resistance is caused by various cellular and molecular mechanisms like overexpression of drug efflux pumps or mutation within the cellular target protein. The commercial applicability of the compounds according to this invention is not limited to $1^{st}$ line treatment of patients. Patients with resistance to defined cancer chemotherapeutics or target specific anti-cancer drugs ($2^{nd}$ or $3^{rd}$ line treatment) can be also amenable for treatment with the compounds according to this invention.

Due to their cellular anti-proliferative properties, compounds according to the present invention may be also commercially usable for treatment of diseases associated with cell cycle and cell proliferation, such as, besides cancer discussed above, for example, fibroproliferative and differentiative disorders, psoriasis, rheumatoid arthritis, atherosclerosis, hyperplasia, restenosis, cardiac hypertrophy, (auto)immune disorders, fungal disorders, bone diseases, or acute or chronic inflammation.

Compounds according to the present invention can be commercially applicable for treatment, prevention or amelioration of the diseases of benign and malignant behavior as described before, such as e.g. benign or malignant neoplasia, particularly cancer (such as e.g. any of those cancer diseases described above), especially a cancer that is susceptible to Eg5 inhibition.

In the context of their properties, functions and usabilities mentioned herein, the compounds according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability.

The invention further includes a method for treating (hyper)proliferative diseases and/or disorders responsive to the induction of apoptosis, particularly those diseases, disorders, conditions or illnesses mentioned above, in mammals, including humans, suffering therefrom comprising administering to said mammals in need thereof a pharmacologically active and therapeutically effective and tolerable amount of one or more of the compounds according to this invention.

The present invention further includes a method useful to modulate apoptosis and/or aberrant cell growth in the therapy of benign or malignant neoplastic diseases, such as e.g. cancer, comprising administering to a subject in need of such therapy a pharmacologically active and therapeutically effective and tolerable amount of one or more of the compounds according to this invention.

The invention further includes a method for modulating, particularly inhibiting, Eg5 activity in cells comprising administering a pharmacologically active and therapeutically effective and tolerable amount of one or more of the compounds according to this invention to a patient in need of such modulation, particularly inhibition.

The present invention further includes a method to modulate the mitotic spindle, i.e., for example, altering mitotic spindle formation, including decreasing spindle formation, or increasing or decreasing spindle pole separation causing malformation of the mitotic spindle poles, comprising administering a pharmacologically active and therapeutically effective and tolerable amount of one or more of the compounds according to this invention to a patient in need of such modulation.

The present invention further includes a method to inhibit mitosis in cells comprising administering a pharmacologically active and therapeutically effective and tolerable amount of one or more of the compounds according to this invention to a patient in need of such inhibition.

The present invention further includes a method for treating, preventing or ameliorating diseases and/or disorders associated with Eg5 kinesin activity, such as, for example, (hyper)proliferative diseases and/or disorders responsive to induction of apoptosis, for example, benign or malignant neoplasia, e.g. cancer, in a mammal comprising administering a pharmacologically active and therapeutically effective and tolerable amount of one or more compounds according to the present invention to said mammal in need thereof.

The present invention further relates to the use of the compounds according to this invention for the production of pharmaceutical compositions which are employed for the treatment, prophylaxis and/or amelioration of one or more of the illnesses mentioned.

The present invention further relates to the use of the compounds according to this invention for the production of pharmaceutical compositions which can be used in the treatment, prevention or amelioration of (hyper)proliferative diseases of benign or malignant behaviour and/or disorders responsive to the induction of apoptosis in a mammal, such as, for example, benign or malignant neoplasia, e.g. cancer.

The present invention further relates to the use of the compounds according to this invention for the production of pharmaceutical compositions which can be used use in the treatment, prevention or amelioration of disorders responsive to arresting of aberrant cell growth and/or induction of apoptosis.

The present invention further relates to the use of the compounds according to this invention for the production of pharmaceutical compositions for treating, preventing or ameliorating benign or malignant neoplasia, particularly cancer, such as e.g. any of those cancer diseases described above.

The present invention further relates to pharmaceutical compositions comprising one or more of the compounds according to this invention and a pharmaceutically acceptable carrier or diluent.

The present invention further relates to pharmaceutical compositions made by combining one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

The present invention further relates to combinations comprising one or more of the compounds according to this invention and pharmaceutically acceptable auxiliaries, excipients and/or vehicles, e.g. for treating, preventing or ameliorating benign or malignant neoplasia, particularly cancer, such as e.g. any of those cancer diseases described above.

The present invention further relates to a combination comprising a compound according to this invention and a pharmaceutically acceptable excipient, carrier and/or diluent, e.g. for treating, preventing or ameliorating benign or malignant neoplasia, particularly cancer, such as e.g. any of those cancer diseases described above.

The present invention further relates to a composition consisting essentially of a therapeutically effective and tolerable amount of one or more compounds according to this invention together with the usual pharmaceutically acceptable vehicles, diluents and/or excipients for use in therapy, e.g. for treating, preventing or ameliorating hyperproliferative diseases, such as e.g. cancer, and/or disorders responsive to induction of apoptosis.

The present invention further relates to compounds according to this invention for use in therapy, such as, for example, in the treatment, prevention or amelioration of (hyper)proliferative diseases of benign or malignant behaviour and/or disorders responsive to the induction of apoptosis, such as e.g. those diseases mentioned herein, particularly cancer.

The present invention further relates to compounds according to this invention having anti-proliferative and/or apoptosis inducing activity.

The present invention further relates to compounds according to this invention having Eg5 inhibiting properties.

The present invention further relates to pharmaceutical compositions according to this invention having Eg5 inhibiting properties.

The present invention further relates to pharmaceutical compositions according to this invention having anti-proliferative activity.

The present invention further relates to pharmaceutical compositions according to this invention having apoptosis inducing activity.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

Additionally, the invention relates to an article of manufacture, which comprises packaging material and a pharmaceutical agent contained within said packaging material, wherein the pharmaceutical agent is therapeutically effective inhibiting Eg5 and/or inhibiting cellular (hyper)proliferation and/or inducing apoptosis, ameliorating the symptoms of a Eg5 mediated disease and/or a (hyper)proliferative disease and/or a disorder responsive to the induction of apoptosis, and wherein the packaging material comprises a label or package insert which indicates that the pharmaceutical agent is useful for preventing or treating a Eg5 mediated disease and/or a (hyper)proliferative disease and/or a disorder responsive to the induction of apoptosis, and wherein said pharmaceutical agent comprises one or more compounds according to the invention. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, dragees, pills, cachets, granules, capsules, caplets, suppositories, patches (e.g. as TTS), emulsions (such as e.g. micro-emulsions or lipid emulsions), suspensions (such as e.g. nano suspensions), gels, solubilisates or solutions (e.g. sterile solutions), or encapsuled in liposomes or as beta-cyclodextrine or beta-cyclodextrin derivative inclusion complexes or the like, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers (such as e.g. polyoxyethylenglyceroltriricinoleat 35, PEG 400, Tween 80, Captisol, Solutol HS15 or the like), colorants, complexing agents, permeation promoters, stabilizers, fillers, binders, thickeners, disintegrating agents, buffers, pH regulators (e.g. to obtain neutral, alkaline or acidic formulations), polymers, lubricants, coating agents, propellants, tonicity adjusting agents, surfactants, flavorings, sweeteners or dyes, can be used.

In particular, auxiliaries and/or excipients of a type appropriate to the desired formulation and the desired mode of administration are used.

The administration of the compounds, pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, the compounds of the invention can be in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, lotions, pastes, gels or solutions.

The pharmaceutical compositions according to the invention can be prepared by processes known per se. The dosage of the compounds of the invention (=active compounds) is carried out in the order of magnitude customary for Eg5 inhibitors, inhibitors for cellular (hyper)proliferation or apoptosis inducers. Topical application forms (such as ointments) for the treatment of dermatoses thus contain the active compounds in a concentration of, for example, 0.1-99%. The customary dose in the case of systemic therapy (p.o.) may be between 0.03 and 60 mg/kg per day, (i. v.) may be between 0.03 and 60 mg/kg/h. In another embodiment, the customary dose in the case of systemic therapy (p.o.) is between 0.3 and 30 mg/kg per day, (i. v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

For example, compounds according to this invention may be combined with one or more standard therapeutic agents used for treatment of the diseases as mentioned before.

In one particular embodiment, compounds according to this invention may be combined with one or more art-known anti-cancer agents, such as e.g. with one or more chemotherapeutic and/or target specific anti-cancer agents as described below.

Examples of known chemotherapeutic anti-cancer agents frequently used in combination therapy include, but not are limited to (i) alkylating/carbamylating agents such as Cyclophosphamid (Endoxan®), Ifosfamid (Holoxan®), Thiotepa (Thiotepa Lederle®), Melphalan (Alkeran®), or chloroethylnitrosourea (BCNU); (ii) platinum derivatives like cis-platin (Platinex® BMS), oxaliplatin, satraplatin or carboplatin (Cabroplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof (like the nanoparticle formulation Abraxane® with paclitaxel bound to albumin), epothilones such as Epothilone B (Patupilone®), Azaepothilone (Ixabepilone®) or ZK-EPO, a fully synthetic epothilone B analog; (iv) topoisomerase inhibitors such as anthracyclines (exemplified by Doxorubicin/Adriblastin®), epipodophyllotoxines (exemplified by Etoposide/Etopophos®) and camptothecin and camptothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) or premetrexed (Alimta®).

Examples of target specific anti-cancer drug classes used in experimental or standard cancer therapy include but are not limited to (i) kinase inhibitors such as e.g. Imatinib (Glivec®), ZD-1839/Gefitinib (Iressa®), Bay43-9006 (Sorafenib, Nexavar®), SU11248/Sunitinib (Sutent®), OSI-774/Erlotinib (Tarceva®), Dasatinib (Sprycel®), Lapatinib (Tykerb®), or, see also below, Vatalanib, Vandetanib (Zactima®) or Pazopanib; (ii) proteasome inhibitors such as PS-341/Bortezumib (Velcade®); (iii) histone deacetylase inhibitors like SAHA (Zolinza®), PXD101, MS275, MGCD0103, Depsipeptide/FK228, NVP-LBH589, NVP-LAQ824, Valproic acid (VPA), CRA/PCI 24781, ITF2357, SB939 and butyrates (iv) heat shock protein 90 inhibitors like 17-allylaminogeldanamycin (17-AAG) or 17-dimethylaminogeldanamycin (17-DMAG); (v) vascular targeting agents (VTAs) like combretastin A4 phosphate or AVE8062/AC7700 and anti-angiogenic drugs like the VEGF antibodies, such as Bevacizumab (Avastin®), or KDR tyrosine kinase inhibitors such as PTK787/ZK222584 (Vatalanib) or Vandetanib (Zactima®) or Pazopanib; (vi) monoclonal antibodies such as Trastuzumab (Herceptin®) or Rituximab (MabThera/Rituxan®) or Alemtuzumab (Campath®) or Tositumomab (Bexxar®) or C225/Cetuximab (Erbitux®) or Avastin (see above) or Panitumumab (Vectibix®) as well as mutants and conjugates of monoclonal antibodies, e.g. Gemtuzumab ozogamicin (Mylotarg®) or Ibritumomab tiuxetan (Zevalin®), and antibody fragments; (vii) oligonucleotide based therapeutics like G-3139/Oblimersen (Genasense®) or the DNMT1 inhibitor MG98; (viii) Toll-like receptor/TLR 7/8 agonists like Promune®, TLR 7 agonists like Imiquimod (Aldara®) or Isatoribine and analogues thereof, or TLR 7/8 agonists like Resiquimod as well as immunostimulatory RNA as TLR 7/8 agonists; (ix) protease inhibitors (x) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors.

Other known target specific anti-cancer agents which may be used for combination therapy include bleomycin, retinoids such as all-trans retinoic acid (ATRA), DNA methyltransferase inhibitors such as 5-Aza-2'-deoxycytidine (Decitabine, Dacogen®) and 5-azacytidine, alanosine, cytokines such as interleukin-2, interferons such as interferon α2 or interferon-γ, death receptor agonists, such as TRAIL, DR4/5 agonistic antibodies, FasL and TNF-R agonists (e.g. TRAIL receptor agonists like mapatumumab or lexatumumab).

As exemplary anti-cancer agents, which may be useful in the combination therapy according to the present invention, any of the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DASATINIB, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LAPATINIB, LETROZOLE, LEUPRORELIN, LOBAPLATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PANITUMUMAB, PATUPILONE, PAZOPANIB, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLI- MUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VANDETANIB, VERTEPORFIN, VINBLASTINE, VINCRISTINE, VINDESINE, VINORELBINE, VOROZOLE and ZEVALIN.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware on the base of his/her expert knowledge of the kind, total daily dosage(s) and administration form(s) of the additional therapeutic agent(s) coadministered. Said total daily dosage(s) can vary within a wide range.

In practicing the present invention, the compounds according to this invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics (chemotherapeutic and/or target specific anti-cancer agents), in particular art-known anti-cancer agents, such as any of e.g. those mentioned above.

In this context, the present invention further relates to a combination comprising
a first active ingredient, which is at least one compound according to this invention, and
a second active ingredient, which is at least one art-known anti-cancer agent, such as e.g. one or more of those mentioned herein above,
for separate, sequential, simultaneous, concurrent or chronologically staggered use in therapy, such as e.g. in therapy of any of those diseases mentioned herein.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously, concurrently or chronologically staggered.

The present invention further relates to a pharmaceutical composition comprising
a first active ingredient, which is at least one compound according to this invention, and
a second active ingredient, which is at least one art-known anti-cancer agent, such as e.g. one or more of those mentioned herein above, and, optionally,
a pharmaceutically acceptable carrier or diluent,
for separate, sequential, simultaneous, concurrent or chronologically staggered use in therapy.

The present invention further relates to a combination product comprising
a.) at least one compound according to this invention formulated with a pharmaceutically acceptable carrier or diluent, and
b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat (hyper)proliferative diseases and/or disorders responsive to the induction of apoptosis, such as e.g. cancer, more precisely, any of those cancer diseases described above.

The present invention further relates to a combined preparation comprising at least one compound according to this invention and at least one art-known anti-cancer agent for simultaneous, concurrent, sequential or separate administration.

The present invention further relates to combinations, compositions, formulations, preparations or kits according to the present invention having Eg5 inhibitory activity and/or anti-proliferative and/or apoptosis inducing properties.

In addition, the present invention further relates to a method for treating in combination therapy (hyper)proliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating (hyper)proliferative diseases of benign or malignant behaviour and/or disorders responsive to the induction of apoptosis, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing or ameliorating (hyper) proliferative diseases, such as e.g. cancer, and/or disorders responsive to the induction of apoptosis, particularly those diseases mentioned herein, such as e.g. malignant or benign neoplasia.

The present invention further relates to a commercial package comprising one or more compounds of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a (hyper)proliferative diseases and/or a disorder responsive to the induction of apoptosis, particularly one of those diseases mentioned herein, such as e.g. malignant or benign neoplasia, especially cancer, like any of those cancer diseases mentioned herein.

In addition, compounds according to the present invention can be used in the pre- or post-surgical treatment of cancer.

In further addition, compounds of the present invention can be used in combination with radiation therapy.

A combination according to this invention can refer to a composition comprising both the compound(s) according to this invention and the other active anti-cancer agent(s) in a fixed combination (fixed unit dosage form), or a medicament pack comprising the two or more active ingredients as discrete separate dosage forms (non-fixed combination). In case of a medicament pack comprising the two or more active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

Biological Investigations

The ATPase activity of Eg5 kinesin motor domains (Cytoskeleton, cat. No. EG01) can be used to monitor the effects of modulating agents. The test compounds are dissolved as 10 mM solutions in dimethylsulfoxide (DMSO). 2 µl of appropriate DMSO dilutions of the test compounds are added to each well of a 96 well flat bottom plate. Each compound dilution is tested as triplicates. The reagents are added and the final reaction of the standard assay contains 15 mM Pipes, pH 6.8, 5.0 mM $MgCl_2$, 0.5 mM KCl, 1 mM EGTA, 0.1 mg/ml BSA, 1 µM Paclitaxel, 250 nM preformed microtubules (Cytoskeleton, cat. No. MT001), 300 µM ATP, and Eg5 protein (50 ng) in a reaction volume of 100 µl. The controls include buffer wells with ATP and 2% DMSO. Reactions are started by the addition of ATP, incubated at room temperature for 30 min., and terminated by removing 20 µl of the reaction volume and adding it to 80 µl of 1 M perchloric acid, followed by the addition of 80 µl Malachite green reagent. Malachite green reagent is prepared by mixing a solution of 4.2 g ammonium molybdate in 100 ml 4 N HCl with a solution of 0.135 g Malachite green in 300 ml $H_2O$. The reactions are incubated for a further 20 min. and then read at 615 nm.

The corresponding $IC_{50}$ values of the compounds for Eg5 inhibition are determined from the concentration-effect curves.

Representative inhibitory values [measured as $-\log IC_{50}$ (mol/l)] determined in the aforementioned assay follow from the following table A, in which the numbers of the compounds correspond to the numbers of the examples.

TABLE A

| Inhibition of Eg5 activity | |
| --- | --- |
| Compound | $-\log IC_{50}$ [mol/l] |
| 1 to 15, 16 to 24, 25, 27 to 35, 37 to 53, 7b | The inhibitory values of these listed compounds are all $\geq 6.3$ |

The anti-proliferative/cytotoxic activity of the compounds described herein can be tested on subclones of RKO human colon adenocarcinoma cells (Schmidt et al., Oncogene 19, 2423-2429; 2000) using the Alamar Blue cell viability assay (described in O'Brien et al. Eur J Biochem 267, 5421-5426, 2000). The compounds are dissolved as 10 mM solutions in DMSO and subsequently diluted in semi-logarithmic steps. DMSO dilutions are further diluted 1:100 into Dulbecco's modified Eagle's medium (DMEM) containing 10% fetal calf serum to a final concentration twice as much as the final concentration in the test. RKO subclones are seeded into 96 well flat bottom plates at a density of 4000 cells per well in a volume of 50 µl per well. 24 hours after seeding the 50 µl each of the compound dilutions in DMEM medium are added into each well of the 96 well plate. Each compound dilution is tested as triplicates. Wells containing untreated control cells are filled with 50 µl DMEM medium containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values. The Graphpad Prism program is used for the calculation of $EC_{50}$ values for anti-proliferative/cytotoxic activity out of the obtained dose-response curves.

To determine the cell cycle specific mode of action, subclones of RKO colon adenocarcinoma cells (RKOp21 or RKOp27 as described by Schmidt et al. in Oncogene 19, 2423-2429; 2000) are seeded into 96 well flat bottom plates at a density of 16000 cells per well in a volume of 50 µl per well in DMEM growth medium with 10% FCS containing 10 µM Ponasterone A. 24 hours after seeding the 50 µl each of the compound dilutions in DMEM medium are added into each well of the 96-well plate. Each compound dilution is tested as triplicates. Wells containing untreated control cells are filled with 50 µl DMEM medium containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values. The Graphpad Prism program (GraphPad Software, Inc) is used for the calculation of $EC_{50}$ values out of the obtained dose-response curves. Viability is compared of proliferating cells grown in the absence of the inducer Ponasterone A, versus viability of cells arrested by the expression of ectopic p27Kip1 induced by Ponasterone A.

Representative values for anti-proliferation/cytotoxicity [measured as $-\log EC_{50}$ (mol/l)] determined in the aforementioned assays follow from the following tables B1, B2 and B3, in which the numbers of the compounds correspond to the numbers of the examples.

TABLE B1

| Anti-proliferative/cytotoxic activity on RKO colon cancer cells | | |
| --- | --- | --- |
| | $-\log EC_{50}$ [mol/l] RKO p27 induced (arrested) $\leq 5.5$ | $-\log EC_{50}$ [mol/l] RKO p27 induced (arrested) $\leq 6.5$ |
| $-\log EC_{50}$ [mol/l] RKO p27 uninduced (proliferating) $\geq 7.4$ | 3, 6, 7, 8, 9, 10, 11, 14, 15, 16 to 20, 23, 25, 27 to 30, 33, 35, 39 to 44, 46 to 53, 7b | 37, 38, 45 |
| $-\log EC_{50}$ [mol/l] RKO p27 uninduced (proliferating) < 7.4 but $\geq 6.6$ | 1, 4, 5, 12, 13, 22, 24, 31, 32, 34, | |

TABLE B2

| Anti-proliferative/cytotoxic activity on RKO colon cancer cells | | |
| --- | --- | --- |
| | $-\log EC_{50}$ [mol/l] RKO p27 or p21 induced (arrested) $\leq 5.5$ | $-\log EC_{50}$ [mol/l] RKO p27 or p21 induced (arrested) $\leq 6.5$ |
| $-\log EC_{50}$ [mol/l] RKO p27 or p21 uninduced (proliferating) $\geq 7.4$ | 67-72, 74, 76-81, 82-84, 86-90, 92-104, 135-141 | 105-115, 117-119, 22, 124, 126-128 130-133, 143, 145-149 |
| $-\log EC_{50}$ [mol/l] RKO p27 or p21 uninduced (proliferating) < 7.4 but $\geq 6.6$ | 73, 75, 81, 85 | 55, 57, 116, 120, 121, 123, 125, 129, 142, 144 |

TABLE B3

| Anti-proliferative/cytotoxic activity on RKO colon cancer cells | |
| --- | --- |
| $-\log EC_{50}$ [mol/l] RKO p21 uninduced (proliferating) $\geq 7.4$ | 150, 152-158, 163, 167-169, 171-182, 185, 211-219, 228, 230-233, 234, 235, 237-239, 242, 243, 247, 249-251, 256, 268-276, 278, 279, 284, 296, 314, 337-339, 341-347, 352, 354, 369-371, 373, 375-379, 383-387, 389-394 397, 426, 453, 462, 467-470, 474, 476, 478, 490, 533-544 |
| $-\log EC_{50}$ [mol/l] RKO p21 uninduced (proliferating) < 7.4 but $\geq 6.6$ | 55a, 151, 159-162, 164-166, 170, 184, 186-208, 210, 220-224, 225, 226, 229, 236, 240, 241, 244-246, 248, 252-255, 257-259, 261-266, 277, 280-283 285-290, 292-295, 297-300, 302-306, 308-313, 315-317, 319, 321-327 329-336, 340, 348-350, 353, 355-357, 359-362, 380-382, 388, 395, 396, 406-408, 410, 413, 414, 451, 452, 454, 456-461, 463-466, 471, 472, 475, 477, 479-483 |

The induction of apoptosis can be measured by using a Cell death detection ELISA (Roche Biochemicals, Mannheim, Germany). NCI-H460 non-small cell lung cancer cells are seeded into 96 well flat bottom plates at a density of 10000 cells per well in a volume of 50 µl RPMI medium (containing 10% fetal calf serum) per well. 24 hours after seeding the 50 µl each of the compound dilutions in RPMI medium are added into each well of the 96 Well plate. Each compound dilution is tested at least as duplicates. Wells containing untreated control cells are filled with 50 µl RPMI medium containing 1% DMSO. The cells are then incubated with the substances for 24 hours at 37° C. in a humidified atmosphere containing 5% carbon dioxide. As a positive control for the induction of apoptosis, cells are treated with 50 µM Cisplatin (Gry Pharmaceuticals, Kirchzarten, Germany). Medium is then removed and the cells are lysed in 200 µl lysis buffer. After centrifugation as described by the manufacturer, 10 µl of cell lysate is processed as described in the protocol. The degree of apoptosis is calculated as follows: The absorbance at 405 nm obtained with lysates from cells treated with 50 µM cisplatin is set as 100 cpu (cisplatin units), while an absorbance at 405 nm of 0.0 is set as 0.0 cpu. The degree of apoptosis is expressed as cpu in relation to the value of 100 cpu reached with the lysates obtained from cells treated with 50 µM cisplatin.

Experimental perturbation of Eg5 function causes a characteristic malformation of the mitotic spindle, which can be examined by confocal laser scanning microscopy. HeLa cervical cancer cells are grown overnight on glass cover slips (Nunc™ Lab-Tek™ Chamber Slides) in 1800 µl DMEM medium containing 10% fetal calf serum. The test compounds are dissolved as 10 mM solutions in DMSO. Appropriate DMSO dilutions of the test compounds are further diluted 1:10 into DMEM medium containing 10% fetal calf serum to a final concentration ten times as much as the final concentration in the test. 24 hours after seeding, 200 µl of the compound dilutions in DMEM medium are added into each well of the cover slip. As a control, 200 µl DMEM medium containing 10% DMSO are added. 24 hours after incubation with the test compounds, the cells are washed with PBS, and fixed with 3.7% formaldehyde in $H_2O$ for 20 min. at 37° C. Subsequently, cells are washed with PBS and incubated with 0.1% Triton X-100 in a buffer containing 1.471 mM $KH_2PO_4$, 8.504 mM $Na_2HPO_4$, 137 mM NaCl, 1.325 mM $CaCl_2$, 2.685 mM KCl, 0.542 mM $MgCl_2$, pH 7.2 for 15 min. at room temperature. For saturation of non-specific binding, cells are incubated in 2% BSA/10% FCS in PBS (=blocking buffer) for 30 min. at room temperature prior to incubation with anti-alpha tubulin monoclonal antibodies (Sigma, #T5168; 1:1000), followed by Cy3-conjugated rabbit anti-mouse IgG (H+L) antibody (Jackson Immuno Research; 1:1000). All antibody incubations are performed for one hour at 37° C. in blocking buffer, and cells are washed three times in PBS between different incubations. DNA is counterstained with Hoechst 33342 (0.1 µg/ml). Coverslips are mounted in Vectashield (Vector Laboratories, Burlingame, Calif.) and examined with a Leica TCS SP2 confocal laser scanning microscope fitted with appropriate filters (Leica Microsystems, Bensheim, Germany).

Some of the compounds according to this invention may be efficacious against p-glycoprotein mediated multidrug-resistant tumour cell lines (e.g. HCT-15), that can be measured as follows:

All cell lines used are cultured at standard conditions in a tissue culture incubator at 37° C., 5% $CO_2$ and 95% humidity. At day 1, cells are detached with Trypsin/EDTA and pelleted by centrifugation. Cells are resuspended at the appropriate density in culture medium, seeded into 96well microtiter plates and incubated over night in a tissue culture incubator at 37° C., 5% $CO_2$ and 95% humidity. Stock solution of all compounds to be tested are dissolved at 10 mM in DMSO and at day 2 added to the microtiter plates in the desired dilutions. The final DMSO concentration in the microtiter plates is kept at 1%. Control cells are treated with DMSO only. The microtiter plates are incubated with the compounds in a tissue culture incubator at 37° C., 5% $CO_2$ and 95% humidity for further 72 hours. To determine the viability of the cells at day 5, an Alamar Blue solution (Biosource) is added at 1/10 culture volume to the microtiter plates. The cells are incubated in a tissue culture incubator at 37° C., 5% $CO_2$ and 95% humidity for additional 3-6 hours and the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values.

The Graphpad Prism program is used for the calculation of $EC_{50}$ values out of the obtained dose-response curves.

The invention claimed is:
1. A compound of formula I

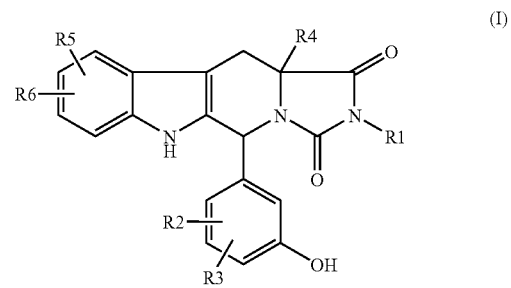

in which
R1 is 1-4C-alkyl, 3-7C-cycloalkyl, 2-4C-alkenyl, 2-4C-alkinyl, 3-7C-cycloalkyl-1-4C-alkyl, or 2-7C-alkyl substituted by R11, in which
R11 is —N(R111)R112, or halogen, in which
R111 is hydrogen, 1-4C-alkyl, 2-4C-alkenyl, 2-4C-alkinyl, 3-7C-cycloalkyl, 3-7C-cycloalkyl-1-4C-alkyl, hydroxy-2-4C-alkyl, 1-4C-alkoxy-2-4C-alkyl, 1N-(1-4C-alkyl)-pyrazolyl, 1N-(H)-pyrazolyl, isoxazolyl, or completely or partially fluorine-substituted 1-4C-alkyl,
R112 is hydrogen, 1-4C-alkyl, 3-7C-cycloalkyl, or 3-7C-cycloalkyl-1-4C-alkyl,
or
R111 and R112 together and with inclusion of the nitrogen atom, to which they are bonded, form a ring Het, in which
Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N-(R113)-piperazin-1-yl, 4N-(R113)-homopiperazin-1-yl, 2,5-dihydro-pyrrol-1-yl, 1,2,3,6-tetrahydropyridin-1-yl, pyrrol-1-yl, pyrazol-1-yl, imidazol-1-yl, triazol-1-yl, or tetrazol-1-yl, in which
R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl,
wherein said Het may be optionally substituted by one or two substituents independently selected from fluorine and 1-4C-alkyl, R2 is hydrogen, 1-4C-alkyl, halogen, trifluoromethyl, 1-4C-alkoxy or hydroxyl, R3 is hydrogen, 1-4C-alkyl, halogen, trifluoromethyl or 1-4C-alkoxy, R4 is 1-4C-alkyl, 3-7C-cycloalkyl or 3-7C-cycloalkyl-1-4C-alkyl, R5 is 1-4C-alkoxy, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, R6 is hydrogen, 1-4C-alkyl or halogen, or a salt, stereoisomer or salt of a stereoisomer thereof.

2. A compound of formula I according to claim 1, in which
R1 is 1-4C-alkyl, 3-7C-cycloalkyl, 3-7C-cycloalkyl-1-4C-alkyl, or 2-7C-alkyl substituted by R11, in which
R11 is —N(R111)R112, or halogen, in which
R111 is hydrogen, 1-4C-alkyl, 3-7C-cycloalkyl, 3-7C-cycloalkyl-1-4C-alkyl, hydroxy-2-4C-alkyl, 1-4C-alkoxy-2-4C-alkyl, or completely or partially fluorine-substituted 1-4C-alkyl,
R112 is hydrogen, 1-4C-alkyl, 3-7C-cycloalkyl, or 3-7C-cycloalkyl-1-4C-alkyl,
or
R111 and R112 together and with inclusion of the nitrogen atom, to which they are bonded, form a ring Het, in which
Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N-(R113)-piperazin-1-yl, 4N-(R113)-homopiperazin-1-yl, pyrrol-1-yl, pyrazol-1-yl, imidazol-1-yl, triazol-1-yl, or tetrazol-1-yl, in which
R113 is hydrogen, 1-4C-alkyl, 3-7C-cycloalkyl or 3-7C-cycloalkyl-1-4C-alkyl, 1-4C-alkylcarbonyl, amidino, or completely or partially fluorine-substituted 1-4C-alkyl,
wherein said Het may be optionally substituted by one or two substituents independently selected from fluorine and 1-4C-alkyl,
R2 is hydrogen, 1-4C-alkyl, halogen, trifluoromethyl, 1-4C-alkoxy or hydroxyl,
R3 is hydrogen, 1-4C-alkyl, halogen, trifluoromethyl or 1-4C-alkoxy,
R4 is 1-4C-alkyl, 3-7C-cycloalkyl or 3-7C-cycloalkyl-1-4C-alkyl,
R5 is 1-4C-alkoxy, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy,
R6 is hydrogen, 1-4C-alkyl or halogen,
or a salt, stereoisomer or salt of a stereoisomer thereof.

3. A compound of formula I according to claim 1, in which
R1 is 1-4C-alkyl, 3-7C-cycloalkyl, 3-7C-cycloalkyl-1-4C-alkyl, or 2-7C-alkyl substituted by R11, in which
R11 is —N(R111)R112, in which
R111 is hydrogen, 1-4C-alkyl, 3-7C-cycloalkyl or 3-7C-cycloalkyl-1-4C-alkyl,
R112 is hydrogen, 1-4C-alkyl, 3-7C-cycloalkyl or 3-7C-cycloalkyl-1-4C-alkyl,
or
R111 and R112 together and with inclusion of the nitrogen atom, to which they are bonded, form a ring Het, in which
Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, 4N-(R113)-piperazin-1-yl, pyrrol-1-yl, pyrazol-1-yl, imidazol-1-yl or triazol-1-yl, in which R113 is 1-4C-alkyl, 3-7C-cycloalkyl or 3-7C-cycloalkyl-1-4C-alkyl,
R2 is hydrogen, 1-4C-alkyl, halogen, trifluoromethyl, 1-4C-alkoxy or hydroxyl,
R3 is hydrogen, 1-4C-alkyl, halogen, trifluoromethyl or 1-4C-alkoxy,
R4 is 1-4C-alkyl, 3-7C-cycloalkyl or 3-7C-cycloalkyl-1-4C-alkyl,
R5 is 1-4C-alkoxy, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy,
R6 is hydrogen, 1-4C-alkyl or halogen,
or a salt, stereoisomer or salt of a stereoisomer thereof.

4. A compound according to claim 1, wherein said compounds have with respect to the positions 3a and 10 the configuration shown in formula I*

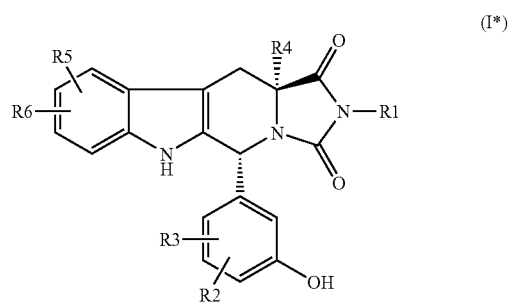

or a salt thereof.

5. A compound of formula I according to claim 1, in which
R1 is methyl, ethyl, propyl, isopropyl, cyclopropyl, cyclopropylmethyl, ethyl substituted by R11, propyl substituted by R11, or butyl substituted by R11, in which
R11 is —N(R111)R112, fluorine, chlorine, or bromine, in which
either
R111 is hydrogen, and
R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is methyl,
or
R111 is ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is ethyl, isopropyl, or cyclopropyl,
or
R111 and R112 together and with inclusion of the nitrogen atom, to which they are bonded, form a ring Het, in which
Het is piperidin-1-yl, morpholin-4-yl, thiomorpholin-4-yl, pyrrolidin-1-yl, azetidin-1-yl, homopiperidin-1-yl, 4N-

(R113)-piperazin-1-yl, 4N-(R113)-homopiperazin-1-yl, pyrrol-1-yl, pyrazol-1-yl, imidazol-1-yl, triazol-1-yl, or tetrazol-1-yl, in which
R113 is hydrogen, methyl, ethyl, propyl, isopropyl, acetyl, 2-fluoroethyl, 2,2-difluoroethyl, or 2,2,2-trifluoroethyl,
wherein said Het may be optionally substituted by one or two substituents independently selected from fluorine and methyl,
R2 is hydrogen,
R3 is hydrogen,
R4 is methyl, ethyl, propyl, isopropyl, cyclopropyl or cyclopropylmethyl,
R5 is methoxy, ethoxy, propoxy, isopropoxy, 2 methoxyethoxy, cyclopropyloxy, cyclopropylmethoxy, or completely or predominantly fluorine-substituted 1-2C-alkoxy,
R6 is hydrogen,
wherein R5 is bonded to the 6-position of the scaffold,
or a salt, stereoisomer or salt of a stereoisomer thereof.

6. A compound according to claim 4, in which
R1 is 2-(R11)-ethyl, or 3-(R11)-propyl, in which
R11 is —N(R111)R112, in which
either
R111 is hydrogen, and
R112 is hydrogen,
or
R111 is methyl, ethyl, propyl, isopropyl, isobutyl, tertbutyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is hydrogen,
or
R111 is methyl, ethyl, propyl, isopropyl, isobutyl, tertbutyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is methyl,
or
R111 is ethyl, propyl, isopropyl, allyl, propargyl, 1-methyl-propargyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is ethyl,
or
R111 and R112 together and with inclusion of the nitrogen atom, to which they are bonded, form a ring Het, in which
either
Het is piperidin-1-yl, morpholin-4-yl, pyrrolidin-1-yl, azetidin-1-yl, homopiperidin-1-yl, 4N-(R113)-piperazin-1-yl, 4N-(R113)-homopiperazin-1-yl, 2,5-dihydro-pyrrol-1-yl, 1,2,3,6-tetrahydropyridin-1-yl, 4-methyl-piperidin-1-yl, 4-fluoro-piperidin-1-yl, 4,4-difluoropiperidin-1-yl, (S)-3-fluoro-pyrrolidin-1-yl, (R)-3-fluoro-pyrrolidin-1-yl, or 3,3-difluoro-pyrrolidin-1-yl, in which
R113 is methyl or acetyl,
or
Het is pyrazol-1-yl, or imidazol-1-yl,
R2 is hydrogen,
R3 is hydrogen,
R4 is methyl,
R5 is ethoxy, methoxy, difluoromethoxy or trifluoromethoxy,
R6 is hydrogen or fluorine,
wherein R5 is bonded to the 6-position of the scaffold, and
wherein R6 is bonded to the 5- or 7-position of the scaffold,
or a salt thereof.

7. A compound according to claim 4, in which
R1 is 2-(R11)-ethyl, or 3-(R11)-propyl, in which
R11 is —N(R111)R112, in which
either
R111 is methyl, ethyl, isopropyl, isobutyl, tertbutyl, allyl, cyclopropyl, cyclobutyl, cyclopropylmethyl, 2-hydroxyethyl, or 2-methoxyethyl, and
R112 is hydrogen,
or
R111 is methyl, ethyl, isopropyl, allyl, cyclopropyl, cyclobutyl, cyclopropylmethyl, 2-hydroxyethyl, or 2-methoxyethyl, and
R112 is methyl,
or
R111 is ethyl, 2-hydroxyethyl, or 2-methoxyethyl, and
R112 is ethyl,
or
R111 and R112 together and with inclusion of the nitrogen atom, to which they are bonded, form a ring Het, in which
Het is piperidin-1-yl, pyrrolidin-1-yl, azetidin-1-yl, 2,5-dihydro-pyrrol-1-yl, or 1,2,3,6-tetrahydropyridin-1-yl,
R2 is hydrogen,
R3 is hydrogen,
R4 is methyl,
R5 is ethoxy, methoxy or difluoromethoxy,
R6 is hydrogen or fluorine,
wherein R5 is bonded to the 6-position of the scaffold, and
wherein R6 is bonded to the 7-position of the scaffold,
or a salt thereof.

8. A compound according to claim 4, in which
R1 is methyl, 2-(R11)-ethyl, or 3-(R11)-propyl, in which
R11 is —N(R111)R112, in which
either
R111 is hydrogen, and
R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is hydrogen,
or
R111 is methyl, ethyl, propyl, isopropyl, isobutyl, cyclopropyl, cyclobutyl, cyclopropylmethyl, 2-hydroxyethyl, 2-methoxyethyl, 2-fluoroethyl, 2,2-difluoroethyl, or 2,2,2-trifluoroethyl, and
R112 is methyl,
or
R111 is ethyl, propyl, isopropyl, cyclopropyl, 2-hydroxyethyl, 2-methoxyethyl, 2-fluoroethyl, 2,2-difluoroethyl, or 2,2,2-trifluoroethyl, and
R112 is ethyl,
or
R111 and R112 together and with inclusion of the nitrogen atom, to which they are bonded, form a ring Het, in which
either
Het is piperidin-1-yl, morpholin-4-yl, pyrrolidin-1-yl, azetidin-1-yl, or 4N-(R113)-piperazin-1-yl, in which
R113 is hydrogen, methyl, ethyl, isopropyl, acetyl, 2-fluoroethyl, 2,2-difluoroethyl, or 2,2,2-trifluoroethyl, wherein said Het may be optionally substituted by one or two substituents independently selected from fluorine and methyl,
or
Het is pyrazol-1-yl, imidazol-1-yl, or triazol-1-yl,
R2 is hydrogen,
R3 is hydrogen,
R4 is methyl, ethyl, isopropyl or cyclopropyl,
R5 is ethoxy, methoxy, propoxy, isopropoxy, cyclopropylmethoxy, or completely or predominantly fluorine-substituted 1-2C-alkoxy,
R6 is hydrogen,
wherein R5 is bonded to 6-position of the scaffold,
or a salt thereof.

9. A compound according to claim 4, in which
R1 is 2-(R11)-ethyl, or 3-(R11)-propyl, in which
R11 is —N(R111)R112, in which either
R111 is hydrogen, and
R112 is hydrogen,
or
R111 is methyl, ethyl, propyl, isopropyl, isobutyl, cyclopropyl, cyclobutyl, or cyclopropylmethyl, and
R112 is hydrogen,
or
R111 is methyl, ethyl, isopropyl, or cyclopropyl, and
R112 is methyl,
or
R111 is ethyl, isopropyl, or cyclopropyl, and
R112 is ethyl,
or
R111 and R112 together and with inclusion of the nitrogen atom, to which they are bonded, form a ring Het, in which
either
Het is piperidin-1-yl, morpholin-4-yl, pyrrolidin-1-yl, azetidin-1-yl, 4N-(R113)-piperazin-1-yl, 4-methyl-piperidin-1-yl, 4-fluoro-piperidin-1-yl, 4,4-difluoropiperidin-1-yl, (S)-3-fluoro-pyrrolidin-1-yl, yl, 3,3-difluoro-pyrrolidin-1-yl, 3-fluoro-azetidin-1-yl, or 3,3-difluoro-azetidin-1-yl, in which
R113 is hydrogen, methyl, or acetyl,
or
Het is pyrazol-1-yl, or imidazol-1-yl,
R2 is hydrogen,
R3 is hydrogen,
R4 is methyl or ethyl,
R5 is ethoxy, methoxy, or completely or predominantly fluorine-substituted 1-2C-alkoxy,
R6 is hydrogen,
wherein R5 is bonded to the 6-position of the scaffold,
or a salt thereof.

10. A compound according to claim 4, in which
R1 is methyl, 2-(R11)-ethyl, or 3-(R11)-propyl, in which
R11 is —N(R111)R112, in which
R111 is methyl,
R112 is methyl,
or
R111 and R112 together and with inclusion of the nitrogen atom, to which they are bonded, form a ring Het, in which
Het is piperidin-1-yl, morpholin-4-yl, pyrrolidin-1-yl, 4-methyl-piperazin-1-yl, pyrazol-1-yl, imidazol-1-yl or triazol-1-yl, in which
R2 is hydrogen,
R3 is hydrogen,
R4 is methyl, ethyl, isopropyl or cyclopropyl,
R5 is methoxy, ethoxy, propoxy, isopropoxy, 2 methoxy-ethoxy, cyclopropylmethoxy, difluoromethoxy or trifluoromethoxy,
R6 is hydrogen,
wherein R5 is bonded to the 6-position of the scaffold,
or a salt thereof.

11. A compound according to claim 1, which is a compound of formulae Ia*, Ib* or Ic*

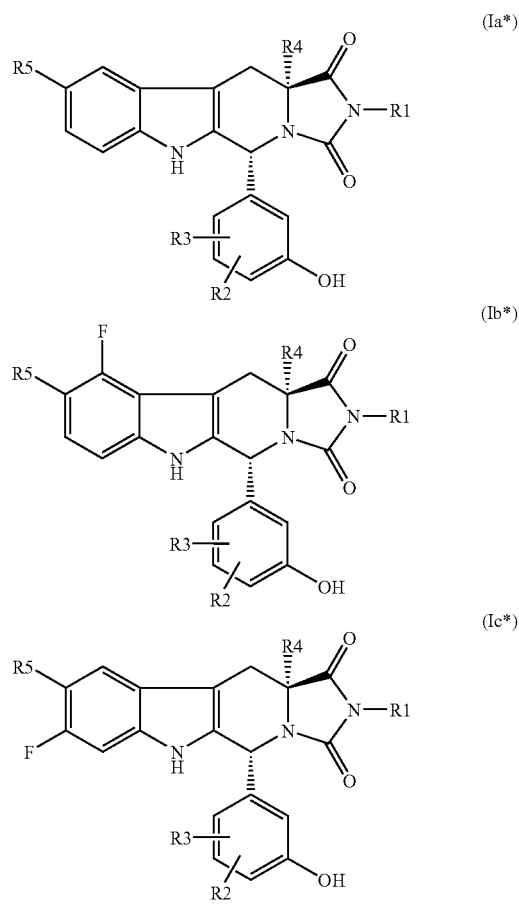

in which
R2 and R3 are both hydrogen,
R4 is methyl or ethyl, and
R1 and R5 have any of the following meanings:

| R1 | R5 |
|---|---|
| methyl | —OCH₃ |
| methyl | —OCH₂CH₃ |
| methyl | —OCH₂CH₂OCH₃ |
| methyl | cyclopropylmethoxy |
| methyl | difluoromethoxy |
| methyl | trifluoromethoxy |
| 2-(dimethylamino)-ethyl | —OCH₃ |
| 2-(dimethylamino)-ethyl | —OCH₂CH₃ |
| 2-(dimethylamino)-ethyl | —OCH₂CH₂OCH₃ |
| 2-(dimethylamino)-ethyl | cyclopropylmethoxy |
| 2-(dimethylamino)-ethyl | difluoromethoxy |
| 2-(dimethylamino)-ethyl | trifluoromethoxy |
| 3-(dimethylamino)-propyl | —OCH₃ |
| 3-(dimethylamino)-propyl | —OCH₂CH₃ |
| 3-(dimethylamino)-propyl | —OCH₂CH₂OCH₃ |

| R1 | R5 |
|---|---|
| 3-(dimethylamino)-propyl | cyclopropylmethoxy |
| 3-(dimethylamino)-propyl | difluoromethoxy |
| 3-(dimethylamino)-propyl | trifluoromethoxy |
| 2-(morpholin-4-yl)-ethyl | —OCH$_3$ |
| 2-(morpholin-4-yl)-ethyl | —OCH$_2$CH$_3$ |
| 2-(morpholin-4-yl)-ethyl | —OCH$_2$CH$_2$OCH$_3$ |
| 2-(morpholin-4-yl)-ethyl | cyclopropylmethoxy |
| 2-(morpholin-4-yl)-ethyl | difluoromethoxy |
| 2-(morpholin-4-yl)-ethyl | trifluoromethoxy |
| 2-(pyrrolidin-1-yl)-ethyl | —OCH$_3$ |
| 2-(pyrrolidin-1-yl)-ethyl | —OCH$_2$CH$_3$ |
| 2-(pyrrolidin-1-yl)-ethyl | —OCH$_2$CH$_2$OCH$_3$ |
| 2-(pyrrolidin-1-yl)-ethyl | cyclopropylmethoxy |
| 2-(pyrrolidin-1-yl)-ethyl | difluoromethoxy |
| 2-(pyrrolidin-1-yl)-ethyl | trifluoromethoxy |
| 2-(imidazol-1-yl)-ethyl | —OCH$_3$ |
| 2-(imidazol-1-yl)-ethyl | —OCH$_2$CH$_3$ |
| 2-(imidazol-1-yl)-ethyl | —OCH$_2$CH$_2$OCH$_3$ |
| 2-(imidazol-1-yl)-ethyl | cyclopropylmethoxy |
| 2-(imidazol-1-yl)-ethyl | difluoromethoxy |
| 2-(imidazol-1-yl)-ethyl | trifluoromethoxy |
| 2-(4-methyl-piperazin-1-yl)-ethyl | —OCH$_3$ |
| 2-(4-methyl-piperazin-1-yl)-ethyl | —OCH$_2$CH$_3$ |
| 2-(4-methyl-piperazin-1-yl)-ethyl | —OCH$_2$CH$_2$OCH$_3$ |
| 2-(4-methyl-piperazin-1-yl)-ethyl | cyclopropylmethoxy |
| 2-(4-methyl-piperazin-1-yl)-ethyl | difluoromethoxy |
| 2-(4-methyl-piperazin-1-yl)-ethyl | trifluoromethoxy |
| 3-(morpholin-4-yl)-propyl | —OCH$_3$ |
| 3-(morpholin-4-yl)-propyl | —OCH$_2$CH$_3$ |
| 3-(morpholin-4-yl)-propyl | —OCH$_2$CH$_2$OCH$_3$ |
| 3-(morpholin-4-yl)-propyl | cyclopropylmethoxy |
| 3-(morpholin-4-yl)-propyl | difluoromethoxy |
| 3-(morpholin-4-yl)-propyl | trifluoromethoxy |
| 3-(pyrrolidin-1-yl)-propyl | —OCH$_3$ |
| 3-(pyrrolidin-1-yl)-propyl | —OCH$_2$CH$_3$ |
| 3-(pyrrolidin-1-yl)-propyl | —OCH$_2$CH$_2$OCH$_3$ |
| 3-(pyrrolidin-1-yl)-propyl | cyclopropylmethoxy |
| 3-(pyrrolidin-1-yl)-propyl | difluoromethoxy |
| 3-(pyrrolidin-1-yl)-propyl | trifluoromethoxy |
| 3-(imidazol-1-yl)-propyl | —OCH$_3$ |
| 3-(imidazol-1-yl)-propyl | —OCH$_2$CH$_3$ |
| 3-(imidazol-1-yl)-propyl | —OCH$_2$CH$_2$OCH$_3$ |
| 3-(imidazol-1-yl)-propyl | cyclopropylmethoxy |
| 3-(imidazol-1-yl)-propyl | difluoromethoxy |
| 3-(imidazol-1-yl)-propyl | trifluoromethoxy |
| 3-(4-methyl-piperazin-1-yl)-propyl | —OCH$_3$ |
| 3-(4-methyl-piperazin-1-yl)-propyl | —OCH$_2$CH$_3$ |
| 3-(4-methyl-piperazin-1-yl)-propyl | —OCH$_2$CH$_2$OCH$_3$ |
| 3-(4-methyl-piperazin-1-yl)-propyl | cyclopropylmethoxy |
| 3-(4-methyl-piperazin-1-yl)-propyl | difluoromethoxy |
| 3-(4-methyl-piperazin-1-yl)-propyl | trifluoromethoxy |
| 3-amino-propyl | —OCH$_3$ |
| 3-amino-propyl | —OCH$_2$CH$_3$ |
| 3-amino-propyl | —OCH$_2$CH$_2$OCH$_3$ |
| 3-amino-propyl | cyclopropylmethoxy |
| 3-amino-propyl | difluoromethoxy |
| 3-amino-propyl | trifluoromethoxy |
| 2-amino-ethyl | —OCH$_3$ |
| 2-amino-ethyl | —OCH$_2$CH$_3$ |
| 2-amino-ethyl | —OCH$_2$CH$_2$OCH$_3$ |
| 2-amino-ethyl | cyclopropylmethoxy |
| 2-amino-ethyl | difluoromethoxy |
| 2-amino-ethyl | trifluoromethoxy |
| 2-(methylamino)-ethyl | —OCH$_3$ |
| 2-(methylamino)-ethyl | —OCH$_2$CH$_3$ |
| 2-(methylamino)-ethyl | —OCH$_2$CH$_2$OCH$_3$ |
| 2-(methylamino)-ethyl | cyclopropylmethoxy |
| 2-(methylamino)-ethyl | difluoromethoxy |
| 2-(methylamino)-ethyl | trifluoromethoxy |
| 2-(ethylamino)-ethyl | —OCH$_3$ |
| 2-(ethylamino)-ethyl | —OCH$_2$CH$_3$ |
| 2-(ethylamino)-ethyl | —OCH$_2$CH$_2$OCH$_3$ |
| 2-(ethylamino)-ethyl | cyclopropylmethoxy |
| 2-(ethylamino)-ethyl | difluoromethoxy |
| 2-(ethylamino)-ethyl | trifluoromethoxy |
| 2-(azetidin-1-yl)-ethyl | —OCH$_3$ |
| 2-(azetidin-1-yl)-ethyl | —OCH$_2$CH$_3$ |
| 2-(azetidin-1-yl)-ethyl | —OCH$_2$CH$_2$OCH$_3$ |
| 2-(azetidin-1-yl)-ethyl | cyclopropylmethoxy |
| 2-(azetidin-1-yl)-ethyl | difluoromethoxy |
| 2-(azetidin-1-yl)-ethyl | trifluoromethoxy |
| 2-(4-acetyl-piperazin-1-yl)-ethyl | —OCH$_3$ |
| 2-(4-acetyl-piperazin-1-yl)-ethyl | —OCH$_2$CH$_3$ |
| 2-(4-acetyl-piperazin-1-yl)-ethyl | —OCH$_2$CH$_2$OCH$_3$ |
| 2-(4-acetyl-piperazin-1-yl)-ethyl | cyclopropylmethoxy |
| 2-(4-acetyl-piperazin-1-yl)-ethyl | difluoromethoxy |
| 2-(4-acetyl-piperazin-1-yl)-ethyl | trifluoromethoxy |
| 2-(3,3-difluoropyrrolidin-1-yl)-ethyl | —OCH$_3$ |
| 2-(3,3-difluoropyrrolidin-1-yl)-ethyl | —OCH$_2$CH$_3$ |
| 2-(3,3-difluoropyrrolidin-1-yl)-ethyl | —OCH$_2$CH$_2$OCH$_3$ |
| 2-(3,3-difluoropyrrolidin-1-yl)-ethyl | cyclopropylmethoxy |
| 2-(3,3-difluoropyrrolidin-1-yl)-ethyl | difluoromethoxy |
| 2-(3,3-difluoropyrrolidin-1-yl)-ethyl | trifluoromethoxy |
| 2-(2-fluoroethylamino)-ethyl | —OCH$_3$ |
| 2-(2-fluoroethylamino)-ethyl | —OCH$_2$CH$_3$ |
| 2-(2-fluoroethylamino)-ethyl | —OCH$_2$CH$_2$OCH$_3$ |
| 2-(2-fluoroethylamino)-ethyl | cyclopropylmethoxy |
| 2-(2-fluoroethylamino)-ethyl | difluoromethoxy |
| 2-(2-fluoroethylamino)-ethyl | trifluoromethoxy |
| 2-(2,2-difluoroethylamino)-ethyl | —OCH$_3$ |
| 2-(2,2-difluoroethylamino)-ethyl | —OCH$_2$CH$_3$ |
| 2-(2,2-difluoroethylamino)-ethyl | —OCH$_2$CH$_2$OCH$_3$ |
| 2-(2,2-difluoroethylamino)-ethyl | cyclopropylmethoxy |
| 2-(2,2-difluoroethylamino)-ethyl | difluoromethoxy |
| 2-(2,2-difluoroethylamino)-ethyl | trifluoromethoxy |
| 2-(2,2,2-trifluoroethylamino)-ethyl | —OCH$_3$ |
| 2-(2,2,2-trifluoroethylamino)-ethyl | —OCH$_2$CH$_3$ |
| 2-(2,2,2-trifluoroethylamino)-ethyl | —OCH$_2$CH$_2$OCH$_3$ |
| 2-(2,2,2-trifluoroethylamino)-ethyl | cyclopropylmethoxy |
| 2-(2,2,2-trifluoroethylamino)-ethyl | difluoromethoxy |
| 2-(2,2,2-trifluoroethylamino)-ethyl | trifluoromethoxy |
| 2-(isopropylamino)-ethyl | —OCH$_3$ |
| 2-(isopropylamino)-ethyl | —OCH$_2$CH$_3$ |
| 2-(isopropylamino)-ethyl | —OCH$_2$CH$_2$OCH$_3$ |
| 2-(isopropylamino)-ethyl | cyclopropylmethoxy |
| 2-(isopropylamino)-ethyl | difluoromethoxy |
| 2-(isopropylamino)-ethyl | trifluoromethoxy |
| 2-(isobutylamino)-ethyl | —OCH$_3$ |
| 2-(isobutylamino)-ethyl | —OCH$_2$CH$_3$ |
| 2-(isobutylamino)-ethyl | —OCH$_2$CH$_2$OCH$_3$ |
| 2-(isobutylamino)-ethyl | cyclopropylmethoxy |
| 2-(isobutylamino)-ethyl | difluoromethoxy |
| 2-(isobutylamino)-ethyl | trifluoromethoxy |
| 2-(N-cyclopropylmethyl-amino)-ethyl | —OCH$_3$ |
| 2-(N-cyclopropylmethyl-amino)-ethyl | —OCH$_2$CH$_3$ |
| 2-(N-cyclopropylmethyl-amino)-ethyl | —OCH$_2$CH$_2$OCH$_3$ |
| 2-(N-cyclopropylmethyl-amino)-ethyl | cyclopropylmethoxy |
| 2-(N-cyclopropylmethyl-amino)-ethyl | difluoromethoxy |
| 2-(N-cyclopropylmethyl-amino)-ethyl | trifluoromethoxy |
| 2-(cyclopropylamino)-ethyl | —OCH$_3$ |
| 2-(cyclopropylamino)-ethyl | —OCH$_2$CH$_3$ |
| 2-(cyclopropylamino)-ethyl | —OCH$_2$CH$_2$OCH$_3$ |
| 2-(cyclopropylamino)-ethyl | cyclopropylmethoxy |
| 2-(cyclopropylamino)-ethyl | difluoromethoxy |
| 2-(cyclopropylamino)-ethyl | trifluoromethoxy |
| 2-(cyclobutylamino)-ethyl | —OCH$_3$ |
| 2-(cyclobutylamino)-ethyl | —OCH$_2$CH$_3$ |
| 2-(cyclobutylamino)-ethyl | —OCH$_2$CH$_2$OCH$_3$ |
| 2-(cyclobutylamino)-ethyl | cyclopropylmethoxy |
| 2-(cyclobutylamino)-ethyl | difluoromethoxy |
| 2-(cyclobutylamino)-ethyl | trifluoromethoxy |
| 2-(N-ethyl-N-methyl-amino)-ethyl | —OCH$_3$ |
| 2-(N-ethyl-N-methyl-amino)-ethyl | —OCH$_2$CH$_3$ |
| 2-(N-ethyl-N-methyl-amino)-ethyl | —OCH$_2$CH$_2$OCH$_3$ |
| 2-(N-ethyl-N-methyl-amino)-ethyl | cyclopropylmethoxy |
| 2-(N-ethyl-N-methyl-amino)-ethyl | difluoromethoxy |
| 2-(N-ethyl-N-methyl-amino)-ethyl | trifluoromethoxy |
| 2-(diethylamino)-ethyl | —OCH$_3$ |
| 2-(diethylamino)-ethyl | —OCH$_2$CH$_3$ |
| 2-(diethylamino)-ethyl | —OCH$_2$CH$_2$OCH$_3$ |
| 2-(diethylamino)-ethyl | cyclopropylmethoxy |
| 2-(diethylamino)-ethyl | difluoromethoxy |
| 2-(diethylamino)-ethyl | trifluoromethoxy |
| 2-(N-isopropyl-N-methyl-amino)-ethyl | —OCH$_3$ |
| 2-(N-isopropyl-N-methyl-amino)-ethyl | —OCH$_2$CH$_3$ |
| 2-(N-isopropyl-N-methyl-amino)-ethyl | —OCH$_2$CH$_2$OCH$_3$ |

| R1 | R5 |
|---|---|
| 2-(N-isopropyl-N-methyl-amino)-ethyl | cyclopropylmethoxy |
| 2-(N-isopropyl-N-methyl-amino)-ethyl | difluoromethoxy |
| 2-(N-isopropyl-N-methyl-amino)-ethyl | trifluoromethoxy |
| 2-((R)-3-fluoro-pyrrolidin-1-yl)-ethyl | —OCH$_3$ |
| 2-((R)-3-fluoro-pyrrolidin-1-yl)-ethyl | —OCH$_2$CH$_3$ |
| 2-((R)-3-fluoro-pyrrolidin-1-yl)-ethyl | —OCH$_2$CH$_2$OCH$_3$ |
| 2-((R)-3-fluoro-pyrrolidin-1-yl)-ethyl | cyclopropylmethoxy |
| 2-((R)-3-fluoro-pyrrolidin-1-yl)-ethyl | difluoromethoxy |
| 2-((R)-3-fluoro-pyrrolidin-1-yl)-ethyl | trifluoromethoxy |
| 2-((S)-3-fluoro-pyrrolidin-1-yl)-ethyl | —OCH$_3$ |
| 2-((S)-3-fluoro-pyrrolidin-1-yl)-ethyl | —OCH$_2$CH$_3$ |
| 2-((S)-3-fluoro-pyrrolidin-1-yl)-ethyl | —OCH$_2$CH$_2$OCH$_3$ |
| 2-((S)-3-fluoro-pyrrolidin-1-yl)-ethyl | cyclopropylmethoxy |
| 2-((S)-3-fluoro-pyrrolidin-1-yl)-ethyl | difluoromethoxy |
| 2-((S)-3-fluoro-pyrrolidin-1-yl)-ethyl | trifluoromethoxy |
| 2-(4-methyl-piperidin-1-yl)-ethyl | —OCH$_3$ |
| 2-(4-methyl-piperidin-1-yl)-ethyl | —OCH$_2$CH$_3$ |
| 2-(4-methyl-piperidin-1-yl)-ethyl | —OCH$_2$CH$_2$OCH$_3$ |
| 2-(4-methyl-piperidin-1-yl)-ethyl | cyclopropylmethoxy |
| 2-(4-methyl-piperidin-1-yl)-ethyl | difluoromethoxy |
| 2-(4-methyl-piperidin-1-yl)-ethyl | trifluoromethoxy |
| 3-(methylamino)-propyl | —OCH$_3$ |
| 3-(methylamino)-propyl | —OCH$_2$CH$_3$ |
| 3-(methylamino)-propyl | —OCH$_2$CH$_2$OCH$_3$ |
| 3-(methylamino)-propyl | cyclopropylmethoxy |
| 3-(methylamino)-propyl | difluoromethoxy |
| 3-(methylamino)-propyl | trifluoromethoxy |
| 3-(ethylamino)-propyl | —OCH$_3$ |
| 3-(ethylamino)-propyl | —OCH$_2$CH$_3$ |
| 3-(ethylamino)-propyl | —OCH$_2$CH$_2$OCH$_3$ |
| 3-(ethylamino)-propyl | cyclopropylmethoxy |
| 3-(ethylamino)-propyl | difluoromethoxy |
| 3-(ethylamino)-propyl | trifluoromethoxy |
| 3-(azetidin-1-yl)-propyl | —OCH$_3$ |
| 3-(azetidin-1-yl)-propyl | —OCH$_2$CH$_3$ |
| 3-(azetidin-1-yl)-propyl | —OCH$_2$CH$_2$OCH$_3$ |
| 3-(azetidin-1-yl)-propyl | cyclopropylmethoxy |
| 3-(azetidin-1-yl)-propyl | difluoromethoxy |
| 3-(azetidin-1-yl)-propyl | trifluoromethoxy |
| 3-(4-acetyl-piperazin-1-yl)-propyl | —OCH$_3$ |
| 3-(4-acetyl-piperazin-1-yl)-propyl | —OCH$_2$CH$_3$ |
| 3-(4-acetyl-piperazin-1-yl)-propyl | —OCH$_2$CH$_2$OCH$_3$ |
| 3-(4-acetyl-piperazin-1-yl)-propyl | cyclopropylmethoxy |
| 3-(4-acetyl-piperazin-1-yl)-propyl | difluoromethoxy |
| 3-(4-acetyl-piperazin-1-yl)-propyl | trifluoromethoxy |
| 3-(3,3-difluoropyrrolidin-1-yl)-propyl | —OCH$_3$ |
| 3-(3,3-difluoropyrrolidin-1-yl)-propyl | —OCH$_2$CH$_3$ |
| 3-(3,3-difluoropyrrolidin-1-yl)-propyl | —OCH$_2$CH$_2$OCH$_3$ |
| 3-(3,3-difluoropyrrolidin-1-yl)-propyl | cyclopropylmethoxy |
| 3-(3,3-difluoropyrrolidin-1-yl)-propyl | difluoromethoxy |
| 3-(3,3-difluoropyrrolidin-1-yl)-propyl | trifluoromethoxy |
| 3-(2-fluoroethylamino)-propyl | —OCH$_3$ |
| 3-(2-fluoroethylamino)-propyl | —OCH$_2$CH$_3$ |
| 3-(2-fluoroethylamino)-propyl | —OCH$_2$CH$_2$OCH$_3$ |
| 3-(2-fluoroethylamino)-propyl | cyclopropylmethoxy |
| 3-(2-fluoroethylamino)-propyl | difluoromethoxy |
| 3-(2-fluoroethylamino)-propyl | trifluoromethoxy |
| 3-(2,2-difluoroethylamino)-propyl | —OCH$_3$ |
| 3-(2,2-difluoroethylamino)-propyl | —OCH$_2$CH$_3$ |
| 3-(2,2-difluoroethylamino)-propyl | —OCH$_2$CH$_2$OCH$_3$ |
| 3-(2,2-difluoroethylamino)-propyl | cyclopropylmethoxy |
| 3-(2,2-difluoroethylamino)-propyl | difluoromethoxy |
| 3-(2,2-difluoroethylamino)-propyl | trifluoromethoxy |
| 3-(2,2,2-trifluoroethylamino)-propyl | —OCH$_3$ |
| 3-(2,2,2-trifluoroethylamino)-propyl | —OCH$_2$CH$_3$ |
| 3-(2,2,2-trifluoroethylamino)-propyl | —OCH$_2$CH$_2$OCH$_3$ |
| 3-(2,2,2-trifluoroethylamino)-propyl | cyclopropylmethoxy |
| 3-(2,2,2-trifluoroethylamino)-propyl | difluoromethoxy |
| 3-(2,2,2-trifluoroethylamino)-propyl | trifluoromethoxy |
| 3-(isopropylamino)-propyl | —OCH$_3$ |
| 3-(isopropylamino)-propyl | —OCH$_2$CH$_3$ |
| 3-(isopropylamino)-propyl | —OCH$_2$CH$_2$OCH$_3$ |
| 3-(isopropylamino)-propyl | cyclopropylmethoxy |
| 3-(isopropylamino)-propyl | difluoromethoxy |
| 3-(isopropylamino)-propyl | trifluoromethoxy |
| 3-(isobutylamino)-propyl | —OCH$_3$ |
| 3-(isobutylamino)-propyl | —OCH$_2$CH$_3$ |
| 3-(isobutylamino)-propyl | —OCH$_2$CH$_2$OCH$_3$ |
| 3-(isobutylamino)-propyl | cyclopropylmethoxy |
| 3-(isobutylamino)-propyl | difluoromethoxy |
| 3-(isobutylamino)-propyl | trifluoromethoxy |
| 3-(N-cyclopropylmethyl-amino)-propyl | —OCH$_3$ |
| 3-(N-cyclopropylmethyl-amino)-propyl | —OCH$_2$CH$_3$ |
| 3-(N-cyclopropylmethyl-amino)-propyl | —OCH$_2$CH$_2$OCH$_3$ |
| 3-(N-cyclopropylmethyl-amino)-propyl | cyclopropylmethoxy |
| 3-(N-cyclopropylmethyl-amino)-propyl | difluoromethoxy |
| 3-(N-cyclopropylmethyl-amino)-propyl | trifluoromethoxy |
| 3-(cyclopropylamino)-propyl | —OCH$_3$ |
| 3-(cyclopropylamino)-propyl | —OCH$_2$CH$_3$ |
| 3-(cyclopropylamino)-propyl | —OCH$_2$CH$_2$OCH$_3$ |
| 3-(cyclopropylamino)-propyl | cyclopropylmethoxy |
| 3-(cyclopropylamino)-propyl | difluoromethoxy |
| 3-(cyclopropylamino)-propyl | trifluoromethoxy |
| 3-(cyclobutylamino)-propyl | —OCH$_3$ |
| 3-(cyclobutylamino)-propyl | —OCH$_2$CH$_3$ |
| 3-(cyclobutylamino)-propyl | —OCH$_2$CH$_2$OCH$_3$ |
| 3-(cyclobutylamino)-propyl | cyclopropylmethoxy |
| 3-(cyclobutylamino)-propyl | difluoromethoxy |
| 3-(cyclobutylamino)-propyl | trifluoromethoxy |
| 3-(N-ethyl-N-methyl-amino)-propyl | —OCH$_3$ |
| 3-(N-ethyl-N-methyl-amino)-propyl | —OCH$_2$CH$_3$ |
| 3-(N-ethyl-N-methyl-amino)-propyl | —OCH$_2$CH$_2$OCH$_3$ |
| 3-(N-ethyl-N-methyl-amino)-propyl | cyclopropylmethoxy |
| 3-(N-ethyl-N-methyl-amino)-propyl | difluoromethoxy |
| 3-(N-ethyl-N-methyl-amino)-propyl | trifluoromethoxy |
| 3-(diethylamino)-propyl | —OCH$_3$ |
| 3-(diethylamino)-propyl | —OCH$_2$CH$_3$ |
| 3-(diethylamino)-propyl | —OCH$_2$CH$_2$OCH$_3$ |
| 3-(diethylamino)-propyl | cyclopropylmethoxy |
| 3-(diethylamino)-propyl | difluoromethoxy |
| 3-(diethylamino)-propyl | trifluoromethoxy |
| 3-(N-isopropyl-N-methyl-amino)-propyl | —OCH$_3$ |
| 3-(N-isopropyl-N-methyl-amino)-propyl | —OCH$_2$CH$_3$ |
| 3-(N-isopropyl-N-methyl-amino)-propyl | —OCH$_2$CH$_2$OCH$_3$ |
| 3-(N-isopropyl-N-methyl-amino)-propyl | cyclopropylmethoxy |
| 3-(N-isopropyl-N-methyl-amino)-propyl | difluoromethoxy |
| 3-(N-isopropyl-N-methyl-amino)-propyl | trifluoromethoxy |
| 3-((R)-3-fluoro-pyrrolidin-1-yl)-propyl | —OCH$_3$ |
| 3-((R)-3-fluoro-pyrrolidin-1-yl)-propyl | —OCH$_2$CH$_3$ |
| 3-((R)-3-fluoro-pyrrolidin-1-yl)-propyl | —OCH$_2$CH$_2$OCH$_3$ |
| 3-((R)-3-fluoro-pyrrolidin-1-yl)-propyl | cyclopropylmethoxy |
| 3-((R)-3-fluoro-pyrrolidin-1-yl)-propyl | difluoromethoxy |
| 3-((R)-3-fluoro-pyrrolidin-1-yl)-propyl | trifluoromethoxy |
| 3-((S)-3-fluoro-pyrrolidin-1-yl)-propyl | —OCH$_3$ |
| 3-((S)-3-fluoro-pyrrolidin-1-yl)-propyl | —OCH$_2$CH$_3$ |
| 3-((S)-3-fluoro-pyrrolidin-1-yl)-propyl | —OCH$_2$CH$_2$OCH$_3$ |
| 3-((S)-3-fluoro-pyrrolidin-1-yl)-propyl | cyclopropylmethoxy |
| 3-((S)-3-fluoro-pyrrolidin-1-yl)-propyl | difluoromethoxy |
| 3-((S)-3-fluoro-pyrrolidin-1-yl)-propyl | trifluoromethoxy |
| 3-(4-methyl-piperidin-1-yl)-propyl | —OCH$_3$ |
| 3-(4-methyl-piperidin-1-yl)-propyl | —OCH$_2$CH$_3$ |
| 3-(4-methyl-piperidin-1-yl)-propyl | —OCH$_2$CH$_2$OCH$_3$ |
| 3-(4-methyl-piperidin-1-yl)-propyl | cyclopropylmethoxy |
| 3-(4-methyl-piperidin-1-yl)-propyl | difluoromethoxy |
| 3-(4-methyl-piperidin-1-yl)-propyl | trifluoromethoxy |
| 3-[N-(2-hydroxyethyl)-amino]-propyl | —OCH$_3$ |
| 3-[N-(2-hydroxyethyl)-amino]-propyl | —OCH$_2$CH$_3$ |
| 3-[N-(2-hydroxyethyl)-amino]-propyl | —OCH$_2$CH$_2$OCH$_3$ |
| 3-[N-(2-hydroxyethyl)-amino]-propyl | cyclopropylmethoxy |
| 3-[N-(2-hydroxyethyl)-amino]-propyl | difluoromethoxy |
| 3-[N-(2-hydroxyethyl)-amino]-propyl | trifluoromethoxy |
| 3-[N-(2-methoxyethyl)-amino]-propyl | —OCH$_3$ |
| 3-[N-(2-methoxyethyl)-amino]-propyl | —OCH$_2$CH$_3$ |
| 3-[N-(2-methoxyethyl)-amino]-propyl | —OCH$_2$CH$_2$OCH$_3$ |
| 3-[N-(2-methoxyethyl)-amino]-propyl | cyclopropylmethoxy |
| 3-[N-(2-methoxyethyl)-amino]-propyl | difluoromethoxy |
| 3-[N-(2-methoxyethyl)-amino]-propyl | trifluoromethoxy |
| 3-(tertbutylamino)-propyl | —OCH$_3$ |
| 3-(tertbutylamino)-propyl | —OCH$_2$CH$_3$ |
| 3-(tertbutylamino)-propyl | —OCH$_2$CH$_2$OCH$_3$ |
| 3-(tertbutylamino)-propyl | cyclopropylmethoxy |
| 3-(tertbutylamino)-propyl | difluoromethoxy |
| 3-(tertbutylamino)-propyl | trifluoromethoxy |
| 3-(allylamino)-propyl | —OCH$_3$ |
| 3-(allylamino)-propyl | —OCH$_2$CH$_3$ |
| 3-(allylamino)-propyl | —OCH$_2$CH$_2$OCH$_3$ |

-continued

| R1 | R5 |
|---|---|
| 3-(allylamino)-propyl | cyclopropylmethoxy |
| 3-(allylamino)-propyl | difluoromethoxy |
| 3-(allylamino)-propyl | trifluoromethoxy |
| 3-(propargylamino)-propyl | —OCH$_3$ |
| 3-(propargylamino)-propyl | —OCH$_2$CH$_3$ |
| 3-(propargylamino)-propyl | —OCH$_2$CH$_2$OCH$_3$ |
| 3-(propargylamino)-propyl | cyclopropylmethoxy |
| 3-(propargylamino)-propyl | difluoromethoxy |
| 3-(propargylamino)-propyl | trifluoromethoxy |
| 3-(N-allyl-N-methyl-amino)-propyl | —OCH$_3$ |
| 3-(N-allyl-N-methyl-amino)-propyl | —OCH$_2$CH$_3$ |
| 3-(N-allyl-N-methyl-amino)-propyl | —OCH$_2$CH$_2$OCH$_3$ |
| 3-(N-allyl-N-methyl-amino)-propyl | cyclopropylmethoxy |
| 3-(N-allyl-N-methyl-amino)-propyl | difluoromethoxy |
| 3-(N-allyl-N-methyl-amino)-propyl | trifluoromethoxy |
| 3-(N-methyl-N-propargyl-amino)-propyl | —OCH$_3$ |
| 3-(N-methyl-N-propargyl-amino)-propyl | —OCH$_2$CH$_3$ |
| 3-(N-methyl-N-propargyl-amino)-propyl | —OCH$_2$CH$_2$OCH$_3$ |
| 3-(N-methyl-N-propargyl-amino)-propyl | cyclopropylmethoxy |
| 3-(N-methyl-N-propargyl-amino)-propyl | difluoromethoxy |
| 3-(N-methyl-N-propargyl-amino)-propyl | trifluoromethoxy |
| 3-[N-(2-hydroxyethyl)-N-methyl-amino]-propyl | —OCH$_3$ |
| 3-[N-(2-hydroxyethyl)-N-methyl-amino]-propyl | —OCH$_2$CH$_3$ |
| 3-[N-(2-hydroxyethyl)-N-methyl-amino]-propyl | —OCH$_2$CH$_2$OCH$_3$ |
| 3-[N-(2-hydroxyethyl)-N-methyl-amino]-propyl | cyclopropylmethoxy |
| 3-[N-(2-hydroxyethyl)-N-methyl-amino]-propyl | difluoromethoxy |
| 3-[N-(2-hydroxyethyl)-N-methyl-amino]-propyl | trifluoromethoxy |
| 3-[N-(2-methoxyethyl)-N-methyl-amino]-propyl | —OCH$_3$ |
| 3-[N-(2-methoxyethyl)-N-methyl-amino]-propyl | —OCH$_2$CH$_3$ |
| 3-[N-(2-methoxyethyl)-N-methyl-amino]-propyl | —OCH$_2$CH$_2$OCH$_3$ |
| 3-[N-(2-methoxyethyl)-N-methyl-amino]-propyl | cyclopropylmethoxy |
| 3-[N-(2-methoxyethyl)-N-methyl-amino]-propyl | difluoromethoxy |
| 3-[N-(2-methoxyethyl)-N-methyl-amino]-propyl | trifluoromethoxy |
| 3-[N-ethyl-N-(2-hydroxyethyl)-amino]-propyl | —OCH$_3$ |
| 3-[N-ethyl-N-(2-hydroxyethyl)-amino]-propyl | —OCH$_2$CH$_3$ |
| 3-[N-ethyl-N-(2-hydroxyethyl)-amino]-propyl | —OCH$_2$CH$_2$OCH$_3$ |
| 3-[N-ethyl-N-(2-hydroxyethyl)-amino]-propyl | cyclopropylmethoxy |
| 3-[N-ethyl-N-(2-hydroxyethyl)-amino]-propyl | difluoromethoxy |
| 3-[N-ethyl-N-(2-hydroxyethyl)-amino]-propyl | trifluoromethoxy |
| 3-[N-ethyl-N-(2-methoxyethyl)-amino]-propyl | —OCH$_3$ |
| 3-[N-ethyl-N-(2-methoxyethyl)-amino]-propyl | —OCH$_2$CH$_3$ |
| 3-[N-ethyl-N-(2-methoxyethyl)-amino]-propyl | —OCH$_2$CH$_2$OCH$_3$ |
| 3-[N-ethyl-N-(2-methoxyethyl)-amino]-propyl | cyclopropylmethoxy |
| 3-[N-ethyl-N-(2-methoxyethyl)-amino]-propyl | difluoromethoxy |
| 3-[N-ethyl-N-(2-methoxyethyl)-amino]-propyl | trifluoromethoxy |
| 3-(piperidin-1-yl)-propyl | —OCH$_3$ |
| 3-(piperidin-1-yl)-propyl | —OCH$_2$CH$_3$ |
| 3-(piperidin-1-yl)-propyl | —OCH$_2$CH$_2$OCH$_3$ |
| 3-(piperidin-1-yl)-propyl | cyclopropylmethoxy |
| 3-(piperidin-1-yl)-propyl | difluoromethoxy |
| 3-(piperidin-1-yl)-propyl | trifluoromethoxy |
| 3-(homopiperidin-1-yl)-propyl | —OCH$_3$ |
| 3-(homopiperidin-1-yl)-propyl | —OCH$_2$CH$_3$ |
| 3-(homopiperidin-1-yl)-propyl | —OCH$_2$CH$_2$OCH$_3$ |
| 3-(homopiperidin-1-yl)-propyl | cyclopropylmethoxy |
| 3-(homopiperidin-1-yl)-propyl | difluoromethoxy |
| 3-(homopiperidin-1-yl)-propyl | trifluoromethoxy |
| 3-(2,5-dihydropyrrol-1-yl)-propyl | —OCH$_3$ |
| 3-(2,5-dihydropyrrol-1-yl)-propyl | —OCH$_2$CH$_3$ |
| 3-(2,5-dihydropyrrol-1-yl)-propyl | —OCH$_2$CH$_2$OCH$_3$ |
| 3-(2,5-dihydropyrrol-1-yl)-propyl | cyclopropylmethoxy |
| 3-(2,5-dihydropyrrol-1-yl)-propyl | difluoromethoxy |
| 3-(2,5-dihydropyrrol-1-yl)-propyl | trifluoromethoxy |
| 3-(1,2,3,6-tetrahydropyridin-1-yl)-propyl | —OCH$_3$ |
| 3-(1,2,3,6-tetrahydropyridin-1-yl)-propyl | —OCH$_2$CH$_3$ |
| 3-(1,2,3,6-tetrahydropyridin-1-yl)-propyl | —OCH$_2$CH$_2$OCH$_3$ |
| 3-(1,2,3,6-tetrahydropyridin-1-yl)-propyl | cyclopropylmethoxy |
| 3-(1,2,3,6-tetrahydropyridin-1-yl)-propyl | difluoromethoxy |
| 3-(1,2,3,6-tetrahydropyridin-1-yl)-propyl | trifluoromethoxy |
| 2-[N-(2-hydroxyethyl)-amino]-ethyl | —OCH$_3$ |
| 2-[N-(2-hydroxyethyl)-amino]-ethyl | —OCH$_2$CH$_3$ |
| 2-[N-(2-hydroxyethyl)-amino]-ethyl | —OCH$_2$CH$_2$OCH$_3$ |
| 2-[N-(2-hydroxyethyl)-amino]-ethyl | cyclopropylmethoxy |
| 2-[N-(2-hydroxyethyl)-amino]-ethyl | difluoromethoxy |
| 2-[N-(2-hydroxyethyl)-amino]-ethyl | trifluoromethoxy |
| 2-[N-(2-methoxyethyl)-amino]-ethyl | —OCH$_3$ |
| 2-[N-(2-methoxyethyl)-amino]-ethyl | —OCH$_2$CH$_3$ |
| 2-[N-(2-methoxyethyl)-amino]-ethyl | —OCH$_2$CH$_2$OCH$_3$ |
| 2-[N-(2-methoxyethyl)-amino]-ethyl | cyclopropylmethoxy |
| 2-[N-(2-methoxyethyl)-amino]-ethyl | difluoromethoxy |
| 2-[N-(2-methoxyethyl)-amino]-ethyl | trifluoromethoxy |
| 2-(tertbutylamino)-ethyl | —OCH$_3$ |
| 2-(tertbutylamino)-ethyl | —OCH$_2$CH$_3$ |
| 2-(tertbutylamino)-ethyl | —OCH$_2$CH$_2$OCH$_3$ |
| 2-(tertbutylamino)-ethyl | cyclopropylmethoxy |
| 2-(tertbutylamino)-ethyl | difluoromethoxy |
| 2-(tertbutylamino)-ethyl | trifluoromethoxy |
| 2-(allylamino)-ethyl | —OCH$_3$ |
| 2-(allylamino)-ethyl | —OCH$_2$CH$_3$ |
| 2-(allylamino)-ethyl | —OCH$_2$CH$_2$OCH$_3$ |
| 2-(allylamino)-ethyl | cyclopropylmethoxy |
| 2-(allylamino)-ethyl | difluoromethoxy |
| 2-(allylamino)-ethyl | trifluoromethoxy |
| 2-(propargylamino)-ethyl | —OCH$_3$ |
| 2-(propargylamino)-ethyl | —OCH$_2$CH$_3$ |
| 2-(propargylamino)-ethyl | —OCH$_2$CH$_2$OCH$_3$ |
| 2-(propargylamino)-ethyl | cyclopropylmethoxy |
| 2-(propargylamino)-ethyl | difluoromethoxy |
| 2-(propargylamino)-ethyl | trifluoromethoxy |
| 2-(N-allyl-N-methyl-amino)-ethyl | —OCH$_3$ |
| 2-(N-allyl-N-methyl-amino)-ethyl | —OCH$_2$CH$_3$ |
| 2-(N-allyl-N-methyl-amino)-ethyl | —OCH$_2$CH$_2$OCH$_3$ |
| 2-(N-allyl-N-methyl-amino)-ethyl | cyclopropylmethoxy |
| 2-(N-allyl-N-methyl-amino)-ethyl | difluoromethoxy |
| 2-(N-allyl-N-methyl-amino)-ethyl | trifluoromethoxy |
| 2-(N-methyl-N-propargyl-amino)-ethyl | —OCH$_3$ |
| 2-(N-methyl-N-propargyl-amino)-ethyl | —OCH$_2$CH$_3$ |
| 2-(N-methyl-N-propargyl-amino)-ethyl | —OCH$_2$CH$_2$OCH$_3$ |
| 2-(N-methyl-N-propargyl-amino)-ethyl | cyclopropylmethoxy |
| 2-(N-methyl-N-propargyl-amino)-ethyl | difluoromethoxy |
| 2-(N-methyl-N-propargyl-amino)-ethyl | trifluoromethoxy |
| 2-[N-(2-hydroxyethyl)-N-methyl-amino]-ethyl | —OCH$_3$ |
| 2-[N-(2-hydroxyethyl)-N-methyl-amino]-ethyl | —OCH$_2$CH$_3$ |
| 2-[N-(2-hydroxyethyl)-N-methyl-amino]-ethyl | —OCH$_2$CH$_2$OCH$_3$ |
| 2-[N-(2-hydroxyethyl)-N-methyl-amino]-ethyl | cyclopropylmethoxy |
| 2-[N-(2-hydroxyethyl)-N-methyl-amino]-ethyl | difluoromethoxy |
| 2-[N-(2-hydroxyethyl)-N-methyl-amino]-ethyl | trifluoromethoxy |
| 2-[N-(2-methoxyethyl)-N-methyl-amino]-ethyl | —OCH$_3$ |
| 2-[N-(2-methoxyethyl)-N-methyl-amino]-ethyl | —OCH$_2$CH$_3$ |
| 2-[N-(2-methoxyethyl)-N-methyl-amino]-ethyl | —OCH$_2$CH$_2$OCH$_3$ |
| 2-[N-(2-methoxyethyl)-N-methyl-amino]-ethyl | cyclopropylmethoxy |
| 2-[N-(2-methoxyethyl)-N-methyl-amino]-ethyl | difluoromethoxy |
| 2-[N-(2-methoxyethyl)-N-methyl-amino]-ethyl | trifluoromethoxy |
| 2-[N-ethyl-N-(2-hydroxyethyl)-amino]-ethyl | —OCH$_3$ |
| 2-[N-ethyl-N-(2-hydroxyethyl)-amino]-ethyl | —OCH$_2$CH$_3$ |
| 2-[N-ethyl-N-(2-hydroxyethyl)-amino]-ethyl | —OCH$_2$CH$_2$OCH$_3$ |
| 2-[N-ethyl-N-(2-hydroxyethyl)-amino]-ethyl | cyclopropylmethoxy |
| 2-[N-ethyl-N-(2-hydroxyethyl)-amino]-ethyl | difluoromethoxy |
| 2-[N-ethyl-N-(2-hydroxyethyl)-amino]-ethyl | trifluoromethoxy |
| 2-[N-ethyl-N-(2-methoxyethyl)-amino]-ethyl | —OCH$_3$ |
| 2-[N-ethyl-N-(2-methoxyethyl)-amino]-ethyl | —OCH$_2$CH$_3$ |
| 2-[N-ethyl-N-(2-methoxyethyl)-amino]-ethyl | —OCH$_2$CH$_2$OCH$_3$ |
| 2-[N-ethyl-N-(2-methoxyethyl)-amino]-ethyl | cyclopropylmethoxy |
| 2-[N-ethyl-N-(2-methoxyethyl)-amino]-ethyl | difluoromethoxy |
| 2-[N-ethyl-N-(2-methoxyethyl)-amino]-ethyl | trifluoromethoxy |
| 2-(piperidin-1-yl)-ethyl | —OCH$_3$ |
| 2-(piperidin-1-yl)-ethyl | —OCH$_2$CH$_3$ |
| 2-(piperidin-1-yl)-ethyl | —OCH$_2$CH$_2$OCH$_3$ |
| 2-(piperidin-1-yl)-ethyl | cyclopropylmethoxy |
| 2-(piperidin-1-yl)-ethyl | difluoromethoxy |
| 2-(piperidin-1-yl)-ethyl | trifluoromethoxy |
| 2-(homopiperidin-1-yl)-ethyl | —OCH$_3$ |
| 2-(homopiperidin-1-yl)-ethyl | —OCH$_2$CH$_3$ |
| 2-(homopiperidin-1-yl)-ethyl | —OCH$_2$CH$_2$OCH$_3$ |
| 2-(homopiperidin-1-yl)-ethyl | cyclopropylmethoxy |
| 2-(homopiperidin-1-yl)-ethyl | difluoromethoxy |
| 2-(homopiperidin-1-yl)-ethyl | trifluoromethoxy |
| 2-(2,5)-dihydropyrrol-1-yl)-ethyl | —OCH$_3$ |
| 2-(2,5)-dihydropyrrol-1-yl)-ethyl | —OCH$_2$CH$_3$ |
| 2-(2,5)-dihydropyrrol-1-yl)-ethyl | —OCH$_2$CH$_2$OCH$_3$ |
| 2-(2,5)-dihydropyrrol-1-yl)-ethyl | cyclopropylmethoxy |
| 2-(2,5)-dihydropyrrol-1-yl)-ethyl | difluoromethoxy |
| 2-(2,5)-dihydropyrrol-1-yl)-ethyl | trifluoromethoxy |
| 2-(1,2,3,6-tetrahydropyridin-1-yl)-ethyl | —OCH$_3$ |
| 2-(1,2,3,6-tetrahydropyridin-1-yl)-ethyl | —OCH$_2$CH$_3$ |
| 2-(1,2,3,6-tetrahydropyridin-1-yl)-ethyl | —OCH$_2$CH$_2$OCH$_3$ |

-continued

| R1 | R5 |
|---|---|
| 2-(1,2,3,6-tetrahydropyridin-1-yl)-ethyl | cyclopropylmethoxy |
| 2-(1,2,3,6-tetrahydropyridin-1-yl)-ethyl | difluoromethoxy |
| 2-(1,2,3,6-tetrahydropyridin-1-yl)-ethyl | trifluoromethoxy | or a salt thereof.

12. A compound, which is one of the following compounds
1. (3aS,10R)-6-Ethoxy-10-(3-hydroxy-phenyl)-2,3a-dimethyl-3a,4,9,10-tetrahydro-2,9,10a-triaza-cyclopenta[b]fluorene-1,3-dione
2. (3aS,10R)-10-(3-Hydroxy-phenyl)-6-(2-methoxy-ethoxy)-2,3a-dimethyl-3a,4,9,10-tetrahydro-2,9,10a-triaza-cyclopenta[b]fluorene-1,3-dione
3. (3aS,10R)-10-(3-Hydroxy-phenyl)-6-methoxy-2,3a-dimethyl-3a,4,9,10-tetrahydro-2,9,10a-triaza-cyclopenta[b]fluorene-1,3-dione
6. (3aS,10R)-2-(2-Dimethylamino-ethyl)-10-(3-hydroxy-phenyl)-6-(2-methoxy-ethoxy)-3a-methyl-3a,4,9,10-tetrahydro-2,9,10a-triaza-cyclopenta[b]fluorene-1,3-dione
7. (3aS,10R)-2-(2-Dimethylamino-ethyl)-10-(3-hydroxy-phenyl)-6-methoxy-3a-methyl-3a,4,9,10-tetrahydro-2,9,10a-triaza-cyclopenta[b]fluorene-1,3-dione
10. (3aS,10R)-10-(3-Hydroxy-phenyl)-6-methoxy-3a-methyl-2-(2-morpholin-4-yl-ethyl)-3a,4,9,10-tetrahydro-2,9,10a-triaza-cyclopenta[b]fluorene-1,3-dione
11. (3aS,10R)-10-(3-Hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione
12. (3aS,10R)-10-(3-Hydroxy-phenyl)-6-methoxy-3a-methyl-2-[2-(4-methyl-piperazin-1-yl)-ethyl]-3a,4,9,10-tetrahydro-2,9,10a-triaza-cyclopenta[b]fluorene-1,3-dione
13. (3aS,10R)-10-(3-Hydroxy-phenyl)-2-(2-imidazol-1-yl-ethyl)-6-methoxy-3a-methyl-3a,4,9,10-tetrahydro-2,9,10a-triaza-cyclopenta[b]fluorene-1,3-dione
14. (3aS,10R)-2-(4-Dimethylamino-butyl)-10-(3-hydroxy-phenyl)-6-methoxy-3a-methyl-3a,4,9,10-tetrahydro-2,9,10a-triaza-cyclopenta[b]fluorene-1,3-dione
15. (3aS,10R)-2-(3-Dimethylamino-propyl)-10-(3-hydroxy-phenyl)-6-methoxy-3a-methyl-3a,4,9,10-tetrahydro-2,9,10a-triaza-cyclopenta[b]fluorene-1,3-dione
18. (3aS,10R)-2-(2-Dimethylamino-ethyl)-3a-ethyl-10-(3-hydroxy-phenyl)-6-methoxy-3a,4,9,10-tetrahydro-2,9,10a-triaza-cyclopenta[b]fluorene-1,3-dione
19. (3aS,10R)-2-(3-Dimethylamino-propyl)-3a-ethyl-10-(3-hydroxy-phenyl)-6-methoxy-3a,4,9,10-tetrahydro-2,9,10a-triaza-cyclopenta[b]fluorene-1,3-dione
20. (3aS,10R)-10-(3-Hydroxy-phenyl)-2-(3-imidazol-1-yl-propyl)-6-methoxy-3a-methyl-3a,4,9,10-tetrahydro-2,9,10a-triaza-cyclopenta[b]fluorene-1,3-dione
21. (3aS,10R)-6-Cyclopropylmethoxy-10-(3-hydroxy-phenyl)-2,3a-dimethyl-3a,4,9,10-tetrahydro-2,9,10a-triaza-cyclopenta[b]fluorene-1,3-dione
22. (3aS,10R)-2-(2-Bromo-ethyl)-6-ethoxy-10-(3-hydroxy-phenyl)-3a-methyl-3a,4,9,10-tetrahydro-2,9,10a-triaza-cyclopenta[b]fluorene-1,3-dione
23. (3aS,10R)-2-(2-Dimethylamino-ethyl)-6-ethoxy-10-(3-hydroxy-phenyl)-3a-methyl-3a,4,9,10-tetrahydro-2,9,10a-triaza-cyclopenta[b]fluorene-1,3-dione
24. (3aS,10R)-2-(2-Bromo-ethyl)-10-(3-hydroxy-phenyl)-6-methoxy-3a-methyl-3a,4,9,10-tetrahydro-2,9,10a-triaza-cyclopenta[b]fluorene-1,3-dione
25. (3aS,10R)-2-(2-Amino-ethyl)-10-(3-hydroxy-phenyl)-6-methoxy-3a-methyl-3a,4,9,10-tetrahydro-2,9,10a-triaza-cyclopenta[b]fluorene-1,3-dione
27. (3aS,10R)-10-(3-Hydroxy-phenyl)-6-methoxy-3a-methyl-2-(2-methylamino-ethyl)-3a,4,9,10-tetrahydro-2,9,10a-triaza-cyclopenta[b]fluorene-1,3-dione
32. (3aS,10R)-2-[2-(4-Acetyl-piperazin-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione
33. (3aS,10R)-2-(2-Azetidin-1-yl-ethyl)-10-(3-hydroxy-phenyl)-6-methoxy-3a-methyl-3a,4,9,10-tetrahydro-2,9,10a-triaza-cyclopenta[b]fluorene-1,3-dione
34. (3aS,10R)-2-[2-(3,3-Difluoro-pyrrolidin-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione
35. (3aS,10R)-2-(2-Ethylamino-ethyl)-10-(3-hydroxy-phenyl)-6-methoxy-3a-methyl-3a,4,9,10-tetrahydro-2,9,10a-triaza-cyclopenta[b]fluorene-1,3-dione
36. (3aS,10R)-2-(2-Bromo-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
41. (3aS,10R)-6-Ethoxy-10-(3-hydroxy-phenyl)-3a-methyl-2-(2-methylamino-ethyl)-3a,4,9,10-tetrahydro-2,9,10a-triaza-cyclopenta[b]fluorene-1,3-dione
42. (3aS, OR)-6-(1,1-Difluoro-methoxy)-10-(3-hydroxy-phenyl)-3a-methyl-2-(2-methylamino-ethyl)-3a,4,9,10-tetrahydro-2,9,10a-triaza-cyclopenta[b]fluorene-1,3-dione
43. (3aS,10R)-6-(1,1-Difluoro-methoxy)-2-(2-dimethylamino-ethyl)-10-(3-hydroxy-phenyl)-3a-methyl-3a,4,9,10-tetrahydro-2,9,10a-triaza-cyclopenta[b]fluorene-1,3-dione
44. (3aS,10R)-2-(2-Azetidin-1-yl-ethyl)-6-(1-difluoro-methoxy)-10-(3-hydroxy-phenyl)-3a-methyl-3a,4,9,10-tetrahydro-2,9,10a-triaza-cyclopenta[b]fluorene-1,3-dione
45. (3aS,10R)-2-(2-Amino-ethyl)-6-ethoxy-10-(3-hydroxy-phenyl)-3a-methyl-3a,4,9,10-tetrahydro-2,9,10a-triaza-cyclopenta[b]fluorene-1,3-dione
46. (3aS,10R)-2-(2-Azetidin-1-yl-ethyl)-6-ethoxy-10-(3-hydroxy-phenyl)-3a-methyl-3a,4,9,10-tetrahydro-2,9,10a-triaza-cyclopenta[b]fluorene-1,3-dione
47. (3aS,10R)-10-(3-Hydroxy-phenyl)-2-(2-isopropylamino-ethyl)-6-methoxy-3a-methyl-3a,4,9,10-tetrahydro-2,9,10a-triaza-cyclopenta[b]fluorene-1,3-dione
48. (3aS,10R)-2-[2-(Cyclopropylmethyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione
49. (3aS,10R)-10-(3-Hydroxy-phenyl)-2-(2-isobutylamino-ethyl)-6-methoxy-3a-methyl-3a,4,9,10-tetrahydro-2,9,10a-triaza-cyclopenta[b]fluorene-1,3-dione
50. (3aS,10R)-2-(2-Cyclobutylamino-ethyl)-10-(3-hydroxy-phenyl)-6-methoxy-3a-methyl-3a,4,9,10-tetrahydro-2,9,10a-triaza-cyclopenta[b]fluorene-1,3-dione
51. (3aS,10R)-2-(3-Ethylamino-propyl)-10-(3-hydroxy-phenyl)-6-methoxy-3a-methyl-3a,4,9,10-tetrahydro-2,9,10a-triaza-cyclopenta[b]fluorene-1,3-dione 52. (3aS,10R)-2-[2-(Ethyl-methyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione,
53. (3aS,10R)-2-(2-Cyclopropylamino-ethyl)-10-(3-hydroxy-phenyl)-6-methoxy-3a-methyl-3a,4,9,10-tetrahydro-2,9,10a-triaza-cyclopenta[b]fluorene-1,3-dione,
55. (3aS,10R)-2-(3-Chloro-propyl)-10-(3-hydroxy-phenyl)-6-methoxy-3a-methyl-3a,4,9,10-tetrahydro-2,9,10a-triaza-cyclopenta[b]fluorene-1,3-dione
56. (3aS,10R)-2-(3-Chloro-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
59. (3aS,10R)-2-(3-Chloro-propyl)-6-ethoxy-10-(3-hydroxy-phenyl)-3a-methyl-3a,4,9,10-tetrahydro-2,9,10a-triaza-cyclopenta[b]fluorene-1,3-dione
60. (3aS,10R)-2-(2-Bromo-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
62. (3aS,10R)-2-(2-Bromo-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
63. (3aS,10R)-2-(3-Chloro-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
65. (3aS,10R)-2-(3-Chloro-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
67. (3aS,10R)-10-(3-Hydroxy-phenyl)-2-(3-isopropylamino-propyl)-6-methoxy-3a-methyl-3a,4,9,10-tetrahydro-2,9,10a-triaza-cyclopenta[b]fluorene-1,3-dione
68. (3aS,10R)-2-[2-(3,6-Dihydro-2H-pyridin-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione
69. (3aS,10R)-2-(2-Diethylamino-ethyl)-10-(3-hydroxy-phenyl)-6-methoxy-3a-methyl-3a,4,9,10-tetrahydro-2,9,10a-triaza-cyclopenta[b]fluorene-1,3-dione
70. (3aS,10R)-10-(3-Hydroxy-phenyl)-2-[2-(isopropyl-methyl-amino)-ethyl]-6-methoxy-3a-methyl-3a,4,9,10-tetrahydro-2,9,10a-triaza-cyclopenta[b]fluorene-1,3-dione
71. (3aS,10R)-10-(3-Hydroxy-phenyl)-6-methoxy-3a-methyl-2-(2-piperidin-1-yl-ethyl)-3a,4,9,10-tetrahydro-2,9,10a-triaza-cyclopenta[b]fluorene-1,3-dione
72. (3aS,10R)-2-(2-tert-Butylamino-ethyl)-10-(3-hydroxy-phenyl)-6-methoxy-3a-methyl-3a,4,9,10-tetrahydro-2,9,10a-triaza-cyclopenta[b]fluorene-1,3-dione
73. (3aS, OR)-2-[2-(2,2-Difluoro-ethylamino)-ethyl]-10-(3-hydroxy-phenyl)-6-methoxy-3a-methyl-3a,4,9,10-tetrahydro-2,9,10a-triaza-cyclopenta[b]fluorene-1,3-dione
74. (3aS,10R)-2-(2-Azepan-1-yl-ethyl)-10-(3-hydroxy-phenyl)-6-methoxy-3a-methyl-3a,4,9,10-tetrahydro-2,9,10a-triaza-cyclopenta[b]fluorene-1,3-dione
75. (3aS, OR)-10-(3-Hydroxy-phenyl)-6-methoxy-3a-methyl-2-[2-(4-methyl-piperidin-1-yl)-ethyl]-3a,4,9,10-tetrahydro-2,9,10a-triaza-cyclopenta[b]fluorene-1,3-dione
76. (3aS,10R)-10-(3-Hydroxy-phenyl)-6-methoxy-3a-methyl-2-(3-methylamino-propyl)-3a,4,9,10-tetrahydro-2,9,10a-triaza-cyclopenta[b]fluorene-1,3-dione
77. (3aS, OR)-2-[3-(Ethyl-methyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione
78. (3aS,10R)-2-{2-[Ethyl-(2-hydroxy-ethyl)-amino]-ethyl}-10-(3-hydroxy-phenyl)-6-methoxy-3a-methyl-3a,4,9,10-tetrahydro-2,9,10a-triaza-cyclopenta[b]fluorene-1,3-dione
79. (3aS,10R)-2-{2-[Ethyl-(2-methoxy-ethyl)-amino]-ethyl}-10-(3-hydroxy-phenyl)-6-methoxy-3a-methyl-3a,4,9,10-tetrahydro-2,9,10a-triaza-cyclopenta[b]fluorene-1,3-dione
80. (3aS,10R)-2-[2-(Allyl-methyl-amino)-ethyl]-10-(3-hydroxy-phenyl)-6-methoxy-3a-methyl-3a,4,9,10-tetrahydro-2,9,10a-triaza-cyclopenta[b]fluorene-1,3-dione
81. (3aS,10R)-10-(3-Hydroxy-phenyl)-6-methoxy-3a-methyl-2-[2-(methyl-prop-2-ynyl-amino)-ethyl]-3a,4,9,10-tetrahydro-2,9,10a-triaza-cyclopenta[b]fluorene-1,3-dione
82. (3aS,10R)-2-[2-(2-Hydroxy-ethylamino)-ethyl]-10-(3-hydroxy-phenyl)-6-methoxy-3a-methyl-3a,4,9,10-tetrahydro-2,9,10a-triaza-cyclopenta[b]fluorene-1,3-dione
83. (3aS, OR)-10-(3-Hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione
84. (3aS,10R)-2-(2-Allylamino-ethyl)-10-(3-hydroxy-phenyl)-6-methoxy-3a-methyl-3a,4,9,10-tetrahydro-2,9,10a-triaza-cyclopenta[b]fluorene-1,3-dione
85. (3aS,10R)-10-(3-Hydroxy-phenyl)-6-methoxy-3a-methyl-2-(2-prop-2-ynylamino-ethyl)-3a,4,9,10-tetrahydro-2,9,10a-triaza-cyclopenta[b]fluorene-1,3-dione
86. (3aS,10R)-2-(3-Cyclobutylamino-propyl)-10-(3-hydroxy-phenyl)-6-methoxy-3a-methyl-3a,4,9,10-tetrahydro-2,9,10a-triaza-cyclopenta[b]fluorene-1,3-dione
87. (3aS,10R)-2-(3-Azetidin-1-yl-propyl)-10-(3-hydroxy-phenyl)-6-methoxy-3a-methyl-3a,4,9,10-tetrahydro-2,9,10a-triaza-cyclopenta[b]fluorene-1,3-dione
88. (3aS,10R)-2-[3-(Allyl-methyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione
89. (3aS,10R)-2-{3-[Ethyl-(2-hydroxy-ethyl)-amino]-propyl}-10-(3-hydroxy-phenyl)-6-methoxy-3a-methyl-3a,4,9,10-tetrahydro-2,9,10a-triaza-cyclopenta[b]fluorene-1,3-dione
90. (3aS,10R)-2-{3-[Ethyl-(2-methoxy-ethyl)-amino]-propyl}-10-(3-hydroxy-phenyl)-6-methoxy-3a-methyl-3a,4,9,10-tetrahydro-2,9,10a-triaza-cyclopenta[b]fluorene-1,3-dione
91. (3aS,10R)-10-(3-Hydroxy-phenyl)-6-methoxy-3a-methyl-2-[2-(1-methyl-1H-pyrazol-3-ylamino)-ethyl]-3a,4,9,10-tetrahydro-2,9,10a-triaza-cyclopenta[b]fluorene-1,3-dione
92. (3aS,10R)-10-(3-Hydroxy-phenyl)-2-(3-isobutylamino-propyl)-6-methoxy-3a-methyl-3a,4,9,10-tetrahydro-2,9,10a-triaza-cyclopenta[b]fluorene-1,3-dione 93. (3aS,10R)-2-(3-Cyclopropylamino-propyl)-10-(3-hydroxy-phenyl)-6-methoxy-3a-methyl-3a,4,9,10-tetrahydro-2,9,10a-triaza-cyclopenta[b]fluorene-1,3-dione
94. (3aS,10R)-10-(3-Hydroxy-phenyl)-2-[3-(isopropyl-methyl-amino)-propyl]-6-methoxy-3a-methyl-3a,4,9,10-tetrahydro-2,9,10a-triaza-cyclopenta[b]fluorene-1,3-dione
95. (3aS,10R)-2-[3-(Cyclopropylmethyl-amino)-propyl]-10-(3-hydroxy-phenyl)-6-methoxy-3a-methyl-3a,4,9,10-tetrahydro-2,9,10a-triaza-cyclopenta[b]fluorene-1,3-dione
96. (3aS,10R)-10-(3-Hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione
105. (3aS,10R)-10-(3-Hydroxy-phenyl)-6-methoxy-3a-methyl-2-(3-piperidin-1-yl-propyl)-3a,4,9,10-tetrahydro-2,9,10a-triaza-cyclopenta[b]fluorene-1,3-dione
106. (3aS,10R)-2-[3-(3,6-Dihydro-2H-pyridin-1-yl)-propyl]-10-(3-hydroxy-phenyl)-6-methoxy-3a-methyl-3a,4,9,10-tetrahydro-2,9,10a-triaza-cyclopenta[b]fluorene-1,3-dione
107. (3aS,10R)-2-(3-Diethylamino-propyl)-10-(3-hydroxy-phenyl)-6-methoxy-3a-methyl-3a,4,9,10-tetrahydro-2,9,10a-triaza-cyclopenta[b]fluorene-1,3-dione
112. (3aS,10R)-10-(3-Hydroxy-phenyl)-6-methoxy-3a-methyl-2-[3-(4-methyl-piperidin-1-yl)-propyl]-3a,4,9,10-tetrahydro-2,9,10a-triaza-cyclopenta[b]fluorene-1,3-dione
113. (3aS,10R)-2-(3-Azepan-1-yl-propyl)-10-(3-hydroxy-phenyl)-6-methoxy-3a-methyl-3a,4,9,10-tetrahydro-2,9,10a-triaza-cyclopenta[b]fluorene-1,3-dione
118. (3aS,10R)-2-{2-[(2-Hydroxy-ethyl)-methyl-amino]-ethyl}-10-(3-hydroxy-phenyl)-6-methoxy-3a-methyl-3a,4,9,10-tetrahydro-2,9,10a-triaza-cyclopenta[b]fluorene-1,3-dione
119. (3aS,10R)-2-[2-(2,5-Dihydro-pyrrol-1-yl)-ethyl]-10-(3-hydroxy-phenyl)-6-methoxy-3a-methyl-3a,4,9,10-tetrahydro-2,9,10a-triaza-cyclopenta[b]fluorene-1,3-dione
134. (3aS,10R)-10-(3-Hydroxy-phenyl)-6-methoxy-3a-methyl-2-[2-(2-methyl-2H-pyrazol-3-ylamino)-ethyl]-3a,4,9,10-tetrahydro-2,9,10a-triaza-cyclopenta[b]fluorene-1,3-dione
142. (3aS,10R)-2-[3-(2,2-Difluoro-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione
143. (3aS,10R)-2-{3-[(2-Hydroxy-ethyl)-methyl-amino]-propyl}-10-(3-hydroxy-phenyl)-6-methoxy-3a-methyl-3a,4,9,10-tetrahydro-2,9,10a-triaza-cyclopenta[b]fluorene-1,3-dione
144. (3aS,10R)-10-(3-Hydroxy-phenyl)-6-methoxy-3a-methyl-2-[3-(methyl-prop-2-ynyl-amino)-propyl]-3a,4,9,10-tetrahydro-2,9,10a-triaza-cyclopenta[b]fluorene-1,3-dione
145. (3aS,10R)-2-[3-(2-Hydroxy-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione
146. (3aS,10R)-2-(3-Allylamino-propyl)-10-(3-hydroxy-phenyl)-6-methoxy-3a-methyl-3a,4,9,10-tetrahydro-2,9,10a-triaza-cyclopenta[b]fluorene-1,3-dione
147. (3aS,10R)-10-(3-Hydroxy-phenyl)-6-methoxy-3a-methyl-2-(3-prop-2-ynylamino-propyl)-3a,4,9,10-tetrahydro-2,9,10a-triaza-cyclopenta[b]fluorene-1,3-dione
148. (3aS,10R)-10-(3-Hydroxy-phenyl)-6-methoxy-3a-methyl-2-(3-morpholin-4-yl-propyl)-3a,4,9,10-tetrahydro-2,9,10a-triaza-cyclopenta[b]fluorene-1,3-dione
149. (3aS,10R)-2-[3-(2,5-Dihydro-pyrrol-1-yl)-propyl]-10-(3-hydroxy-phenyl)-6-methoxy-3a-methyl-3a,4,9,10-tetrahydro-2,9,10a-triaza-cyclopenta[b]fluorene-1,3-dione
150. (3aS,10R)-10-(3-Hydroxy-phenyl)-6-methoxy-3a-methyl-2-[3-(4-methyl-piperazin-1-yl)-propyl]-3a,4,9,10-tetrahydro-2,9,10a-triaza-cyclopenta[b]fluorene-1,3-dione
151. (3aS,10R)-2-[3-(4-Acetyl-piperazin-1-yl)-propyl]-10-(3-hydroxy-phenyl)-6-methoxy-3a-methyl-3a,4,9,10-tetrahydro-2,9,10a-triaza-cyclopenta[b]fluorene-1,3-dione
152. (3aS,10R)-6-Ethoxy-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione
153. (3aS,10R)-6-Ethoxy-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione
154. (3aS,10R)-2-[2-(Cyclopropylmethyl-amino)-ethyl]-6-ethoxy-10-(3-hydroxy-phenyl)-3a-methyl-3a,4,9,10-tetrahydro-2,9,10a-triaza-cyclopenta[b]fluorene-1,3-dione
155. (3aS,10R)-2-(2-Cyclobutylamino-ethyl)-6-ethoxy-10-(3-hydroxy-phenyl)-3a-methyl-3a,4,9,10-tetrahydro-2,9,10a-triaza-cyclopenta[b]fluorene-1,3-dione
156. (3aS,10R)-2-(2-tert-Butylamino-ethyl)-6-ethoxy-10-(3-hydroxy-phenyl)-3a-methyl-3a,4,9,10-tetrahydro-2,9,10a-triaza-cyclopenta[b]fluorene-1,3-dione
157. (3aS,10R)-2-(2-Allylamino-ethyl)-6-ethoxy-10-(3-hydroxy-phenyl)-3a-methyl-3a,4,9,10-tetrahydro-2,9,10a-triaza-cyclopenta[b]fluorene-1,3-dione
158. (3aS,10R)-6-Ethoxy-2-[2-(ethyl-methyl-amino)-ethyl]-10-(3-hydroxy-phenyl)-3a-methyl-3a,4,9,10-tetrahydro-2,9,10a-triaza-cyclopenta[b]fluorene-1,3-dione
159. (3aS,10R)-6-Ethoxy-2-[2-(2-hydroxy-ethylamino)-ethyl]-10-(3-hydroxy-phenyl)-3a-methyl-3a,4,9,10-tetrahydro-2,9,10a-triaza-cyclopenta[b]fluorene-1,3-dione
160. (3aS,10R)-6-Ethoxy-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione
161. (3aS,10R)-2-(2-Cyclopropylamino-ethyl)-6-ethoxy-10-(3-hydroxy-phenyl)-3a-methyl-3a,4,9,10-tetrahydro-2,9,10a-triaza-cyclopenta[b]fluorene-1,3-dione
162. (3aS,10R)-2-(2-Diethylamino-ethyl)-6-ethoxy-10-(3-hydroxy-phenyl)-3a-methyl-3a,4,9,10-tetrahydro-2,9,10a-triaza-cyclopenta[b]fluorene-1,3-dione
163. (3aS,10R)-6-Ethoxy-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione
164. (3aS,10R)-6-Ethoxy-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione
165. (3aS,10R)-2-[2-(3,6-Dihydro-2H-pyridin-1-yl)-ethyl]-6-ethoxy-10-(3-hydroxy-phenyl)-3a-methyl-3a,4,9,10-tetrahydro-2,9,10a-triaza-cyclopenta[b]fluorene-1,3-dione 166. (3aS,10R)-2-(2-Azepan-1-yl-ethyl)-6-ethoxy-10-(3-hydroxy-phenyl)-3a-methyl-3a,4,9,10-tetrahydro-2,9,10a-triaza-cyclopenta[b]fluorene-1,3-dione
167. (3aS,10R)-2-(3-tert-Butylamino-propyl)-10-(3-hydroxy-phenyl)-6-methoxy-3a-methyl-3a,4,9,10-tetrahydro-2,9,10a-triaza-cyclopenta[b]fluorene-1,3-dione
176. (3aS,10R)-2-(3-Diethylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
177. (3aS,10R)-6-(1,1-Difluoro-methoxy)-2-{3-[ethyl-(2-hydroxy-ethyl)-amino]-propyl}-10-(3-hydroxy-phenyl)-3a-methyl-3a,4,9,10-tetrahydro-2,9,10a-triaza-cyclopenta[b]fluorene-1,3-dione
178. (3aS,10R)-6-(1,1-Difluoro-methoxy)-2-{3-[ethyl-(2-methoxy-ethyl)-amino]-propyl}-10-(3-hydroxy-phenyl)-3a-methyl-3a,4,9,10-tetrahydro-2,9,10a-triaza-cyclopenta[b]fluorene-1,3-dione
179. (3aS,10R)-6-(1,1-Difluoro-methoxy)-10-(3-hydroxy-phenyl)-2-[3-(isopropyl-methyl-amino)-propyl]-3a-methyl-3a,4,9,10-tetrahydro-2,9,10a-triaza-cyclopenta[b]fluorene-1,3-dione
182. (3aS,10R)-2-(3-tert-Butylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
183. (3aS,10R)-6-(1,1-Difluoro-methoxy)-10-(3-hydroxy-phenyl)-3a-methyl-2-[3-(methyl-prop-2-ynyl-amino)-propyl]-3a,4,9,10-tetrahydro-2,9,10a-triaza-cyclopenta[b]fluorene-1,3-dione
184. (3aS,10R)-2-[3-(Allyl-methyl-amino)-propyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
186. (3aS,10R)-6-Ethoxy-10-(3-hydroxy-phenyl)-3a-methyl-2-(3-methylamino-propyl)-3a,4,9,10-tetrahydro-2,9,10a-triaza-cyclopenta[b]fluorene-1,3-dione
187. (3aS,10R)-6-Ethoxy-2-(3-ethylamino-propyl)-10-(3-hydroxy-phenyl)-3a-methyl-3a,4,9,10-tetrahydro-2,9,10a-triaza-cyclopenta[b]fluorene-1,3-dione
188. (3aS,10R)-2-[3-(Cyclopropylmethyl-amino)-propyl]-6-ethoxy-10-(3-hydroxy-phenyl)-3a-methyl-3a,4,9,10-tetrahydro-2,9,10a-triaza-cyclopenta[b]fluorene-1,3-dione
189. (3aS,10R)-6-Ethoxy-10-(3-hydroxy-phenyl)-2-[3-(2-methoxy-ethylamino)-propyl]-3a-methyl-3a,4,9,10-tetrahydro-2,9,10a-triaza-cyclopenta[b]fluorene-1,3-dione
190. (3aS,10R)-2-(3-Cyclopropylamino-propyl)-6-ethoxy-10-(3-hydroxy-phenyl)-3a-methyl-3a,4,9,10-tetrahydro-2,9,10a-triaza-cyclopenta[b]fluorene-1,3-dione
191. (3aS,10R)-2-(3-Allylamino-propyl)-6-ethoxy-10-(3-hydroxy-phenyl)-3a-methyl-3a,4,9,10-tetrahydro-2,9,10a-triaza-cyclopenta[b]fluorene-1,3-dione
192. (3aS,10R)-6-Ethoxy-2-[3-(ethyl-methyl-amino)-propyl]-10-(3-hydroxy-phenyl)-3a-methyl-3a,4,9,10-tetrahydro-2,9,10a-triaza-cyclopenta[b]fluorene-1,3-dione
193. (3aS,10R)-6-Ethoxy-2-{3-[(2-hydroxy-ethyl)-methyl-amino]-propyl}-10-(3-hydroxy-phenyl)-3a-methyl-3a,4,9,10-tetrahydro-2,9,10a-triaza-cyclopenta[b]fluorene-1,3-dione
194. (3aS,10R)-6-Ethoxy-2-{3-[ethyl-(2-hydroxy-ethyl)-amino]-propyl}-10-(3-hydroxy-phenyl)-3a-methyl-3a,4,9,10-tetrahydro-2,9,10a-triaza-cyclopenta[b]fluorene-1,3-dione
195. (3aS,10R)-6-Ethoxy-2-{3-[ethyl-(2-methoxy-ethyl)-amino]-propyl}-10-(3-hydroxy-phenyl)-3a-methyl-3a,4,9,10-tetrahydro-2,9,10a-triaza-cyclopenta[b]fluorene-1,3-dione
196. (3aS,10R)-2-[3-(Allyl-methyl-amino)-propyl]-6-ethoxy-10-(3-hydroxy-phenyl)-3a-methyl-3a,4,9,10-tetrahydro-2,9,10a-triaza-cyclopenta[b]fluorene-1,3-dione
197. (3aS,10R)-6-Ethoxy-10-(3-hydroxy-phenyl)-2-[3-(isopropyl-methyl-amino)-propyl]-3a-methyl-3a,4,9,10-tetrahydro-2,9,10a-triaza-cyclopenta[b]fluorene-1,3-dione
198. (3aS,10R)-2-(3-Azetidin-1-yl-propyl)-6-ethoxy-10-(3-hydroxy-phenyl)-3a-methyl-3a,4,9,10-tetrahydro-2,9,10a-triaza-cyclopenta[b]fluorene-1,3-dione
199. (3aS,10R)-6-(1,1-Difluoro-methoxy)-10-(3-hydroxy-phenyl)-2-(3-isobutylamino-propyl)-3a-methyl-3a,4,9,10-tetrahydro-2,9,10a-triaza-cyclopenta[b]fluorene-1,3-dione
200. (3aS,10R)-2-[3-(Cyclopropylmethyl-amino)-propyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
201. (3aS,10R)-6-(1,1-Difluoro-methoxy)-2-[3-(2-hydroxy-ethylamino)-propyl]-10-(3-hydroxy-phenyl)-3a-methyl-3a,4,9,10-tetrahydro-2,9,10a-triaza-cyclopenta[b]fluorene-1,3-dione
202. (3aS,10R)-2-(3-Cyclopropylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
203. (3aS,10R)-6-(1,1-Difluoro-methoxy)-10-(3-hydroxy-phenyl)-3a-methyl-2-(3-methylamino-propyl)-3a,4,9,10-tetrahydro-2,9,10a-triaza-cyclopenta[b]fluorene-1,3-dione
204. (3aS,10R)-6-(1,1-Difluoro-methoxy)-2-(3-ethylamino-propyl)-10-(3-hydroxy-phenyl)-3a-methyl-3a,4,9,10-tetrahydro-2,9,10a-triaza-cyclopenta[b]fluorene-1,3-dione
205. (3aS,10R)-6-(1,1-Difluoro-methoxy)-10-(3-hydroxy-phenyl)-2-[3-(2-methoxy-ethylamino)-propyl]-3a-methyl-3a,4,9,10-tetrahydro-2,9,10a-triaza-cyclopenta[b]fluorene-1,3-dione
206. (3aS,10R)-2-(3-Allylamino-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
207. (3aS,10R)-6-Ethoxy-10-(3-hydroxy-phenyl)-3a-methyl-2-(3-morpholin-4-yl-propyl)-3a,4,9,10-tetrahydro-2,9,10a-triaza-cyclopenta[b]fluorene-1,3-dione
208. (3aS,10R)-2-[3-(3,6-Dihydro-2H-pyridin-1-yl)-propyl]-6-ethoxy-10-(3-hydroxy-phenyl)-3a-methyl-3a,4,9,10-tetrahydro-2,9,10a-triaza-cyclopenta[b]fluorene-1,3-dione
209. (3aS,10R)-2-[3-(4-Acetyl-piperazin-1-yl)-propyl]-6-ethoxy-10-(3-hydroxy-phenyl)-3a-methyl-3a,4,9,10-tetrahydro-2,9,10a-triaza-cyclopenta[b]fluorene-1,3-dione
210. (3aS,10R)-2-(3-Azepan-1-yl-propyl)-6-ethoxy-10-(3-hydroxy-phenyl)-3a-methyl-3a,4,9,10-tetrahydro-2,9,10a-triaza-cyclopenta[b]fluorene-1,3-dione 221. (3aS,10R)-6-Ethoxy-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione
222. (3aS,10R)-2-[3-(2,5-Dihydro-pyrrol-1-yl)-propyl]-6-ethoxy-10-(3-hydroxy-phenyl)-3a-methyl-3a,4,9,10-tetrahydro-2,9,10a-triaza-cyclopenta[b]fluorene-1,3-dione
223. (3aS,10R)-6-Ethoxy-10-(3-hydroxy-phenyl)-3a-methyl-2-(3-piperidin-1-yl-propyl)-3a,4,9,10-tetrahydro-2,9,10a-triaza-cyclopenta[b]fluorene-1,3-dione
224. (3aS,10R)-6-Ethoxy-10-(3-hydroxy-phenyl)-3a-methyl-2-[3-(4-methyl-piperidin-1-yl)-propyl]-3a,4,9,10-tetrahydro-2,9,10a-triaza-cyclopenta[b]fluorene-1,3-dione
225. (3aS,10R)-6-Ethoxy-10-(3-hydroxy-phenyl)-3a-methyl-2-(3-prop-2-ynylamino-propyl)-3a,4,9,10-tetrahydro-2,9,10a-triaza-cyclopenta[b]fluorene-1,3-dione
226. (3aS,10R)-2-(3-Dimethylamino-propyl)-6-ethoxy-10-(3-hydroxy-phenyl)-3a-methyl-3a,4,9,10-tetrahydro-2,9,10a-triaza-cyclopenta[b]fluorene-1,3-dione
227. (3aS,10R)-6-Ethoxy-10-(3-hydroxy-phenyl)-3a-methyl-2-[3-(methyl-prop-2-ynyl-amino)-propyl]-3a,4,9,10-tetrahydro-2,9,10a-triaza-cyclopenta[b]fluorene-1,3-dione
229. (3aS,10R)-6-Ethoxy-10-(3-hydroxy-phenyl)-3a-methyl-2-[3-(4-methyl-piperazin-1-yl)-propyl]-3a,4,9,10-tetrahydro-2,9,10a-triaza-cyclopenta[b]fluorene-1,3-dione
236. (3aS,10R)-6-(1,1-Difluoro-methoxy)-10-(3-hydroxy-phenyl)-3a-methyl-2-(3-morpholin-4-yl-propyl)-3a,4,9,10-tetrahydro-2,9,10a-triaza-cyclopenta[b]fluorene-1,3-dione
237. (3aS,10R)-6-(1,1-Difluoro-methoxy)-10-(3-hydroxy-phenyl)-3a-methyl-2-(3-pyrrolidin-1-yl-propyl)-3a,4,9,10-tetrahydro-2,9,10a-triaza-cyclopenta[b]fluorene-1,3-dione
238. (3aS,10R)-6-(1,1-Difluoro-methoxy)-2-[3-(2,5-dihydro-pyrrol-1-yl)-propyl]-10-(3-hydroxy-phenyl)-3a-methyl-3a,4,9,10-tetrahydro-2,9,10a-triaza-cyclopenta[b]fluorene-1,3-dione
239. (3aS,10R)-6-(1,1-Difluoro-methoxy)-10-(3-hydroxy-phenyl)-3a-methyl-2-(3-piperidin-1-yl-propyl)-3a,4,9,10-tetrahydro-2,9,10a-triaza-cyclopenta[b]fluorene-1,3-dione
240. (3aS,10R)-6-(1,1-Difluoro-methoxy)-10-(3-hydroxy-phenyl)-3a-methyl-2-[3-(4-methyl-piperazin-1-yl)-propyl]-3a,4,9,10-tetrahydro-2,9,10a-triaza-cyclopenta[b]fluorene-1,3-dione
241. (3aS,10R)-2-[3-(4-Acetyl-piperazin-1-yl)-propyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
242. (3aS,10R)-6-(1,1-Difluoro-methoxy)-2-[3-(3,6-dihydro-2H-pyridin-1-yl)-propyl]-10-(3-hydroxy-phenyl)-3a-methyl-3a,4,9,10-tetrahydro-2,9,10a-triaza-cyclopenta[b]fluorene-1,3-dione
243. (3aS,10R)-2-(3-Azepan-1-yl-propyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione
244. (3aS,10R)-6-(1,1-Difluoro-methoxy)-10-(3-hydroxy-phenyl)-3a-methyl-2-[3-(4-methyl-piperidin-1-yl)-propyl]-3a,4,9,10-tetrahydro-2,9,10a-triaza-cyclopenta[b]fluorene-1,3-dione
245. (3aS,10R)-7-Fluoro-2-[2-(2-hydroxy-ethylamino)-ethyl]-10-(3-hydroxy-phenyl)-6-methoxy-3a-methyl-3a,4,9,10-tetrahydro-2,9,10a-triaza-cyclopenta[b]fluorene-1,3-dione
246. (3aS,10R)-7-Fluoro-2-{2-[(2-hydroxy-ethyl)-methyl-amino]-ethyl}-10-(3-hydroxy-phenyl)-6-methoxy-3a-methyl-3a,4,9,10-tetrahydro-2,9,10a-triaza-cyclopenta[b]fluorene-1,3-dione
247. (3aS,10R)-6-(1,1-Difluoro-methoxy)-2-[3-(ethyl-methyl-amino)-propyl]hydroxy-phenyl)-3a-methyl-3a,4,9,10-tetrahydro-2,9,10a-triaza-cyclopenta[b]fluorene-1,3-dione
248. (3aS,10R)-7-Fluoro-10-(3-hydroxy-phenyl)-6-methoxy-3a-methyl-2-(2-methylamino-ethyl)-3a,4,9,10-tetrahydro-2,9,10a-triaza-cyclopenta[b]fluorene-1,3-dione
249. (3aS,10R)-2-(2-Ethylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
250. (3aS,10R)-7-Fluoro-10-(3-hydroxy-phenyl)-2-(2-isopropylamino-ethyl)-6-methoxy-3a-methyl-3a,4,9,10-tetrahydro-2,9,10a-triaza-cyclopenta[b]fluorene-1,3-dione
251. (3aS,10R)-2-[2-(Cyclopropylmethyl-amino)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
252. (3aS,10R)-7-Fluoro-10-(3-hydroxy-phenyl)-2-(2-isobutylamino-ethyl)-6-methoxy-3a-methyl-3a,4,9,10-tetrahydro-2,9,10a-triaza-cyclopenta[b]fluorene-1,3-dione
253. (3aS,10R)-7-Fluoro-10-(3-hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione
254. (3aS,10R)-2-(2-Allylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
255. (3aS,10R)-2-(2-Dimethylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
256. (3aS,10R)-2-(2-tert-Butylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
257. (3aS,10R)-2-[2-(Ethyl-methyl-amino)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
258. (3aS,10R)-2-(2-Diethylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
259. (3aS,10R)-7-Fluoro-10-(3-hydroxy-phenyl)-2-[2-(isopropyl-methyl-amino)-ethyl]-6-methoxy-3a-methyl-3a,4,9,10-tetrahydro-2,9,10a-triaza-cyclopenta[b]fluorene-1,3-dione
260. (3aS,10R)-7-Fluoro-10-(3-hydroxy-phenyl)-6-methoxy-3a-methyl-2-(2-morpholin-4-yl-ethyl)-3a,4,9,10-tetrahydro-2,9,10a-triaza-cyclopenta[b]fluorene-1,3-dione 261. (3aS,10R)-7-Fluoro-10-(3-hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione 262. (3aS,10R)-2-[2-(2,5-Dihydro-pyrrol-1-yl)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione 263. (3aS,10R)-7-Fluoro-10-(3-hydroxy-phenyl)-6-methoxy-3a-methyl-2-(2-piperidin-1-yl-ethyl)-3a,4,9,10-tetrahydro-2,9,10a-triaza-cyclopenta[b]fluorene-1,3-dione 264. (3aS,10R)-7-Fluoro-10-(3-hydroxy-phenyl)-6-methoxy-3a-methyl-2-[2-(4-methyl-piperidin-1-yl)-ethyl]-3a,4,9,10-tetrahydro-2,9,10a-triaza-cyclopenta[b]fluorene-1,3-dione 265. (3aS,10R)-2-[2-(3,6-Dihydro-2H-pyridin-1-yl)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione 266. (3aS,10R)-7-Fluoro-10-(3-hydroxy-phenyl)-6-methoxy-3a-methyl-2-[2-(4-methyl-piperazin-1-yl)-ethyl]-3a,4,9,10-tetrahydro-2,9,10a-triaza-cyclopenta[b]fluorene-1,3-dione 267. (3aS,10R)-2-[2-(4-Acetyl-piperazin-1-yl)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione 268. (3aS,10R)-6-(1,1-Difluoro-methoxy)-10-(3-hydroxy-phenyl)-2-(2-isopropylamino-ethyl)-3a-methyl-3a,4,9,10-tetrahydro-2,9,10a-triaza-cyclopenta[b]fluorene-1,3-dione 269. (3aS,10R)-6-(1,1-Difluoro-methoxy)-10-(3-hydroxy-phenyl)-2-(2-isobutylamino-ethyl)-3a-methyl-3a,4,9,10-tetrahydro-2,9,10a-triaza-cyclopenta[b]fluorene-1,3-dione 270. (3aS,10R)-2-[2-(Cyclopropylmethyl-amino)-ethyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione 271. (3aS,10R)-6-(1,1-Difluoro-methoxy)-10-(3-hydroxy-phenyl)-2-[2-(2-methoxy-ethylamino)-ethyl]-3a-methyl-3a,4,9,10-tetrahydro-2,9,10a-triaza-cyclopenta[b]fluorene-1,3-dione 272. (3aS,10R)-2-(2-Cyclobutylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione 273. (3aS,10R)-2-(2-tert-Butylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione 274. (3aS,10R)-2-(2-Allylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione 275. (3aS,10R)-6-(1,1-Difluoro-methoxy)-2-[2-(ethyl-methyl-amino)-ethyl]hydroxy-phenyl)-3a-methyl-3a,4,9,10-tetrahydro-2,9,10a-triaza-cyclopenta[b]fluorene-1,3-dione 276. (3aS,10R)-2-(2-Diethylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione 277. (3aS,10R)-6-(1,1-Difluoro-methoxy)-2-{2-[ethyl-(2-hydroxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione 278. (3aS,10R)-6-(1,1-Difluoro-methoxy)-10-(3-hydroxy-phenyl)-2-[2-(isopropyl-methyl-amino)-ethyl]-3a-methyl-3a,4,9,10-tetrahydro-2,9,10a-triaza-cyclopenta[b]fluorene-1,3-dione 279. (3aS,10R)-6-(1,1-Difluoro-methoxy)-10-(3-hydroxy-phenyl)-3a-methyl-2-(2-pyrrolidin-1-yl-ethyl)-3a,4,9,10-tetrahydro-2,9,10a-triaza-cyclopenta[b]fluorene-1,3-dione 280. (3aS,10R)-6-(1,1-Difluoro-methoxy)-10-(3-hydroxy-phenyl)-3a-methyl-2-(2-piperidin-1-yl-ethyl)-3a,4,9,10-tetrahydro-2,9,10a-triaza-cyclopenta[b]fluorene-1,3-dione 281. (3aS,10R)-6-(1,1-Difluoro-methoxy)-2-[2-(3,6-dihydro-2H-pyridin-1-yl)-ethyl]hydroxy-phenyl)-3a-methyl-3a,4,9,10-tetrahydro-2,9,10a-triaza-cyclopenta[b]fluorene-1,3-dione 282. (3aS,10R)-2-(2-Azepan-1-yl-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione 283. (3aS,10R)-2-(2-Amino-ethyl)-6-(1-difluoro-methoxy)-10-(3-hydroxy-phenyl)-3a-methyl-3a,4,9,10-tetrahydro-2,9,10a-triaza-cyclopenta[b]fluorene-1,3-dione 284. (3aS,10R)-6-(1,1-Difluoro-methoxy)-2-(2-ethylamino-ethyl)-10-(3-hydroxy-phenyl)-3a-methyl-3a,4,9,10-tetrahydro-2,9,10a-triaza-cyclopenta[b]fluorene-1,3-dione 285. (3aS,10R)-6-(1,1-Difluoro-methoxy)-2-[2-(2-hydroxy-ethylamino)-ethyl]-10-(3-hydroxy-phenyl)-3a-methyl-3a,4,9,10-tetrahydro-2,9,10a-triaza-cyclopenta[b]fluorene-1,3-dione 286. (3aS,10R)-2-(2-Cyclopropylamino-ethyl)-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione 287. (3aS,10R)-6-(1,1-Difluoro-methoxy)-10-(3-hydroxy-phenyl)-3a-methyl-2-(2-prop-2-ynylamino-ethyl)-3a,4,9,10-tetrahydro-2,9,10a-triaza-cyclopenta[b]fluorene-1,3-dione 288. (3aS,10R)-6-(1,1-Difluoro-methoxy)-2-{2-[(2-hydroxy-ethyl)-methyl-amino]-ethyl}-10-(3-hydroxy-phenyl)-3a-methyl-3a,4,9,10-tetrahydro-2,9,10a-triaza-cyclopenta[b]fluorene-1,3-dione 289. (3aS,10R)-6-(1,1-Difluoro-methoxy)-2-{2-[ethyl-(2-methoxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione 290. (3aS,10R)-2-[2-(Allyl-methyl-amino)-ethyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione 291. (3aS,10R)-6-(1,1-Difluoro-methoxy)-10-(3-hydroxy-phenyl)-3a-methyl-2-[2-(methyl-prop-2-ynyl-amino)-ethyl]-3a,4,9,10-tetrahydro-2,9,10a-triaza-cyclopenta[b]fluorene-1,3-dione 292. (3aS,10R)-6-(1,1-Difluoro-methoxy)-10-(3-hydroxy-phenyl)-3a-methyl-2-(2-morpholin-4-yl-ethyl)-3a,4,9,10-tetrahydro-2,9,10a-triaza-cyclopenta[b]fluorene-1,3-dione 293. (3aS,10R)-6-(1,1-Difluoro-methoxy)-10-(3-hydroxy-phenyl)-3a-methyl-2-[2-(4-methyl-piperidin-1-yl)-ethyl]-3a,4,9,10-tetrahydro-2,9,10a-triaza-cyclopenta[b]fluorene-1,3-dione 294. (3aS,10R)-6-(1,1-Difluoro-methoxy)-10-(3-hydroxy-phenyl)-3a-methyl-2-[2-(4-methyl-piperazin-1-yl)-ethyl]-3a,4,9,10-tetrahydro-2,9,10a-triaza-cyclopenta[b]fluorene-1,3-dione 295. (3aS,10R)-2-[2-(4-Acetyl-piperazin-1-yl)-ethyl]-6-(1,1-difluoro-methoxy)-10-(3-hydroxy-phenyl)-3a-methyl-3a,4,9,10-tetrahydro-2,9,10a-triaza-cyclopenta[b]fluorene-1,3-dione 296. (3aS,10R)-6-Ethoxy-2-(2-ethylamino-ethyl)-10-(3-hydroxy-phenyl)-3a-methyl-3a,4,9,10-tetrahydro-2,9,10a-triaza-cyclopenta[b]fluorene-1,3-dione 297. (3aS,10R)-6-Ethoxy-2-{2-[(2-hydroxy-ethyl)-methyl-amino]-ethyl}-10-(3-hydroxy-phenyl)-3a-methyl-3a,4,9,10-tetrahydro-2,9,10a-triaza-cyclopenta[b]fluorene-1,3-dione 298. (3aS,10R)-6-Ethoxy-2-{2-[ethyl-(2-hydroxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione 299. (3aS,10R)-6-Ethoxy-2-{2-[ethyl-(2-methoxy-ethyl)-amino]-ethyl}-10-(3-hydroxy-phenyl)-3a-methyl-3a,4,9,10-tetrahydro-2,9,10a-triaza-cyclopenta[b]fluorene-1,3-dione 300. (3aS,10R)-2-[2-(Allyl-methyl-amino)-ethyl]-6-ethoxy-10-(3-hydroxy-phenyl)-3a-methyl-3a,4,9,10-tetrahydro-2,9,10a-triaza-cyclopenta[b]fluorene-1,3-dione 301. (3aS,10R)-6-Ethoxy-10-(3-hydroxy-phenyl)-3a-methyl-2-[2-(methyl-prop-2-ynyl-amino)-ethyl]-3a,4,9,10-tetrahydro-2,9,10a-triaza-cyclopenta[b]fluorene-1,3-dione 302. (3aS,10R)-6-Ethoxy-10-(3-hydroxy-phenyl)-3a-methyl-2-[2-(4-methyl-piperidin-1-yl)-ethyl]-3a,4,9,10-tetrahydro-2,9,10a-triaza-cyclopenta[b]fluorene-1,3-dione 303. (3aS,10R)-7-Fluoro-10-(3-hydroxy-phenyl)-6-methoxy-3a-methyl-2-(3-methylamino-propyl)-3a,4,9,10-tetrahydro-2,9,10a-triaza-cyclopenta[b]fluorene-1,3-dione 304. (3aS,10R)-2-[3-(Cyclopropylmethyl-amino)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione 305. (3aS,10R)-7-Fluoro-2-[3-(2-hydroxy-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione 306. (3aS,10R)-7-Fluoro-10-(3-hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione 307. (3aS,10R)-2-(3-Cyclopropylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 308. (3aS,10R)-2-(3-tert-Butylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 309. (3aS,10R)-7-Fluoro-10-(3-hydroxy-phenyl)-6-methoxy-3a-methyl-2-(3-prop-2-ynylamino-propyl)-3a,4,9,10-tetrahydro-2,9,10a-triaza-cyclopenta[b]fluorene-1,3-dione 310. (3aS,10R)-2-(3-Dimethylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 311. (3aS,10R)-2-[3-(Ethyl-methyl-amino)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione 312. (3aS,10R)-7-Fluoro-2-{3-[(2-hydroxy-ethyl)-methyl-amino]-propyl}-10-(3-hydroxy-phenyl)-6-methoxy-3a-methyl-3a,4,9,10-tetrahydro-2,9,10a-triaza-cyclopenta[b]fluorene-1,3-dione 313. (3aS,10R)-2-(3-Diethylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 314. (3aS,10R)-6-(1,1-Difluoro-methoxy)-2-(3-dimethylamino-propyl)-10-(3-hydroxy-phenyl)-3a-methyl-3a,4,9,10-tetrahydro-2,9,10a-triaza-cyclopenta[b]fluorene-1,3-dione 315. (3aS,10R)-2-[3-[Ethyl-(2-hydroxy-ethyl)-amino]-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione 316. (3aS,10R)-2-{3-[Ethyl-(2-methoxy-ethyl)-amino]-propyl}-7-fluoro-10-(3-hydroxy-phenyl)-6-methoxy-3a-methyl-3a,4,9,10-tetrahydro-2,9,10a-triaza-cyclopenta[b]fluorene-1,3-dione 317. (3aS,10R)-2-[3-(Allyl-methyl-amino)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione 318. (3aS,10R)-7-Fluoro-10-(3-hydroxy-phenyl)-6-methoxy-3a-methyl-2-[3-(methyl-prop-2-ynyl-amino)-propyl]-3a,4,9,10-tetrahydro-2,9,10a-triaza-cyclopenta[b]fluorene-1,3-dione 319. (3aS,10R)-7-Fluoro-10-(3-hydroxy-phenyl)-2-[3-(isopropyl-methyl-amino)-propyl]-6-methoxy-3a-methyl-3a,4,9,10-tetrahydro-2,9,10a-triaza-cyclopenta[b]fluorene-1,3-dione 320. (3aS,10R)-2-(3-Azetidin-1-yl-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 321. (3aS,10R)-7-Fluoro-10-(3-hydroxy-phenyl)-6-methoxy-3a-methyl-2-(3-morpholin-4-yl-propyl)-3a,4,9,10-tetrahydro-2,9,10a-triaza-cyclopenta[b]fluorene-1,3-dione 322. (3aS,10R)-7-Fluoro-10-(3-hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione 323. (3aS,10R)-2-[3-(2,5-Dihydro-pyrrol-1-yl)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione 324. (3aS,10R)-7-Fluoro-10-(3-hydroxy-phenyl)-6-methoxy-3a-methyl-2-(3-piperidin-1-yl-propyl)-3a,4,9,10-tetrahydro-2,9,10a-triaza-cyclopenta[b]fluorene-1,3-dione 325. (3aS,10R)-7-Fluoro-10-(3-hydroxy-phenyl)-6-methoxy-3a-methyl-2-[3-(4-methyl-piperazin-1-yl)-propyl]-3a,4,9,10-tetrahydro-2,9,10a-triaza-cyclopenta[b]fluorene-1,3-dione 326. (3aS,10R)-2-[3-(3,6-Dihydro-2H-pyridin-1-yl)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione 327. (3aS,10R)-7-Fluoro-10-(3-hydroxy-phenyl)-6-methoxy-3a-methyl-2-[3-(4-methyl-piperidin-1-yl)-propyl]-3a,4,9,10-tetrahydro-2,9,10a-triaza-cyclopenta[b]fluorene-1,3-dione 328. (3aS,10R)-2-[3-(4-Acetyl-piperazin-1-yl)-propyl]-7-fluoro-10-(3-hydroxy-phenyl)-6-methoxy-3a-methyl-3a,4,9,10-tetrahydro-2,9,10a-triaza-cyclopenta[b]fluorene-1,3-dione 329. (3aS,10R)-2-(3-Azepan-1-yl-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 330. (3aS,10R)-2-(3-Ethylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 331. (3aS,10R)-7-Fluoro-10-(3-hydroxy-phenyl)-2-(3-isopropylamino-propyl)-6-methoxy-3a-methyl-3a,4,9,10-tetrahydro-2,9,10a-triaza-cyclopenta[b]fluorene-1,3-dione 332. (3aS,10R)-7-Fluoro-10-(3-hydroxy-phenyl)-2-(3-isobutylamino-propyl)-6-methoxy-3a-methyl-3a,4,9,10-tetrahydro-2,9,10a-triaza-cyclopenta[b]fluorene-1,3-dione 333. (3aS,10R)-2-(3-Cyclobutylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 334. (3aS,10R)-2-(3-Allylamino-propyl)-7-fluoro-10-(3-hydroxy-phenyl)-6-methoxy-3a-methyl-3a,4,9,10-tetrahydro-2,9,10a-triaza-cyclopenta[b]fluorene-1,3-dione 363. (3aS,10R)-2-(3-Allylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione 364. (3aS,10R)-2-[3-(Ethyl-methyl-amino)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione 365. (3aS,10R)-2-{3-[Ethyl-(2-methoxy-ethyl)-amino]-propyl}-5-fluoro-10-(3-hydroxy-phenyl)-6-methoxy-3a-methyl-3a,4,9,10-tetrahydro-2,9,10a-triaza-cyclopenta[b]fluorene-1,3-dione 366. (3aS,10R)-5-Fluoro-10-(3-hydroxy-phenyl)-6-methoxy-3a-methyl-2-(3-piperidin-1-yl-propyl)-3a,4,9,10-tetrahydro-2,9,10a-triaza-cyclopenta[b]fluorene-1,3-dione 367. (3aS,10R)-5-Fluoro-10-(3-hydroxy-phenyl)-6-methoxy-3a-methyl-2-[3-(4-methyl-piperidin-1-yl)-propyl]-3a,4,9,10-tetrahydro-2,9,10a-triaza-cyclopenta[b]fluorene-1,3-dione 368. (3aS,10R)-2-[3-(3,6-Dihydro-2H-pyridin-1-yl)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione 398. (3aS,10R)-2-(2-Azepan-1-yl-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione 399. (3aS,10R)-2-[2-(4-Acetyl-piperazin-1-yl)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione 400. (3aS,10R)-5-Fluoro-10-(3-hydroxy-phenyl)-6-methoxy-3a-methyl-2-[2-(4-methyl-piperazin-1-yl)-ethyl]-3a,4,9,10-tetrahydro-2,9,10a-triaza-cyclopenta[b]fluorene-1,3-dione 401. (3aS,10R)-2-[2-(3,6-Dihydro-2H-pyridin-1-yl)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione 402. (3aS,10R)-5-Fluoro-10-(3-hydroxy-phenyl)-6-methoxy-3a-methyl-2-[2-(4-methyl-piperidin-1-yl)-ethyl]-3a,4,9,10-tetrahydro-2,9,10a-triaza-cyclopenta[b]fluorene-1,3-dione 403. (3aS,10R)-5-Fluoro-10-(3-hydroxy-phenyl)-6-methoxy-3a-methyl-2-(2-piperidin-1-yl-ethyl)-3a,4,9,10-tetrahydro-2,9,10a-triaza-cyclopenta[b]fluorene-1,3-dione 404. (3aS,10R)-2-[2-(2,5-Dihydro-pyrrol-1-yl)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione 405. (3aS,10R)-5-Fluoro-10-(3-hydroxy-phenyl)-6-methoxy-3a-methyl-2-(2-pyrrolidin-1-yl-ethyl)-3a,4,9,10-tetrahydro-2,9,10a-triaza-cyclopenta[b]fluorene-1,3-dione 406. (3aS,10R)-5-Fluoro-10-(3-hydroxy-phenyl)-6-methoxy-3a-methyl-2-(2-methylamino-ethyl)-3a,4,9,10-tetrahydro-2,9,10a-triaza-cyclopenta[b]fluorene-1,3-dione 407. (3aS,10R)-2-(2-Ethylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione 408. (3aS,10R)-5-Fluoro-10-(3-hydroxy-phenyl)-2-(2-isopropylamino-ethyl)-6-methoxy-3a-methyl-3a,4,9,10-tetrahydro-2,9,10a-triaza-cyclopenta[b]fluorene-1,3-dione 409. (3aS,10R)-5-Fluoro-10-(3-hydroxy-phenyl)-2-(2-isobutylamino-ethyl)-6-methoxy-3a-methyl-3a,4,9,10-tetrahydro-2,9,10a-triaza-cyclopenta[b]fluorene-1,3-dione 410. (3aS,10R)-2-[2-(Cyclopropylmethyl-amino)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione 411. (3aS,10R)-2-[2-(2,5-Dihydro-pyrrol-1-yl)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione 412. (3aS,10R)-5-Fluoro-10-(3-hydroxy-phenyl)-6-methoxy-2-[2-(2-methoxy-ethylamino)-ethyl]-3a-methyl-3a,4,9,10-tetrahydro-2,9,10a-triaza-cyclopenta[b]fluorene-1,3-dione 413. (3aS,10R)-2-(2-Cyclobutylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione 414. (3aS,10R)-2-(2-tert-Butylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione 415. (3aS,10R)-2-(2-Allylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
416. (3aS,10R)-5-Fluoro-10-(3-hydroxy-phenyl)-6-methoxy-3a-methyl-2-(2-prop-2-ynylamino-ethyl)-3a,4,9,10-tetrahydro-2,9,10a-triaza-cyclopenta[b]fluorene-1,3-dione
417. (3aS,10R)-2-(2-Dimethylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
418. (3aS,10R)-2-[2-(Ethyl-methyl-amino)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
419. (3aS,10R)-5-Fluoro-2-{2-[(2-hydroxy-ethyl)-methyl-amino]-ethyl}-10-(3-hydroxy-phenyl)-6-methoxy-3a-methyl-3a,4,9,10-tetrahydro-2,9,10a-triaza-cyclopenta[b]fluorene-1,3-dione
420. (3aS,10R)-2-(2-Diethylamino-ethyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
421. (3aS,10R)-2-{2-[Ethyl-(2-hydroxy-ethyl)-amino]-ethyl}-5-fluoro-10-(3-hydroxy-phenyl)-6-methoxy-3a-methyl-3a,4,9,10-tetrahydro-2,9,10a-triaza-cyclopenta[b]fluorene-1,3-dione
422. (3aS,10R)-2-{2-[Ethyl-(2-methoxy-ethyl)-amino]-ethyl}-5-fluoro-10-(3-hydroxy-phenyl)-6-methoxy-3a-methyl-3a,4,9,10-tetrahydro-2,9,10a-triaza-cyclopenta[b]fluorene-1,3-dione
423. (3aS,10R)-2-[2-(Allyl-methyl-amino)-ethyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
424. (3aS,10R)-5-Fluoro-10-(3-hydroxy-phenyl)-6-methoxy-3a-methyl-2-[2-(methyl-prop-2-ynyl-amino)-ethyl]-3a,4,9,10-tetrahydro-2,9,10a-triaza-cyclopenta[b]fluorene-1,3-dione
425. (3aS,10R)-5-Fluoro-10-(3-hydroxy-phenyl)-2-[2-(isopropyl-methyl-amino)-ethyl]-6-methoxy-3a-methyl-3a,4,9,10-tetrahydro-2,9,10a-triaza-cyclopenta[b]fluorene-1,3-dione
426. (3aS,10R)-2-(2-Cyclobutylamino-ethyl)-7-fluoro-10-(3-hydroxy-phenyl)-6-methoxy-3a-methyl-3a,4,9,10-tetrahydro-2,9,10a-triaza-cyclopenta[b]fluorene-1,3-dione
427. (3aS,10R)-5-Fluoro-10-(3-hydroxy-phenyl)-6-methoxy-3a-methyl-2-(3-methylamino-propyl)-3a,4,9,10-tetrahydro-2,9,10a-triaza-cyclopenta[b]fluorene-1,3-dione
428. (3aS,10R)-2-(3-Ethylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
429. (3aS,10R)-5-Fluoro-10-(3-hydroxy-phenyl)-2-(3-isopropylamino-propyl)-6-methoxy-3a-methyl-3a,4,9,10-tetrahydro-2,9,10a-triaza-cyclopenta[b]fluorene-1,3-dione
430. (3aS,10R)-5-Fluoro-10-(3-hydroxy-phenyl)-2-(3-isobutylamino-propyl)-6-methoxy-3a-methyl-3a,4,9,10-tetrahydro-2,9,10a-triaza-cyclopenta[b]fluorene-1,3-dione
431. (3aS,10R)-2-[3-(Cyclopropylmethyl-amino)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
432. (3aS,10R)-5-Fluoro-2-[3-(2-hydroxy-ethylamino)-propyl]-10-(3-hydroxy-phenyl)-6-methoxy-3a-methyl-3a,4,9,10-tetrahydro-2,9,10a-triaza-cyclopenta[b]fluorene-1,3-dione
433. (3aS,10R)-5-Fluoro-10-(3-hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione
434. (3aS,10R)-2-(3-Cyclopropylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
435. (3aS,10R)-2-(3-Cyclobutylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
436. (3aS,10R)-2-(3-tert-Butylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
437. (3aS,10R)-5-Fluoro-10-(3-hydroxy-phenyl)-6-methoxy-3a-methyl-2-(3-prop-2-ynylamino-propyl)-3a,4,9,10-tetrahydro-2,9,10a-triaza-cyclopenta[b]fluorene-1,3-dione
438. (3aS,10R)-2-(3-Dimethylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
439. (3aS,10R)-5-Fluoro-2-{3-[(2-hydroxy-ethyl)-methyl-amino]-propyl}-10-(3-hydroxy-phenyl)-6-methoxy-3a-methyl-3a,4,9,10-tetrahydro-2,9,10a-triaza-cyclopenta[b]fluorene-1,3-dione
440. (3aS,10R)-2-(3-Diethylamino-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
441. (3aS,10R)-2-{3-[Ethyl-(2-hydroxy-ethyl)-amino]-propyl}-5-fluoro-10-(3-hydroxy-phenyl)-6-methoxy-3a-methyl-3a,4,9,10-tetrahydro-2,9,10a-triaza-cyclopenta[b]fluorene-1,3-dione
442. (3aS,10R)-2-[3-(Allyl-methyl-amino)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
443. (3aS,10R)-5-Fluoro-10-(3-hydroxy-phenyl)-6-methoxy-3a-methyl-2-[3-(methyl-prop-2-ynyl-amino)-propyl]-3a,4,9,10-tetrahydro-2,9,10a-triaza-cyclopenta[b]fluorene-1,3-dione
444. (3aS,10R)-5-Fluoro-10-(3-hydroxy-phenyl)-2-[3-(isopropyl-methyl-amino)-propyl]-6-methoxy-3a-methyl-3a,4,9,10-tetrahydro-2,9,10a-triaza-cyclopenta[b]fluorene-1,3-dione
445. (3aS,10R)-5-Fluoro-10-(3-hydroxy-phenyl)-6-methoxy-3a-methyl-2-(3-morpholin-4-yl-propyl)-3a,4,9,10-tetrahydro-2,9,10a-triaza-cyclopenta[b]fluorene-1,3-dione
446. (3aS,10R)-5-Fluoro-10-(3-hydroxy-phenyl)-6-methoxy-3a-methyl-2-(3-pyrrolidin-1-yl-propyl)-3a,4,9,10-tetrahydro-2,9,10a-triaza-cyclopenta[b]fluorene-1,3-dione 447. (3aS,10R)-2-[3-(2,5-Dihydro-pyrrol-1-yl)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
448. (3aS,10R)-5-Fluoro-10-(3-hydroxy-phenyl)-6-methoxy-3a-methyl-2-[3-(4-methyl-piperazin-1-yl)-propyl]-3a,4,9,10-tetrahydro-2,9,10a-triaza-cyclopenta[b]fluorene-1,3-dione
449. (3aS,10R)-2-[3-(4-Acetyl-piperazin-1-yl)-propyl]-5-fluoro-10-(3-hydroxy-phenyl)-6-methoxy-3a-methyl-3a,4,9,10-tetrahydro-2,9,10a-triaza-cyclopenta[b]fluorene-1,3-dione
450. (3aS,10R)-2-(3-Azepan-1-yl-propyl)-5-fluoro-10-(3-hydroxy-phenyl)-6-methoxy-3a-methyl-3a,4,9,10-tetrahydro-2,9,10a-triaza-cyclopenta[b]fluorene-1,3-dione
451. (3aS,10R)-2-{2-[Ethyl-(2-hydroxy-ethyl)-amino]-ethyl}-7-fluoro-10-(3-hydroxy-phenyl)-6-methoxy-3a-methyl-3a,4,9,10-tetrahydro-2,9,10a-triaza-cyclopenta[b]fluorene-1,3-dione
452. (3aS,10R)-2-[2-(Allyl-methyl-amino)-ethyl]-7-fluoro-10-(3-hydroxy-phenyl)-6-methoxy-3a-methyl-3a,4,9,10-tetrahydro-2,9,10a-triaza-cyclopenta[b]fluorene-1,3-dione
453. (3aS,10R)-6-(1,1-Difluoro-methoxy)-2-{3-[(2-hydroxy-ethyl)-methyl-amino]-propyl}-10-(3-hydroxy-phenyl)-3a-methyl-3a,4,9,10-tetrahydro-2,9,10a-triaza-cyclopenta[b]fluorene-1,3-dione
454. (3aS,10R)-2-{2-[Ethyl-(2-methoxy-ethyl)-amino]-ethyl}-7-fluoro-10-(3-hydroxy-phenyl)-6-methoxy-3a-methyl-3a,4,9,10-tetrahydro-2,9,10a-triaza-cyclopenta[b]fluorene-1,3-dione
455. (3aS,10R)-7-Fluoro-10-(3-hydroxy-phenyl)-6-methoxy-3a-methyl-2-[2-(methyl-prop-2-ynyl-amino)-ethyl]-3a,4,9,10-tetrahydro-2,9,10a-triaza-cyclopenta[b]fluorene-1,3-dione
490. (3aS,10R)-10-(3-Hydroxy-phenyl)-6-methoxy-2-[3-(2-methoxy-ethylamino)-propyl]-3a-methyl-3a,4,9,10-tetrahydro-2,9,10a-triaza-cyclopenta[b]fluorene-1,3-dione, or a salt thereof.

13. A compound according to claim 1, wherein
R1 is 2-(R11)-ethyl or 3-(R11)-propyl;
R2 and R3 are both hydrogen;
R4 is methyl;
R5 is bonded to the 6-position of the scaffold, and is chlorine, bromine, ethoxy, methoxy or difluoromethoxy; and
R6 is hydrogen;
or a salt, stereoisomer or salt of a stereoisomer thereof.

14. A compound according to claim 1, wherein
R1 is 2-(R11)-ethyl;
R2 and R3 are both hydrogen;
R4 is methyl;
R5 is bonded to the 6-position of the scaffold, and is chlorine, ethoxy, methoxy or difluoromethoxy; and
R6 is hydrogen;
or a salt, stereoisomer or salt of a stereoisomer thereof.

15. A method for treating a disease selected from the group consisting of benign neoplasia and malignant neoplasia, comprising administering to a patient in need thereof an effective amount of a compound according to claim 1.

16. A pharmaceutical composition comprising a compound according to claim 1 and a pharmaceutically acceptable carrier, auxiliary and/or excipient.

17. A method for treating a (hyper)proliferative disease and/or disorder responsive to induction of apoptosis selected from the group consisting of tumors; tumors selected from the group consisting of tumors of the breast, bladder, bone, brain, central and peripheral nervous system, colon, endocrine glands, thyroid, adrenal cortex, esophagus, endometrium, germ cells, head and neck, kidney, liver, lung, larynx, hypopharynx, mesothelioma, sarcoma, ovary, pancreas, prostate, rectum, renal, small intestine, soft tissue, testis, stomach, skin, ureter, vagina, and vulva;
malignant neoplasia;
malignant neoplasia selected from the group consisting of inherited cancers, retinoblastoma, Wilms tumor, primary tumors and secondary tumors;
hematological tumors;
hematological tumors selected from the group consisting of aggressive forms of leukemia, aggressive forms of lymphoma, indolent forms of leukemia, indolent forms of lymphoma, non-Hodgkins disease, chronic myeloid leukemia, acute myeloid leukemia, acute lymphoblastic leukemia, Hodgkins disease, multiple myeloma and T-cell lymphoma;
myelodysplastic syndrome;
plasma cell neoplasia;
paraneoplastic syndromes;
cancers of unknown primary site, and
AIDS related malignancies, in a mammal, comprising administering a therapeutically effective and tolerable amount of one or more compounds according to claim 1 to said mammal in need thereof.

18. A method for treating or ameliorating a (hyper)proliferative disease and/or disorder responsive to induction of apoptosis selected from the group consisting of
benign hyperplasia, benign hyperplasia of the prostate and benign hyperplasia of the colon epithelium, in a mammal comprising administering a therapeutically effective and tolerable amount of one or more compounds according to claim 1 to said mammal in need thereof.

19. A method for modulating Eg5 kinesin activity comprising administering a therapeutically effective and tolerable amount of one or more compounds according to claim 1 to a mammal in need of said modulation.

20. A combination comprising
a first active ingredient, which is at least one compound according to claim 1, and
a second active ingredient, which is at least one anti-cancer agent selected from the group consisting of chemotherapeutic anti-cancer agents and target-specific anti-cancer agents.

21. A method for treating or ameliorating a disease selected from the group consisting of benign neoplasia and malignant neoplasia, in a patient, comprising administering separately, simultaneously, concurrently, sequentially or chronologically staggered to said patient in need thereof an amount of a first active compound, which is a compound according to claim 1, and an amount of at least one second active compound, said second active compound being an anti-cancer agent selected from the group consisting of chemotherapeutic anti-cancer agents and target-specific anti-cancer agents, wherein the amounts of the first active compound and said second active compound result in a therapeutic effect.

22. The combination according to claim 20, in which said chemotherapeutic anti-cancer agents are selected from the group consisting of alkylating/carbamylating agents, Cyclophosphamid, Ifosfamid, Thiotepa, Melphalan, chloroethylnitrosourea; platinum derivatives, cis-platin, oxaliplatin, satraplatin, carboplatin;
antimitotic agents/tubulin inhibitors, vinca alkaloids, vincristine, vinblastine, vinorelbine, taxanes, Paclitaxel, Docetaxel, analogs and formulations and conjugates of taxanes Abraxane, epothilones, Epothilone B, Aza-epothilone, ZK-EPO; topoisomerase inhibitors, anthracyclines, Doxorubicin, epipodophyllotoxines, Etoposide, camptothecin, camptothecin analogs, Irinotecan, Topotecan; pyrimidine antagonists, 5-fluorouracil, Capecitabine, Arabinosylcytosine/Cytarabin, Gemcitabine; purin antagonists, 6-mercaptopurine, 6-thioguanine, fludarabine; folic acid antagonists, methotrexate and pemetrexed.

23. The combination according to claim 20, in which said target-specific anti-cancer agents are selected from the group consisting of kinase inhibitors, Imatinib, ZD-1839/Gefitinib, BAY43-9006/Sorafenib, SU11248/Sunitinib, OSI-774/Erlotinib, Dasatinib, Lapatinib, Vatalanib, Vandetanib, Pazopanib; proteasome inhibitors, PS-341/Bortezomib; histone deacetylase inhibitors, SAHA, PXD101, MS275, MGCD0103, Depsipeptide/FK228, NVP-LBH589, NVP-LAQ824, Valproic acid (VPA), CRA/PCI-24781, ITF2357, SB939, butyrates; heat shock protein 90 inhibitors, 17-allylaminogeldanamycin (17-AAG), 17-dimethylaminogeldanmycin (17-DMAG); vascular targeting agents (VAT), combretastatin A4 phosphate, AVE8062/AC7700, anti-angiogenic drugs, VEGF antibodies, Bevacizumab, KDR tyrosine kinase inhibitors, PTK787/ZK222584 (Vatalanib), Vandetanib, Pazopanib; monoclonal antibodies, Trastuzumab, Rituximab, Alemtuzumab, Tositumomab, Cetuximab, Bevacizumab, Panitumumab, mutants of monoclonal antibodies, conjugates of monoclonal antibodies, Gemtuzumab ozogamicin, Ibritumomab tiuxetan, antibody fragments; oligonucleotide based therapeutics, G-3139/Oblimersen, DNMT1 inhibitor MG98; Toll-like receptor/TLR 9 agonists, CPG-7909, TLR 7 agonists, Imiquimod, Isatoribine, analogues of TLR 7 agonists, TLR 7/8 agonists, Resiquimod, immunostimulatory RNA as TLR 7/8 agonists; protease inhibitors; hormonal therapeutics, anti-estrogens, Tamoxifen, Raloxifen, anti-androgens, Flutamide, Casodex, LHRH analogs, Luprolide, Goserelin, Triptorelin, aromatase inhibitors; bleomycin; retinoids, all-trans retinoic acid (ATRA); DNA methyltransferase inhibitors, 2-deoxycytidine derivative Decitabine, 5-azacytidine; alanosine; cytokines, interleukin-2; interferons, interferon α2, interferon-γ; death receptor agonists, TRAIL, DR4/5 agonistic antibodies, FasL, TNF-R agonists, TRAIL receptor agonists, mapatumumab and lexatumumab.

24. A method for treating cancer selected from the group consisting of
cancer of the breast, bladder, bone, brain, central peripheral nervous system, peripheral nervous system, colon, endocrine glands, esophagus, endometrium, germ cells, head and neck, kidney, liver, lung, larynx, hypopharynx, mesothelioma, sarcoma, ovary, pancreas, prostate, rectum, renal, small intestine, soft tissue, testis, stomach, skin, ureter, vagina, vulva;
inherited cancers, retinomblastoma, Wilms tumor;
leukemia, lymphoma, non-Hodgkins disease, chronic myeloid leukaemia, acute myeloid leukaemia, acute lymphoblastic leukemia, Hodgkins disease, multiple myeloma, T-cell lymphoma;
myelodysplastic syndrome, plasma cell neoplasia, paraneoplastic syndromes, cancers of unknown primary site and AIDS related malignancies, in a mammal, comprising
administering a therapeutically effective and tolerable amount of one or more compounds according to claim 1 to said mammal in need thereof.

25. A method for treating colon cancer in a mammal, comprising administering a therapeutically effective and tolerable amount of one or more compounds according to claim 1 to said mammal in need thereof.

26. A method for treating cancer of the breast, bladder, bone, brain, central peripheral nervous system, peripheral nervous system, colon, endocrine glands, esophagus, endometrium, germ cells, head and neck, kidney, liver, lung, larynx, hypopharynx, mesothelioma, sarcoma, ovary, pancreas, prostate, rectum, renal, small intestine, soft tissue, testis, stomach, skin, ureter, vagina, or vulva;
retinomblastoma, Wilms tumor;
leukemia, lymphoma, non-Hodgkins disease, chronic myeloid leukaemia, acute myeloid leukaemia, acute lymphoblastic leukemia, Hodgkins disease, multiple myeloma, or T-cell lymphoma,
comprising administering a therapeutically effective and tolerable amount of one or more compounds according to claim 1 to said mammal in need thereof.

27. A compound of formula I according to claim 1, in which R1 is 2-4C-alkenyl, 2-4C-alkinyl or 3-7C-cycloalkyl-1-4C-alkyl, or a salt thereof.

28. A compound of formula I

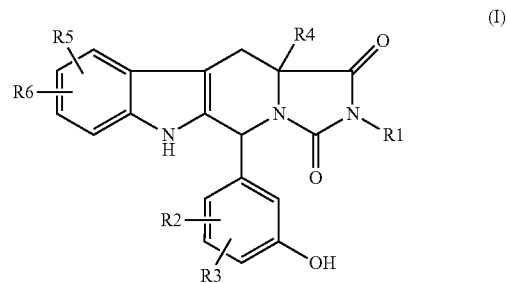

in which
R1 is 1-4C-alkyl, 3-7C-cycloalkyl, 2-4C-alkenyl, 2-4C-alkinyl, 3-7C-cycloalkyl-1-4C-alkyl, or 2-7C-alkyl substituted by R11, in which
R11 is —N(R111)R112, or halogen, in which
R111 is hydrogen, 1-4C-alkyl, 2-4C-alkenyl, 2-4C-alkinyl, 3-7C-cycloalkyl, 3-7C-cycloalkyl-1-4C-alkyl, hydroxy-2-4C-alkyl, 1-4C-alkoxy-2-4C-alkyl, 1N-(1-4C-alkyl)-pyrazolyl, 1N-(H)-pyrazolyl, isoxazolyl, or completely or partially fluorine-substituted 1-4C-alkyl,
R112 is hydrogen, 1-4C-alkyl, 3-7C-cycloalkyl, or 3-7C-cycloalkyl-1-4C-alkyl,
or
R111 and R112 together and with inclusion of the nitrogen atom, to which they are bonded, form a ring Het, in which
Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N-(R113)-piperazin-1-yl, 4N-(R113)-homopiperazin-1-yl, 2,5-dihydro-pyrrol-1-yl, 1,2,3,6-tetrahydropyridin-1-yl, pyrrol-1-yl, pyrazol-1-yl, imidazol-1-yl, triazol-1-yl, or tetrazol-1-yl, in which
R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl,
wherein said Het may be optionally substituted by one or two substituents independently selected from fluorine and 1-4C-alkyl, R2 is hydrogen, 1-4C-alkyl, halogen, trifluoromethyl, 1-4C-alkoxy or hydroxyl, R3 is hydrogen, 1-4C-alkyl, halogen, trifluoromethyl or 1-4C-alkoxy, R4 is 3-7C-cycloalkyl or 3-7C-cycloalkyl-1-4C-alkyl, R5 is 3-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, and R6 is hydrogen, 1-4C-alkyl or halogen, or a salt thereof.

29. A compound of formula I

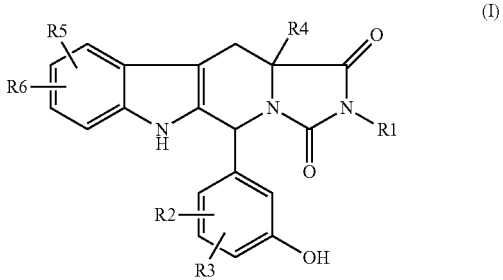

in which

R1 is 1-4C-alkyl, 3-7C-cycloalkyl, 2-4C-alkenyl, 2-4C-alkinyl, 3-7C-cycloalkyl-1-4C-alkyl, or 2-7C-alkyl substituted by R11, in which R11 is —N(R111)R112, or halogen, in which R111 is hydrogen, 1-4C-alkyl, 2-4C-alkenyl, 2-4C-alkinyl, 3-7C-cycloalkyl, 3-7C-cycloalkyl-1-4C-alkyl, hydroxy-2-4C-alkyl, 1-4C-alkoxy-2-4C-alkyl, 1N-(1-4C-alkyl)-pyrazolyl, 1N-(H)-pyrazolyl, isoxazolyl, or completely or partially fluorine-substituted 1-4C-alkyl, R112 is hydrogen, 1-4C-alkyl, 3-7C-cycloalkyl, or 3-7C-cycloalkyl-1-4C-alkyl, or R111 and R112 together and with inclusion of the nitrogen atom, to which they are bonded, form a ring Het, in which Het is piperidin-1-yl, morpholin-4-yl, thiomorpholin-4-yl, S-oxo-thiomorpholin-4-yl, S,S-dioxo-thiomorpholin-4-yl, pyrrolidin-1-yl, azetidin-1-yl, homopiperidin-1-yl, 4N-(R113)-piperazin-1-yl, 4N-(R113)-homopiperazin-1-yl, 2,5-dihydro-pyrrol-1-yl, 1,2,3,6-tetrahydropyridin-1-yl, pyrrol-1-yl, pyrazol-1-yl, imidazol-1-yl, triazol-1-yl, or tetrazol-1-yl, in which R113 is hydrogen, 1-4C-alkyl, 3-7C-cycloalkyl, 3-7C-cycloalkyl-1-4C-alkyl, 1-4C-alkylcarbonyl, amidino, or completely or partially fluorine-substituted 1-4C-alkyl, wherein said Het may be optionally substituted by one or two substituents independently selected from fluorine and 1-4C-alkyl, R2 is hydrogen, 1-4C-alkyl, halogen, trifluoromethyl, 1-4C-alkoxy or hydroxyl, R3 is hydrogen, 1-4C-alkyl, halogen, trifluoromethyl or 1-4C-alkoxy, R4 is 1-4C-alkyl, 3-7C-cycloalkyl or 3-7C-cycloalkyl-1-4C-alkyl, R5 is 3-4C-alkyl, halogen, 1-4C-alkoxy, trifluoromethyl, cyano, hydroxyl, phenyl-1-4C-alkoxy, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, and R6 is 1-4C-alkyl or halogen, or a salt thereof.

30. A compound of formula I according to claim 1, in which

R5 is 1-4C-alkoxy-2-4C-alkoxy, 3-7C-cycloalkyl-1-4C-alkoxy, or completely or predominantly fluorine-substituted 1-4C-alkoxy.

31. A compound of formula I according to claim 1, in which

R5 is 1-4C-alkoxy.

32. A compound of formula I according to claim 1, in which

R5 is methoxy.

33. A compound, which is a compound of formulae Ib* or Ic*

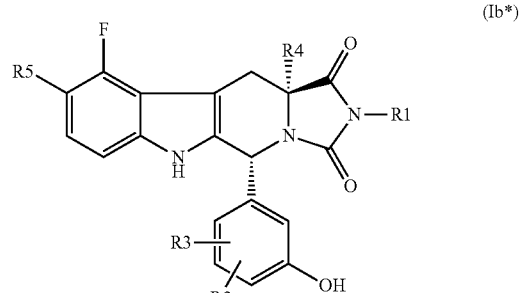

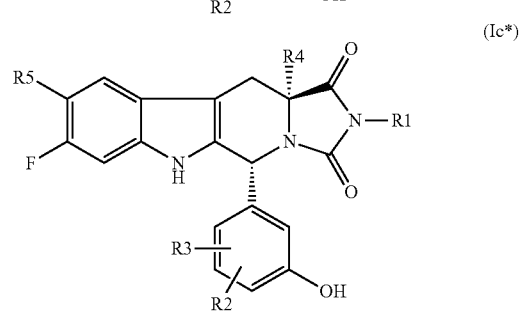

in which

R2 and R3 are both hydrogen,

R4 is methyl or ethyl, and

R1 and R5 have any of the following meanings:

| R1 | R5 |
|---|---|
| methyl | —CH₃ |
| 2-(dimethylamino)-ethyl | —CH₃ |
| 3-(dimethylamino)-propyl | —CH₃ |
| 2-(morpholin-4-yl)-ethyl | —CH₃ |
| 2-(pyrrolidin-1-yl)-ethyl | —CH₃ |
| 2-(imidazol-1-yl)-ethyl | —CH₃ |
| 2-(4-methyl-piperazin-1-yl)-ethyl | —CH₃ |
| 3-(morpholin-4-yl)-propyl | —CH₃ |
| 3-(pyrrolidin-1-yl)-propyl | —CH₃ |
| 3-(imidazol-1-yl)-propyl | —CH₃ |
| 3-(4-methyl-piperazin-1-yl)-propyl | —CH₃ |
| 3-amino-propyl | —CH₃ |
| 2-amino-ethyl | —CH₃ |
| 2-(methylamino)-ethyl | —CH₃ |
| 2-(ethylamino)-ethyl | —CH₃ |
| 2-(azetidin-1-yl)-ethyl | —CH₃ |
| 2-(4-acetyl-piperazin-1-yl)-ethyl | —CH₃ |

-continued

| R1 | R5 |
|---|---|
| 2-(3,3-difluoropyrrolidin-1-yl)-ethyl | —CH₃ |
| 2-(2-fluoroethylamino)-ethyl | —CH₃ |
| 2-(2,2-difluoroethylamino)-ethyl | —CH₃ |
| 2-(2,2,2-trifluoroethylamino)-ethyl | —CH₃ |
| 2-(isopropylamino)-ethyl | —CH₃ |
| 2-(isobutylamino)-ethyl | —CH₃ |
| 2-(N-cyclopropylmethyl-amino)-ethyl | —CH₃ |
| 2-(cyclopropylamino)-ethyl | —CH₃ |
| 2-(cyclobutylamino)-ethyl | —CH₃ |
| 2-(N-ethyl-N-methyl-amino)-ethyl | —CH₃ |
| 2-(diethylamino)-ethyl | —CH₃ |
| 2-(N-isopropyl-N-methyl-amino)-ethyl | —CH₃ |
| 2-((R)-3-fluoro-pyrrolidin-1-yl)-ethyl | —CH₃ |
| 2-((S)-3-fluoro-pyrrolidin-1-yl)-ethyl | —CH₃ |
| 2-(4-methyl-piperidin-l-yl)-ethyl | —CH₃ |
| 3-(methylamino)-propyl | —CH₃ |
| 3-(ethylamino)-propyl | —CH₃ |
| 3-(azetidin-1-yl)-propyl | —CH₃ |
| 3-(4-acetyl-piperazin-1-yl)-propyl | —CH₃ |
| 3-(3,3-difluoropyrrolidin-1-yl)-propyl | —CH₃ |
| 3-(2-fluoroethylamino)-propyl | —CH₃ |
| 3-(2,2-difluoroethylamino)-propyl diploma | —CH₃ |
| 3-(2,2,2-trifluoroethylamino)-propyl | —CH₃ |
| 3-(isopropylamino)-propyl | —CH₃ |
| 3-(isobutylamino)-propyl | —CH₃ |
| 3-(N-cyclopropylmethyl-amino)-propyl versitale | —CH₃ |
| 3-(cyclopropylamino)-propyl | —CH₃ |
| 3-(cyclobutylamino)-propyl | —CH₃ |
| 3-(N-ethyl-N-methyl-amino)-propyl | —CH₃ |
| 3-(diethylamino)-propyl | —CH₃ |
| 3-(N-isopropyl-N-methyl-amino)-propyl | —CH₃ |
| 3-((R)-3-fluoro-pyrrolidin-1-yl)-propyl | —CH₃ |
| 3-((S)-3-fluoro-pyrrolidin-1-yl)-propyl | —CH₃ |
| 3-(4-methyl-piperidin-l-yl)-propyl | —CH₃ |
| 3-[N-(2-hydroxyethyl)-amino]-propyl | —CH₃ |

-continued

| R1 | R5 |
|---|---|
| 3-[N-(2-methoxyethyl)-amino]-propyl | —CH₃ |
| 3-(tertbutylamino)-propyl | —CH₃ |
| 3-(allylamino)-propyl | —CH₃ |
| 3-(propargylamino)-propyl | —CH₃ |
| 3-(N-allyl-N-methyl-amino)-propyl | —CH₃ |
| 3-(N-methyl-N-propargyl-amino)-propyl | —CH₃ |
| 3-[N-(2-hydroxyethyl)-N-methyl-amino]-propyl | —CH₃ |
| 3-[N-(2-methoxyethyl)-N-methyl-amino]-propyl | —CH₃ |
| 3-[N-ethyl-N-(2-hydroxyethyp-amino]-propyl | —CH₃ |
| 3-[N-ethyl-N-(2-methoxyethyl)-amino]-propyl | —CH₃ |
| 3-(piperidin-1-yl)-propyl | —CH₃ |
| 3-(homopiperidin-1-yl)-propyl | —CH₃ |
| 3-(2,5-dihydropyrrol-1-yl)-propyl | —CH₃ |
| 3-(1,2,3,6-tetrahydropyridin-1-yl)-propyl | —CH₃ |
| 2-[N-(2-hydroxyethyl)-amino]-ethyl | —CH₃ |
| 2-[N-(2-methoxyethyl)-amino]-ethyl | —CH₃ |
| 2-(tertbutylamino)-ethyl | —CH₃ |
| 2-(allylamino)-ethyl | —CH₃ |
| 2-(propargylamino)-ethyl | —CH₃ |
| 2-(N-allyl-N-methyl-amino)-ethyl | —CH₃ |
| 2-(N-methyl-N-propargyl-amino)-ethyl | —CH₃ |
| 2-[N-(2-hydroxyethyl)-N-methyl-amino]-ethyl | —CH₃ |
| 2-[N-(2-methoxyethyl)-N-methyl-amino]-ethyl | —CH₃ |
| 2-[N-ethyl-N-(2-hydroxyethyl)-amino]-ethyl | —CH₃ |
| 2-[N-ethyl-N-(2-methoxyethyl)-amino]-ethyl | —CH₃ |
| 2-(piperidin-1-yl)-ethyl | —CH₃ |
| 2-(homopiperidin-1-yl)-ethyl | —CH₃ |
| 2-(2,5-dihydropyrrol-1-yl)-ethyl | —CH₃ |
| 2-(1,2,3,6-tetrahydropyridin-1-yl)-ethyl | —CH₃ | or a salt thereof.

\* \* \* \* \*

UNITED STATES PATENT AND TRADEMARK OFFICE
CERTIFICATE OF CORRECTION

PATENT NO. : 8,530,493 B2
APPLICATION NO. : 12/280424
DATED : September 10, 2013
INVENTOR(S) : Matthias Vennemann et al.

Page 1 of 1

It is certified that error appears in the above-identified patent and that said Letters Patent is hereby corrected as shown below:

In the Claims:

Column 441, line 39 reads "yl", should read --(R)-3-fluoro-pyrrolidin-l-yl--;

Column 467, lines 46 and 47 read "is chlorine, bromine, ethoxy, methoxy", should read
--is ethoxy, methoxy--;

Column 467, lines 54 and 55 read "is chlorine, ethoxy, methoxy", should read
--is ethoxy, methoxy--.

Signed and Sealed this
Thirteenth Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,530,493 B2 | Page 1 of 1 |
| APPLICATION NO. | : 12/280424 | |
| DATED | : September 10, 2013 | |
| INVENTOR(S) | : Matthias Vennemann et al. | |

It is certified that error appears in the above-identified patent and that said Letters Patent is hereby corrected as shown below:

In the Claims:

Column 441, line 39 reads "1-yl, (S)-3-fluoro-pyrrolidin-1-yl, yl, 3,3-difluoro-" should read -- 1-yl, (S)-3-fluoro-pyrrolidin-1-yl, (R)-3-fluoro-pyrrolidin-1-yl, 3,3-difluoro- --

Column 467, line 46 reads "R5 is bonded to the 6-position of the scaffold, and is chlo-" should read -- R5 is bonded to the 6-position of the scaffold, and is --

Column 467, line 47 reads "rine, bromine, ethoxy, methoxy or difluoromethoxy; and" should read -- ethoxy, methoxy or difluoromethoxy; and --

Column 467, line 54 reads "R5 is bonded to the 6-position of the scaffold, and is chlo-" should read -- R5 is bonded to the 6-position of the scaffold, and is --

Column 467, line 55 reads "rine, ethoxy, methoxy or difluoromethoxy; and" should read -- ethoxy, methoxy or difluoromethoxy; and --

This certificate supersedes the Certificate of Correction issued May 13, 2014.

Signed and Sealed this
Ninth Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,530,493 B2  Page 1 of 1
APPLICATION NO. : 12/280424
DATED : September 10, 2013
INVENTOR(S) : Vennemann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1217 days.

Signed and Sealed this

Fifteenth Day of September, 2015

Michelle K. Lee
*Director of the United States Patent and Trademark Office*